US012807737B2

(12) United States Patent
Glaser et al.

(10) Patent No.: US 12,807,737 B2
(45) Date of Patent: Nov. 24, 2026

(54) MULTISPECIFIC BINDING AGENTS AND USES THEREOF

(71) Applicant: EXELIXIS, INC., Alameda, CA (US)

(72) Inventors: Bryan Glaser, Madison, WI (US); Bonnie Hammer, Madison, WI (US); Seema Kantak, Pacifica, CA (US)

(73) Assignee: EXELIXIS, INC., Alameda, CA (US)

( * ) Notice: Subject to any disclaimer, the term of this patent is extended or adjusted under 35 U.S.C. 154(b) by 821 days.

(21) Appl. No.: 18/018,864

(22) PCT Filed: Aug. 3, 2021

(86) PCT No.: PCT/US2021/044356

§ 371 (c)(1),
(2) Date: Jan. 30, 2023

(87) PCT Pub. No.: WO2022/031710

PCT Pub. Date: Feb. 10, 2022

(65) Prior Publication Data

US 2024/0010751 A1 Jan. 11, 2024

Related U.S. Application Data

(60) Provisional application No. 63/061,112, filed on Aug. 4, 2020.

(51) Int. Cl.
*A61P 37/02* (2006.01)
*C07K 16/46* (2006.01)

(52) U.S. Cl.
CPC ............ *C07K 16/468* (2013.01); *A61P 37/02* (2018.01); *C07K 2317/31* (2013.01); *C07K 2317/565* (2013.01)

(58) Field of Classification Search
CPC .... C07K 16/468; C07K 2317/31; A61P 37/02
USPC .......................................................... 424/136.1
See application file for complete search history.

(56) References Cited

U.S. PATENT DOCUMENTS

| | | | |
|---|---|---|---|
| 10,239,862 | B2 | 3/2019 | Coburn et al. |
| 10,344,091 | B2 | 7/2019 | Koide et al. |
| 11,739,151 | B2 | 8/2023 | Liu et al. |
| 12,110,332 | B2 | 10/2024 | Guo |
| 2007/0218069 | A1 | 9/2007 | Gordon et al. |
| 2009/0094717 | A1 | 4/2009 | Troukhan et al. |
| 2010/0028354 | A1 | 2/2010 | McKinnon et al. |
| 2010/0203056 | A1 | 8/2010 | Irving et al. |
| 2016/0046711 | A1 | 2/2016 | Bialucha et al. |
| 2016/0304591 | A1 | 10/2016 | Kelley et al. |
| 2017/0368169 | A1 | 12/2017 | Loew et al. |
| 2019/0062306 | A1 | 2/2019 | Coburn et al. |
| 2019/0106494 | A1 | 4/2019 | Wang et al. |
| 2019/0127472 | A1 | 5/2019 | Koide et al. |
| 2020/0270345 | A1 | 8/2020 | Solovyev et al. |
| 2021/0332131 | A1 | 10/2021 | De Boer et al. |
| 2023/0303699 | A1* | 9/2023 | Glaser ................ C07K 16/2827 |
| 2023/0357391 | A1* | 11/2023 | Glaser .................... C12N 15/63 |
| 2025/0197502 | A1 | 6/2025 | Glaser et al. |

FOREIGN PATENT DOCUMENTS

| | | | |
|---|---|---|---|
| JP | 2019528083 | A | 10/2019 |
| JP | 2019532013 | A | 11/2019 |
| JP | 2020511133 | A | 4/2020 |
| JP | 2020517239 | A | 6/2020 |
| WO | WO 2002004520 | A2 | 1/2002 |
| WO | WO 2002004520 | A3 | 1/2002 |
| WO | WO 2007064919 | A2 | 6/2007 |
| WO | WO 2007064919 | A3 | 6/2007 |
| WO | WO 2011016238 | A1 | 2/2011 |
| WO | WO 2012170438 | A2 | 12/2012 |
| WO | WO 2012170438 | A3 | 12/2012 |
| WO | WO 2013055998 | A1 | 4/2013 |
| WO | WO 2017161976 | A1 | 9/2017 |
| WO | WO 2017220990 | A1 | 12/2017 |
| WO | WO 2017220990 | A9 | 12/2017 |
| WO | WO 2018005682 | A2 | 1/2018 |
| WO | WO 2018005682 | A3 | 1/2018 |
| WO | WO 2018162749 | A1 | 9/2018 |
| WO | WO 2018195226 | A1 | 10/2018 |
| WO | WO 2019040791 | A1 | 2/2019 |
| WO | WO 2019095358 | A1 | 5/2019 |
| WO | WO 2019109876 | A1 | 6/2019 |
| WO | WO 2019129211 | A1 | 7/2019 |
| WO | WO 2019144895 | A1 | 8/2019 |
| WO | WO 2019179434 | A1 | 9/2019 |
| WO | WO 2019185035 | A1 | 10/2019 |
| WO | WO 2021142448 | A2 | 7/2021 |
| WO | WO 2021142448 | A3 | 7/2021 |
| WO | WO 2022031680 | A1 | 2/2022 |
| WO | WO 2022031695 | A1 | 2/2022 |

(Continued)

OTHER PUBLICATIONS

Almagro & Franssen, Frontiers in Bioscience, 13:1619-33 (2008).*
Edwards et al., J Mol Biol 334:103-118 (2003).*
Marchalonis et al., Dev & Comp Immunol. 30:223-247 (2006).*
Lippow et al., Nature Biotechnology, 25(10):1171-1176 (2007).*
Sulea et al., Scientific Reports, 8(260):1-11 (2018).*
Hasegawa et al., MABS, vol. 9, No. 5, pp. 854-873 (2017).*
Altshuler et al., Biochemistry (Moscow), 75(13):1584-1605 (2010).*
Vajda et al., Current Opinion in Structural Biology, 67 pp. 226-231 (2021).*
Marks et al., J. Biol. Chem. 295(29) 9823-9837 (2020).*
Akbar et al., Cell Reports 34, 108856, (Mar. 16, 2021).*

(Continued)

*Primary Examiner* — Lynn A Bristol
(74) *Attorney, Agent, or Firm* — JONES DAY

(57) ABSTRACT

The present disclosure provides multispecific binding agents, e.g., antibodies, such as bispecific antibodies, that have a first binding domain that binds to CD47, including human CD47, and one or more additional binding domains that bind to one or more targets that are not CD47, such as PD-L1 and uses thereof.

28 Claims, 71 Drawing Sheets

Specification includes a Sequence Listing.

(56) References Cited

FOREIGN PATENT DOCUMENTS

| | | | | |
|---|---|---|---|---|
| WO | WO 2023154730 | A2 | | 8/2023 |
| WO | WO 2023154730 | A3 | * | 8/2023 |
| WO | WO 2023245022 | A2 | * | 12/2023 |

OTHER PUBLICATIONS

Lo et al., BMC Genomics vol. 22, Article No. 116 (2021).*

Cembrola et al., 2019, "Rapid Affinity Maturation of Novel Anti-PD-L1 Antibodies by a Fast Drop of the Antigen Concentration and FACS Selection of Yeast Libraries," Biomed. Res. Int., 2019:6051870 (22 pages).

International Searching Authority, International Search Report and Written Opinion for International Patent Application No. PCT/US2021/044310 (Pub No. WO 2022031680) mailed Dec. 30, 2021 (13 pages).

International Searching Authority, International Search Report and Written Opinion for International Patent Application No. PCT/US2021/044330 (Pub No. WO 2022031695) mailed Jan. 5, 2022 (13 pages).

International Searching Authority, International Search Report and Written Opinion for International Patent Application No. PCT/US2021/044356 (Pub No. WO 2022031710) mailed Jan. 31, 2022 (13 pages).

International Searching Authority, International Search Report and Written Opinion for International Patent Application No. PCT/US2023/062185 (Pub No. WO 2023154730) mailed Jul. 28, 2023 (14 pages).

Lakhani et al., 2020, "A phase 1b study of the anti-CD47 antibody magrolimab with the PD-L1 inhibitor avelumab (A) in solid tumor (ST) and ovarian cancer (OC) patients," Meeting Abstract, 2020 ASCO-SITC Clinical Immuno-Oncology Symposium, J. Clin. Oncol., 38(5_Suppl):Abstract 18 (2 pages).

Lian et al., 2019, "Dual blockage of both PD-L1 and CD47 enhances immunotherapy against circulating tumor cells," Sci. Rep., 9(1):4532.

Lin et al., 2011, "Improved affinity of a chicken single-chain antibody to avian infectious bronchitis virus by site-directed mutagenesis of complementarity-determining region H 3," African Journal of Biotechnology, 10(79):18294-18303.

Liu et al., 2018, "Elimination of tumor by CD47/PD-L1 dual-targeting fusion protein that engages innate and adaptive immune responses," MAbs, 10(2):315-324 and supplemental material (Epub 2017) (15 pages).

Mariuzza et al., 1987, "The structural basis of antigen-antibody recognition," Annu. Rev. Biophys. Biophys. Chem., 16:139-159.

McCarthy et al., 2001, "Altering the fine specificity of an anti-Legionella single chain antibody by a single amino acid insertion," J. Immunol. Methods, 251(1-2):137-149.

Shi et al., 2020, "The identification of a CD47-blocking "hotspot" and design of a CD47/PD-L1 dual-specific antibody with limited hemagglutination," Signal Transduct Target Ther., 5(1):16 (3 pages).

Chen et al., 2021, "Dual checkpoint blockade of CD47 and PD-L1 using an affinity-tuned bispecific antibody maximizes antitumor immunity," J. Immunother. Cancer, 9(10):e003464 (17 pages).

Wang et al., 2022, "Abstract CT513: Phase I study of IBI322 (anti-CD47/PD-L1 bispecific antibody) monotherapy therapy in patients with advanced solid tumors in China," Cancer Research, 82(12_Suppl):CT513.

Yang et al., 2021, "Potential Role of CD47-Directed Bispecific Antibodies in Cancer Immunotherapy," Front Immunol., 12:686031 (10 pages).

* cited by examiner

Cell Binding

C40xP31.2

Cell Binding

C59xP31.2

Cell Binding

| # | Time | Area | Height | Width | Symmetry |
|---|---|---|---|---|---|
| 1 | 7.497 | 18.7 | 4.1E-1 | 0.5351 | 1.163 |
| 2 | 8.814 | 932.2 | 41.7 | 0.3441 | 0.848 |
| 3 | 9.5 | 22.8 | 1.3 | 0.2508 | 0.543 |
| 4 | 12.811 | 7.1 | 4.3E-1 | 0.2192 | 0.991 |

| # | Time | Area | Height | Width | Symmetry |
|---|---|---|---|---|---|
| 1 | 7.383 | 79.7 | 1.6 | 0.5953 | 0.678 |
| 2 | 8.798 | 805.8 | 34.9 | 0.3536 | 0.859 |
| 3 | 12.837 | 11.3 | 6.8E-1 | 0.2218 | 1.037 |

| # | Time | Area | Height | Width | Symmetry |
|---|---|---|---|---|---|
| 1 | 7.598 | 176.4 | 4.6 | 0.5426 | 0.755 |
| 2 | 8.784 | 698.6 | 28.5 | 0.3746 | 0.798 |
| 3 | 12.765 | 11 | 7.7E-1 | 0.1959 | 0.8 |

| # | Time | Area | Height | Width | Area% | Symmetry |
|---|---|---|---|---|---|---|
| 1 | 10.228 | 821.5 | 40.8 | 0.2889 | 100.000 | 0.329 |

| # | Time | Area | Height | Width | Area% | Symmetry |
|---|---|---|---|---|---|---|
| 1 | 10.502 | 558.4 | 26.6 | 0.3006 | 100.000 | 0.373 |

| # | Time | Area | Height | Width | Area% | Symmetry |
|---|---|---|---|---|---|---|
| 1 | 10.371 | 740.3 | 39.2 | 0.2804 | 100.000 | 1.094 |

| # | Time | Area | Height | Width | Area% | Symmetry |
|---|---|---|---|---|---|---|
| 1 | 9.594 | 611.2 | 28.3 | 0.3081 | 75.741 | 0.338 |
| 2 | 10.481 | 195.8 | 4.6 | 0.5303 | 24.259 | 0.167 |

| # | Time | Area | Height | Width | Area% | Symmetry |
|---|---|---|---|---|---|---|
| 1 | 8.563 | 154.9 | 3.2 | 0.6328 | 8.198 | 4.413 |
| 2 | 9.221 | 1714 | 94.6 | 0.2834 | 90.724 | 0.9 |
| 3 | 12.226 | 20.4 | 1.7 | 0.1855 | 1.078 | 1.317 |

| # | Time | Area | Height | Width | Area% | Symmetry |
|---|---|---|---|---|---|---|
| 1 | 5.664 | 11.8 | 5.4E-1 | 0.3206 | 0.516 | 0.646 |
| 2 | 7.478 | 40 | 7.9E-1 | 0.6695 | 1.745 | 0.544 |
| 3 | 9.583 | 2200.8 | 83 | 0.3812 | 96.036 | 0.643 |
| 4 | 12.243 | 39 | 2.6 | 0.2179 | 1.703 | 2.136 |

| # | Time | Area | Height | Width | Area% | Symmetry |
|---|---|---|---|---|---|---|
| 1 | 9.173 | 2072.1 | 58.6 | 0.5005 | 100.000 | 0.554 |

C59xP22

| # | Time | Area | Height | Width | Area% | Symmetry |
|---|---|---|---|---|---|---|
| 1 | 7.268 | 122.9 | 4.3 | 0.3903 | 5.723 | 3.475 |
| 2 | 7.7 | 374 | 14.4 | 0.374 | 17.408 | 0.639 |
| 3 | 8.793 | 1625.5 | 97.5 | 0.2585 | 75.664 | 0.851 |
| 4 | 12.224 | 25.9 | 2.2 | 0.185 | 1.205 | 1.31 |

```
VH Domain
Kabat      1      10          22        31--35   40          50--a------60---65
AbM        1      10          22   26-------35   40          50--a----58     65
Chothia    1      10          22   26----32      40              a-55        65
Contact    1      10          22       30---35   40      47------a----58     65
IMGT       1                  23   27-----38  41              56-----65      74
C40        EVQLVESGGGLVQPGGSLRLSCAAS GFTFSYYYIH WVRQAPGKGLEWVA WIDPYGHSTTYADSVKG
C56        EVQLVESGGGLVQPGGSLRLSCAAS GFTFTYYYIH WVRQAPGKGLEWVA FIDPYSGSTEYADSVKG
C59        EVQLVESGGGLVQPGGSLRLSCAAS GFTFTSYYIH WVRQAPGKGLEWVA YIDSKHGTTQYADSVKG
                                     GFTFtyYYIH                -IDpy-gsT-YADSVKG

Kabat         70        80  abc      90    95----102      110
AbM           70        80  abc      90    95----102      110
Chothia       70        80  abc      90     96--101       110
Contact       70        80  abc      90 93------101       110
IMGT      75               89          105-------117
C40        RFTISADTSKNTAYLQMNSLRAEDTAVYYCAR GGRGAMDY WGQGTLVT (SEQ ID NO:25)
C56        RFTISADTSKNTAYLQMNSLRAEDTAVYYCAR GGLYALDY WGQGTLVT (SEQ ID NO:51)
C59        RFTISADTSKNTAYLQMNSLRAEDTAVYYCAR GGRSAMDY WGQGTLVT (SEQ ID NO:77)
                                            GGr-AmDY          (SEQ ID NO:212)
```

FIG. 22A

```
VL Domain
Kabat       1      10       20   24-27-----34     40        50----56
AbM         1      10       20   24----30--34     40        50----56
Chothia     1      10       20     26----32       40        50--
Contact     1      10       20         30-----36  40    46--------55
IMGT        1                  23     27---38  41           56-65 69
                                                             |  |
C40.        DIQMTQSPSSLSASVGDRVTITC RASQSVSSAVA WYQQKPGKAPKLLIY SASSLYS
C56         DIQMTQSPSSLSASVGDRVTITC RASQSVSSAVA WYQQKPGKAPKLLIY SASSLYS
C59         DIQMTQSPSSLSASVGDRVTITC RASQSVSSAVA WYQQKPGKAPKLLIY SASSLYS
                                    RASQSVSSAVA                 SASSLYS


Kabat         60        70        80       89------97
AbM           60        70        80       89------97
Chothia       60        70        80         91---96
Contact       60        70        80       89-----96
IMGT        70               89           105-----117
C40.        GVPSRFSGSRSGTDFTLTISSLQPEDFATYYC QQRYSSLLT FGQGTKVEIK (SEQ ID NO:26)
C56         GVPSRFSGSRSGTDFTLTISSLQPEDFATYYC QQGRSDLRT FGQGTKVEIK (SEQ ID NO:52)
C59         GVPSRFSGSRSGTDFTLTISSLQPEDFATYYC QQRTTSLLT FGQGTKVEIK (SEQ ID NO:78)
                                             QQr-ssLlT            (SEQ ID NO:213)
```

FIG. 22B

VH Domain

| | | | | |
|---|---|---|---|---|
| Kabat | 1 10 22 | **31--35** | 40 | **50--a------60---65** |
| AbM | 1 10 22 | **26-------35** | 40 | **50--a----58** 65 |
| Chothia | 1 10 22 | **26----32** | 40 | **a-55** 65 |
| Contact | 1 10 22 | **30---35** | 40 | **47------a----58** 65 |
| IMGT | 1 23 | **27-----38** | 41 | **56-----65** 74 |
| P24 | EVQLVESGGGLVQPGGSLRLSCAAS | GFTFDQYYIH | WVRQAPGKGLEWVA | EIYPAGSYTYYADSVKG |
| P22 | EVQLVESGGGLVQPGGSLRLSCAAS | GFTFSSYYIH | WVRQAPGKGLEWVA | WITSHGYSTKYADSVKG |
| P31.2 | EVQLVESGGGLVQPGGSLRLSCAAS | GFTFSSYYIH | WVRQAPGKGLEWVA | TISSGGGFTYYADSVKG |
| | | GFTFssYYIH | | -I---G--TyYADSVKG |

| | | | | |
|---|---|---|---|---|
| Kabat | 70 80 abc 90 | **95-------102** | 110 | |
| AbM | 70 80 abc 90 | **95-------102** | 110 | |
| Chothia | 70 80 abc 90 | **96-----101** | 110 | |
| Contact | 70 80 abc 90 | **93---------101** | 110 | |
| IMGT | 75 89 | **105----------117** | | |
| P24 | RFTISADTSKNTAYLQMNSLRAEDTAVYYCAR | GPYSVRYALDY | WGQGTLVT | (SEQ ID NO:129) |
| P22 | RFTISADTSKNTAYLQMNSLRAEDTAVYYCAR | DSVIYG--LDY | WGQGTLVT | (SEQ ID NO:103) |
| P31.2 | RFTISADTSKNTAYLQMNSLRAEDTAVYYCAR | GYTLTPV-LDY | WGQGTLVT | (SEQ ID NO:155) |
| | | g-------LDY | | (SEQ ID NO:214) |

FIG. 23A

```
VL Domain
Kabat      1      10       20   24-27-----34     40         50----56
AbM        1      10       20   24----30--34     40         50----56
Chothia    1      10       20     26----32       40         50--
Contact    1      10       20         30-----36  40     46--------55
IMGT       1                  23   27---38   41             56-65 69
                                                             |  |
P24        DIQMTQSPSSLSASVGDRVTITC RASQSVSSAVA WYQQKPGKAPKLLIY SASSLYS
P22        DIQMTQSPSSLSASVGDRVTITC RASQSVSSAVA WYQQKPGKAPKLLIY SASSLYS
P31.2      DIQMTQSPSSLSASVGDRVTITC RASQSVSSAVA WYQQKPGKAPKLLIY SASSLYS
                                   RASQSVSSAVA                 SASSLYS


Kabat        60       70       80      89------97
AbM          60       70       80      89------97
Chothia      60       70       80        91---96
Contact      60       70       80      89-----96
IMGT      70             89           105-----117
P24        GVPSRFSGSRSGTDFTLTISSLQPEDFATYYC QQVSYSPYT FGQGTKVEIK (SEQ ID NO:130)
P22        GVPSRFSGSRSGTDFTLTISSLQPEDFATYYC QQYYTSPYT FGQGTKVEIK (SEQ ID NO:104)
P31.2      GVPSRFSGSRSGTDFTLTISSLQPEDFATYYC QQFGAEPIT FGQGTKVEIK (SEQ ID NO:156)
                                            QQ---sPyT            (SEQ ID NO:215)
```

FIG. 23B

MULTISPECIFIC BINDING AGENTS AND USES THEREOF

CROSS-REFERENCE TO RELATED APPLICATIONS

This application is a U.S. National Stage Application under 35 U.S.C. § 371 of International Patent Application No. PCT/US2021/044356, filed Aug. 3, 2021, which claims the benefit of U.S. Provisional Application No. 63/061,112, filed Aug. 4, 2020, the disclosure of each of which is incorporated by reference herein in its entirety.

SEQUENCE LISTING

This application incorporates by reference a Sequence Listing submitted with this application as a text file, entitled 14529-008-228_SEQ_LISTING.txt, created on Jul. 30, 2021, and is 172,431 bytes in size.

FIELD

The present disclosure relates generally to multispecific binding agents, such as bispecific antibodies, that have a first binding domain that binds to CD47, including human CD47, and one or more additional binding domains that bind to one or more targets that are not CD47, such as PD-L1, and methods of their use.

BACKGROUND

Tumor cells have been shown to utilize both innate and adaptive checkpoints to evade anti-tumor immune responses. CD47 and PD-L1 are two targets widely expressed on the cell surface of tumor cells, which may coordinately suppress innate and adaptive sensing, respectively, to evade immune control.

CD47 is a cell surface glycoprotein that functions as a regulator of phagocytosis mediated by cells of the innate immune system. CD47 interacts with multiple ligands, such as integrins, signal regulatory protein alpha (SIRPα), signal regulatory protein gamma (SIRPγ) and thrombospondins. CD47 inhibits phagocytosis by interacting with SIRPα on the surface of macrophages and dendritic cells, triggering a "don't eat me" signal.

Expressing CD47 enables tumor cells to evade phagocytosis and escape from innate immune surveillance. Thus, CD47 has been a target for possible therapeutics. However, CD47 is broadly expressed on normal cells, such as hematopoietic cells, red blood cells (RBCs) and platelets. The broad expression of CD47 by healthy cells presents safety and efficacy challenges because targeting CD47 with a neutralizing antibody could affect healthy cells, possibly leading to toxic effects. Additionally, broad expression of CD47 could also lead to a rapid elimination of CD47 binding agents, leading to poor pharmacokinetics and decreased efficacy.

Additionally, activation or loss of CD47 can result in enhanced proliferation in a cell type dependent manor. For example, astrocytoma cells have been shown to have increased proliferation following activation of CD47 and TSP-1, whereas the normal astroglial cells have not. It has also been proposed that CD47 may facilitate proliferation of cancer cells through a PI3K/Akt pathway.

Many of the anti-CD47 antibodies that have been reported are known to cause agglutination of RBCs upon blocking CD47 binding to SIRPα, which significantly lowers the therapeutic effect of such antibodies.

Programmed death ligand 1 (PD-L1) is a cell surface glycoprotein ligand that specifically binds to programmed death receptor 1 (PD-1), a key immune checkpoint receptor. PD-1 is upregulated on activated T cells, B cells, and monocytes and mediates immunosuppression. While PD-L2, the other PD-1 ligand, is expressed primarily on activated antigen-presenting cells (APCs), PD-L1 is broadly expressed, including in cells of hematopoietic lineage, such as activated T cells, B cells, monocytes, dendritic cells and macrophages, and peripheral tissues such as heart, skeletal, muscle, placenta, lung, kidney and liver tissues.

The binding of PD-L1 to PD-1 is a negative checkpoint that can activate the downstream signaling of PD-1 receptor in T cells, thus inhibiting the proliferation, cytokine generation and release, and cytotoxicity of T cells. This inhibition of T cell activation and secretion of effector cytokines can prevent autoimmunity and chronic infection.

However, many tumor cells use this mechanism to protect themselves from immune attack, resulting in tumor immune evasion. Many cancers overexpress PD-L1, and its overexpression is often associated with poor prognosis. In cancer, the PD-1/PD-L1 interaction stimulates the downstream signals to suppress T cell activation, resulting in tumor cell survival.

The blockade of PD-1 interaction with its ligands has been proposed as an immunotherapeutic method of enhancing T cell immune responses against tumor cells. Current strategies of PD-1/PD-L1 based immunotherapy have shown efficacy in treating some advanced carcinoma, but have limited effects on many solid tumors and on certain PD-L1 functions. Accordingly, there remains an urgent need in the art for agents that can block or prevent PD-1/PD-L1 interaction.

Accordingly, there remains a need in the art for agents that overcome these concerns and which target CD47 and other targets, such as PD-L1, to treat, prevent, or alleviate immune cell dysfunctional diseases, disorders, or conditions, including those involving tumor cells expressing CD47 and/or PD-L1. The multispecific binding agents, compositions and methods provide herein satisfy this need and provide related advantages.

SUMMARY

The present disclosure provides multispecific binding agents (e.g., antibodies, such as bispecific antibodies) that have a first binding domain that binds to CD47, including human CD47, and one or more additional binding domains that bind to one or more targets that are not CD47 (e.g., PD-L1). Such agents include multispecific antibodies (e.g., antibodies, such as bispecific antibodies) that bind to CD47 and one or more additional targets that are not CD47 (e.g., PD-L1), for example, multispecific antibodies that have a first binding domain that binds to CD47, including human CD47, and one or more additional binding domains that bind to one or more targets that are not CD47 (e.g., PD-L1). Such agents, in some embodiments, include multispecific antibodies (e.g., bispecific antibodies) that bind to CD47 and one or more additional targets that are not CD47 (e.g., PD-L1), for example, multispecific antibodies that have a first binding domain that binds to CD47, including human CD47, and one or more additional binding domains that bind to one or more targets that are not CD47 (e.g., PD-L1) and compete for the binding of human CD47 with an antibody having a heavy chain variable region and a light chain variable region described herein (e.g., Table 1-3).

The present disclosure also provides compositions comprising a multispecific binding agent described herein. Such compositions, in some embodiments, include multispecific antibodies (e.g., antibodies, such as bispecific antibodies) that bind to CD47 and one or more additional targets that are not CD47 (e.g., PD-L1), for example, multispecific antibodies that have a first binding domain that binds to CD47, including human CD47, and one or more additional binding domains that bind to one or more targets that are not CD47 (e.g., PD-L1). Such compostions, in some embodiments, include multispecific antibodies (e.g., antibodies, such as bispecific antibodies) that bind to CD47 and one or more additional targets that are not CD47 (e.g., PD-L1), for example, multispecific antibodies that have a first binding domain that binds to CD47, including human CD47, and one or more additional binding domains that bind to one or more targets that are not CD47 (e.g., PD-L1) and compete for the binding of human CD47 with an antibody having a heavy chain variable region and a light chain variable region described herein (e.g., Table 1-3).

The present disclosure also provides methods of treating, preventing, or alleviating an immune cell dysfunctional disease, disorder or condition (e.g., a phagocytic cell dysfunctional disease, disorder, or condition or a T cell dysfunctional disease, disorder, or condition), including one or more symptoms of the immune cell dysfunctional disease, disorder, or condition with a multispecific binding agent or a composition comprising the multispecific binding agent, including a bispecific antibody or composition comprising the bispecific antibody, as described herein. Such compositions include multispecific antibodies (e.g., antibodies, such as bispecific antibodies) that bind to CD47 and one or more additional targets that are not CD47 (e.g., PD-L1), for example, multispecific antibodies that have a first binding domain that binds to CD47, including human CD47, and one or more additional binding domains that bind to one or more targets that are not CD47 (e.g., PD-L1). Such compostions, in some embodiments, include multispecific antibodies (e.g., antibodies, such as bispecific antibodies) that bind to CD47 and one or more additional targets that are not CD47 (e.g., PD-L1), for example, multispecific antibodies that have a first binding domain that binds to CD47, including human CD47, and one or more additional binding domains that bind to one or more targets that are not CD47 (e.g., PD-L1) and compete for the binding of human CD47 with an antibody having a heavy chain variable region and a light chain variable region described herein (e.g., Table 1-3).

BRIEF DESCRIPTION OF THE DRAWINGS

FIG. 1A illustrates results and $EC_{50}$ for C40×P24, compared to control antibodies C40×D (the corresponding monospecific antibody having only one binding domain capable of targeting CD47), D×P24 (the corresponding monospecific antibody having only one binding domain capable of targeting PD-L1), and a secondary antibody-only negative control. FIG. 1B illustrates results and $EC_{50}$ for C56×P22, compared to control antibodies C56×D (the corresponding monospecific antibody having only one binding domain capable of targeting CD47), D×P22 (the corresponding monospecific antibody having only one binding domain capable of targeting PD-L1), and a secondary antibody-only negative control. FIG. 1C illustrates results and $EC_{50}$ for C40×P31.2, compared to control antibodies C40×D (the corresponding monospecific antibody having only one binding domain capable of targeting CD47), D×P31.2 (the corresponding monospecific antibody having only one binding domain capable of targeting PD-L1), and a secondary antibody-only negative control. FIG. 1D illustrates results and $EC_{50}$ for C59×P22, compared to control antibodies C59×D (the corresponding monospecific antibody having only one binding domain capable of targeting CD47), D×P22 (the corresponding monospecific antibody having only one binding domain capable of targeting PD-L1), and a secondary antibody-only negative control.

FIG. 2A illustrates results and $EC_{50}$ for C40×P24. FIG. 2B illustrates results and $EC_{50}$ for C56×P22. FIG. 2C illustrates results and $EC_{50}$ for C40×P31.2. FIG. 2D illustrates results and $EC_{50}$ for C59×P22. FIG. 2E illustrates results and $EC_{50}$ for C59×P31.2.

FIG. 5A illustrates an exemplary image of labeled JeKo-PD-L1 cells co-cultured with M2 macrophages at 0 hour. FIG. 5B illustrates an exemplary image of labeled JeKo-PD-L1 cells after co-culturing with M2 macrophages for 5 hours. FIG. 5C illustrates the level of phagocytosis of JeKo-PD-L1 cells by M2 macrophages after 5 hours of co-incubation with C40×P24, compared to the control with no antibody. FIG. 5D illustrates the level of phagocytosis of JeKo-PD-L1 cells by M2 macrophages after 5 hours of co-incubation with C56×P22, compared to the control with no antibody. FIG. 5E illustrates the level of phagocytosis of JeKo-PD-L1 cells by M2 macrophages after 5 hours of co-incubation with C40×P31.2, compared to the control with no antibody. FIG. 5F illustrates the level of phagocytosis of JeKo-PD-L1 cells by M2 macrophages after 5 hours of co-incubation with C59×P22, compared to the control with no antibody. FIG. 5G illustrates the level of phagocytosis of JeKo-PD-L1 cells by M2 macrophages after 5 hours of co-incubation with C59×P31.2, compared to the control with no antibody. For FIGS. 5C-5G, the X-axis is log molar concentration of antibody (Log [Ab]M), and the Y-axis is total red object area ($\mu m^2$/image).

FIG. 6A illustrates an exemplary image of labeled A375 cells co-cultured with M2 macrophages at 0 hour. FIG. 6B illustrates an exemplary image of labeled A375 cells after co-culturing with M2 macrophages for 48 hours. FIG. 6C illustrates the level of phagocytosis of A375 cells by M2 macrophages after 48 hours of co-incubation with C40×P24, compared to the control with no antibody. FIG. 6D illustrates the level of phagocytosis of A375 cells by M2 macrophages after 48 hours of co-incubation with C56×P22, compared to the control with no antibody. FIG. 6E illustrates the level of phagocytosis of A375 cells by M2 macrophages after 48 hours of co-incubation with C40×P31.2, compared to the control with no antibody. FIG. 6F illustrates the level of phagocytosis of A375 cells by M2 macrophages after 48 hours of co-incubation with C59×P22, compared to the control with no antibody. FIG. 6G illustrates the level of phagocytosis of A375 cells by M2 macrophages after 48 hours of co-incubation with C59×P31.2, compared to the control with no antibody. For FIGS. 6C-6G, the X-axis is log molar concentration of antibody (Log [Ab]M), and the Y-axis is total red object area ($\mu m^2$/image).

FIG. 9A illustrates results of red blood cells. FIG. 9B illustrates results of platelet. FIG. 9C illustrates results of white blood cells. FIG. 9D illustrates results of lymphocytes. FIG. 9E illustrates results of monocytes. G1: treated with PBS (vehicle control). G3: treated with 10 mg/kg C40×P24. G4: treated with 3 mg/kg C40×P24. G5: treated with 10 mg/kg C56×P22. G6: treated with 3 mg/kg C56×P22. G7: treated with 10 mg/kg C40×P24s (s=silent Fc).

FIG. 10A illustrates results of haemoglobin. FIG. 10B illustrates results of mean platelet volume. FIG. 10C illustrates results of hematocrit. FIG. 10D illustrates results of red cell distribution width. FIG. 10E illustrates results of mean corpuscular volume. FIG. 10F illustrates results of mean corpuscular haemoglobin. FIG. 10G illustrates results of mean corpuscular haemoglobin concentration. G1: treated with PBS (vehicle control). G3: treated with 10 mg/kg C40×P24. G4: treated with 3 mg/kg C40×P24. G5: treated with 10 mg/kg C56×P22. G6: treated with 3 mg/kg C56×P22. G7: treated with 10 mg/kg C40×P24s (s=silent Fc).

FIG. 12A illustrates results of mean tumor volume for different treatment groups. FIG. 12B illustrates results of tumor volume for individual mice treated with vehicle control. FIG. 12C illustrates results of tumor volume for individual mice treated with C56×P22. FIG. 12D illustrates results of tumor volume for individual mice treated with C59×P22. FIG. 12E illustrates results of mean body weight for different treatment groups.

FIG. 13A illustrates results of CD4+ cell count per gram of tumor. FIG. 13B illustrates results of CD8+ cell count per gram of tumor. FIG. 13C illustrates results of Treg cell count per gram of tumor. FIG. 13D illustrates results of macrophage count per gram of tumor.

FIG. 15A illustrates results of mean tumor volume for different treatment groups. FIG. 15B illustrates results of median tumor volume for different treatment groups. FIG. 15C illustrates results of tumor volume for individual mice treated with vehicle control. FIG. 15D illustrates results of tumor volume for individual mice treated with C40×P24. FIG. 15E illustrates results of tumor volume for individual mice treated with C40×P24s. FIG. 15F illustrates results of tumor volume for individual mice treated with C40×P31.2. FIG. 15G illustrates results of tumor volume for individual mice treated with C59×P31.2. FIG. 15H illustrates results of mean body weight for different treatment groups.

FIG. 16A illustrates results of mean tumor volume for different treatment groups. FIG. 16B illustrates results of mean body weight for different treatment groups.

FIG. 18A illustrates results of mean tumor volume for different treatment groups. FIG. 18B illustrates results of mean body weight for different treatment groups.

FIG. 19A illustrates results for C40×P24. FIG. 19B illustrates results for C56×P22. FIG. 19C illustrates results for C59×P22.

FIG. 20A illustrates results for C40×P24. FIG. 20B illustrates results for C56×P22. FIG. 20C illustrates results for C40×P31.2. FIG. 20D illustrates results for C59×P22.

FIG. 21A illustrates results for C40×P24. FIG. 21B illustrates results for C56×P22. FIG. 21C illustrates results for C40×P31.2. FIG. 21D illustrates results for C59×P22.

FIGS. 22A-22B show a sequence alignment of heavy chain variable regions and light chain variable regions of C40, C56, and C59, including consensus sequences for VH CDR1, VH CDR2, VH CDR3, VL CDR1, VL CDR2, and VL CDR3. Boundaries of CDRs are indicated by Kabat, AbM, Chothia, Contact, and IMGT numbering. FIG. 22A shows the sequence alignment of heavy chain variable regions. FIG. 22B shows the sequence alignment of light chain variable regions.

FIGS. 23A-23B show a sequence alignment of heavy chain variable regions and light chain variable regions of P22, P24, and P31.2, including consensus sequences for VH CDR1, VH CDR2, VH CDR3, VL CDR1, VL CDR2, and VL CDR3. Boundaries of CDRs are indicated by Kabat, AbM, Chothia, Contact, and IMGT numbering. FIG. 23A shows the sequence alignment of heavy chain variable regions. FIG. 23B shows the sequence alignment of light chain variable regions.

DETAILED DESCRIPTION

Figure 1A:
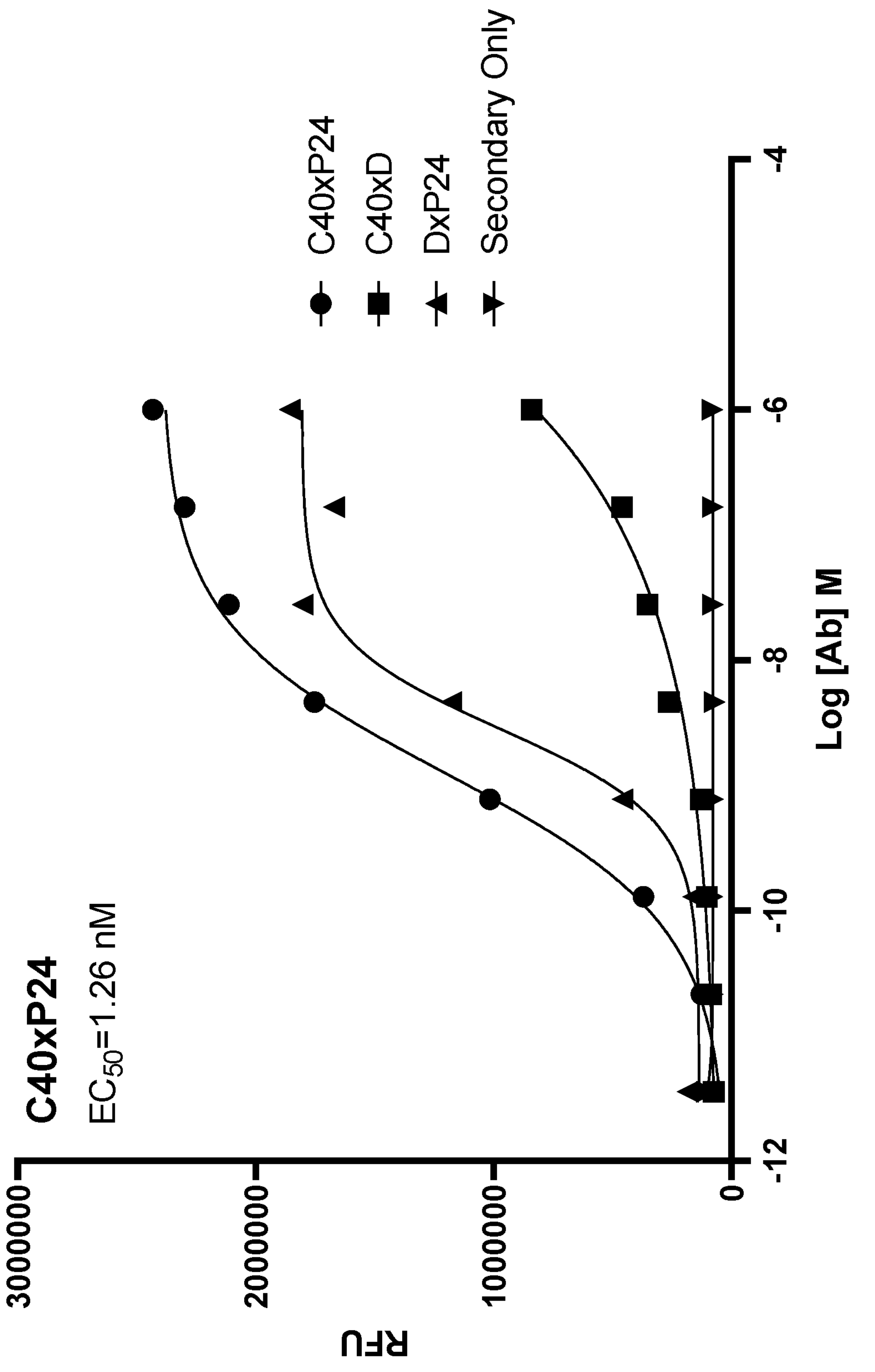
FIGS. 1A-1D illustrate exemplary results from cell binding assays, showing log molar concentration of antibody (Log [Ab]M) on the X-axis and relative fluorescence unit (RFU) on the Y-axis for different antibodies as indicated, further described in Example 3.
Figure 1B:
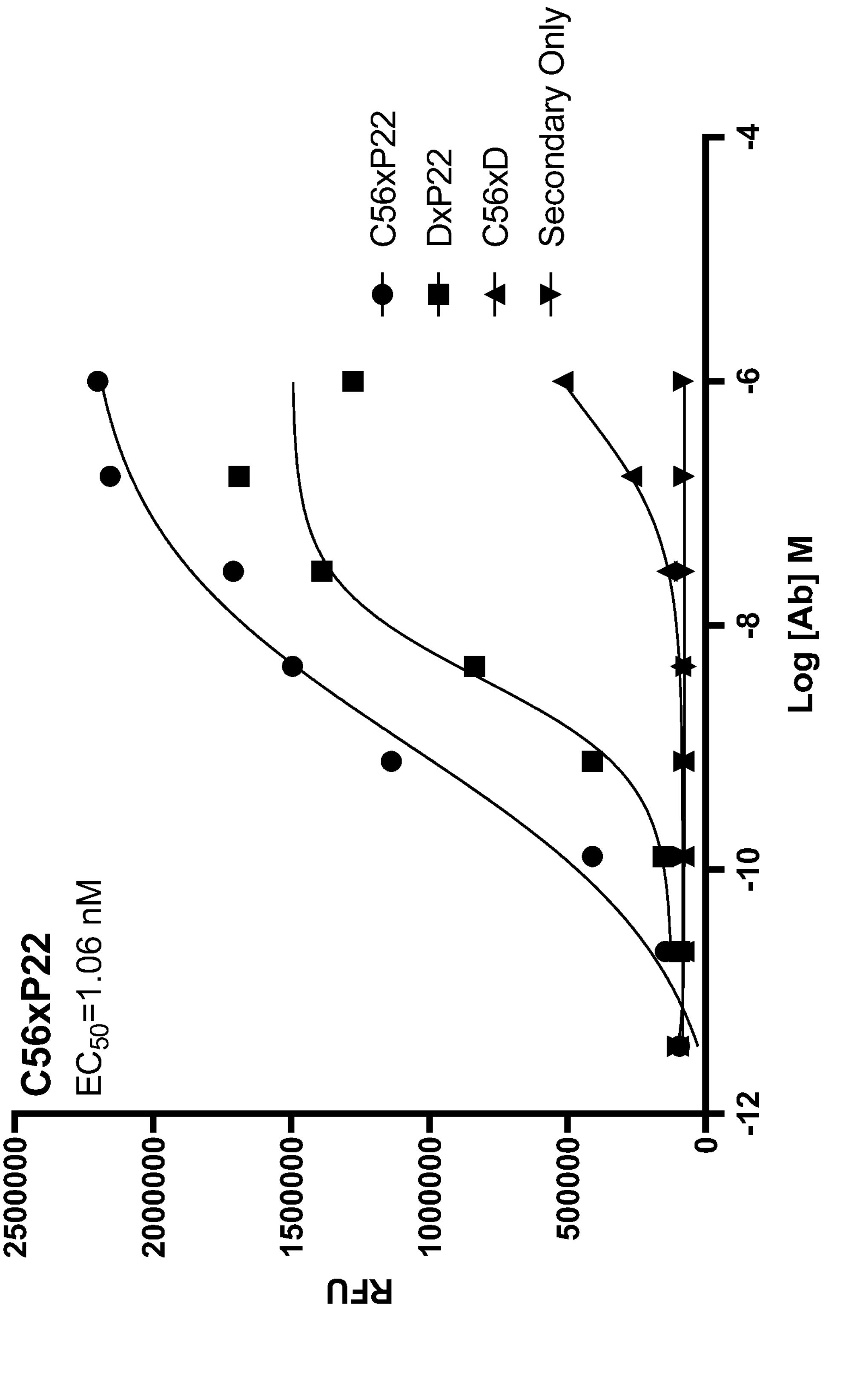
Figure 1C:
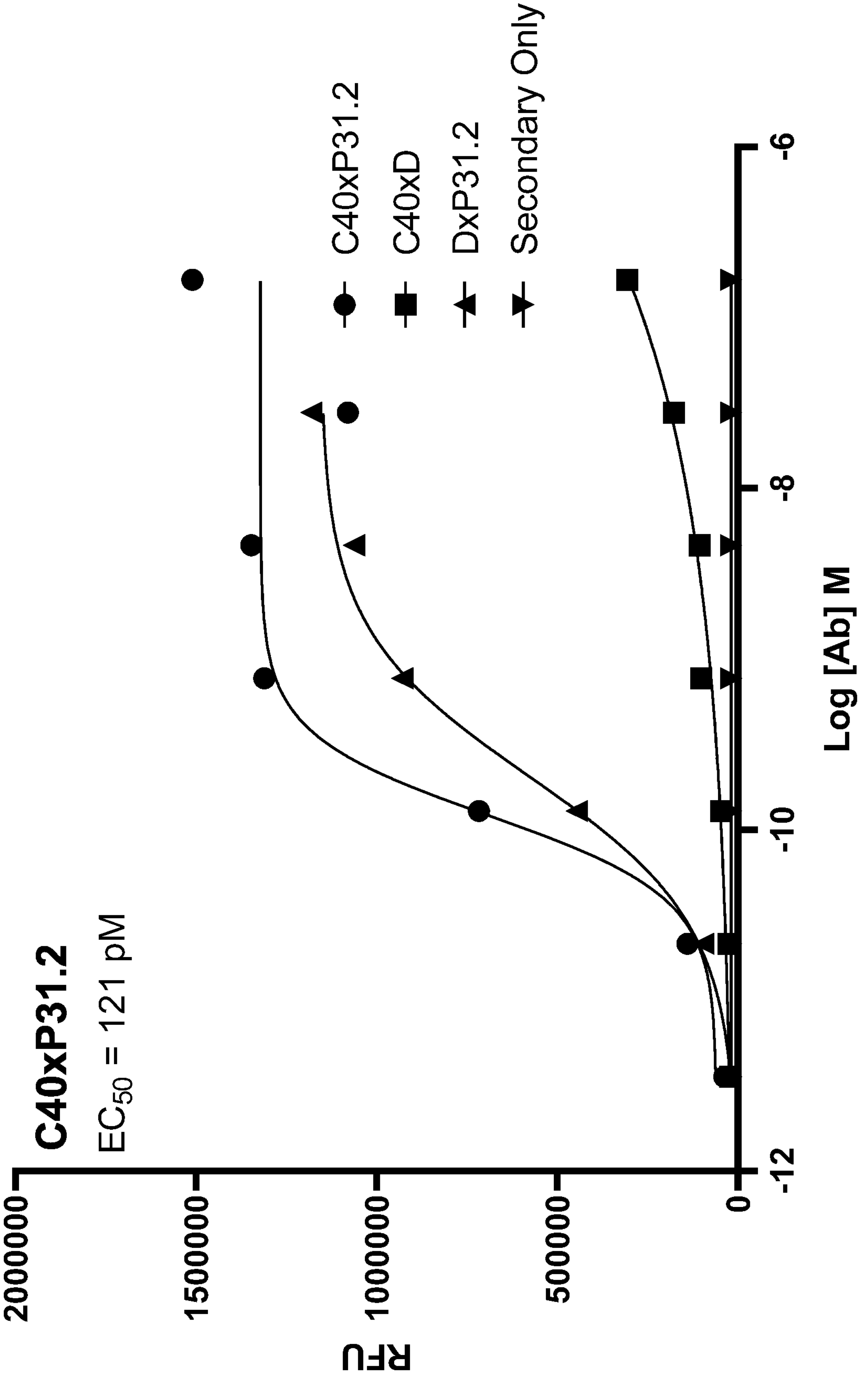
Figure 1D:
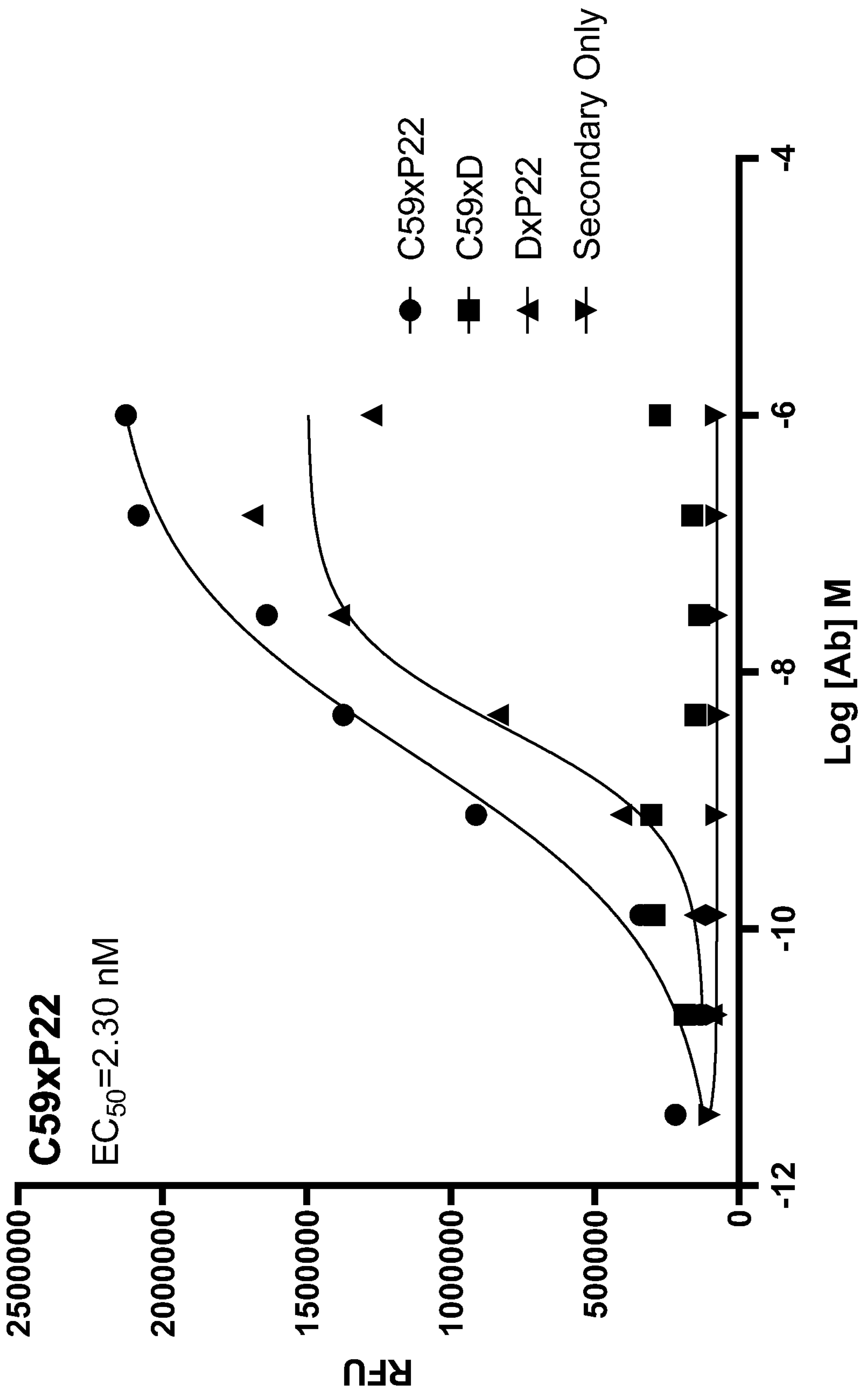
Figure 2A:
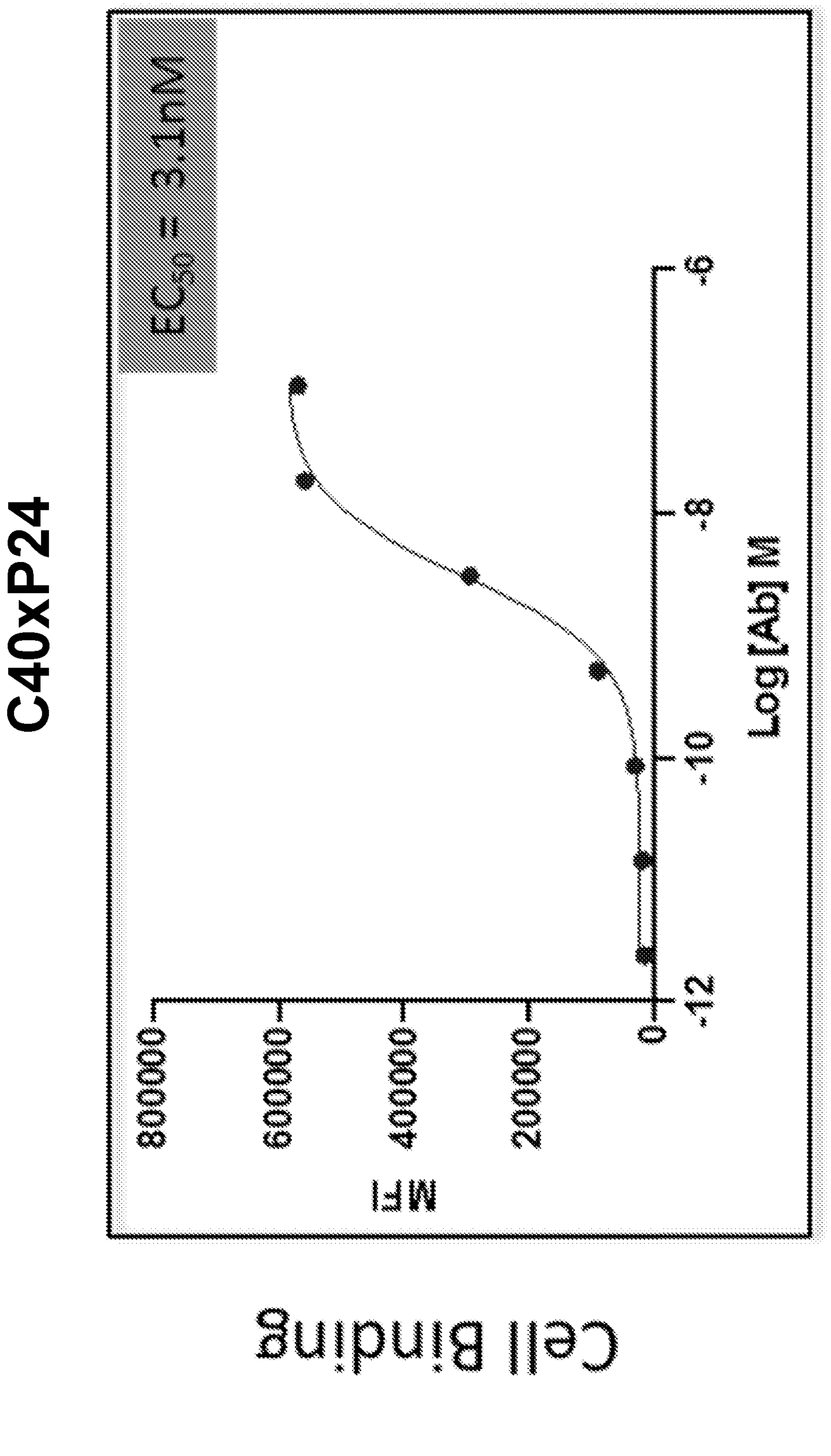
FIGS. 2A-2E illustrate exemplary results from additional cell binding assays, showing log molar concentration of antibody (Log [Ab]M) on the X-axis and cell binding (mean fluorescence intensity, MFI) on the Y-axis for different antibodies as indicated, further described in Example 3.
Figure 2B:
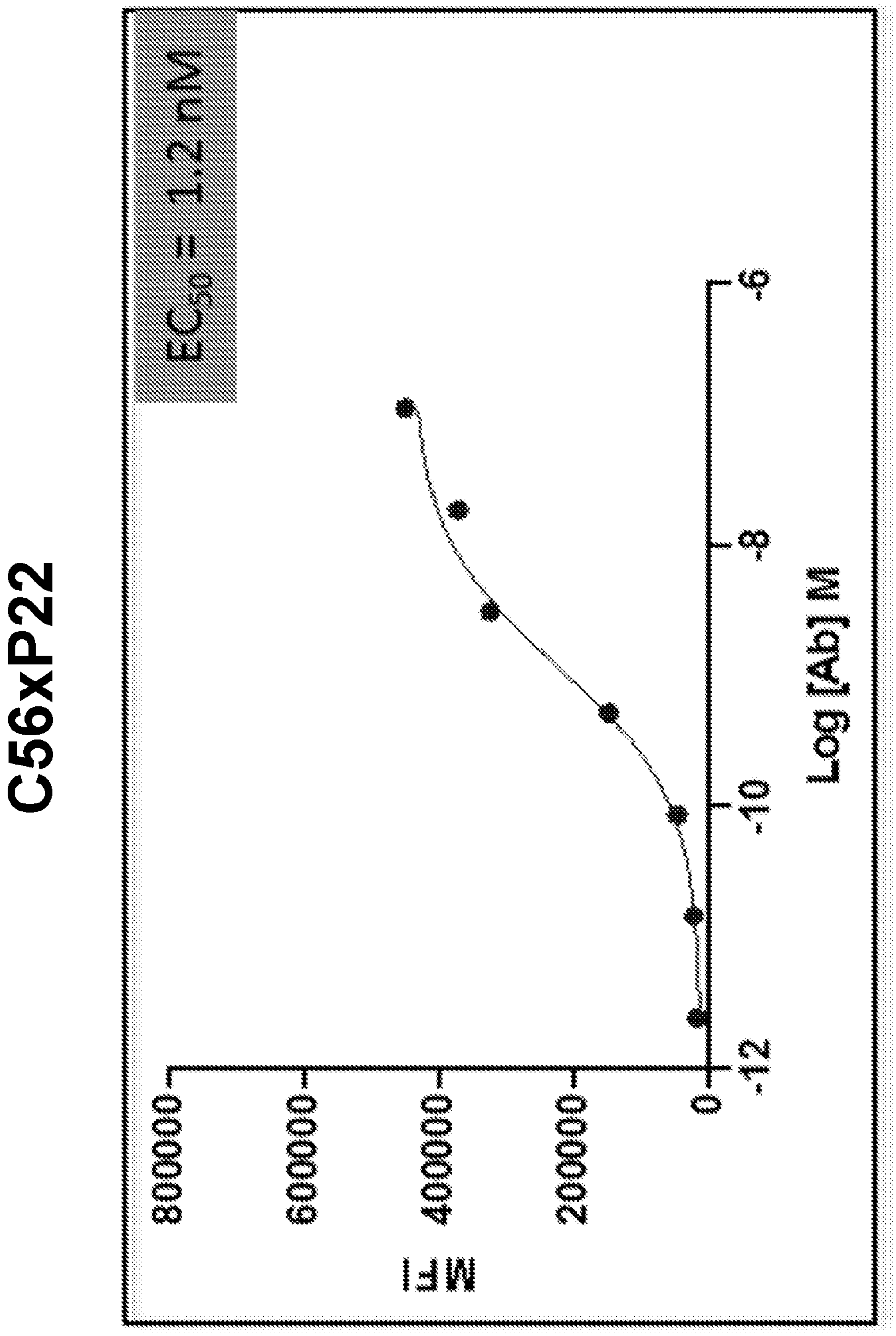
Figure 2C:
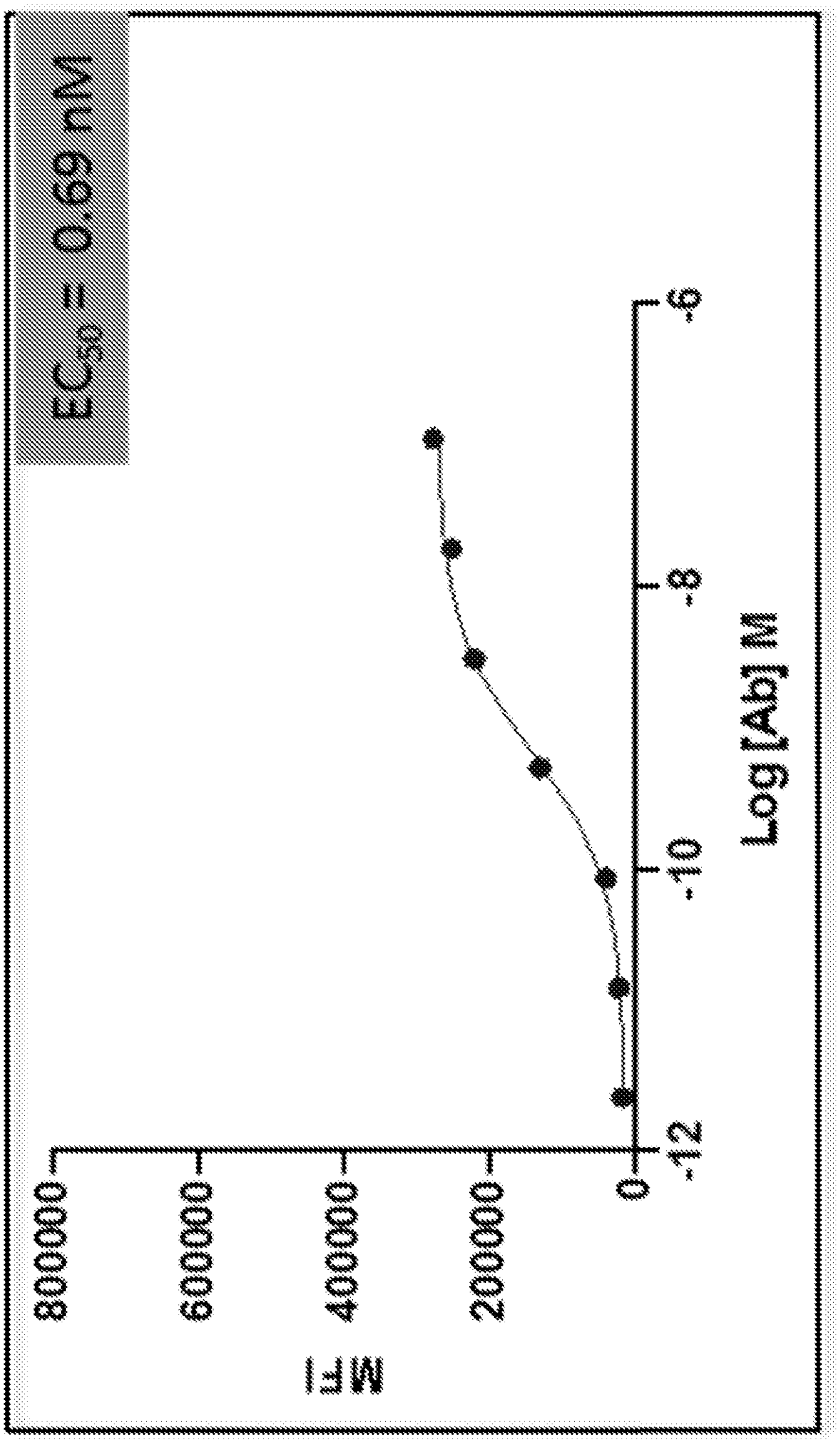
Figure 2D:
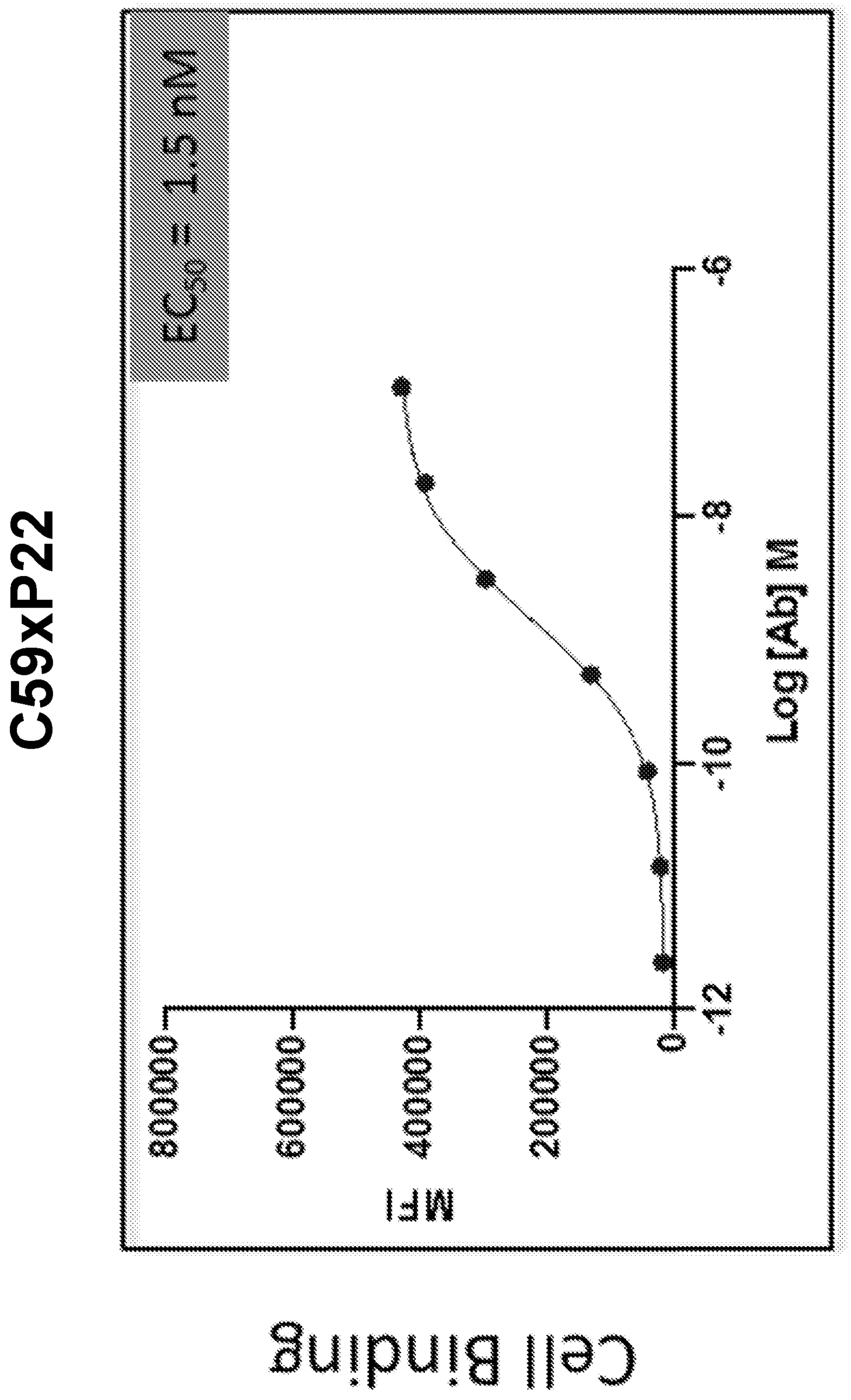
Figure 2E:
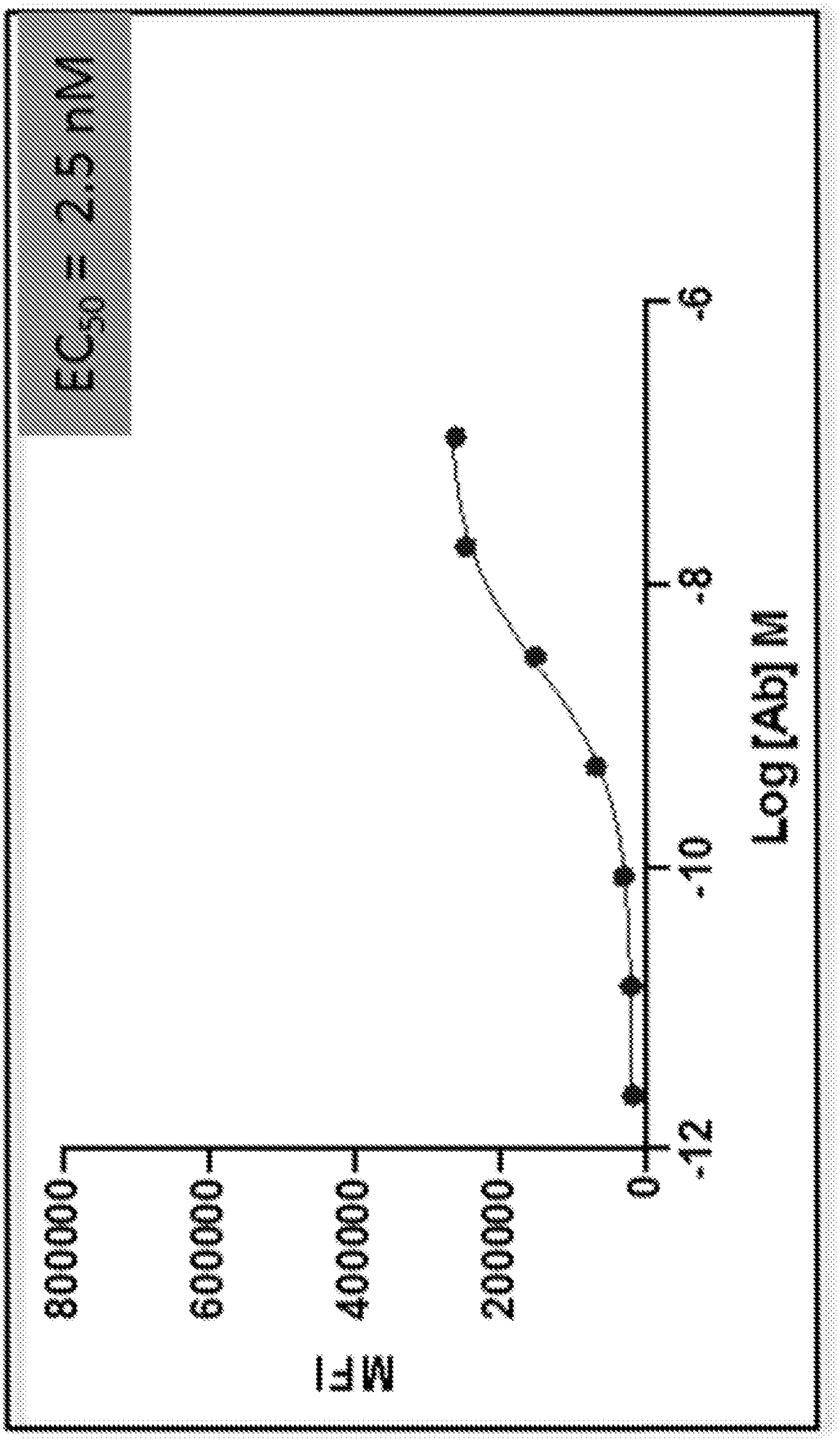

The present disclosure provides multispecific binding agents (e.g., antibodies, such as bispecific antibodies) that bind to CD47 and one or more additional targets that are not CD47 (e.g., PD-L1). Such multispecific binding agents include antibodies (e.g., antibodies, such as bispecific antibodies) that bind to CD47, including antibodies that bind to human CD47, and one or more additional targets that are not CD47 (e.g., PD-L1). Such multispecific binding agents are useful in compositions and in methods of treating, preventing, or alleviating an immune cell dysfunctional disease, disorder or condition (e.g., a phagocytic cell dysfunctional disease, disorder, or condition or a T cell dysfunctional disease, disorder, or condition), including one or more symptoms of the disease, disorder, or condition. Phagocytic cell dysfunctional diseases, disorders, and conditions include tumor immunity and associated cancers, including, but not limited to, any cancer wherein the tumor cells express or overexpress CD47. T cell dysfunctional diseases, disorders, and conditions include tumor immunity and associated cancers, including, but not limited to, any cancer wherein the tumor cells express or overexpress PD-L1. Such CD47 and/or PD-L1 expressing tumor cells may help tumor cells escape immune surveillance and clearance (e.g., tumor immunity). In addition, multispecific binding agents described herein, such as multispecific antibodies (e.g., antibodies, such as bispecific antibodies), that bind to CD47 and one or more additional targets that are not CD47 (e.g., PD-L1), are useful to inhibit SIRPα signaling and/or PD-1 signaling, enhance phagocytic cell function and/or immune surveillance, and enhance removal of tumor cells. Multispecific binding agents (e.g., antibodies, such as bispecific antibodies) described herein, such as multispecific binding antibodies (e.g., bispecific antibodies), are useful in compositions and in methods for enhancing phagocytic cell function and T cell function, including the upregulation of cell-mediated immune responses.

The term "CD47," "Cluster of Differentiation 47," or "CD47 polypeptide" and similar terms refers to a polypeptide ("polypeptide" and "protein" are used interchangeably herein) or any native CD47 from any vertebrate source, including mammals such as primates (e.g., humans, cynomolgus monkey (cyno)), dogs, and rodents (e.g., mice and rats), unless otherwise indicated. CD47, also known in the art as integrin associated protein (IAP), has an extracellular N-terminal IgV domain, five transmembrane domains, and a short C-terminal intracellular tail. The term CD47 encompasses "full-length," unprocessed CD47, as well as any form of CD47 or any fragment thereof that results from processing in the cell, including the four known alternatively spliced isoforms of CD47 that differ in the length of the intracellular tail. The term CD47 also encompasses naturally occurring variants of CD47, such as SNP variants, splice variants and allelic variants. CD47 is known in the art to interact with SIRPα and this interaction leads to cell signaling that includes, among other things, inhibition of phagocytosis by macrophages. The full-length amino acid sequence of human CD47 is provided below (exemplary extracellular domain=underline text):

(SEQ ID NO: 184)

MWPLVAALLLGSACCGSAQLLENKTKSVEFTECNDTVVIPCEVTNMEAQ

NTTEVYVKWKFKGRDIYTEDGALNKSTVPTDFSSAKIEVSQLLKGDASL

KMDKSDAVSHTGNYTCEVTELTREGETIIELKYRVVSWFSPNENILIVI

FPIFAILLFWGQFGIKTLKYRSGGMDEKTIALLVAGLVITVIVIVGAIL

FVPGEYSLKNATGLGLIVTSTGILILLHYYVFSTAIGLTSFVIAILVIQ

VIAYILAVVGLSLCIAACIPMHGPLLISGLSILALAQLLGLVYMKFVAS

NQKTIQPPRKAVEEPLNAFKESKGMMNDE

Other related CD47 polypeptides that are also encompassed by the term CD47 include fragments, derivatives (e.g., substitution, deletion, truncations, and insertion variants), fusion polypeptides, and interspecies homologs that retain CD47 activity and/or are sufficient to generate an anti-CD47 immune response. As those skilled in the art will appreciate, a multispecific binding agent (e.g., an antibody, such as a bispecific antibody) described herein can bind to a CD47 polypeptide, a CD47 polypeptide fragment, a CD47 antigen, and/or a CD47 epitope. An epitope may be part of a larger CD47 antigen, which may be part of a larger CD47 polypeptide fragment, which, in turn, may be part of a larger CD47 polypeptide. CD47 may exist in a native or denatured form. CD47 polypeptides described herein may be isolated from a variety of sources, such as from human tissue types or from another source, or prepared by recombinant or synthetic methods. A CD47 polypeptide may comprise a polypeptide having the same amino acid sequence as a corresponding CD47 polypeptide derived from nature. Orthologs to the CD47 polypeptide are also well known in the art.

The term "SIRPα," "Signal-regulatory protein alpha," or "Signal-regulatory protein a" and similar terms refers to a polypeptide ("polypeptide" and "protein" are used interchangeably herein) or any native SIRPα from any vertebrate source, including mammals such as primates (e.g., humans, cynomolgus monkey (cyno)), dogs, and rodents (e.g., mice and rats), unless otherwise indicated. SIRPα has an extracellular region, which includes three immunoglobulin superfamily domains—single V-set and two C1-set IgSF domains, a transmembrane domain and a cytoplasmic region containing an immunoreceptor tyrosine-based inhibition motif (ITIM). The term SIRPα also encompasses naturally occurring variants of SIRPα, such as SNP variants, splice variants and allelic variants. SIRPα is known in the art to interact with CD47, leading to phosphorization of the ITIM, which mediates its association with the phosphatase SH2-domain-containing protein tyrosine phosphatase 2 (SHP2). The full-length amino acid sequence of human SIRPα is provided below:

(SEQ ID NO: 185)

```
MEPAGPAPGRLGPLLCLLLAASCAWSGVAGEEELQVIQPDKSVLVAAGE
TATLRCTATSLIPVGPIQWFRGAGPGRELIYNQKEGHFPRVTTVSDLTK
RNNMDFSIRIGNITPADAGTYYCVKFRKGSPDDVEFKSGAGTELSVRAK
PSAPVVSGPAARATPQHTVSFTCESHGFSPRDITLKWFKNGNELSDFQT
NVDPVGESVSYSIHSTAKVVLTREDVHSQVICEVAHVTLQGDPLRGTAN
LSETIRVPPTLEVTQQPVRAENQVNVTCQVRKFYPQRLQLTWLENGNVS
RTETASTVTENKDGTYNWMSWLLVNVSAHRDDVKLTCQVEHDGQPAVSK
SHDLKVSAHPKEQGSNTAAENTGSNERNIYIVVGVVCTLLVALLMAALY
LVRIRQKKAQGSTSSTRLHEPEKNAREITQDTNDITYADLNLPKGKKPA
PQAAEPNNHTEYASIQTSPQPASEDTLTYADLDMVHLNRTPKQPAPKPE
PSFSEYASVQVPRK.
```

The term "Programmed Cell Death Ligand-1 (PD-L1)," "Programmed Death Ligand-1," "PD-1 ligand 1" or similar terms refers to a polypeptide ("polypeptide" and "protein" are used interchangeably herein) or any native PD-L1 from any vertebrate source, including mammals such as primates (e.g., humans, cynomolgus monkey (cyno)), dogs, and rodents (e.g., mice and rats), unless otherwise indicated. PD-L1, also known as cluster of differentiation 274 (CD274) or B7 homolog 1 (B7-H1) is a protein that in humans is encoded by the CD274 gene. PD-L1 is a one of two naturally-occurring cell surface glycoprotein ligands for PD-1 (the other is PD-L2). Like PD-1, PD-L1 belongs to the immunoglobulin superfamily and consist of two extracellular Ig domains, an N-terminal V domain, and a C-terminal constant domain. PD-L1 is known in the art to downregulate T cell activation and cytokine secretion upon binding to PD-1. The term PD-L1 encompasses "full-length," PD-L1, as well as any form of PD-L1 or any fragment thereof that results from processing in the cell. The term PD-L1 also encompasses naturally occurring variants of PD-L1, such as SNP variants, splice variants and allelic variants. The full-length amino acid sequence of human PD-L1 is provided below (exemplary extracellular domain=underline text):

(SEQ ID NO: 186)

```
MRIFAVFIFMTYWHLLNAFTVTVPKDLYVVEYGSNMTIECKFPVEKQLD
LAALIVYWEMEDKNIIQFVHGEEDLKVQHSSYRQRARLLKDQLSLGNAA
LQITDVKLQDAGVYRCMISYGGADYKRITVKVNAPYNKINQRILVVDPV
```

-continued

```
TSEHELTCQAEGYPKAEVIWTSSDHQVLSGKTTTTNSKREEKLFNVTST
LRINTTTNEIFYCTFRRLDPEENHTAELVIPELPLAHPPNERTHLVILG
AILLCLGVALTFIFRLRKGRMMDVKKCGIQDTNSKKQSDTHLEET.
```

Other related PD-L1 polypeptides that are also encompassed by the term PD-L1 include fragments, derivatives (e.g., substitution, deletion, truncations, and insertion variants), fusion polypeptides, and interspecies homologs that retain PD-L1 activity and/or are sufficient to generate an anti-PD-L1 immune response. As those skilled in the art will appreciate, a PD-L1 binding agent (e.g., an antibody) described herein can bind to a PD-L1 polypeptide, a PD-L1 polypeptide fragment, a PD-L1 antigen, and/or a PD-L1 epitope. An epitope may be part of a larger PD-L1 antigen, which may be part of a larger PD-L1 polypeptide fragment, which, in turn, may be part of a larger PD-L1 polypeptide. PD-L1 may exist in a native or denatured form. PD-L1 polypeptides described herein may be isolated from a variety of sources, such as from human tissue types or from another source, or prepared by recombinant or synthetic methods. A PD-L1 polypeptide may comprise a polypeptide having the same amino acid sequence as a corresponding PD-L1 polypeptide derived from nature. Orthologs to the PD-L1 polypeptide are also well known in the art.

The term "Programmed Cell Death-1 (PD-1)," "Programmed Death-1," "PD-1 receptor" or similar terms refers to a polypeptide ("polypeptide" and "protein" are used interchangeably herein) or any native PD-1 from any vertebrate source, including mammals such as primates (e.g., humans, cynomolgus monkey (cyno)), dogs, and rodents (e.g., mice and rats), unless otherwise indicated. PD-1, also known as CD279 (cluster of differentiation 279), is an immunoinhibitory receptor belonging to the CD28 family. PD-1 is expressed predominantly on previously activated T cells in vivo, and binds to two ligands, PD-L1 and PD-L2. PD-1 belongs to the immunoglobulin superfamily and consist of two extracellular Ig domains, an N-terminal V domain, and a C-terminal constant domain. PD-1 contains two cytoplasmic tyrosine-based signaling motifs, an immunoreceptor tyrosine-based inhibition motif (ITIM) and an immunoreceptor tyrosine-based switch motif (ITSM). The term PD-1 encompasses "full-length," PD-1, as well as any form of PD-1 or any fragment thereof that results from processing in the cell. The term PD-1 also encompasses naturally occurring variants of PD-1, such as SNP variants, splice variants and allelic variants. Following T cell stimulation, PD-1 is known in the art to recruit the tyrosine phosphatase SHP-2 to the ITSM motif within its cytoplasmic tail, leading to, among other things, the dephosphorylation of effector molecules such as CD3 Zeta, PKC theta and ZAP70 that are involved in the CD3 T cell signaling cascade (Carter et al. (2002) Eur J Immunol 32:634-43). The full-length amino acid sequence of human PD-1 is provided below:

(SEQ ID NO: 187)

```
MQIPQAPWPVVWAVLQLGWRPGWFLDSPDRPWNPPTFSPA
LLVVTEGDNATFTCSFSNTSESFVLNWYRMSPSNQTDKLA
AFPEDRSQPGQDCRFRVTQLPNGRDFHMSVVRARRNDSGT
YLCGAISLAPKAQIKESLRAELRVTERRAEVPTAHPSPSP
RPAGQFQTLVVGVVGGLLGSLVLLVWVLAVICSRAARGTI
```

-continued

```
GARRTGQPLKEDPSAVPVFSVDYGELDFQWREKTPEPPVP
CVPEQTEYATIVFPSGMGTSSPARRGSADGPRSAQPLRPE
DGHCSWPL.
```

As used herein, the term "binding agent" or a grammatical equivalent thereof refers to a molecule (e.g., an antibody, such as a bispecific antibody) with one or more antigen binding sites that binds an antigen. In some embodiments, a multispecific binding agent as described herein is an antibody, antibody fragment, or other peptide-based molecule that binds to CD47, such as human CD47.

The term "antibody," "immunoglobulin," or "Ig" is used interchangeably herein, and is used in the broadest sense and specifically covers, for example polyclonal antibodies, monoclonal antibodies (including agonist, antagonist, neutralizing antibodies, full length monoclonal antibodies), antibody compositions with polyepitopic or monoepitopic specificity, recombinantly produced antibodies, monospecific antibodies, multispecific antibodies (including bispecific antibodies), synthetic antibodies, chimeric antibodies, humanized antibodies, or human versions of antibodies having full length heavy and/or light chains. The present disclosure also includes antibody fragments (and/or polypeptides that comprise antibody fragments) that retain CD47 binding characteristics. Non-limiting examples of antibody fragments include antigen-binding regions and/or effector regions of the antibody, e.g., Fab, Fab', $F(ab')_2$, Fv, scFv, $(scFv)_2$, single chain antibody molecule, dual variable region antibody, single variable region antibody, linear antibody, V region, a multispecific antibody formed from antibody fragments, $F(ab)_2$, Fd, Fc, diabody, di-diabody, disulfide-linked Fvs (dsFv), single-domain antibody (e.g., NANOBODY®) or other fragments (e.g., fragments consisting of the variable regions of the heavy and light chains that are non-covalently coupled). In general terms, a variable (V) region domain may be any suitable arrangement of immunoglobulin heavy (VH) and/or light (VL) chain variable domains. For example, the present disclosure also includes tetrameric antibodies comprising two heavy chain and two light chain molecules, an antibody light chain monomer, and an antibody heavy chain monomer. Thus, for example, the V region domain may be dimeric and contain VH-VH, VH-VL, or VL-VL dimers that bind CD47. If desired, the VH and VL chains may be covalently coupled either directly or through a linker to form a single chain Fv (scFv). For ease of reference, scFv proteins are referred to herein as included in the category "antibody fragments." Another form of an antibody fragment is a peptide comprising one or more complementarity determining regions (CDRs) of an antibody. CDRs (also termed "minimal recognition units" or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology, 2:106 (1991); Courtenay-Luck, "Genetic Manipulation of Monoclonal Antibodies," in Monoclonal Antibodies Production, Engineering and Clinical Application, Ritter et al. (eds.), page 166, Cambridge University Press (1995); and Ward et al., "Genetic Manipulation and Expression of Antibodies," in Monoclonal Antibodies: Principles and Applications, Birch et al., (eds.), page 137, Wiley-Liss, Inc. (1995)). Antibody fragments may be incorporated into single domain antibodies, maxibodies, minibodies, intrabodies, diabodies, triabodies, tetrabodies, variable domains of new antigen receptors (v-NAR), and bis-single chain Fv regions (see, e.g., Hollinger and Hudson, Nature Biotechnology, 23(9):1126-1136, 2005). The binding agent, in some embodiments, contains a light chain and/or a heavy chain constant region, such as one or more constant regions, including one or more IgG1, IgG2, IgG3 and/or IgG4 constant regions. In some embodiments, antibodies can include epitope-binding fragments of any of the above. The antibodies described herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies.

The term "monospecific" when used in reference to a binding agent (e.g., an antibody) as used herein denotes a binding agent that has one or more binding sites each of which bind to the same epitope of the same antigen.

The term "multispecific" when used in reference to a binding agent (e.g., an antibody) means that the binding agent has binding specificities for at least two different antigens or at least two different epitopes on the same antigen (e.g., a bispecific antibody directed to CD47 with a first binding site for a first epitope of a CD47, and a second binding site for a second epitope of CD47).

The term "bispecific" when used in reference to a binding agent (e.g., an antibody) means that the binding agent is able to specifically bind to two distinct antigenic determinants, for example, two binding sites each formed by a pair of an antibody heavy chain variable domain (VH) and an antibody light chain variable domain (VL) binding to different antigens or to different epitopes on the same antigen. Such a bispecific binding agent may have a 1+1 format. Other bispecific binding agent (e.g., an antibody) formats may be 2+1 or 1+2 formats (comprising two binding sites for a first antigen or epitope and one binding site for a second antigen or epitope) or 2+2 formats (comprising two binding sites for a first antigen or epitope and two binding sites for a second antigen or epitope). When a bispecific binding agent (e.g., an antibody) comprises two antigen binding sites, each may bind to a different antigenic determinant. Such a bispecific binding agent (e.g., an antibody) may bind to two different epitopes on the same antigen (e.g., epitopes on CD47).

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, MegAlign®, BestFit, GCG Wisconsin Package, and variants thereof. In some embodiments, two nucleic acids or polypeptides are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

A "conservative amino acid substitution" is one in which one amino acid 'residue is replaced with another amino acid residue having a side chain with similar chemical characteristics. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies of the disclosure do not abrogate the binding of the polypeptide, soluble protein, or antibody containing the amino acid sequence, to the target binding site. Methods of identifying amino acid conservative substitutions which do not eliminate binding are well-known in the art.

The terms "polypeptide" refers to polymers of amino acids of any length. The polymer can be linear or branched, it can comprise modified amino acids, and it can include (e.g., be interrupted by) non-amino acids. The terms also encompass an amino acid polymer that has been modified naturally or by intervention; for example, disulfide bond formation, glycosylation, lipidation, acetylation, phosphorylation, or any other manipulation or modification, such as linkage to or conjugation with (directly or indirectly) a moiety such as a labeling component. Also included within the definition are, for example, polypeptides containing one or more analogs of an amino acid (including, for example, unnatural amino acids), as well as other modifications known in the art. It is understood that, because the polypeptides of this disclosure can be based upon antibodies or other members of the immunoglobulin superfamily, in some embodiments, the polypeptides can occur as single chains.

As used herein, an "antigen" is a moiety or molecule that contains an epitope to which a binding agent (e.g., an antibody, such as a bispecific antibody) can bind. As such, an antigen can be bound by an antibody. In some embodiments, the antigen, to which a binding agent (e.g., an antibody, such as a bispecific antibody) described herein binds, is CD47 (e.g., human CD47), or a fragment thereof.

As used herein, an "epitope" is a term in the art and refers to a localized region of an antigen to which an antibody can bind. An epitope can be a linear epitope or a conformational, non-linear, or discontinuous, epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope), e.g., human CD47. It will be appreciated by one of skill in the art that, in general, a linear epitope may or may not be dependent on secondary, tertiary, or quaternary structure. For example, in some embodiments, an antibody binds to a group of amino acids regardless of whether they are folded in a natural three dimensional protein structure. In other embodiments, an antibody requires amino acid residues making up the epitope to exhibit a particular conformation (e.g., bend, twist, turn or fold) in order to recognize and bind the epitope.

An antibody binds "an epitope" or "essentially the same epitope" or "the same epitope" as a reference antibody, when the two antibodies recognize identical, overlapping or adjacent epitopes in a three-dimensional space. The most widely used and rapid methods for determining whether two antibodies bind to identical, overlapping or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies is measured using radioactive, fluorescent or enzyme labels.

"Epitope binning" is the process of grouping antibodies based on the epitopes they recognize. More particularly, epitope binning comprises methods and systems for discriminating the epitope recognition properties of different antibodies, using competition assays combined with computational processes for clustering antibodies based on their epitope recognition properties and identifying antibodies having distinct binding specificities.

As used herein, the terms "specifically binds," "specifically recognizes," "immunospecifically binds," "selectively binds," "immunospecifically recognizes" and "immunospecific" are analogous terms in the context of antibodies and refer to molecules that bind to an antigen (e.g., epitope) as such binding is understood by one skilled in the art. In some embodiments, "specifically binds" means, for instance that a polypeptide or molecule interacts more frequently, more rapidly, with greater duration, with greater affinity, or with some combination of the above to the epitope, protein, or target molecule than with alternative substances, including related and unrelated proteins. For example, a molecule that specifically binds to an antigen may bind to other peptides or polypeptides, generally with lower affinity as determined by, e.g., immunoassays, Biacore™, KinExA® 3000 instrument (Sapidyne Instruments, Boise, ID), or other assays known in the art. In some embodiments, an antibody or antigen binding domain binds to or specifically binds to an antigen when it binds to an antigen with higher affinity than to any cross-reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., Fundamental Immunology 332-36 (Paul ed., 2d ed. 1989) for a discussion regarding binding specificity. In some embodiments, the extent of binding of an antibody or antigen binding domain to a "non-target" protein is less than about 10% of the binding of the antibody or antigen binding domain to its particular target antigen, for example, as determined by fluorescence activated cell sorting (FACS) analysis or RIA. In some embodiments, molecules that specifically bind to an antigen bind to the antigen with a Ka that is at least 2 logs, 2.5 logs, 3 logs, 4 logs or greater than the Ka when the molecules bind to another antigen. In some embodiments, molecules that specifically bind to an antigen do not cross react with other proteins. In another specific embodiment, molecules that specifically bind to an antigen do not cross react with other non-CD47 proteins. In some embodiments "specifically binds" means, for instance, that a polypeptide or molecule binds a protein or target with a KD of about 0.1 mM or less, but more usually less than about 1 μM. In some embodiments, "specifically binds" means that a polypeptide or molecule binds a target with a KD of at least about 0.1 μM or less, at least about 0.01 μM or less, or at least about 1 nM or less. Because of the sequence identity between homologous proteins in different species, specific binding can include a polypeptide or molecule that recognizes a protein or target in more than one species. Likewise, because of homology within certain regions of polypeptide sequences of different proteins, specific binding can include a polypeptide or molecule that recognizes more than one protein or target. It is understood that, in some embodiments, a polypeptide or molecule that specifically binds a first target may or may not specifically bind a second target. As such, "specific binding" does not necessarily require (although it can include) exclusive binding, e.g., binding to a single target. Thus, a polypeptide or molecule can, in some embodiments, specifically bind more than one target. In some embodiments, multiple targets can be bound by the same antigen-binding site on the polypeptide or molecule. For example, an antibody can, in certain instances, comprise two identical antigen-binding sites, each of which specifically binds the same epitope on two or more proteins. In certain alternative embodiments, an antibody can be bispecific and comprise at least two antigen-binding sites with differing specificities. Generally, but not necessarily, reference to "binding" means "specific binding".

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. In one embodiment, the "$K_D$" or "Ko value" may be measured by assays known in the art, for example by a binding assay. The $K_D$ values reported herein were determined by biolayer interferometry (BLI) using, for example, the Octet®QK384 system (ForteBio, Menlo Park, CA). Alternatively, the Ko may be also be measured in a radiolabeled antigen binding assay (RIA), for example, performed with the Fab version of an antibody of interest and its antigen (Chen, et al., (1999) J. Mol Biol 293:865-881) or using surface plasmon resonance (SPR) assays by Biacore™, using, for example, a BIAcore™ TM-2000 or a BIAcore™ TM-3000 BIAcore, Inc., Piscataway, NJ). An "on-rate" or "rate of association" or "association rate" or "$k_{on}$," as well as an "off-rate" or "rate of dissociation" or "dissociation rate" or "$k_{off}$," may can also be determined with the same SPR or BLI techniques described above using, for example, the Octet®QK384 system (ForteBio, Menlo Park, CA) or a BIAcore™ TM-2000 or a BIAcore™ TM-3000 (BIAcore, Inc., Piscataway, NJ), respectively.

The term "compete" when used in the context of multi-specific binding agents (e.g., antibodies, such as bispecific antibodies) means binding agents that compete for the same epitope or binding site on a target, which includes competition between such binding agents as determined by an assay in which the binding agent under study prevents or inhibits the specific binding of a reference molecule (e.g., a reference ligand, or reference antigen binding protein, such as a reference antibody) to a common antigen (e.g., CD47). Numerous types of competitive binding assays can be used to determine if a test binding agent competes with a reference molecule for binding to CD47 (e.g., human CD47). Examples of assays that can be employed include solid phase direct or indirect radioimmunoassay (RIA), solid phase direct or indirect enzyme immunoassay (EIA), sandwich competition assay (see, e.g., Stahli et al., (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane, (1988) Antibodies, A Laboratory Manual, Cold Spring Harbor Press); solid phase direct label RIA using 1-125 label (see, e.g., Morel et al., (1988) Molec. Immunol. 25:7-15); solid phase direct biotin-avidin EIA (see, e.g., Cheung, et al., (1990) Virology 176:546-552); and direct labeled RIA (Moldenhauer et al., (1990) Scand. J. Immunol. 32:77-82). Typically, such an assay involves the use of a purified antigen (e.g., CD47, such as human CD47) bound to a solid surface or cells bearing either of an unlabelled test antigen binding protein (e.g., test CD47 antibody) or a labeled reference antigen binding protein (e.g., reference CD47 antibody). Competitive inhibition may be measured by determining the amount of label bound to the solid surface or cells in the presence of the test antigen binding protein. Usually the test antigen binding protein is present in excess. Antibodies identified by competition assay (competing antibodies) include antibodies binding to the same epitope as the reference antibody and/or antibodies binding to an adjacent epitope sufficiently proximal to the epitope bound by the reference for antibodies steric hindrance to occur (e.g., similar epitope or overlapping epitope). Usually, when a competing antibody is present in excess, it will inhibit specific binding of a reference antibody to a common antigen by at least 20%, for example, at least 20%, 25%, 30%, 35%, 40%, 45%, 50%, 55%, 60%, 65%, 70% or 75%. In some instance, binding is inhibited by at least 80%, 85%, 90%, 95%, 96% or 97%, 98%, 99% or more.

As used herein, the term "constant region" or "constant domain" is a well-known antibody term of art and refers to an antibody portion, e.g., for example, a carboxyl terminal portion of a light and/or heavy chain which is not directly involved in binding of an antibody to antigen but which can exhibit various effector functions, such as interaction with the Fc receptor. The term include the portion of an immunoglobulin molecule having a generally more conserved amino acid sequence relative to an immunoglobulin variable domain.

Antibody "effector functions" refer to those biological activities attributable to the Fc region (e.g., a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226 (according to the EU numbering system), or from Pro230 (according to the EU numbering system), to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. An exemplary Fc region sequence is provided below (CH2 domain=bold text; CH3 domain=underline text):

(SEQ ID NO: 188)
CPPCPAPELLGGPSVFLFPPKPKDTLMISRTPEVTCVVVD

VSHEDPEVKFNWYVDGVEVHNAKTKPREEQYNSTYRVVSV

LTVLHQDWLNGKEYKCKVSNKALPAPIEKTISKAKGQPRE

PQVYTLPPSRDELTKNQVSLTCLVKGFYPSDIAVEWESNG

QPENNYKTTPPVLDSDGSFFLYSKLTVDKSRWQQGNVFSC

SVMHEALHNHYTQKSLSLSPGK.

A "functional Fc region" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding region or binding domain (e.g., an antibody variable region or domain) and can be assessed using various assays as disclosed.

A "native sequence Fc region" comprises an amino acid sequence identical to the amino acid sequence of an Fc region found in nature, and not manipulated, modified, and/or changed (e.g., isolated, purified, selected, including or combining with other sequences such as variable region sequences) by a human. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, (e.g., substituting, addition, or deletion) preferably one or more amino acid substitution(s). In some embodiments, the variant Fc region has at least one amino acid substitution compared to a native sequence Fc region or to the Fc region of a parent polypeptide, for example, from about one to about ten amino acid substitutions, and preferably from about one to about five amino acid substitutions in a native sequence Fc region or in the Fc region of the parent polypeptide. The variant Fc region herein can possess at least about 80% homology with a native sequence Fc region and/or with an Fc region of a parent polypeptide, or at least about 90% homology therewith, for example, at least about 95% homology therewith.

The variant Fc region herein described herein may have a loss of effector function (e.g., silent Fc). An exemplary variant Fc region ("silent Fc") sequence is provided below (CH2 domain=bold text with amino acid changes underlined; CH3 domain=underline text):

(SEQ ID NO: 189)
CPPCPAPEAAGGPSVFLFPPKPKDTLMISRTPEVTCVVVD

VSHEDPEVKFNWYVDGVEVHNAKTKPREEQYNSTYRVVSV

LTVLHQDWLNGKEYKCKVSNKALKAPIEKTISKAKGQPRE

PQVYTLPPSRDELTKNQVSLTCLVKGFYPSDIAVEWESNG

QPENNYKTTPPVLDSDGSFFLYSKLTVDKSRWQQGNVFSC

SVMHEALHNHYTQKSLSLSPGK.

An exemplary variant CH2 domain (e.g., silent CH2) sequence useful for multispecific (e.g., bispecific) binding agents described herein is provided below (amino acid changes underlined):

(SEQ ID NO: 190)
APEAAGGPSVFLFPPKPKDTLMISRTPEVTCVVVDVSHED

PEVKFNWYVDGVEVHNAKTKPREEQYNSTYRVVSVLTVLH

QDWLNGKEYKCKVSNKALKAPIEKTISKAK.

As used herein, the term "heavy chain" when used in reference to an antibody refers to a polypeptide chain of about 50-70 kDa, wherein the amino-terminal portion includes a variable region of about 120 to 130 or more amino acids, and a carboxy-terminal portion includes one or more constant regions. The "heavy chain" can refer to any distinct types, e.g., for example, alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, e.g., kappa (κ) of lambda (λ) based on the amino acid sequence of the constant domains. Light chain amino acid sequences are well known in the art.

The terms "antigen binding fragment," "antigen binding domain," "antigen binding region," and similar terms refer to that portion of an antibody, which comprises the amino acid residues that interact with an antigen and confer on the binding fragment, domain, or region its specificity and affinity for the antigen (e.g., the CDRs). "Antigen binding fragment" as used herein include "antibody fragment," which comprise a portion of an antibody including one or more CDRs, such as the antigen binding or variable region of the antibody.

Antibodies described herein include, but are not limited to, synthetic antibodies, monoclonal antibodies, recombinantly produced antibodies, multispecific antibodies (e.g., including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In some embodiments, antibodies described herein include immunoglobulin molecules and immunologically active portions of immunoglobulin molecules, including molecules that contain one or more antigen binding domains that bind to a CD47 antigen and one or more antigen binding domains that bind to one or more targets other than CD47 (e.g., PD-L1).

Antibodies can be of any type (e.g., IgG, IgE, IgM, IgD, IgA or IgY), any class, (e.g., IgG1, IgG2, IgG3, IgG4, IgA1 or IgA2), or any subclass (e.g., IgG2a or IgG2b) of immunoglobulin molecule. In some embodiments, antibodies described herein are IgG antibodies (e.g., human IgG), or a class (e.g., human IgG1, IgG2, IgG3 or IgG4) or subclass thereof.

In some embodiments, an antibody is a 4-chain antibody unit comprising two heavy (H) chain/light (L) chain pairs, wherein the amino acid sequences of the H chains are identical and the amino acid sequences of the L chains are identical. In some embodiments, the H and L chains comprise constant regions, for example, human constant regions. In some embodiments, the L chain constant region of such antibodies is a kappa or lambda light chain constant region, for example, a human kappa or lambda light chain constant region. In some embodiments, the H chain constant region of such antibodies comprise a gamma heavy chain constant region, for example, a human gamma heavy chain constant region. In some embodiments, such antibodies comprise IgG constant regions, for example, human IgG constant regions (e.g., IgG1, IgG2, IgG3, and/or IgG4 constant regions).

An antibody or fragment thereof may preferentially bind to CD47, such as human CD47, meaning that the antibody or fragment thereof binds CD47 with greater affinity than it binds to an unrelated control protein and/or binds human CD47 with greater affinity than it binds to an unrelated control protein. For example, the antibody or fragment thereof may specifically recognize and bind CD47 or a portion thereof. "Specific binding" means that the antibody or fragment thereof binds to CD47 with an affinity that is at least 5, 10, 15, 20, 25, 50, 100, 250, 500, 1000, or 10,000 times greater than the affinity for an unrelated control protein (e.g., hen egg white lysozyme). In some embodiments, the antibody or fragment thereof may bind CD47 substantially exclusively (e.g., is able to distinguish CD47 from other known polypeptides, for example, by virtue of measurable differences in binding affinity). In some embodiments, a multispecific binding agent (e.g., an antibody, such as a bispecific antibody) may react with CD47 sequences other than human CD47 sequences (e.g., cynomolgous CD47 sequences).

The term "variable region" or "variable domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" or alternatively called "complementarity determining regions." The variable regions of heavy and light chains each comprise four FRs (FR1, FR2, FR3 and FR4), largely adopting a p sheet configuration, connected by three hypervariable regions, which form loops connecting, and in some cases forming part of, the p sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, MD, 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. The variability in sequence is concentrated in the CDRs while the less variable portions in the variable region are referred to as framework regions (FR). The CDRs of the light and heavy chains are primarily responsible for the interaction of the antibody with antigen. In specific embodiments, the variable region is a human variable region.

The term "hypervariable region," "HVR," "HV," "complementarity determining region," or "CDR" when used herein refers to the regions of an antibody variable region that are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat CDRs are based on sequence variability and are the most commonly used (see, e.g., Kabat et al., Sequences of Proteins of Immunological Interest, 5th Ed. Public Health Service, National Institutes of Health, Bethesda, MD. (1991)). Chothia refers instead to the location of the structural loops (see, e.g., Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). The "contact" hypervariable regions are based on an analysis of the available complex crystal structures. The residues from each of these hypervariable regions or CDRs are noted below.

A universal numbering system has been developed and widely adopted, ImMunoGeneTics (IMGT) Information System® (Lefranc et al., Dev. Comp. Immunol. 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Plückthun, *J. Mol. Biol.* 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra) and is also illustrated below. An Exemplary system, shown herein, combines Kabat and Chothia.

| | Exemplary | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 52a/53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (L1), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. As used herein, the terms "hypervariable region," "HVR," "HV," "complementarity determining region," or "CDR" are used interchangeably.

The term "vector" refers to a substance that is used to carry or include a nucleic acid sequences, including for example, in order to introduce a nucleic acid sequence into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain or an antibody VH and VL) both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g., a multispecific binding agent as described herein), and it is further understood that expression levels can be optimized to obtain sufficient expression using methods well known in the art.

An "immune cell dysfunctional disease" and "immune cell dysfunctional disorder" and "immune cell dysfunctional condition" are used interchangeably and refer to any disease, disorder or condition that is completely or partially caused by or is the result of improper signaling to an immune cell and/or alternatively any disease, disorder, or condition in which it is desirable to inhibit the in vivo effects of the interaction of an immune cell receptor (e.g., SIRPα or PD-1) with its ligand (e.g., CD47 or PD-L1). An immune cell dysfunctional disease includes a phagocytic cell dysfunctional disease and a T cell dysfunctional disease.

A "phagocytic cell dysfunctional disease" and "phagocytic cell dysfunctional disorder" and "phagocytic cell dysfunctional condition" are used interchangeably and refer to any disease, disorder or condition that is completely or partially caused by or is the result of CD47 or the interaction of CD47 with SIRPα and/or alternatively any disease, disorder, or condition in which it is desirable to inhibit the in vivo effects of the interaction of CD47 with SIRPα. A phagocytic cell dysfunctional disease includes a disease, disorder or condition that is characterized by or associated with decreased phagocytic activity of immune cells (e.g., neutrophils, macrophages, dendritic cells, B lymphocytes). In some embodiments, a phagocytic cell dysfunctional disease is a disease, disorder or condition that is specifically associated with inappropriate increased signaling through SIRPα. In some embodiments, a phagocytic cell dysfunctional disease is one in which phagocytic cells (e.g., macrophages) have decreased ability to ingest or engulf other cells (e.g., a tumor cell) or particles. In some embodiments, the decreased ability to ingest or engulf other cells or particles results in ineffective control of a pathogen or tumor, including but not limited to tumors expressing CD47. Examples of a phagocytic cell dysfunctional disease characterized by phagocytic cell dysfunction include unresolved acute infection, chronic infection and tumor immunity (e.g., any cancers, including but not limited to cancers that express or overexpress CD47).

A "T cell dysfunctional disease" and "T cell dysfunctional disorder" and "T cell dysfunctional condition" are used interchangeably and refer to any disease, disorder or condition of T cells characterized by decreased responsiveness to antigenic stimulation. A T cell dysfunctional disease includes a disease, disorder or condition that is completely or partially caused by or is the result of PD-L1 or the interaction of PD-L1 with PD-1 and/or alternatively any disease, disorder, or condition in which it is desirable to inhibit the in vivo effects of the interaction of PD-L1 with PD-1. In some embodiments, a T cell dysfunctional disease is a disease, disorder or condition that is specifically associated with inappropriate increased signaling through PD-1. In some embodiments, a T cell dysfunctional disease is one in which T cells are anergic or have decreased ability to secrete cytokines, proliferate, or execute cytolytic activity. In some embodiments, the decreased responsiveness results in ineffective control of a pathogen or tumor, including but not limited to tumors expressing PD-L1. Examples of a T cell dysfunctional disease characterized by T cell dysfunction include unresolved acute infection, chronic infection and tumor immunity (e.g., from any cancers, including but not limited to cancers that express or overexpress PD-L1).

"Tumor immunity" refers to the process in which tumors evade immune recognition and clearance. Thus, as a therapeutic concept, tumor immunity is "treated" when such evasion is attenuated and the tumors are recognized and attacked by the immune system. Examples of tumor recognition include tumor binding, tumor shrinkage and tumor clearance.

"Enhancing T cell function" means to induce, cause or stimulate a T cell to have a sustained or increased biological function, or renew or reactivate exhausted or inactive T cells. Examples of enhancing T cell function include: increased secretion of cytokines (e.g., TNFα, IFNγ) from $CD8^+$ T cells, increased proliferation, increased antigen responsiveness (e.g., tumor cell removal) relative to such levels before the intervention. In some embodiments, the level of enhancement is as least 50%, alternatively 60%, 70%, 80%, 90%, 100%, 120%, 150%, 200%. The manner of measuring this enhancement is known to one of ordinary skill in the art.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition. In some embodiments, the effective amount is a therapeutically effective amount or a prophylactically effective amount.

The term "therapeutically effective amount" as used herein refers to the amount of an agent (e.g., an antibody described herein or any other agent described herein) that is sufficient to reduce and/or ameliorate the severity and/or duration of a given disease, disorder or condition, and/or a symptom related thereto. A therapeutically effective amount of an agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody described herein). A "therapeutically effective amount" of a substance/molecule/agent of the present disclosure (e.g., a CD47 antibody) may vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of an antibody or other agent (e.g., or drug) effective to "treat" a disease, disorder, or condition, in a subject or mammal.

A "prophylactically effective amount" is an amount of a pharmaceutical composition that, when administered to a subject, will have the intended prophylactic effect, e.g., preventing or delaying the onset (or reoccurrence) of a disease, disorder or condition, or reducing the likelihood of the onset (or reoccurrence) of a disease, disorder, or condition or associated symptom(s). The full therapeutic or prophylactic effect does not necessarily occur by administration of one dose, and may occur only after administration of a series of doses. Thus, a therapeutically or prophylactically effective amount may be administered in one or more administrations.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

"Carriers" as used herein include carriers, excipients, or stabilizers that are nontoxic to the cell or mammal being exposed thereto at the dosages and concentrations employed. Often the carrier is an aqueous pH buffered solution. Examples of carriers include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The term "carrier" can also refer to a diluent, adjuvant (e.g., Freund's adjuvant (complete or incomplete)), excipient, or vehicle with which the therapeutic is administered. Such carriers can be sterile liquids, such as water and oils, including those of petroleum, animal, vegetable or synthetic origin, such as peanut oil, soybean oil, mineral oil, sesame oil and the like. Water is an exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Compositions can take the form of solutions, suspensions, emulsion, tablets, pills, capsules, powders, sustained-release formulations and the like. Oral compositions, including formulations, can include standard carriers such as pharmaceutical grades of mannitol, lactose, starch, magnesium stearate, sodium saccharine, cellulose, magnesium carbonate, etc. Examples of suitable carriers are described in Remington's Pharmaceutical Sciences (1990) Mack Publishing Co., Easton, PA. Compositions, including pharmaceutical compounds, may contain a prophylactically or therapeutically effective amount of a multispecific binding agent (e.g., an antibody, such as a bispecific antibody), for example, in isolated or purified form, together with a suitable amount of carrier so as to provide the form for proper administration to the subject (e.g., patient). The formulation should suit the mode of administration.

In some embodiments, the present disclosure provides multispecific binding agents that can be used herein as therapeutic agents. Such agents include multispecific antibodies (e.g., antibodies, such as bispecific antibodies) comprising a first binding domain that binds to CD47, including human CD47, and a second binding domain that binds one or more additional targets that are not CD47 (e.g., PD-L1). Exemplary antibodies include humanized, human, bispecific, and heteroconjugate antibodies, as well as variants thereof having increased or decreased affinity or other properties.

In some embodiments, described herein are multispecific binding agents (e.g., antibodies, such as bispecific antibodies) comprising a first binding domain that binds to CD47, including a CD47 polypeptide, a CD47 polypeptide fragment, a CD47 peptide or a CD47 epitope. In some embodiments, the multispecific binding agents are human or humanized antibodies (e.g., comprising human constant regions) comprising a first binding domain that binds CD47, including a CD47 polypeptide, a CD47 polypeptide fragment, a CD47 peptide or a CD27 epitope. In some embodiments, a multispecific binding agent (e.g., an antibody, such as a bispecific antibody) can bind to CD47 expressed on the surface of a mammalian (e.g., human) cell, including a CD47 expressing tumor cell. In some embodiments, a multispecific binding agent (e.g., an antibody, such as a bispecific antibody) binds a CD47 extracellular epitope exposed on a cell such as a tumor cell (e.g., a CD47 epitope). In some embodiments, described herein is a multispecific binding agent (e.g., an antibody, such as a bispecific antibody) that binds to CD47, such as human CD47 or portions thereof. In some embodiments, CD47 is a human CD47. In some embodiments, a multispecific binding agent is a multispecific binding agent that binds to CD47 (e.g., an antibody that binds to human CD47). An exemplary amino acid sequence of human CD47 is described herein.

In some embodiments, described herein are multispecific binding agents (e.g., antibodies, such as bispecific antibodies) comprising a second binding domain that bind to PD-L1, including a PD-L1 polypeptide, a PD-L1 polypeptide fragment, a PD-L1 peptide or a PD-L1 epitope. In some embodiments, the multispecific binding agents are humanized antibodies (e.g., comprising human constant regions) comprising a second binding domain that binds PD-L1, including a PD-L1 polypeptide, a PD-L1 polypeptide fragment, a PD-L1 peptide or a PD-L1 epitope. In some embodiments, a multispecific binding agent (e.g., an antibody, such as a bispecific antibody) can bind to PD-L1 expressed on the surface of a mammalian (e.g., human) cell, including a PD-L1 expressing antigen presenting cells and tumor cells. In some embodiments, a multispecific binding agent (e.g., an antibody, such as a bispecific antibody) binds a PD-L1 extracellular epitope exposed on a cell such as a tumor cell (e.g., a CD47 epitope). In some embodiments, described herein is a multispecific binding agent (e.g., an antibody, such as a bispecific antibody) comprising a second binding domain that binds to PD-L1, such as human PD-L1 or portions thereof. In some embodiments, PD-L1 is a human PD-L1. In some embodiments, a multispecific binding agent is a multispecific binding agent that binds to human PD-L1 (e.g., an antibody that binds to human PD-L1). An exemplary amino acid sequence of human PD-L1 is described herein.

In some embodiments, the multispecific binding agents (e.g., antibodies, such as bispecific antibodies) described herein compete for the binding to CD47, such as human CD47, with a binding agent (e.g., an antibody, such as a bispecific antibody) that comprises a VH region, VL region, VH CDR1, VH CDR2, VH CDR3, VL CDR1, VL CDR2, and/or VL CDR3 of any one of the antibodies described herein, such as an amino acid sequence of a VH region, VL region, VH CDR1, VH CDR2, VH CDR3, VL CDR1, VL CDR2, and/or VL CDR3 depicted in Tables 1-3. Accordingly, in some embodiments, a multispecific binding agent (e.g., an antibody, such as a bispecific antibody) described herein competes for the binding to CD47, such as human CD47, with an binding agent (e.g., an antibody, such as a bispecific antibody) that comprises one, two, and/or three VH CDRs and/or one, two, and/or three VL CDRs from: (a) the antibody designated C40; (b) the antibody designated C56; or (c) the antibody designated C59, as shown in Tables 1-3. In some embodiments, a multispecific binding agent (e.g., an antibody, such as a bispecific antibody) described herein competes for the binding to CD47, such as human CD47, with a binding agent (e.g., an antibody, such as a bispecific antibody) that comprises one, two, and/or three VH CDRs and one, two, and/or three VL CDRs from: (a) the antibody designated C40; (b) the antibody designated C56; or (c) the antibody designated C59, as shown in Tables 1-3. In some embodiments, a multispecific binding agent (e.g., an antibody, such as a bispecific antibody) described herein competes for the binding to CD47, such as human CD47, with a binding agent (e.g., an antibody, such as a bispecific antibody) that comprises a VH region and VL region from: (a) the antibody designated C40; (b) the antibody designated C56; or (c) the antibody designated C59, as shown in Tables 1-3. In some embodiments, a multispecific binding agent (e.g., an antibody, such as a bispecific antibody) described herein competes for the binding to CD47, such as human CD47, with a binding agent (e.g., an antibody, such as a bispecific antibody) that comprises: (a) a VH region comprising the amino acid sequence of SEQ ID NO:25 and a VL region comprising the amino acid sequence of SEQ ID NO:26; (b) a VH region comprising the amino acid sequence of SEQ ID NO:51 and a VL region comprising the amino acid sequence of SEQ ID NO:52; or (c) a VH region comprising the amino acid sequence of SEQ ID NO:77 and a VL region comprising the amino acid sequence of SEQ ID NO:78.

In some embodiments, the multispecific binding agents (e.g., antibodies, such as bispecific antibodies) described herein comprise a VH region, VL region, VH CDR1 VH CDR2, VH CDR3, VL CDR1, VL CDR2, and/or VL CDR3 of any one of the antibodies described herein, such as an amino acid sequence of a VH region, VL region, VH CDR1, VH CDR2, VH CDR3, VL CDR1, VL CDR2, and/or VL CDR3 depicted in Tables 1-6. Accordingly, in some embodiments, the multispecific binding agent (e.g., an antibody, such as a bispecific antibody) described herein comprises a first binding domain that comprises one, two, and/or three heavy chain CDRs and/or one, two, and/or three light chain CDRs from: (a) the antibody designated C40; (b) the antibody designated C56; or (c) the antibody designated C59, as shown in Tables 1-3. In some embodiments, the multispecific binding agent (e.g., an antibody, such as a bispecific antibody) described herein comprises a second binding domain that comprises one, two, and/or three heavy chain CDRs and/or one, two, and/or three light chain CDRs from: (a) the antibody designated P22; (b) the antibody designated P24; or (c) the antibody designated P31.2, as shown in Tables 4-6. In some embodiments, the multispecific binding agent (e.g., an antibody, such as a bispecific antibody) described herein comprises a first binding domain that comprises one, two, and/or three heavy chain CDRs and/or one, two, and/or three light chain CDRs from: (a) the antibody designated C40; (b) the antibody designated C56; or (c) the antibody designated C59, as shown in Tables 1-3, and a second binding domain that comprises one, two, and/or three heavy chain CDRs and/or one, two, and/or three light chain CDRs from: (a) the antibody designated P22; (b) the antibody designated P24; or (c) the antibody designated P31.2, as shown in Tables 4-6. In some embodiments, the multispecific binding agent (e.g., an antibody, such as a bispecific antibody) described herein comprises a first binding domain that comprises one, two, and/or three heavy chain CDRs and one, two, and/or three light chain CDRs from: (a) the antibody designated C40; (b) the antibody designated C56; or (c) the antibody designated C59, as shown in Tables 1-3, and a second binding domain that comprises one, two, and/or three heavy chain CDRs and one, two, and/or three light chain CDRs from: (a) the antibody designated P22; (b) the antibody designated P24; or (c) the antibody designated P31.2, as shown in Tables 4-6.

In some embodiments, a multispecific binding agent (e.g., an antibody, such as a bispecific antibody) comprises a first binding domain that binds to CD47 and comprises a VH region, which comprises VH CDR1, VH CDR2, and/or VH CDR3, and a VL region, which comprises VL CDR1, VL CDR2, and/or VL CDR3, of any one of the binding agents described in Table 1, Table 2, and Table 3, and a second binding domain that binds to PD-L1 and comprises a VH region, which comprises VH CDR1, VH CDR2, and/or VH CDR3, and a VL region, which comprises VL CDR1, VL CDR2, and/or VL CDR3, of any one of the binding agents described in Table 4, Table 5 and Table 6. Accordingly, in some embodiments, a multispecific binding agent (e.g., an antibody, such as a bispecific antibody) described herein comprises a first binding domain that comprises one, two, and/or three heavy chain CDRs and/or one, two, and/or three light chain CDRs from Table 1. In some embodiments, the multispecific binding agent described herein comprises a first binding domain that comprises one, two, and/or three heavy chain CDRs and/or one, two, and/or three light chain CDRs from Table 2. In some embodiments, a multispecific binding agent (e.g., an antibody, such as a bispecific antibody) described herein comprises a first binding domain that comprises one, two, and/or three heavy chain CDRs and/or one, two, and/or three light chain CDRs from Table 3. In some embodiments, the multispecific binding agent (e.g., an antibody, such as a bispecific antibody) described herein comprises a second binding domain that comprises one, two, and/or three heavy chain CDRs and/or one, two, and/or three light chain CDRs from Table 4. In some embodiments, a multispecific binding agent (e.g., an antibody, such as a bispecific antibody) described herein comprises a second binding domain that comprises one, two, and/or three heavy chain CDRs and/or one, two, and/or three light chain CDRs from Table 5. In some embodiments, a multispecific binding agent (e.g., an antibody, such as a bispecific antibody) described herein comprises a second binding domain that comprises one, two, and/or three heavy chain CDRs and/or one, two, and/or three light chain CDRs from Table 6. In some embodiments, a multispecific binding agent (e.g., an antibody, such as a bispecific antibody) described herein is bispecific and comprises a first binding domain that comprises one, two, and/or three heavy chain CDRs and/or one, two, and/or three light chain CDRs from Table 1, Table 2, or Table 3 and a second binding domain that comprises one, two, and/or three heavy chain CDRs and/or one, two, and/or three light chain CDRs from a binding agent that binds to a second target antigen that is not CD47. In some embodiments, a multispecific binding agent (e.g., an antibody, such as a bispecific antibody) described herein is bispecific and comprises a first binding domain that comprises one, two, and/or three heavy chain CDRs and one, two, and/or three light chain CDRs from Table 1, Table 2, or Table 3, and a second binding domain that comprises one, two, and/or three heavy chain CDRs and one, two, and/or three light chain CDRs from Table 4, Table 5, or Table 6.

The antibody designated C40 comprises a VH sequence that is SEQ ID NO:25 and a VL sequence that is SEQ ID NO:26.

The antibody designated C56 comprises a VH sequence that is SEQ ID NO:51 and a VL sequence that is SEQ ID NO:52.

The antibody designated C59 comprises a VH sequence that is SEQ ID NO:77 and a VL sequence that is SEQ ID NO:78.

The antibody designated P22 comprises a VH sequence that is SEQ ID NO:103 and a VL sequence that is SEQ ID NO:104.

The antibody designated P24 comprises a VH sequence that is SEQ ID NO:129 and a VL sequence that is SEQ ID NO:130.

The antibody designated P31.2 comprises a VH sequence that is SEQ ID NO:155 and a VL sequence that is SEQ ID NO:156.

In some embodiments, a multispecific binding agent (e.g., an antibody) that binds to CD47 comprises (i) a VH domain wherein the VH domain comprises a VH sequence that is SEQ ID NO:26 (C40 VH), SEQ ID NO:51 (C56 VH), or SEQ ID NO:77 (C59 VH) and (ii) a VL domain wherein the VL domain comprises a VL sequence that is SEQ ID NO:26 (C40 VL), SEQ ID NO:52 (C56 VL), or SEQ ID NO:78 (C59 VL). In some embodiments, such VH and VL domains were used to construct bispecific binding agents (e.g., antibodies) each with a first binding domain that bind to CD47, including wherein the first binding domain comprises (i) the C40 VH and C40 VL domains, (ii) the C56 VH and C56 VL domains, or (iii) the C59 VH and C59 VL domains.

In some embodiments, a multispecific binding agent (e.g., an antibody) that binds to PD-L1 comprises (i) a VH domain wherein the VH domain comprises a VH sequence that is SEQ ID NO:103 (P22 VH), SEQ ID NO:129 (P24 VH), or SEQ ID NO:155 (P31.2 VH) and (ii) a VL domain wherein the VL domain comprises a VL sequence that is SEQ ID NO:104 (P22 VL), SEQ ID NO:130 (P24 VL), or SEQ ID NO:156 (P31.2 VL). In some embodiments, such VH and VL domains were used to construct bispecific binding agents (e.g., antibodies) each with a first binding domain that bind to PD-L1, including wherein the first binding domain comprises (i) the P22 VH and P22 VL domains, (ii) the P24 VH and P24 VL domains, or (iii) the P31.2 VH and P31.2 VL domains.

In some embodiments, such VH and VL domains were used to construct bispecific antibodies comprising four polypeptide chains, wherein (i) polypeptide chain 1 comprises a VL domain (e.g., C40 VL, C56 VL, or C59 VL), polypeptide chain 2 comprises a VH domain (e.g., C40 VH, C56 VH, or C59 VH), wherein the VL and VH domains form a first binding domain that binds to CD47, and (ii) polypeptide chain 3 comprises a VL domain (e.g., P22 VL, P24 VL, or P31.2 VL), polypeptide chain 4 comprises a VH domain (e.g., P22 VH, P24 VH, or P31.2 VH), wherein the VL and VH domains form a second binding domain that binds to PD-1.

In a first series of embodiments, a CD47×PD-L1 binding agent (e.g., an antibody) has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence (e.g., SEQ ID NO:26 for C40 VL, SEQ ID NO:52 for C56 VL, SEQ ID NO:78 for C59 VL), domain B has a human IgG1 CH3 amino acid sequence with a T366K mutation and a C-terminal extension incorporating a KSC tripeptide sequence that is followed by the DKTHT motif of an IgG1 hinge region, domain D has a human IgG1 CH2 amino acid sequence, and domain E has human IgG1 CH3 amino acid with a S354C and T366W mutation; (b) the second polypeptide chain has a domain F and a domain G, wherein the domains are arranged, from N-terminus to C-terminus, in a F-G orientation, and wherein domain F has a first VH amino acid sequence (e.g., SEQ ID NO:25 for C40 VH, SEQ ID NO:51 for C56 VH, SEQ ID NO:77 for C59 VH) and domain G has a human IgG1 CH3 amino acid sequence with a L351 D mutation and a C-terminal extension incorporating a GEC amino acid disulfide motif; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence (e.g., SEQ ID NO:104 for P22 VL, SEQ ID NO:130 for P24 VL, SEQ ID NO:156 for P31.2 VL), domain I has a human CL kappa amino acid sequence, domain J has a human IgG1 CH2 amino acid sequence, and K has a human IgG1 CH3 amino acid sequence with a Y349C, a D356E, a L358M, a T366S, a L368A, and a Y407V mutation; (d) the fourth polypeptide chain has a domain L and a domain M, wherein the domains are arranged, from N-terminus to C-terminus, in a L-M orientation, and wherein domain L has a second VH amino acid sequence (e.g., SEQ ID NO:103 for P22 VH, SEQ ID NO:129 for P24 VH, SEQ ID NO:155 for P31.2 VH) and domain M has a human IgG1 CH1 amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; (g) the first and the third polypeptides are associated through an interaction between the D and the J domains and an interaction between the E and the K domains to form a bispecific binding agent (e.g., an antibody); (h) domain A and domain F form a first binding domain that binds to CD47; and (i) domain H and domain L form a second binding domain that binds to PD-L1.

Such a four polypeptide chain format is designated as a BC1 B-Body format:

first polypeptide chain:
 Domain A = Target 1 (e.g., CD47) VL
 Domain B = CH3 (T366K; 445K, 446S, 447C tripeptide insertion)
 Domain D = CH2
 Domain E = CH3 (T366W, S354C)
second polypeptide chain:
 Domain F = Target 1 (e.g., CD47) VH
 Domain G = CH3 (L351D; 445G, 446E, 447C tripeptide insertion)
third polypeptide chain:
 Domain H = Target 2 (e.g., PD-L1) VL
 Domain I = CL
 Domain J = CH2
 Domain K = CH3 (Y349C, D356E, L358M, T366S, L368A, Y407V)
fourth polypeptide chain:
 Domain L = Target 2 (e.g., PD-L1) VH
 Domain M = CH1.

>BC1 chain 1
Domain arrangement:
A- B- Hinge- D- E
VL- CH3- Hinge- CH2- CH3(knob)
Mutations in first CH3 (Domain B):
T366K; 445K, 446S, 447C insertion
Mutations in second CH3 (Domain E):
S354C, T366W
>BC1 chain 2
Domain arrangement:
F- G
VH- CH3
Mutations in CH3 (Domain G):
L351D; 445G, 446E, 447C insertion
>BC1 chain 3

-continued

Domain arrangement:
H- I- Hinge-J- K
VL- CL- Hinge-CH2- CH3(hole)
Mutations in CH3 (Domain K):
Y349C, D356E, L358M, T366S, L368A, Y407V
>BC1 chain 4
Domain arrangement:
L- M
VH- CH1

In an exemplary embodiment of a bispecific binding agent (e.g., an antibody), the first polypeptide chain has the sequence SEQ ID NO:157, the second polypeptide chain has the sequence SEQ ID NO:158, the third polypeptide chain has the sequence SEQ ID NO:159, and the fourth polypeptide chain has the sequence SEQ ID NO:160. Alternatively, the first polypeptide chain has the sequence SEQ ID NO:169, and the third polypeptide chain has the sequence SEQ ID NO:170.

In an exemplary embodiment of a bispecific binding agent (e.g., an antibody), the first polypeptide chain has the sequence SEQ ID NO:157, the second polypeptide chain has the sequence SEQ ID NO:158, the third polypeptide chain has the sequence SEQ ID NO:161, and the fourth polypeptide chain has the sequence SEQ ID NO:162. Alternatively, the first polypeptide chain has the sequence SEQ ID NO:169, and the third polypeptide chain has the sequence SEQ ID NO:171.

In an exemplary embodiment of a bispecific binding agent (e.g., an antibody), the first polypeptide chain has the sequence SEQ ID NO:157, the second polypeptide chain has the sequence SEQ ID NO:158, the third polypeptide chain has the sequence SEQ ID NO:163, and the fourth polypeptide chain has the sequence SEQ ID NO:164. Alternatively, the first polypeptide chain has the sequence SEQ ID NO:169, and the third polypeptide chain has the sequence SEQ ID NO:172.

In an exemplary embodiment of a bispecific binding agent (e.g., an antibody), the first polypeptide chain has the sequence SEQ ID NO:165, the second polypeptide chain has the sequence SEQ ID NO:166, the third polypeptide chain has the sequence SEQ ID NO:159, and the fourth polypeptide chain has the sequence SEQ ID NO:160. Alternatively, the first polypeptide chain has the sequence SEQ ID NO:173, and the third polypeptide chain has the sequence SEQ ID NO:170.

In an exemplary embodiment of a bispecific binding agent (e.g., an antibody), the first polypeptide chain has the sequence SEQ ID NO:165, the second polypeptide chain has the sequence SEQ ID NO:166, the third polypeptide chain has the sequence SEQ ID NO:161, and the fourth polypeptide chain has the sequence SEQ ID NO:162. Alternatively, the first polypeptide chain has the sequence SEQ ID NO:173, and the third polypeptide chain has the sequence SEQ ID NO:171.

In an exemplary embodiment of a bispecific binding agent (e.g., an antibody), the first polypeptide chain has the sequence SEQ ID NO:165, the second polypeptide chain has the sequence SEQ ID NO:166, the third polypeptide chain has the sequence SEQ ID NO:163, and the fourth polypeptide chain has the sequence SEQ ID NO:164. Alternatively, the first polypeptide chain has the sequence SEQ ID NO:173, and the third polypeptide chain has the sequence SEQ ID NO:172.

In an exemplary embodiment of a bispecific binding agent (e.g., an antibody), the first polypeptide chain has the sequence SEQ ID NO:167, the second polypeptide chain has the sequence SEQ ID NO:168, the third polypeptide chain has the sequence SEQ ID NO:159, and the fourth polypeptide chain has the sequence SEQ ID NO:160. Alternatively, the first polypeptide chain has the sequence SEQ ID NO:174, and the third polypeptide chain has the sequence SEQ ID NO:170.

In an exemplary embodiment of a bispecific binding agent (e.g., an antibody), the first polypeptide chain has the sequence SEQ ID NO:167, the second polypeptide chain has the sequence SEQ ID NO:168, the third polypeptide chain has the sequence SEQ ID NO:161, and the fourth polypeptide chain has the sequence SEQ ID NO:162. Alternatively, the first polypeptide chain has the sequence SEQ ID NO:174, and the third polypeptide chain has the sequence SEQ ID NO:171.

In an exemplary embodiment of a bispecific binding agent (e.g., an antibody), the first polypeptide chain has the sequence SEQ ID NO:167, the second polypeptide chain has the sequence SEQ ID NO:168, the third polypeptide chain has the sequence SEQ ID NO:163, and the fourth polypeptide chain has the sequence SEQ ID NO:164. Alternatively, the first polypeptide chain has the sequence SEQ ID NO:174, and the third polypeptide chain has the sequence SEQ ID NO:172.

In a second series of embodiments, a CD47×PD-L1 binding agent (e.g., an antibody) has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence (e.g., SEQ ID NO:26 for C40 VL, SEQ ID NO:52 for C56 VL, SEQ ID NO:78 for C59 VL), domain B has a human IgG1 CH3 amino acid sequence with a Y349C mutation, a P343V mutation, and a C-terminal extension incorporating a PGK tripeptide sequence that is followed by the DKTHT motif of an IgG1 hinge region, domain D has a human IgG1 CH2 amino acid sequence, and domain E has human IgG1 CH3 amino acid with a S354C mutation and a T366W mutation; (b) the second polypeptide chain has a domain F and a domain G, wherein the domains are arranged, from N-terminus to C-terminus, in a F-G orientation, and wherein domain F has a first VH amino acid sequence (e.g., SEQ ID NO:25 for C40 VH, SEQ ID NO:51 for C56 VH, SEQ ID NO:77 for C59 VH) and domain G has a human IgG1 CH3 amino acid sequence with a S354C mutation and a C-terminal extension incorporating a PGK tripeptide sequence; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence (e.g., SEQ ID NO:104 for P22 VL, SEQ ID NO:130 for P24 VL, SEQ ID NO:156 for P31.2 VL), domain I has a human CL kappa amino acid sequence, domain J has a human IgG1 CH2 amino acid sequence, and K has a human IgG1 CH3 amino acid sequence with a Y349C, T366S, L368A, and a Y407V; (d) the fourth polypeptide chain has a domain L and a domain M, wherein the domains are arranged, from N-terminus to C-terminus, in a L-M orientation, and wherein domain L has a second VH amino acid sequence (e.g., SEQ ID NO:103 for P22 VH, SEQ ID NO:129 for P24 VH, SEQ ID NO:155 for P31.2 VH) and domain M has a human IgG1 amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; and (g) the first and the third polypeptides are associated through an interaction between the D and the J domains and an interaction between the E and the K domains to form a bispecific binding agent (e.g., an antibody); (h) domain A and domain F form a first binding domain that binds to CD47; and (i) domain H and domain L form a second binding domain that binds to PD-L1.

Such a four polypeptide chain format is designated as a BC44 B-Body format:

first polypeptide chain
  Domain A = Target 1 (e.g., CD47) VL
  Domain B = CH3 (P343V; Y349C; 445P, 446G, 447K insertion)
  Domain D = CH2
  Domain E = CH3 (S354C, T366W)
second polypeptide chain
  Domain F = Target 1 (e.g., CD47) VH
  Domain G = CH3 (S354C; 445P, 446G, 447K insertion)
third polypeptide chain
  Domain H = Target 2 (e.g., PD-L1) VL
  Domain I = CL (Kappa)
  Domain J = CH2
  Domain K = CH3 (Y349C, D356E, L358M, T366S, L368A, Y407V)
fourth polypeptide chain
  Domain L = Target 2 (e.g., PD-L1) VH
  Domain M = CH1

>BC44 chain 1
  Domain arrangement:
    A- B- Hinge- D- E
    VL- CH3- Hinge- CH2- CH3(knob)
  Mutations in first CH3 (Domain B):
    P343V; Y349C; 445P, 446G, 447K insertion
  Mutations in second CH3 (Domain E):
    S354C, T366W
>BC44 chain 2
  Domain arrangement:
    F- G
    VH- CH3
    Mutations in CH3 (Domain G):
      S354C; 445P, 446G, 447K insertion
>BC44 chain 3
  Domain arrangement:
    H- I- Hinge-J- K
    VL- CL- Hinge-CH2- CH3(hole)
    Mutations in CH3 (Domain K):
      Y349C, D356E, L358M, T366S, L368A, Y407V
>BC44 chain 4
  Domain arrangement:
    L- M
    VH- CH1

In an exemplary embodiment of a bispecific binding agent (e.g., an antibody), the first polypeptide chain has the sequence SEQ ID NO:175, the second polypeptide chain has the sequence SEQ ID NO:176, the third polypeptide chain has the sequence SEQ ID NO:159, and the fourth polypeptide chain has the sequence SEQ ID NO:160. Alternatively, the first polypeptide chain has the sequence SEQ ID NO:181, and the third polypeptide chain has the sequence SEQ ID NO:170.

In an exemplary embodiment of a bispecific binding agent (e.g., an antibody), the first polypeptide chain has the sequence SEQ ID NO:175, the second polypeptide chain has the sequence SEQ ID NO:176, the third polypeptide chain has the sequence SEQ ID NO:161, and the fourth polypeptide chain has the sequence SEQ ID NO:162. Alternatively, the first polypeptide chain has the sequence SEQ ID NO:181, and the third polypeptide chain has the sequence SEQ ID NO:171.

In an exemplary embodiment of a bispecific binding agent (e.g., an antibody), the first polypeptide chain has the sequence SEQ ID NO:175, the second polypeptide chain has the sequence SEQ ID NO:176, the third polypeptide chain has the sequence SEQ ID NO:163, and the fourth polypeptide chain has the sequence SEQ ID NO:164. Alternatively, the first polypeptide chain has the sequence SEQ ID NO:181, and the third polypeptide chain has the sequence SEQ ID NO:172.

In an exemplary embodiment of a bispecific binding agent (e.g., an antibody), the first polypeptide chain has the sequence SEQ ID NO:177, the second polypeptide chain has the sequence SEQ ID NO:178, the third polypeptide chain has the sequence SEQ ID NO:159, and the fourth polypeptide chain has the sequence SEQ ID NO:160. Alternatively, the first polypeptide chain has the sequence SEQ ID NO:182, and the third polypeptide chain has the sequence SEQ ID NO:170.

In an exemplary embodiment of a bispecific binding agent (e.g., an antibody), the first polypeptide chain has the sequence SEQ ID NO:177, the second polypeptide chain has the sequence SEQ ID NO:178, the third polypeptide chain has the sequence SEQ ID NO:161, and the fourth polypeptide chain has the sequence SEQ ID NO:162. Alternatively, the first polypeptide chain has the sequence SEQ ID NO:182, and the third polypeptide chain has the sequence SEQ ID NO:171.

In an exemplary embodiment of a bispecific binding agent (e.g., an antibody), the first polypeptide chain has the sequence SEQ ID NO:177, the second polypeptide chain has the sequence SEQ ID NO:178, the third polypeptide chain has the sequence SEQ ID NO:163, and the fourth polypeptide chain has the sequence SEQ ID NO:164. Alternatively, the first polypeptide chain has the sequence SEQ ID NO:182, and the third polypeptide chain has the sequence SEQ ID NO:172.

In an exemplary embodiment of a bispecific binding agent (e.g., an antibody), the first polypeptide chain has the sequence SEQ ID NO:179, the second polypeptide chain has the sequence SEQ ID NO:180, the third polypeptide chain has the sequence SEQ ID NO:159, and the fourth polypeptide chain has the sequence SEQ ID NO:160. Alternatively, the first polypeptide chain has the sequence SEQ ID NO:183, and the third polypeptide chain has the sequence SEQ ID NO:170.

In an exemplary embodiment of a bispecific binding agent (e.g., an antibody), the first polypeptide chain has the sequence SEQ ID NO:179, the second polypeptide chain has the sequence SEQ ID NO:180, the third polypeptide chain has the sequence SEQ ID NO:161, and the fourth polypeptide chain has the sequence SEQ ID NO:162. Alternatively, the first polypeptide chain has the sequence SEQ ID NO:183, and the third polypeptide chain has the sequence SEQ ID NO:171.

In an exemplary embodiment of a bispecific binding agent (e.g., an antibody), the first polypeptide chain has the sequence SEQ ID NO:179, the second polypeptide chain has the sequence SEQ ID NO:180, the third polypeptide chain has the sequence SEQ ID NO:163, and the fourth polypeptide chain has the sequence SEQ ID NO:164. Alternatively, the first polypeptide chain has the sequence SEQ ID NO:183, and the third polypeptide chain has the sequence SEQ ID NO:172.

TABLE 1

Antibody C40

| | | Exemplary | IMGT | Kabat | Chothia | Contact | AbM |
|---|---|---|---|---|---|---|---|
| VH CDR Seq. | VH CDR1 | GFTFSYYYIH (SEQ ID NO: 1) | GFTFSYYY (SEQ ID NO: 7) | YYYIH (SEQ ID NO: 12) | GFTFSYY (SEQ ID NO: 13) | SYYYIH (SEQ ID NO: 18) | GFTFSYYYIH (SEQ ID NO: 1) |
| | VH CDR2 | WIDPYGHSTTYADSVKG (SEQ ID NO: 2) | IDPYGHST (SEQ ID NO: 8) | WIDPYGHSTTYADSVKG (SEQ ID NO: 2) | PYGH (SEQ ID NO: 14) | WVAWIDPYGHSTT (SEQ ID NO: 19) | WIDPYGHSTT (SEQ ID NO: 24) |
| | VH CDR3 | GGRGAMDY (SEQ ID NO: 3) | ARGGRGAMDY (SEQ ID NO: 9) | GGRGAMDY (SEQ ID NO: 3) | GRGAMD (SEQ ID NO: 15) | ARGGRGAMD (SEQ ID NO: 20) | GGRGAMDY (SEQ ID NO: 3) |
| VL CDR Seq. | VL CDR1 | RASQSVSSAVA (SEQ ID NO: 4) | QSVSSA (SEQ ID NO: 10) | RASQSVSSAVA (SEQ ID NO: 4) | SQSVSSA (SEQ ID NO: 16) | SSAVAWY (SEQ ID NO: 21) | RASQSVSSAVA (SEQ ID NO: 4) |
| | VL CDR2 | SASSLYS (SEQ ID NO: 5) | SAS (SEQ ID NO: 11) | SASSLYS (SEQ ID NO: 5) | SAS (SEQ ID NO: 11) | LLIYSASSLY (SEQ ID NO: 22) | SASSLYS (SEQ ID NO: 5) |
| | VL CDR3 | QQRYSSLLT (SEQ ID NO: 6) | QQRYSSLLT (SEQ ID NO: 6) | QQRYSSLLT (SEQ ID NO: 6) | RYSSLL (SEQ ID NO: 17) | QQRYSSLL (SEQ ID NO: 23) | QQRYSSLLT (SEQ ID NO: 6) |

VH Sequence:
EVQLVESGGGLVQPGGSLRLSCAASGFTFSYYYIHWVRQ
APGKGLEWVAWIDPYGHSTTYADSVKGRFTISADTSKNT
AYLQMNSLRAEDTAVYYCARGGRGAMDYWGQGTLVT
(SEQ ID NO: 25)

VL Sequence:
DIQMTQSPSSLSASVGDRVTITCRASQSVSSAVAWYQQK
PGKAPKLLIYSASSLYSGVPSRFSGSRSGTDFTLTISSL
QPEDFATYYCQQRYSSLLTFGQGTKVEIK
(SEQ ID NO: 26)

TABLE 2

Antibody C56

| | | Exemplary | IMGT | Kabat | Chothia | Contact | AbM |
|---|---|---|---|---|---|---|---|
| VH CDR Seq. | VH CDR1 | GFTFTYYYIH | GFTFTYYY (SEQ | YYYIH (SEQ | GFTFTYY (SEQ | TYYYIH (SEQ | GFTFTYYYIH |

TABLE 2-continued

| Antibody C56 | | | | | | | |
|---|---|---|---|---|---|---|---|
| | | Exemplary | IMGT | Kabat | Chothia | Contact | AbM |
| | | (SEQ ID NO: 27) | ID NO: 33) | ID NO: 38) | ID NO: 39) | ID NO: 44) | (SEQ ID NO: 27) |
| | VH CDR2 | FIDPYSGSTEYADSVKG (SEQ ID NO: 28) | IDPYSGST (SEQ ID NO: 34) | FIDPYSGSTEYADSVKG (SEQ ID NO: 28) | PYSG (SEQ ID NO: 40) | WVAFIDPYSGSTE (SEQ ID NO: 45) | FIDPYSGSTE (SEQ ID NO: 50) |
| | VH CDR3 | GGLYALDY (SEQ ID NO: 29) | ARGGLYALDY (SEQ ID NO: 35) | GGLYALDY (SEQ ID NO: 29) | GLYALD (SEQ ID NO: 41) | ARGGLYALD (SEQ ID NO: 46) | GGLYALDY (SEQ ID NO: 29) |
| VL CDR Seq. | VL CDR1 | RASQSVSSAVA (SEQ ID NO: 30) | QSVSSA (SEQ ID NO: 36) | RASQSVSSAVA (SEQ ID NO: 30) | SQSVSSA (SEQ ID NO: 42) | SSAVAWY (SEQ ID NO: 47) | RASQSVSSAVA (SEQ ID NO: 30) |
| | VL CDR2 | SASSLYS (SEQ ID NO: 31) | SAS (SEQ ID NO: 37) | SASSLYS (SEQ ID NO: 31) | SAS (SEQ ID NO: 37) | LLIYSASSLY (SEQ ID NO: 48) | SASSLYS (SEQ ID NO: 31) |
| | VL CDR3 | QQGRSDLRT (SEQ ID NO: 32) | QQGRSDLRT (SEQ ID NO: 32) | QQGRSDLRT (SEQ ID NO: 32) | GRSDLR (SEQ ID NO: 43) | QQGRSDLR (SEQ ID NO: 49) | QQGRSDLRT (SEQ ID NO: 32) |

VH Sequence:
EVQLVESGGGLVQPGGSLRLSCAASGFTFTYYYIHWVRQA
PGKGLEWVAFIDPYSGSTEYADSVKGRFTISADTSKNTAY
LQMNSLRAEDTAVYYCARGGLYALDYWGQGTLVT
(SEQ ID NO: 51)

VL Sequence:
DIQMTQSPSSLSASVGDRVTITCRASQSVSSAVAWYQQKP
GKAPKLLIYSASSLYSGVPSRFSGSRSGTDFTLTISSLQP
EDFATYYCQQGRSDLRTFGQGTKVEIK (SEQ ID NO: 52)

TABLE 3

| Antibody C59 | | | | | | | |
|---|---|---|---|---|---|---|---|
| | | Exemplary | IMGT | Kabat | Chothia | Contact | AbM |
| VH CDR Seq. | VH CDR1 | GFTFTSYYIH (SEQ ID NO: 53) | GFTFTSYY (SEQ ID NO: 59) | SYYIH (SEQ ID NO: 64) | GFTFTSY (SEQ ID NO: 65) | TSYYIH (SEQ ID NO: 70) | GFTFTSYYIH (SEQ ID NO: 53) |

TABLE 3 -continued

| Antibody C59 | | | | | | | |
|---|---|---|---|---|---|---|---|
| | | Exemplary | IMGT | Kabat | Chothia | Contact | AbM |
| | VH CDR2 | YIDSKHGTTQYADSVKG (SEQ ID NO: 54) | IDSKHGTT (SEQ ID NO: 60) | YIDSKHGTTQYADSVKG (SEQ ID NO: 54) | SKHG (SEQ ID NO: 66) | WVAYIDSKHGTTQ (SEQ ID NO: 71) | YIDSKHGTTQ (SEQ ID NO: 76) |
| | VH CDR3 | GGRSAMDY (SEQ ID NO: 55) | ARGGRSAMDY (SEQ ID NO: 61) | GGRSAMDY (SEQ ID NO: 55) | GRSAMD (SEQ ID NO: 67) | ARGGRSAMD (SEQ ID NO: 72) | GGRSAMDY (SEQ ID NO: 55) |
| VL CDR Seq. | VL CDR1 | RASQSVSSAVA (SEQ ID NO: 56) | QSVSSA (SEQ ID NO: 62) | RASQSVSSAVA (SEQ ID NO: 56) | SQSVSSA (SEQ ID NO: 68) | SSAVAWY (SEQ ID NO: 73) | RASQSVSSAVA (SEQ ID NO: 56) |
| | VL CDR2 | SASSLYS (SEQ ID NO: 57) | SAS (SEQ ID NO: 63) | SASSLYS (SEQ ID NO: 57) | SAS (SEQ ID NO: 63) | LLIYSASSLY (SEQ ID NO: 74) | SASSLYS (SEQ ID NO: 57) |
| | VL CDR3 | QQRTTSLLT (SEQ ID NO: 58) | QQRTTSLLT (SEQ ID NO: 58) | QQRTTSLLT (SEQ ID NO: 58) | RTTSLL (SEQ ID NO: 69) | QQRTTSLL (SEQ ID NO: 75) | QQRTTSLLT (SEQ ID NO: 58) |

VH Sequence:
EVQLVESGGGLVQPGGSLRLSCAASGFTFTSYYIHWVRQA
PGKGLEWVAYIDSKHGTTQYADSVKGRFTISADTSKNTAY
LQMNSLRAEDTAVYYCARGGRSAMDYWGQGTLVT
(SEQ ID NO: 77)

VL Sequence:
DIQMTQSPSSLSASVGDRVTITCRASQSVSSAVAWYQQKP
GKAPKLLIYSASSLYSGVPSRFSGSRSGTDFTLTISSLQP
EDFATYYCQQRTTSLLTFGQGTKVEIK (SEQ ID NO: 78)

TABLE 4

| Antibody P22 | | | | | | | |
|---|---|---|---|---|---|---|---|
| | | Exemplary | IMGT | Kabat | Chothia | Contact | AbM |
| VH CDR Seq. | VH CDR1 | GFTFSSYYIH (SEQ ID NO: 79) | GFTFSSYY (SEQ ID NO: 85) | SYYIH (SEQ ID NO: 90) | GFTFSSY (SEQ ID NO: 91) | SSYYIH (SEQ ID NO: 96) | GFTFSSYYIH (SEQ ID NO: 79) |
| | VH CDR2 | WITSHGYSTKYA | ITSHGYST (SEQ | WITSHGYSTKYA | SHGY (SEQ ID | WAWITSHGYS | WITSHGYSTK |

TABLE 4-continued

Antibody P22

| | | Exemplary | IMGT | Kabat | Chothia | Contact | AbM |
|---|---|---|---|---|---|---|---|
| | | DSVKG (SEQ ID NO: 80) | ID NO: 86) | DSVKG (SEQ ID NO: 80) | NO: 92) | TK (SEQ ID NO: 97) | (SEQ ID NO: 102) |
| | VH CDR3 | DSVIYGLDY (SEQ ID NO: 81) | ARDSVIYGLDY (SEQ ID NO: 87) | DSVIYGLDY (SEQ ID NO: 81) | SVIYGLD (SEQ ID NO: 93) | ARDSVIYGLD (SEQ ID NO: 98) | DSVIYGLDY (SEQ ID NO: 81) |
| VL CDR Seq. | VL CDR1 | RASQSVSSAVA (SEQ ID NO: 82) | QSVSSA (SEQ ID NO: 88) | RASQSVSSAVA (SEQ ID NO: 82) | SQSVSSA (SEQ ID NO: 94) | SSAVAWY (SEQ ID NO: 99) | RASQSVSSAVA (SEQ ID NO: 82) |
| | VL CDR2 | SASSLYS (SEQ ID NO: 83) | SAS (SEQ ID NO: 89) | SASSLYS (SEQ ID NO: 83) | SAS (SEQ ID NO: 89) | LLIYSASSLY (SEQ ID NO: 100) | SASSLYS (SEQ ID NO: 83) |
| | VL CDR3 | QQYYTSPYT (SEQ ID NO: 84) | QQYYTSPYT (SEQ ID NO: 84) | QQYYTSPYT (SEQ ID NO: 84) | YYTSPY (SEQ ID NO: 95) | QQYYTSPY (SEQ ID NO: 101) | QQYYTSPYT (SEQ ID NO: 84) |

VH Sequence:
EVQLVESGGGLVQPGGSLRLSCAASGFTFSSYYIHWVRQA
PGKGLEWVAWITSHGYSTKYADSVKGRFTISADTSKNTAY
LQMNSLRAEDTAVYYCARDSVIYGLDYWGQGTLVT
(SEQ ID NO: 103)

VL Sequence:
DIQMTQSPSSLSASVGDRVTITCRASQSVSSAVAWYQQKP
GKAPKLLIYSASSLYSGVPSRFSGSRSGTDFTLTISSLQP
EDFATYYCQQYYTSPYTFGQGTKVEIK (SEQ ID NO: 104)

TABLE 5

Antibody P24

| | | Exemplary | IMGT | Kabat | Chothia | Contact | AbM |
|---|---|---|---|---|---|---|---|
| VH CDR Seq. | VH CDR1 | GFTFDQYYIH (SEQ ID NO: 105) | GFTFDQYY (SEQ ID NO: 111) | QYYIH (SEQ ID NO: 116) | GFTFDQY (SEQ ID NO: 117) | DQYYIH (SEQ ID NO: 122) | GFTFDQYYIH (SEQ ID NO: 105) |
| | VH CDR2 | EIYPAGSYTYYADSVKG (SEQ ID NO: 106) | IYPAGSYT (SEQ ID NO: 112) | EIYPAGSYTYYADSVKG (SEQ ID NO: 106) | PAGS (SEQ ID NO: 118) | WVAEIYPAGSYTY (SEQ ID NO: 123) | EIYPAGSYTY (SEQ ID NO: 128) |
| | VH CDR3 | GPYSVRYALDY (SEQ ID NO: 107) | ARGPYSVRYALDY (SEQ ID NO: 113) | GPYSVRYALDY (SEQ ID NO: 107) | PYSVRYALD (SEQ ID NO: 119) | ARGPYSVRYALD (SEQ ID NO: 124) | GPYSVRYALDY (SEQ ID NO: 107) |
| VL CDR Seq. | VL CDR1 | RASQSVSSAVA (SEQ ID NO: 108) | QSVSSA (SEQ ID NO: 114) | RASQSVSSAVA (SEQ ID NO: 108) | SQSVSSA (SEQ ID NO: 120) | SSAVAWY (SEQ ID NO: 125) | RASQSVSSAVA (SEQ ID NO: 108) |
| | VL CDR2 | SASSLYS (SEQ ID NO: 109) | SAS (SEQ ID NO: 115) | SASSLYS (SEQ ID NO: 109) | SAS (SEQ ID NO: 115) | LLIYSASSLY (SEQ ID NO: 126) | SASSLYS (SEQ ID NO: 109) |
| | VL CDR3 | QQVSYSPYT (SEQ ID NO: 110) | QQVSYSPYT (SEQ ID NO: 110) | QQVSYSPYT (SEQ ID NO: 110) | VSYSPY (SEQ ID NO: 121) | QQVSYSPY (SEQ ID NO: 127) | QQVSYSPYT (SEQ ID NO: 110) |

VH Sequence:
EVQLVESGGGLVQPGGSLRLSCAASGFTFDQYYIHWVRQA
PGKGLEWVAEIYPAGSYTYYADSVKGRFTISADTSKNTAY
LQMNSLRAEDTAVYYCARGPYSVRYALDYWGQGTLVT
(SEQ ID NO: 129)

VL Sequence:
DIQMTQSPSSLSASVGDRVTITCRASQSVSSAVAWYQQKP
GKAPKLLIYSASSLYSGVPSRFSGSRSGTDFTLTISSLQP
EDFATYYCQQVSYSPYTFGQGTKVEIK (SEQ ID NO: 130)

TABLE 6

Antibody P31.2

| | | Exemplary | IMGT | Kabat | Chothia | Contact | AbM |
|---|---|---|---|---|---|---|---|
| VH CDR Seq. | VH CDR1 | GFTFSSYYIH (SEQ ID NO: 131) | GFTFSSYY (SEQ ID NO: 137) | SYYIH (SEQ ID NO: 142) | GFTFSSY (SEQ ID NO: 143) | SSYYIH (SEQ ID NO: 148) | GFTFSSYYIH (SEQ ID NO: 131) |
| | VH CDR2 | TISSGGGFTYYADSVKG (SEQ ID NO: 132) | ISSGGGFT (SEQ ID NO: 138) | TISSGGGFTYYADSVKG (SEQ ID NO: 132) | SGGG (SEQ ID NO: 144) | WATISSGGGFTY (SEQ ID NO: 149) | TISSGGGFTY (SEQ ID NO: 154) |

TABLE 6 -continued

| Antibody P31.2 | | | | | | | |
|---|---|---|---|---|---|---|---|
| | | Exemplary | IMGT | Kabat | Chothia | Contact | AbM |
| | VH CDR3 | GYTLTPVLDY (SEQ ID NO: 133) | ARGYTLTPVLDY (SEQ ID NO: 139) | GYTLTPVLDY (SEQ ID NO: 133) | YTLTPVLD (SEQ ID NO: 145) | ARGYTLTPVLD (SEQ ID NO: 150) | GYTLTPVLDY (SEQ ID NO: 133) |
| VL CDR Seq. | VL CDR1 | RASQSVSSAVA (SEQ ID NO: 134) | QSVSSA (SEQ ID NO: 140) | RASQSVSSAVA (SEQ ID NO: 134) | SQSVSSA (SEQ ID NO: 146) | SSAVAWY (SEQ ID NO: 151) | RASQSVSSAVA (SEQ ID NO: 134) |
| | VL CDR2 | SASSLYS (SEQ ID NO: 135) | SAS (SEQ ID NO: 141) | SASSLYS (SEQ ID NO: 135) | SAS (SEQ ID NO: 141) | LLIYSASSLY (SEQ ID NO: 152) | SASSLYS (SEQ ID NO: 135) |
| | VL CDR3 | QQFGAEPIT (SEQ ID NO: 136) | QQFGAEPIT (SEQ ID NO: 136) | QQFGAEPIT (SEQ ID NO: 136) | FGAEPI (SEQ ID NO: 147) | QQFGAEPI (SEQ ID NO: 153) | QQFGAEPIT (SEQ ID NO: 136) |

VH Sequence:
EVQLVESGGGLVQPGGSLRLSCAASGFTFSSYYIHWVRQA
PGKGLEWVATISSGGGFTYYADSVKGRFTISADTSKNTAY
LQMNSLRAEDTAVYYCARGYTLTPVLDYWGQGTLVT
(SEQ ID NO: 155)

VL Sequence:
DIQMTQSPSSLSASVGDRVTITCRASQSVSSAVAWYQQKP
GKAPKLLIYSASSLYSGVPSRFSGSRSGTDFTLTISSLQP
EDFATYYCQQFGAEPITFGQGTKVEIK (SEQ ID NO: 156)

In some embodiments, multispecific binding agents (e.g., antibodies, such as bispecific antibodies) described herein comprise a first binding domain that binds to CD47, including human CD47, and a second binding domain that binds to one or more targets that are not CD47 (e.g., PD-L1, including human PD-L1), wherein the first binding domain and/or the second binding domain comprise a VH region or VH domain. In other embodiments, multispecific binding agents (e.g., antibodies, such as bispecific antibodies) described herein comprise a first binding domain that binds to CD47, including human CD47, and a second binding domain that binds to one or more targets that are not CD47 (e.g., PD-L1, including human PD-L1), wherein the first binding domain and/or the second binding domain comprise a VL region or VL domain. In some embodiments, multispecific binding agents (e.g., antibodies, such as bispecific antibodies) described herein comprise a first binding domain that binds to CD47, including human CD47, and a second binding domain that binds to one or more targets that are not CD47 (e.g., PD-L1, including human PD-L1), wherein the first binding domain and/or the second binding domain have a combination of (i) a VH domain or VH region; and/or (ii) a VL domain or VL region.

In some embodiments, multispecific binding agents (e.g., antibodies, such as bispecific antibodies) described herein have a combination of (i) a VH domain or VH region; and (ii) a VL domain or VL region. For example, an exemplary bispecific IgG antibody comprises (i) a heavy chain having a combination of a VH domain or VH region as described herein; and one or more heavy chain constant domains or contant regions (e.g., CH1, Hinge, CH2, and CH3), and (ii) a light chain having a combination of a VL domain or VL region as described herein and a light chain constant domain or constant region (CL). An exemplary IgG heavy chain comprises any VH domain as described herein and the following CH1, Hinge, CH2, and CH3 amino acid sequence:

(SEQ ID NO: 191)
ASTKGPSVFPLAPSSKSTSGGTAALGCLVKDYFPEPVTVS
WNSGALTSGVHTFPAVLQSSGLYSLSSVVTVPSSSLGTQT
YICNVNHKPSNTKVDKKVEPKSCDKTHTCPPCPAPELLGG
PSVFLFPPKPKDTLMISRTPEVTCVVVDVSHEDPEVKFNW
YVDGVEVHNAKTKPREEQYNSTYRVVSVLTVLHQDWLNGK
EYKCKVSNKALPAPIEKTISKAKGQPREPQVYTLPPSRDE
LTKNQVSLTCLVKGFYPSDIAVEWESNGQPENNYKTTPPV
LDSDGSFFLYSKLTVDKSRWQQGNVFSCSVMHEALHNHYT
QKSLSLSPGK

Another exemplary IgG heavy chain comprises any VH domain as described herein and the following CH1, Hinge, CH2, and CH3 amino acid sequence:

(SEQ ID NO: 192)
ASTKGPSVFPLAPSSKSTSGGTAALGCLVKDYFPEPVTVS
WNSGALTSGVHTFPAVLQSSGLYSLSSVVTVPSSSLGTQT
YICNVNHKPSNTKVDKKVEPKSCDKTHTCPPCPAPEAAGG
PSVFLFPPKPKDTLMISRTPEVTCVVVDVSHEDPEVKFNW
YVDGVEVHNAKTKPREEQYNSTYRVVSVLTVLHQDWLNGK
EYKCKVSNKALKAPIEKTISKAKGQPREPQVYTLPPSRDE
LTKNQVSLTCLVKGFYPSDIAVEWESNGQPENNYKTTPPV
LDSDGSFFLYSKLTVDKSRWQQGNVFSCSVMHEALHNHYT
QKSLSLSPGK

An exemplary light chain (e.g., for pairing with an IgG heavy chain) comprises any VL domain as described herein and the following CL amino acid sequence:

(SEQ ID NO: 193)
RTVAAPSVFIFPPSDSQLKSGTASVVCLLNNFYPREAKVQ
WKVDNALQSGNSQESVTEQDSKDSTYSLSSTLTLSKADYE
KHKVYACEVTHQGLSSPVTKSFNRGEC.

In some embodiments, multispecific binding agents (e.g., antibodies, such as bispecific antibodies) described herein comprise a first binding domain that binds to CD47, including human CD47, and second binding domain that binds one or more targets that are not CD47 (e.g., PD-L1, including human PD-L1), wherein the first binding domain comprises one or more CDRs, including six CDRs, for example, VH CDR1, VH CDR2, VH CDR3, VL CDR1, VL CDR2, and/or VL CDR3 identified in Table 1. In some embodiments, multispecific binding agents (e.g., antibodies, such as bispecific antibodies) described herein comprise a first binding domain that binds to CD47, including human CD47, and a second binding domain that binds one or more targets that are not CD47 (e.g., PD-L1, including human PD-L1), wherein the first binding domain comprises one or more, including six CDRs, for example, VH CDR1, VH CDR2, VH CDR3, VL CDR1, VL CDR2, and/or VL CDR3 identified in Table 2. In some embodiments, multispecific binding agents (e.g., antibodies, such as bispecific antibodies) described herein comprise a first binding domain that binds to CD47, including human CD47, and a second binding domain that binds one or more targets that are not CD47 (e.g., PD-L1, including human PD-L1), wherein the first binding domain comprises one or more, including six CDRs, for example, VH CDR1, VH CDR2, VH CDR3, VL CDR1, VL CDR2, and/or VL CDR3 identified in Table 3. In some embodiments, multispecific binding agents (e.g., antibodies, such as bispecific antibodies) described herein comprise a first binding domain that binds to CD47, including human CD47, and a second binding domain that binds one or more targets that are not CD47 (e.g., PD-L1, including human PD-L1), wherein the first binding domain comprises one or more, including six CDRs, for example, VH CDR1, VH CDR2, VH CDR3, VL CDR1, VL CDR2, and/or VL CDR3 identified in Tables 1, 2 and/or 3.

In some embodiments, multispecific binding agents (e.g., antibodies, such as bispecific antibodies), including multispecific binding agent that binds to CD47, including human CD47, and one or more targets that are not CD47 (e.g., PD-L1, including human PD-L1), described herein comprise a first binding domain comprising one or more CDRs, including three VH CDRs, for example, VH CDR1, VH CDR2, VH CDR3, listed in Table 1. In other embodiments, multispecific binding agents (e.g., antibodies, such as bispecific antibodies), including multispecific binding agents that bind to CD47, including human CD47, and one or more targets that are not CD47 (e.g., PD-L1, including human PD-L1), described herein comprise a first binding domain comprising one or more CDRs, including three CDRs, for example, VL CDR1, VL CDR2, and/or VL CDR3, listed in Table 1. In yet other embodiments, multispecific binding agents (e.g., antibodies, such as bispecific antibodies), including multispecific binding agents that bind to CD47, including human CD47, and one or more targets that are not CD47 (e.g., PD-1, including human PD-L1), described herein comprise a first binding domain comprising one or more CDRs, including three VH CDRs, for example, VH CDR1, VH CDR2, VH CDR3, listed in Table 1 and one or more CDRs, including three VL CDRs, for example, VL CDR1, VL CDR2, and/or VL CDR3, listed in Table 1.

In some embodiments, multispecific binding agents (e.g., antibodies, such as bispecific antibodies), including multispecific binding agent that binds to CD47, including human CD47, and one or more targets that are not CD47 (e.g., PD-L1, including human PD-L1), described herein comprise a first binding domain comprising one or more CDRs, including three VH CDRs, for example, VH CDR1, VH CDR2, VH CDR3, listed in Table 2. In other embodiments, multispecific binding agents (e.g., antibodies, such as bispecific antibodies), including multispecific binding agents that bind to CD47, including human CD47, and one or more targets that are not CD47 (e.g., PD-1, including human PD-L1), described herein comprise a first binding domain comprising one or more CDRs, including three CDRs, for example, VL CDR1, VL CDR2, and/or VL CDR3, listed in Table 2. In yet other embodiments, multispecific binding agents (e.g., antibodies, such as bispecific antibodies), including multispecific binding agents that bind to CD47, including human CD47, and one or more targets that are not CD47 (e.g., PD-L1, including human PD-L1), described herein comprise a first binding domain comprising one or more CDRs, including three VH CDRs, for example, VH CDR1, VH CDR2, VH CDR3, listed in Table 2 and one or more CDRs, including three VL CDRs, for example, VL CDR1, VL CDR2, and/or VL CDR3, listed in Table 2.

In some embodiments, multispecific binding agents (e.g., antibodies, such as bispecific antibodies), including multispecific binding agent that binds to CD47, including human CD47, and one or more targets that are not CD47 (e.g., PD-L1, including human PD-L1), described herein comprise a first binding domain comprising one or more CDRs, including three VH CDRs, for example, VH CDR1, VH CDR2, VH CDR3, listed in Table 3. In other embodiments, multispecific binding agents (e.g., antibodies, such as bispecific antibodies), including multispecific binding agents that bind to CD47, including human CD47, and one or more targets that are not CD47 (e.g., PD-1, including human PD-L1), described herein comprise a first binding domain comprising one or more CDRs, including three CDRs, for example, VL CDR1, VL CDR2, and/or VL CDR3, listed in Table 3. In yet other embodiments, multispecific binding agents (e.g., antibodies, such as bispecific antibodies), including multispecific binding agents that bind to CD47, including human CD47, and one or more targets that are not CD47 (e.g., PD-L1, including human PD-L1), described herein comprise a first binding domain comprising one or more CDRs, including three VH CDRs, for example, VH CDR1, VH CDR2, VH CDR3, listed in Table 3 and one or more CDRs, including three VL CDRs, for example, VL CDR1, VL CDR2, and/or VL CDR3, listed in Table 3.

In some embodiments, multispecific binding agents (e.g., antibodies, such as bispecific antibodies), including multispecific binding agent that binds to CD47, including human CD47, and PD-L1, including human PD-L1, described herein comprise a second binding domain comprising one or more CDRs, including three VH CDRs, for example, VH CDR1, VH CDR2, VH CDR3, listed in Table 4. In other embodiments, multispecific binding agents (e.g., antibodies, such as bispecific antibodies), including multispecific binding agents that bind to CD47, including human CD47, and PD-L1, including human PD-L1, described herein comprise a second binding domain comprising one or more CDRs, including three CDRs, for example, VL CDR1, VL CDR2, and/or VL CDR3, listed in Table 4. In yet other embodiments, multispecific binding agents (e.g., antibodies, such as bispecific antibodies), including multispecific binding agents that bind to CD47, including human CD47, and PD-L1, including human PD-L1, described herein comprise a second binding domain comprising one or more CDRs, including three VH CDRs, for example, VH CDR1, VH CDR2, VH CDR3, listed in Table 4 and one or more CDRs, including three VL CDRs, for example, VL CDR1, VL CDR2, and/or VL CDR3, listed in Table 4.

In some embodiments, multispecific binding agents (e.g., antibodies, such as bispecific antibodies), including multispecific binding agent that binds to CD47, including human CD47, and PD-L1, including human PD-L1, described herein comprise a second binding domain comprising one or more CDRs, including three VH CDRs, for example, VH CDR1, VH CDR2, VH CDR3, listed in Table 5. In other embodiments, multispecific binding agents (e.g., antibodies, such as bispecific antibodies), including multispecific binding agents that bind to CD47, including human CD47, and PD-L1, including human PD-L1, described herein comprise a second binding domain comprising one or more CDRs, including three CDRs, for example, VL CDR1, VL CDR2, and/or VL CDR3, listed in Table 5. In yet other embodiments, multispecific binding agents (e.g., antibodies, such as bispecific antibodies), including multispecific binding agents that bind to CD47, including human CD47, and PD-L1, including human PD-L1, described herein comprise a second binding domain comprising one or more CDRs, including three VH CDRs, for example, VH CDR1, VH CDR2, VH CDR3, listed in Table 5 and one or more CDRs, including three VL CDRs, for example, VL CDR1, VL CDR2, and/or VL CDR3, listed in Table 5.

In some embodiments, multispecific binding agents (e.g., antibodies, such as bispecific antibodies), including multispecific binding agent that binds to CD47, including human CD47, and PD-L1, including human PD-L1, described herein comprise a second binding domain comprising one or more CDRs, including three VH CDRs, for example, VH CDR1, VH CDR2, VH CDR3, listed in Table 6. In other embodiments, multispecific binding agents (e.g., antibodies, such as bispecific antibodies), including multispecific binding agents that bind to CD47, including human CD47, and PD-L1, including human PD-L1, described herein comprise a second binding domain comprising one or more CDRs, including three CDRs, for example, VL CDR1, VL CDR2, and/or VL CDR3, listed in Table 6. In yet other embodiments, multispecific binding agents (e.g., antibodies, such as bispecific antibodies), including multispecific binding agents that bind to CD47, including human CD47, and PD-L1, including human PD-L1, described herein comprise a second binding domain comprising one or more CDRs, including three VH CDRs, for example, VH CDR1, VH CDR2, VH CDR3, listed in Table 6 and one or more CDRs, including three VL CDRs, for example, VL CDR1, VL CDR2, and/or VL CDR3, listed in Table 6.

In some embodiments, a multispecific binding agent (e.g., an antibody, such as a bispecific antibody) described herein comprises a first binding domain that binds to CD47 and comprises one or more complementarity determining regions (CDRs) comprising an amino acid sequence selected from a group consisting of SEQ ID NOS: 1-24, 27-50, and 53-76. In some embodiments, a multispecific binding agent (e.g., an antibody, such as a bispecific antibody) described herein comprises a first binding domain that binds to CD47 and comprises two or more complementarity determining regions (CDRs) comprising an amino acid sequence selected from a group consisting of SEQ ID NOS: 1-24, 27-50, and 53-76. In some embodiments, a multispecific binding agent (e.g., an antibody, such as a bispecific antibody) described herein comprises a first binding domain that binds to CD47 and comprises three or more complementarity determining regions (CDRs) comprising an amino acid sequence selected from a group consisting of SEQ ID NOS: 1-24, 27-50, and 53-76. In some embodiments, the multispecific binding agent (e.g., an antibody, such as a bispecific antibody) described herein comprises a second binding domain that binds to PD-L1 and comprises one or more complementarity determining regions (CDRs) comprising an amino acid sequence selected from a group consisting of SEQ ID NOS: 79-102, 105-128, and 131-154. In some embodiments, a multispecific binding agent (e.g., an antibody, such as a bispecific antibody) described herein comprises a second binding domain that binds to PD-L1 and comprises two or more complementarity determining regions (CDRs) comprising an amino acid sequence selected from a group consisting of SEQ ID NOS: 79-102, 105-128, and 131-154. In some embodiments, a multispecific binding agent (e.g., an antibody, such as a bispecific antibody) described herein comprises a second binding domain that binds to PD-L1 and comprises three or more complementarity determining regions (CDRs) comprising an amino acid sequence selected from a group consisting of SEQ ID NOS: 79-102, 105-128, and 131-154.

In some embodiments, a multispecific binding agent (e.g., an antibody, such as a bispecific antibody) described herein comprises a first binding domain that binds to CD47 and comprises a VH with one or more (e.g., one, two or three) VH CDRs listed in Tables 1-3. In other embodiments, a multispecific binding agent (e.g., an antibody, such as a bispecific antibody) described herein comprises a first binding domain that binds to CD47 and comprises a VL with one or more (e.g., one, two or three) VL CDRs listed in Tables 1-3. In yet other embodiments, the multispecific binding agent (e.g., an antibody, such as a bispecific antibody) described herein comprises a first binding domain that binds to CD47 and comprises one or more (e.g., one, two or three) VH CDRs listed in Tables 1-3 and one or more VL CDRs listed in Tables 1-3. Accordingly, in some embodiments, a multispecific binding agent (e.g., an antibody, such as a bispecific antibody) described herein comprises a first binding domain that binds to CD47 and comprises a VH CDR1 having the amino acid sequence of any one of SEQ ID NOS: 1, 7, 12, 13, 18, 27, 33, 38, 39, 44, 53, 59, 64, 65, and 70. In some embodiments, a multispecific binding agent (e.g., an antibody, such as a bispecific antibody) described herein comprises a first binding domain that binds to CD47 and comprises a VH CDR2 having the amino acid sequence of any one of SEQ ID NOS: 2, 8, 14, 19, 24, 28, 34, 40, 45, 50, 54, 60, 66, 71, and 76. In some embodiments, a multispecific binding agent (e.g., an antibody, such as a bispecific antibody) described herein a first binding domain that binds to CD47 and comprises comprises a VH CDR3 having the amino acid sequence of any one of SEQ ID NOS: 3, 9, 15, 20, 29, 35, 41, 46, 55, 61, 67, and 72. In some embodiments, a multispecific binding agent (e.g., an antibody, such as a bispecific antibody) described herein comprises a first binding domain that binds to CD47 and comprises a VH CDR1 and/or a VH CDR2 and/or a VH CDR3 independently selected from a VH CDR1, VH CDR2, VH CDR3 as depicted in any one of the amino acid sequences depicted in Table 1-3. In some embodiments, a multispecific binding agent (e.g., an antibody, such as a bispecific antibody) described herein comprises a first binding domain that binds to CD47 and comprises a VL CDR1 having the amino acid sequence of any one of SEQ ID NOS: 4, 10, 16, 21, 30, 36, 42, 47, 56, 62, 68, and 73. In another embodiment, a multispecific binding agent (e.g., an antibody, such as a bispecific antibody) described herein comprises a first binding domain that binds to CD47 and comprises a VL CDR2 having the amino acid sequence of any one of SEQ ID NOS: 5, 11, 22, 31, 37, 48, 57, 63, and 74. In some embodiments, a multispecific binding agent (e.g., an antibody, such as a bispecific antibody) described herein comprises a first binding domain that binds to CD47 and comprises a VL CDR3 having the amino acid sequence of any one of SEQ ID NOS: 6, 17, 23, 32, 43, 49, 58, 69, and 75. In some embodiments, a multispecific binding agent (e.g., an antibody, such as a bispecific antibody) described herein comprises a first binding domain that binds to CD47 and comprises a VL CDR1 and/or a VL CDR2 and/or a VL CDR3 independently selected from a VL CDR1, VL CDR2, VL CDR3 as depicted in any one of the amino acid sequences depicted in Tables 1-3.

In some embodiments, a multispecific binding agent (e.g., an antibody, such as a bispecific antibody) described herein comprises a second binding domain that binds to PD-L1 and comprises a VH with one or more (e.g., one, two or three) VH CDRs listed in Tables 4-6. In other embodiments, a multispecific binding agent (e.g., an antibody, such as a bispecific antibody) described herein comprises a second binding domain that binds to PD-L1 and comprises a VL with one or more (e.g., one, two or three) VL CDRs listed in Tables 4-6. In yet other embodiments, the multispecific binding agent (e.g., an antibody, such as a bispecific antibody) described herein comprises a second binding domain that binds to PD-L1 and comprises one or more (e.g., one, two or three) VH CDRs listed in Tables 4-6 and one or more VL CDRs listed in Tables 4-6. Accordingly, in some embodiments, a multispecific binding agent (e.g., an antibody, such as a bispecific antibody) described herein comprises a second binding domain that binds to PD-L1 and comprises a VH CDR1 having the amino acid sequence of any one of SEQ ID NOS: 79, 85, 90, 91, 96, 105, 11, 116, 117, 122, 131, 137, 142, 143, and 148. In some embodiments, a multispecific binding agent (e.g., an antibody, such as a bispecific antibody) described herein comprises a second binding domain that binds to PD-L1 and comprises a VH CDR2 having the amino acid sequence of any one of SEQ ID NOS: 80, 86, 92, 97, 102, 106, 112, 118, 123, 128, 132, 138, 44, 149, and 154. In some embodiments, a multispecific binding agent (e.g., an antibody, such as a bispecific antibody) described herein a second binding domain that binds to PD-L1 and comprises comprises a VH CDR3 having the amino acid sequence of any one of SEQ ID NOS: 81, 87, 93, 98, 107, 113, 119, 124, 133, 139, 145, and 150. In some embodiments, a multispecific binding agent (e.g., an antibody, such as a bispecific antibody) described herein comprises a second binding domain that binds to PD-L1 and comprises a VH CDR1 and/or a VH CDR2 and/or a VH CDR3 independently selected from a VH CDR1, VH CDR2, VH CDR3 as depicted in any one of the amino acid sequences depicted in Table 4-6. In some embodiments, a multispecific binding agent (e.g., an antibody, such as a bispecific antibody) described herein comprises a second binding domain that binds to PD-L1 and comprises a VL CDR1 having the amino acid sequence of any one of SEQ ID NOS: 82, 88, 94, 99, 108, 114, 120, 125, 134, 140, 146, and 151. In another embodiment, a multispecific binding agent (e.g., an antibody, such as a bispecific antibody) described herein comprises a second binding domain that binds to PD-L1 and comprises a VL CDR2 having the amino acid sequence of any one of SEQ ID NOS: 83, 89, 100, 109, 115, 126, 135, 141, and 152. In some embodiments, a multispecific binding agent (e.g., an antibody, such as a bispecific antibody) described herein comprises a second binding domain that binds to PD-L1 and comprises a VL CDR3 having the amino acid sequence of any one of SEQ ID NOS: 84, 95, 101, 110, 121, 127, 136, 147, and 153. In some embodiments, a multispecific binding agent (e.g., an antibody, such as a bispecific antibody) described herein comprises a second binding domain that binds to PD-L1 and comprises a VL CDR1 and/or a VL CDR2 and/or a VL CDR3 independently selected from a VL CDR1, VL CDR2, VL CDR3 as depicted in any one of the amino acid sequences depicted in Tables 4-6.

In some embodiments, a multispecific binding agent (e.g., an antibody, such as a bispecific antibody) described herein comprises a first binding domain that binds to CD47 and comprises a heavy chain variable (VH) region comprising: (1) a VH CDR1 having an amino acid sequence of selected from the group consisting of: (i) SEQ ID NO:1, 27, or 53, (ii) SEQ ID NO:7, 33, or 59, (iii) SEQ ID NO:12, 38, or 64, (iv) SEQ ID NO:13, 39, or 65, and (v) SEQ ID NO:18, 44, or 70; (2) a VH CDR2 having an amino acid sequence of selected from the group consisting of: (i) SEQ ID NO:2, 28, or 54, (ii) SEQ ID NO:8, 34, or 60, (iii) SEQ ID NO:14, 40, or 66, (iv) SEQ ID NO:19, 45, or 71, and (v) SEQ ID NO:24, 50, or 76; and (3) a VH CDR3 having an amino acid sequence of selected from the group consisting of: (i) SEQ ID NO:3, 29, or 55, (ii) SEQ ID NO:9, 35, or 61, (iii) SEQ ID NO:15, 41, or 67, and (iv) SEQ ID NO:20, 46, or 72; and/or a light chain variable (VL) region comprising: (1) a VL CDR1 having an amino acid sequence of selected from the group consisting of: (i) SEQ ID NO:4, 30, or 56, (ii) SEQ ID NO:10, 36, or 62, (iii) SEQ ID NO:16, 42, or 68, and (iv) SEQ ID NO:21, 47, or 73; (2) a VL CDR2 having an amino acid sequence of selected from the group consisting of: (i) SEQ ID NO:5, 31, or 57, (ii) SEQ ID NO:11, 37, or 63, and (iii) SEQ ID NO:22, 48, or 74; and (3) a VL CDR3 having an amino acid sequence of selected from the group consisting of: (i) SEQ ID NO:6, 32, or 58, (ii) SEQ ID NO:17, 43, or 69, and (iii) SEQ ID NO:23, 49, or 75.

In some embodiments, a multispecific binding agent (e.g., an antibody, such as a bispecific antibody) described herein comprises a first binding domain that binds to CD47 and comprises a heavy chain variable (VH) region comprising: (1) a VH CDR1 having an amino acid sequence of selected from the group consisting of: (i) SEQ ID NO:1, 27, or 53, (ii) SEQ ID NO:7, 33, or 59, (iii) SEQ ID NO:12, 38, or 64, (iv) SEQ ID NO:13, 39, or 65, and (v) SEQ ID NO:18, 44, or 70; (2) a VH CDR2 having an amino acid sequence of selected from the group consisting of: (i) SEQ ID NO:2, 28, or 54, (ii) SEQ ID NO:8, 34, or 60, (iii) SEQ ID NO:14, 40, or 66, (iv) SEQ ID NO:19, 45, or 71, and (v) SEQ ID NO:24, 50, or 76; and (3) a VH CDR3 having an amino acid sequence of selected from the group consisting of: (i) SEQ ID NO:3, 29, or 55, (ii) SEQ ID NO:9, 35, or 61, (iii) SEQ ID NO:15, 41, or 67, and (iv) SEQ ID NO:20, 46, or 72.

In some embodiments, a multispecific binding agent (e.g., an antibody, such as a bispecific antibody) described herein comprises a first binding domain that binds to CD47 and comprises a light chain variable (VL) region comprising: (1) a VL CDR1 having an amino acid sequence of selected from the group consisting of: (i) SEQ ID NO:4, 30, or 56, (ii) SEQ ID NO:10, 36, or 62, (iii) SEQ ID NO:16, 42, or 68, and (iv) SEQ ID NO:21, 47, or 73; (2) a VL CDR2 having an amino acid sequence of selected from the group consisting of: (i) SEQ ID NO:5, 31, or 57, (ii) SEQ ID NO:11, 37, or 63, and (iii) SEQ ID NO:22, 48, or 74; and (3) a VL CDR3 having an amino acid sequence of selected from the group consisting of: (i) SEQ ID NO:6, 32, or 58, (ii) SEQ ID NO:17, 43, or 69, and (iii) SEQ ID NO:23, 49, or 75.

In some embodiments, a multispecific binding agent (e.g., an antibody, such as a bispecific antibody) described herein comprises a second binding domain that binds to PD-L1 and comprises (a) a heavy chain variable (VH) region comprising (1) a VH CDR1 having an amino acid sequence selected from the group consisting of: (i) SEQ ID NO:79, 105, or 131 (ii) SEQ ID NO:85, 111, or 137 (iii) SEQ ID NO:90, 116, or 142, (iv) SEQ ID NO:91, 117, or 143 (v) SEQ ID NO:96, 122, or 148; (2) a VH CDR2 having an amino acid sequence selected from the group consisting of: (i) SEQ ID NO:80, 106, or 132, (ii) SEQ ID NO:86, 112, or 138, (iii) SEQ ID NO:92, 118, or 144, (iv) SEQ ID NO:97, 123, or 149, (v) SEQ ID NO:102, 128, or 159; and (3) a VH CDR3 having an amino acid sequence selected from the group consisting of: (i) SEQ ID NO:81, 107, or 133, (ii) SEQ ID NO:87, 113, or 139, (iii) SEQ ID NO:93, 119, or 145, (iv) SEQ ID NO:98, 124, or 150; and/or (b) a light chain variable (VL) region comprising: (1) a VL CDR1 having an amino acid sequence selected from the group consisting of: (i) SEQ ID NO:82, 108, or 134, (ii) SEQ ID NO:88, 114, or 140, (iii) SEQ ID NO:94, 120, or 146, (iv) SEQ ID NO:99, 125, or 151; (2) a VL CDR2 having an amino acid sequence selected from the group consisting of: (i) SEQ ID NO:83, 109, or 135, (ii) SEQ ID NO:89, 115, or 141, (iii) SEQ ID NO:100, 126, or 152; (3) a VL CDR3 having an amino acid sequence selected from the group consisting of: (i) SEQ ID NO:84, 110, or 136, (ii) SEQ ID NO:95, 121, or 147, (iii) SEQ ID NO:101, 127, or 153.

In some embodiments, a multispecific binding agent (e.g., an antibody, such as a bispecific antibody) described herein comprises a second binding domain that binds to PD-L1 and comprises a heavy chain variable (VH) region comprising (1) a VH CDR1 having an amino acid sequence selected from the group consisting of: (i) SEQ ID NO:79, 105, or 131 (ii) SEQ ID NO:85, 11, 1 or 137 (iii) SEQ ID NO:90, 116, or 142, (iv) SEQ ID NO:91, 117, or 143 (v) SEQ ID NO:96, 122, or 148; (2) a VH CDR2 having an amino acid sequence selected from the group consisting of: (i) SEQ ID NO:80, 106, or 132, (ii) SEQ ID NO:86, 112, or 138, (iii) SEQ ID NO:92, 118, or 144, (iv) SEQ ID NO:97, 123, or 149, (v) SEQ ID NO:102, 128, or 159; and (3) a VH CDR3 having an amino acid sequence selected from the group consisting of: (i) SEQ ID NO:81, 107, or 133, (ii) SEQ ID NO:87, 113, or 139, (iii) SEQ ID NO:93, 119, or 145, (iv) SEQ ID NO:98, 124, or 150.

In some embodiments, a multispecific binding agent (e.g., an antibody, such as a bispecific antibody) described herein comprises a second binding domain that binds to PD-L1 and comprises a light chain variable (VL) region comprising: (1) a VL CDR1 having an amino acid sequence selected from the group consisting of: (i) SEQ ID NO:82, 108, or 134, (ii) SEQ ID NO:88, 114, or 140, (iii) SEQ ID NO:94, 120, or 146, (iv) SEQ ID NO:99, 125, or 151; (2) a VL CDR2 having an amino acid sequence selected from the group consisting of: (i) SEQ ID NO:83, 109, or 135, (ii) SEQ ID NO:89, 115 or 141, (iii) SEQ ID NO:100, 126, or 152; (3) a VL CDR3 having an amino acid sequence selected from the group consisting of: (i) SEQ ID NO:84, 110, or 136, (ii) SEQ ID NO:95, 121, or 147, (iii) SEQ ID NO:101, 127, or 153.

Also described herein are multispecific binding agents (e.g., antibodies, such as bispecific antibodies) comprising a first binding domain that binds to CD47 and comprises one or more (e.g., one, two or three) VH CDRs and one or more (e.g., one, two or three) VL CDRs listed in Tables 1-3. In particular, described herein is a multispecific binding agent (e.g., an antibody, such as a bispecific antibody) comprising: a VH CDR1 (SEQ ID NOS: 1, 7, 12, 13, 18, 27, 33, 38, 39, 44, 53, 59, 64, 65, and 70) and a VL CDR1 (SEQ ID NOS: 4, 10, 16, 21, 30, 36, 42, 47, 56, 62, 68, and 73); a VH CDR1 (SEQ ID NOS: 1, 7, 12, 13, 18, 27, 33, 38, 39, 44, 53, 59, 64, 65, and 70) and a VL CDR2 (SEQ ID NOS: 5, 11, 22, 31, 37, 48, 57, 63, and 74); a VH CDR1 (SEQ ID NOS: 1, 7, 12, 13, 18, 27, 33, 38, 39, 44, 53, 59, 64, 65, and 70) and a VL CDR3 (SEQ ID NOS: 6, 17, 23, 32, 43, 49, 58, 69, and 75); a VH CDR2 (SEQ ID NOS: 2, 8, 14, 19, 24, 28, 34, 40, 45, 50, 54, 60, 66, 71, and 76) and a VL CDR1 (SEQ ID NOS: 4, 10, 16, 21, 30, 36, 42, 47, 56, 62, 68, and 73); a VH CDR2 (SEQ ID NOS: 2, 8, 14, 19, 24, 28, 34, 40, 45, 50, 54, 60, 66, 71, and 76) and a VL CDR2 (SEQ ID NOS: 5, 11, 22, 31, 37, 48, 57, 63, and 74); a VH CDR2 (SEQ ID NOS: 2, 8, 14, 19, 24, 28, 34, 40, 45, 50, 54, 60, 66, 71, and 76) and a VL CDR3 (SEQ ID NOS: 6, 17, 23, 32, 43, 49, 58, 69, and 75); a VH CDR3 (SEQ ID NOS: 3, 9, 15, 20, 29, 35, 41, 46, 55, 61, 67, and 72) and a VL CDR1 (SEQ ID NOS: 4, 10, 16, 21, 30, 36, 42, 47, 56, 62, 68, and 73); a VH CDR3 (SEQ ID NOS: 3, 9, 15, 20, 29, 35, 41, 46, 55, 61, 67, and 72) and a VL CDR2 (SEQ ID NOS: 5, 11, 22, 31, 37, 48, 57, 63, and 74); a VH CDR3 (SEQ ID NOS: 3, 9, 15, 20, 29, 35, 41, 46, 55, 61, 67, and 72) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76) and a VL CDR1 (SEQ ID NOS: 4, 10, 16, 21, 30, 36, 42, 47, 56, 62, 68, and 73); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76) and a VL CDR2 (SEQ ID NOS: 5, 11, 22, 31, 37, 48, 57, 63, and 74); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76) and a VL CDR3 (SEQ ID NOS: 6, 17, 23, 32, 43, 49, 58, 69, and 75); a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72) and a VL CDR1 (SEQ ID NOS: 4, 10, 16, 21, 30, 36, 42, 47, 56, 62, 68, and 73), a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72) and a VL CDR2 (SEQ ID NOS: 5, 11, 22, 31, 37, 48, 57, 63, and 74); a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VL CDR1 (SEQ ID NOS: 4, 10, 16, 21, 30, 36, 42, 47, 56, 62, 68, and 73) and a VL CDR2 (SEQ ID NOS: 5, 11, 22, 31, 37, 48, 57, 63, and 74); a VH CDR1 (SEQ ID NOS: 1, 7, 12, 13, 18, 27, 33, 38, 39, 44, 53, 59, 64, 65, and 70), a VL CDR1 (SEQ ID NOS: 4, 10, 16, 21, 30, 36, 42, 47, 56, 62, 68, and 73) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VL CDR2 (SEQ ID NOS: 5, 11, 22, 31, 37, 48, 57, 63, and 74) and a VL CDR3 (SEQ ID NOS: 6, 17, 23, 32, 43, 49, 58, 69, and 75); a VH CDR2 (SEQ ID NOS: 2, 8, 14, 19, 24, 28, 34, 40, 45, 50, 54, 60, 66, 71, and 76), a VL CDR1 (SEQ ID NOS: 4, 10, 16, 21, 30, 36, 42, 47, 56, 62, 68, and 73) and a VL CDR2 (SEQ ID NOS: 5, 11, 22, 31, 37, 48, 57, 63, and 74); a VH CDR2 (SEQ ID NOS: 2, 8, 14, 19, 24, 28, 34, 40, 45, 50, 54, 60, 66, 71, and 76), a VL CDR1 (SEQ ID NOS: 4, 10, 16, 21, 30, 36, 42, 47, 56, 62, 68, and 73) and a VL CDR3 (SEQ ID NOS: 6, 17, 23, 32, 43, 49, 58, 69, and 75); a VH CDR2 (SEQ ID NOS: 2, 8, 14, 19, 24, 28, 34, 40, 45, 50, 54, 60, 66, 71, and 76), a VL CDR2 (SEQ ID NOS: 5, 11, 22, 31, 37, 48, 57, 63, and 74) and a VL CDR3 (SEQ ID NOS: 6, 17, 23, 32, 43, 49, 58, 69, and 75); a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73) and a VL CDR2 (SEQ ID NOS: 5, 11, 22, 31, 37, 48, 57, 63, and 74); a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73) and a VL CDR3 (SEQ ID NOS: 6, 17, 23, 32, 43, 49, 58, 69, and 75); a VH CDR3 (SEQ ID NOS: 3, 9, 15, 20, 29, 35, 41, 46, 55, 61, 67, and 72), a VL CDR2 (SEQ ID NOS: 5, 11, 22, 31, 37, 48, 57, 63, and 74) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72) and a VL CDR1 (SEQ ID NOS: 4, 10, 16, 21, 30, 36, 42, 47, 56, 62, 68, and 73); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72) and a VL CDR2 (SEQ ID NOS: 5, 11, 22, 31, 37, 48, 57, 63, and 74); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VL CDR1 (SEQ ID NOS: 4, 10, 16, 21, 30, 36, 42, 47, 56, 62, 68, and 73) and a VL CDR2 (SEQ ID NOS: 5, 11, 22, 31, 37, 48, 57, 63, and 74); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VL CDR1 (SEQ ID NOS: 4, 10, 16, 21, 30, 36, 42, 47, 56, 62, 68, and 73) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VL CDR2 (SEQ ID NOS: 5, 11, 22, 31, 37, 48, 57, 63, and 74) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73) and a VL CDR2 (SEQ ID NOS: 5, 11, 22, 31, 37, 48, 57, 63, and 74); a VH CDR1 (SEQ ID NOS: 1, 7, 12, 13, 18, 27, 33, 38, 39, 44, 53, 59, 64, 65, and 70), a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR3 (SEQ ID NOS: 3, 9, 15, 20, 29, 35, 41, 46, 55, 61, 67, and 72), a VL CDR2 (SEQ ID NOS: 5, 11, 22, 31, 37, 48, 57, 63, and 74) and a VL CDR3 (SEQ ID NOS: 6, 17, 23, 32, 43, 49, 58, 69, and 75); a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73) and a VL CDR2 (SEQ ID NOS: 5, 11, 22, 31, 37, 48, 57, 63, and 74); a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73) and a VL CDR3 (SEQ ID NOS: 6, 17, 23, 32, 43, 49, 58, 69, and 75); a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72), a VL CDR2 (SEQ ID NOS: 5, 11, 22, 31, 37, 48, 57, 63, and 74) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73) and a VL CDR2 (SEQ ID NOS: 5, 11, 22, 31, 37, 48, 57, 63, and 74); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72), a VL CDR2 (SEQ ID NOS: 5, 11, 22, 31, 37, 48, 57, 63, and 74) and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR2 (SEQ ID NOS: 2, 8, 14, 19, 24, 28, 34, 40, 45, 50, 54, 60, 66, 71, and 76), a VL CDR1 (SEQ ID NOS: 4, 10, 16, 21, 30, 36, 42, 47, 56, 62, 68, and 73), a VL CDR2 (SEQ ID NOS: 5, 11, 22, 31, 37, 48, 57, 63, and 74), and a VL CDR3 (SEQ ID NOS: 6, 17, 23, 32, 43, 49, 58, 69, and 75); a VH CDR1 (SEQ ID NOS: 1, 7, 12, 13, 18, 27, 33, 38, 39, 44, 53, 59, 64, 65, and 70), a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73), a VL CDR2 (SEQ ID NOS: 5, 11, 22, 31, 37, 48, 57, 63, and 74), and a VL CDR3 (SEQ ID NOS: 6, 17, 23, 32, 43, 49, 58, 69, and 75); a VH CDR2 (SEQ ID NOS: 2, 8, 14, 19, 24, 28, 34, 40, 45, 50, 54, 60, 66, 71, and 76), a VH CDR3 (SEQ ID NOS: 3, 9, 15, 20, 29, 35, 41, 46, 55, 61, 67, and 72), a VL CDR1 (SEQ ID NOS: 4, 10, 16, 21, 30, 36, 42, 47, 56, 62, 68, and 73), a VL CDR2 (SEQ ID NOS: 5, 11, 22, 31, 37, 48, 57, 63, and 74), and a VL CDR3 (SEQ ID NOS: 6, 17, 23, 32, 43, 49, 58, 69, and 75); or any combination thereof of the VH CDRs (SEQ ID NOS: 1, 7, 12, 13, 18, 27, 33, 38, 39, 44, 53, 59, 64, 65, 70, 2, 8, 14, 19, 24, 28, 34, 40, 45, 50, 54, 60, 66, 71, 76, 3, 9, 15, 20, 29, 35, 41, 46, 55, 61, 67, and 72) and VL CDRs (SEQ ID NOS: 4, 10, 16, 21, 30, 36, 42, 47, 56, 62, 68, 73, 5, 11, 22, 31, 37, 48, 57, 63, 74, 6, 17, 23, 32, 43, 49, 58, 69, and 75) listed in Tables 1-3.

Also described herein are multispecific binding agents (e.g., antibodies) comprising a second binding domain that binds to PD-L1 and comprises one or more (e.g., one, two or three) VH CDRs and one or more (e.g., one, two or three) VL CDRs listed in Tables 4-6. In particular, described herein is a multispecific binding agent (e.g., an antibody) comprising: a VH CDR1 (SEQ ID NOS: 79, 85, 90, 91, 96, 105, 11, 116, 117, 122, 131, 137, 142, 143, or 148) and a VL CDR1 (SEQ ID NOS: 82, 88, 94, 99, 108, 114, 120, 125, 134, 140, 146, or 151); a VH CDR1 (SEQ ID NOS: 79, 85, 90, 91, 96, 105, 11, 116, 117, 122, 131, 137, 142, 143, or 148) and a VL CDR2 (SEQ ID NOS: 83, 89, 100, 109, 115, 126, 135, 141, or 152); a VH CDR1 (SEQ ID NOS: 79, 85, 90, 91, 96, 105, 11, 116, 117, 122, 131, 137, 142, 143, or 148) and a VL CDR3 (SEQ ID NOS: 84, 95, 101, 110, 121, 127, 136, 147, or 153); a VH CDR2 (SEQ ID NOS: 80, 86, 92, 97, 102, 106, 112, 118, 123, 128, 132, 138, 144, 149, or 154) and a VL CDR1 (SEQ ID NOS: 82, 88, 94, 99, 108, 114, 120, 125, 134, 140, 146, or 151); a VH CDR2 (SEQ ID NOS: 80, 86, 92, 97, 102, 106, 112, 118, 123, 128, 132, 138, 144, 149, or 154) and a VL CDR2 (SEQ ID NOS: 83, 89, 100, 109, 115, 126, 135, 141, or 152); a VH CDR2 (SEQ ID NOS: 80, 86, 92, 97, 102, 106, 112, 118, 123, 128, 132, 138, 144, 149, or 154) and a VL CDR3 (SEQ ID NOS: 84, 95, 101, 110, 121, 127, 136, 147, or 153); a VH CDR3 (SEQ ID NOS: 81, 87, 93, 98, 107, 113, 119, 124, 133, 139, 145, or 150) and a VL CDR1 (SEQ ID NOS: 82, 88, 94, 99, 108, 114, 120, 125, 134, 140, 146, or 151); a VH CDR3 (SEQ ID NOS: 81, 87, 93, 98, 107, 113, 119, 124, 133, 139, 145, or 150) and a VL CDR2 (SEQ ID NOS: 83, 89, 100, 109, 115, 126, 135, 141, or 152); a VH CDR3 (SEQ ID NOS: 81, 87, 93, 98, 107, 113, 119, 124, 133, 139, 145, or 150) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154) and a VL CDR1 (SEQ ID NOS: 82, 88, 94, 99, 108, 114, 120, 125, 134, 140, 146, or 151); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154) and a VL CDR2 (SEQ ID NOS: 83, 89, 100, 109, 115, 126, 135, 141, or 152); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154) and a VL CDR3 (SEQ ID NOS: 84, 95, 101, 110, 121, 127, 136, 147, or 153); a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150) and a VL CDR1 (SEQ ID NOS: 82, 88, 94, 99, 108, 114, 120, 125, 134, 140, 146, or 151), a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150) and a VL CDR2 (SEQ ID NOS: 83, 89, 100, 109, 115, 126, 135, 141, or 152); a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VL CDR1 (SEQ ID NOS: 82, 88, 94, 99, 108, 114, 120, 125, 134, 140, 146, or 151) and a VL CDR2 (SEQ ID NOS: 83, 89, 100, 109, 115, 126, 135, 141, or 152); a VH CDR1 (SEQ ID NOS: 79, 85, 90, 91, 96, 105, 11, 116, 117, 122, 131, 137, 142, 143, or 148), a VL CDR1 (SEQ ID NOS: 82, 88, 94, 99, 108, 114, 120, 125, 134, 140, 146, or 151) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VL CDR2 (SEQ ID NOS: 83, 89, 100, 109, 115, 126, 135, 141, or 152) and a VL CDR3 (SEQ ID NOS: 84, 95, 101, 110, 121, 127, 136, 147, or 153); a VH CDR2 (SEQ ID NOS: 80, 86, 92, 97, 102, 106, 112, 118, 123, 128, 132, 138, 144, 149, or 154), a VL CDR1 (SEQ ID NOS: 82, 88, 94, 99, 108, 114, 120, 125, 134, 140, 146, or 151) and a VL CDR2 (SEQ ID NOS: 83, 89, 100, 109, 115, 126, 135, 141, or 152); a VH CDR2 (SEQ ID NOS: 80, 86, 92, 97, 102, 106, 112, 118, 123, 128, 132, 138, 144, 149, or 154), a VL CDR1 (SEQ ID NOS: 82, 88, 94, 99, 108, 114, 120, 125, 134, 140, 146, or 151) and a VL CDR3 (SEQ ID NOS: 84, 95, 101, 110, 121, 127, 136, 147, or 153); a VH CDR2 (SEQ ID NOS: 80, 86, 92, 97, 102, 106, 112, 118, 123, 128, 132, 138, 144, 149, or 154), a VL CDR2 (SEQ ID NOS: 83, 89, 100, 109, 115, 126, 135, 141, or 152) and a VL CDR3 (SEQ ID NOS: 84, 95, 101, 110, 121, 127, 136, 147, or 153); a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151) and a VL CDR2 (SEQ ID NOS: 83, 89, 100, 109, 115, 126, 135, 141, or 152); a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151) and a VL CDR3 (SEQ ID NOS: 84, 95, 101, 110, 121, 127, 136, 147, or 153); a VH CDR3 (SEQ ID NOS: 81, 87, 93, 98, 107, 113, 119, 124, 133, 139, 145, or 150), a VL CDR2 (SEQ ID NOS: 83, 89, 100, 109, 115, 126, 135, 141, or 152) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150) and a VL CDR1 (SEQ ID NOS: 82, 88, 94, 99, 108, 114, 120, 125, 134, 140, 146, or 151); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150) and a VL CDR2 (SEQ ID NOS: 83, 89, 100, 109, 115, 126, 135, 141, or 152); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VL CDR1 (SEQ ID NOS: 82, 88, 94, 99, 108, 114, 120, 125, 134, 140, 146, or 151) and a VL CDR2 (SEQ ID NOS: 83, 89, 100, 109, 115, 126, 135, 141, or 152); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VL CDR1 (SEQ ID NOS: 82, 88, 94, 99, 108, 114, 120, 125, 134, 140, 146, or 151) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VL CDR2 (SEQ ID NOS: 83, 89, 100, 109, 115, 126, 135, 141, or 152) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151) and a VL CDR2 (SEQ ID NOS: 83, 89, 100, 109, 115, 126, 135, 141, or 152); a VH CDR1 (SEQ ID NOS: 79, 85, 90, 91, 96, 105, 11, 116, 117, 122, 131, 137, 142, 143, or 148), a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR3 (SEQ ID NOS: 81, 87, 93, 98, 107, 113, 119, 124, 133, 139, 145, or 150), a VL CDR2 (SEQ ID NOS: 83, 89, 100, 109, 115, 126, 135, 141, or 152) and a VL CDR3 (SEQ ID NOS: 84, 95, 101, 110, 121, 127, 136, 147, or 153); a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151) and a VL CDR2 (SEQ ID NOS: 83, 89, 100, 109, 115, 126, 135, 141, or 152); a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151) and a VL CDR3 (SEQ ID NOS: 84, 95, 101, 110, 121, 127, 136, 147, or 153); a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150), a VL CDR2 (SEQ ID NOS: 83, 89, 100, 109, 115, 126, 135, 141, or 152) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151) and a VL CDR2 (SEQ ID NOS: 83, 89, 100, 109, 115, 126, 135, 141, or 152); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150), a VL CDR2 (SEQ ID NOS: 83, 89, 100, 109, 115, 126, 135, 141, or 152) and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR2 (SEQ ID NOS: 80, 86, 92, 97, 102, 106, 112, 118, 123, 128, 132, 138, 144, 149, or 154), a VL CDR1 (SEQ ID NOS: 82, 88, 94, 99, 108, 114, 120, 125, 134, 140, 146, or 151), a VL CDR2 (SEQ ID NOS: 83, 89, 100, 109, 115, 126, 135, 141, or 152), and a VL CDR3 (SEQ ID NOS: 84, 95, 101, 110, 121, 127, 136, 147, or 153); a VH CDR1 (SEQ ID NOS: 79, 85, 90, 91, 96, 105, 11, 116, 117, 122, 131, 137, 142, 143, or 148), a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151), a VL CDR2 (SEQ ID NOS: 83, 89, 100, 109, 115, 126, 135, 141, or 152), and a VL CDR3 (SEQ ID NOS: 84, 95, 101, 110, 121, 127, 136, 147, or 153); a VH CDR2 (SEQ ID NOS: 80, 86, 92, 97, 102, 106, 112, 118, 123, 128, 132, 138, 144, 149, or 154), a VH CDR3 (SEQ ID NOS: 81, 87, 93, 98, 107, 113, 119, 124, 133, 139, 145, or 150), a VL CDR1 (SEQ ID NOS: 82, 88, 94, 99, 108, 114, 120, 125, 134, 140, 146, or 151), a VL CDR2 (SEQ ID NOS: 83, 89, 100, 109, 115, 126, 135, 141, or 152), and a VL CDR3 (SEQ ID NOS: 84, 95, 101, 110, 121, 127, 136, 147, or 153); or any combination thereof of the VH CDRs (SEQ ID NOS: 79, 85, 90, 91, 96, 105, 11, 116, 117, 122, 131, 137, 142, 143,148, 80, 86, 92, 97, 102, 106, 112, 118, 123, 128, 132, 138,144, 149, 154, 81, 87, 93, 98, 107, 113, 119, 124, 133, 139, 145, or 150) and VL CDRs (SEQ ID NOS: 82, 88, 94, 99, 108, 114, 120, 125, 134, 140, 146, 151, 83, 89, 100, 109, 115, 126, 135, 141,152, 84, 95, 101, 110, 121, 127, 136, 147, or 153) listed in Tables 4-6.

In some embodiments, described herein is a multispecific antibody or fragment thereof with a first binding domain that binds to CD47, wherein the first binding domain comprises:

(a) a heavy chain variable ($V_H$) region comprising: (1) a $V_H$ CDR1 having an amino acid sequence selected from the group consisting of: (i) SEQ ID NO:1, 27, or 53, (ii) SEQ ID NO:7, 33, or 59, (iii) SEQ ID NO:12, 38, or 64, (iv) SEQ ID NO:13, 39, or 65, and (v) SEQ ID NO:18, 44, or 70; (2) a $V_H$ CDR2 having an amino acid sequence selected from the group consisting of: (i) SEQ ID NO:2, 28, or 54, (ii) SEQ ID NO:8, 34, or 60, (iii) SEQ ID NO:14, 40, or 66, (iv) SEQ ID NO:19, 45, or 71, and (v) SEQ ID NO:24, 50, or 76; and (3) a $V_H$ CDR3 having an amino acid sequence selected from the group consisting of: (i) SEQ ID NO:3, 29, or 55, (ii) SEQ ID NO:9, 35, or 61, (iii) SEQ ID NO:15, 41, or 67, and (iv) SEQ ID NO:20, 46, or 72; and (b) a light chain variable ($V_L$) region comprising: (1) a $V_L$ CDR1 having an amino acid sequence selected from the group consisting of: (i) SEQ ID NO:4, 30, or 56, (ii) SEQ ID NO:10, 36, or 62, (iii) SEQ ID NO:16, 42, or 68, and (iv) SEQ ID NO:21, 47, or 73; (2) a $V_L$ CDR2 having an amino acid sequence selected from the group consisting of: (i) SEQ ID NO:5, 31, or 57, (ii) SEQ ID NO:11, 37, or 63, and (iii) SEQ ID NO:22, 48, or 74; and (3) a $V_L$ CDR3 having an amino acid sequence selected from the group consisting of: (i) SEQ ID NO:6, 32, or 58, (ii) SEQ ID NO:17, 43, or 69, and (iii) SEQ ID NO:23, 49, or 75. In some embodiments, the multispecific antibody comprises a second binding domain that binds to PD-L1. In some embodiments, the multispecific antibody or fragment is a bispecific antibody. In some embodiments, the second binding domain comprises: (a) a heavy chain variable ($V_H$) region comprising: (1) a $V_H$ CDR1 having an amino acid sequence selected from the group consisting of: (i) SEQ ID NO:79, 105, or 131, (ii) SEQ ID NO:85, 111, or 137, (iii) SEQ ID NO:90, 116, or 142, (iv) SEQ ID NO:91, 117, or 143, and (v) SEQ ID NO:96, 122, or 148; (2) a $V_H$ CDR2 having an amino acid sequence selected from the group consisting of: (i) SEQ ID NO:80, 106, or 132, (ii) SEQ ID NO:86, 112, or 138, (iii) SEQ ID NO:92, 118, or 144, (iv) SEQ ID NO:97, 123, or 149, and (v) SEQ ID NO:102, 128, or 159; and (3) a $V_H$ CDR3 having an amino acid sequence selected from the group consisting of: (i) SEQ ID NO:81, 107, or 133, (ii) SEQ ID NO:87, 113, or 139, (iii) SEQ ID NO:93, 119, or 145, (iv) SEQ ID NO:98, 124, or 150; and (b) a light chain variable ($V_L$) region comprising: (1) a $V_L$ CDR1 having an amino acid sequence selected from the group consisting of: (i) SEQ ID NO:82, 108, or 134, (ii) SEQ ID NO:88, 114, or 140, (iii) SEQ ID NO:94, 120, or 146, and (iv) SEQ ID NO:99, 125, or 151; (2) a $V_L$ CDR2 having an amino acid sequence selected from the group consisting of: (i) SEQ ID NO:83, 109, or 135, (ii) SEQ ID NO:89, 115, or 141, and (iii) SEQ ID NO:100, 126, or 152; and (3) a $V_L$ CDR3 having an amino acid sequence selected from the group consisting of: (i) SEQ ID NO:84, 110, or 136, (ii) SEQ ID NO:95, 121, or 147, (iii) SEQ ID NO:101, 127, or 153. In some embodiments, described herein is a multispecific antibody or fragment thereof with a first binding domain that binds to CD47, wherein the first binding domain comprises a heavy chain variable ($V_H$) region comprising: (1) a $V_H$ CDR1 having an amino acid sequence selected from the group consisting of: (i) SEQ ID NO:1, 27, or 53, (ii) SEQ ID NO:7, 33, or 59, (iii) SEQ ID NO:12, 38, or 64, (iv) SEQ ID NO:13, 39, or 65, and (v) SEQ ID NO:18, 44, or 70; (2) a $V_H$ CDR2 having an amino acid sequence selected from the group consisting of: (i) SEQ ID NO:2, 28, or 54, (ii) SEQ ID NO:8, 34, or 60, (iii) SEQ ID NO:14, 40, or 66, (iv) SEQ ID NO:19, 45, or 71, and (v) SEQ ID NO:24, 50, or 76; and (3) a $V_H$ CDR3 having an amino acid sequence selected from the group consisting of: (i) SEQ ID NO:3, 29, or 55, (ii) SEQ ID NO:9, 35, or 61, (iii) SEQ ID NO:15, 41, or 67, and (iv)

SEQ ID NO:20, 46, or 72. In some embodiments, the multispecific antibody comprises a second binding domain that binds to PD-L1. In some embodiments, the multispecific antibody or fragment thereof of is a bispecific antibody. In some embodiments, the second binding domain comprises: (a) a heavy chain variable ($V_H$) region comprising: (1) a $V_H$ CDR1 having an amino acid sequence selected from the group consisting of: (i) SEQ ID NO:79, 105, or 131, (ii) SEQ ID NO:85, 111, or 137, (iii) SEQ ID NO:90, 116, or 142, (iv) SEQ ID NO:91, 117, or 143, and (v) SEQ ID NO:96, 122, or 148; (2) a $V_H$ CDR2 having an amino acid sequence selected from the group consisting of: (i) SEQ ID NO:80, 106, or 132, (ii) SEQ ID NO:86, 112, or 138, (iii) SEQ ID NO:92, 118, or 144, (iv) SEQ ID NO:97, 123, or 149, and (v) SEQ ID NO:102, 128, or 159; and (3) a $V_H$ CDR3 having an amino acid sequence selected from the group consisting of: (i) SEQ ID NO:81, 107, or 133, (ii) SEQ ID NO:87, 113, or 139, (iii) SEQ ID NO:93, 119, or 145, and (iv) SEQ ID NO:98, 124, or 150.

In some embodiments, described herein is a multispecific antibody or fragment thereof with a first binding domain that binds to CD47, wherein the first binding domain comprises a light chain variable ($V_L$) region comprising: (1) a $V_L$ CDR1 having an amino acid sequence selected from the group consisting of: (i) SEQ ID NO:4, 30, or 56, (ii) SEQ ID NO:10, 36, or 62, (iii) SEQ ID NO:16, 42, or 68, and (iv) SEQ ID NO:21, 47, or 73; (2) a $V_L$ CDR2 having an amino acid sequence selected from the group consisting of: (i) SEQ ID NO:5, 31, or 57, (ii) SEQ ID NO:11, 37, or 63, and (iii) SEQ ID NO:22, 48, or 74; (3) a $V_L$ CDR3 having an amino acid sequence selected from the group consisting of: (i) SEQ ID NO:6, 32, or 58, (ii) SEQ ID NO:17, 43, or 69, and (iii) SEQ ID NO:23, 49, or 75. In some embodiments, the multispecific antibody comprises a second binding domain that binds to PD-L1. In some embodiments, the multispecific antibody or fragment thereof is a bispecific antibody. In some embodiments, the second binding domain comprises: (a) a light chain variable ($V_L$) region comprising: (1) a $V_L$ CDR1 having an amino acid sequence selected from the group consisting of: (i) SEQ ID NO:82, 108, or 134, (ii) SEQ ID NO:88, 114, or 140, (iii) SEQ ID NO:94, 120, or 146, and (iv) SEQ ID NO:99, 125, or 151; (2) a $V_L$ CDR2 having an amino acid sequence selected from the group consisting of: (i) SEQ ID NO:83, 109, or 135, (ii) SEQ ID NO:89, 115, or 141, and (iii) SEQ ID NO:100, 126, or 152; and (3) a $V_L$ CDR3 having an amino acid sequence selected from the group consisting of: (i) SEQ ID NO:84, 110, or 136, (ii) SEQ ID NO:95, 121, or 147, (iii) SEQ ID NO:101, 127, or 153.

In some embodiments, described herein is a multispecific antibody or fragment thereof with a first binding domain that binds to CD47, wherein the first binding domain comprises all three heavy chain complementarity determining regions (CDRs) or all three light chain CDRs from: the antibody designated C40 that comprises a VH sequence that is SEQ ID NO:25 and a VL sequence that is SEQ ID NO:26; the antibody designated C56 that comprises a VH sequence that is SEQ ID NO:51 and a VL sequence that is SEQ ID NO:52; or the antibody designated C59 that comprises a VH sequence that is SEQ ID NO:77 and a VL sequence that is SEQ ID NO:78. In some embodiments, the multispecific antibody comprises a second binding domain that binds to PD-L1. In some embodiments, the multispecific antibody is a bispecific antibody. In some embodiments, the second binding domain comprises all three heavy chain complementarity determining regions (CDRs) or all three light chain CDRs from: the antibody designated P22 that comprises a VH sequence that is SEQ ID NO:103 and a VL sequence that is SEQ ID NO:104; the antibody designated P24 that comprises a VH sequence that is SEQ ID NO:129 and a VL sequence that is SEQ ID NO:130; or the antibody designated P31.2 that comprises a VH sequence that is SEQ ID NO:155 and a VL sequence that is SEQ ID NO:156.

In some embodiments, described herein is a multispecific antibody or fragment thereof with a first binding domain that binds to CD47, wherein the first binding domain comprises all three heavy chain CDRs and/or all three light chain CDRs from the antibody designated C40. In some embodiments, the multispecific antibody comprises a second binding domain that binds to PD-L1. In some embodiments, the multispecific antibody or fragment thereof of is a bispecific antibody. In some embodiments, the second binding domain comprises all three heavy chain CDRs and all three light chain CDRs from the antibody designated P22. In some embodiments, the second binding domain comprises all three heavy chain CDRs and all three light chain CDRs from the antibody designated P24. In some embodiments, the second binding domain comprises all three heavy chain CDRs and all three light chain CDRs from the antibody designated P31.2.

In some embodiments, described herein is a multispecific antibody or fragment thereof with a first binding domain that binds to CD47, wherein the first binding domain comprises all three heavy chain CDRs and all three light chain CDRs from the antibody designated C56. In some embodiments, the multispecific antibody comprises a second binding domain that binds to PD-L1. In some embodiments, the multispecific antibody or fragment thereof is a bispecific antibody. In some embodiments, the second binding domain comprises all three heavy chain CDRs and all three light chain CDRs from the antibody designated P22. In some embodiments, the second binding domain comprises all three heavy chain CDRs and all three light chain CDRs from the antibody designated P24. In some embodiments, the second binding domain comprises all three heavy chain CDRs and all three light chain CDRs from the antibody designated P31.2.

In some embodiments, described herein is a multispecific antibody or fragment thereof with a first binding domain that binds to CD47, wherein the first binding domain comprises all three heavy chain CDRs and all three light chain CDRs from the antibody designated C59. In some embodiments, the multispecific antibody comprises a second binding domain that binds to PD-L1. In some embodiments, the multispecific antibody or fragment thereof is a bispecific antibody. In some embodiments, the second binding domain comprises all three heavy chain CDRs and all three light chain CDRs from the antibody designated P22. In some embodiments, the second binding domain comprises all three heavy chain CDRs and all three light chain CDRs from the antibody designated P24. In some embodiments, the second binding domain comprises all three heavy chain CDRs and all three light chain CDRs from the antibody designated P31.2.

In some embodiments, described herein is a multispecific antibody or fragment thereof with a first binding domain that binds to CD47, wherein the first binding domain comprises: (a) a heavy chain variable ($V_H$) region comprising a $V_H$ CDR1, a $V_H$ CDR2, and a $V_H$ CDR3 amino acid sequence depicted in Tables 1-3; or (b) a light chain variable ($V_L$) region comprising a $V_L$ CDR1, a $V_L$ CDR2, and a $V_L$ CDR3 amino acid sequence depicted in Tables 1-3. In some embodiments, the first binding domain comprises: (a) a heavy chain variable ($V_H$) region comprising a $V_H$ CDR1, a $V_H$ CDR2, and a $V_H$ CDR3 amino acid sequence depicted in Tables 1-3; and (b) a light chain variable ($V_L$) region comprising a $V_L$ CDR1, a $V_L$ CDR2, and a $V_L$ CDR3 amino acid sequence depicted in Tables 1-3. In some embodiments, the multispecific antibody comprises a second binding domain that binds to PD-L1. In some embodiments, the multispecific antibody or fragment thereof is a bispecific antibody. In some embodiments, the second binding domain comprises: (a) a heavy chain variable ($V_H$) region comprising a $V_H$ CDR1, a $V_H$ CDR2, and a $V_H$ CDR3 amino acid sequence depicted in Tables 4-6; and/or (b) a light chain variable ($V_L$) region comprising a $V_L$ CDR1, a $V_L$ CDR2, and a $V_L$ CDR3 amino acid sequence depicted in Tables 4-6. In some embodiments, the first binding domain comprises a heavy chain variable ($V_H$) region comprising a $V_H$ CDR1, a $V_H$ CDR2, and a $V_H$ CDR3 amino acid sequence depicted in Tables 1-3. In some embodiments, the multispecific antibody comprises a second binding domain that binds to PD-L1. In some embodiments, the multispecific antibody or fragment thereof is a bispecific antibody. In some embodiments, the second binding domain comprises a heavy chain variable ($V_H$) region comprising a $V_H$ CDR1, a $V_H$ CDR2, and a $V_H$ CDR3 amino acid sequence depicted in Tables 4-6. In some embodiments, the first binding domain comprises a light chain variable ($V_L$) region comprising a $V_L$ CDR1, a $V_L$ CDR2, and a $V_L$ CDR3 amino acid sequence depicted in Tables 1-3. In some embodiments, the multispecific antibody comprises a second binding domain that binds to PD-L1. In some embodiments, the multispecific antibody or fragment thereof is a bispecific antibody. In some embodiments, the second binding domain comprises a light chain variable ($V_L$) region comprising a $V_L$ CDR1, a $V_L$ CDR2, and a $V_L$ CDR3 amino acid sequence depicted in Tables 4-6

In some embodiments, described herein is a multispecific antibody or fragment thereof with a first binding domain that binds to CD47, wherein the first binding domain comprises: (a) a heavy chain variable ($V_H$) region comprising: (1) a $V_H$ CDR1 having an amino acid sequence selected from the group consisting of SEQ ID NO:1, 7, 12, 13, and 18; (2) a $V_H$ CDR2 having an amino acid sequence selected from the group consisting of SEQ ID NO:2, 8, 14, 19 and 24; and (3) a $V_H$ CDR3 having an amino acid sequence selected from the group consisting of SEQ ID NO:3, 9, 15 and 20; and (b) a light chain variable ($V_L$) region comprising: (1) a $V_L$ CDR1 having an amino acid sequence selected from the group consisting of SEQ ID NO:4, 10, 16 and 21; (2) a $V_L$ CDR2 having an amino acid sequence selected from the group consisting of SEQ ID NO:5, 11, and 22; and (3) a $V_L$ CDR3 having an amino acid sequence selected from the group consisting of SEQ ID NO:6, 17, and 23. In some embodiments, the multispecific antibody comprises a second binding domain that binds to PD-L1. In some embodiments, the first binding domain comprises: (a) a heavy chain variable ($V_H$) region comprising: (1) a $V_H$ CDR1 having the amino acid sequence of SEQ ID NO:1; (2) a $V_H$ CDR2 having the amino acid sequence of SEQ ID NO:2; and (3) a $V_H$ CDR3 having the amino acid sequence of SEQ ID NO:3; and (b) a light chain variable ($V_L$) region comprising: (1) a $V_L$ CDR1 having the amino acid sequence of SEQ ID NO:4; (2) a $V_L$ CDR2 having the amino acid sequence of SEQ ID NO:5; and (3) a $V_L$ CDR3 having the amino acid sequence of SEQ ID NO:6. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, wherein the first binding domain comprises: (a) a heavy chain variable ($V_H$) region comprising: (1) a $V_H$ CDR1 having the amino acid sequence of SEQ ID NO:7; (2) a $V_H$ CDR2 having the amino acid sequence of SEQ ID NO:8; and (3) a $V_H$ CDR3 having the amino acid sequence of SEQ ID NO:9; and (b) a light chain variable ($V_L$) region comprising: (1) a $V_L$ CDR1 having the amino acid sequence of SEQ ID NO:10; (2) a $V_L$ CDR2 having the amino acid sequence of SEQ ID NO:11; and (3) a $V_L$ CDR3 having the amino acid sequence of SEQ ID NO:6. In some embodiments, the second binding domain comprises: (a) a heavy chain variable ($V_H$) region comprising: (1) a $V_H$ CDR1 having the amino acid sequence of SEQ ID NO:85; (2) a $V_H$ CDR2 having the amino acid sequence of SEQ ID NO:86; and (3) a $V_H$ CDR3 having the amino acid sequence of SEQ ID NO:87; and (b) a light chain variable ($V_L$) region comprising: (1) a $V_L$ CDR1 having the amino acid sequence of SEQ ID NO:88; (2) a $V_L$ CDR2 having the amino acid sequence of SEQ ID NO:89; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:111; (2) a $V_H$ CDR2 having the amino acid sequence of SEQ ID NO:112; and (3) a $V_H$ CDR3 having the amino acid sequence of SEQ ID NO:113; and (b) a light chain variable ($V_L$) region comprising: (1) a $V_L$ CDR1 having the amino acid sequence of SEQ ID NO:114; (2) a $V_L$ CDR2 having the amino acid sequence of SEQ ID NO:115; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:137; (2) a $V_H$ CDR2 having the amino acid sequence of SEQ ID NO:138; and (3) a $V_H$ CDR3 having the amino acid sequence of SEQ ID NO:139; and (b) a light chain variable ($V_L$) region comprising: (1) a $V_L$ CDR1 having the amino acid sequence of SEQ ID NO:140; (2) a $V_L$ CDR2 having the amino acid sequence of SEQ ID NO:141; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:12; (2) a $V_H$ CDR2 having the amino acid sequence of SEQ ID NO:2; and (3) a $V_H$ CDR3 having the amino acid sequence of SEQ ID NO:3; and (b) a light chain variable ($V_L$) region comprising: (1) a $V_L$ CDR1 having the amino acid sequence of SEQ ID NO:4; (2) a $V_L$ CDR2 having the amino acid sequence of SEQ ID NO:5; and (3) a $V_L$ CDR3 having the amino acid sequence of SEQ ID NO:6. In some embodiments, the second binding domain comprises: (a) a heavy chain variable ($V_H$) region comprising: (1) a $V_H$ CDR1 having the amino acid sequence of SEQ ID NO:90; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:116; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:142; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, first binding domain comprises: (a) a heavy chain variable ($V_H$) region comprising: (1) a $V_H$ CDR1 having the amino acid sequence of SEQ ID NO:13; (2) a $V_H$ CDR2 having the amino acid sequence of SEQ ID NO:14; and (3) a $V_H$ CDR3 having the amino acid sequence of SEQ ID NO:15; and (b) a light chain variable ($V_L$) region comprising: (1) a $V_L$ CDR1 having the amino acid sequence of SEQ ID NO:16; (2) a $V_L$ CDR2 having the amino acid sequence of SEQ ID NO:11; and (3) a $V_L$ CDR3 having the amino acid sequence of SEQ ID NO:17. In some embodiments, the second binding domain comprises: (a) a heavy chain variable ($V_H$) region comprising: (1) a $V_H$ CDR1 having the amino acid sequence of SEQ ID NO:91; (2) a $V_H$ CDR2 having the amino acid sequence of SEQ ID NO:92; and (3) a $V_H$ CDR3 having the amino acid sequence of SEQ ID NO:93; and (b) a light chain variable ($V_L$) region comprising: (1) a $V_L$ CDR1 having the amino acid sequence of SEQ ID NO:94; (2) a $V_L$ CDR2 having the amino acid sequence of SEQ ID NO:89; and (3) a $V_L$ CDR3 having the amino acid sequence of SEQ ID NO:95. In some embodiments, the second binding domain comprises: (a) a heavy chain variable ($V_H$) region comprising: (1) a $V_H$ CDR1 having the amino acid sequence of SEQ ID NO:117; (2) a $V_H$ CDR2 having the amino acid sequence of SEQ ID NO:118; and (3) a $V_H$ CDR3 having the amino acid sequence of SEQ ID NO:119; and (b) a light chain variable ($V_L$) region comprising: (1) a $V_L$ CDR1 having the amino acid sequence of SEQ ID NO:120; (2) a $V_L$ CDR2 having the amino acid sequence of SEQ ID NO:115; and (3) a $V_L$ CDR3 having the amino acid sequence of SEQ ID NO:128. In some embodiments, the second binding domain comprises: (a) a heavy chain variable ($V_H$) region comprising: (1) a $V_H$ CDR1 having the amino acid sequence of SEQ ID NO:143; (2) a $V_H$ CDR2 having the amino acid sequence of SEQ ID NO:144; and (3) a $V_H$ CDR3 having the amino acid sequence of SEQ ID NO:145; and (b) a light chain variable ($V_L$) region comprising: (1) a $V_L$ CDR1 having the amino acid sequence of SEQ ID NO:146; (2) a $V_L$ CDR2 having the amino acid sequence of SEQ ID NO:141; and (3) a $V_L$ CDR3 having the amino acid sequence of SEQ ID NO:147. In some embodiments, first binding domain comprises: (a) a heavy chain variable ($V_H$) region comprising: (1) a $V_H$ CDR1 having the amino acid sequence of SEQ ID NO:18; (2) a $V_H$ CDR2 having the amino acid sequence of SEQ ID NO:19; and (3) a $V_H$ CDR3 having the amino acid sequence of SEQ ID NO:20; and (b) a light chain variable ($V_L$) region comprising: (1) a $V_L$ CDR1 having the amino acid sequence of SEQ ID NO:21; (2) a $V_L$ CDR2 having the amino acid sequence of SEQ ID NO:22; and (3) a $V_L$ CDR3 having the amino acid sequence of SEQ ID NO:23. In some embodiments, the second binding domain comprises: (a) a heavy chain variable ($V_H$) region comprising: (1) a $V_H$ CDR1 having the amino acid sequence of SEQ ID NO:96; (2) a $V_H$ CDR2 having the amino acid sequence of SEQ ID NO:97; and (3) a $V_H$ CDR3 having the amino acid sequence of SEQ ID NO:98; and (b) a light chain variable ($V_L$) region comprising: (1) a $V_L$ CDR1 having the amino acid sequence of SEQ ID NO:99; (2) a $V_L$ CDR2 having the amino acid sequence of SEQ ID NO:100; and (3) a $V_L$ CDR3 having the amino acid sequence of SEQ ID NO:101. In some embodiments, the second binding domain comprises: (a) a heavy chain variable ($V_H$) region comprising: (1) a $V_H$ CDR1 having the amino acid sequence of SEQ ID NO:122; (2) a $V_H$ CDR2 having the amino acid sequence of SEQ ID NO:123; and (3) a $V_H$ CDR3 having the amino acid sequence of SEQ ID NO:124; and (b) a light chain variable ($V_L$) region comprising: (1) a $V_L$ CDR1 having the amino acid sequence of SEQ ID NO:125; (2) a $V_L$ CDR2 having the amino acid sequence of SEQ ID NO:126; and (3) a $V_L$ CDR3 having the amino acid sequence of SEQ ID NO:127. In some embodiments, the second binding domain comprises: (a) a heavy chain variable ($V_H$) region comprising: (1) a $V_H$ CDR1 having the amino acid sequence of SEQ ID NO:148; (2) a $V_H$ CDR2 having the amino acid sequence of SEQ ID NO:149; and (3) a $V_H$ CDR3 having the amino acid sequence of SEQ ID NO:150; and (b) a light chain variable ($V_L$) region comprising: (1) a $V_L$ CDR1 having the amino acid sequence of SEQ ID NO:151; (2) a $V_L$ CDR2 having the amino acid sequence of SEQ ID NO:152; and (3) a $V_L$ CDR3 having the amino acid sequence of SEQ ID NO:153. In some embodiments, the first binding domain comprises: (a) a heavy chain variable ($V_H$) region comprising: (1) a $V_H$ CDR1 having the amino acid sequence of SEQ ID NO:1; (2) a $V_H$ CDR2 having the amino acid sequence of SEQ ID NO:24; and (3) a $V_H$ CDR3 having the amino acid sequence of SEQ ID NO:3; and (b) a light chain variable ($V_L$) region comprising: (1) a $V_L$ CDR1 having the amino acid sequence of SEQ ID NO:4; (2) a $V_L$ CDR2 having the amino acid sequence of SEQ ID NO:5; and (3) a $V_L$ CDR3 having the amino acid sequence of SEQ ID NO:6. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:102; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:128; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:154; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, a multispecific antibody or fragment thereof described above is a bispecific antibody.

In some embodiments, described herein is a multispecific antibody or fragment thereof with a first binding domain that binds to CD47, wherein the first binding domain comprises: (a) a heavy chain variable ($V_H$) region comprising: (1) a $V_H$ CDR1 having an amino acid sequence selected from the group consisting of SEQ ID NO:27, 33, 38, 39, and 44; (2) a $V_H$ CDR2 having an amino acid sequence selected from the group consisting of SEQ ID NO:28, 34, 40, 45, and 50; and (3) a $V_H$ CDR3 having an amino acid sequence selected from the group consisting of SEQ ID NO:29, 35, 41, and 46; and (b) a light chain variable ($V_L$) region comprising: (1) a $V_L$ CDR1 having an amino acid sequence selected from the group consisting of SEQ ID NO:30, 36, 42, and 47; (2) a $V_L$ CDR2 having an amino acid sequence selected from the group consisting of SEQ ID NO:31, 37, and 48 and (3) a $V_L$ CDR3 having an amino acid sequence selected from the group consisting of SEQ ID NO:32, 43, and 49. In some embodiments, the multispecific antibody comprises a second binding domain that binds to PD-L1. In some embodiments, the first binding domain comprises: (a) a heavy chain variable ($V_H$) region comprising: (1) a $V_H$ CDR1 having the amino acid sequence of SEQ ID NO:27; (2) a $V_H$ CDR2 having the amino acid sequence of SEQ ID NO:28; and (3) a $V_H$ CDR3 having the amino acid sequence of SEQ ID NO:29; and (b) a light chain variable ($V_L$) region comprising: (1) a $V_L$ CDR1 having the amino acid sequence of SEQ ID NO:30; (2) a $V_L$ CDR2 having the amino acid sequence of SEQ ID NO:31; and (3) a $V_L$ CDR3 having the amino acid sequence of SEQ ID NO:32. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: 1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:33; (2) a $V_H$ CDR2 having the amino acid sequence of SEQ ID NO:34; and (3) a $V_H$ CDR3 having the amino acid sequence of SEQ ID NO:35; and (b) a light chain variable ($V_L$) region comprising: (1) a $V_L$ CDR1 having the amino acid sequence of SEQ ID NO:36; (2) a $V_L$ CDR2 having the amino acid sequence of SEQ ID NO:37; and (3) a $V_L$ CDR3 having the amino acid sequence of SEQ ID NO:32. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:38; (2) a $V_H$ CDR2 having the amino acid sequence of SEQ ID NO:28; and (3) a $V_H$ CDR3 having the amino acid sequence of SEQ ID NO:29; and (b) a light chain variable ($V_L$) region comprising: (1) a $V_L$ CDR1 having the amino acid sequence of SEQ ID NO:30; (2) a $V_L$ CDR2 having the amino acid sequence of SEQ ID NO:31; and (3) a $V_L$ CDR3 having the amino acid sequence of SEQ ID NO:32. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:39; (2) a $V_H$ CDR2 having the amino acid sequence of SEQ ID NO:40; and (3) a $V_H$ CDR3 having the amino acid sequence of SEQ ID NO:41; and (b) a light chain variable ($V_L$) region comprising: (1) a $V_L$ CDR1 having the amino acid sequence of SEQ ID NO:42; (2) a $V_L$ CDR2 having the amino acid sequence of SEQ ID NO:37; and (3) a $V_L$ CDR3 having the amino acid sequence of SEQ ID NO:43. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:44; (2) a $V_H$ CDR2 having the amino acid sequence of SEQ ID NO:45; and (3) a $V_H$ CDR3 having the amino acid sequence of SEQ ID NO:46; and (b) a light chain variable ($V_L$) region comprising: (1) a $V_L$ CDR1 having the amino acid sequence of SEQ ID NO:47; (2) a $V_L$ CDR2 having the amino acid sequence of SEQ ID NO:48; and (3) a $V_L$ CDR3 having the amino acid sequence of SEQ ID NO:49. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:27; (2) a $V_H$ CDR2 having the amino acid sequence of SEQ ID NO:50; and (3) a $V_H$ CDR3 having the amino acid sequence of SEQ ID NO:29; and (b) a light chain variable ($V_L$) region comprising: (1) a $V_L$ CDR1 having the amino acid sequence of SEQ ID NO:30; (2) a $V_L$ CDR2 having the amino acid sequence of SEQ ID NO:31; and (3) a $V_L$ CDR3 having the amino acid sequence of SEQ ID NO:32. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, a multispecific antibody or fragment thereof described above is a bispecific antibody.

In some embodiments, described herein is a multispecific antibody or fragment thereof with a first binding domain that binds to CD47, wherein the first binding domain comprises: (a) a heavy chain variable ($V_H$) region comprising: (1) a $V_H$ CDR1 having an amino acid sequence selected from the group consisting of SEQ ID NO:53, 59, 64, 65, and 70; (2) a $V_H$ CDR2 having an amino acid sequence selected from the group consisting of SEQ ID NO:54, 60, 66, 71, and 76; and (3) a $V_H$ CDR3 having an amino acid sequence selected from the group consisting of SEQ ID NO:55, 61, 67, and 72; and (b) a light chain variable ($V_L$) region comprising: (1) a $V_L$ CDR1 having an amino acid sequence selected from the group consisting of SEQ ID NO:56, 62, 68, and 73; (2) a $V_L$ CDR2 having an amino acid sequence selected from the group consisting of SEQ ID NO:57, 63, and 74; and (3) a $V_L$ CDR3 having an amino acid sequence selected from the group consisting of SEQ ID NO:58, 69, and 75. In some embodiments, the multispecific antibody comprises a second binding domain that binds to PD-L1. In some embodiments, the first binding domain comprises: (a) a heavy chain variable ($V_H$) region comprising: (1) a $V_H$ CDR1 having the amino acid sequence of SEQ ID NO:53; (2) a $V_H$ CDR2 having the amino acid sequence of SEQ ID NO:54; and (3) a $V_H$ CDR3 having the amino acid sequence of SEQ ID NO:55; and (b) a light chain variable ($V_L$) region comprising: (1) a $V_L$ CDR1 having the amino acid sequence of SEQ ID NO:56; (2) a $V_L$ CDR2 having the amino acid sequence of SEQ ID NO:57; and (3) a $V_L$ CDR3 having the amino acid sequence of SEQ ID NO:58. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:59; (2) a $V_H$ CDR2 having the amino acid sequence of SEQ ID NO:60; and (3) a $V_H$ CDR3 having the amino acid sequence of SEQ ID NO:61; and (b) a light chain variable ($V_L$) region comprising: (1) a $V_L$ CDR1 having the amino acid sequence of SEQ ID NO:62; (2) a $V_L$ CDR2 having the amino acid sequence of SEQ ID NO:63; and (3) a $V_L$ CDR3 having the amino acid sequence of SEQ ID NO:58. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, first binding domain comprises: (a) a heavy chain variable ($V_H$) region comprising: (1) a $V_H$ CDR1 having the amino acid sequence of SEQ ID NO:64; (2) a $V_H$ CDR2 having the amino acid sequence of SEQ ID NO:54; and (3) a $V_H$ CDR3 having the amino acid sequence of SEQ ID NO:55; and (b) a light chain variable ($V_L$) region comprising: (1) a $V_L$ CDR1 having the amino acid sequence of SEQ ID NO:56; (2) a $V_L$ CDR2 having the amino acid sequence of SEQ ID NO:57; and (3) a $V_L$ CDR3 having the amino acid sequence of SEQ ID NO:58. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:65; (2) a $V_H$ CDR2 having the amino acid sequence of SEQ ID NO:66; and (3) a $V_H$ CDR3 having the amino acid sequence of SEQ ID NO:67; and (b) a light chain variable ($V_L$) region comprising: (1) a $V_L$ CDR1 having the amino acid sequence of SEQ ID NO:68; (2) a $V_L$ CDR2 having the amino acid sequence of SEQ ID NO:63; and (3) a $V_L$ CDR3 having the amino acid sequence of SEQ ID NO:69. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, the first binding domain comprises: (a) a heavy chain variable ($V_H$) region comprising: (1) a $V_H$ CDR1 having the amino acid sequence of SEQ ID NO:70; (2) a $V_H$ CDR2 having the amino acid sequence of SEQ ID NO:71; and (3) a $V_H$ CDR3 having the amino acid sequence of SEQ ID NO:72; and (b) a light chain variable ($V_L$) region comprising: (1) a $V_L$ CDR1 having the amino acid sequence of SEQ ID NO:73; (2) a $V_L$ CDR2 having the amino acid sequence of SEQ ID NO:74; and (3) a $V_L$ CDR3 having the amino acid sequence of SEQ ID NO:75. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and In some embodiments, the first binding domain comprises: (a) a heavy chain variable ($V_H$) region comprising: (1) a $V_H$ CDR1 having the amino acid sequence of SEQ ID NO:53; (2) a $V_H$ CDR2 having the amino acid sequence of SEQ ID NO:76; and (3) a $V_H$ CDR3 having the amino acid sequence of SEQ ID NO:55; and (b) a light chain variable ($V_L$) region comprising: (1) a $V_L$ CDR1 having the amino acid sequence of SEQ ID NO:56; (2) a $V_L$ CDR2 having the amino acid sequence of SEQ ID NO:57; and (3) a $V_L$ CDR3 having the amino acid sequence of SEQ ID NO:58. In some embodiments, the second binding domain comprises: (a) a heavy chain variable ($V_H$) region comprising: (1) a $V_H$ CDR1 having the amino acid sequence of SEQ ID NO:79; (2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising: (1) a $V_L$ CDR1 having the amino acid sequence of SEQ ID NO:82; (2) a $V_L$ CDR2 having the amino acid sequence of SEQ ID NO:83; and (3) a $V_L$ CDR3 having the amino acid sequence of SEQ ID NO:84. In some embodiments, the second binding domain comprises: (a) a heavy chain variable ($V_H$) region comprising: (1) a $V_H$ CDR1 having the amino acid sequence of SEQ ID NO:105; (2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising: (1) a $V_L$ CDR1 having the amino acid sequence of SEQ ID NO:108; (2) a $V_L$ CDR2 having the amino acid sequence of SEQ ID NO:109; and (3) a $V_L$ CDR3 having the amino acid sequence of SEQ ID NO:110. In some embodiments, the second binding domain comprises: (a) a heavy chain variable ($V_H$) region comprising: (1) a $V_H$ CDR1 having the amino acid sequence of SEQ ID NO:131; (2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising: (1) a $V_L$ CDR1 having the amino acid sequence of SEQ ID NO:134; (2) a $V_L$ CDR2 having the amino acid sequence of SEQ ID NO:135; and (3) a $V_L$ CDR3 having the amino acid sequence of SEQ ID NO:136. In some embodiments, a multispecific antibody or fragment thereof described above is a bispecific antibody.

In some embodiments, described herein is a multispecific antibody comprising a VH region and/or VL region described herein, which further comprises human framework sequences. In some embodiment, the VH region and/or VL region further comprises a framework 1 (FR1), a framework 2 (FR2), a framework 3 (FR3) and/or a framework 4 (FR4) sequence.

Figure 16A:
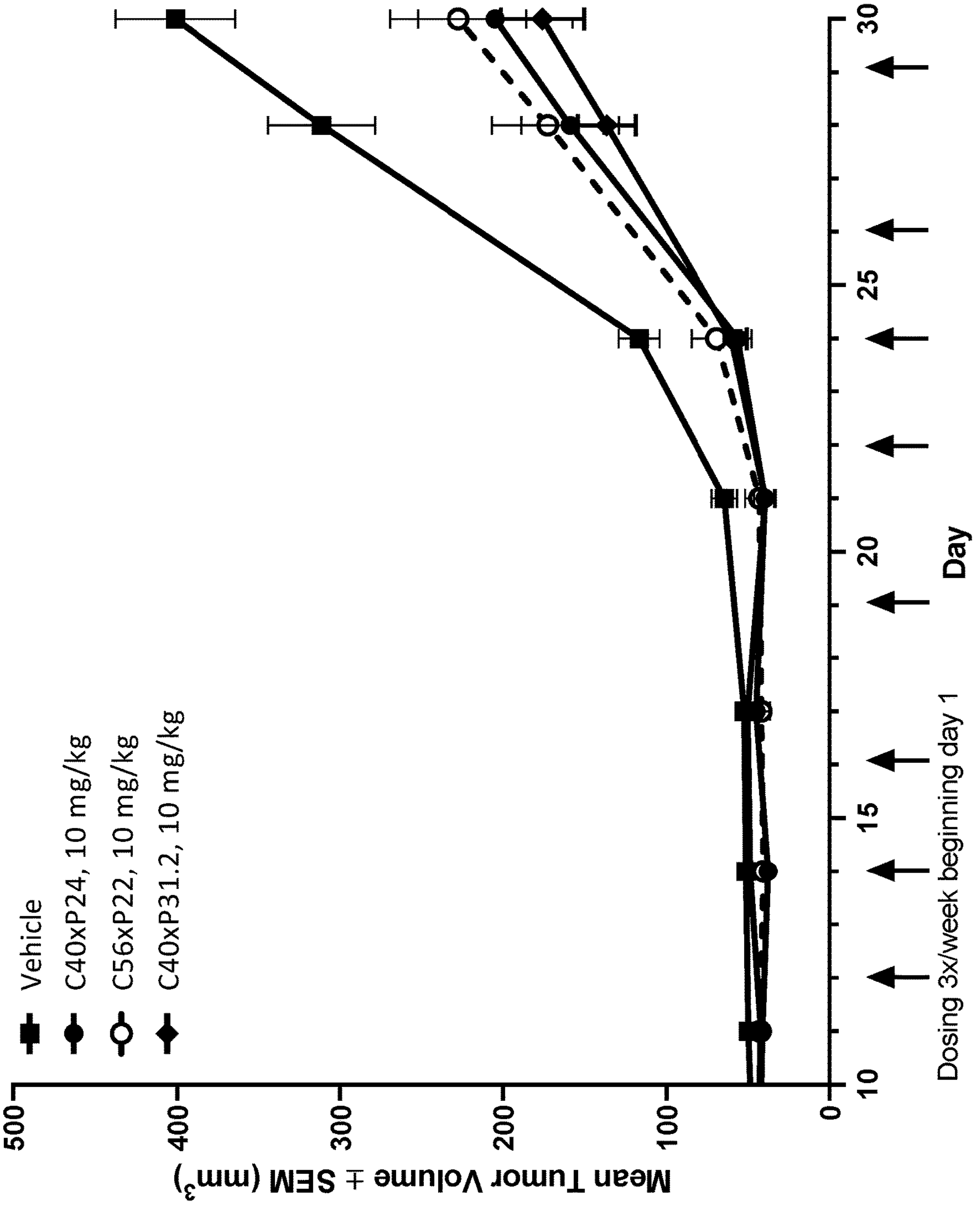
FIGS. 16A-16B illustrate exemplary results from additional in vivo animal studies related to tumor volume and body weight from different animal groups treated with vehicle control, C40×P24, C56×P22, or C40×P31.2 as indicated, further described in Example 7.
Figure 16B:
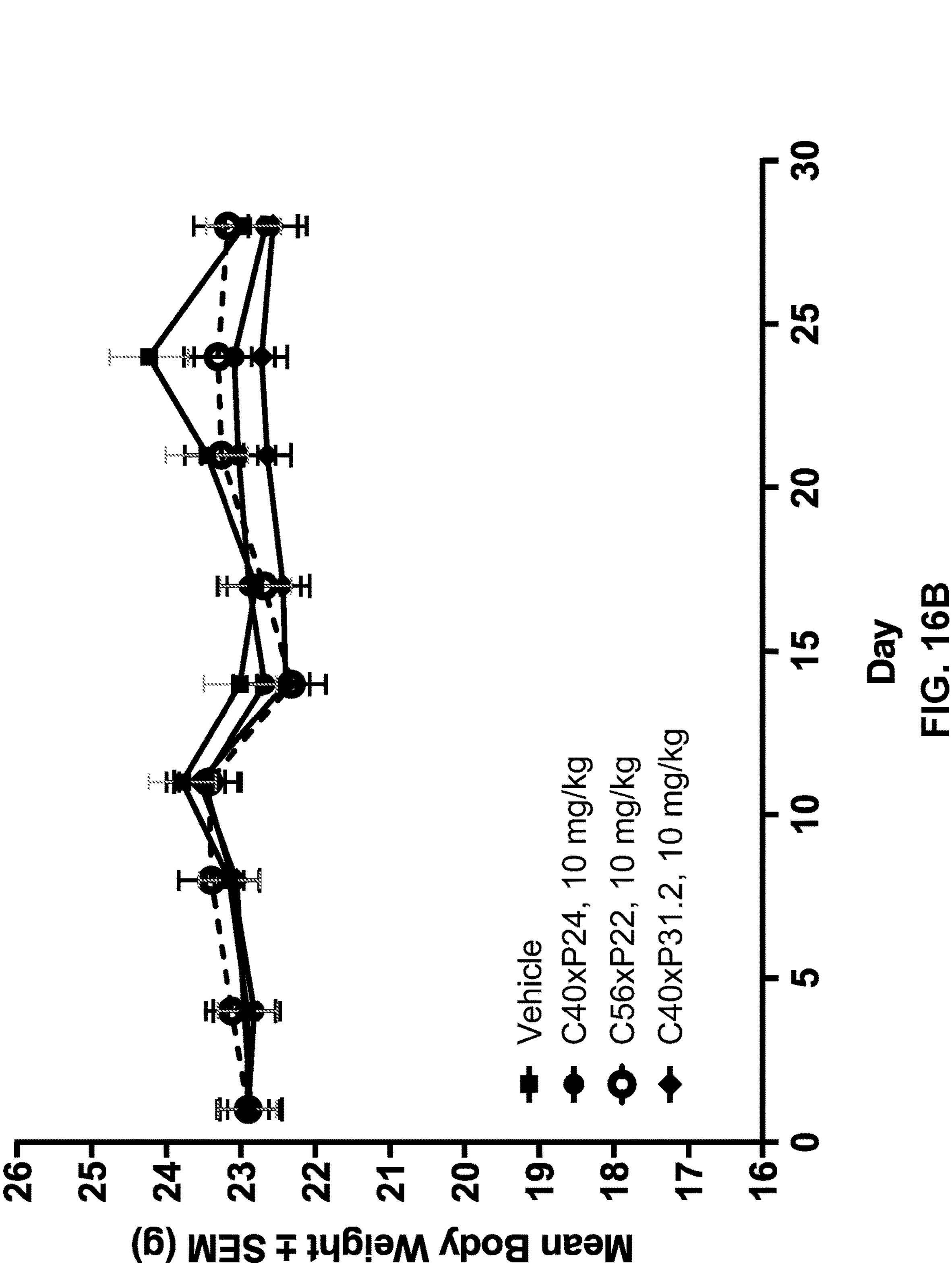

In some embodiments, the multispecific antibody described herein is a monoclonal antibody. In some embodiments, the monoclonal antibody is a humanized, human or chimeric antibody. In some embodiments, the multispecific antibody described herein is a Fab, Fab', F(ab')2, Fv, scFv, (scFv)2, single chain antibody molecule, dual variable region antibody, single variable region antibody, linear antibody, V region, or a multispecific antibody formed from antibody fragments. In some embodiments, the multispecific antibody described herein is a recombinant antibody, which is optionally a humanized, human or chimeric antibody In some embodiments, the CDRs disclosed herein for the first binding domain that binds to CD47 include consensus sequences derived from groups of related antibodies (see, e.g., Tables 1-3). As described herein, a "consensus sequence" refers to amino acid sequences having conserved amino acids common among a number of sequences and variable amino acids that vary within a given amino acid sequences. The CDR consensus sequences provided include CDRs corresponding to CDRH1, CDRH2, CDRH3, CDRL1, CDRL2 and/or CDRL3. Consensus sequences of CDRs of multispecific binding agents (e.g., antibodies, such as bispecific antibodies) for the first binding domain that binds to CD47 are shown in FIGS. 16A and 16B. Accordingly, in some embodiments, a multispecific binding agent (e.g., an antibody, such as a bispecific antibody) described herein comprises a first binding domain that binds to CD47 and comprises (a) a heavy chain variable (VH) region comprising: (1) a VH CDR1 having the amino acid sequence GFTF$X_1X_2$YYIH (SEQ ID NO:194), wherein $X_1$ and $X_2$ are each independently a naturally occurring amino acid; (2) a $V_H$ CDR2 having the amino acid sequence of $X_1$ID$X_2X_3X_4X_5X_6$T$X_7$YADSVKG (SEQ ID NO:195), wherein $X_1$, $X_2$, $X_3$ $X_4$, $X_5$, $X_6$, and $X_7$ are each independently a naturally occurring amino acid; and (3) a $V_H$ CDR3 having the amino acid of GG$X_1X_2$A$X_3$DY (SEQ ID NO:196), wherein $X_1$, $X_2$, and $X_3$ are each independently a naturally occurring amino acid, and/or (b) a light chain variable ($V_L$) region comprising: (1) a $V_L$ CDR1 having the amino acid sequence RASQSVSSAVA (SEQ ID NO:197); (2) a $V_L$ CDR2 having the amino acid sequence SASSLYS (SEQ ID NO:198); and (3) a $V_L$ CDR3 having the amino acid sequence QQ$X_1X_2X_3X_4$L$X_5$T (SEQ ID NO:199), wherein $X_1$, $X_2$, $X_3$ $X_4$, and $X_5$ are each independently a naturally occurring amino acid. In some embodiments, the $V_H$ CDR1 of a multispecific binding agent described herein has the amino acid sequence of GFTF$X_1X_2$YYIH (SEQ ID NO:216), wherein $X_1$ is a S or T, and $X_2$ is a Y or S. In some embodiments, the $V_H$ CDR2 of a multispecific binding agent described herein has the amino acid sequence of $X_1$ID$X_2X_3X_4X_5X_6$T$X_7$YADSVKG (SEQ ID NO:206), wherein $X_1$ is a W, F or Y, $X_2$ is a P or S, $X_3$ is a Y or K, $X_4$ is a G, S or H, $X_5$ is a H or G, $X_6$ is a S or T, and $X_7$ is a T, E or Q. In some embodiments, the $V_H$ CDR3 of a multispecific binding agent described herein has the amino acid sequence of GG$X_1X_2$A$X_3$DY (SEQ ID NO:207), wherein $X_1$ is a R or L, $X_2$ is a G, Y or S, and $X_3$ is a M or L. In some embodiments, the $V_L$ CDR1 of a multispecific binding agent described herein has the amino acid sequence of RASQSVSSAVA (SEQ ID NO:197). In some embodiments, the $V_L$ CDR2 of a multispecific binding agent described herein has the amino acid sequence of SASSLYS (SEQ ID NO:198). In some embodiments, the $V_L$ CDR3 of a multispecific binding agent described herein has the amino acid sequence of QQ$X_1X_2X_3X_4$L$X_5$T (SEQ ID NO:208), wherein $X_1$ is a R or G, $X_2$ is Y, R or T, $X_3$ is a S or T, $X_4$ is a S or D, and $X_5$ is a L or R.

In some embodiments, consensus sequences of CDRs of multispecific binding agents (e.g., antibodies, such as bispecific antibodies) for the second binding domain that binds to PD-L1 are shown in FIGS. 17A and 17B. Accordingly, in some embodiments, a multispecific binding agent (e.g., an antibody, such as a bispecific antibody) described herein comprises a second binding domain that binds to PD-L1 and comprises (a) a heavy chain variable ($V_H$) region comprising: (1) a $V_H$ CDR1 having the amino acid sequence GFTF$X_1X_2$YYIH (SEQ ID NO:200), wherein $X_1$ and $X_2$ are each independently a naturally occurring amino acid; (2) a $V_H$ CDR2 having the amino acid sequence of $X_1$I$X_2X_3X_4$G$X_5X_6$T$X_7$YADSVKG (SEQ ID NO:201), wherein $X_1$, $X_2$, $X_3$, $X_4$, $X_5$, $X_6$, and $X_7$ are each independently a naturally occurring amino acid; and (3) a $V_H$ CDR3 having the amino acid of $X_1X_2X_3X_4X_5X_6X_7X_8$LDY (SEQ ID NO:202), wherein $X_1$, $X_2$, $X_3$, $X_4$, $X_5$, $X_6$, $X_7$ and $X_8$ are each independency a naturally occurring amino acid, and/or (b) a light chain variable ($V_L$) region comprising: (1) a $V_L$ CDR1 having the amino acid sequence RASQSVSSAVA (SEQ ID NO:197); (2) a $V_L$ CDR2 having the amino acid sequence SASSLYS (SEQ ID NO:198); and (3) a $V_L$ CDR3 having the amino acid sequence QQ$X_1X_2X_3X_4$P$X_5$T (SEQ ID NO:203), wherein $X_1$, $X_2$, $X_3$, $X_4$, and $X_5$ are each independently a naturally occurring amino acid. In some embodiments, the $V_H$ CDR1 of a multispecific binding agent described herein has the amino acid sequence of GFTF$X_1X_2$YYIH (SEQ ID NO:217), wherein $X_1$ is a D or S, $X_2$ is a Q or S. In some embodiments, the $V_H$ CDR2 of a multispecific binding agent described herein has the amino acid sequence of $X_1$I$X_2X_3X_4$G$X_5X_6$T$X_7$YADSVKG (SEQ ID NO:209), wherein $X_1$ is a E, W, or T, $X_2$ is a Y, T, or S, $X_3$ is a P or S, $X_4$ is a A, H, or G, $X_5$ is a S, Y, or G, $X_6$ is a Y, S, or F, and $X_7$ is Y or K. In some embodiments, the $V_H$ CDR3 of a multispecific binding agent described herein has the amino acid sequence of $X_1X_2X_3X_4X_5X_6X_7X_8$LDY (SEQ ID NO:210), wherein $X_1$ is a G or D, $X_2$ is a P, S, or Y, $X_3$ is a Y, V, or T, $X_4$ is a S, I, or L, $X_5$ is a V, Y, or T, $X_6$ is a R, G or P, $X_7$ is a Y or V (or not present), and $X_8$ is an A (or not present). In some embodiments, the $V_L$ CDR1 of a multispecific binding agent described herein has the amino acid sequence of RASQSVSSAVA (SEQ ID NO:197). In some embodiments, the $V_L$ CDR2 of a multispecific binding agent described herein has the amino acid sequence of SASSLYS (SEQ ID NO:198). In some embodiments, the $V_L$ CDR3 of a multispecific binding agent described herein has the amino acid sequence of QQ$X_1X_2X_3X_4$P$X_5$T (SEQ ID NO:211), wherein $X_1$ is a V, Y, or F, $X_2$ is a S, Y, or G, $X_3$ is a Y, T, or A, $X_4$ is a S or E, and $X_5$ is a Y or I.

In some embodiments, described herein is a binding agent that binds to essentially the same epitope as an antibody or fragment thereof of any one of the antibodies described herein. In some embodiments, described hereins is a binding agent that competes for binding to human PD-L1 with an antibody or fragment thereof of any one described herein. In some embodiments, the binding agent is an antibody or fragment thereof.

In certain aspects, the CDRs of a multispecific binding agent (e.g., an antibody, such as a bispecific antibody), including a multispecific binding agent that binds to CD47, including human CD47, and one or more targets that are not CD47 (e.g., PD-L1, including human PD-L1), can be determined according to the Kabat system (Kabat et al. (1971) Ann. NY Acad. Sci. 190:382-391 and, Kabat et al. (1991) *Sequences of Proteins of Immunological Interest*, Fifth Edition, U.S. Department of Health and Human Services, NIH Publication No. 91-3242).

In certain aspects, the CDRs of a multispecific binding agent (e.g., an antibody, such as a bispecific antibody), including a multispecific binding agent that binds to CD47, including human CD47, and one or more targets that are not CD47 (e.g., PD-L1, including human PD-L1), can be determined according to the Chothia system, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709,226).

In certain aspects, the CDRs of a multispecific binding agent (e.g., an antibody, such as a bispecific antibody), including a multispecific binding agent that binds to CD47, including human CD47, and one or more targets that are not CD47 (e.g., PD-L1, including human PD-L1), can be determined according to the ImMunoGeneTics (IMGT) system, for example, as described in Lefranc, M.-P., 1999, The Immunologist, 7:132-136 and Lefranc, M.-P. et al., 1999, Nucleic Acids Res., 27:209-212 ("IMGT CDRs").

In certain aspects, the CDRs of a multispecific binding agent (e.g., an antibody, such as a bispecific antibody), including a multispecific binding agent that binds to CD47, including human CD47, and one or more targets that are not CD47 (e.g., PD-L1, including human PD-L1), can be determined according to the AbM system, which will be referred to herein as the "AbM CDRs," for example as described in MacCallum et al., 1996, J. Mol. Biol., 262:732-745. See also, e.g., Martin, A., "Protein Sequence and Structure Analysis of Antibody Variable Domains," in Antibody Engineering, Kontermann and Dübel, eds., Chapter 31, pp. 422-439, Springer-Verlag, Berlin (2001).

In certain aspects, the CDRs of a multispecific binding agent (e.g., an antibody, such as a bispecific antibody), including a multispecific binding agent that binds to CD47, including human CD47, and one or more targets that are not CD47 (e.g., PD-L1, including human PD-L1), can be determined according to the Contact system, which will be referred to herein as the "Contact CDRs" (see, e.g., MacCallum R M et al., 1996, J Mol Biol 5: 732-745). The Contact CDRs are based on an analysis of the available complex crystal structures.

In some embodiments, the position of one or more CDRs along the VH (e.g., CDR1, CDR2, or CDR3) and/or VL (e.g., CDR1, CDR2, or CDR3) region of a first binding domain of a multispecific binding agent (e.g., an antibody, such as a bispecific antibody), including a multispecific binding agent that binds to CD47, including human CD47, and one or more targets that are not CD47 (e.g., PD-L1, including human PD-L1), described herein may vary by one, two, three, four, five, or six amino acid positions so long as binding to CD47 (e.g., human CD47) is maintained (e.g., substantially maintained, for example, at least 50%, at least 60%, at least 70%, at least 80%, at least 90%, at least 95%). For example, in some embodiments, the position defining a CDR of any of Table 1, 2 or 3 may vary by shifting the N-terminal and/or C-terminal boundary of the CDR by one, two, three, four, five, or six amino acids, relative to the current CDR position, so long as binding to CD47 (e.g., human CD47) is maintained (e.g., substantially maintained, for example, at least 50%, at least 60%, at least 70%, at least 80%, at least 90%, at least 95%). In other embodiments, the length of one or more CDRs along the VH (e.g., CDR1, CDR2, or CDR3) and/or VL (e.g., CDR1, CDR2, or CDR3) region of a first binding domain of a multispecific binding agent (e.g., an antibody, such as a bispecific antibody), including a multispecific binding agent that binds to CD47, including human CD47, and one or more targets that are not CD47 (e.g., PD-1, including human PD-L1), described herein may vary (e.g., be shorter or longer) by one, two, three, four, five, or more amino acids, so long as binding to CD47 (e.g., human CD47) is maintained (e.g., substantially maintained, for example, at least 50%, at least 60%, at least 70%, at least 80%, at least 90%, at least 95%). For example, in some embodiments, a VH and/or VL CDR1, CDR2, and/or CDR3 described herein may be one, two, three, four, five or more amino acids shorter than one or more of the CDRs described by SEQ ID NOS: 1-24, 27-50, or 53-76, so long as binding to CD47 (e.g., human CD47) is maintained (e.g., substantially maintained, for example, at least 50%, at least 60%, at least 70%, at least 80%, at least 90%, at least 95%). In other embodiments, a VH and/or VL CDR1, CDR2, and/or CDR3 described herein may be one, two, three, four, five or more amino acids longer than one or more of the CDRs described by SEQ ID NOS: 1-24, 27-50, or 53-76, so long as binding to CD47 (e.g., human CD47) is maintained (e.g., substantially maintained, for example, at least 50%, at least 60%, at least 70%, at least 80%, at least 90%, at least 95%). In other embodiments, the amino terminus of a VH and/or VL CDR1, CDR2, and/or CDR3 of a first binding domain described herein may be extended by one, two, three, four, five or more amino acids compared to one or more of the CDRs described by SEQ ID NOS: 1-24, 27-50, or 53-76, so long as binding to CD47 (e.g., human CD47) is maintained (e.g., substantially maintained, for example, at least 50%, at least 60%, at least 70%, at least 80%, at least 90%, at least 95%). In other embodiments, the carboxy terminus of a VH and/or VL CDR1, CDR2, and/or CDR3 of a first binding domain described herein may be extended by one, two, three, four, five or more amino acids compared to one or more of the CDRs described by SEQ ID NOS: 1-24, 27-50, or 53-76, so long as binding to CD47 (e.g., human CD47) is maintained (e.g., substantially maintained, for example, at least 50%, at least 60%, at least 70%, at least 80%, at least 90%, at least 95%). In other embodiments, the amino terminus of a VH and/or VL CDR1, CDR2, and/or CDR3 of a first binding domain described herein may be shortened by one, two, three, four, five or more amino acids compared to one or more of the CDRs described by SEQ ID NOS: 1-24, 27-50, or 53-76, so long as binding to CD47 (e.g., human CD47) is maintained (e.g., substantially maintained, for example, at least 50%, at least 60%, at least 70%, at least 80%, at least 90%, at least 95%). In some embodiments, the carboxy terminus of a VH and/or VL CDR1, CDR2, and/or CDR3 of a first binding domain described herein may be shortened by one, two, three, four, five or more amino acids compared to one or more of the CDRs described by SEQ ID NOS: 1-24, 27-50, or 53-76, so long as binding to CD47 (e.g., human CD47) is maintained (e.g., substantially maintained, for example, at least 50%, at least 60%, at least 70%, at least 80%, at least 90%, at least 95%). Any method known in the art can be used to ascertain whether binding to CD47 (e.g., human CD47) is maintained, for example, the binding assays and conditions described in the "Examples" section described herein.

In some embodiments, the position of one or more CDRs along the VH (e.g., CDR1, CDR2, or CDR3) and/or VL (e.g., CDR1, CDR2, or CDR3) region of a second binding domain of a multispecific binding agent (e.g., an antibody, such as a bispecific antibody), including a multispecific binding agent that binds to CD47, including human CD47, and PD-L1, including human PD-L1, described herein may vary by one, two, three, four, five, or six amino acid positions so long as binding to PD-L1 (e.g., human PD-L1) is maintained (e.g., substantially maintained, for example, at least 50%, at least 60%, at least 70%, at least 80%, at least 90%, at least 95%). For example, in some embodiments, the position defining a CDR of any of Table 4, 5 or 6 may vary by shifting the N-terminal and/or C-terminal boundary of the CDR by one, two, three, four, five, or six amino acids, relative to the current CDR position, so long as binding to PD-L1 (e.g., human PD-L1) is maintained (e.g., substantially maintained, for example, at least 50%, at least 60%, at least 70%, at least 80%, at least 90%, at least 95%). In other embodiments, the length of one or more CDRs along the VH (e.g., CDR1, CDR2, or CDR3) and/or VL (e.g., CDR1, CDR2, or CDR3) region of a second binding domain of a multispecific binding agent (e.g., an antibody, such as a bispecific antibody), including a multispecific binding agent that binds to CD47, including human CD47, and PD-1, including human PD-L1, described herein may vary (e.g., be shorter or longer) by one, two, three, four, five, or more amino acids, so long as binding to PD-L1 (e.g., human PD-L1) is maintained (e.g., substantially maintained, for example, at least 50%, at least 60%, at least 70%, at least 80%, at least 90%, at least 95%). For example, in some embodiments, a VH and/or VL CDR1, CDR2, and/or CDR3 described herein may be one, two, three, four, five or more amino acids shorter than one or more of the CDRs described by SEQ ID NOS: 79-102, 105-128, or 131-154, so long as binding to PD-L1 (e.g., human PD-L1) is maintained (e.g., substantially maintained, for example, at least 50%, at least 60%, at least 70%, at least 80%, at least 90%, at least 95%). In other embodiments, a VH and/or VL CDR1, CDR2, and/or CDR3 described herein may be one, two, three, four, five or more amino acids longer than one or more of the CDRs described by SEQ ID NOS: 79-102, 105-128, or 131-154, so long as binding to PD-L1 (e.g., human PD-L1) is maintained (e.g., substantially maintained, for example, at least 50%, at least 60%, at least 70%, at least 80%, at least 90%, at least 95%). In other embodiments, the amino terminus of a VH and/or VL CDR1, CDR2, and/or CDR3 of a second binding domain described herein may be extended by one, two, three, four, five or more amino acids compared to one or more of the CDRs described by SEQ ID NOS: 79-102, 105-128, or 131-154, so long as binding to PD-L1 (e.g., human PD-L1) is maintained (e.g., substantially maintained, for example, at least 50%, at least 60%, at least 70%, at least 80%, at least 90%, at least 95%). In other embodiments, the carboxy terminus of a VH and/or VL CDR1, CDR2, and/or CDR3 of a second binding domain described herein may be extended by one, two, three, four, five or more amino acids compared to one or more of the CDRs described by SEQ ID NOS: 79-102, 105-128, or 131-154, so long as binding to PD-L1 (e.g., human PD-L1) is maintained (e.g., substantially maintained, for example, at least 50%, at least 60%, at least 70%, at least 80%, at least 90%, at least 95%). In other embodiments, the amino terminus of a VH and/or VL CDR1, CDR2, and/or CDR3 of a second binding domain described herein may be shortened by one, two, three, four, five or more amino acids compared to one or more of the CDRs described by SEQ ID NOS: 79-102, 105-128, or 131-154, so long as binding to PD-L1 (e.g., human PD-L1) is maintained (e.g., substantially maintained, for example, at least 50%, at least 60%, at least 70%, at least 80%, at least 90%, at least 95%). In some embodiments, the carboxy terminus of a VH and/or VL CDR1, CDR2, and/or CDR3 of a second binding domain described herein may be shortened by one, two, three, four, five or more amino acids compared to one or more of the CDRs described by SEQ ID NOS: 79-102, 105-128, or 131-154, so long as binding to PD-L1 (e.g., human PD-L1) is maintained (e.g., substantially maintained, for example, at least 50%, at least 60%, at least 70%, at least 80%, at least 90%, at least 95%). Any method known in the art can be used to ascertain whether binding to PD-L1 (e.g., human PD-L1) is maintained, for example, the binding assays and conditions described in the "Examples" section described herein.

In other embodiments, the multispecific binding agents (e.g., antibodies, such as bispecific antibodies), including multispecific binding agents that bind to CD47, including human CD47, and one or more targets that are not CD47 (e.g., PD-L1, including human PD-L1), presented herein that bind to CD47, comprise conservative sequence modifications. With respect to polypeptides that are multispecific binding agents (e.g., antibodies, such as bispecific antibodies), such as multispecific binding agents that bind to CD47, including human CD47, and one or more targets that are not CD47 (e.g., PD-L1, including human PD-L1), conservative sequence modifications include conservative amino acid substitutions that include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, in some embodiments, a predicted nonessential amino acid residue in a CD47 or PD-L1 is replaced with another amino acid residue from the same side chain family. Methods of identifying nucleotide and amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)). In some embodiments, the conservative sequence modifications described herein modify the amino acid sequences of the multispecific binding agents (e.g., antibodies, such as bispecific antibodies), including multispecific binding agents that bind to CD47, including human CD47, and one or more targets that are not CD47 (e.g., PD-L1, including human PD-L1), by 50%, or 55%, or 60%, or 65%, or 70%, or 75%, or 80%, or 85%, or 90%, or 95%, or 98%, or 99%. In some embodiments, the nucleotide and amino acid sequence modifications refer to at most 1, 2, 3, 4, 5, or 6 amino acid substitutions to the CDRs described in Table 1, Table 2, Table 3, Table 4, Table 5, or Table 6. Thus, for example, each such CDR may contain up to 5 conservative amino acid substitutions, for example up to (not more than) 4 conservative amino acid substitutions, for example up to (not more than) 3 conservative amino acid substitutions, for example up to (not more than) 2 conservative amino acid substitutions, or no more than 1 conservative amino acid substitution.

The present disclosure provides multispecific binding agents (e.g., antibodies, such as bispecific antibodies), including multispecific binding agents that bind to CD47, including human CD47, and one or more targets that are not CD47 (e.g., PD-L1, including human PD-L1) with a masking moiety and/or cleavable moiety in which one or more of the CD47 and/or other target binding domains of the multispecific binding agent (e.g., an antibody) are masked (e.g., via a masking moiety) and/or activatable (e.g., via a cleavable moiety). Technologies for masking of a multispecific binding agent (e.g., an antibody, such as a bispecific antibody) are well known in the art, including SAFE body masking technology (see, e.g., US Patent Application Publication No. 2019/0241886) and Probody masking technology (see, e.g., US Patent Application Publication No. 2015/0079088). Such technologies can be used to generate a multispecific binding agent (e.g., an antibody, such as a bispecific antibody) that is masked and/or activatable. Such masked and/or activatable multispecific binding agents (e.g., antibodies, such as bispecific antibodies), including multispecific binding agents that bind to CD47, including human CD47, and one or more targets that are not CD47 (e.g., PD-L1, including human PD-L1) are useful for the preparation of conjugates, including immunoconjugates, antibody-drug conjugates (ADCs), masked ADCs and activatable antibody-drug conjugates (AADCs), comprising any one of the multispecific binding agents (e.g., antibodies, such as bispecific antibodies), including multispecific binding agents that bind to CD47, including human CD47, and one or more targets that are not CD47 (e.g., PD-L1, including human PD-L1), such as human CD47 binding agents, of the present disclosure, including those directly or indirectly linked another agent such as a drug. For example, multispecific binding agents (e.g., antibodies, such as bispecific antibodies), including multispecific binding agents that bind to CD47, including human CD47, and one or more targets that are not CD47 (e.g., PD-L1, including human PD-L1), such as human CD47 binding agents, of the present disclosure may be covalently bound by a synthetic linker to one or more agents such as drugs.

If desired, a multispecific binding agent (e.g., an antibody, such as a bispecific antibody) is linked or conjugated (directly or indirectly) to a moiety with effector function, such as cytotoxic activity (e.g., a chemotherapeutic moiety or a radioisotope) or immune recruitment activity. Moieties that are linked or conjugated (directly or indirectly) include drugs that are cytotoxic (e.g., toxins such as aurostatins) or non-cytotoxic (e.g., signal transduction modulators such as kinases or masking moieties that mask one or more binding domains of a multispecific binding agent (e.g., an antibody, such as a bispecific antibody), or cleavable moieties that allow for activating a multispecific binding agent by cleaving of a cleavable moiety to unmask one or more binding domains of a multispecific binding agent (e.g., an antibody, such as a bispecific antibody) in the tumor microenvironment) in the form of masked conjugates. Moieties that promote immune recruitment can include other antigen-binding agents, such as viral proteins that bind selectively to cells of the innate immune system. Alternatively or in addition, a multispecific binding agent (e.g., an antibody, such as a bispecific antibody) is optionally linked or conjugated (directly or indirectly) to a moiety that facilitates isolation from a mixture (e.g., a tag) or a moiety with reporter activity (e.g., a detection label or reporter protein). It will be appreciated that the features of a multispecific binding agent (e.g., an antibody, such as a bispecific antibody) described herein extend also to a polypeptide comprising a binding agent fragment.

In some embodiments, multispecific binding agents (e.g., antibodies, such as bispecific antibodies), including multispecific binding agents that bind to CD47, including human CD47, and one or more targets that are not CD47 (e.g., PD-L1, including human PD-L1) described herein may be linked or conjugated (directly or indirectly) to a polypeptide, which can result in the generation of an activatable antibody. In some embodiments, a multispecific binding agent (e.g., an antibody, such as a bispecific antibody) is linked or conjugated (directly or indirectly) to an agent. In some embodiments, the agent is a drug, resulting in an ADC or an AADC when the antibody of the ADC comprises a masking moiety and a cleavable moiety.

In some embodiments, multispecific binding agents (e.g., antibodies, such as bispecific antibodies), including multispecific binding agents that bind to CD47, including human CD47, and one or more targets that are not CD47 (e.g., PD-L1, including human PD-L1) described herein are conjugated or recombinantly linked (directly or indirectly) to a therapeutic agent (e.g., a cytotoxic agent) or to a diagnostic or detectable agent. The conjugated or recombinantly linked antibodies, including masked or activatable conjugates, can be useful, for example, for treating or preventing a disease or disorder such as an immune cell dysfunctional disease, disorder or condition. The conjugated or recombinantly linked multispecific binding agents (e.g., antibodies, such as bispecific antibodies), including multispecific binding agents that bind to CD47, including human CD47, and one or more targets that are not CD47 (e.g., PD-L1, including human PD-L1), including masked or activatable conjugates, can be useful, for example, for monitoring or prognosing the onset, development, progression, and/or severity of an immune cell dysfunctional disease.

Such diagnosis and detection can be accomplished, for example, by coupling the multispecific binding agent (e.g., an antibody, such as a bispecific antibody) to detectable substances including, for example: enzymes, including, but not limited to, horseradish peroxidase, alkaline phosphatase, beta-galactosidase, or acetylcholinesterase; prosthetic groups, including, but not limited to, streptavidin/biotin or avidin/biotin; fluorescent materials, including, but not limited to, umbelliferone, fluorescein, fluorescein isothiocynate, rhodamine, dichlorotriazinylamine fluorescein, dansyl chloride, or phycoerythrin; luminescent materials, including, but not limited to, luminol; bioluminescent materials, including, but not limited to, luciferase, luciferin, or aequorin; chemiluminescent material, including, but not limited to, an acridinium based compound or a HALOTAG; radioactive materials, including, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga and 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, or 117Sn; positron emitting metals using various positron emission tomographies; and non-radioactive paramagnetic metal ions.

Also described herein are multispecific binding agents (e.g., antibodies, such as bispecific antibodies) that are recombinantly linked or conjugated (covalent or non-covalent conjugations, directly or indirectly) to a heterologous protein or polypeptide (or fragment thereof, for example, to a polypeptide (e.g., of about 10, about 20, about 30, about 40, about 50, about 60, about 70, about 80, about 90, or about 100 amino acids) to generate fusion proteins, as well as uses thereof. In particular, described herein are fusion proteins comprising an antigen-binding fragment of a multispecific binding agent (e.g., an antibody, such as a bispecific antibody), including a multispecific binding agent that binds to CD47, including human CD47, and one or more targets that are not CD47 (e.g., PD-L1, including human PD-L1), described herein (e.g., comprising CDR1, CDR2, and/or CDR3 of VH and/or VL) and a heterologous protein, polypeptide, or peptide. In some embodiments, the heterologous protein, polypeptide, or peptide that a multispecific binding agent (e.g., an antibody, such as a bispecific antibody) is linked to is useful for targeting the multispecific binding agent to a particular cell (e.g., a CD47 expressing cell and/or PD-L1 expressing cell, including a tumor cell).

Moreover, multispecific binding agents (e.g., antibodies, such as bispecific antibodies), including multispecific binding agents that bind to CD47, including human CD47, and one or more targets that are not CD47 (e.g., PD-L1, including human PD-L1), described herein can be linked (directly or indirectly) to marker or "tag" sequences, such as a peptide, to facilitate purification. In some embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-24, hexa-histidine provides for convenient purification of a fusion protein. Other peptide tags useful for purification include, but are not limited to, the hemagglutinin ("HA") tag, which corresponds to an epitope derived from the influenza hemagglutinin protein (Wilson et al., 1984, Cell 37:767-78), and the "FLAG" tag.

Methods for linking or conjugating (directly or indirectly) moieties (including polypeptides) to antibodies are well known in the art, any one of which can be used to make an antibody-drug conjugate or fusion protein described herein.

In some embodiments, a multispecific binding agent (e.g., an antibody) described herein is a fusion protein. The term "fusion protein" as used herein refers to a polypeptide that comprises an amino acid sequence of a binding agent (e.g., an antibody) and an amino acid sequence of a heterologous polypeptide or protein (e.g., a polypeptide or protein not normally a part of the antibody (e.g., a non-CD47 binding antibody or a non-PD-L1 binding antibody)). In certain embodiments, the fusion protein retains the biological activity of a multispecific binding agent. In certain embodiments, the fusion protein comprises a first binding domain that comprises CD47 antibody VH region, VL region, VH CDR (one, two or three VH CDRs), and/or VL CDR (one, two or three VL CDRs), wherein the fusion protein binds to a CD47 epitope, a CD47 fragment and/or a CD47 polypeptide. In certain embodiments, the fusion protein comprises a second binding domain that comprises PD-L1 antibody VH region, VL region, VH CDR (one, two or three VH CDRs), and/or VL CDR (one, two or three VL CDRs), wherein the fusion protein binds to a PD-L1 epitope, a PD-L1 fragment and/or a PD-L1 polypeptide.

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the multispecific binding agents (e.g., antibodies, such as bispecific antibodies), including multispecific binding agents that bind to CD47, including human CD47, and one or more targets that are not CD47 (e.g., PD-L1, including human PD-L1), as described herein, including, for example, multispecific binding agents with higher affinities and lower dissociation rates (see, e.g., U.S. Pat. Nos. 5,605,793; 5,811,238; 5,830,721; 5,834,252; and U.S. Pat. No. 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-13). In some embodiments, multispecific binding agents, including multispecific binding agents that bind to CD47, including human CD47, and one or more targets that are not CD47 (e.g., PD-L1, including human PD-L1), may be altered by being subjected to random mutagenesis by error-prone PCR, random nucleotide insertion, or other methods prior to recombination. A polynucleotide encoding a multispecific binding agent described herein may be recombined with one or more components, motifs, sections, parts, domains, fragments, etc. of one or more heterologous molecules.

Multispecific binding agents (e.g., antibodies, such as bispecific antibodies), including multispecific binding agents that bind to CD47, including human CD47, and one or more targets that are not CD47 (e.g., PD-L1, including human PD-L1), described herein may also be attached to solid supports, which are useful for immunoassays or purification of the target antigen. Such solid supports include, but are not limited to, glass, cellulose, polyacrylamide, nylon, polystyrene, polyvinyl chloride, or polypropylene.

Multispecific binding agents (e.g., antibodies, such as bispecific antibodies), including multispecific binding agents that bind to CD47, including human CD47, and one or more targets that are not CD47 (e.g., PD-L1, including human PD-L1), described herein can also be linked or conjugated (directly or indirectly) to a second antibody to form an antibody heteroconjugate.

The linker may be a "cleavable moiety" facilitating release of the linked or conjugated agent in a cell, but non-cleavable linkers are also contemplated herein. Linkers for use in conjugates (e.g., antibody-drug conjugates) of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers, thioether linkers, or hydrophilic linkers designed to evade multidrug transporter-mediated resistance.

Conjugates of an antibody and agent, including wherein the agent is a drug for the preparation of an ADC or an AADC, may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate). The present disclosure further contemplates that conjugates of antibodies and agents, including wherein the agent is a drug for the preparation of an ADC or an AADC, may be prepared using any suitable methods as disclosed in the art (see, e.g., Bioconjugate Techniques (Hermanson ed., 2d ed. 2008)).

Conventional conjugation strategies for antibodies and agents, including wherein the agent is a drug for the preparation of an ADC or an AADC, have been based on random conjugation chemistries involving the ε-amino group of Lys residues or the thiol group of Cys residues, which results in heterogeneous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (see, e.g., Junutula et al., 2008, J. Immunol. Meth. 332: 41-52; and Junutula et al., 2008, Nature Biotechnol. 26:925-32). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., 2008, Proc. Natl. Acad. Sci. USA 105:12451-56; and Hofer et al., 2009, Biochemistry 48(50):12047-57).

In some embodiments, a multispecific binding agent (e.g., an antibody, such as a bispecific antibody), including a multispecific binding agent that binds to CD47, including human CD47, and one or more targets that are not CD47 (e.g., PD-L1, including human PD-L1), described herein is conjugated to a cytotoxic agent. In some embodiments, a multispecific binding agent (e.g., an antibody, such as a bispecific antibody), including a multispecific binding agent that binds to CD47, including human CD47, and one or more targets that are not CD47 (e.g., PD-L1, including human PD-L1), disclosed herein can be optionally conjugated with one or more cytotoxic agent(s) disclosed herein or known in the art in order to generate an ADC or an AADC. In some embodiments, the cytotoxic agent is a chemotherapeutic agent including, but not limited to, methotrexate, adriamycin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated agent. A variety of radionuclides are available for the production of radioconjugated agents including, but not limited to, 90Y, 125I, 131I, 123I, 111In, 131In, 105Rh, 153Sm, 67Cu, 67Ga, 166Ho, 177Lu, 186Re, 188Re, and 212Bi. Conjugates of a polypeptide or molecule and one or more small molecule toxins, such as a calicheamicin, maytansinoids, a trichothene, and CC1065, and the derivatives of these toxins that have toxin activity, can also be used. Conjugates of a polypeptide or molecule and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, a multispecific binding agent (e.g., an antibody, such as a bispecific antibody), including a multispecific binding agent that binds to CD47, including human CD47, and one or more targets that are not CD47 (e.g., PD-L1, including human PD-L1), described herein is conjugated to a drug such as a signal transduction modulator, a pro-apoptotic agent, a mitotic inhibitor, an anti-tumor antibiotic, an immunomodulating agent, a nucleic acid for gene therapy, an alkylating agent, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In some embodiments, the mitotic inhibitor is a dolastatin, an auristatin, a maytansinoid, and a plant alkaloid. In some embodiments, the drug is a dolastatin, an auristatin, a maytansinoid, and a plant alkaloid. An example of an auristatin is monomethylaurisatin F (MMAF) or monomethyauristatin E (MMAE). Examples of maytansinoids include, but are not limited to, DM1, DM2, DM3, and DM4. In some embodiments, the anti-tumor antibiotic is selected from the group consisting of an actinomycine, an anthracycline, a calicheamicin, and a duocarmycin. In some embodiments, the actinomycine is a pyrrolobenzodiazepine (PBD).

Multispecific binding agents (e.g., antibodies, such as bispecific antibodies), including multispecific binding agents that bind to CD47, including human CD47, and one or more targets that are not CD47 (e.g., PD-L1, including human PD-L1), described herein may be monospecific, bispecific, trispecific or of greater multispecificity. Such agents may include antibodies. Multispecific antibodies, such as bispecific antibodies, are monoclonal antibodies that have binding specificities for at least two different targets (e.g., antigens) or two different epitopes on the same target (e.g., a bispecific antibody directed to CD47 with a first binding domain for a first epitope of a CD47, and a second binding domain for a second epitope of CD47). In some embodiments, the first binding domain of multispecific (e.g., bispecific) antibodies described herein can be constructed based on the sequences of the antibodies described herein, e.g., the CDR sequences listed in Table 1, Table 2, and Table 3. In some embodiments, the second binding domain of multispecific (e.g., bispecific) antibodies described herein can be constructed based on the sequences of the antibodies described herein, e.g., the CDR sequences listed in Table 4, Table 5, and Table 6. In some embodiments, the multispecific antibodies described herein are bispecific antibodies. In some embodiments, bispecific antibodies are mouse, chimeric, human or humanized antibodies. In some embodiments, one of the binding specificities of the multispecific antibody is for CD47 and the other is for any other target (e.g., antigen). In some embodiments, a multispecific (e.g., bispecific) antibody can comprise more than one target binding domain, in which different domains are specific for different targets (e.g., a first binding domain that binds CD47 and a second binding domain that binds another target (e.g., antigen), such as an immune check point regulator (e.g., a negative checkpoint regulator). In some embodiments, a multispecific (e.g., bispecific) antibody can bind more than one (e.g., two or more) epitopes on the same target (e.g., antigen). In some embodiments, one of the binding specificities is for CD47 and the other is for any other target (e.g., antigen). In some embodiments, one of the binding specificities is CD47 and the other is for one or more of Cytotoxic T-lymphocyte antigen-4 (CTLA-4), CD80, CD86, Programmed cell death 1 (PD-1), Programmed cell death ligand 1 (PD-L1), Programmed cell death ligand 2 (PD-L2), Lymphocyte activation gene-3 (LAG-3; also known as CD223), Galectin-3, B and T lymphocyte attenuator (BTLA), T-cell membrane protein 3 (TIM3), Galectin-9 (GAL9), B7-H1, B7-H3, B7-H4, T-Cell immunoreceptor with Ig and ITIM domains (TIGIT/Vstm3/WUCAM/VSIG9), V-domain Ig suppressor of T-Cell activation (VISTA), Glucocorticoid-induced tumor necrosis factor receptor-related (GITR) protein, Herpes Virus Entry Mediator (HVEM), OX40, CD27, CD28, CD137. CGEN-15001T, CGEN-15022, CGEN-15027, CGEN-15049, CGEN-15052, and CGEN-15092.

Methods for making multispecific antibodies are known in the art, such as, by co-expression of two immunoglobulin heavy chain-light chain pairs, where the two heavy chains have different specificities (see, e.g., Milstein and Cuello, 1983, Nature 305:537-40). For further details of generating multispecific antibodies (e.g., bispecific antibodies), see, for example, Bispecific Antibodies (Kontermann ed., 2011).

Exemplary structures of multispecific antibodies are known in the art and are further described in Weidle et al., 2013, Cancer Genomics & Proteomics 10: 1-18; Brinkman et al., 2017, MABS, 9:2, 182-212; Godar et al., 2018, Expert Opinion on Therapeutic Patents, 28:3, 251-276; and Spiess et al., 2015, Mol. Immunol. 67 95-106.

For example, bispecific antibody molecules can be classified into different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates. As a non-limiting example, BsIgG formats can include crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, KA-body, orthogonal Fab.

In some embodiments, BsIgG comprises heavy chains that are engineered for heterodimerization. For example, heavy chains can be engineered for heterodimerization using a "knobs-into-holes" strategy, a SEED platform, a common heavy chain (e.g., in κλ-bodies), and use of heterodimeric Fc regions. Strategies are known in the art to avoid heavy chain pairing of homodimers in BsIgG, including knobs-into-holes, DuoBody®, azymetric, charge pair, HA-TF, SEEDbody, and differential protein A affinity.

Another bispecific antibody format is IgG appended with an additional antigen-binding moiety. For example, monospecific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable domains (e.g., single chain variable fragments or variable fragments). Non-limiting examples of appended IgG formats include dual variable domain IgG (DVD-Ig), IgG(H)-scFv, scFv-(H)IgG, IgG(L)-scFv, scFv-(L)IgG, IgG(L,H)-Fv, IgG(H)-V, V(H)-IgG, IgG (L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67(2015):95-106. In some embodiments, an exemplary antibody format is a B-Body format for monospecific or multispecific (e.g., bispecific antibodies) as described in e.g. International Patent Application Publication No. WO 2018/075692 and US Patent Application Publication No. 2018/0118811.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Non-limiting examples of bispecific antibody fragments include, but are not limited to, NANOBODY®, NANOBODY®-HAS, BiTE®, Diabody, DART©, TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv-Fc, tetravalent HCAb, scDiabody-Fc, Diabody-Fc, tandem scFv-Fc, and intrabody.

Bispecific fusion proteins include antibody fragments linked to other proteins. For example bispecific fusion proteins can be linked to other proteins to add additional specificity and/or functionality. In some embodiments, the dock-and-lock (DNL) method can be used to generate bispecific antibody molecules with higher valency. For example, bispecific antibody fusions to albumin binding proteins or human serum albumin can be extend the serum half-life of antibody fragments. In embodiments, chemical conjugation, e.g., chemical conjugation of antibodies and/or antibody fragments, can be used to create BsAb molecules. An exemplary bispecific antibody conjugate includes the CovX-body format, in which a low molecular weight drug is conjugated site-specifically to a single reactive lysine in each Fab arm or an antibody or fragment thereof. In embodiments, the conjugation improves the serum half-life.

Methods of production of multispecific antibodies, including bispecific antibodies, are known in the art. For example, multispecific antibodies, including bispecific antibodies, can be produced by separate expression of the component antibodies in different host cells and subsequent purification/assembly or by expression of the component antibodies in a single host cell. Purification of multispecific (e.g., bispecific) antibody molecules can be performed by various methods known in the art, including affinity chromatography.

In some embodiments, multispecific binding agents (e.g., antibodies, such as bispecific antibodies), including multispecific binding agents that bind to CD47, including human CD47, and one or more targets that are not CD47 (e.g., PD-L1, including human PD-L1), disclosed herein can be provided in any antibody format disclosed herein or known in the art. As a non-limiting example, in some embodiments, the multispecific binding agents (e.g., antibodies, such as bispecific antibodies), including multispecific binding agents that bind to CD47, including human CD47, and one or more targets that are not CD47 (e.g., PD-L1, including human PD-L1), can be selected from Fabs-in-tandem-Ig (FIT-Ig); DVD-Ig; hybrid hybridoma (quadroma or tetradoma); anticalin platform (*Pieris*); diabodies; single chain diabodies; tandem single chain Fv fragments; TandAbs, Trispecific Abs (Affimed); Darts dual affinity retargeting (Macrogenics); Bispecific Xmabs (Xencor); Bispecific T cell engagers (BiTE®; Amgen; 55 kDa); Triplebodies; Tribody=Fab-scFv Fusion Protein multifunctional recombinant antibody derivates (CreativeBiolabs); DuoBody® platform (Genmab); dock and lock platform; knobs-into-holes (KIH) platform; Humanized bispecific IgG antibody (REGN1979) (Regeneron); Mab2 bispecific antibodies (F-Star); DVD-Ig=dual variable domain immunoglobulin (Abbott); kappa-lambda bodies; TBTI=tetravalent bispecific tandem Ig; and CrossMab (Roche).

In some embodiments, a multispecific (e.g., bispecific) antibody disclosed herein comprises a CD47 binding domain and one or more additional binding domains that bind to one or more targets that are not CD47. In some embodiments, a multispecific (e.g., bispecific) antibody disclosed herein comprises a CD47 binding domain that comprises the VH and/or VL amino acid sequences of Table 1. In some embodiments, a multispecific (e.g., bispecific) antibody disclosed herein comprises a CD47 binding domain that comprises the VH and/or VL amino acid sequences of Table 2. In some embodiments, a multispecific (e.g., bispecific) antibody disclosed herein comprises a CD47 binding domain that comprises the VH and/or VL amino acid sequences of Table 3.

In some embodiments, described herein is a multispecific (e.g., bispecific) antibody comprising a binding domain which binds to CD47 that comprises VH and VL CDRs as set forth in Table 1. In some embodiments, described herein is a multispecific (e.g., bispecific) antibody comprising a binding domain which binds to CD47 that comprises VH and VL CDRs as set for in Table 2. In some embodiments, described herein is a multispecific (e.g., bispecific) antibody comprising a binding domain which binds to CD47 that comprises VH and VL CDRs as set for in Table 3.

In some embodiments, a multispecific (e.g., bispecific) antibody disclosed herein comprises a CD47 binding domain and PD-L1 binding domain. In some embodiments, a multispecific (e.g., bispecific) antibody disclosed herein comprises a CD47 binding domain that comprises the VH and/or VL amino acid sequences of Table 1 and a PD-L1 binding domain that comprises the VH and/or VL amino acid sequences of Table 4. In some embodiments, a multispecific (e.g., bispecific) antibody disclosed herein comprises a CD47 binding domain that comprises the VH and/or VL amino acid sequences of Table 1 and a PD-L1 binding domain that comprises the VH and/or VL amino acid sequences of Table 5. In some embodiments, a multispecific (e.g., bispecific) antibody disclosed herein comprises a CD47 binding domain that comprises the VH and/or VL amino acid sequences of Table 1 and a PD-L1 binding domain that comprises the VH and/or VL amino acid sequences of Table 6. In some embodiments, a multispecific (e.g., bispecific) antibody disclosed herein comprises a CD47 binding domain that comprises the VH and/or VL amino acid sequences of Table 2 and a PD-L1 binding domain that comprises the VH and/or VL amino acid sequences of Table 4. In some embodiments, a multispecific (e.g., bispecific) antibody disclosed herein comprises a CD47 binding domain that comprises the VH and/or VL amino acid sequences of Table 2 and a PD-L1 binding domain that comprises the VH and/or VL amino acid sequences of Table 5. In some embodiments, a multispecific (e.g., bispecific) antibody disclosed herein comprises a CD47 binding domain that comprises the VH and/or VL amino acid sequences of Table 2 and a PD-L1 binding domain that comprises the VH and/or VL amino acid sequences of Table 6. In some embodiments, a multispecific (e.g., bispecific) antibody disclosed herein comprises a CD47 binding domain that comprises the VH and/or VL amino acid sequences of Table 3 and a PD-L1 binding domain that comprises the VH and/or VL amino acid sequences of Table 4. In some embodiments, a multispecific (e.g., bispecific) antibody disclosed herein comprises a CD47 binding domain that comprises the VH and/or VL amino acid sequences of Table 3 and a PD-L1 binding domain that comprises the VH and/or VL amino acid sequences of Table 5. In some embodiments, a multispecific (e.g., bispecific) antibody disclosed herein comprises a CD47 binding domain that comprises the VH and/or VL amino acid sequences of Table 3 and a PD-L1 binding domain that comprises the VH and/or VL amino acid sequences of Table 6.

In some embodiments, a multispecific (e.g., bispecific) antibody disclosed herein comprises a CD47 binding domain that comprises the VH and VL amino acid sequences of Table 1 and a PD-L1 binding domain that comprises the VH and VL amino acid sequences of Table 4. In some embodiments, a multispecific (e.g., bispecific) antibody disclosed herein comprises a CD47 binding domain that comprises the VH and VL amino acid sequences of Table 1 and a PD-L1 binding domain that comprises the VH and VL amino acid sequences of Table 5. In some embodiments, a multispecific (e.g., bispecific) antibody disclosed herein comprises a CD47 binding domain that comprises the VH and VL amino acid sequences of Table 1 and a PD-L1 binding domain that comprises the VH and VL amino acid sequences of Table 6. In some embodiments, a multispecific (e.g., bispecific) antibody disclosed herein comprises a CD47 binding domain that comprises the VH and VL amino acid sequences of Table 2 and a PD-L1 binding domain that comprises the VH and VL amino acid sequences of Table 4. In some embodiments, a multispecific (e.g., bispecific) antibody disclosed herein comprises a CD47 binding domain that comprises the VH and VL amino acid sequences of Table 2 and a PD-L1 binding domain that comprises the VH and VL amino acid sequences of Table 5. In some embodiments, a multispecific (e.g., bispecific) antibody disclosed herein comprises a CD47 binding domain that comprises the VH and VL amino acid sequences of Table 2 and a PD-L1 binding domain that comprises the VH and VL amino acid sequences of Table 6. In some embodiments, a multispecific (e.g., bispecific) antibody disclosed herein comprises a CD47 binding domain that comprises the VH and VL amino acid sequences of Table 3 and a PD-L1 binding domain that comprises the VH and VL amino acid sequences of Table 4. In some embodiments, a multispecific (e.g., bispecific) antibody disclosed herein comprises a CD47 binding domain that comprises the VH and VL amino acid sequences of Table 3 and a PD-L1 binding domain that comprises the VH and VL amino acid sequences of Table 5. In some embodiments, a multispecific (e.g., bispecific) antibody disclosed herein comprises a CD47 binding domain that comprises the VH and VL amino acid sequences of Table 3 and a PD-L1 binding domain that comprises the VH and VL amino acid sequences of Table 6.

Antibodies that bind CD47 and/or PD-L1 may be obtained by any suitable method, such as (but not limited to) immunization with whole tumor cells comprising CD47 and/or PD-L1 and collection of antibodies, recombinant techniques, or screening libraries of antibodies or antibody fragments using CD47 extracellular domain epitopes or PD-L1 extracellular domain epitopes. Monoclonal antibodies may be generated using a variety of known techniques (see, for example, Coligan et al. (eds.), *Current Protocols in Immunology,* 1:2.5.12.6.7 (John Wiley & Sons 1991); *Monoclonal Antibodies, Hybridomas: A New Dimension in Biological Analyses*, Plenum Press, Kennett, McKearn, and Bechtol (eds.) (1980); *Antibodies: A Laboratory Manual*, Harlow and Lane (eds.), Cold Spring Harbor Laboratory Press (1988); and Picksley et al., "Production of monoclonal antibodies against proteins expressed in *E. coli*," in *DNA Cloning* 2*: Expression Systems,* 2nd Edition, Glover et al. (eds.), page 93 (Oxford University Press 1995)). One exemplary technique for generating monoclonal antibodies comprises immunizing an animal with a human CD47 antigen and generating a hybridoma from spleen cells taken from the animal. A hybridoma may produce a monoclonal antibody or antibody fragment that binds CD47. One exemplary technique for generating monoclonal antibodies comprises immunizing an animal with a human PD-L1 antigen and generating a hybridoma from spleen cells taken from the animal. A hybridoma may produce a monoclonal antibody or antibody fragment that binds PD-L1.

In a further embodiment, monoclonal antibodies or antibody fragments can be isolated from antibody phage libraries generated using the techniques described in, for example, *Antibody Phage Display: Methods and Protocols*, P. M. O'Brien and R. Aitken, eds, Humana Press, Totawa N.J., 2002. In principle, synthetic antibody clones are selected by screening phage libraries containing phage that display various fragments of antibody variable region (Fv) fused to phage coat protein. Such phage libraries are screened for against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., *Ann. Rev. Immunol.,* 12: 433-455 (1994).

Repertoires of VH and VL genes can be separately cloned by polymerase chain reaction (PCR) and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J,* 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, *J. Mol. Biol.,* 227: 381-388 (1992).

Screening of the libraries can be accomplished by various techniques known in the art. For example, CD47 (e.g., a CD47 polypeptide, fragment or epitope) or PD-L1 (e.g., a PD-L1 polypeptide, fragment or epitope) can be used to coat the wells of adsorption plates, expressed on host cells affixed to adsorption plates or used in cell sorting, or conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

Multispecific binding agents can be obtained by designing a suitable antigen screening procedure to select for the phage clone of interest followed by construction of a full length multispecific binding agent (e.g., an antibody) clone using VH and/or VL sequences (e.g., the Fv sequences), or various CDR sequences from VH and VL sequences, from the phage clone of interest and suitable constant region (e.g., Fc) sequences described in Kabat et al., *Sequences of Proteins of Immunological Interest*, Fifth Edition, NIH Publication 91-3242, Bethesda MD (1991), vols. 1-3.

Likewise, human antibodies that bind CD47 and/or PD-L1 may be generated by any of a number of techniques including, but not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. Methods for obtaining human antibodies from transgenic animals are further described, for example, in Bruggemann et al., *Curr. Opin. Biotechnol.,* 8: 455 58, 1997; Jakobovits et al., *Ann. N. Y. Acad. Sci.,* 764: 525 35, 1995; Green et al., *Nature Genet.,* 7: 13-21, 1994; Lonberg et al., *Nature,* 368: 856-859, 1994; Taylor et al., *Int. Immun.* 6: 579-591, 1994; and U.S. Pat. No. 5,877,397.

For example, human antibodies that bind CD47 and/or PD-L1 may be obtained from transgenic animals that have been engineered to produce specific human antibodies in response to antigenic challenge. For example, International Patent Publication No. WO 98/24893 discloses transgenic animals having a human Ig locus, wherein the animals do not produce functional endogenous immunoglobulins due to the inactivation of endogenous heavy and light chain loci. Transgenic non-primate mammalian hosts capable of mounting an immune response to an immunogen, wherein the antibodies have primate constant and/or variable regions, and wherein the endogenous immunoglobulin encoding loci are substituted or inactivated, also have been described. International Patent Publication No. WO 96/30498 discloses the use of the Cre/Lox system to modify the immunoglobulin locus in a mammal, such as to replace all or a portion of the constant or variable region to form a modified antibody molecule. International Patent Publication No. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. Using a transgenic animal, such as a transgenic animal described herein, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in International Patent Publication No. WO 96/33735. The monoclonal antibodies can be tested for the ability to inhibit or neutralize the biological activity or physiological effect of the corresponding protein.

The present disclosure provides humanized antibodies that bind CD47, including human CD47, and one or more targets that are not CD47 (e.g., PD-L1, including human PD-L1). Humanized antibodies of the present disclosure may comprise a first binding domain that binds to CD47 and comprises one or more CDRs as shown in Tables 1-3.

Humanized antibodies of the present disclosure may comprise a second binding domain that binds to PD-L1 and comprises one or more CDRs as shown in Tables 4-6. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanized antibodies that bind CD47 may be produced using techniques known to those skilled in the art (Zhang et al., *Molecular Immunology,* 42(12): 1445-1451, 2005; Hwang et al., *Methods,* 36(1): 35-42, 2005; Dall'Acqua et al., Methods, 36(1): 43-60, 2005; Clark, *Immunology Today,* 21(8): 397-402, 2000, and U.S. Pat. Nos. 6,180,370; 6,054,927; 5,869,619; 5,861,155; 5,712,120; and 4,816,567, all of which are all hereby expressly incorporated herein by reference).

In some cases, the humanized antibodies are constructed by CDR grafting, in which the amino acid sequences of the six complementarity determining regions (CDRs) of the parent non-human antibody (e.g., rodent) are grafted onto a human antibody framework. For example, Padlan et al. (*FASEB J.* 9:133-139, 1995) determined that only about one third of the residues in the CDRs actually contact the antigen, and termed these the "specificity determining residues," or SDRs. In the technique of SDR grafting, only the SDR residues are grafted onto the human antibody framework (see, e.g., Kashmiri et al., *Methods* 36: 25-34, 2005).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence which is closest to that of the rodent may be selected as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623. In some cases, the framework is derived from the consensus sequences of the most abundant human subclasses, $V_L6$ subgroup I ($V_L6I$) and $V_H$ subgroup III ($V_HIII$). In another method, human germline genes are used at the source of the framework regions.

In an alternative paradigm based on comparison of CDRs, called Superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., *J. Immunol.* 169: 1119-1125, 2002).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, *Protein Eng.* 13: 819-824, 2000), Modeller (Sali and Blundell, *J. Mol. Biol.* 234: 779-815, 1993), and Swiss PDB Viewer (Guex and Peitsch, Electrophoresis 18: 2714-2713, 1997). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes and the differences are scored as HSC. The target sequence is then humanized by maximizing its HSC rather than using a global identity measure to generate multiple diverse humanized variants. (Lazar et al., *Mol. Immunol.* 44: 1986-1998, 2007).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome and yeast display libraries as well as by bacterial colony screening (see, e.g., Hoogenboom, *Nat. Biotechnol.* 23: 1105-1116, 2005; Dufner et al., *Trends Biotechnol.* 24: 523-529, 2006; Feldhaus et al., *Nat. Biotechnol.* 21: 163-70, 2003; Schlapschy et al., *Protein Eng. Des. Sel.* 17: 847-60, 2004).

In the FR library approach, a collection of residue variants are introduced at specific positions in the FR followed by selection of the library to select the FR that best supports the grafted CDR. The residues to be substituted may include some or all of the "Vernier" residues identified as potentially contributing to CDR structure (see, e.g., Foote and Winter, *J. Mol. Biol.* 224: 487-499, 1992), or from the more limited set of target residues identified by Baca et al. (*J. Biol. Chem.* 272: 10678-10684, 1997).

In FR shuffling, whole FRs are combined with the non-human CDRs instead of creating combinatorial libraries of selected residue variants (see, e.g., Dall'Acqua et al., Methods 36: 43-60, 2005). The libraries may be screened for binding in a two-step selection process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity and thermal stability (see, e.g., Damschroder et al., *Mol. Immunol.* 44: 3049-60, 2007).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple sub-classes with distinct human V-segment CDRs. Humaneering allows for isolation of antibodies that are 91-96% homologous to human germline gene antibodies. (see, e.g., Alfenito, Cambridge Healthtech Institute's Third Annual PEGS, The Protein Engineering Summit, 2007).

The "human engineering" method involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or are substituted with human residues. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering, 7: 805-814 (1994), U.S. Pat. Nos. 5,766,886, 5,770,196, 5,821,123, and 5,869,619, and PCT Application Publication WO 93/11794.

In some embodiments, a multispecific binding agent described herein comprises a non-antibody protein scaffold. Non-limiting examples of such a non-antibody protein scaffold include a fibronectin scaffold, an anticalin, an adnectin, an Affibody®, a DARPin®, a fynomer, an affitin, an Affilin®, an avimer, a cysteine-rich knottin peptide, or an engineered Kunitz-type inhibitor. Methods for generating such non-antibody protein scaffolds are well known in the art, any one of which can be used to generate a multispecific binding agent comprising a non-antibody protein scaffold (see, e.g., Simeon and Chen, *Protein Cell,* 9(1):3-14 (2018); Yang et al., *Annu Rev Anal Chem* (Palo Alto Calif). 10(1): 293-320 (2017)).

Further provided are the materials for generating multispecific binding agents and fragments thereof. For example, an isolated cell (e.g., a hybridoma) may produce a multispecific binding agent (e.g., antibody or antibody fragment). In this regard, a cell (e.g., an isolated cell) may produce an antibody or fragment thereof comprising a first binding domain comprising a VH and a VL as shown in Table 1, 2, or 3 for C40, C56, or C59, respectively. Alternatively or additionally, a cell (e.g., an isolated cell) may produce an antibody or fragment thereof comprising a second binding domain comprising a VH and a VL as shown in Table 4, 5, or 6 for P22, P24, or P31.2, respectively. In some embodiments, polynucleotides described herein may comprise one or more nucleic acid sequences encoding the multispecific binding agent (e.g., antibody or antibody fragment). In some embodiments, the polynucleotide is an isolated and/or recombinant polynucleotide. In various aspects, the isolated polynucleotide comprises a nucleotide sequence that encodes an antibody heavy chain variable region (VH) and/or an antibody light chain variable region ($V_L$), wherein the $V_H$ and the $V_L$ comprise complementarity determining regions (CDRs) identical to CDRs as shown in Table 1, CDRs as shown in Table 2, or CDRs as shown in Table 3. In various aspects, the isolated polynucleotide comprises a nucleotide sequence that encodes an antibody heavy chain variable region (VH) and/or an antibody light chain variable region ($V_L$), wherein the $V_H$ and the $V_L$ comprise complementarity determining regions (CDRs) identical to CDRs as shown in Table 4, CDRs as shown in Table 5, or CDRs as shown in Table 6.

In some embodiments, one or more vectors (e.g., expression vectors) may comprise one or more polynucleotides for expression of the one or more polynucleotides in a suitable host cell. Such vectors are useful, e.g., for amplifying the polynucleotides in host cells to create useful quantities thereof, and for expressing binding agents, such as antibodies or antibody fragments, using recombinant techniques.

In some embodiments, one or more vectors are expression vectors wherein one or more polynucleotides are operatively linked to one or more polynucleotides comprising expression control sequences. Autonomously replicating recombinant expression constructs such as plasmid and viral DNA vectors incorporating one or more polynucleotides encoding antibody sequences that bind CD47 are specifically contemplated. Expression control DNA sequences include promoters, enhancers, and operators, and are generally selected based on the expression systems in which the expression construct is to be utilized. Promoter and enhancer sequences are generally selected for the ability to increase gene expression, while operator sequences are generally selected for the ability to regulate gene expression. Expression constructs may also include sequences encoding one or more selectable markers that permit identification of host cells bearing the construct. Expression constructs may also include sequences that facilitate, and preferably promote, homologous recombination in a host cell. In some embodiments, expression constructs of the can also include sequences necessary for replication in a host cell.

Exemplary expression control sequences include promoter/enhancer sequences, e.g., cytomegalovirus promoter/enhancer (Lehner et al., *J. Clin. Microbiol.,* 29: 2494-2502, 1991; Boshart et al., *Cell,* 41: 521-530, 1985); Rous sarcoma virus promoter (Davis et al., *Hum. Gene Ther.,* 4: 151, 1993); Tie promoter (Korhonen et al., *Blood,* 86(5): 1828-1835, 1995); simian virus 40 promoter; DRA (downregulated in adenoma; Alrefai et al., *Am. J. Physiol. Gastrointest. Liver Physiol.,* 293: G923-G934, 2007); MCT1 (monocarboxylate transporter 1; Cuff et al., *Am. J. Physiol. Gastrointet. Liver Physiol., G*977-G979. 2005); and Math1 (mouse atonal homolog 1; Shroyer et al., *Gastroenterology,* 132: 2477-2478, 2007), for expression in mammalian cells, the promoter being operatively linked upstream (e.g., 5') of a polypeptide coding sequence. In another variation, the promoter is an epithelial-specific promoter or endothelial-specific promoter. Polynucleotides may also optionally include a suitable polyadenylation sequence (e.g., the SV40 or human growth hormone gene polyadenylation sequence) operably linked downstream (e.g., 3') of the polypeptide coding sequence.

If desired, the one or more polynucleotides also optionally comprise nucleotide sequences encoding secretory signal peptides fused in frame with the polypeptide sequences. The secretory signal peptides direct secretion of the antibody polypeptides by the cells that express the one or more polynucleotides, and are cleaved by the cell from the secreted polypeptides. The one or more polynucleotides may further optionally comprise sequences whose only intended function is to facilitate large scale production of the vector. One can manufacture and administer polynucleotides for gene therapy using procedures that have been described in the literature for a variety of transgenes. See, e.g., Isner et al., *Circulation,* 91: 2687-2692, 1995; and Isner et al., *Human Gene Therapy,* 7: 989-1011, 1996.

In some embodiments, polynucleotides may further comprise additional sequences to facilitate uptake by host cells and expression of the antibody or fragment thereof (and/or any other peptide). In some embodiments, a "naked" transgene encoding an antibody or fragment thereof described herein (e.g., a transgene without a viral, liposomal, or other vector to facilitate transfection) is employed.

Any suitable vectors may be used to introduce one or more polynucleotides that encode an antibody or fragment thereof into the host. Exemplary vectors that have been described include replication deficient retroviral vectors, including but not limited to lentivirus vectors (Kim et al., *J. Virol.,* 72(1): 811-816, 1998; Kingsman & Johnson, *Scrip Magazine, October,* 1998, pp. 43-46); parvoviral vectors, such as adeno-associated viral (AAV) vectors (U.S. Pat. Nos. 5,474,935I; 5,139,941; 5,622,856; 5,658,776; 5,773,289; 5,789,390; 5,834,441; 5,863,541; 5,851,521; 5,252,479; Gnatenko et al., *J. Invest. Med.,* 45: 87-98, 1997); adenoviral (AV) vectors (U.S. Pat. Nos. 5,792,453; 5,824,544; 5,707,618; 5,693,509; 5,670,488; 5,585,362; Quantin et al., *Proc. Natl. Acad. Sci. USA,* 89: 2581-2584, 1992; Stratford Perricaudet et al., *J. Clin. Invest.,* 90: 626-630, 1992; and Rosenfeld et al., *Cell,* 68: 143-155, 1992); an adenoviral adeno-associated viral chimeric (U.S. Pat. No. 5,856,152) or a vaccinia viral or a herpesviral vector (U.S. Pat. Nos. 5,879,934; 5,849,571; 5,830,727; 5,661,033; 5,328,688); Lipofectin mediated gene transfer (BRL); liposomal vectors (U.S. Pat. No. 5,631,237); and combinations thereof. Any of these expression vectors can be prepared using standard recombinant DNA techniques described in, e.g., Sambrook et al., *Molecular Cloning, a Laboratory Manual,* 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994). Optionally, viral vectors are rendered replication-deficient by, e.g., deleting or disrupting select genes required for viral replication.

Other non-viral delivery mechanisms contemplated include calcium phosphate precipitation (Graham and Van Der Eb, Virology, 52: 456-467, 1973; Chen and Okayama, *Mol. Cell Biol.,* 7: 2745-2752, 1987; Rippe et al., *Mol. Cell Biol.,* 10: 689-695, 1990) DEAE-dextran (Gopal, *Mol. Cell Biol.,* 5: 1188-1190, 1985), electroporation (Tur-Kaspa et al., *Mol. Cell Biol.,* 6: 716-718, 1986; Potter et al., *Proc. Nat. Acad. Sci. USA,* 81: 7161-7165, 1984), direct microinjection (Harland and Weintraub, *J. Cell Biol.,* 101: 1094-1099, 1985, DNA-loaded liposomes (Nicolau and Sene, *Biochim. Biophys. Acta,* 721: 185-190, 1982; Fraley et al., *Proc. Natl. Acad. Sci. USA,* 76: 3348-3352, 1979; Felgner, *Sci Am.,* 276(6): 102-6, 1997*; Felgner, Hum Gene Ther.,* 7(15): 1791-3, 1996), cell sonication (Fechheimer et al., *Proc. Natl. Acad. Sci. USA,* 84: 8463-8467, 1987), gene bombardment using high velocity microprojectiles (Yang et al., *Proc. Natl. Acad Sci USA,* 87: 9568-9572, 1990), and receptor-mediated transfection (Wu and Wu, *J. Biol. Chem.,* 262: 4429-4432, 1987; Wu and Wu, *Biochemistry,* 27: 887-892, 1988; Wu and Wu, *Adv. Drug Delivery Rev.,* 12: 159-167, 1993).

An expression vector (or the antibody or fragment thereof discussed herein) may be entrapped in a liposome. See, e.g., Ghosh and Bachhawat, In: *Liver diseases, targeted diagnosis and therapy using specific receptors and ligands*, Wu G, Wu C ed., New York: Marcel Dekker, pp. 87-104 (1991); Radler et al., *Science,* 275(5301): 810-814, 1997). Also contemplated are various commercial approaches involving "lipofection" technology. In some embodiments, the liposome may be complexed with a hemagglutinating virus (HVJ). This has been shown to facilitate fusion with the cell membrane and promote cell entry of liposome-encapsulated DNA (Kaneda et al., *Science,* 243: 375-378, 1989). In some embodiments, the liposome is complexed or employed in conjunction with nuclear nonhistone chromosomal proteins (HMG-1) (Kato et al., *J. Biol. Chem.,* 266: 3361-3364, 1991). In some embodiments, the liposome are complexed or employed in conjunction with both HVJ and HMG-1. Such expression constructs have been successfully employed in transfer and expression of nucleic acid in vitro and in vivo. In some embodiments, a multispecific binding agent (e.g., an antibody), including a multispecific binding agent that binds to CD47, including human CD47, and one or more targets that are not CD47 (e.g., PD-L1, including human PD-L1), is included in the liposome to target the liposome to cells (such as tumor cells) expressing CD47 and/or PD-L1 on their surface.

A cell may comprise one or more polynucleotides or one or more vectors, e.g., the cell is transformed or transfected with one or more polynucleotides encoding a multispecific binding agent (e.g., an antibody), including a multispecific binding agent that binds to CD47, including human CD47, and one or more targets that are not CD47 (e.g., PD-L1, including human PD-L1), or the one or more vectors comprising the one or more polynucleotides. In some embodiments, cells express a multispecific binding agent, including a multispecific binding agent that binds to CD47, including human CD47, and one or more targets that are not CD47 (e.g., PD-L1, including human PD-L1), having at least 75% identity to the CDRs of C40 (see, e.g., Table 1). In some embodiments, cells express a multispecific binding agent, including a multispecific binding agent that binds to CD47, including human CD47, and one or more targets that are not CD47 (e.g., PD-L1, including human PD-L1), having at least 75% identity to the CDRs of C56 (see, e.g., Table 2). In some embodiments, cells express a multispecific binding agent, including a multispecific binding agent that binds to CD47, including human CD47, and one or more targets that are not CD47 (e.g., PD-L1, including human PD-L1), having at least 75% identity to the CDRs of C59 (see, e.g., Table 3). In some embodiments, cells express a multispecific binding agent, including a multispecific binding agent that binds to CD47, including human CD47, and PD-L1, including human PD-L1, having at least 75% identity to the CDRs of P22 (see, e.g., Table 4). In some embodiments, cells express a multispecific binding agent, including a multispecific binding agent that binds to CD47, including human CD47, and PD-L1, including human PD-L1, having at least 75% identity to the CDRs of P24 (see, e.g., Table 5). In some embodiments, cells express a multispecific binding agent, including a multispecific binding agent that binds to CD47, including human CD47, and PD-L1, including human PD-L1, having at least 75% identity to the CDRs of P31.2 (see, e.g., Table 6). The cells may be prokaryotic cells, such as *Escherichia coli* (see, e.g., Pluckthun et al., *Methods Enzymol.,* 178: 497-515, 1989), or eukaryotic cells, such as an animal cell (e.g., a myeloma cell, Chinese Hamster Ovary (CHO) cell, or hybridoma cell), yeast (e.g., *Saccharomyces cerevisiae*), or a plant cell (e.g., a tobacco, corn, soybean, or rice cell). Use of mammalian host cells may provide for translational modifications (e.g., glycosylation, truncation, lipidation, and phosphorylation) that may be desirable to confer optimal biological activity on recombinant expression products. Similarly, polypeptides (e.g., multispecific binding agents (e.g., antibodies, such as bispecific antibodies), including multispecific binding agents that bind to CD47, including human CD47, and one or more targets that are not CD47 (e.g., PD-L1, including human PD-L1)) may be glycosylated or non-glycosylated and/or have been covalently modified to include one or more water soluble polymer attachments such as polyethylene glycol, polyoxyethylene glycol, or polypropylene glycol.

Methods for introducing DNA or RNA into host cells are well known and include transformation, transfection, electroporation, nuclear injection, or fusion with carriers such as liposomes, micelles, ghost cells, and protoplasts. Such host cells are useful for amplifying polynucleotides and also for expressing polypeptides encoded by the polynucleotides. In this regard, a process for the production of a multispecific binding agent (e.g., an antibody) may comprise culturing a host cell and isolating the multispecific binding agent. Transferring a naked DNA expression construct into cells can be accomplished using particle bombardment, which depends on the ability to accelerate DNA coated microprojectiles to a high velocity allowing them to pierce cell membranes and enter cells without killing them (Klein et al., *Nature,* 327: 70-73, 1987). Several devices for accelerating small particles have been developed. One such device relies on a high voltage discharge to generate an electrical current, which in turn provides the motive force (Yang et al., *Proc. Natl. Acad. Sci USA,* 87: 9568-9572, 1990). The microprojectiles used have consisted of biologically inert substances such as tungsten or gold beads. A host cell may be isolated and/or purified. A host cell also may be a cell transformed in vivo to cause transient or permanent expression of the polypeptide in vivo. A host cell may also be an isolated cell transformed ex vivo and introduced post-transformation, e.g., to produce the polypeptide in vivo for therapeutic purposes. The definition of host cell explicitly excludes a transgenic human being.

A variety of methods for producing antibodies from polynucleotides are generally well-known. For example, basic molecular biology procedures are described by Maniatis et al., *Molecular Cloning, A Laboratory Manual,* 2nd ed., Cold Spring Harbor Laboratory, New York, 1989 (see also Maniatis et al, 3rd ed., Cold Spring Harbor Laboratory, New York, 2001). Additionally, numerous publications describe techniques suitable for the preparation of antibodies by manipulation of DNA, creation of expression vectors, and transformation and culture of appropriate cells (see, e.g., Mountain and Adair, Chapter 1 in *Biotechnology and Genetic Engineering Reviews*, Tombs ed., Intercept, Andover, UK, 1992); and *Current Protocols in Molecular Biology*, Ausubel ed., Wiley Interscience, New York, 1999).

A multispecific binding agent (e.g., an antibody), including a multispecific binding agent that binds to CD47, including human CD47, and one or more targets that are not CD47 (e.g., PD-L1, including human PD-L1), is produced using any suitable method, e.g., isolated from an immunized animal, recombinantly or synthetically generated, or genetically-engineered, including as described above. Antibody fragments derived from an antibody are obtained by, e.g., proteolytic hydrolysis of an antibody. For example, papain or pepsin digestion of whole antibodies yields a 5S fragment termed $F(ab')_2$ or two monovalent Fab fragments and an Fc fragment, respectively. $F(ab)_2$ can be further cleaved using a thiol reducing agent to produce 3.5S Fab monovalent fragments. Methods of generating antibody fragments are further described in, for example, Edelman et al., *Methods in Enzymology,* 1: 422 Academic Press (1967); Nisonoff et al., *Arch. Biochem. Biophys.,* 89: 230-244, 1960; Porter, Biochem. J., 73: 119-127, 1959; U.S. Pat. No. 4,331,647; and by Andrews, S. M. and Titus, J. A. in Current Protocols in Immunology (Coligan et al., eds), John Wiley & Sons, New York (2003), pages 2.8.1 2.8.10 and 2.10A.1 2.10A.5.

A multispecific binding agent (e.g., an antibody), including a multispecific binding agent that binds to CD47, including human CD47, and one or more targets that are not CD47 (e.g., PD-L1, including human PD-L1), can be genetically engineered. For example, a multispecific binding agent (e.g., an antibody), including a multispecific binding agent that binds to CD47, including human CD47, and one or more targets that are not CD47 (e.g., PD-L1, including human PD-L1) comprises, for example, a variable region domain generated by recombinant DNA engineering techniques. In this regard, a variable region is optionally modified by insertions, deletions, or changes in the amino acid sequence of the antibody to produce an antibody of interest, including as described above. Polynucleotides encoding complementarity determining regions (CDRs) of interest are prepared, for example, by using polymerase chain reaction to synthesize variable regions using mRNA of antibody producing cells as a template (see, for example, Courtenay Luck, "Genetic Manipulation of Monoclonal Antibodies," in *Monoclonal Antibodies: Production, Engineering and Clinical Application*, Ritter et al. (eds.), page 166 (Cambridge University Press 1995); Ward et al., "Genetic Manipulation and Expression of Antibodies," in *Monoclonal Antibodies: Principles and Applications*, Birch et al., (eds.), page 137 (Wiley Liss, Inc. 1995); and Larrick et al., *Methods: A Companion to Methods in Enzymology,* 2: 106-110, 1991). Current antibody manipulation techniques allow construction of engineered variable region domains containing at least one CDR and, optionally, one or more framework amino acids from a first antibody and the remainder of the variable region domain from a second antibody. Such techniques are used, e.g., to humanize an antibody or to improve its affinity for a binding target.

"Humanized antibodies" are antibodies in which CDRs of heavy and light variable chains of non-human immunoglobulins are transferred into a human variable domain. Constant regions need not be present, but if they are, they optionally are substantially identical to human immunoglobulin constant regions, e.g., at least about 85-90%, about 95%, 96%, 97%, 98%, 99% or more identical, in some embodiments. Hence, in some instances, all parts of a humanized immunoglobulin, except possibly the CDRs, are substantially identical to corresponding parts of natural human immunoglobulin sequences. For example, humanized antibodies are human immunoglobulins (e.g., host antibody) in which hypervariable region residues of the host antibody are replaced by hypervariable region residues from a non-human species (donor antibody) such as mouse, rat, rabbit, or a non-human primate having the desired specificity, affinity, and capacity.

In some embodiments, multispecific binding agents (e.g., antibodies), including multispecific binding agents that binds to CD47, including human CD47, and one or more targets that are not CD47 (e.g., PD-L1, including human PD-L1) described herein are useful in compositions and in methods of treating, preventing, or alleviating an immune cell dysfunctional disease, disorder or condition (e.g., a phagocytic cell dysfunctional disease, disorder, or condition or a T cell dysfunctional disease, disorder or condition), including one or more symptoms of the disease, disorder, or condition. Phagocytic cell dysfunctional diseases, disorders, and conditions include tumor immunity and associated cancers, including, but not limited to, any cancer wherein the tumor cells overexpress CD47. T cell dysfunctional diseases, disorders, and conditions include tumor immunity and associated cancers, including, but not limited to, any cancer wherein the tumor cells express or overexpress PD-L1. Such CD47 and/or PD-L1 expressing tumor cells may help tumor cells escape immune surveillance and clearance (e.g., tumor immunity). In addition, multispecific binding agents described herein, such as multispecific antibodies (e.g., antibodies, such as bispecific antibodies), that bind to CD47 and one or more additional targets that are not CD47 (e.g., PD-L1), are useful to inhibit SIRPα signaling and/or PD-1 signaling, enhance phagocytic cell function and/or immune surveillance, and enhance removal of tumor cells.

In some embodiments, described herein is a method for treating tumor immunity in a subject comprising administering to the subject a multispecific binding agent (e.g., an antibody), including a multispecific binding agent that binds to CD47, including human CD47, and one or more targets that are not CD47 (e.g., PD-L1, including human PD-L1), described herein or fragment thereof or a pharmaceutical composition comprising the binding agent (e.g., antibody) described herein.

In some embodiments, described herein is a method for treating a cancer or a tumor in a subject comprising administering to the subject a multispecific binding agent (e.g., an antibody), including a multispecific binding agent that binds to CD47, including human CD47, and one or more targets that are not CD47 (e.g., PD-L1, including human PD-L1), described herein or fragment thereof or a pharmaceutical composition comprising the binding agent (e.g., antibody) described herein.

In some embodiments, described herein is a method for alleviating one or more symptoms associated with a cancer or a tumor in a subject comprising administering to the subject a multispecific binding agent (e.g., an antibody), including a multispecific binding agent that binds to CD47, including human CD47, and one or more targets that are not CD47 (e.g., PD-L1, including human PD-L1), described herein or fragment thereof or a pharmaceutical composition comprising the binding agent (e.g., antibody) described herein.

In some embodiments, described herein is a method for decreasing tumor size in a subject with a tumor comprising administering to the subject a multispecific binding agent (e.g., an antibody), including a multispecific binding agent that binds to CD47, including human CD47, and one or more targets that are not CD47 (e.g., PD-1, including human PD-L1), described herein or fragment thereof or a pharmaceutical composition comprising the binding agent (e.g., an antibody) described herein.

In some embodiments, described herein is a method for enhancing tumor cell removal in a subject with a tumor comprising administering to the subject a multispecific binding agent (e.g., an antibody), including a multispecific binding agent that binds to CD47, including human CD47, and one or more targets that are not CD47 (e.g., PD-1, including human PD-L1), described herein or fragment thereof or a pharmaceutical composition comprising the binding agent (e.g., an antibody) described herein.

In some embodiments, described herein is a method for treating a phagocytic cell dysfunctional disease, disorder or condition in a subject comprising administering to the subject a multispecific binding agent (e.g., an antibody), including a multispecific binding agent that binds to CD47, including human CD47, and one or more targets that are not CD47 (e.g., PD-L1, including human PD-L1), described herein or fragment thereof or a pharmaceutical composition comprising the binding agent (e.g., an antibody) described herein.

In some embodiments, described herein is a method for increasing immune cell phagocytosis in a subject comprising administering to the subject a multispecific binding agent (e.g., an antibody), including a multispecific binding agent that binds to CD47, including human CD47, and one or more targets that are not CD47 (e.g., PD-1, including human PD-L1), described herein or fragment thereof or a pharmaceutical composition comprising the binding agent (e.g., an antibody) described herein. In some embodiments, the immune cell is a macrophage, a neutrophil, a dendritic cell, or a B lymphocyte. In some embodiments, the subject is diagnosed with a cancer or a tumor.

In some embodiments, described herein is a method for treating a T cell dysfunctional disease, disorder or condition in a subject comprising administering to the subject a multispecific binding agent (e.g., an antibody), including a multispecific binding agent that binds to CD47, including human CD47, and one or more targets that are not CD47 (e.g., PD-L1, including human PD-L1), described herein or fragment thereof or a pharmaceutical composition comprising the binding agent (e.g., an antibody) described herein. In some embodiments, the T cell dysfunctional disease, disorder or condition is tumor immunity.

In some embodiments, described herein is a method for enhancing T cell function in a subject comprising administering to the subject a multispecific binding agent (e.g., an antibody), including a multispecific binding agent that binds to CD47, including human CD47, and one or more targets that are not CD47 (e.g., PD-1, including human PD-L1), described herein or fragment thereof or a pharmaceutical composition comprising the binding agent (e.g., an antibody) described herein. In some embodiments, the T cell function is secretion of cytokines. In some embodiments, the T cell function is removal of tumor cells. In some embodiments, the subject is diagnosed with a cancer or a tumor.

The subject of a method described above can be administered one or more therapeutic agents described herein in combination with a multispecific binding agent (e.g., an antibody), including a multispecific binding agent that binds to CD47, including human CD47, and one or more targets that are not CD47 (e.g., PD-L1, including human PD-L1), described herein or fragment thereof or a pharmaceutical composition comprising the binding agent (e.g., an antibody) described herein.

In some embodiments, the antibody is a human antibody, including, but not limited to, an antibody having variable regions in which both the framework and CDR regions are derived from human germline immunoglobulin sequences as described, for example, in Kabat et al. (1991) *Sequences of proteins of Immunological Interest*, Fifth Edition, U.S. Department of Health and Human Services, NIH Publication No. 91-3242. If the antibody contains a constant region, the constant region also preferably is derived from human germline immunoglobulin sequences. Human antibodies may comprise amino acid residues not encoded by human germline immunoglobulin sequences, for example, to enhance the activity of the antibody, but do not comprise CDRs derived from other species (e.g., a mouse CDR placed within a human variable framework region).

In some embodiments, a multispecific binding agent (e.g., an antibody), including a multispecific binding agent that binds to CD47, including human CD47, and one or more targets that are not CD47 (e.g., PD-L1, including human PD-L1), increases phagocytosis and/or enhances phagocytic activity of cells in cell culture. For example, such cell culture may include tumor cells expressing or overexpressing CD47. In some embodiments, a multispecific binding agent (e.g., an antibody), including a multispecific binding agent that binds to CD47, including human CD47, and PD-L1, including human PD-L1, increases T cell function and/or enhances cytolytic activity of cells in cell culture. Such cell culture may include tumor cells expressing or overexpressing PD-L1. In some embodiments, a multispecific binding agent (e.g., an antibody), including a multispecific binding agent that binds to CD47, including human CD47, and PD-L1, including human PD-L1, increases phagocytosis, enhances phagocytic activity, increases T cell function and/or enhances cytolytic activity of cells in cell culture. Such cell culture may include tumor cells expressing or overexpressing CD47 and PD-L1. Tumor cells include, but are not limited to, breast cancer cells, bladder cancer cells, melanoma cells, prostate cancer cells, mesothelioma cells, lung cancer cells, testicular cancer cells, thyroid cancer cells, squamous cell carcinoma cells, glioblastoma cells, neuroblastoma cells, uterine cancer cells, colorectal cancer cells, and pancreatic cancer cells.

In some embodiments, described herein is a method of inhibiting proliferation of tumor cells in a subject. For example, the method comprises administering an amount of a multispecific binding agent (e.g., an antibody) such as a multispecific binding agent that binds to CD47, including human CD47, and one or more targets that are not CD47 (e.g., PD-L1, including human PD-L1) described herein effective to inhibit proliferation of the tumor cells. In some embodiments, the method includes administering a multispecific binding agent (e.g., an antibody) that competes for binding with antibody C40, antibody C56, and/or antibody C59 (see, e.g., CDRs and VH/VL of Tables 1, 2 and/or 3), to human CD47 and/or binds the region of a CD47 recognized by antibody C40, antibody C56, and/or antibody C59 (see, e.g., CDRs and VH/VL of Tables 1, 2 and/or 3), resulting in resulting in enhancement of the removal of tumor cells. In some embodiments, the method includes administering a multispecific binding agent (e.g., an antibody) that competes for binding with antibody P22, antibody P24, and/or antibody P31.2 (see, e.g., CDRs and VH/VL of Tables 4, 5 and/or 6), to human PD-L1 and/or binds the region of a PD-L1 recognized by antibody P22, antibody P24, and/or antibody P31.2 (see, e.g., CDRs and VH/VL of Tables 4, 5 and/or 6), resulting in resulting in enhancement of the removal of tumor cells. In some embodiments, one or more polynucleotides, vectors, and/or cells as described above can be used in methods of enhancing the removal of tumor cells in vivo (e.g., in a method of treating cancer in a subject).

A method of modulating (e.g., inhibiting, reducing, preventing) tumor growth in a subject also is provided. For example, the method comprises administering to the subject a composition comprising a multispecific binding agent (e.g., an antibody) in an amount effective to modulate tumor growth in the subject. "Tumor" refers to any neoplastic cell growth or proliferation, whether malignant or benign, and to all pre-cancerous and cancerous cells and tissues. The terms "cancer" and "cancerous" refer to or describe the physiological condition in mammals that is typically characterized by unregulated cell growth. Examples of cancers include, but are not limited to: breast cancer, colon cancer, renal cancer, lung cancer, squamous cell myeloid leukemia, hemangiomas, melanomas, astrocytomas, and glioblastomas as well as other cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia, renal cell carcinoma), bladder and urethra (squamous cell carcinoma, transitional cell carcinoma, adenocarcinoma), prostate (adenocarcinoma, sarcoma, small cell carcinoma of the prostate), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma) serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; as well as cancers of the thyroid including medullary thyroid cancer. Also provided is a method of treating cancer by administering a multispecific binding agent (e.g., an antibody) such as a multispecific binding agent that binds to CD47, including human CD47, and one or more targets that are not CD47 (e.g., PD-L1, including human PD-L1), to a subject in need thereof, alone or in combination with another agent.

"Enhancing" tumor cell removal does not require a 100% enhancement of removal. Any enhancement in the rate of removal is contemplated. Similarly, "modulating" tumor growth refers to reducing the size of the tumor, slowing tumor growth, or inhibiting an increase in the size of an existing tumor. Complete abolition of a tumor is not required; any decrease in tumor size or slowing of tumor growth constitutes a beneficial biological effect in a subject. In this regard, tumor cell removal may be enhanced by, for example, at least about 5%, at least about 10% or at least about 20% compared to levels of removal observed in the absence of the method (e.g., in a biologically-matched control subject or specimen that is not exposed to the agent of the method). The effect is detected by, for example, a reduction in tumor size, a decrease or maintenance of the levels of tumor markers, or reduction or maintenance of a tumor cell population. In some embodiments, removal of tumor cells is enhanced by, for example, at least about 30%, at least about 40%, at least about 50%, at least about 60%, at least about 70%, at least about 80%, at least about 90%, or more (about 100%) compared to the removal of tumor cells in the absence of a multispecific binding agent (e.g., an antibody) of the method.

Additionally, multispecific binding agents (e.g., antibodies, such as bispecific antibodies) may be used to alleviate or reduce side effects associated with cancer such as, for example, bone deterioration, vertebral collapse, and paralysis. In one aspect, the subject suffers from or is at risk of suffering from bone metastases and a multispecific binding agent (e.g., an antibody) is administered in an amount to reduce deterioration of surrounding bone. Accordingly, in some aspects, a multispecific binding agent prevents bone deterioration due to bone metastases, wherein tumor cell proliferation is or is not reduced. In some aspects, a multispecific binding agent (e.g., an antibody) both prevents bone deterioration due to bone metastases and reduces tumor cell proliferation. In general, the effect on tumor cell proliferation (e.g., inhibition of proliferation or no effect on proliferation) depends on the microenvironment of a particular metastasis. For example, proliferation of metastases located in microenvironments with substantial amounts of type 1 collagen may be inhibited. In contrast, proliferation of metastases located in microenvironments lacking substantial amounts of type 1 collagen may not be inhibited, yet bone deterioration in the vicinity of the metastasis is reduced or prevented.

A particular administration regimen of a multispecific binding agent (e.g., an antibody) for a particular subject will depend, in part, upon the agent used, the amount of agent administered, the route of administration, and the cause and extent of any side effects. The amount of agent (e.g., an antibody) administered to a subject (e.g., a mammal, such as a human) should be sufficient to effect the desired response over a reasonable time frame. According, in some embodiments, the amount of a multispecific binding agent (e.g., an antibody) or pharmaceutical composition described herein administered to a subject is an effective amount. In some embodiments, the amount of a multispecific binding agent (e.g., an antibody) or pharmaceutical composition described herein administered to a subject is a therapeutically effective amount. In some aspects, the method comprises administering, e.g., from about 0.1 μg/kg to up to about 100 mg/kg or more. In some embodiments, the dosage ranges from about 1 μg/kg up to about 100 mg/kg; or about 5 μg/kg up to about 100 mg/kg; or about 10 μg/kg up to about 100 mg/kg; or about 1 mg/kg up to about 50 mg/kg; or about 2 mg/kg up to about 30 mg/kg; or about 3 mg/kg up to about 25 mg/kg; or about 3 mg/kg up to about 25 mg/kg; or about 5 mg/kg up to about 10 mg/kg; or about 10 mg/kg up to about 20 mg/kg; or about 10 mg/kg up to about 30 mg/kg. Some conditions or disease states require prolonged treatment, which may or may not entail administering doses of multispecific binding agents (e.g., antibodies, such as bispecific antibodies), including multispecific binding agents that bind to CD47, including human CD47, and one or more targets that are not CD47 (e.g., PD-L1, including human PD-L1) (e.g., antibodies, such as bispecific antibodies), over multiple administrations (e.g., every day, three times a week, once a week, once every two weeks, or once every month for a treatment period of three days, seven days, two weeks, three weeks, one month, three months, six months, nine months, 12 months, 15 months, 18 months, 21 months, two years, or more).

Suitable routes of administering a composition comprising a multispecific binding agent (e.g., an antibody), such as a multispecific binding agent that binds to CD47, including human CD47, and one or more targets that are not CD47 (e.g., PD-1, including human PD-L1) (e.g., an antibody), are well known in the art. Although more than one route can be used to administer an agent (e.g., an antibody), a particular route can provide a more immediate and more effective reaction than another route. Depending on the circumstances, a composition comprising a multispecific binding agent (e.g., an antibody) such as a multispecific binding agent that binds to CD47, including human CD47, and one or more targets that are not CD47 (e.g., PD-1, including human PD-L1) is applied or instilled into body cavities, absorbed through the skin or mucous membranes, ingested, inhaled, and/or introduced into circulation. For example, it may be desirable to deliver a composition comprising a multispecific binding agent (e.g., an antibody) such as a multispecific binding agent that binds to CD47, including human CD47, and one or more targets that are not CD47 (e.g., PD-1, including human PD-L1) through injection by intravenous, subcutaneous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, a multispecific binding agent (e.g., an antibody) such as a multispecific binding agent that binds to CD47, including human CD47, and one or more targets that are not CD47 (e.g., PD-L1, including human PD-L1) is administered regionally via intraarterial or intravenous administration feeding the region of interest, e.g., via the hepatic artery for delivery to the liver. Alternatively, a multispecific binding agent (e.g., an antibody) such as a multispecific binding agent that binds to CD47, including human CD47, and one or more targets that are not CD47 (e.g., PD-1, including human PD-L1) is administered locally via implantation of a membrane, sponge, or another appropriate material on to which the binding agent has been absorbed or encapsulated. Where an implantation device is used, the device is, one aspect, implanted into any suitable tissue or organ, and delivery of a multispecific binding agent (e.g., an antibody) such as a multispecific binding agent that binds to CD47, including human CD47, and one or more targets that are not CD47 (e.g., PD-L1, including human PD-L1) is, for example, via diffusion, timed-release bolus, or continuous administration. In other aspects, the multispecific binding agent is administered directly to exposed tissue during tumor resection or other surgical procedures.

The present disclosure provides a composition, such as pharmaceutical composition, comprising a multispecific binding agent (e.g., an antibody) such as a multispecific binding agent that binds to CD47, including human CD47, and one or more targets that are not CD47 (e.g., PD-L1, including human PD-L1) and a carrier (e.g., a pharmaceutically acceptable carrier). The particular carrier employed may depend on chemico-physical considerations, such as solubility and lack of reactivity with the binding agent or co-therapy, and by the route of administration. Pharmaceutically acceptable carriers are well-known in the art, examples of which are described herein. Illustrative pharmaceutical forms suitable for injectable use include sterile aqueous solutions or dispersions and sterile powders for the extemporaneous preparation of sterile injectable solutions or dispersions. Injectable formulations are further described in, e.g., *Pharmaceutics and Pharmacy Practice*, J. B. Lippincott Co., Philadelphia. Pa., Banker and Chalmers. eds., pages 238-250 (1982), and *ASHP Handbook on Injectable Drugs*, Toissel, 4th ed., pages 622-630 (1986)). A pharmaceutical composition comprising a multispecific binding agent (e.g., an antibody) such as a multispecific binding agent that binds to CD47, including human CD47, and one or more targets that are not CD47 (e.g., PD-L1, including human PD-L1) is, in one aspect, placed within containers, along with packaging material that provides instructions regarding the use of such pharmaceutical compositions. Generally, such instructions include a tangible expression describing the reagent concentration, as well as, in some embodiments, relative amounts of excipient ingredients or diluents (e.g., water, saline or PBS) that may be necessary to reconstitute the pharmaceutical composition.

In some aspects, a method described herein further comprises administering one or more additional agents, including therapeutic agents (e.g., combination therapy), which may be present in a composition or may be administered with a multispecific binding agent (e.g., an antibody) such as a multispecific binding agent that binds to CD47, including human CD47, and one or more targets that are not CD47 (e.g., PD-L1, including human PD-L1) or provided in a separate composition using the same or a different route of administration. The one or more additional agents, including therapeutic agents, may be administered together or separately (e.g., simultaneously, alternatively, sequentially) with a multispecific binding agent (e.g., an antibody). Such additional therapeutic agents include, but are not limited to, therapeutic antibodies, immunotherapies, cytotoxic agents, chemotherapeutic agents, and inhibitors.

Therapeutic antibodies that can be used include, but are not limited to, trastuzumab; abciximab; daclizumab; BEC2; IMC-C22; vitaxin; Campath 1H/LDP-03; Smart M195; epratuzumab; bectumomab; visilizumab; CM3, a humanized anti-ICAM3 antibody; IDEC-I 14; ibritumomab tiuxetan; IDEC-131; IDEC-151; IDEC-152; SMART anti-CD3; eculizumab; adalimumab; certolizumab; IDEC-I 51; MDX-CD4; CD20-sreptdavidin; CDP571; LDP-02; OrthoClone OKT4A; ruplizumab; natalizumab; and lerdelimumab.

Immunotherapies that can be used include, but are not limited to, cytokines, such as granulocyte-macrophage colony-stimulating factor (GM-CSF), granulocyte-colony stimulating factor (G-CSF), macrophage inflammatory protein (MIP)-I-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IF A); QS-21; DETOX; Levamisole; and Dinitrophenyl (DNP), and combinations thereof, such as, for example, combinations of, interleukins, for example, IL-2 with other cytokines, such as IFN-alpha. In some embodiments, the immunotherapy includes an immunotherapeutic agent that modulates immune responses, for example, a checkpoint inhibitor or a checkpoint agonist. In some embodiments, the immunotherapeutic agent is an antibody modulator that targets PD-1, PD-L1, PD-L2, CEACAM (e g., CEACAM-I, -3 and/or -5), CTLA-4, TIM-3, LAG-3, VISTA, BTLA, TIGIT, LAIR1, CD160, 2B4, TGF beta, OX40, 41BB, LIGHT, CD40, GITR, TGF-beta, TIM-3, SIRP-alpha, VSIG8, BTLA, SIGLEC7, SIGLEC9, ICOS, B7H3, B7H4, FAS, and/or BTNL2 among others known in the art. In some embodiments, the immunotherapeutic agent is an agent that increases natural killer (NK) cell activity, inhibits suppression of an immune response, inhibits suppressor cells or suppressor cell activity, inhibits Treg activity, or inhibits the activity of inhibitory immune checkpoint receptors.

In some embodiments, the immunotherapeutic agent includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g., SLAMF7), HVEM, LIGHT, CD2, CD27, CD28, CDS, ICAM-1, LFA-I (CD1 Ia/CDI8), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

Cytotoxic agents that can be used include a substance that inhibits or prevents a cellular function and/or causes cell death or destruction. Exemplary cytotoxic agents include, but are not limited to, radioactive isotopes (e.g., At211, 1131, 1125, Y90, Re186, Re188, Sm153, Bi212, P32, Pb212 and radioactive isotopes of Lu); growth inhibitory agents; enzymes and fragments thereof such as nucleolytic enzymes; and toxins such as small molecule toxins or enzymatically active toxins of bacterial, fungal, plant or animal origin, including fragments and/or variants thereof. Other exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

Chemotherapeutic agents that can be used include chemical compounds useful in the treatment of cancer. Examples of chemotherapeutic agents include, but are not limited to, erlotinib, bortezomib, disulfiram, epigallocatechin gallate, salinosporamide A, carfilzomib, 17-AAG (geldanamycin), radicicol, lactate dehydrogenase A (LDH-A), fulvestrant, sunitib, letrozole, imatinib mesylate, fmasunate, oxaliplatin, 5-FET (5-fluorouracil), leucovorin, Rapamycin, Lapatinib, Lonafamib (SCH 66336), sorafenib, Bayer Labs), gefitinib, AG1478; alkylating agents such as thiotepa and CYTOXAN®; cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; cally statin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5 alpha-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancrati statin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma II and calicheamicin omega I (Angew Chem. Inti. Ed. Engl. 1994 33: 183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Ore.); razoxane; rhizoxin; sizofuran; spirogermanium; tenuazonic acid; triaziquone; 2,2',2"-trichlorotriethylamine; trichothecenes especially T-2 toxin, verracurin A, roridin A and anguidine); urethan; vindesine; dacarbazine; mannomustine; mitobronitol; mitolactol; pipobroman; gacytosine; arabinoside “Ara-C”); cyclophosphamide; thiotepa; taxoids, e.g., paclitaxel, ABRAXANE® (Cremophor-free), albumin-engineered nanoparticle formulations of paclitaxel (American Pharmaceutical Partners, Schaumberg, III.), and docetaxel/doxetaxel; chloranmbucil; gemcitabine; 6-thioguanine; mercaptopurine; methotrexate; platinum analogs such as cisplatin and carboplatin; vinblastine; etoposide (VP-16); ifosfamide; mitoxantrone; vincristine; vinorelbine; novantrone; teniposide; edatrexate; daunomycin; aminopterin; capecitabine; ibandronate; CPT-I I; topoisomerase inhibitor RFS 2000; difluorom ethyl ornithine (DMFO); retinoids such as retinoic acid; and pharmaceutically acceptable salts, acids and derivatives of any of the above. Chemotherapeutic agent also includes (i) anti-hormonal agents that act to regulate or inhibit hormone action on tumors such as anti-estrogens and selective estrogen receptor modulators (SERMs), including, for example, tamoxifen (including tamoxifen citrate), raloxifene, droloxifene, iodoxyfene, 4-hydroxytamoxifen, trioxifene, keoxifene, LY117018, onapristone, and toremifme citrate; (ii) aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LEIRTOTECAN®; ABARELIX®; and (ix) pharmaceutically acceptable salts, acids and derivatives of any of the above.

Chemotherapeutic agents also include antibodies, as described above, including alemtuzumab, bevacizumab; cetuximab; panitumumab, rituximab, pertuzumab, tositumomab, and the antibody drug conjugate, gemtuzumab ozogamicin. Additional humanized monoclonal antibodies with therapeutic potential as agents in combination with the multispecific binding agents (e.g., antibodies) as described herein include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nivolumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-8744695, Wyeth Research and Abbott Laboratories) which is a recombinant exclusively human-sequence, full-length IgGI λ antibody genetically modified to recognize interleukin-12 p40 protein. Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-1 7-butyrate, clobetasol-d 7-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF alpha) blockers such as etanercept, infliximab, adalimumab, certolizumab pegol, golimumab (Simponi), Interleukin 1 (IL-1) blockers such as anakinra, T cell costimulation blockers such as abatacept, Interleukin 6 (IL-6) blockers such as tocilizumab; Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-MI prime; Secreted homotrimeric LTa3 and membrane bound heterotrimer LTaI/I32 blockers such as Anti-lymphotoxin alpha (LTa); miscellaneous investigational agents such as thioplatin, PS-341, phenylbutyrate, ET-18-OCH3, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol); beta-lapachone; lapachol; colchicines; betulinic acid; acetylcamptothecin, scopolectin, and 9-aminocamptothecin); podophyllotoxin; tegafur; bexarotene; bisphosphonates such as clodronate, etidronate, NE-58095, zoledronic acid/zoledronate, alendronate, pamidronate, tiludronate, or risedronate; and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifamib (R11577); orafenib, ABT510; Bcl-2 inhibitor such as oblimersen sodium pixantrone; farnesyltransferase inhibitors such as lonafamib (SCH 6636); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin combined with 5-FU and leucovorin. Chemotherapeutic agents also include Poly ADP ribose polymerase (PARP) inhibitors: olaparib, rucaprib niraparib, talzoparib.

Inhibitors that can be used include, but are not limited to, kinase inhibitors such as imatinib, baricitinib gefitinib, erlotinib, sorafenib, dasatinib, sunitinib, lapatinib, nilotinib, pirfenidone, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, abemaciclib, acalabrutinib, alectinib, binimetinib, brigatinib, encorafenib, erdafitinib, everolimus, fostamatinib, gilter, larotrectinib, lorlatinib, netarsudil, osimertinib, pemigatinib, pexidartinib, ribociclib, temsirolimus, XL-092, XL-147, XL-765, XL-499, and XL-880. In some embodiments, a compound as described herein can be used in combination with a HSP90 inhibitor (e.g., XL888), liver X receptor (LXR) modulators, retinoid-related orphan receptor gamma (RORy) modulators, checkpoint inhibitors such as a CK1 inhibitor or aCK1a inhibitor, a Wnt pathway inhibitor (e.g., SST-215), or a mineralocorticoid receptor inhibitor, (e.g., esaxerenone) or XL-888 for the treatment of a disease disclosed herein such as cancer. In some embodiments, a multispecific binding agent (e.g., an antibody) as disclosed herein can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, 1NS-R, IGF-1R, IR-R, PDGFαR, PDGFβ/R, CSFIR, KIT, FLK-II, KDR/FLK-1, FLK-4, flt-1, FGFR1, FGFR2, FGFR3, FGFR4, Ron, Sea, TRKA, TRKB, TRKC, FLT3, VEGFR/Flt2, Flt4, EphAI, EphA2, EphA3, EphB2, EphB4, Tie2, Src, Fyn, Lck, Fgr, Btk, Fak, SYR, FRK, JAK (JAK1 and or JAK2), ABL, ALK, CDK7, CDK12, KRAS, and B-Raf.

Additional non-limiting examples of inhibitors that can be combined with a multispecific binding agent (e.g., an antibody) of the present disclosure for treatment of cancer include an FGFR inhibitor (FGFR1, FGFR2, FGFR3 or FGFR4, e.g., pemigatinib, an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, vandetanib, ramucirumab, lenvatinib, ziv-aflibercept), a PARP inhibitor (e.g. olaparib, rucaparib, veliparib or niraparib), a JAK inhibitor (e.g., ruxolitinib, baricitinib, itacitinib), an IDO inhibitor (e.g., epacadostat, NLG919, or BMS-986205, MK7162), an LSD1 inhibitor, a TDO inhibitor, a PI3K-delta inhibitor (e.g., parsaclisib), a PI3K-gamma inhibitor such as PI3K-gamma selective inhibitor, a Pim inhibitor, a CSF1R inhibitor, a TAM receptor tyrosine kinases (Tyro-3, Ax1, and Mer), an adenosine receptor antagonist (e.g., A2a/A2b receptor antagonist), an HPK1 inhibitor, a chemokine receptor inhibitor (e.g. CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors, or combinations thereof.

In some embodiments, a multispecific binding agent as disclosed herein can be used in combination with inhibitors of PD-1 or inhibitors of PD-L1, e.g., an anti-PD-1 monoclonal antibody or an anti-PD-L1 monoclonal antibody, for example, nivolumab (Opdivo®), pembrolizumab (Keytruda®, MK-3475), atezolizumab, avelumab, cemiplimab, spartalizumab, camrelizumab, cetrelimab, toripalimab, sintilimab, AB122, JTX-4014, BGB-108, BCD-100, BAT1306, LZM009, AK105, HLX10, and TSR-042, AMP-224, AMP-514, PDR001, durvalumab, pidilizumab (Imfinzi®, CT-011), CK-301, BMS 936559, MPDL3280A, tislelizumab, BMS-935559, MED14736, FAZ053, KN035, CS1001, CBT-502, A167, STI-A101, BGB-A333, MSB-2311, HLX20, AUNP12, CA-170, BMS-986189, LY3300054, and MSB0010718C.

In some embodiments, a multispecific binding agent as disclosed herein can be used in combination with CTLA-4 inhibitors, e.g., an anti-CTLA-4 antibody, for example, ipilimumab (Yervoy®), tremelimumab and AGEN1884, or with phosphatidylserine inhibitors, for example, bavituximab (PGN401), or with antibodies to cytokines (IL-10, TGF-b, and the like), or with bispecific antibodies that bind to PD-L1 and CTLA-4 (e.g., AK104) or PD-1 and CTLA-4, or with other anti-cancer agents such as cemiplimab.

The additional agent may be a pharmaceutically acceptable salt, ester, amide, hydrate, and/or prodrug of any of these therapeutic agents described above or other agents.

It is understood that modifications which do not substantially affect the activity of the various embodiments described herein are also provided within the definition of the subject matter described herein. Accordingly, the following examples are intended to illustrate but not limit the present disclosure.

EXAMPLES

Example 1. Antibody Generation

Phage Display

To obtain binders for human CD47 and PD-L1, antibody discovery was conducted by phage display of human Fab libraries was carried out using standard protocols. The extracellular domain of human CD47 was purchased from Acro Biosystems (biotinylated human CD47 His-Avitag Acro Cat No. CD7-H82E9 and human CD47 His-tag Acro Cat No. CD7-5227). The extracellular domain of human PD-L1 was purchased from Acro Biosystems (human PD-L1-His tag Acro Cat. No. PD1H5229, biotinylated human PD-L1-His Avitag Acro Cat. No. PDL-H82E4). The non-biotinylated extracellular domain of CD47 or PD-L1 was biotinylated using EZ-Link NHS-PEG12-Biotin (ThermoScientific Cat. No. 21312) using standard protocol as needed. Phage clones were screened for the ability to bind to biotinylated human CD47 or biotinylated human PD-L1 by phage ELISA using standard protocols. Briefly, Fab-formatted phage libraries were constructed using expression vectors capable of replication and expression in phage (also referred to as a phagemid). Both the heavy chain and the light chain were encoded in the same expression vector, where the heavy chain was fused to a truncated variant of the phage coat protein pIII. The light chain and heavy chain-pIII fusion were expressed as separate polypeptides and assembled in the bacterial periplasm, where the redox potential enables disulfide bond formation, to form the antigen binding domain (Fab) of the candidate antibody.

The library was created using sequences derived from a specific human heavy chain variable domain (VH3-23) and a specific human light chain variable domain (Vk-1). Light chain variable domains within the screened library were generated with diversity was introduced into the VL CDR3 (L3) and where the light chain VL CDR1 (1) and CDR2 (L2) remained the human germline sequence. For the screened library, all three CDRs of the VH domain were diversified to match the positional amino acid frequency by CDR length found in the human antibody repertoire. The phage display heavy chain (SEQ ID NO:204) and light chain (SEQ ID NO:205) scaffolds used in the library are listed below, where a lower case "x" represents CDR amino acids that were varied to create the library, and bold italic represents the CDR sequences that were constant.

The sequence for SEQ ID NO: 204 was
EVQLVESGGGLVQPGGSLRLSCAASGFTFSXXXXXWVRQA

PGKGLEWVAXXXXXXXXXXXXXXXXXXRFTISADTSKNTAY

LQMNSLRAEDTAVYYCARXXXXXXXXXXXXXXXWGQGTLVT

VSSASTKGPSVFPLAPSSKSTSGGTAALGCLVKDYFPEPV

TVSWNSGALTSGVHTFPAVLQSSGLYSLSSVVTVPSSSLG

TQTYICNVNHKPSNTKVDKKVEPKSC.

The sequence for SEQ ID NO: 205 was
DIQMTQSPSSLSASVGDRVTITC*RASQSVSSAVA*WYQQKP

GKAPKLLIY*SASSLYS*GVPSRFSGSRSGTDFTLTISSLQP

EDFATYYCXXXXXXXXXFGQGTKVEIKRTVAAPSVFIFPP

SDSQLKSGTASVVCLLNNFYPREAKVQWKVDNALQSGNSQ

ESVTEQDSKDSTYSLSSTLTLSKADYEKHKVYACEVTHQG

LSSPVTKSFNRGEC.

Diversity was created through mutagenesis using degenerate DNA oligonucleotide primers to introduce diversity into VL CDR3 and VH CDR1 (H1), CDR2 (H2) and CDR3 (H3) to mimic the diversity found in the natural antibody repertoire, as described in more detail in Kunkel, TA (PNAS Jan. 1, 1985. 82 (2) 488-492), herein incorporated by reference in its entirety. Briefly, uracil-incorporated single-stranded circular DNA were prepared from isolated phage using standard procedures and Kunkel mutagenesis carried out to introduce diversity to the four CDRs. Chemically-synthesized DNA was then electroporated into TG1 cells, followed by recovery. Recovered cells were sub-cultured and infected with M13K07 helper phage to produce the phage library.

Phage panning was performed using standard procedures. Briefly, the first round of phage panning was performed with target immobilized on streptavidin magnetic beads which were subjected to approximately $1\times10^2$ phages from the prepared library in a volume of 1 mL in PBST-2% BSA. After a one-hour incubation, the bead-bound phage were separated from the supernatant using a magnetic stand. Beads were washed three times to remove non-specifically bound phage and were then added to ER2738 cells (5 mL) at $OD_{600}$ of approximately 0.6. After 20 minutes incubation at room temperature, infected cells were sub-cultured in 25 mL 2×YT+Ampicillin and M13K07 helper phage (final concentration of approximately $1\times10^{10}$ pfu/ml) and allowed to grow overnight at 37° C. with vigorous shaking. The next day, phage were prepared using standard procedures by PEG precipitation. Pre-clearance of phage specific to SAV-coated beads was performed prior to panning. The second round of panning was performed using the KingFisher magnetic bead handler with bead-immobilized CD47 or PD-L1 target antigen using standard procedures (round 3:100 nM CD-47 and 50 nM PD-L1, round 4: 50 nM CD-47 and 25 nM PD-L1). In total, 3-4 rounds of phage panning were performed to enrich in phage displaying Fabs specific for the target antigen. Target-specific enrichment was confirmed using polyclonal ELISA and individual clones were isolated and further verified by performing monoclonal phage ELISA. DNA sequencing was used to determine the sequence of the CDRs of isolated Fab clones containing a candidate antibodies.

To measure binding affinity in CD47 or PD-L1 binder discovery campaigns, the VL and VH domains identified in the phage screen described above were formatted into a bivalent monospecific native human full-length IgG1 architecture and immobilized to a biosensor on an Octet® (Pall ForteBio) biolayer interferometer as described in Example 2. Soluble antigens (e.g., CD47 or PD-L1) were then added to the system and binding was measured.

For experiments performed using bispecific antibodies in a B-Body format as described herein, VL variable regions of individual clones were formatted into Domain A and/or H, and VH region into Domain F and/or L of a bivalent B-Body in a BC1 format and/or a BC44 format as described herein.

Antibodies were affinity purified using anti-IgG10-CH1 resign by batch-mode gravity filtration. Clarified supernatants generated from 500 mL or 1000 mL transfection volumes were affinity purified using CaptureSelect™ CH1-XLAffinity Matrix bulk resin (ThermoFisher PN 194346201L). Supernatants from 1000 mL transfections were divided into 500 mL portions and all supernatants were transferred to 1 L sterile shake flasks. Resin was washed free of storage buffer using Dulbecco's PBS (pH 7.4, without Ca2+/Mg2+) by gravity filtration using disposable 10 mL columns (ThermoFisher Scientific PN 29924) and resuspended in PBS as a 50% slurry. Resin was aliquoted to shake flasks on a scale of 6 mL of 50% resin slurry per 500 mL of supernatant. Supernatant was incubated with resin for 1-2 hours at room temperature on a flask shaker operated at 170 RPM. Resin was captured on a gravity filtration column equipped with reservoir attachment (GE Healthcare Life Sciences PN 18-3216-03) and washed with 30 mL DPBS (10× settled resin bed volume). The resin bed was stringently washed with 30 mL with DPBS containing 500 mM NaCl. An additional wash was performed using 30 mL DPBS to reduce the concentration of NaCl prior to elution. Bound antibody was eluted from the gravity column using 9 mL 0.1 M sodium acetate (pH 3.5) into 2.25 mL neutralization buffer (2 M Tris-HCl (tris(hydroxymethyl)aminomethane hydrochloride), pH 7.5; Sigma PN T2944) contained in a 50 mL conical tube. Samples in neutralized elution buffer were dialyzed into DPBS overnight at 4° C. using a dialysis cassette with a 3.5 kDa molecular weight cutoff (Slide-A-Lyzer™; ThermoFisher Scientific, PN 66110).

For C40×P24, C40×P24s, and C56×P22 antibodies, affinity-purified antibodies from two separate lots were pooled prior to polishing. C40×P31.2, C59×P22, and C59×P31.2 antibodies utilized single lots for polishing. Each single or pooled lot was polished by strong cation exchange (SCX) using an AKTA pure fast protein liquid chromatography instrument (FPLC, GE Healthcare Life Sciences) running GE Unicorn™ v7.2 software. Aseptic techniques were used at all times. Prior to the day of purification, the entire flow-path (including the mobile phase reservoirs, samples loop, column, and switching valves) was cleaned using 500 mM NaOH in 20% ethanol by slowly pumping the cleaning solution through the instrument (0.1 mL/min for 2 hours). The instrument was then flushed with 20% ethanol and stored overnight. Just prior to polishing, a sample was buffer exchanged into 20 mM MES buffer [pH 6.0, MES=(2-(Nmorpholino)ethanesulfonic acid]. A buffer exchange method was employed using molecular weight cutoff (MWCO) filters with buffer exchange performed within 1-2 hours of polishing with storage at room temperature until polishing commenced. Approximately 35 mg of antibody (~4 mg/mL) in DPBS was added to a 15 mL, 30 kDa MWCO centrifugal spin filter (Amicon® Ultra 30) and brought up to volume with MES buffer. Sample was centrifuged at 4 k RPM for 15 minutes or until the original sample volume was achieved. MES buffer was added to bring the volume up to 15 mL and the sample was centrifuged again. This process was repeated three more times. 10 mL of low-endotoxin sample representing ~35 mg of protein at 3.5 mg/mL was loaded onto an MonoS 5/50 GL SCX column (0.5 cm×5 cm, 1 mL, 10 μm particle diameter; GE Healthcare Life Sciences, PN17516801) at 0.5 mL/min in mobile phase A (20 mM MES, pH 6.0) using 12 mL of mobile phase A. An additional 2 CV (column volume) of mobile phase A was used to remove unbound sample at a flow rate of 2.0 mL/min. 1.0 CV was 0.982 mL, as defined in GE Unicorn software for this particular column. Sample was eluted at 2.0 mL/min using a linear gradient from 0 to 30% mobile phase B (20 mM MES/1 M NaCl, pH 6.0) over 50 CV with fractions collected at 1-mL intervals. The system was washed with 7 CV of 100% B at 2.0 mL/min. Fractions from each major peak were pooled and assessed by non-reducing SDS-PAGE. The pooled sample was buffer exchanged into 1×DPBS as described in the procedure above, sterile filtered through a 0.2 pm filter, and re-tested for endotoxin using the ToxinSensor Chromogenic LAL Endotoxin Assay Kit from GenScript® (PN L00350).

This process was repeated several times until unpolished input material was exhausted. A master pool was created from purified material from each injection and was subjected to full analytics screening and freeze/thaw analysis.

Example 2. Screening and Selection

Antibodies to CD47 or PD-L1 were generated by phage display, for example, such as described in Example 1. For example, to determine qualitative binding affinity, bio-layer interferometry (BLI) was used to confirm the specific interaction of the antigens to the candidate antibodies obtained in Example 1.

The bivalent interaction of binders to biotinylated human CD47 or biotinylated human PD-L1 (see Example 1) immobilized on a streptavidin biosensor was monitored using Octet® (Pall ForteBio) instrument. To monitor monovalent interaction, full-length IgG molecule was immobilized to a Fc capture biosensor and its interaction with soluble antigen was monitored using an Octet® instrument.

Briefly, accurate measurements of affinity (such as Ko values) for the top PD-L1 antibodies was obtained using Octet® in a monovalent binding format. First, the antibodies were immobilized on an Fc capture sensor. In the next association step, the binding interaction of antigen to the immobilized IgG was measured. To obtain accurate kinetic constants, a dilution series involving of at least seven concentrations of the analyte (ranging from approximately 10 to 20× $K_D$ to 0.1× $K_D$ value, 2-fold dilutions) were measured in the association step. In the next dissociation step, the sensor was dipped into buffer solution that did not contain the analyte, where the bound analyte on the surface of the sensor was allowed to dissociate. Octet® kinetic analysis software was used to calculate the kinetic and equilibrium binding constants from the rate of association and dissociation curves. The analysis was performed using global curve fit where kinetic constants were derived simultaneously from all analyte concentration included in the experiment.

Example 3. Additional Screening and Selection

Bispecific antibodies that were selected for binding to CD47 and PD-L1, for example, such as those described in Examples 1 and 2, were evaluated for binding to various cell types expressing CD47 and/or PD-L1, including TCA CHO cells, MDA-MB-231 cells, Raji cells, and Jeko1 cells.

Exemplary bispecific antibodies C40×P24, C56×P22, C40×P31.2, C59×P22, and C59×P31.2 were tested using flow cytometry for binding to cells expressing CD47 and PD-L1 in various surface copy numbers. In some analyses, C40×P24s was also tested.

Cells were harvested at 70-90% confluence on the day of the assay. Cells were collected by centrifugation at 200×g for 5 minutes and media was removed. Cells were resuspended at $2\times10^6$ cells per mL in cold PBS. An 8-point antibody dilution series (2× concentration) was prepared in PBS to cover the expected binding affinities of the antibodies being tested. 50 μL per well of the antibody dilution was plated in a 96 well V-bottom plate (Costar 3897). 50 μL per well of cell suspension was added. Plates were placed at 4° C. for 45-60 minutes.

Cells were collected by centrifugation at 400×g for 7 minutes and primary antibody was removed. 50 μL per well of AF488 goat anti human IgG Fab (Jackson Immuno Research 109-547-003) at 1:100 dilution was added. Plates were placed at 4° C. for 30 minutes.

Cells were collected by centrifugation at 400×g for 7 minutes and secondary antibody was removed. Cells were resuspended in 50 μL per well of PBS and analyzed by flow cytometry. Binding curves were calculated using the mean fluorescence intensity (MFI) of the FITC fluorescence signal on the cells.

CD47- and PD-L1-expressing TCA CHO cells (CD47 PD-L1 TCA CHO cells) were used to screen antibodies for binding to CD47 and PD-L1. These cells have a CD47 surface protein copy number of approximately 612,000 and a PD-L1 surface protein copy number of approximately 674,000. For these experiments, the tested bispecific antibodies, each with a first binding domain for CD47 and a second binding domain for PD-L1, were in a BC1 format. Additional monospecific antibody constructs were prepared each with a first binding domain for CD47 or for PD-L1 and a second binding domain for an irrelevant target (designated as a "dummy" binding domain or "D"). Cells were harvested and assayed for binding as described above. Exemplary binding curves are depicted in FIGS. 1A-1D. Half maximal effective concentration ($EC_{50}$) of cell binding for the assayed antibodies are also summarized in Table 7. Monospecific antibodies having only one binding domain capable of targeting CD47 (C40×D) or PD-L1 (D×P24) were also assayed as controls and a secondary antibody-only sample was used as a negative control. Results indicate that the exemplary bispecific antibodies had a higher avidity for binding to CD47 PD-L1 TCA CHO cells than antibodies targeting only CD47 or PD-L1 (FIGS. 1A-1D).

TABLE 7

| $EC_{50}$ of Bispecific Antibody Binding to CD47 PD-L1 TCA CHO Cells | | | | |
|---|---|---|---|---|
| Antibody | C40 × P24 | C56 × P22 | C40 × P31.2 | C59 × P22 |
| $EC_{50}$ (nM) | 1.3 | 1.1 | 0.13 | 2.3 |

Bispecific antibody binding was tested in MDA-MB-231 cells expressing PD-L1 (PD-L1 MDA-MB-231 cells), which have a CD47 surface protein copy number of approximately 500,000 and a PD-L1 surface protein copy number of approximately 1,500,000. For these experiments, the tested bispecific antibodies, each with a first binding domain for CD47 and a second binding domain for PD-L1, were in a BC44 format as described herein. Cells were harvested and assayed for binding as described above. Exemplary binding curves are depicted in FIGS. 2A-2E. $EC_{50}$ of cell binding for indicated antibodies are listed in Table 8.

TABLE 8

| $EC_{50}$ of Bispecific Antibody Binding to PD-L1 MDA-MB-231 Cells | | | | | |
|---|---|---|---|---|---|
| Antibody | C40 × P24 | C56 × P22 | C40 × P31.2 | C59 × P22 | C59 × P31.2 |
| $EC_{50}$ (nM) | 3.1 | 1.2 | 0.69 | 1.5 | 2.5 |

Bispecific antibody binding was tested in Jeko1 cells expressing PD-L1 (Jeko-PD-L1 cells). These cells have a CD47 surface protein copy number of approximately 200,000 to 500,000 and a PD-L1 surface protein copy number of approximately 100,000 to 300,000. For these experiments, the tested exemplary bispecific antibodies, each with a first binding domain for CD47 and a second binding domain for PD-L1, were in a BC44 format as described herein. $EC_{50}$ of cell binding for the assayed antibodies are listed in Table 9.

TABLE 9

| $EC_{50}$ of Bispecific Antibody Binding to Jeko-PD-L1 Cells | | | | |
|---|---|---|---|---|
| Antibody | C40 × P24 | C56 × P22 | C40 × P31.2 | C59 × P31.2 |
| $EC_{50}$ (nM) | 0.703 | 0.218 | 0.227 | 0.256 |

Example 4. Functional Assays

Bispecific antibodies that were selected for binding to CD47 and PD-L1, for example, such as those described in Examples 1-3, were evaluated for inhibition of a CD47/SIRPα signaling and PD-1/PD-L1 signaling in cell types expressing CD47 and/or PD-L1, including TCA CHO cells, MDA-MB-231 cells, Raji cells, and Jeko1 cells.

To test the ability of bispecific antibodies to inhibit CD47/SIRPα signaling, bispecific antibodies in a BC44 format as described herein were assayed using a CD47/SIRPα Signaling Bioassay Kit (93-1135C19, Eurofins DiscoverX) using the manufacturer protocol. Assays were conducted separately using MDA-MB-231-PD-L1 and Jeko-PD-L1 target cells.

The signaling assays are engineered to co-express a ProLink™ (PK) tagged immune checkpoint receptor and an Enzyme Acceptor (EA) tagged SH2 domain. Ligand engagement leads to receptor activation and phosphorylation, resulting in SH2-EA recruitment to the receptor, and forcing complementation of the two β-galactosidase enzyme fragments (EA and PK). The resulting functional enzyme hydrolyzes substrate to generate a chemiluminescent signal. Blocking of the ligand engagement leads to a drop in chemiluminescent signal.

Briefly, 30,000 target cells were added to wells in 40 μL Cell Plating Reagent in White Bottom 96-well Plates (Corning 3917). Antibody dilutions were prepared in cell plating reagent and 20 μL of antibody dilution were added to cells. Next, 10,000 freshly thawed SIRPα Jurkat cells in 40 μL Cell Plating Reagent were added to each well. Plates were incubated for 24 hours at 37° C. Following incubation, 10 μL BioAssay Reagent 1 was added to wells and plates were incubated for 15 minutes at room temp in the dark. Then, 40 μL BioAssay Reagent 2 was added to wells and plates were incubated for 1 hour at room temperature in the dark. Plates were read on a ClarioStar® Plate Reader (BMG Labtech).

Figure 3:
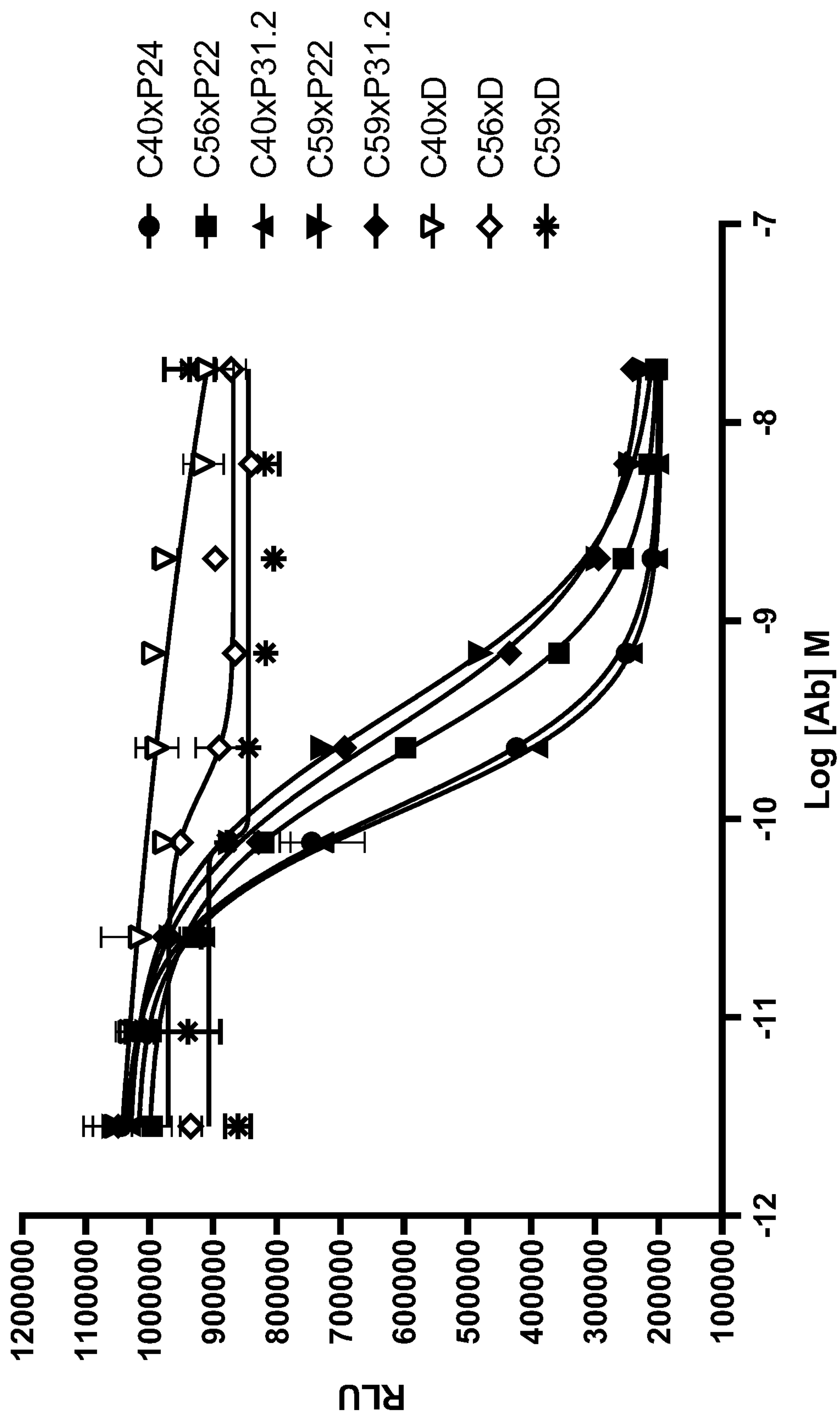
FIG. 3 illustrates exemplary results from CD47/SIRPα inhibiting assays, showing log molar concentration of antibody (Log [Ab]M) on the X-axis and relative light unit (RLU) on the Y-axis for C40×P24, C56×P22, C40×P31.2, C59×P22, and C59×P31.2, compared to control antibodies C40×D, C56×D, and C59×D, further described in Example 4.

Exemplary results of the CD47/SIRPα signaling assay are shown in FIG. 3. Antibodies having only one binding site capable of targeting CD47 (C40×D, C56×D, and C59×D) were assayed as controls and showed minimal inhibition. $IC_{50}$ values for assays in MDA-MB-231-PD-L1 are shown in Table 10. Results indicate that all tested exemplary bispecific antibodies showed a reduction in the chemiluminescent signal compared to the antibodies targeting only CD47. Thus, the assayed bispecific antibodies efficiently blocked the engagement of CD47 ligand on the SIRPα receptor, inhibiting signaling.

TABLE 10

CD47/SIRPα Inhibition Assay in PD-L1 MDA-MB-231 Cells

| Bispecific Antibody | $IC_{50}$ (nM) |
|---|---|
| C40 × P24 | 0.112 |
| C56 × P22 | 0.218 |
| C40 × P31.2 | 0.108 |
| C59 × P22 | 0.350 |
| C59 × P31.2 | 0.266 |

The ability of bispecific antibodies to inhibit CD47/SIRPα signaling in Jeko-PD-L1 cells was also determined. The CD47/SIRPα signaling assay was conducted in these cells as described above. $IC_{50}$ values for the assay in Jeko target cells are shown in Table 11. These results show that the assayed exemplary bispecific antibodies inhibit CD47/SIRPα signaling, with the C40×P24 (silent Fc) bispecific antibody showing the most efficient inhibition of CD47/SIRPα signaling of the several tested in these assays.

TABLE 11

CD47/SIRPα Inhibition Assay in Jeko cells and Jeko-PD-L1 cells

| Bispecific Antibody | JeKo-PD-L1 Cells $IC_{50}$ (nM) |
|---|---|
| C40 × P24 | 1.26 |
| C40 × P24s | 0.26 |
| C56 × P22 | 1.20 |

s = silent Fc

To test the ability of bispecific antibodies to block PD-1/PD-L1 signaling, bispecific antibodies were assayed using a PD-1/PD-L1 Signaling Bioassay Kit (93-1104Y19-00117, Eurofins DiscoverX) using the manufacturer protocol. The assay was conducted in PD-L1 MDA-MB-231 cells, PD-L1 Jeko cells, and Raji-PD-L1 cells.

Briefly, 40 μL of target cells (30,000 cells per 40 μL) was added to each well of a white 96-well plate in Cell Plating Reagent 0 (CPO). Plates were incubated at 37° C. overnight. PathHunter® PD-1 Jurkat cells were thawed for overnight recovery from thaw by adding 9.6 mL of pre-warmed Cell Plating Reagent (CPO) to a T25 flask, removing two cryovials of PD-1 Jurkat cells from liquid nitrogen, and thawing the pellet by immediately adding 1 mL of pre-warmed CPO from the T25 flask to the cryovial. Cells were mixed by gently pipetting up and down several times to break up any clumps. The cell suspension was transferred to the T25 flask containing the remaining CPO and any media/suspension left in the cryovial was removed to ensure complete recovery of all the cells from the vial. Cells were incubated at 37° C. overnight.

Following the incubation, 20 μL of bispecific antibody was added to each well and plates were incubated at 37° C. for 1 hour. 40 μL of PathHunter® PD-1 Jurkat cells in CPO was added to each well of the 96-well plate and the plate was incubated at room temp in the dark for 1 hour. Then, 10 μL of PathHunter® Bioassay Detection Reagent 1 was added to each well and plates were incubated for 15 minutes at room temperature in the dark. Next, 40 μL of PathHunter® Bioassay Detection Reagent 2 as added to each well of the assay plate and the plate was incubated for 3 hours at room temperature in the dark. Plates were analyzed on a ClarioStar® Plate Reader (BMG Labtech).

Figure 4:
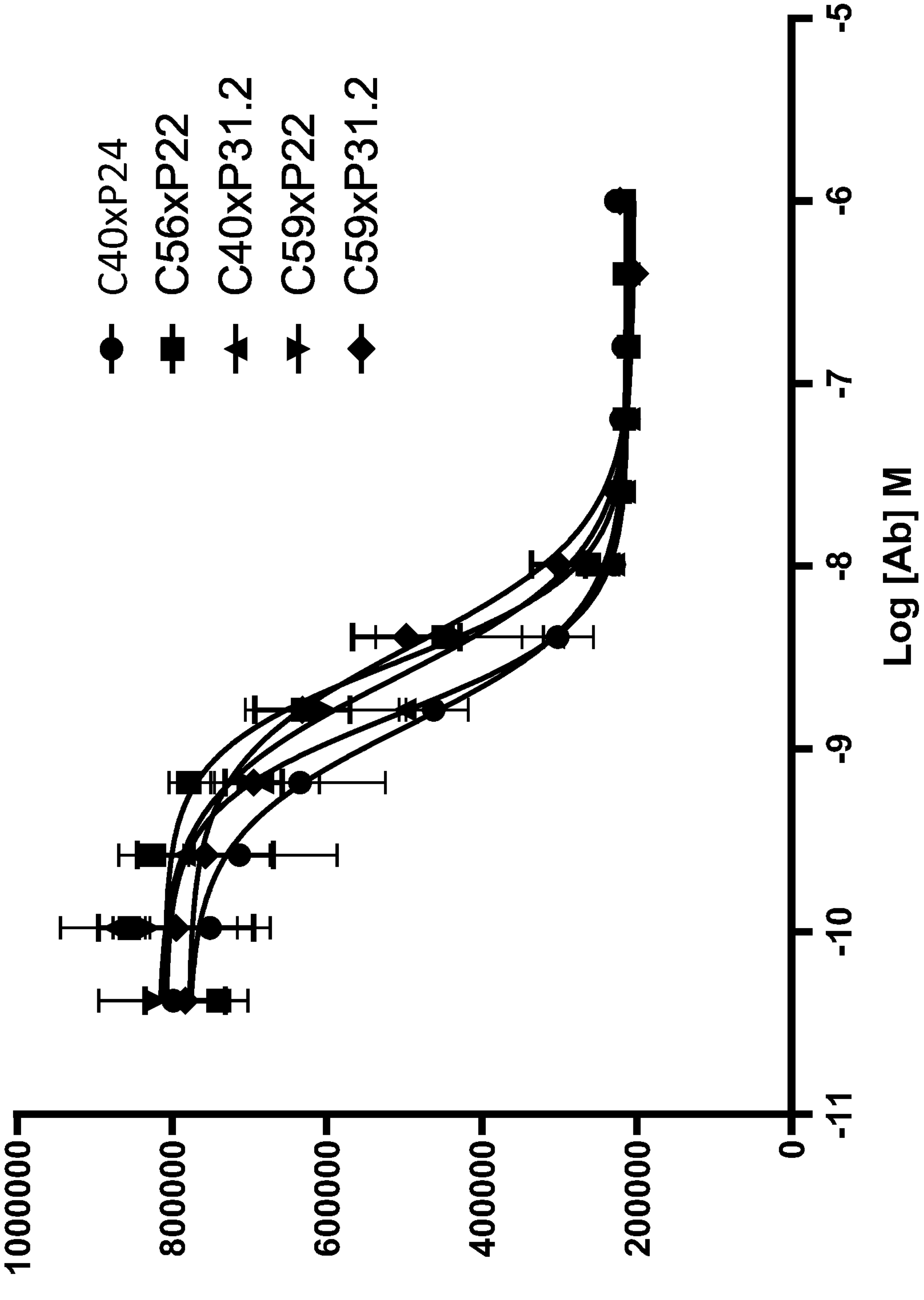
FIG. 4 illustrates exemplary results from PD-L1/PD-1 inhibiting assays, showing log molar concentration of antibody (Log [Ab]M) on the X-axis and relative light unit (RLU) on the Y-axis for C40×P24, C56×P22, C40×P31.2, C59×P22, and C59×P31.2, further described in Example 4.

Exemplary results of the PD-1/PD-L1 checkpoint signaling assay in PD-L1 MDA-MB-231 cells are shown in FIG. 4. $IC_{50}$ values for the assay in PD-L1 MDA-MB-231 cells and Jeko-PD-L1 cells are shown in Table 12. These results show that in JeKo-PD-L1 cells, exemplary bispecific antibodies C40×P31.2, C59×P22, and C59×P31.2 resulted in lower $IC_{50}$ values than other tested bispecific antibodies. In MDA-MB-231-PD-L1 cells, bispecific antibody C40×P24 (silent Fc) showed a higher $IC_{50}$ than other bispecific antibodies tested.

TABLE 12

PD-1/PD-L1 Inhibition Assay in MDA-MB-231 PD-L1 Cells and Jeko-PD-L1 Cells

| $IC_{50}$ (nM) | MDA-MB-231 PD-L1 | Jeko-PD-L1 |
|---|---|---|
| C40 × P24 | 1.3 | 0.275 |
| C40 × P24 | 14.7 | 0.274 |
| C56 × P22 | 3 | 1.99 |
| C40 × P31.2 | 1.5 | 0.0115 |
| C59 × P22 | 2.5 | 0.0481 |
| C59 × P31.2 | 3.7 | 0.0268 |

s = silent Fc

To determine the effect of PD-L1 copy number on the ability of bispecific antibodies to inhibit PD-1/PD-L1 signaling, JeKo cells and JeKo-PD-L1 cells were compared. The PD-1/PD-L1 Checkpoint Signaling Assay was conducted in these cells, as described above. $IC_{50}$ values for assays in Jeko-PD-L1 target cells are shown in Table 12 above. $IC_{50}$ values for assays in Jeko cells were below the measurement threshold, indicating that the inhibitory effect of the bispecific antibody can be affected by the total number of ligand and receptor available on the cells.

Example 5. Additional Functional Assays

Bispecific antibodies that were selected for binding to CD47, for example, such as those described in Examples 1-3, were evaluated for their effect in blocking interaction of CD47 ligand with SIRPα receptor and in promoting phagocytosis. For example, a primary M2 macrophage phagocytosis assay was conducted to determine the effect of bispecific antibodies on phagocytosis. JeKo-PD-L1 target cells were labeled with pHrodo Red Cell Labeling Kit for Flow Cytometry (A10026, ThermoFisher Scientific) and analyzed by flow cytometry according to the manufacturer protocol. Using this method, labeled target cells show little or no fluorescence while apoptotic cells remain in the pH 7.4 extracellular environment. Following CD47 receptor activation, phagocytosis is initiated by formation of the phagocytic cup. After engulfment of labeled cells by pinching off, the cell is within the acidic environment of the phagosome (pH 4.5-5.5), which leads to increased fluorescence.

Following labeling of target cells, cells were incubated with bispecific antibodies in a BC44 format as described herein to allow binding to cell surface CD47. Bispecific antibody-bound labeled cells were then co-cultured with M2 macrophage cells in the Incucyte live cell imaging system (Sartorius) and phase and fluorescent images were taken every 30 minutes for 24 hours.

Figure 5A:
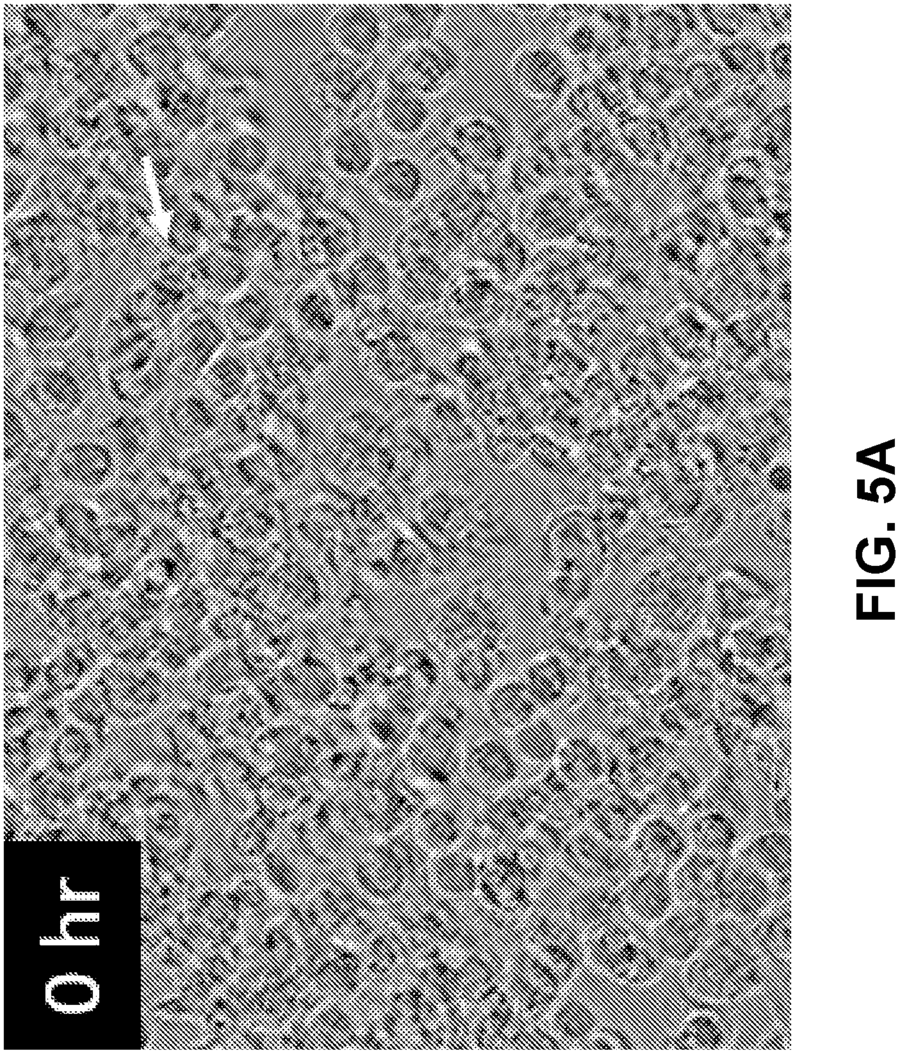
FIGS. 5A-5G illustrate exemplary results from phagocytosis assays, further described in Example 5.
Figure 5B:
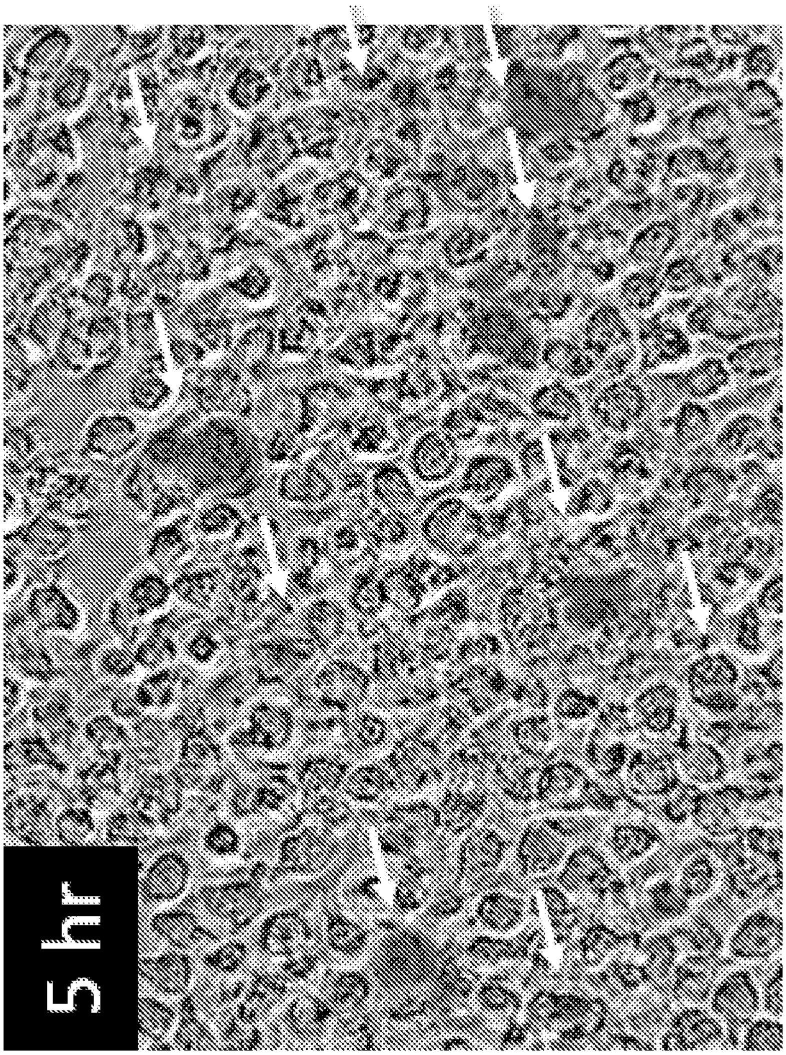
Figure 5C:
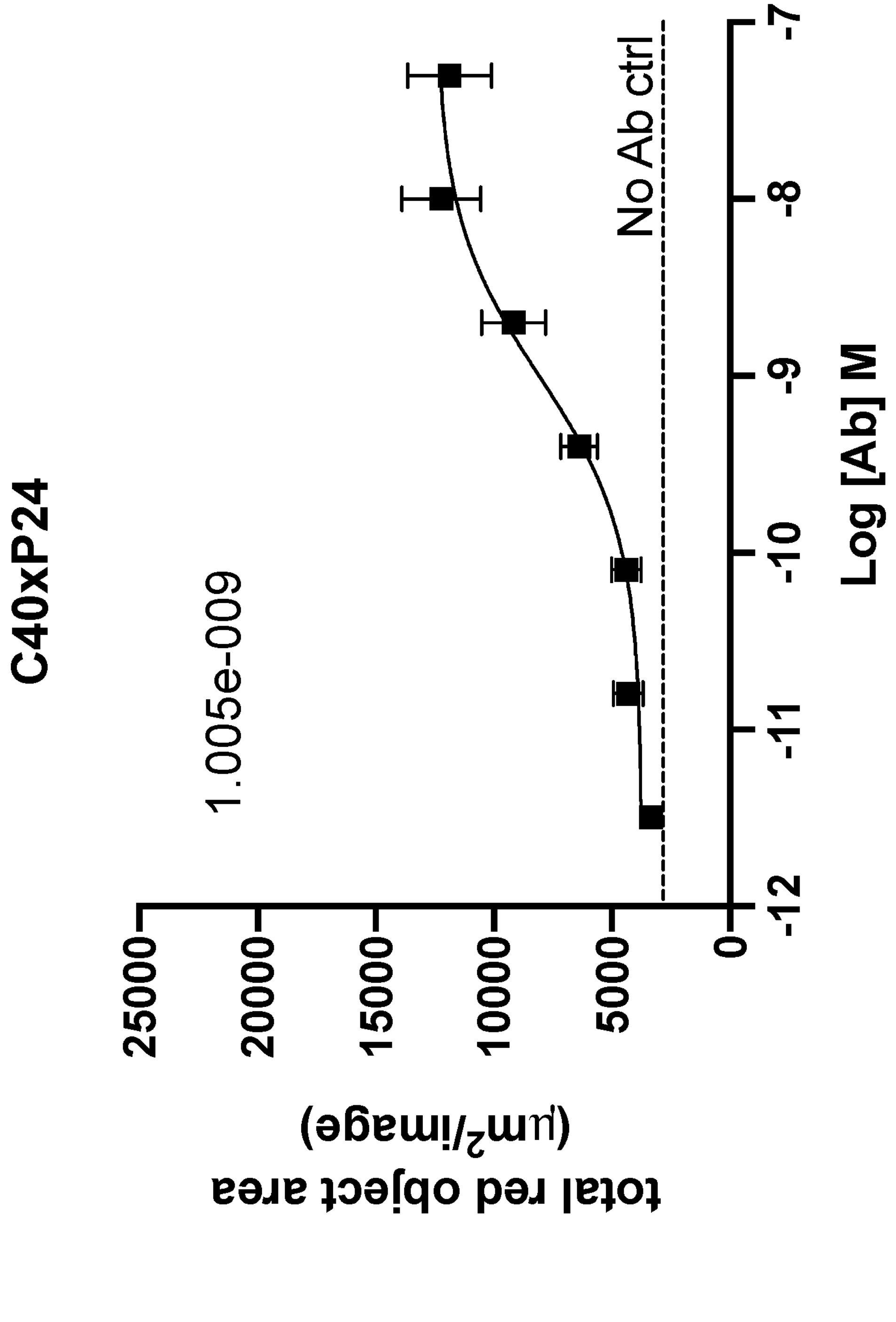
Figure 5D:
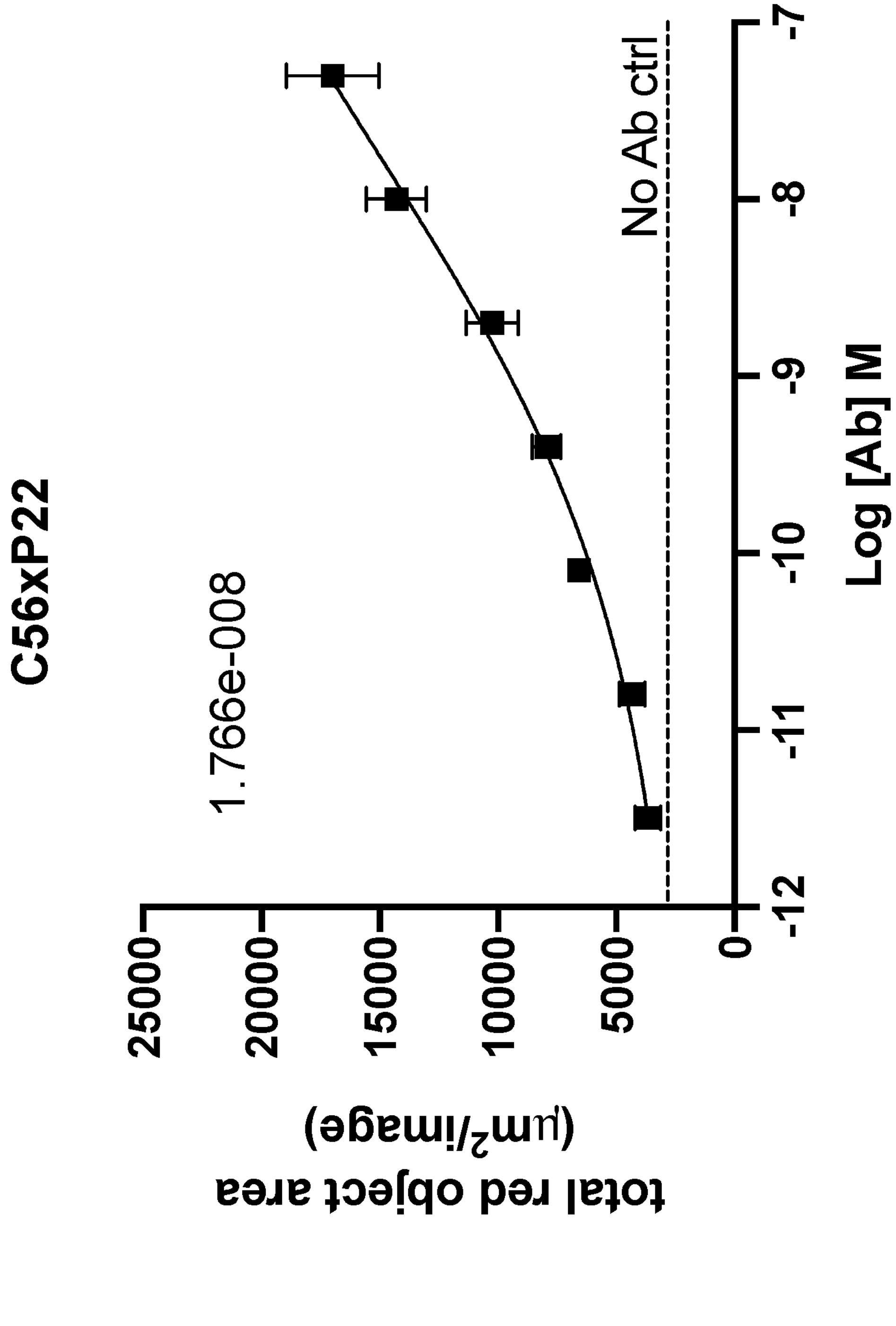
Figure 5E:
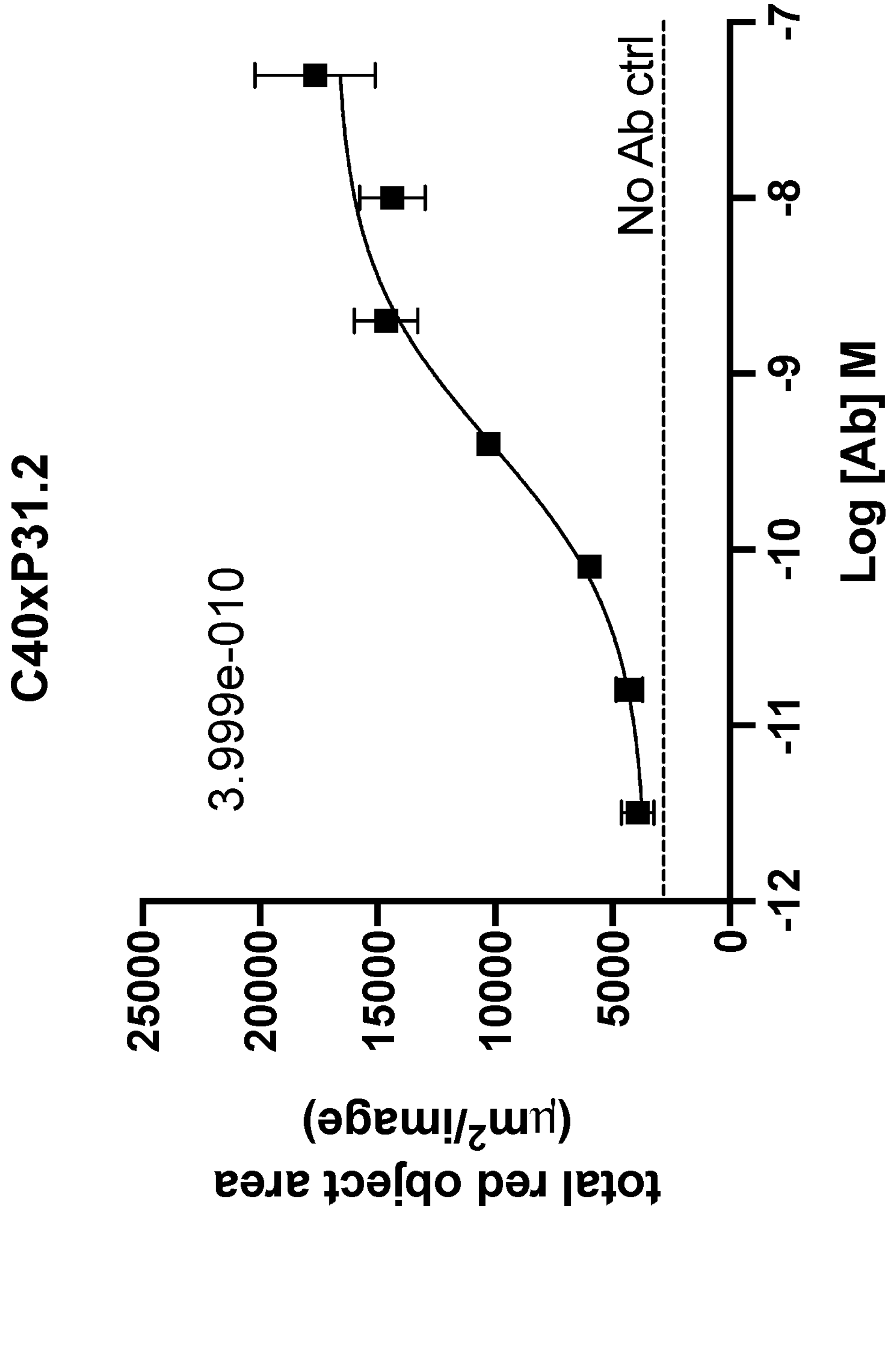
Figure 5F:
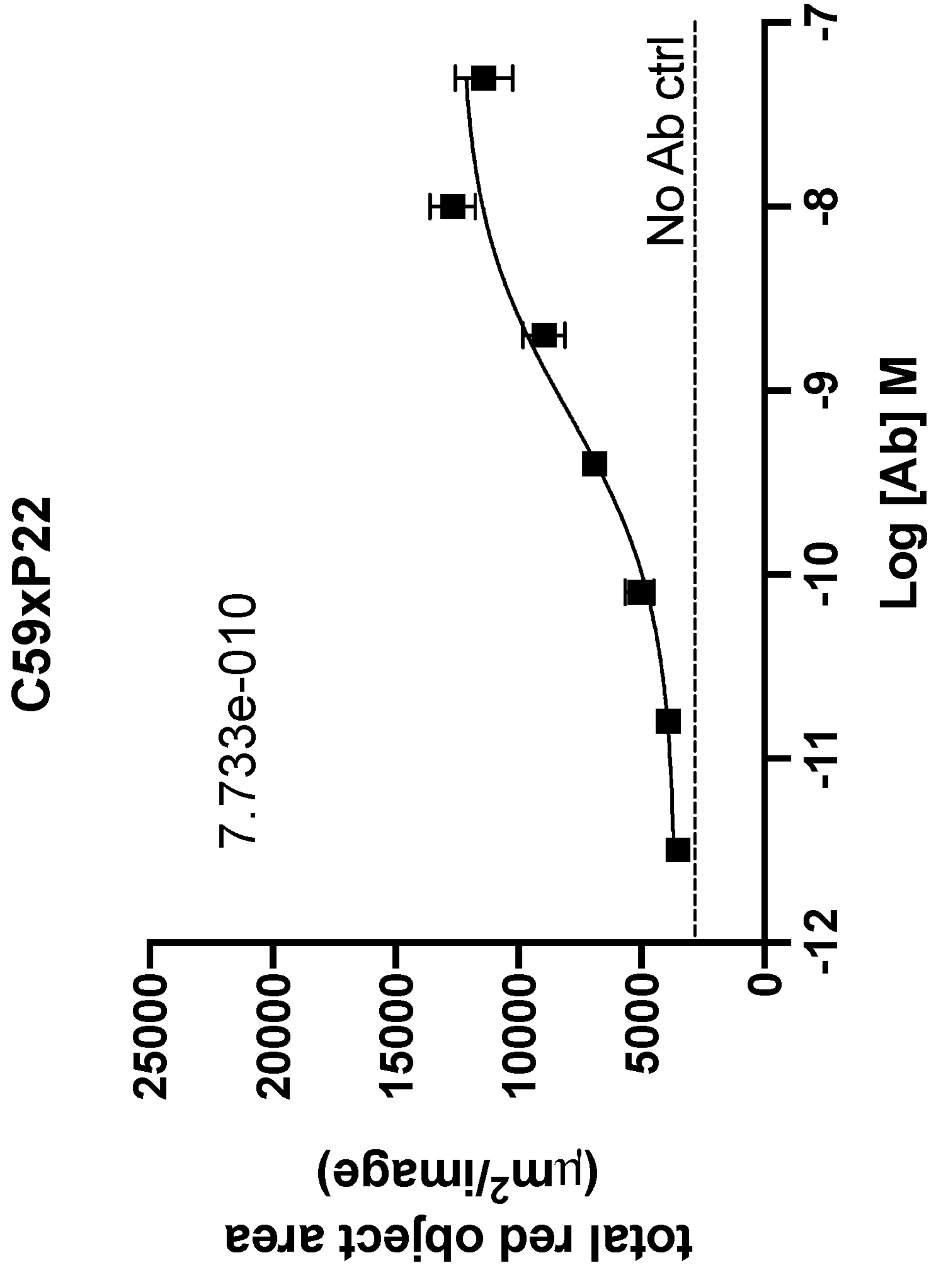
Figure 5G:
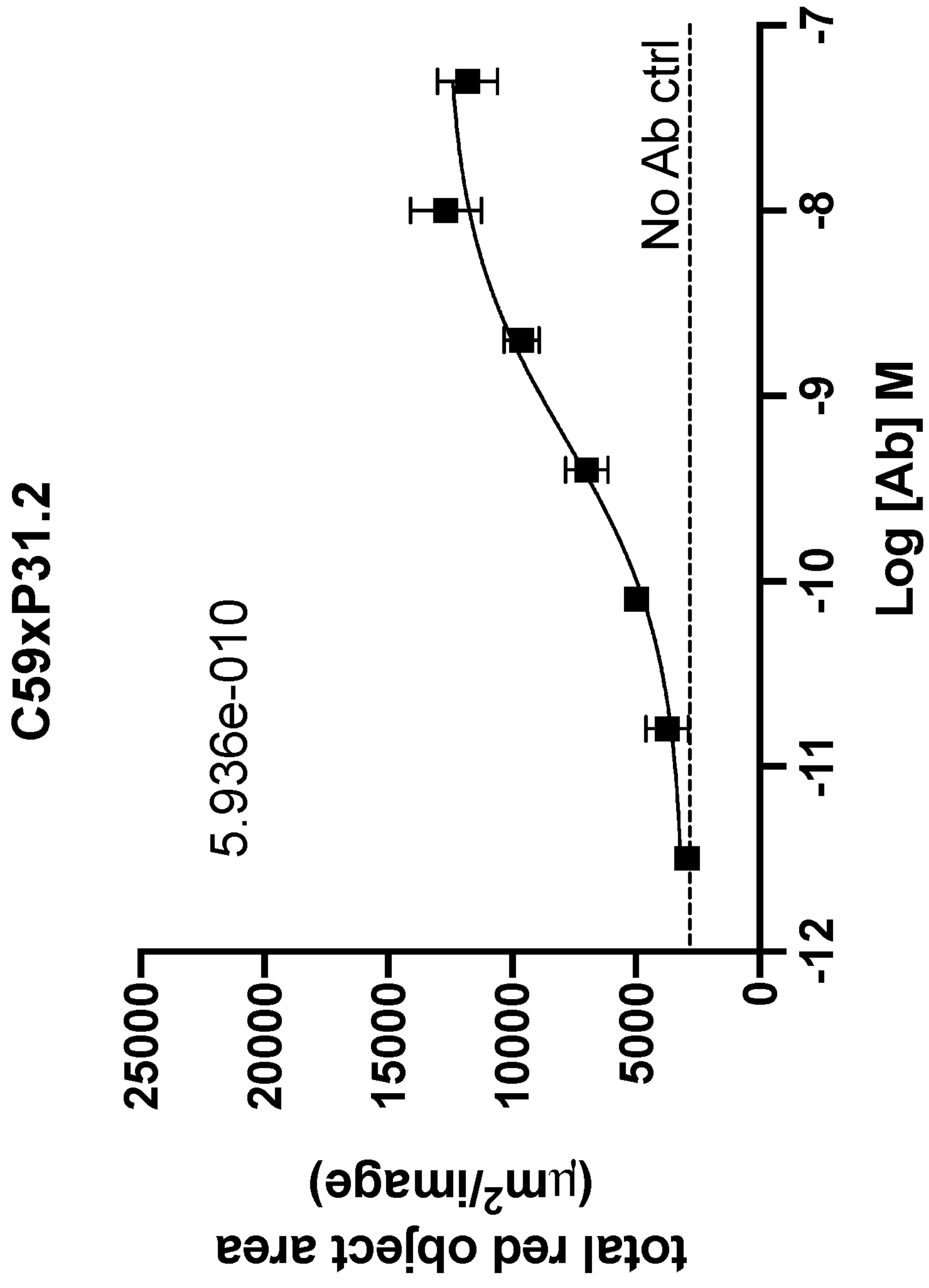

Exemplary fluorescent microscopy images of labeled JeKo-PD-L1 cells at 0 hours and 5 hours after co-culturing with M2 macrophages are shown in FIGS. 5A and 5B. Exemplary results are shown in FIGS. 5C-5G for exemplary bispecific antibodies C40×P24 (FIG. 5C), C56×P22 (FIG. 5D), C40×P31.2 (FIG. 5E), C59×P22 (FIG. 5F), and C59×P31.2 (FIG. 5G) after 5 hours co-incubation. Results indicate that after five hours of co-incubation, there is an increase in phagocytosis (e.g., phagocytic activity or function) of JeKo-PD-L1 cells by M2 macrophages in the presence of all tested bispecific antibodies compared to the control with no antibody.

The effect of bispecific antibodies on phagocytosis was also tested using A375 target cells, which have a CD47 surface copy number of approximately 200,000 and a PD-L1 surface copy number of approximately 25,000. Cells were labeled with pHrodo Red Cell Labeling Kit for Flow Cytometry and analyzed by flow cytometry as described above.

Figure 6A:
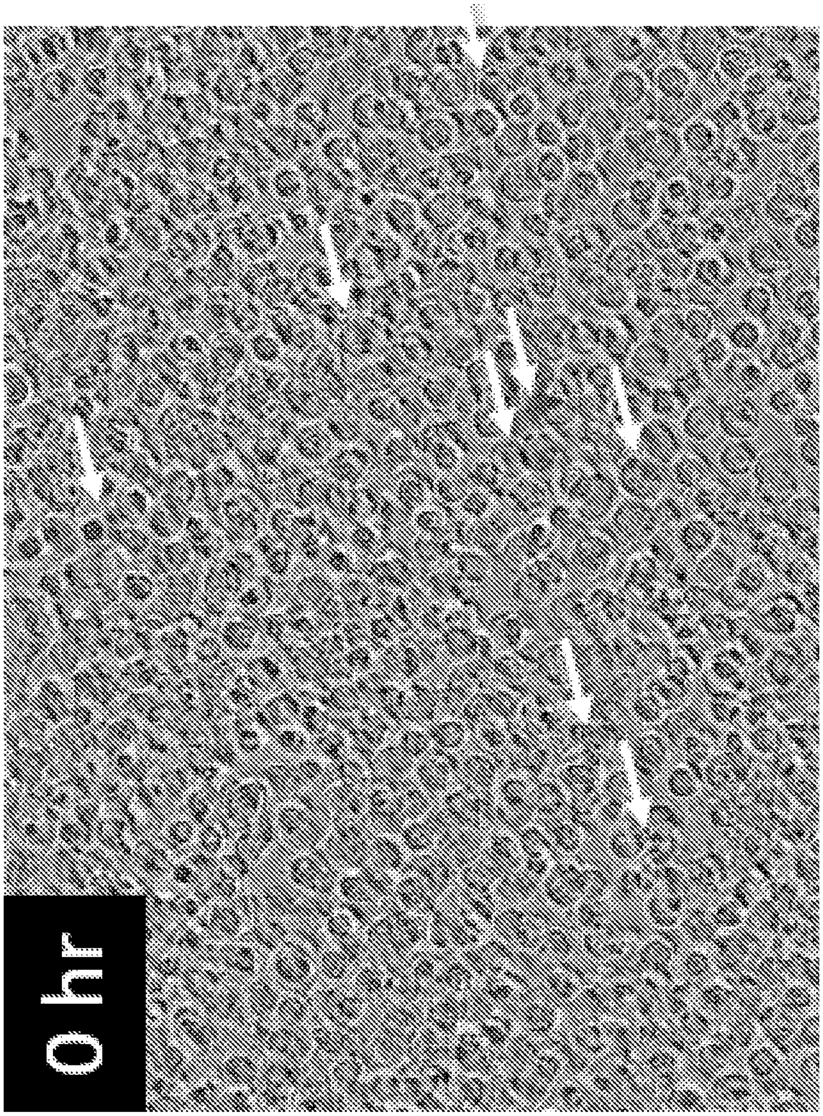
FIGS. 6A-6G illustrate exemplary results from additional phagocytosis assays, further described in Example 5.
Figure 6B:
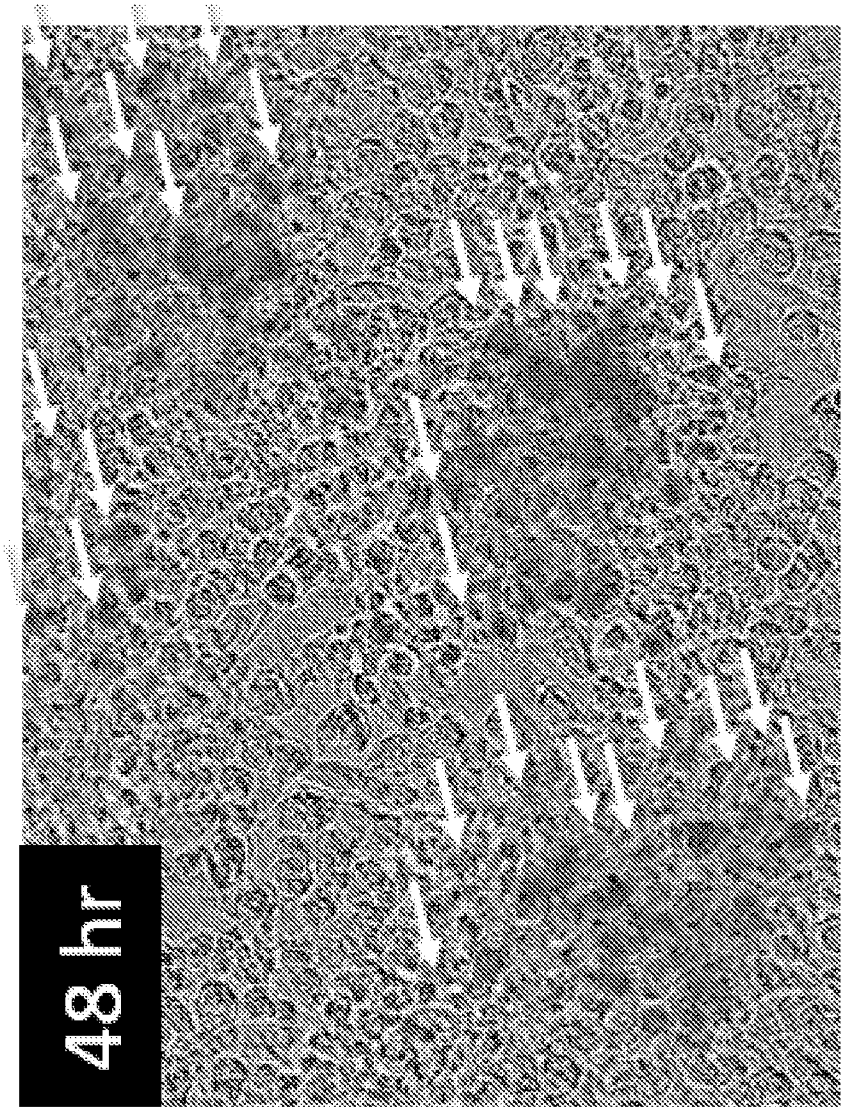
Figure 6C:
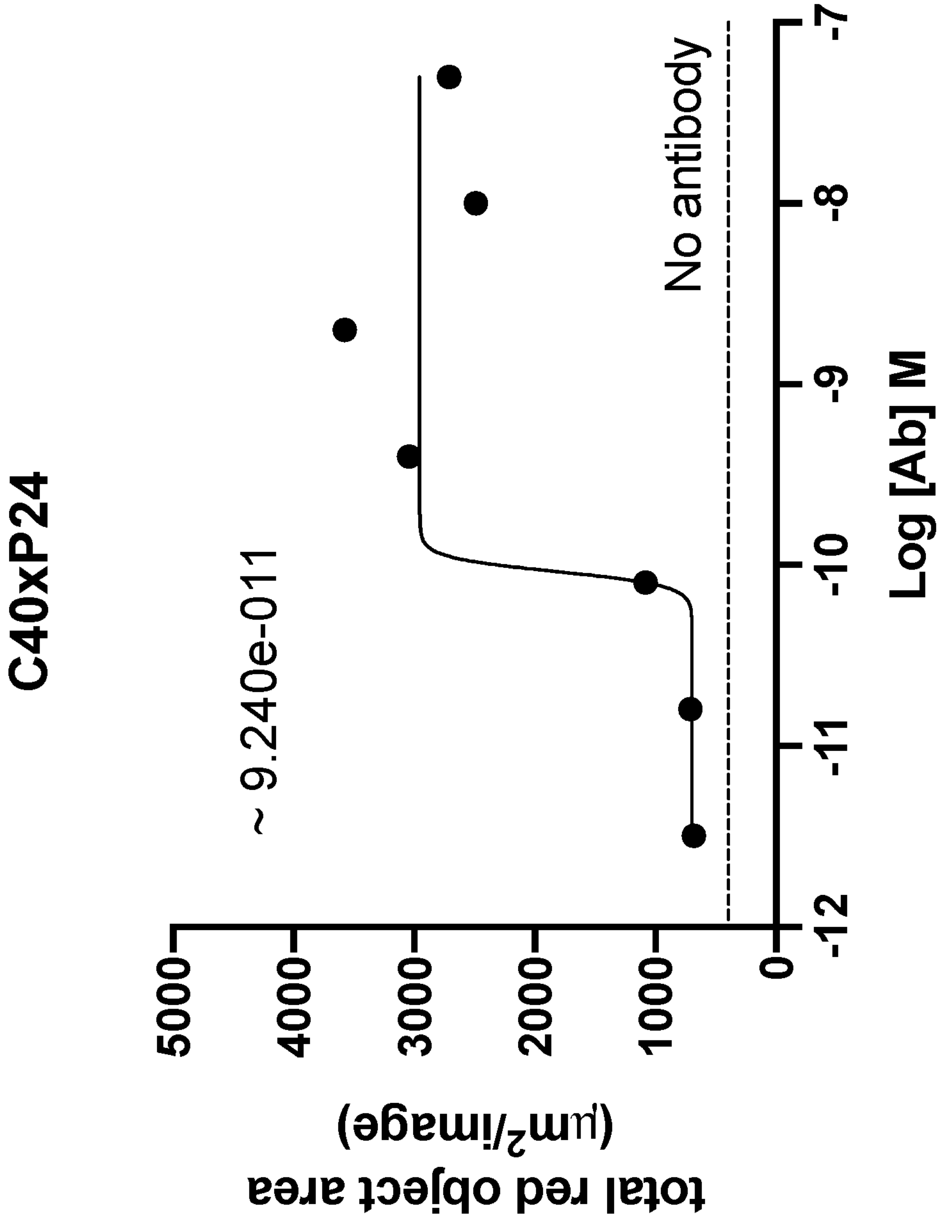
Figure 6D:
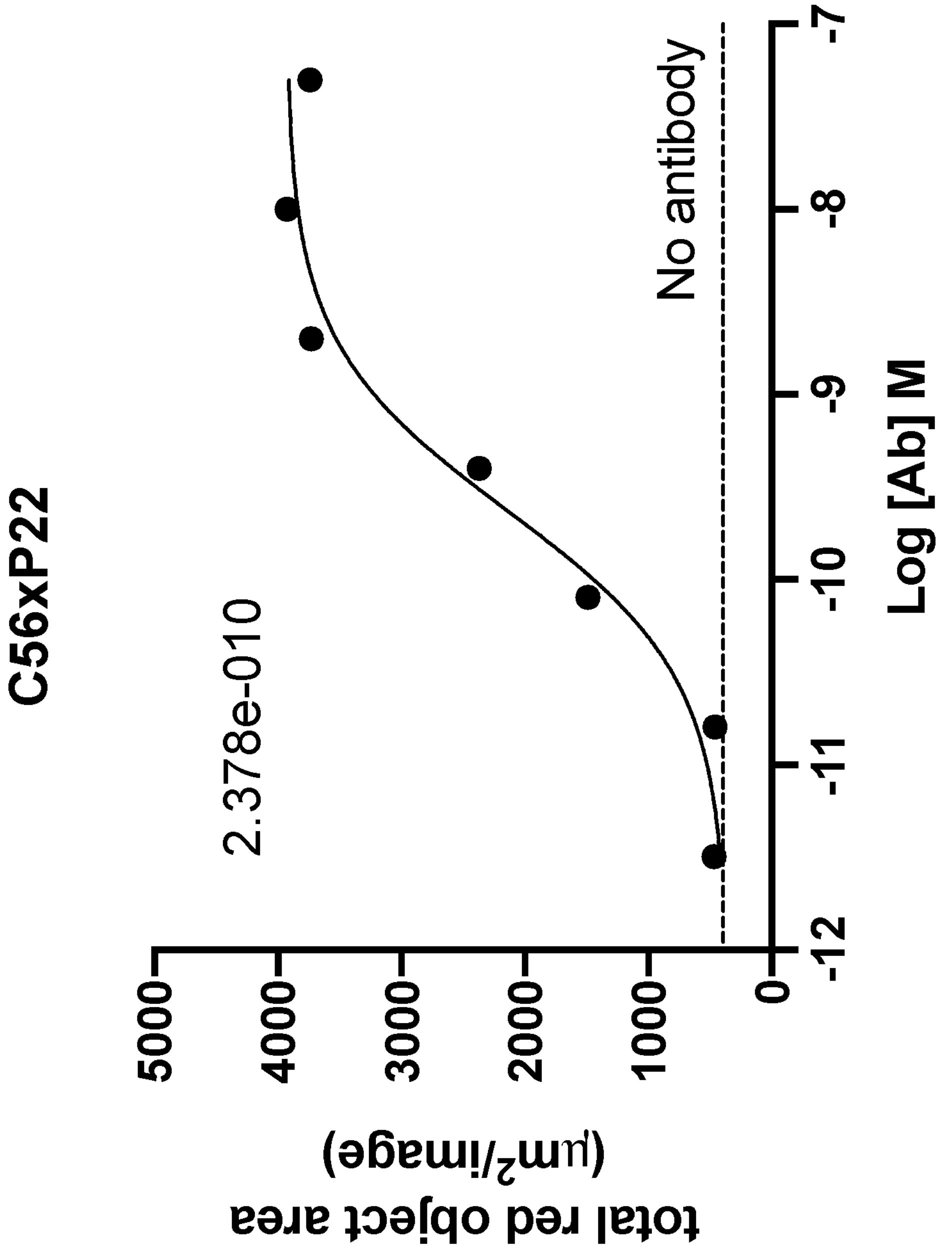
Figure 6E:
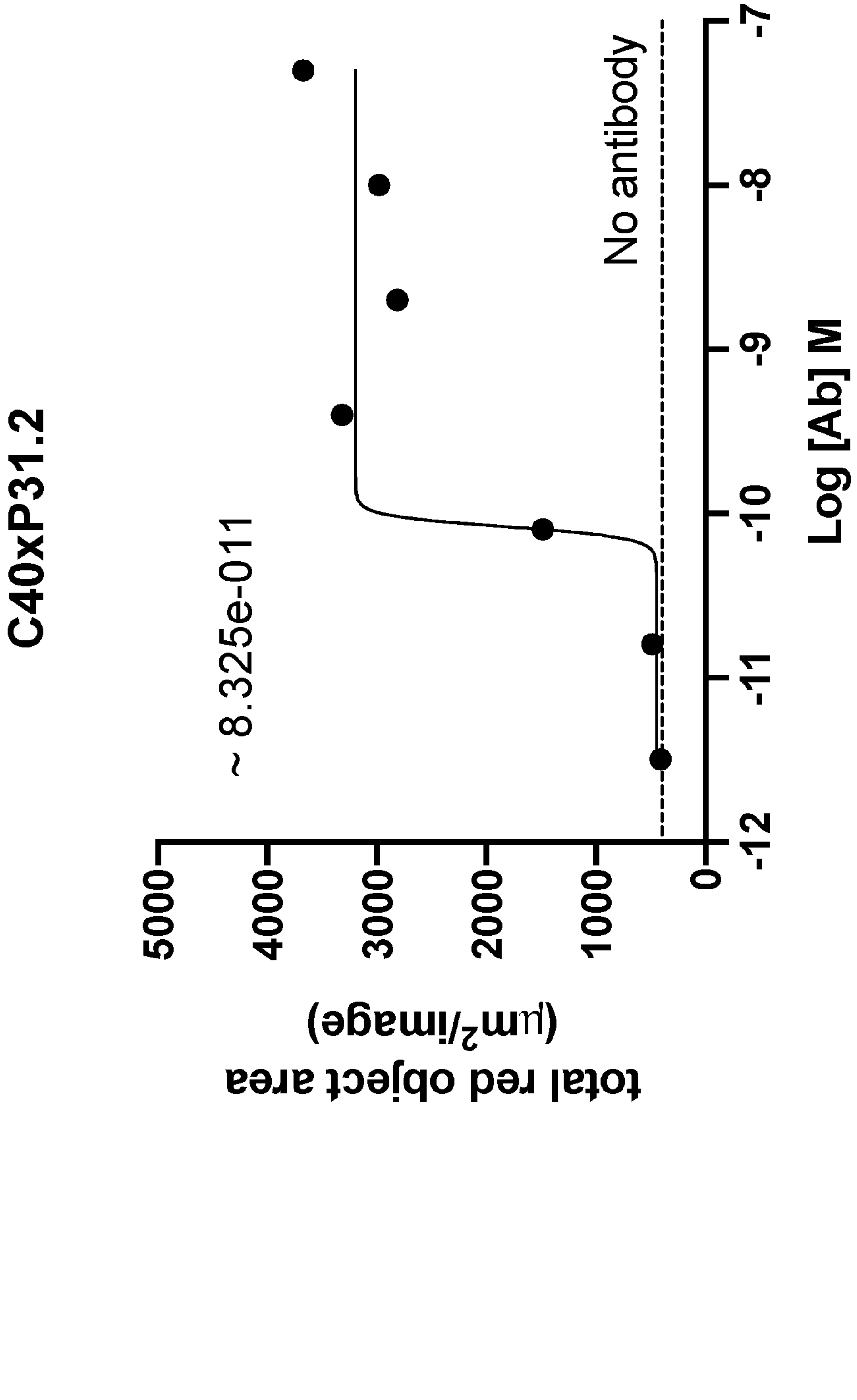
Figure 6F:
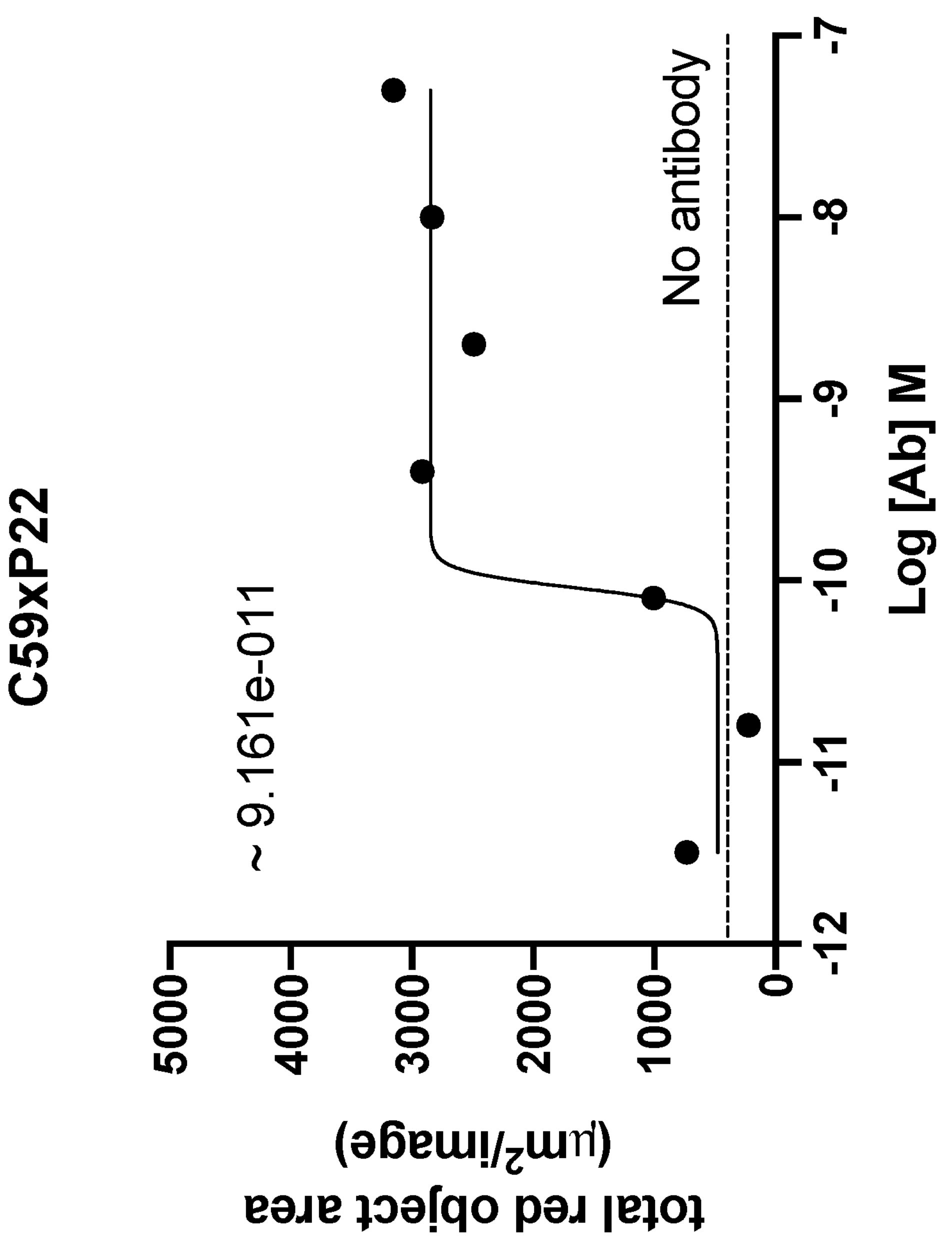
Figure 6G:
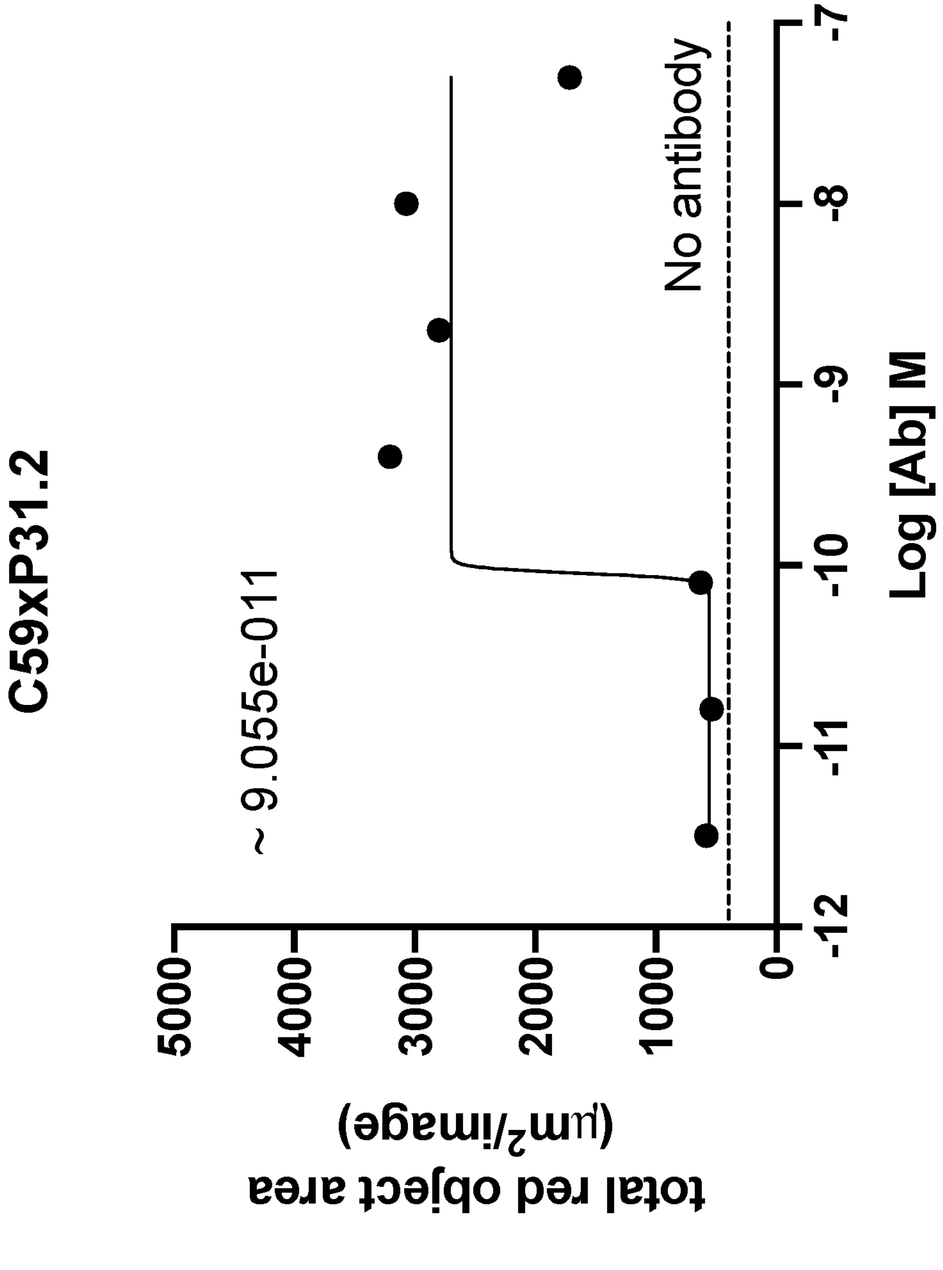

Exemplary fluorescent microscopy images of labeled A375 cells at 0 hours and 48 hours after co-culturing with M2 macrophages are shown in FIGS. 6A and 6B, respectively. Exemplary results are shown in FIGS. 6C-6G for exemplary bispecific antibodies C40×P24 (FIG. 6C), C56×P22 (FIG. 6D), C40×P31.2 (FIG. 6E), C59×P22 (FIG. 6F), and C59×P31.2 (FIG. 6G) after 48 hours co-incubation. Results indicate that after 48 hours of co-incubation, there is an increase in phagocytosis of A375 cells by M2 macrophages in response to all tested exemplary bispecific antibodies compared to the controls with no antibody.

Example 6. Red Blood Cell Binding Assay

Bispecific antibodies that were selected for binding to CD47 and PD-L1, for example, such as those described in Examples 1-3, were evaluated for their binding to red blood cells. Anti-CD47 antibodies may cause red blood cell agglutination, which limits their therapeutic applications. Bispecific antibodies disclosed herein were tested using a red blood cell binding assay to determine the effect on red blood cell agglutination.

100,000 fresh human erythrocyte cells (SER-10MLRBC-SDS, Zen-Bio) were transferred to each well of a V-bottom plate. Plates were centrifuged at 500×g for 5 minutes at room temperature and supernatant was discarded. Bispecific antibodies in a BC44 format as described herein were diluted in BD Stain Buffer (BD Biosciences) and transferred 100 μL to each well of the plate. Plates were incubated for 45 minutes at 4° C. Following incubation, 100 μL PBS was added to each well, plates were centrifuged at 500×g for 5 minutes at room temperature, and supernatant was discarded.

Next, 100 μL anti-human IgG Fab Alexa Fluor® 488 (Jackson Immuno Research 109-547-003) diluted at 1:100 in BD Stain Buffer was added to each well. Plates were incubated for 45 minutes at 4° C., centrifuged at 500×g for 5 minutes at room temperature, and supernatant was discarded. Cells were washed once with 200 μL/well PBS and resuspended in 50 μL/well PBS. Samples were analyzed by flow cytometry on a Sartorius iQue Screener Plus instrument (Sartorius).

All tested exemplary bispecific antibodies resulted in no red blood cell binding compared to a positive control, which is predictive of little interaction with red blood cells in vivo.

Example 7. In Vivo Studies

To evaluate in vivo therapeutic efficacy, bispecific antibodies were tested in a syngeneic MC38-hPDL1/hCD47 murine colon carcinoma model in female B-hPD-L1/hSIRα/hCD47 mice. The efficacy of the treatment was evaluated based on tumor volume (TV) changes. The overall health of animals was also evaluated based on body weight (BW).

Mice were homozygous B-hPD-L1/hSIRPα/hCD47 (h/h; h/h; h/h) mice in a C57BL/6 background). The strain genotype was C57BL/6-$Cd274^{tm1(CD274)}Sirp\alpha^{tm1(SIRPA)}$ $Cd47^{tm1(CD47)}$/Bcgen. These mice are a triple knock-in mouse model generated by crossing 3 genetically engineered mouse strains B-hPD-L1, B-hSIRPA and B-hCD47 mice to triple homozygosity. The extracellular region of endogenous PD-L1 (exon 3), Sirpa (exon 2) and CD47 (exon 2) have been replaced with the respective human counterparts in C57BL/6 mice.

Animals were housed in a specific pathogen-free barrier in individual ventilated cages. The animals were acclimatized for 7 days before the experiment. Temperature and humidity were controlled as follows: 20-26° C., 40-70% humidity, and lighting every 12 hours. Cages contained pressure sterilized corncob bedding material that was changed once per week. Mice had free access to autoclaved sterilized dry granule food and water during the entire study period. Food was SPF grade and water was purified by ultrafiltration.

Bispecific antibodies in a BC44 format as described herein were kept in a stock concentration of 1 mg/mL and stored at −80° C. Thaw was initiated one day prior to use. On the day of use, antibody vials were transferred to clear conical bottom 1.7 mL microcentrifuge tubes and centrifuged at maximum speed (21,130 rcf) for 2 minutes at 4° C. Antibody dilutions were made in Ca2+ and Mg2+ free PBS (Cat #20012027, Gibco).

7-10 days prior to treatment, the mice were implanted with a murine colon carcinoma cell line, MC38-hPD-L1/hCD47 cells. Each mouse was subcutaneously injected with MC38-hPD-L1/hCD47 tumor cells ($5.0\times10^5$) in 0.1 mL PBS in the right flank. The age of animals at inoculation was 7-10 weeks (date of birth of mice was within ±3 days within the cohort) and body weight at inoculation was 18-25 grams. Tumor-bearing animals were randomly enrolled into study groups when mean tumor size reached approximately 125 $mm^3$. Each group consisted of 8 mice. The study groups and number of animals per group for the efficacy cohort are shown in Table 13. Treatment was started at Treatment Day 0 and the study endpoint was up to 28 days. TV and BW were monitored twice weekly.

TABLE 13

Efficacy Cohort Group Designation, Dose Levels, and Dosing Schedule

| Group | Treatment | Number | Dose (mg/kg) | Route of Administration | Frequency | Dosing Schedule (Day) |
|---|---|---|---|---|---|---|
| G1 | DPBS (Vehicle Control) | 8 | 0 | IP | TIW × 6 | 0, 2, 4, 7, 9, 11 |
| G3 | C40 × P24 | 8 | 10 | IP | TIW × 6 | 0, 2, 4, 7, 9, 11 |
| G4 | C40 × P24 | 8 | 3 | IP | TIW × 6 | 0, 2, 4, 7, 9, 11 |
| G5 | C56 × P22 | 8 | 10 | IP | TIW × 6 | 0, 2, 4, 7, 9, 11 |
| G6 | C56 × P22 | 8 | 3 | IP | TIW × 6 | 0, 2, 4, 7, 9, 11 |
| G7 | C40 × P24s | 8 | 10 | IP | TIW × 6 | 0, 2, 4, 7, 9, 11 |

s = silent Fc

At the study end point, blood was collected from 4 mice in each group of the efficacy study by cardiac puncture (terminal bleed) for subsequent analyses.

Tumor size was measured at least twice weekly with a caliper and the tumor volume ($mm^3$) was estimated using the formula: $TV=a \times b^2/2$, where "a" and "b" were long and short diameters of a tumor, respectively. The TVs were used for calculation of the tumor growth inhibition (TGI, an indicator of antitumor effectiveness) and tumor regression (TR) values using the formulae:

$$TGI\ (\%)=[1-(T_t-T_0)/(C_t-C_0)]\times 100\%$$

$$TR\ (\%)=[1-(T_t-T_0)]\times 100\%$$

$T_t$=mean TV of treated mice at time t, $T_0$=mean TV of treated at time 0 (baseline), $C_t$=mean TV of control at time t and $C_0$=mean TV of control at time 0 (baseline).

Figure 7:
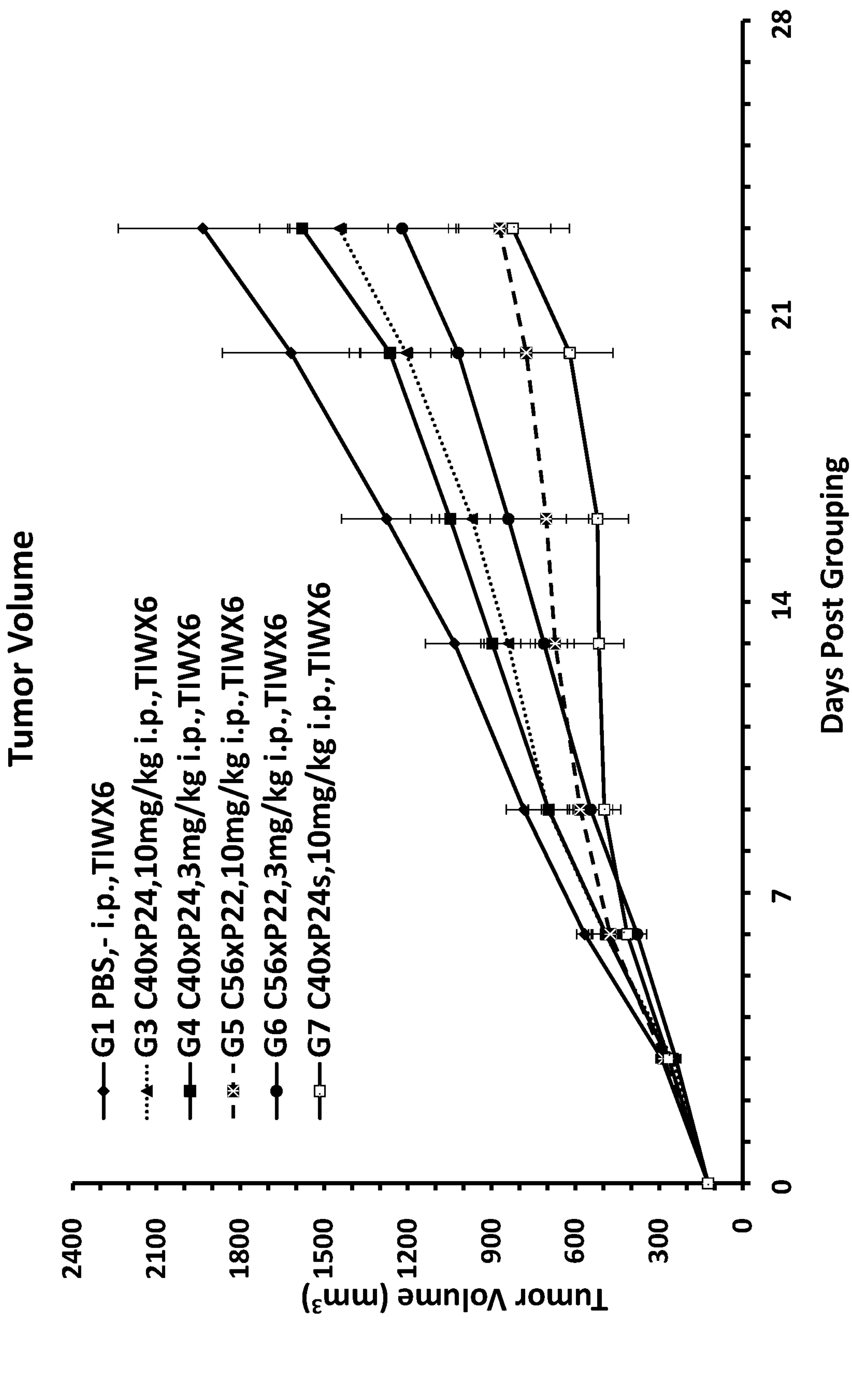
FIG. 7 illustrates exemplary results from in vivo animal studies related to tumor volume, showing days post grouping in the X-axis and tumor volume ($mm^3$) in the Y-axis, from different animal groups as indicated, further described in Example 7. G1: treated with PBS (vehicle control). G3: treated with 10 mg/kg C40×P24. G4: treated with 3 mg/kg C40×P24. G5: treated with 10 mg/kg C56×P22. G6: treated with 3 mg/kg C56×P22. G7: treated with 10 mg/kg C40×P24s (s=silent Fc).

Exemplary results for tumor volume ($mm^3$) are shown in FIG. 7.

Body weights of mice were measured at least twice weekly throughout the study. Body weight (BW) change, expressed in %, was calculated using the following formula:

$$BW\ change\ (\%)=((BW_t-BW_0)/BW_0)\times 100$$

"$BW_t$" and "$BW_0$" were the BW at time t and time 0 (baseline), respectively.

Figure 8:
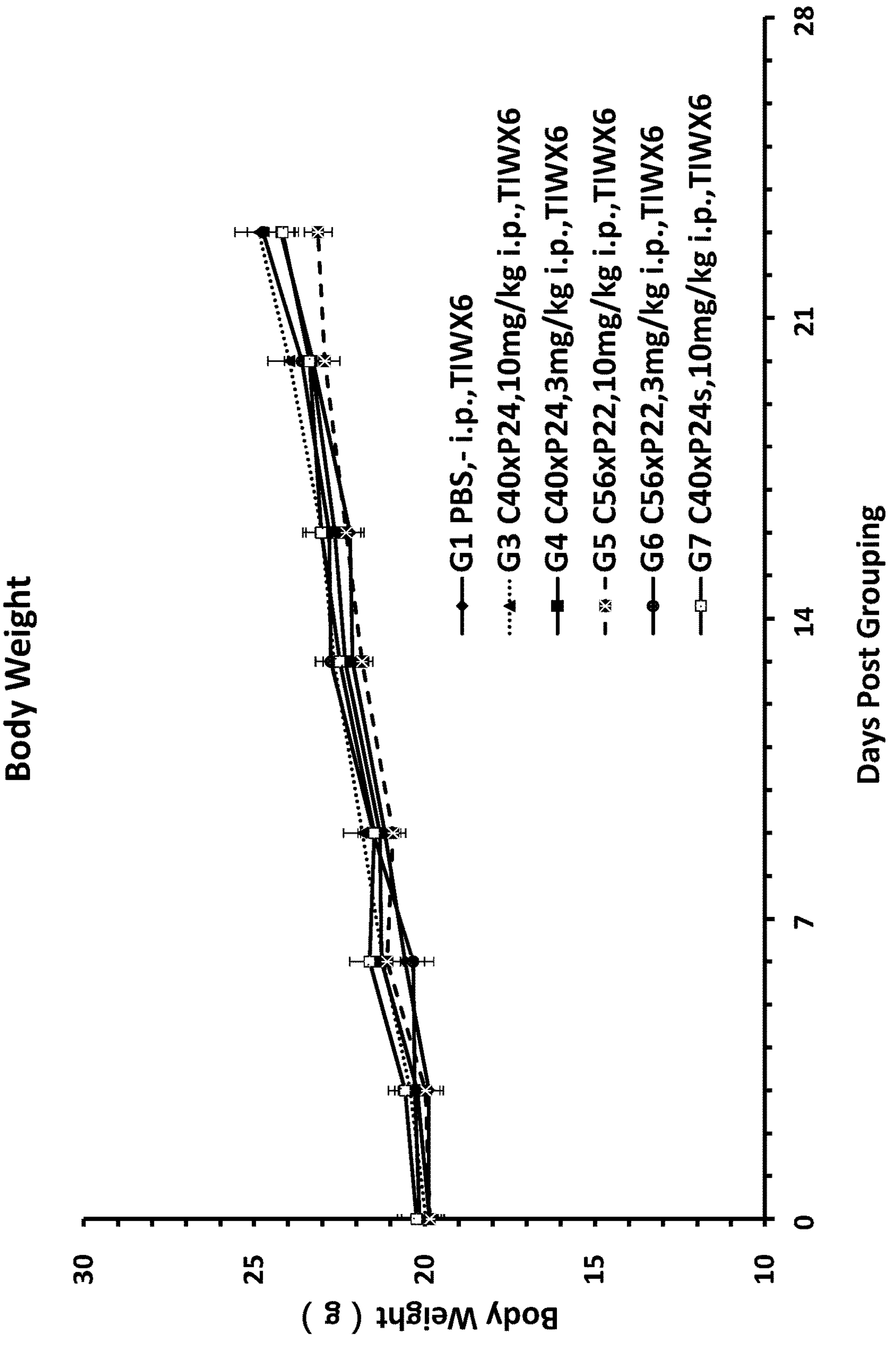
FIG. 8 illustrates exemplary results from in vivo animal studies related to body weight, showing days post grouping in the X-axis and body weight (g) in the Y-axis, from different animal groups as indicated, further described in Example 7. G1: treated with PBS (vehicle control). G3: treated with 10 mg/kg C40×P24. G4: treated with 3 mg/kg C40×P24. G5: treated with 10 mg/kg C56×P22. G6: treated with 3 mg/kg C56×P22. G7: treated with 10 mg/kg C40×P24s (s=silent Fc).

Exemplary results for body weight (grams) are shown in FIG. 8.

In order to evaluate toxicity, an additional toxicity cohort of 24 tumor-bearing mice were treated as described in Table 14. Mice were sacrificed 2 days after the first dose for a complete blood count (CBC) analysis (e.g., to assess platelet and/or red blood cell (RBC) depletion). CBC results were compared to four mice from the efficacy study described above from samples taken at the end of the study.

Blood was collected by cardiac puncture (terminal bleed) for subsequent analyses on Day 2 from the toxicity cohort described in Table 14.

TABLE 14

Toxicity Cohort Group Designation, Dose Levels, and Dosing Schedule

| Group | Treatment | Number | Dose (mg/kg) | Route of Administration | Frequency | Dosing Schedule (Day) |
|---|---|---|---|---|---|---|
| G1 | DPBS (Vehicle Control) | 4 | 0 | IP | once | 0 |
| G3 | C40 × P24 | 4 | 10 | IP | once | 0 |
| G4 | C40 × P24 | 4 | 3 | IP | once | 0 |
| G5 | C56 × P22 | 4 | 10 | IP | once | 0 |
| G6 | C56 × P22 | 4 | 3 | IP | once | 0 |
| G7 | C40 × P24s | 4 | 10 | IP | once | 0 |

s = silent Fc

Whole blood was collected by cardiac puncture at two time points, Day 2 (post-single dose) from mice in the toxicity cohort and at the study endpoint for 4 mice from each group of the efficacy cohort, for CBC and bispecific antibody level analyses.

For collection of blood for CBC analysis, 250 μL of blood was collected into a heparin-coated tube and mixed thoroughly by inversion. After mixing, the blood sample was maintained at 2-8° C.

For serum collection, the remaining whole blood (250 μL or more) was collected into a serum collection tube. The blood was then allowed to clot by leaving it undisturbed at room temperature for 30 minutes. The clot was removed by centrifuging at 12,000×g for 90 seconds in a refrigerated centrifuge per manufacturer's protocol. Following centrifugation, the resulting supernatant (serum) was immediately transferred into a clean labelled polypropylene tube, divided into 2 aliquots (~60 μL×2) and stored at −80° C. until analyzed by ELISA. The serum samples were maintained at 2-8° C. while handling.

Anti-CD47 antibodies may cause red blood cell agglutination, which limits their therapeutic applications. Bispecific antibodies disclosed herein were tested using a red blood cell binding assay to determine the effect on red blood cell agglutination.

RBCs and platelets are reported to have high expression of CD47. 48 hours after dosing, red blood cells and platelet concentrations were analyzed to determine if there was depletion of these cell types.

CBC was measured on HEMAVET950 (Drew Scientific) with blood collected via cardiac puncture as described. Hematological parameters on RBC, WBC (with counts of subtypes), platelets, hemoglobin, and hematocrit were determined for each sample (FIGS. 9A-9E). Information of red cell distribution width (RDW), mean corpuscular volume (MCV), mean corpuscular hemoglobin (MCH), reticulocyte count was determined (FIGS. 10A-10G).

Figure 9A:
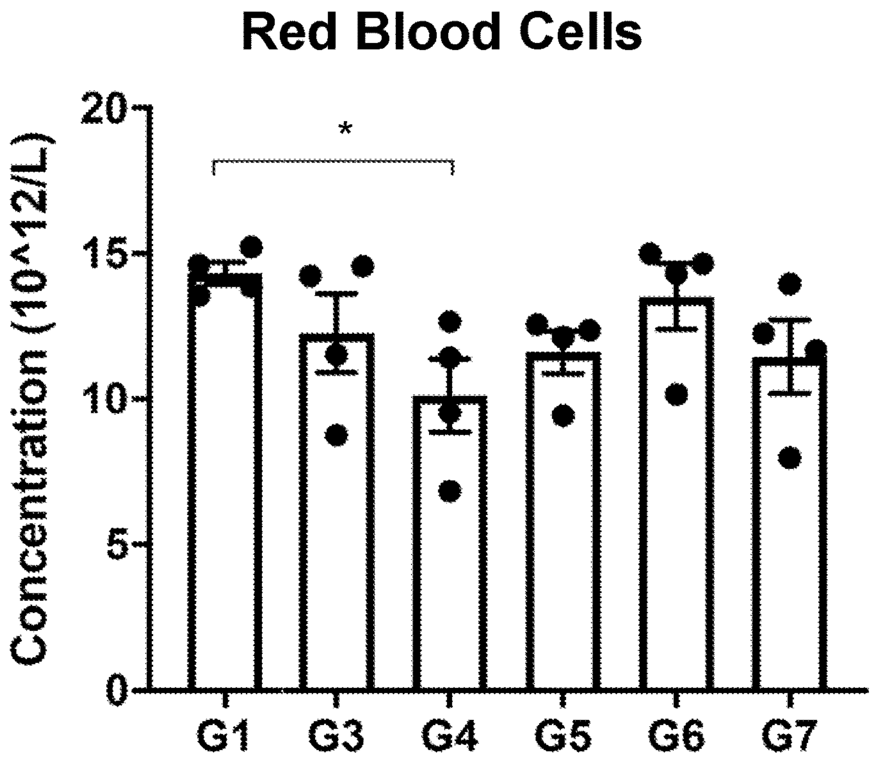
FIGS. 9A-9E illustrate exemplary results from in vivo animal studies related to blood parameters from different animal groups as indicated, further described in Example 7.
Figure 9B:
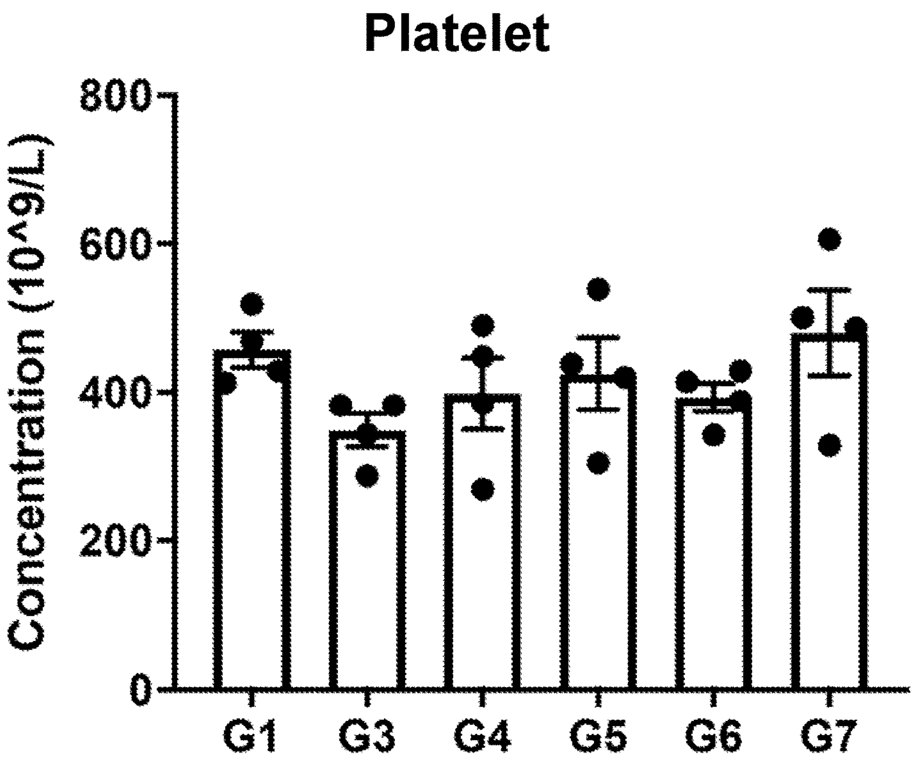
Figure 9C:
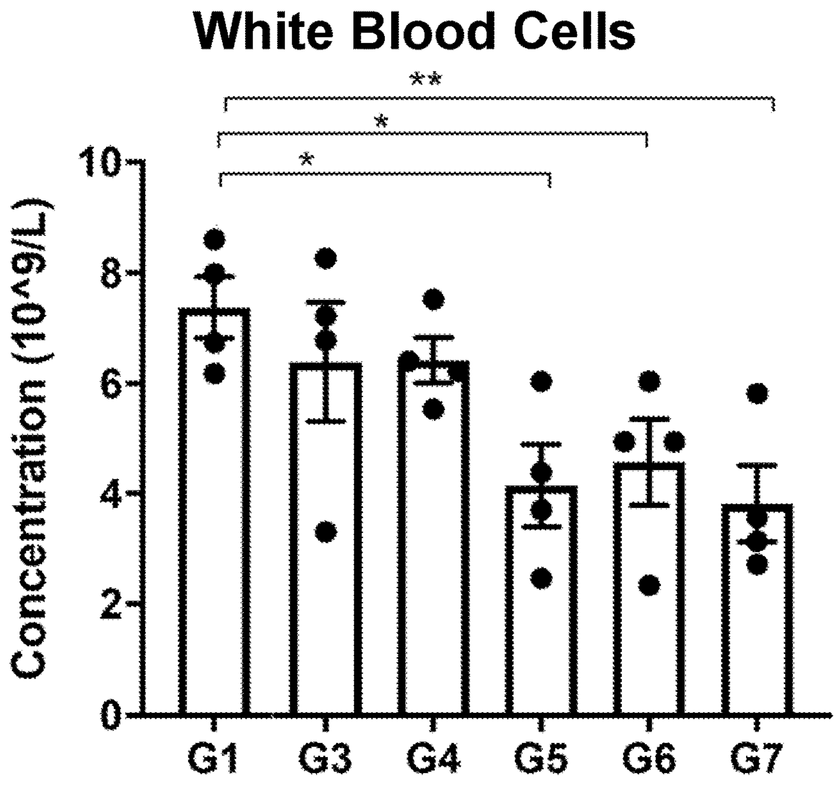
Figure 9D:
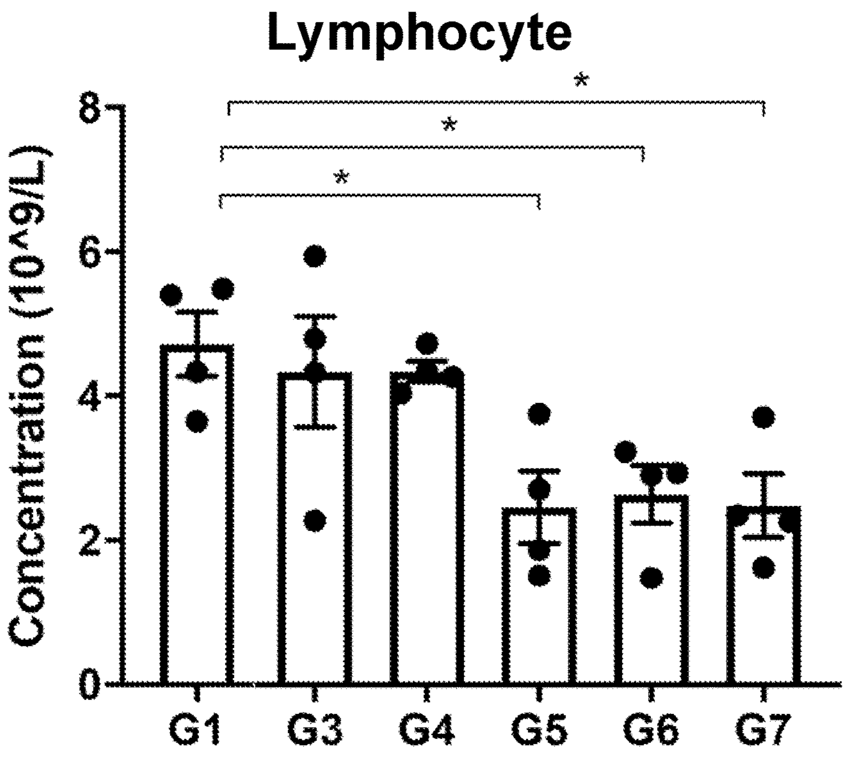
Figure 9E:
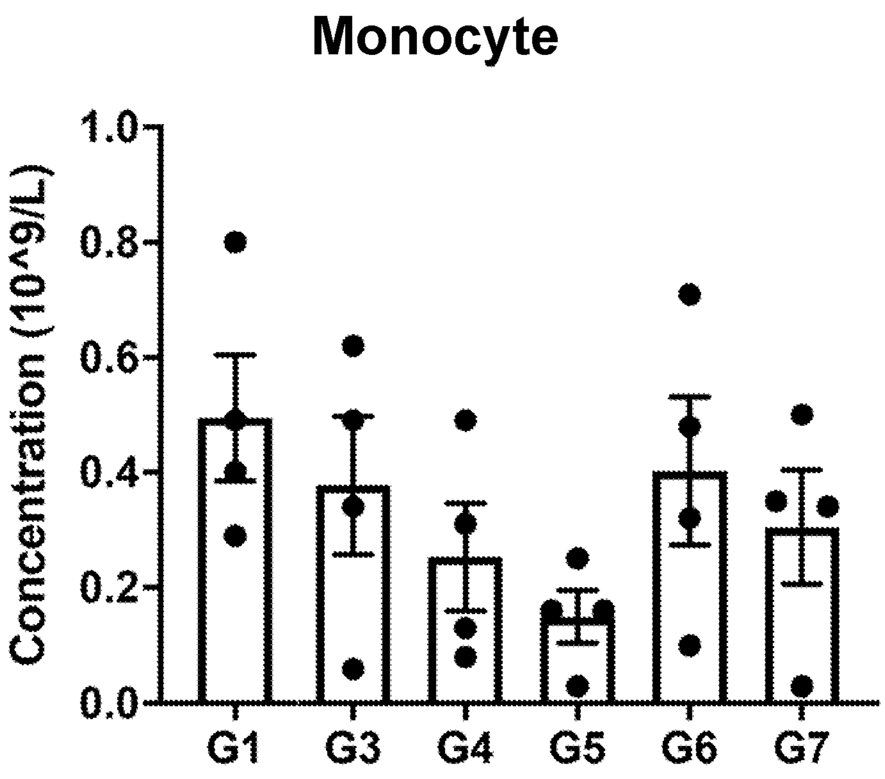
Figure 10A:
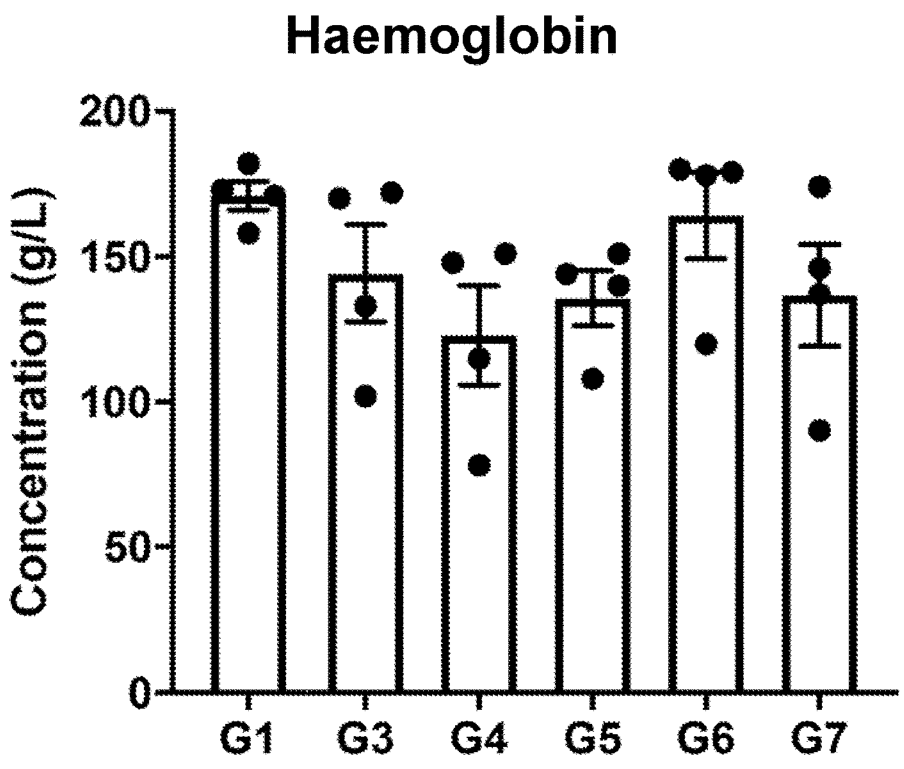
FIGS. 10A-10G illustrate exemplary results from in vivo animal studies related to additional blood parameters from different animal groups as indicated, further described in Example 7.
Figure 10B:
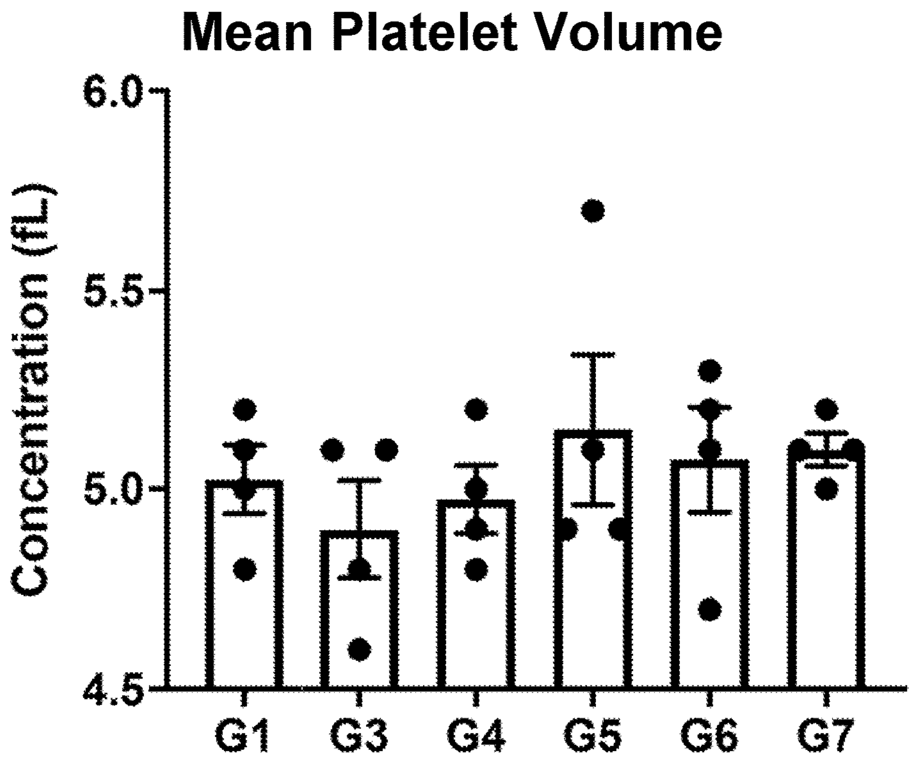
Figure 10C:
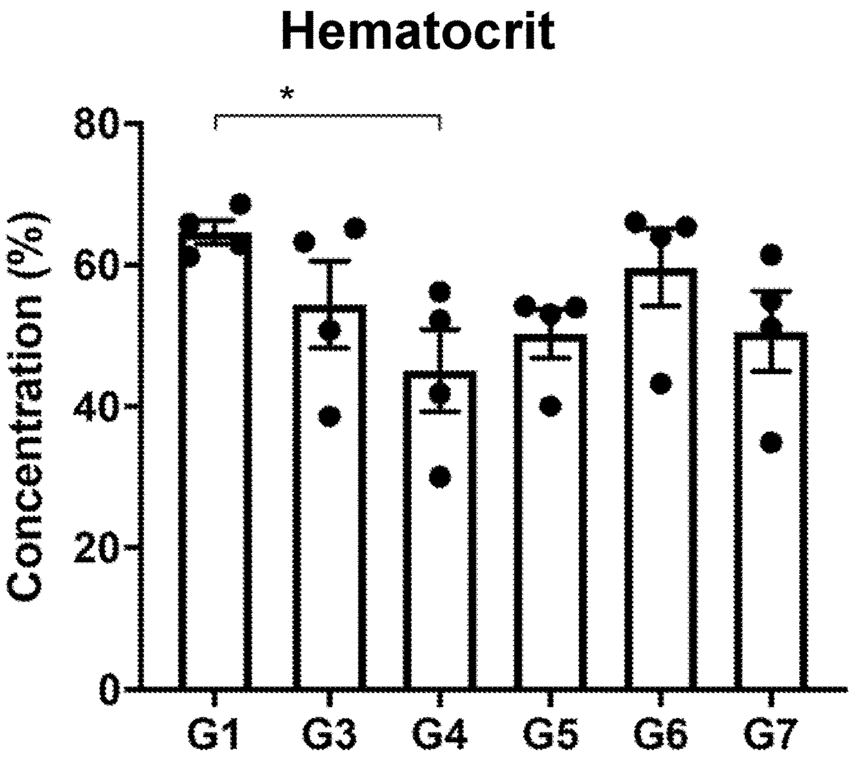
Figure 10D:
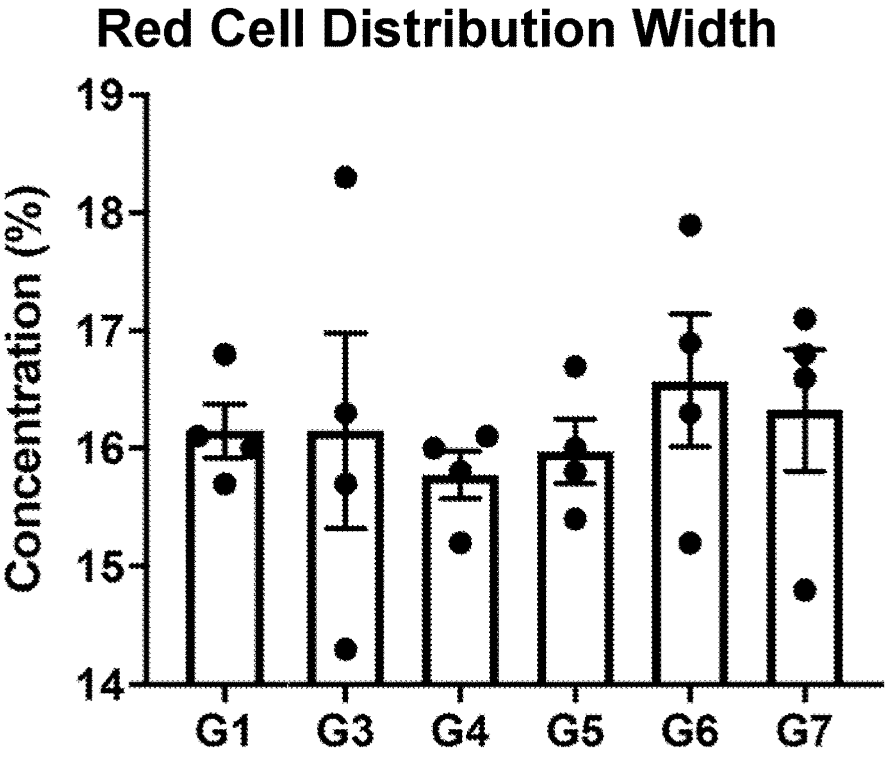
Figure 10E:
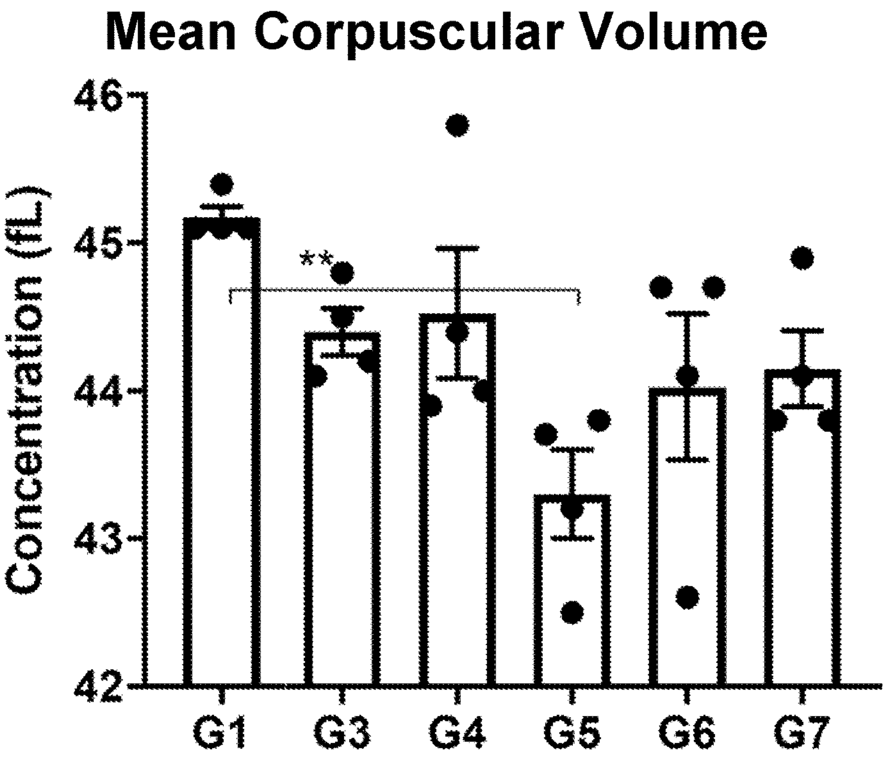
Figure 10F:
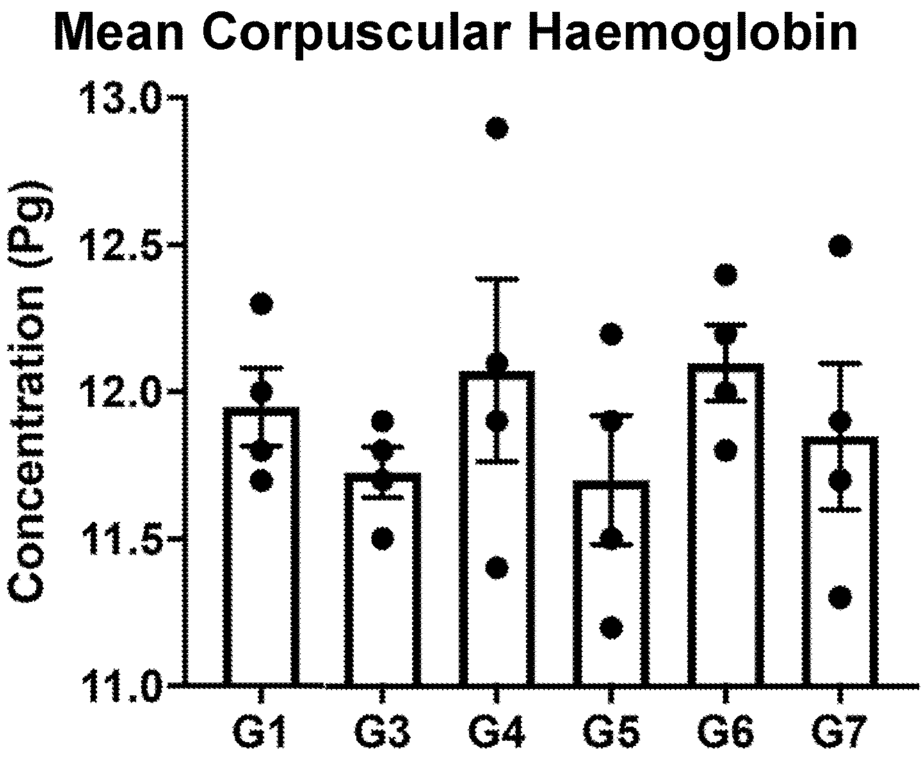
Figure 10G:
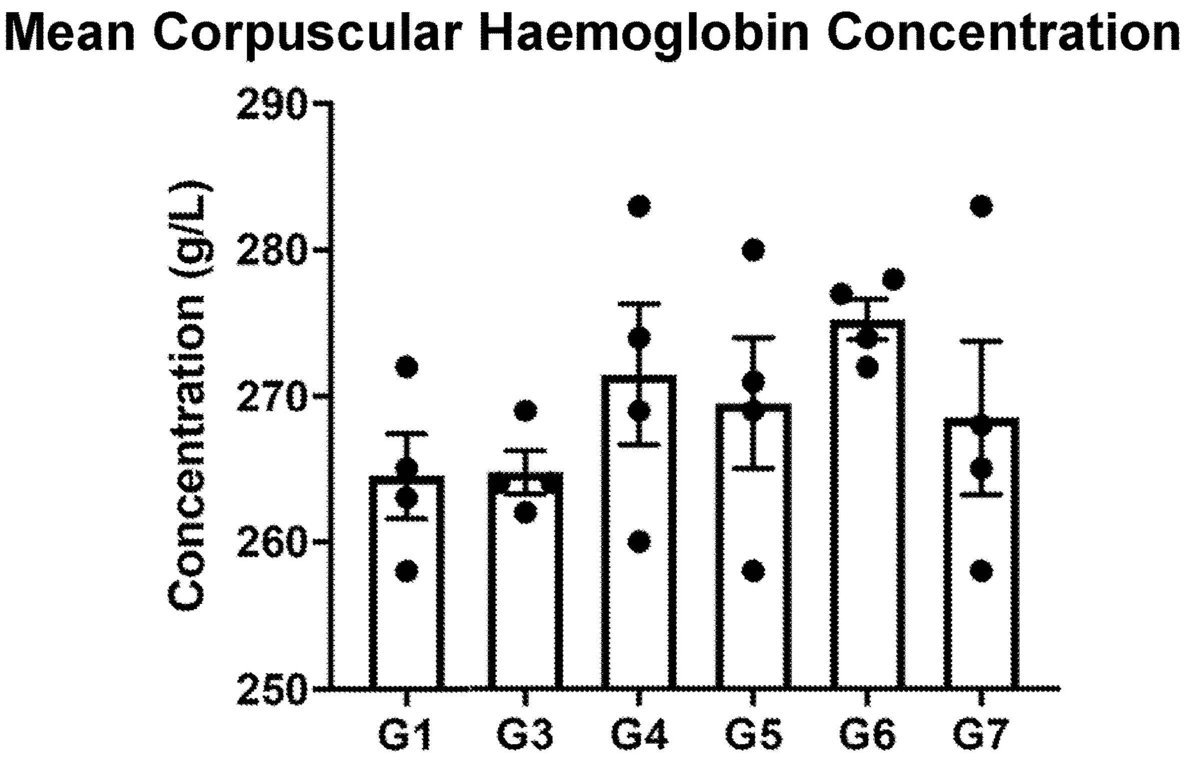

White blood cell and lymphocyte reduction was observed with C56×P22 (G5 and G6), and C40×P24s (G7) (FIGS. 9C and 9D).

An enzyme-linked immune sorbent assay (ELISA) was used to quantitatively determine the amount of human IgG1 antibody in serum prepared from mice in the toxicity cohort described above.

This assay employed affiniPure Goat Anti-Human IgG (H+L) (Cat #109-005-003, Jackson ImmunoResearch) specific for human IgG antibody coated on a 96-well plate. Standards, quality control samples and test specimens are pipetted into the wells and human IgG in a sample is bound to the wells by the immobilized antibody. The wells were washed and peroxidase-conjugated affiniPureF(ab')2 fragment Goat Anti-Human IgG Fc antibody was added (Cat #109-0036-003, Jackson ImmunoResearch). After washing away unbound peroxidase-conjugated antibody, a TMB substrate solution was added to the wells and color developed in proportion to the amount of human IgG bound. The Stop Solution changed the color from blue to yellow, and the intensity of the color was measured at 450 nm and 570 nm. The Lower limit of quantitation (LLOQ) of the sandwich method for determining the human antibody concentration was approximately 1.56 ng/mL.

Figure 11:
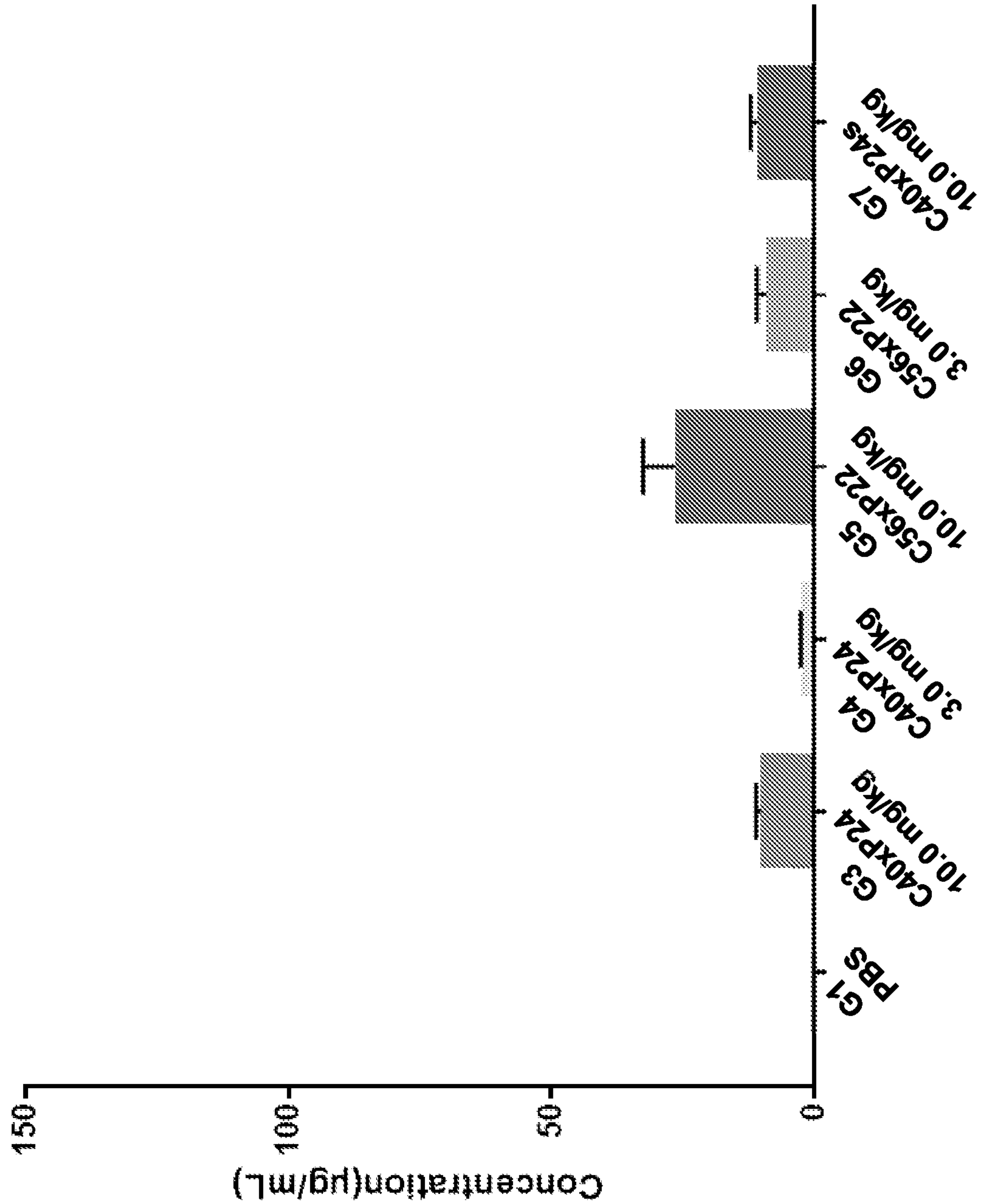
FIG. 11 illustrates exemplary results from in vivo animal studies related to antibody concentrations in blood from different animal groups as indicated, further described in Example 7. G1: treated with PBS (vehicle control). G3: treated with 10 mg/kg C40×P24. G4: treated with 3 mg/kg C40×P24. G5: treated with 10 mg/kg C56×P22. G6: treated with 3 mg/kg C56×P22. G7: treated with 10 mg/kg C40×P24s (s=silent Fc).

The concentration of indicated human antibody in the blood of mice from study groups of the toxicity cohort are shown in FIG. 11. Results indicate a slightly higher blood concentration for C56×P22 (G5) than for other tested bispecific antibodies.

To further evaluate in vivo therapeutic efficacy, bispecific antibodies were tested in an additional study with the syngeneic MC38-hPDL1/hCD47 murine colon carcinoma model in the female B-hPD-L1/hSIRα/hCD47 mice as described in the previous study above. The efficacy of the treatment was again evaluated based on tumor volume (TV) changes. The overall health of animals was again evaluated based on body weight (BW).

Animals were housed and fed as described in the previous study above, and antibody dilutions of the bispecific antibodies in a BC44 format as described herein were prepared as described above but from a stock concentration of 2 mg/mL.

In this additional study, 7-10 days prior to treatment, the mice were implanted with a murine colon carcinoma cell line, MC38-hPD-L1/hCD47 cells. Each mouse was subcutaneously injected with MC38-hPD-L1/hCD47 tumor cells ($5.0\times10^5$) in 0.1 mL PBS in the right front flank. The age of animals at inoculation was 7-10 weeks (date of birth of mice was within ±3 days within the cohort) and body weight at inoculation was 18-25 grams. Tumor-bearing animals were randomly enrolled into study groups when mean tumor size reached approximately 117 mm$^3$. Each group consisted of 8 mice. The study groups and number of animals per group for the efficacy cohort are shown in Table 15. Treatment was started at Treatment Day 0 and the study endpoint was up to 28 days. TV and BW were monitored twice weekly.

TABLE 15

Efficacy Cohort Group Designation, Dose Levels, and Dosing Schedule

| Group | Treatment | Number | Dose (mg/kg) | Route of Administration | Frequency | Total Number of Doses |
|---|---|---|---|---|---|---|
| G1 | DPBS (Vehicle Control) | 8 | 0 | IP | Every other day | 6 |
| G3 | C56 × P22 | 8 | 20 | IP | Every other day | 6 |
| G4 | C59 × P22 | 8 | 20 | IP | Every other day | 6 |

Tumor size was measured at least twice weekly with a caliper and the tumor volume (mm$^3$) was estimated as described in the previous study above.

Figure 12A:
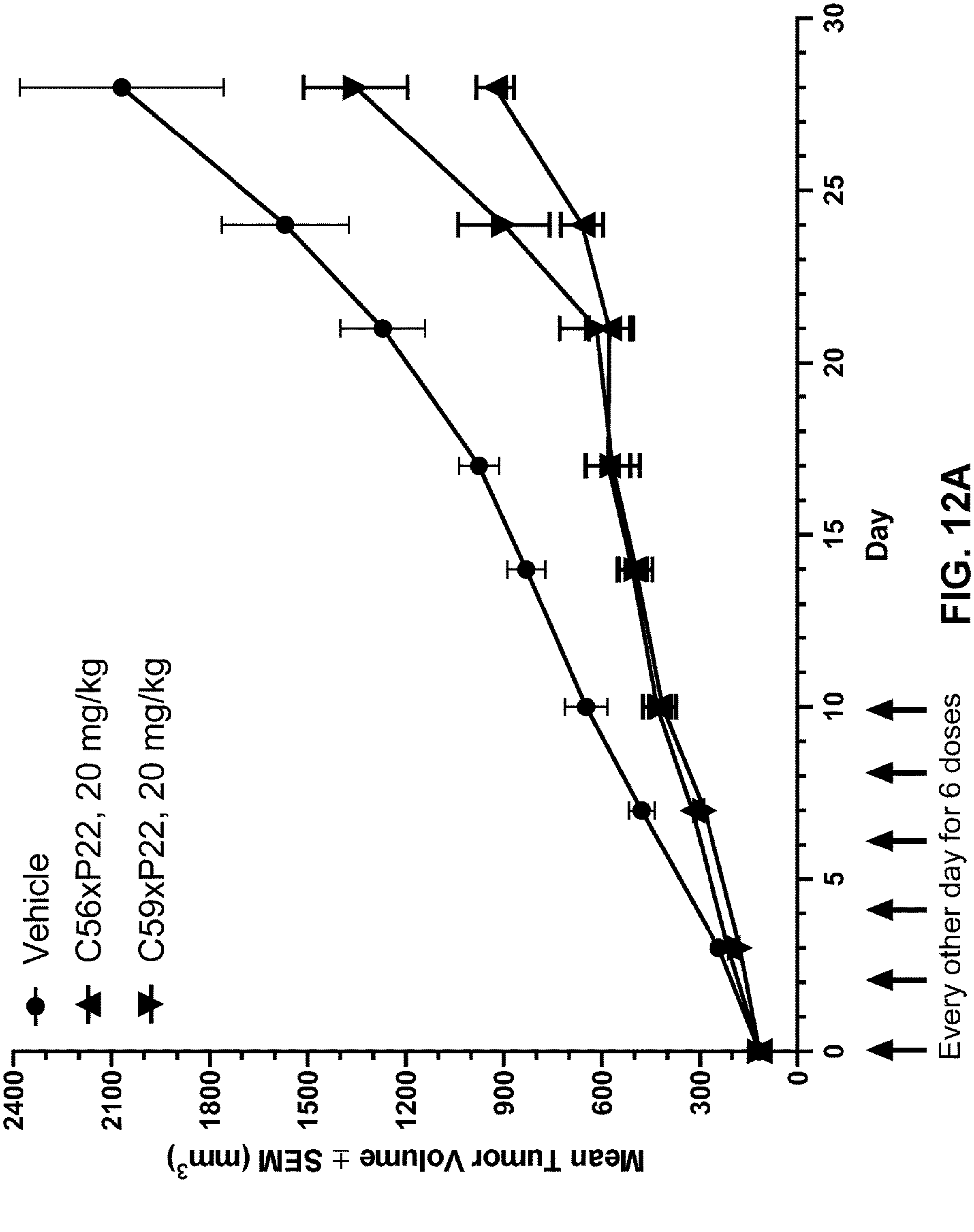
FIGS. 12A-12E illustrate exemplary results from additional in vivo animal studies related to tumor volume and body weight from different animal groups treated with vehicle control, C56×P22, or C59×P22 as indicated, further described in Example 7.
Figure 12B:
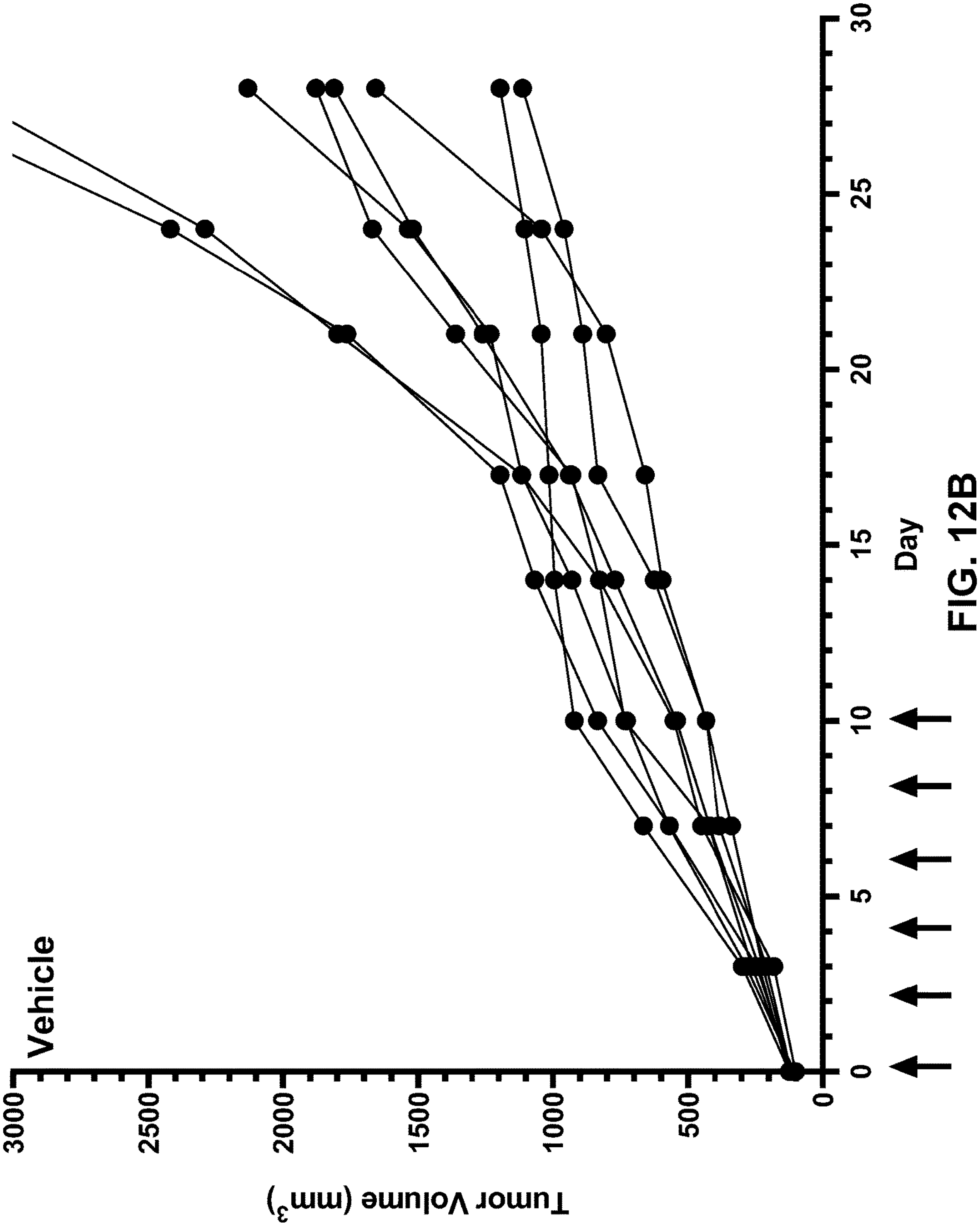
Figure 12C:
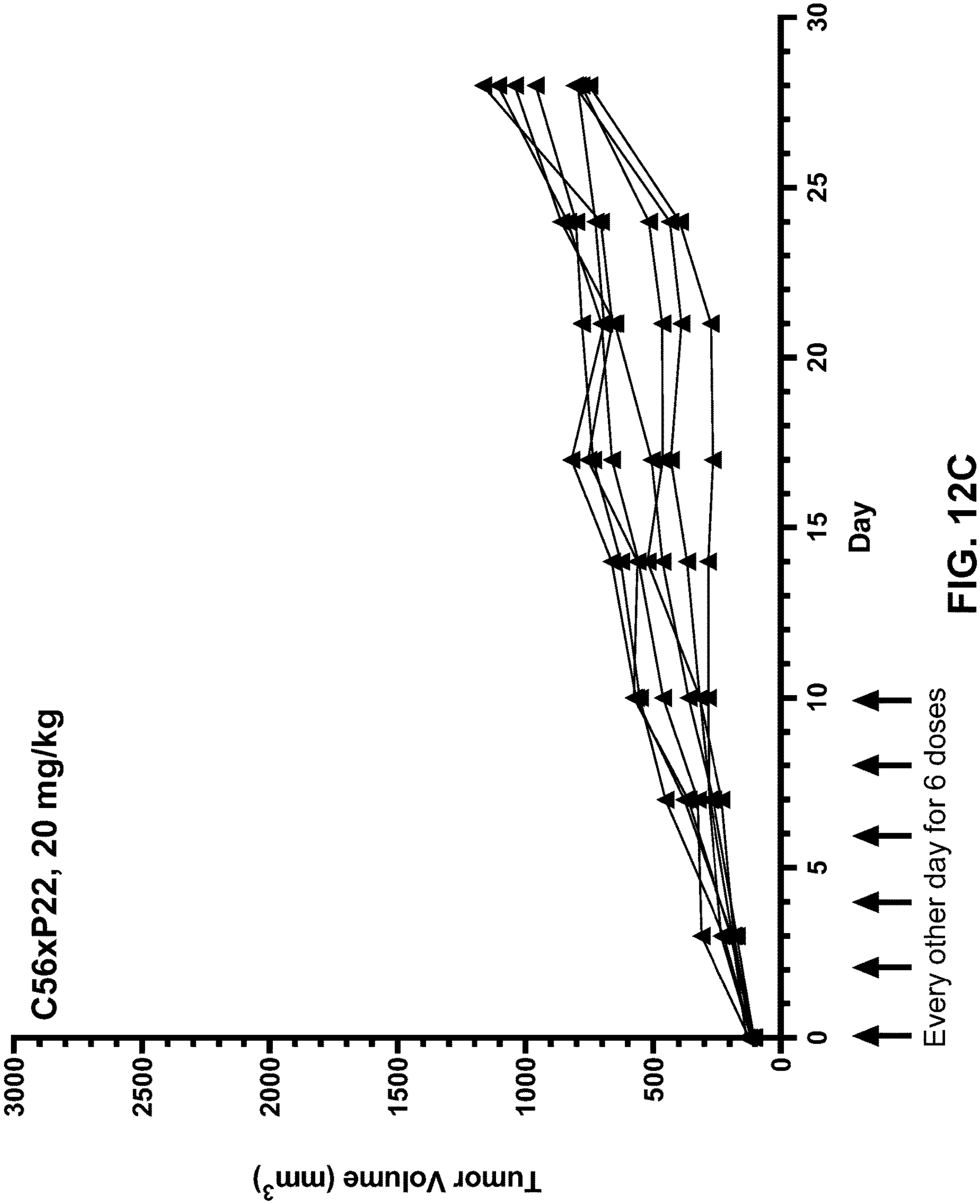
Figure 12D:
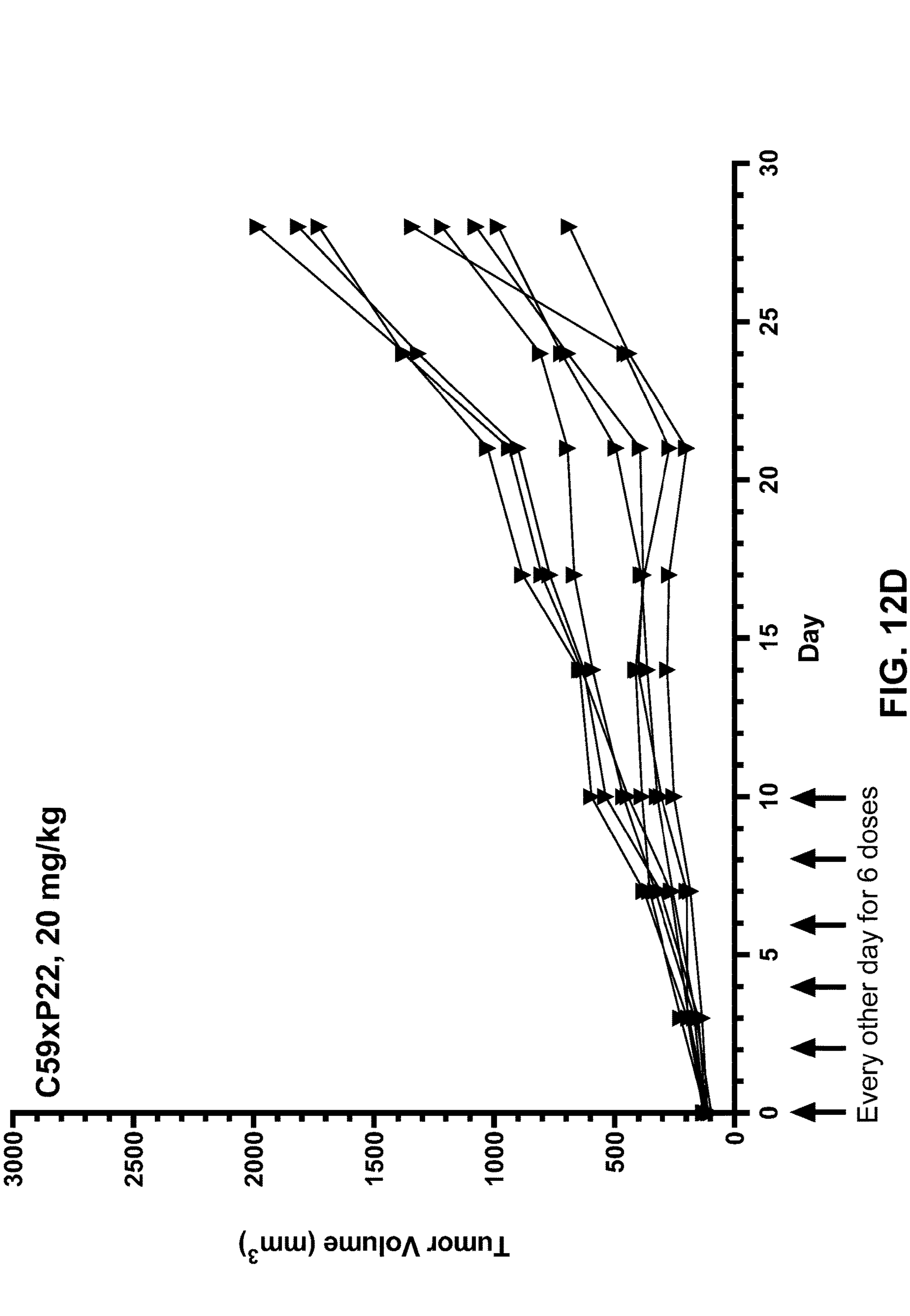

Exemplary tumor volume (mm$^3$) results for mice in indicated treatment groups with the exemplary bispecific antibodies are shown in FIG. 12A. Exemplary tumor volume results for individual mice are shown in FIGS. 12B-12D. Tumor growth inhibition (TGI) was calculated as described above for the previous study. For example, at the end of this study (day 28 post start of treatment), exemplary results showed that C56×P22 (20 mg/kg, IP) demonstrated anti-tumor activity as indicated by effects on tumor volume with % TGI of 58.5% ($P<0.05$), and C59×P22 (20 mg/kg, IP) demonstrated anti-tumor activity with % TGI of 36.6% ($P>0.05$).

Body weights of mice were measured at least twice weekly throughout the study. Body weight (BW) change, expressed in %, was calculated using the following formula:

$$\text{BW change (\%)}=((BW_t-BW_0)/BW_0)\times100$$

"$BW_t$" and "$BW_0$" were the BW at time t and time 0 (baseline), respectively.

Figure 12E:
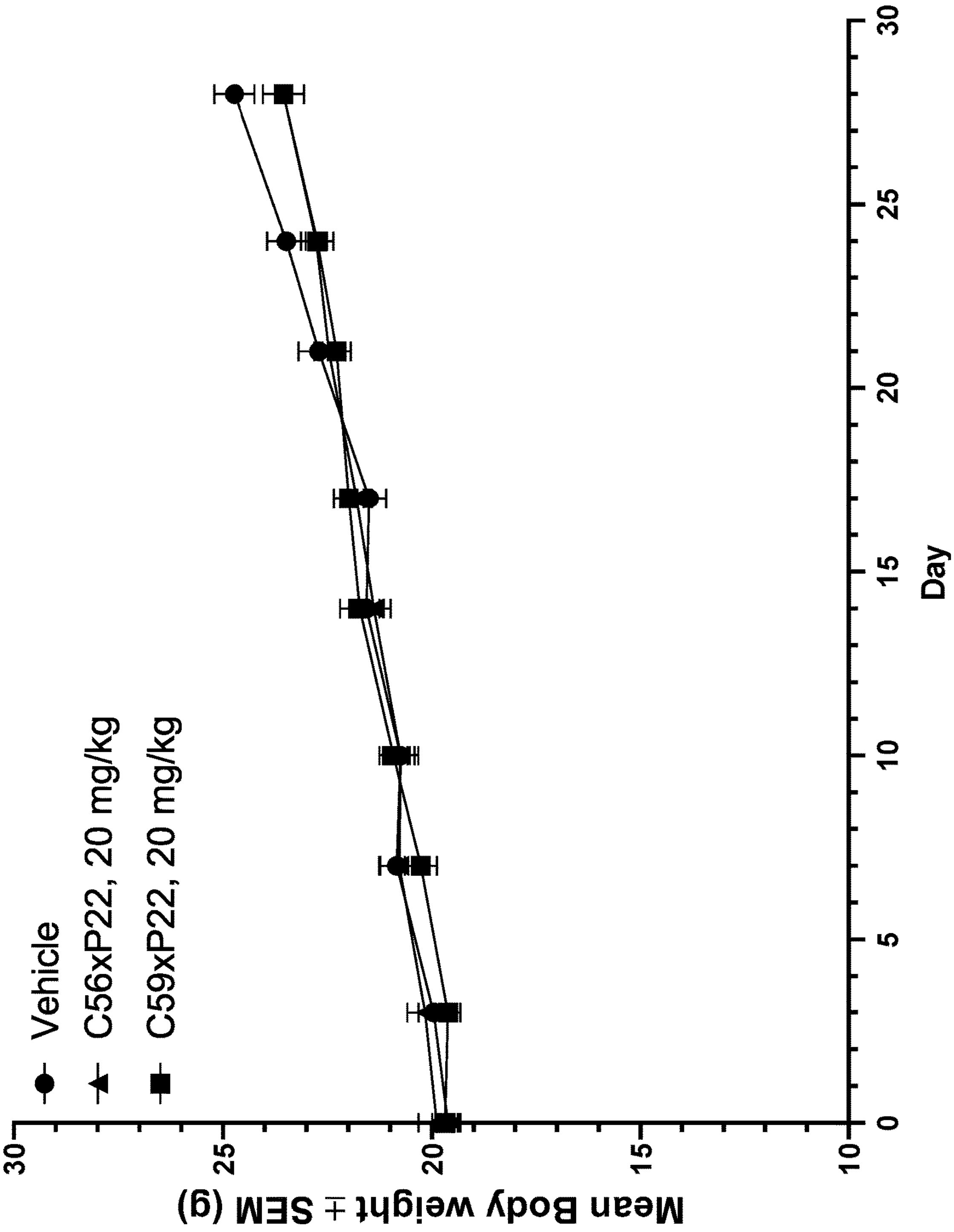

Exemplary mean body weight (grams) results for mice in indicated treatment groups with the exemplary bispecific antibodies are shown in FIG. 12E.

In order to evaluate tumor infiltrating leukocytes (TIL), at the study endpoint, a single cell suspension of tumors was prepared to analyze by FACS. Tumors were cut into small pieces of 2-4 mm, transferred to tube containing enzyme mix (Miltenyi Biotec, cat #130-096-730) and incubated at 37° C. for 40 minutes. Tumor slices were then ground with a sterile syringe plunger in 10 mL RPMI-1640 at 4° C. Cell suspensions were centrifuged at 300 g for 7 minutes at 4° C.

Supernatants were aspirated completely, cell pellets were resuspended in PBS at an appropriate volume and counted using a blood cell counting chamber. Tumor cells were resuspended in PBS to the required concentration for further FACS analysis.

For FACS analysis, the cell suspension of each tumor sample was incubated with anti-mouse CD16/32 antibody, a fixable viability dye for Fc receptor blocking, and live/dead staining at room temperature for 10 minutes. Samples were then stained with fluorescence conjugated antibodies for surface markers including mouse(m) CD45, mCD11b, mCD3, mCD4, mCD8 and mF4/80 at 4° C. for 30 minutes. After staining, samples were washed twice with PBS. After being fixed and permeabilized, samples were stained with fluorescence conjugated anti-mouse Foxp3 antibody at 4° C. for 30 minutes. Samples were washed with PBS, resuspended in PBS and analyzed by flow cytometry (Attune NxT, Thermo Fisher Scientific).

Figure 13B:
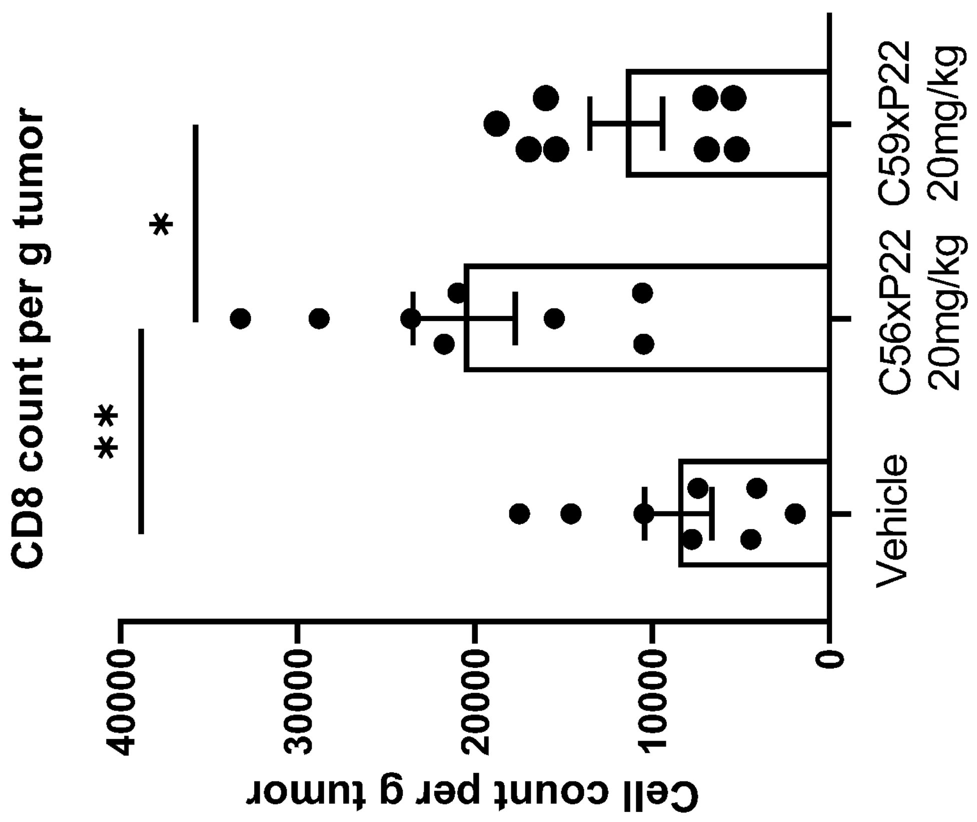
FIGS. 13A-13D illustrate exemplary results from additional in vivo animal studies related to tumor infiltrating leukocytes from different animal groups treated with vehicle control, C56×P22, or C59×P22 as indicated, further described in Example 7.
Figure 13A:
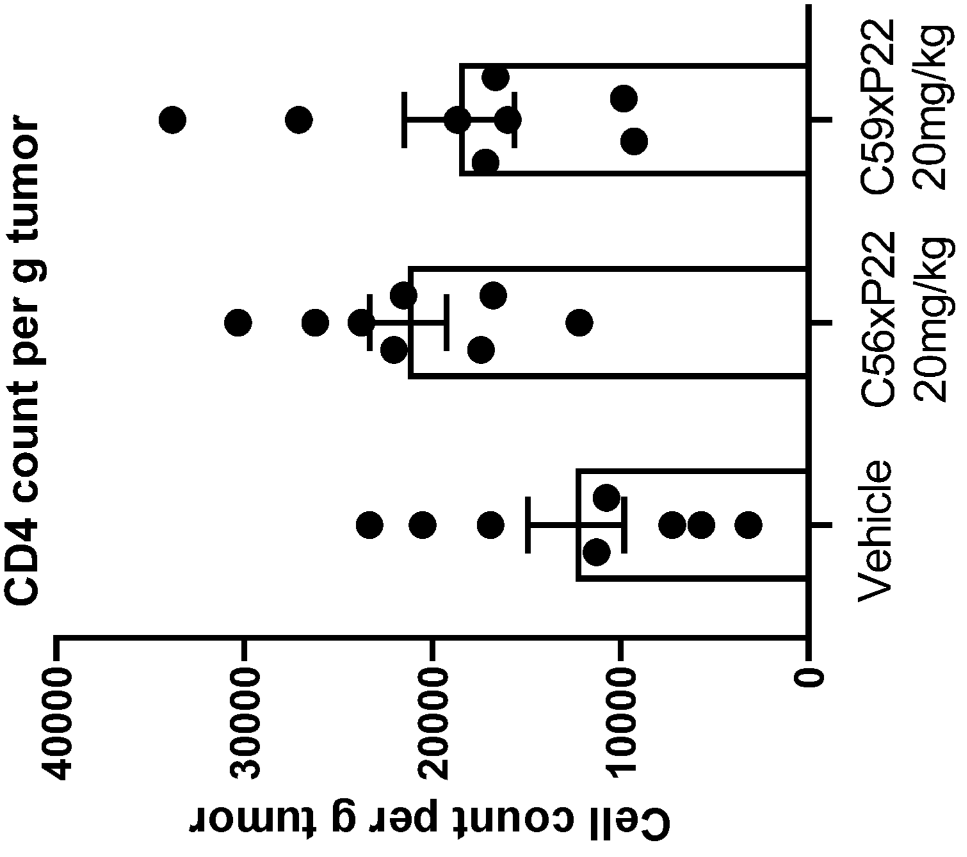
Figure 13D:
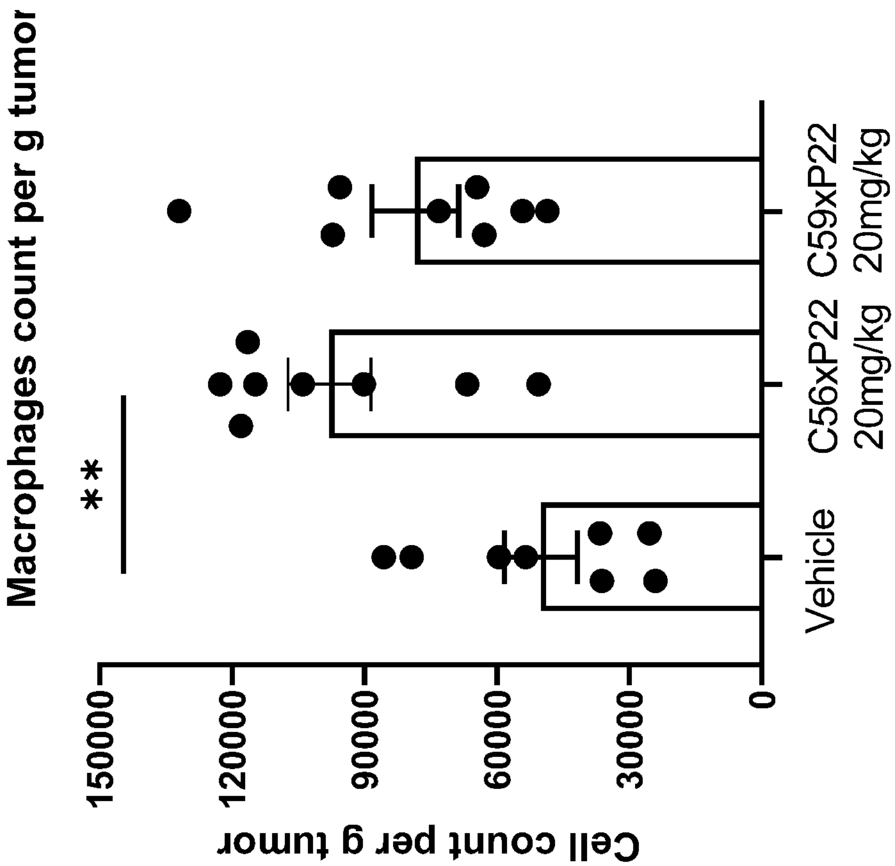
Figure 13C:
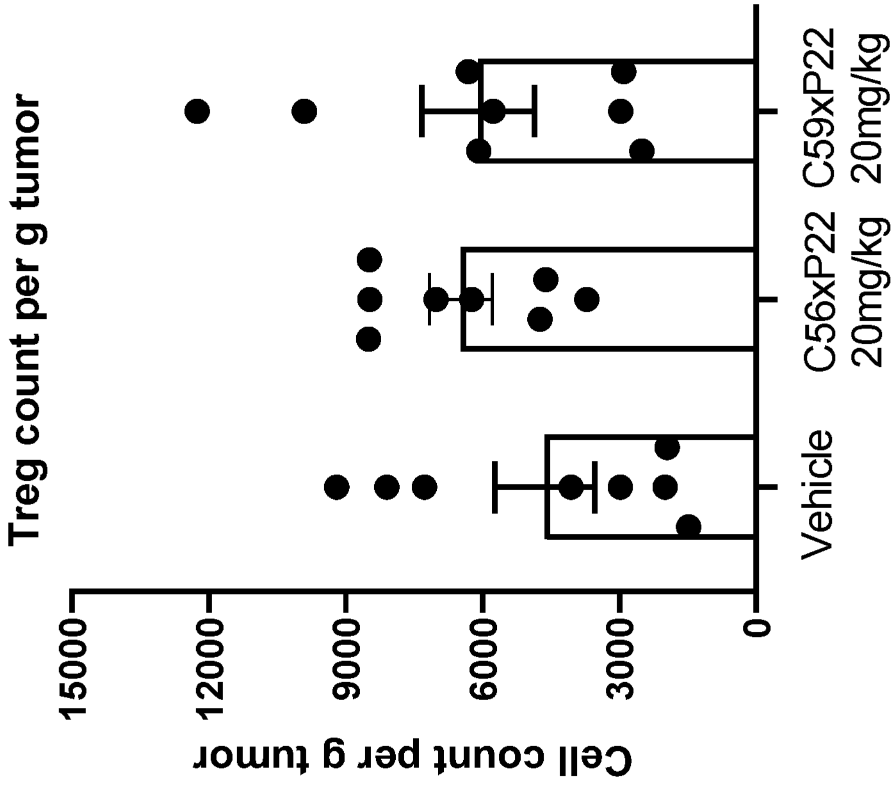

FACS analysis was used to determine the percentages of CD4+ T cells, CD8+ T cells, regulatory T cells (Treg), and macrophages in all live cells, and the cell count per gram of tumor were calculated for each cell type. CD4+ T cell count was determined by gating for CD45+CD3+CD4+CD8−, and exemplary results for cell CD4+ T cells per gram tumor are shown in FIG. 13A. CD8+ T cell (CTL) count was by determined by gating CD45+CD3+CD4−CD8+, and exemplary results for CD8+ cells per gram tumor are shown in FIG. 13B. Treg count was determined by gating CD45+ CD3+CD4+CD8−Foxp3+, and exemplary results for Treg cells per gram tumor are shown in FIG. 13C. Macrophage count was determined by gating CD45+CD11 b+ F4/80+, and exemplary results for macrophage count per gram tumor are shown in FIG. 13D. An increase in TILs was observed with C56×P22 and C59×P22 compared to the vehicle alone control group, as shown in FIGS. 13A-13D.

In vivo therapeutic efficacy was also evaluated in a humanized NOD-SCID mouse model bearing A-375 melanoma tumors. A-375 cells have a CD47 surface copy number of approximately 200,000 and a PD-L1 surface copy number of approximately 25,000.

Animals were housed in specific pathogen-free conditions at an animal facility. The animals were acclimatized for 7 days before the experiment. Temperature and humidity were controlled as follows: 20-24° C., 45-65% humidity, and lighting every 12 hours. Top filter cages contained HEPA filtered air with minimum 15 air exchanges per hour with no recirculation. Cages contained poplar bedding and animals were fed an irradiated diet 25 kGy and sterile filtered (5, 1, 0.2 μm) tap water.

Bispecific antibodies in a BC44 format were provided at 1 mg/mL concentration and were stored at −80° C. Prior to use, bispecific antibodies were thawed and used neat for the 10 mg/kg dose, with doses kept at 4° C. until in vivo injection. Vehicle was Ca++ and Mg++ free Dulbecco's PBS, pH7.4.

The A-375 cell line is a human skin melanoma (American Type Culture Collection, USA, cat #CRL1619) and was isolated from a 54 year-old female patient with melanoma by Giard et al. (D. J. Giard et al., "In vitro cultivation of human tumors: establishment of cell lines derived from a series of solid tumors," *J. Natl. Cancer Inst., vol.* 51, no. 5, pp. 1417-1423, November 1973.). Tumor cells were grown as monolayer at 37° C. in a humidified atmosphere (5% $CO_2$, 95% air) in a RPMI culture medium containing 2 g/L glucose, 2 mM L-glutamine, 2 g/L bicarbonate sodium and supplemented with 10% fetal bovine serum. Tumor cells were adherent to plastic flasks. For experimental use, medium was be removed, and cells rinsed with Ca++& Mg++ free-Dulbecco's PBS before adding trypsin-EDTA and incubating culture flasks for 5 to 15 minutes at room temperature. Cells were then collected and mixed with complete medium before centrifugation for 5 minutes at 300 g. The pelleted cells were washed, resuspended in RPMI without phenol red, counted and their viability assessed by 0.25% trypan blue exclusion assay. Tumor cell culture with a viability of >80% was used for in-vivo implant.

Peripheral blood mononuclear cells (PBMCs) were prepared from buffy coats using established procedures. Three (3) freshly collected buffy coat samples from healthy volunteer donors were obtained. The PBMCs were purified using gradient centrifugation according to Ficoll-Paque® plus procedure within 48 hours after total blood collection. PBMCs were used for in vivo injection only if viability was >80%, as determined by 0.25% trypan blue exclusion assay.

Fifty-seven (57) healthy female NOD-SCID (NOD.CB17-Prkdcscid/NCrCrl) mice, 5 weeks old at reception, were obtained from Charles River Laboratories. PBMCs were injected on Day−3 (D−3), 3 days prior to tumor induction. The fifty-seven mice were split into 3 sub-groups of 19 mice each, and with each sub-group allocated to one PBMCs donor (donor A, B and C). The three sub-groups had equivalent mean body weight at time of PBMC inoculation. PBMCs from each donor were injected into one sub-group of 19 mice on the same day. Each mouse received one single intravenous (IV) injection of $1\times10^7$ PBMCs in 200 μL RPMI without phenol red.

On Day−0 (D0), tumors were induced in all fifty-seven NOD SCID female mice by subcutaneous injection of $1\times10^7$ A-375 cells in 200 μL RPMI 1640 without phenol red into the right flank of each animal. Animals were randomized on Day 1 (D1) by individual body weight. Three (3) mice from each sub-group were randomized into 6 groups according to their individual body weight using Vivo Manager® software. This distribution yielded 6 groups of 9 mice, 3 mice per donor per group. A statistical test (analysis of variance, ANOVA) was performed to test for homogeneity between groups for each donor.

The treatment was administered on Day 1 (D1) by injection into the peritoneal cavity (IP), with an IP formulation of pH 7.4 and an administration volume of 10 mL/kg, adjusted to the most recent individual body weight. Group designations, dosage levels, administration, and treatment schedule (TIW×3, thrice per week for 3 weeks) are described in Table 16.

TABLE 16

NOD-SCID Mouse Model with A-375 Tumors - Group Designation, Dose Levels, and Treatment Schedule

| Group/ PBMC Donor | Number of Animals | Treatment | Dose (mg/kg/ injection) | Administration Route | Treatment Schedule (first treatment on D1) |
|---|---|---|---|---|---|
| 1/A | 3 | Vehicle | N/A | IP | TIWx3 |
| 1/B | 3 | Vehicle | N/A | IP | TIWx3 |
| 1/C | 3 | Vehicle | N/A | IP | TIWx3 |
| 2/A | 3 | C40 × P24 | 10 | IP | TIWx3 |
| 2/B | 3 | C40 × P24 | 10 | IP | TIWx3 |
| 2/C | 3 | C40 × P24 | 10 | IP | TIWx3 |
| 3/A | 3 | C40 × P24s | 10 | IP | TIWx3 |
| 3/B | 3 | C40 × P24s | 10 | IP | TIWx3 |
| 3/C | 3 | C40 × P24s | 10 | IP | TIWx3 |
| 4/A | 3 | C40 × P31.2 | 10 | IP | TIWx3 |
| 4/B | 3 | C40 × P31.2 | 10 | IP | TIWx3 |
| 4/C | 3 | C40 × P31.2 | 10 | IP | TIWx3 |
| 5/A | 3 | C59 × P31.2 | 10 | IP | TIWx3 |
| 5/B | 3 | C59 × P31.2 | 10 | IP | TIWx3 |
| 5/C | 3 | C59 × P31.2 | 10 | IP | TIWx3 |

s = silent Fc

Tumors were collection based on homogeneity of tumor growth, with one tumor per donor per group collected when tumor reach 500 $mm^3$ before study termination. For all other mice, tumors were collected when mice reach humane endpoints or at study endpoint (a maximum of 8 weeks after tumor cell injection). Tumors collected were cut into slices of 4 mm thick, fixed in 4% neutral buffered formalin for 24 to 48 hours, and subsequently embedded in paraffin (Histowax®, Histolab, Sweden) with the aim of allowing serial sectioning of the whole tumor. The level of tumor necrosis was evaluated and noted in the autopsy report.

Figure 14:
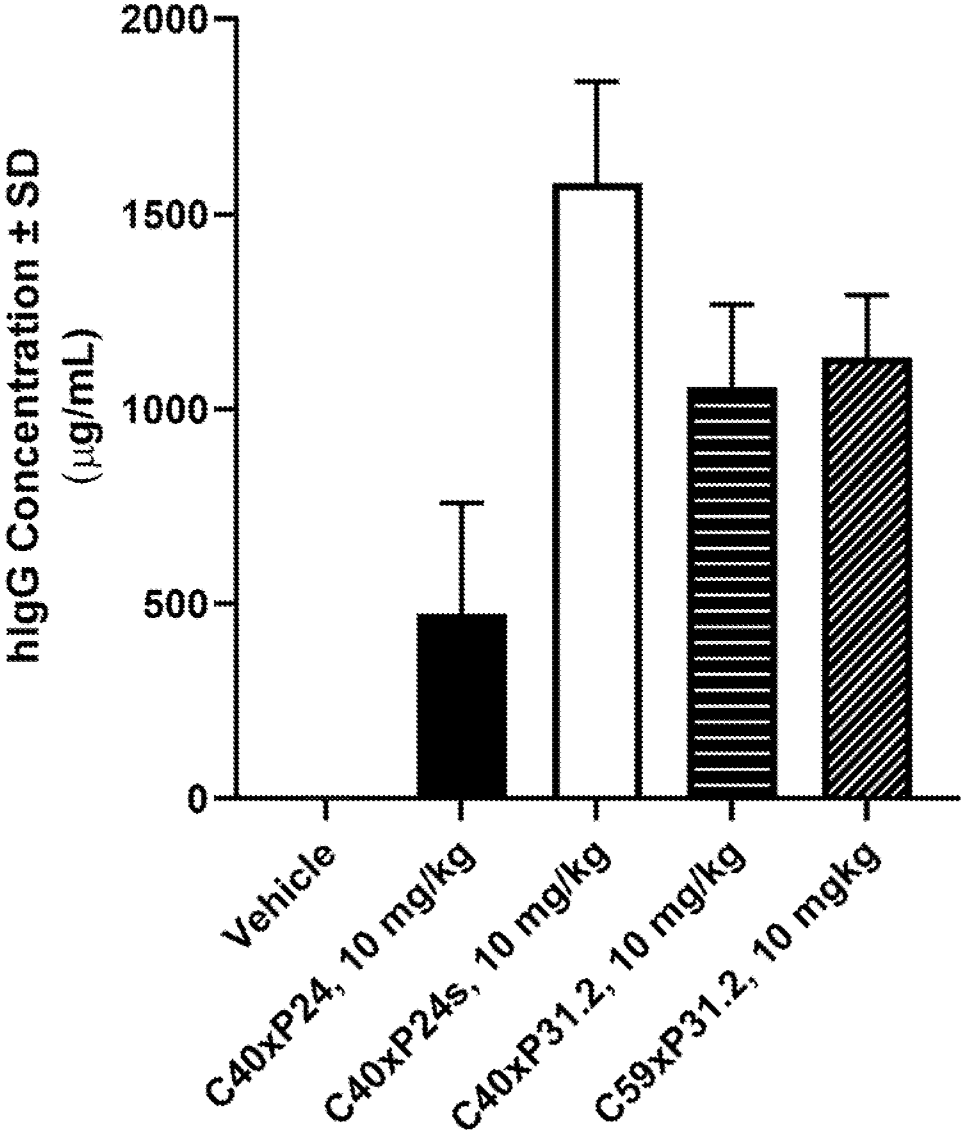
FIG. 14 illustrates exemplary results from additional in vivo animal studies related to antibody concentrations in blood from different animal groups treated with vehicle control, C40×P24, C40×P24s, C40×P31.2, or C59×P31.2 as indicated, further described in Example 7.

Animals were monitored for parameters including animal body weight measurements, tumor volume, clinical and mortality records, and animal viability and behavior was observed daily. Body weights were measured a minimum of twice a week. The length (L) and width (W) of tumors were measured twice a week with calipers and volume calculated with the formula (L×W2)/2. The monitoring of mice was done for a maximum of 8 weeks post tumor induction and all surviving mice were euthanized no later than Day 56 (D56). In addition, bispecific antibody levels in the blood were analyzed by a Human Therapeutic IgG1 ELISA (Cayman Chemical, Kit Item No. 500910). Exemplary results are shown in FIG. 14.

Figure 15A:
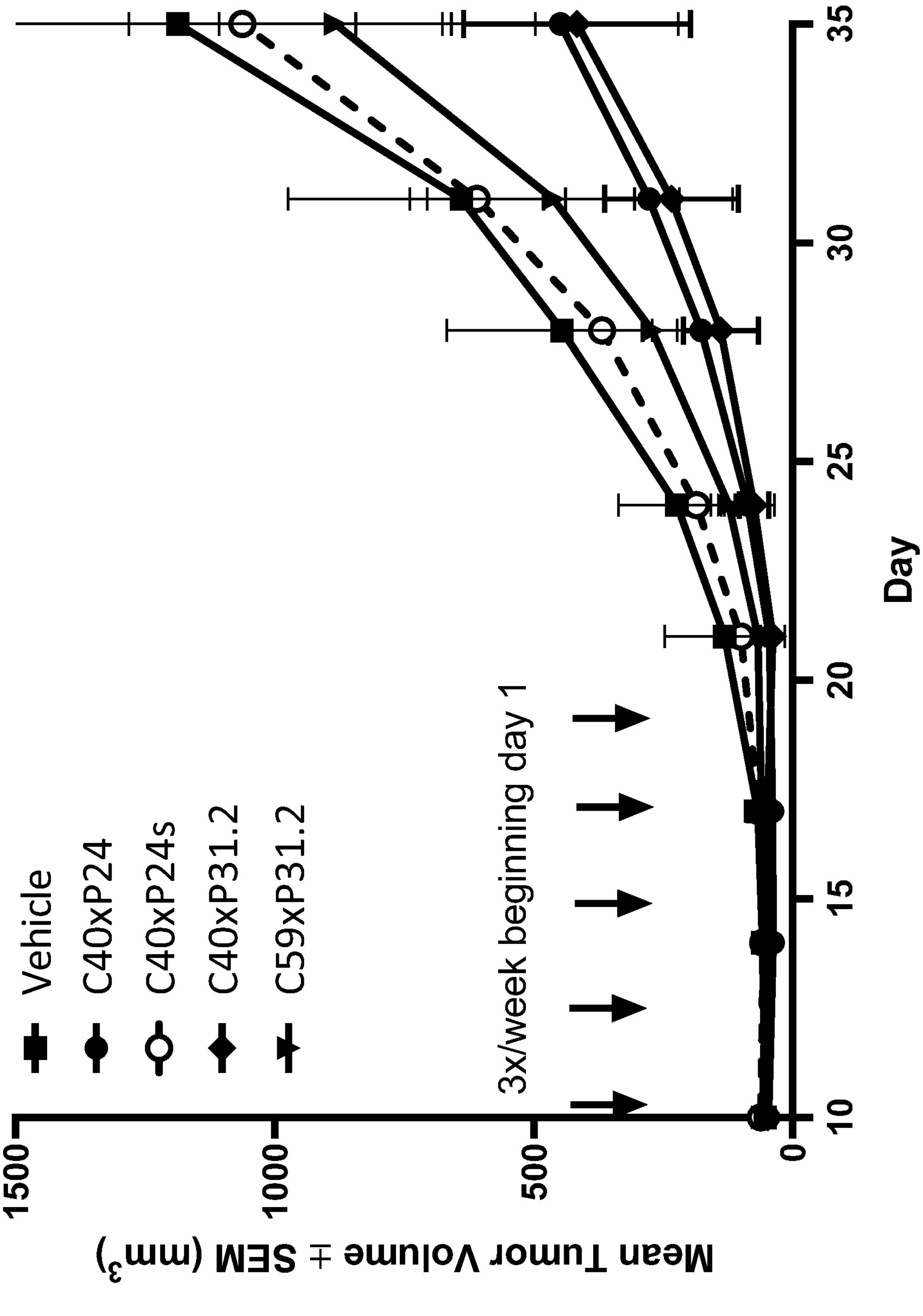
FIGS. 15A-15H illustrate exemplary results from additional in vivo animal studies related to tumor volume and body weight from different animal groups treated with vehicle control, C40×P24, C40×P24s, C40×P31.2, or C59×P31.2 as indicated, further described in Example 7.
Figure 15B:
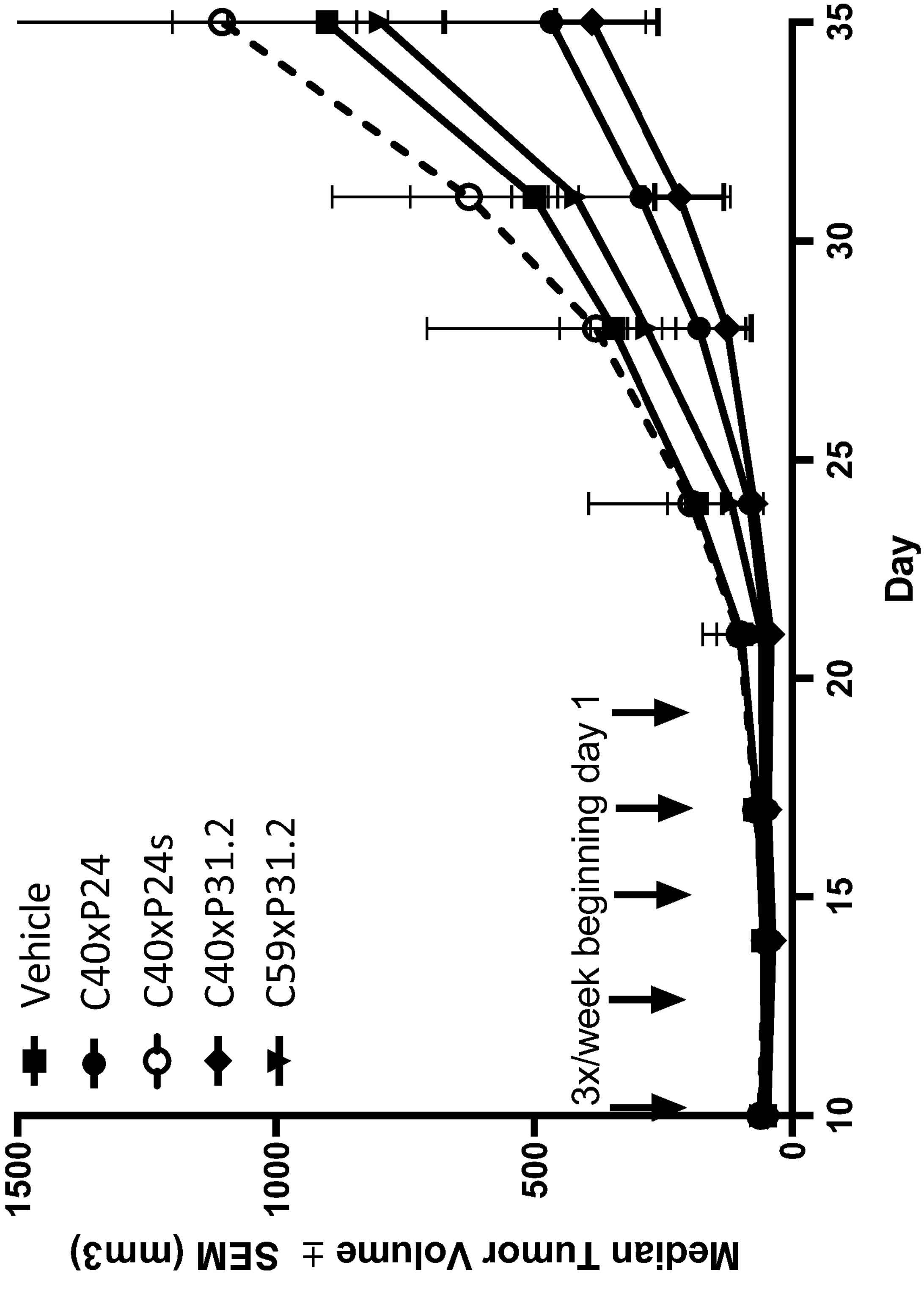
Figure 15C:
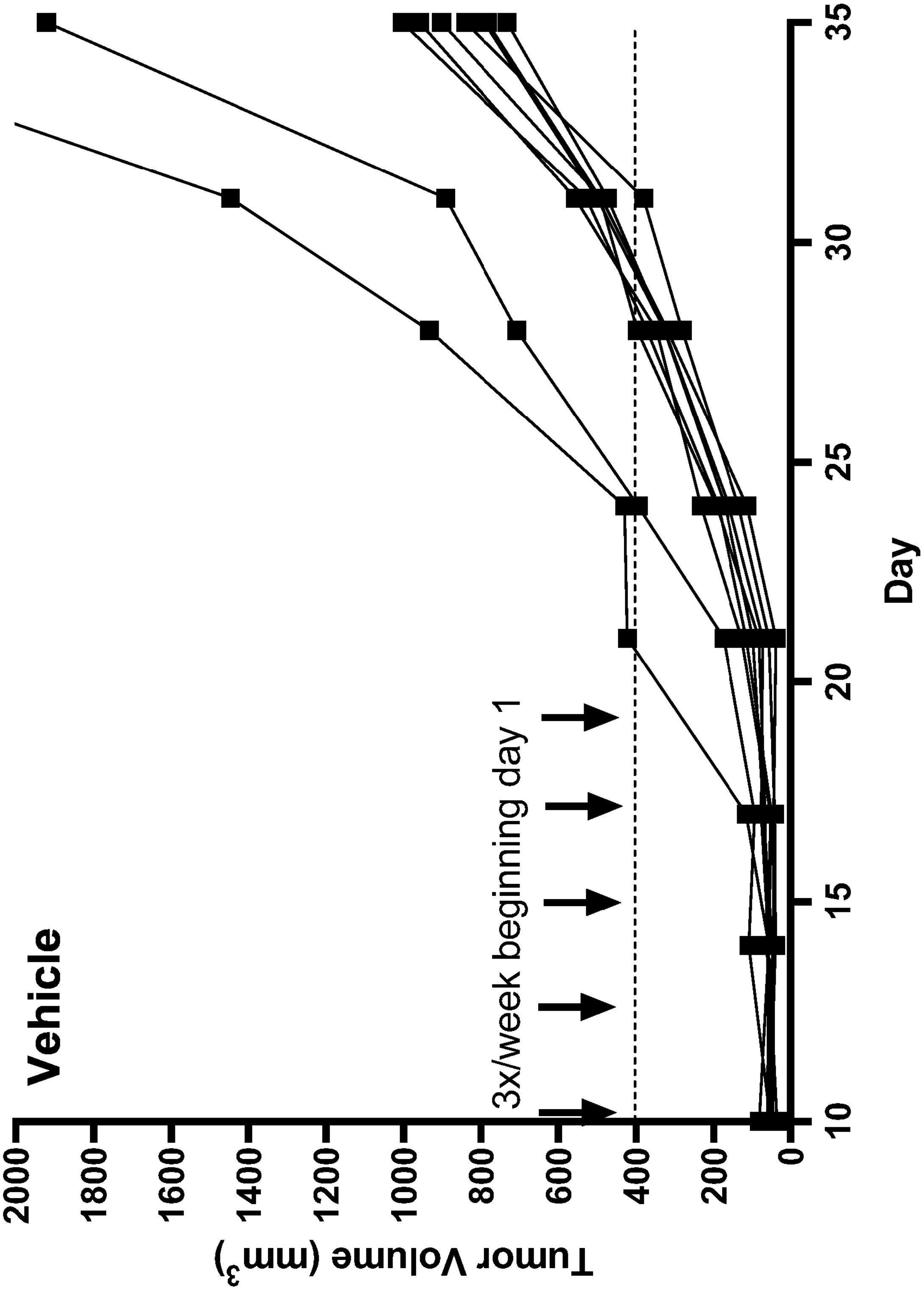
Figure 15D:
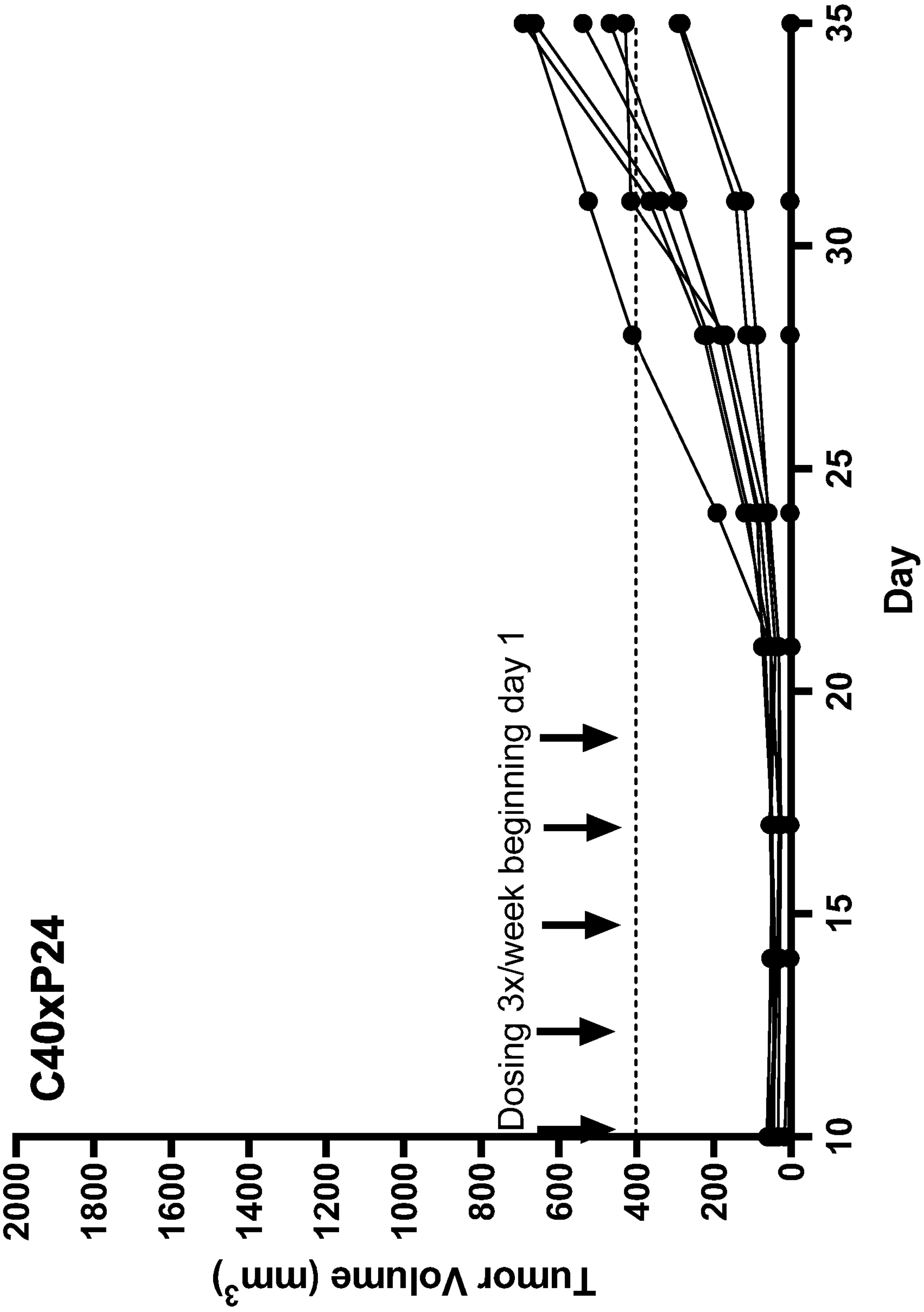
Figure 15E:
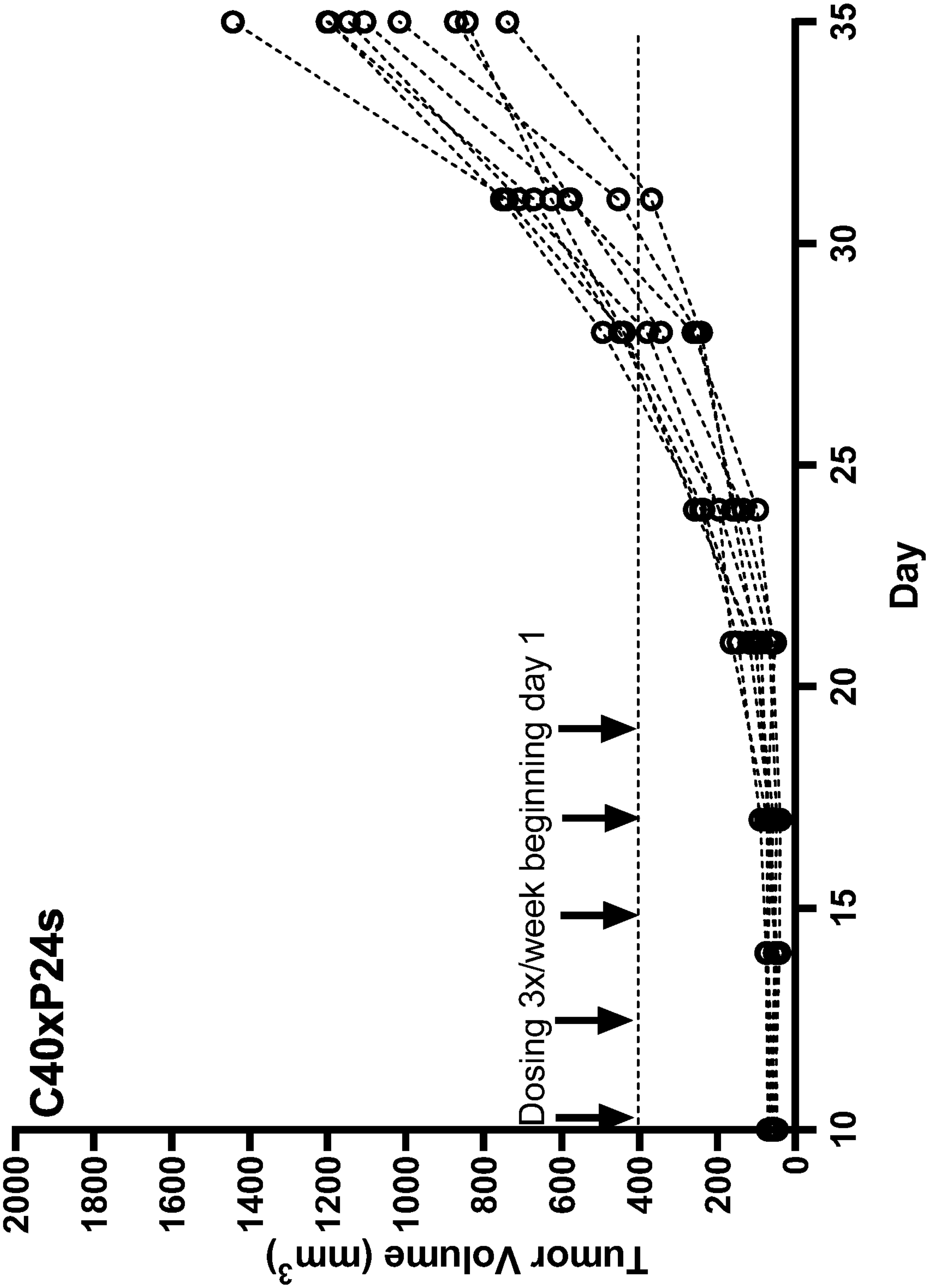
Figure 15F:
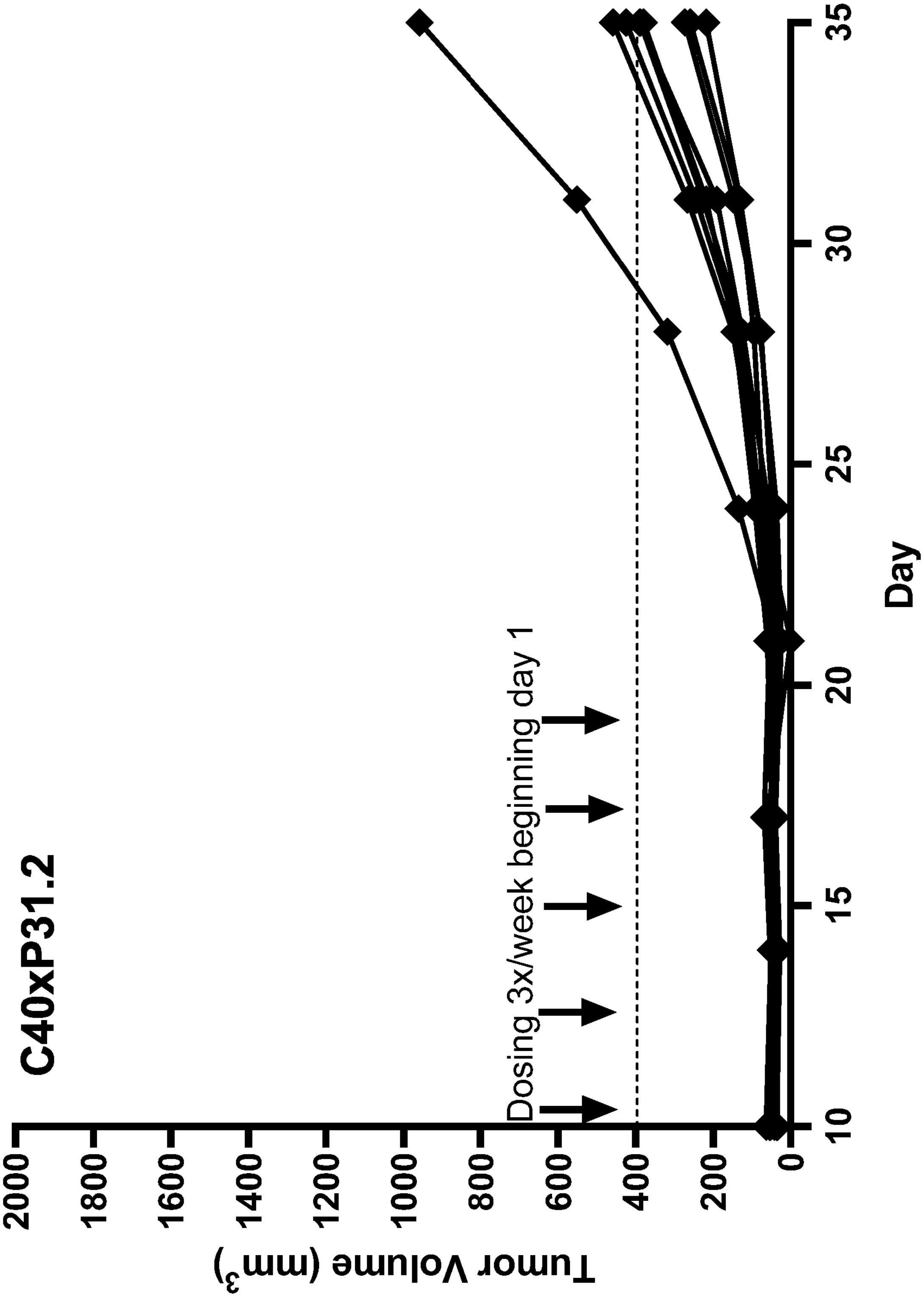
Figure 15G:
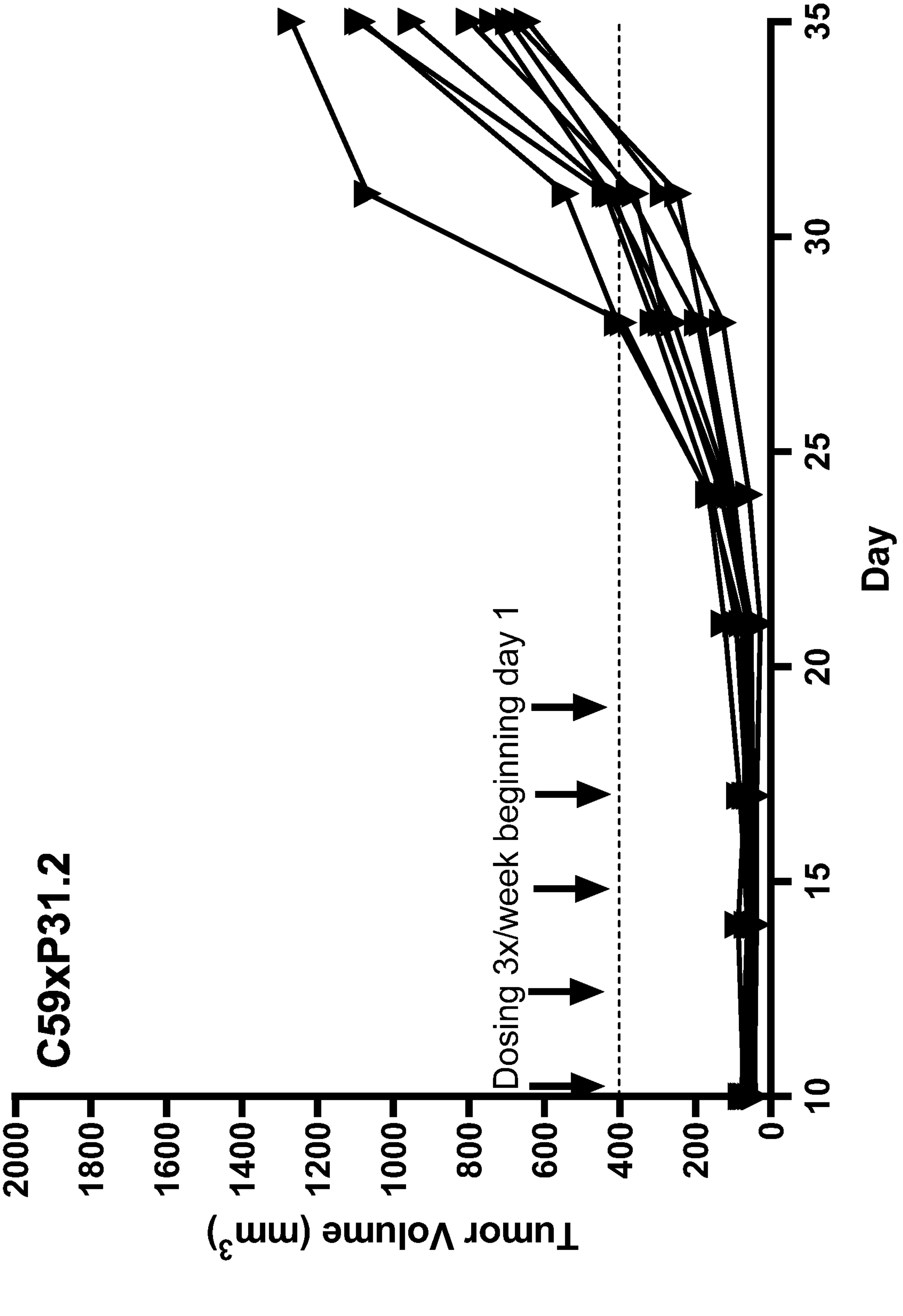
Figure 15H:
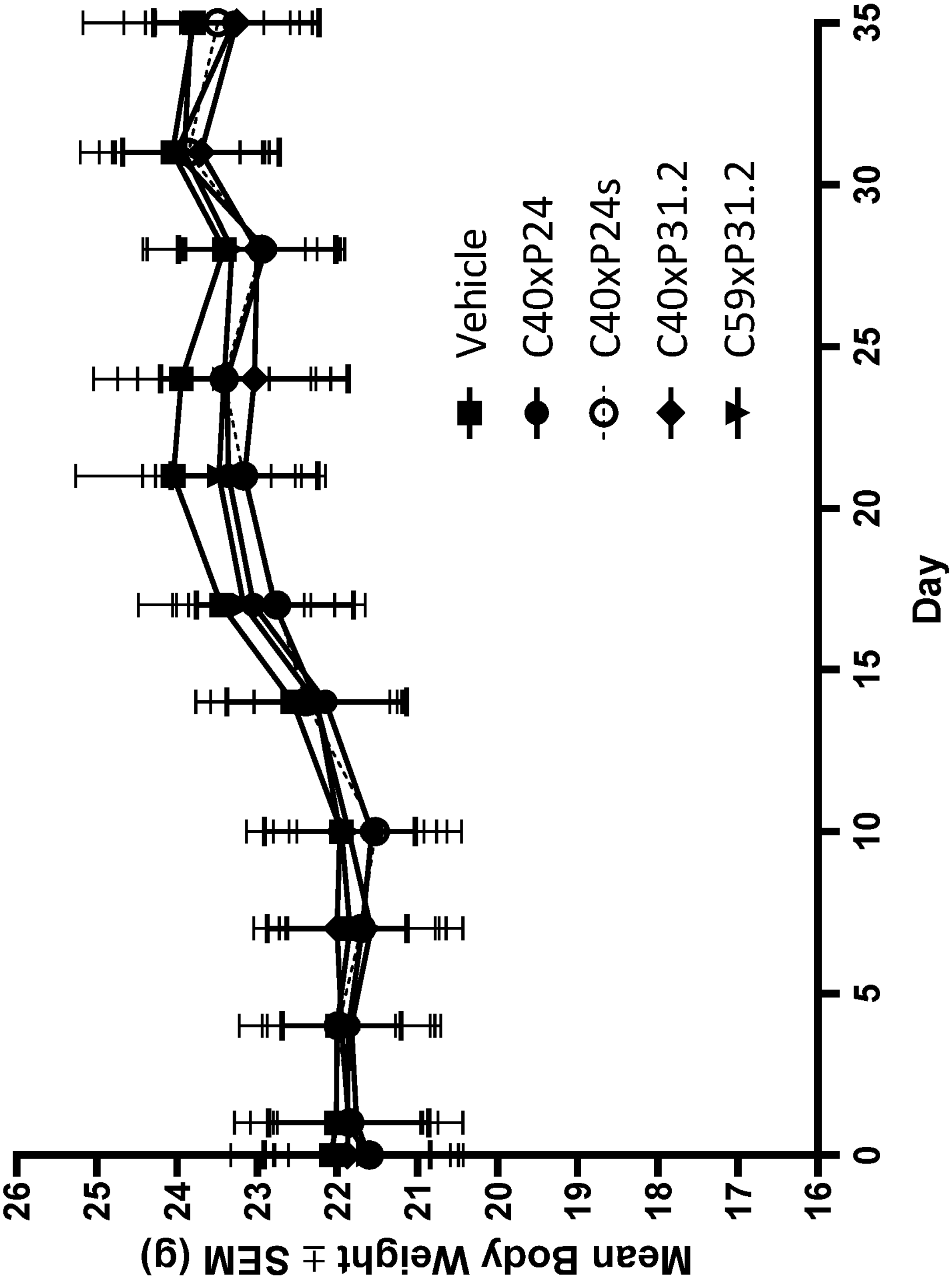

Exemplary mean tumor volume (Mean TV) and median tumor volume (Median TV) results for mice in indicated treatment groups with the exemplary bispecific antibodies are shown in FIG. 15A and FIG. 15B, respectively. Exemplary tumor volume results for individual mice are shown in FIGS. 15C-15G. Exemplary mean body weight results for mice in indicated treatment groups with the exemplary bispecific antibodies are shown in FIG. 15H.

In vivo therapeutic efficacy of bispecific antibodies was further evaluated in the humanized NOD-SCID mouse model bearing the A-375 melanoma tumors in an additional study.

Animals were housed and fed as described above in the previous A-375 study and bispecific antibodies in a BC44 format as described herein were prepared as described above.

PBMCs used for in vivo injection were prepared also as described in the previous A-375 study above.

Fifty-four healthy female NOD-SCID (NOD.CB17-Prkdcscid/NCrCrl) mice, 7 to 8 weeks old at reception, were obtained from Charles River Laboratories. PBMCs were injected on Day−3 (D−3), 3 days prior to tumor induction. The fifty-four mice were split into 6 sub-groups of 9 mice each, and with each sub-group was allocated to one PBMCs donor (donor A, B and C). The three sub-groups had equivalent mean body weight at time of PBMC inoculation. PBMCs from each donor were injected into one sub-group of 9 mice on the same day. Each mouse received one single intravenous (IV) injection of $1\times10^7$ PBMCs in 200 μL RPMI without phenol red.

On Day−0 (DO), tumors were induced in all fifty-four NOD SCID female mice by subcutaneous injection of $1\times10^7$ A-375 cells in 200 μL RPMI 1640 without phenol red into the right flank of each animal. Animals were randomized on Day 1 (D1) by individual body weight. Three (3) mice from each sub-group were randomized into 6 groups according to their individual body weight using Vivo Manager® software. This distribution yielded 6 groups of 9 mice, 3 mice per donor per group. A statistical test (analysis of variance, ANOVA) was performed to test for homogeneity between groups for each donor.

The treatment was administered on Day 1 (D1) by injection into the peritoneal cavity (IP), with an IP formulation of pH 7.3-7.4 and an administration volume of 10 mL/kg, adjusted to the most recent individual body weight. Group designations, dosage levels, administration, and treatment schedule with the exemplary bispecific antibodies (TIW×4, thrice per week for 4 weeks) is described in Table 17.

TABLE 17

NOD-SCID Mouse Model with A-375 Tumors - Group Designation, Dose Levels, and Treatment Schedule

| Group/ PBMC Donor | Number of Animals | Treatment | Dose (mg/kg/ injection) | Administration Route | Treatment Schedule (first treatment on D1) |
|---|---|---|---|---|---|
| 1/A | 3 | Vehicle | N/A | IP | TIWx4 (12 doses) + 13th dose on D 29 |
| 1/B | 3 | Vehicle | N/A | IP | TIWx4 (12 doses) + 13th dose on D 29 |
| 1/C | 3 | Vehicle | N/A | IP | TIWx4 (12 doses) + 13th dose on D 29 |
| 3/A | 3 | C40 × P24 | 10 | IP | TIWx4 (12 doses) + 13th dose on D 29 |
| 3/B | 3 | C40 × P24 | 10 | IP | TIWx4 (12 doses) + 13th dose on D 29 |
| 3/C | 3 | C40 × P24 | 10 | IP | TIWx4 (12 doses) + 13th dose on D 29 |
| 4/A | 3 | C56 × P22 | 10 | IP | TIWx4 (12 doses) + 13th dose on D 29 |
| 4/B | 3 | C56 × P22 | 10 | IP | TIWx4 (12 doses) + 13th dose on D 29 |
| 4/C | 3 | C56 × P22 | 10 | IP | TIWx4 (12 doses) + 13th dose on D 29 |
| 5/A | 3 | C40 × P31.2 | 10 | IP | TIWx4 (12 doses) + 13th dose on D 29 |
| 5/B | 3 | C40 × P31.2 | 10 | IP | TIWx4 (12 doses) + 13th dose on D 29 |
| 5/C | 3 | C40 × P31.2 | 10 | IP | TIWx4 (12 doses) + 13th dose on D 29 |

Tumors were collected at Day 31 (D31) after a final dose on Day 29 (D29), weighed, and used to evaluate tumor infiltrates by flow cytometry analysis. Animals were monitored for parameters including animal body weight measurements, tumor volume, clinical and mortality records, and animal viability and behavior was observed daily. Body weights were measured a minimum of twice a week. The length (L) and width (W) of tumors were measured twice a week with calipers and volume calculated with the formula (L×W2)/2. The monitoring of mice was done for a maximum of 8 weeks post tumor induction and all surviving mice were euthanized no later than Day 56 (D56).

Exemplary mean tumor volume (Mean TV) results for mice in indicated treatment groups with the exemplary bispecific antibodies are shown in FIG. 16A. Exemplary mean body weight results for mice in indicated treatment groups with the exemplary bispecific antibodies are shown in FIG. 16B.

Macrophage infiltration into tumors was analyzed by flow cytometry. For the evaluation of the tumor infiltrates, the excised and weighed tumors were dissected into smaller fragments using scalpels, further dissociated into single cell suspensions in a non-enzymatic cell dissociation buffer, incubated at 37° C. for 30 minutes and mechanically separated through a 70 μm cell strainer. Viable cells were enriched using ficoll-based gradient centrifugation. Prior to any staining, cell suspensions were enumerated and one million cells (when possible) were distributed per well/tube. Cells were stained in a final staining volume of 100 μL per well. A first step of staining with a viability dye was performed to allow dead cell exclusion at the analysis. Non-specific binding was minimized using the FcR blocking reagent (human and mouse). Fluorescent labeled surface target antibodies were added, according to the procedure described by the supplier for each antibody (or a titrated dose if it was a standardized panel). The mixture was incubated for 30 minutes at 4° C. protected from light. After one wash, intracellular staining was performed using the FoxP3 staining buffer following the manufacturer's instructions. This step included both fixation and permeabilization steps allowing intracytoplasmic and intranuclear staining. Fluorescent-labeled antibodies directed against the intracellular targets were added, according to the procedure described by the supplier. The staining solution was incubated for 30 minutes at 4° C. protected from light, washed with permeabilization buffer and finally resuspended in 200 μL PBS 1% formaldehyde containing PKH26 beads. All samples were stored at +4° C. and protected from light until acquisition on cytometer.

Figure 17:
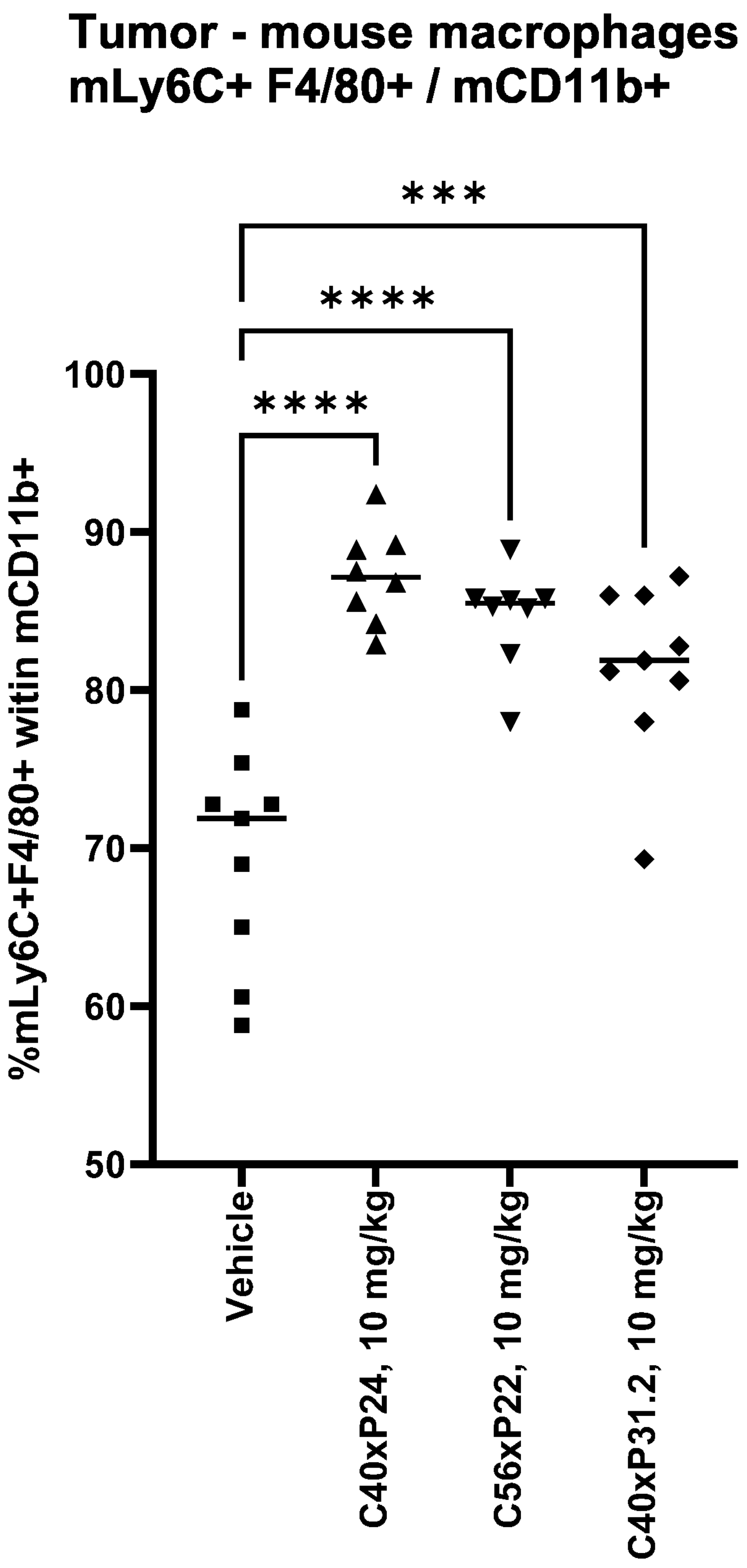
FIG. 17 illustrates exemplary results from additional in vivo animal studies related to macrophage infiltration into tumors from different animal groups treated with vehicle control, C40×P24, C56×P22, or C40×P31.2 as indicated, further described in Example 7.

For identification of positive and negative populations, the fluorescence minus one ("FMO") principle was used to account for background antibody fluorescence. FMO controls were done using excluded tumors from randomization for efficacy study. Compensation was performed using compensation beads and/or single stained cells. Acquisition of each well (150 μL) was performed with a Fortessa X20 cytometer (BD Biosciences) equipped with three excitation lasers. All events were saved during acquisition. Flow cytometry data were analyzed using FlowJo™ software (Becton Dickinson). Exemplary results are shown in FIG. 17.

In vivo therapeutic efficacy of bispecific antibodies was also evaluated in a Jeko-PD-L1 model. In this study, one hundred (100) female NSG (NOD.Cg-PrkdcscidlL2rgtm1Wjl/SzJ; Jackson Lab) mice were inoculated subcutaneously in the rear right flank with a Jeko-PD-L1 lymphoma cell line at 4 million cells per mouse. At a mean tumor volume of 100 $mm^3$, 64 mice were randomized into 8 study groups of n=8 each, based on tumor volumes and dosed intraperitoneally (i.p.) with either vehicle or bispecific antibodies in a BC44 format as described herein every other day for 6 doses. The study was terminated at Day 21 after start of dosing on Day 0.

The study groups and number of animals per group for the efficacy cohort are shown in Table 18.

TABLE 18

| NSG Mouse Model with Jeko-PD-L1 Tumors-Group Designation, Dose Levels, and Treatment Schedule | | | | | | |
|---|---|---|---|---|---|---|
| Group | Treatment | N | Dose Route | Dosing Frequency & Duration | Dose Level (mg/kg) | Dose Volume (mL/kg) |
| 1 | Vehicle | 8 | i.p. | Every other day for 6 doses | N/A | N/A |
| 2 | C40 × P24 | 8 | i.p. | Every other day for 6 doses | 10 | 10 |
| 3 | C56 × P22 | 8 | i.p. | Every other day for 6 doses | 10 | 10 |
| 4 | C40 × P31.2 | 8 | i.p. | Every other day for 6 doses | 10 | 10 |
| 5 | C59 × P22 | 8 | i.p. | Every other day for 6 doses | 10 | 10 |
| 6 | C59 × P31.2 | 8 | i.p. | Every other day for 6 doses | 10 | 10 |

All animals enrolled in the study were randomized by tumor volume on Day 0 to the study groups shown in Table 18 and the mean tumor volume at randomization was similar across the groups (approximately 100 $mm^3$).

Figure 18A:
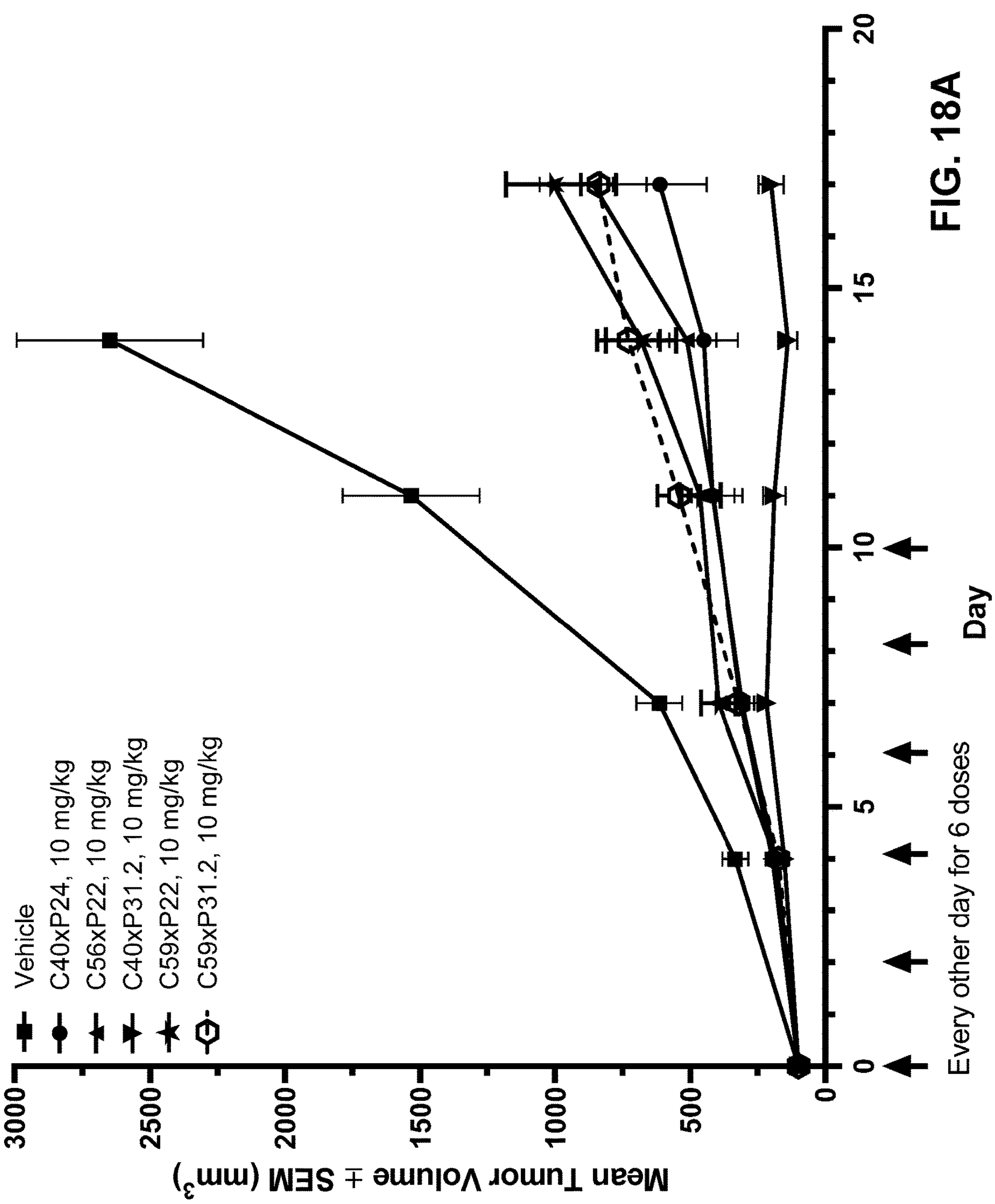
FIGS. 18A-18B illustrate exemplary results from additional in vivo animal studies related to tumor volume and body weight from different animal groups treated with vehicle control, C40×P24, C56×P22, C40×P31.2, C59×P22, or C59×P31.2 as indicated, further described in Example 7.
Figure 18B:
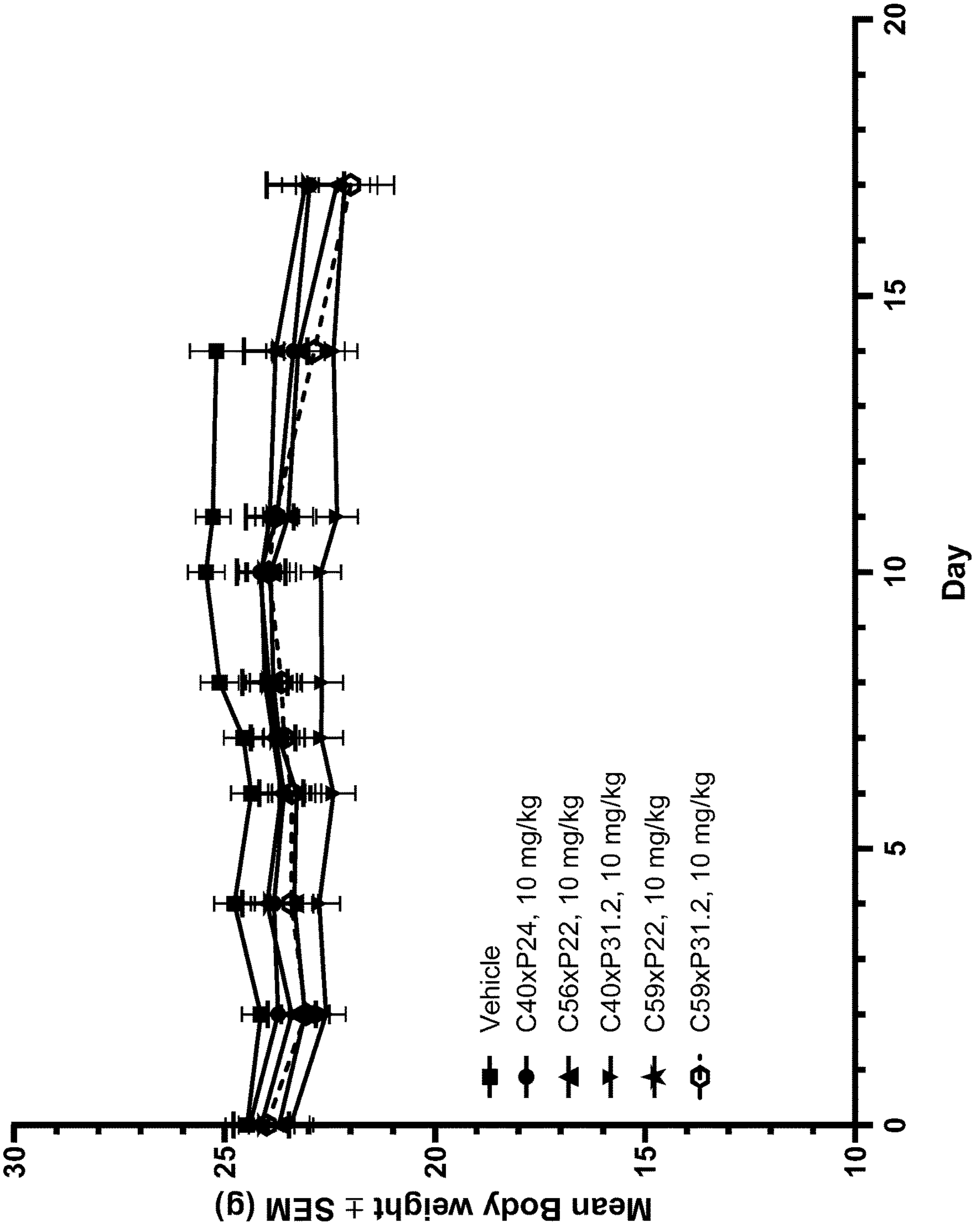

Exemplary Jeko-PD-L1 tumor volumes are shown in FIG. 18A by treatment group (mean±SEM) from randomization (day 0) to Day 14 or 17. Exemplary body weights are also shown in FIG. 18B by treatment group (mean±SEM) from randomization (day 0) to Day 14 or 17. As shown in FIG. 18A and FIG. 18B, compared to the vehicle group, all treatment groups showed significant tumor inhibition 2 weeks after start of dosing and no treatment group had mean body weight loss of over 10%.

Percent tumor growth inhibition (TGI) was also calculated using the following formula: % TGI=(1−(Ti−T1)/(Vi−V1))×100, where Ti is the mean tumor volume of the treatment group on the measurement day; T1 is the mean tumor volume of the treatment group on Day 0; Vi is the mean tumor volume of vehicle-treated group on the measurement day; V1 is the tumor volume of the vehicle-treated group on Day 0.

TABLE 19

| TGI with data collected on Day 14 | |
|---|---|
| Group | % TGI |
| 2 (C40 × P24) | 86.23 |
| 3 (C56 × P22) | 83.79 |
| 4 (C40 × P31.2) | 98.48 |
| 5 (C59 × P22) | 77.12 |
| 6 (C59 × P31.2) | 75.30 |

Exemplary results showed that the exemplary bispecific antibodies had anti-tumor activity as indicated by effects on tumor volume with % TGIs shown in Table 19.

Example 8. Developability Assays

Bispecific antibodies that were selected for binding to CD47 and PD-L1, for example, such as those described in Examples 1-3, were tested in various developability methods. For example, various chromatographic methods, including size exclusion chromatography (SEC), hydrophobic interaction chromatography (HIC), and standup monolayer adsorption chromatography (SMAC) were employed to assess developability factors, such as monomer percentage, solubility, and antibody aggregation or precipitation.

Size exclusion chromatography (SEC) analysis was performed using a 7.8 mm ID×30 cm TSKgel® G3000SWXL column (Tosoh Bioscience LLC, PN 08541) on an Agilent 1100 HPLC. Bispecific antibodies in a BC44 format as described herein were normalized to 1 mg/mL concentration in Dulbecco's PBS (pH 7.4, without Ca2+/Mg2+) and clarified via centrifugation to pellet particulates while still retaining soluble aggregates. The mobile phase buffer was Dulbecco's PBS (pH 7.4, without Ca2+/Mg2+). For each sample, 10 μL was loaded and isocratically eluted at 1.0 mL/min over 20 minutes. Absorbance was monitored at 280 nm. Chromatographic peaks were integrated to determine % homogeneity and retention time. The column stationary phase along with choice of mobile phase supports hydrophobic interaction in addition to molecular sizing (hydrophobic interaction much milder compared to SMAC). Data analysis was performed using Agilent ChemStation B.04.03.

Figure 19A:
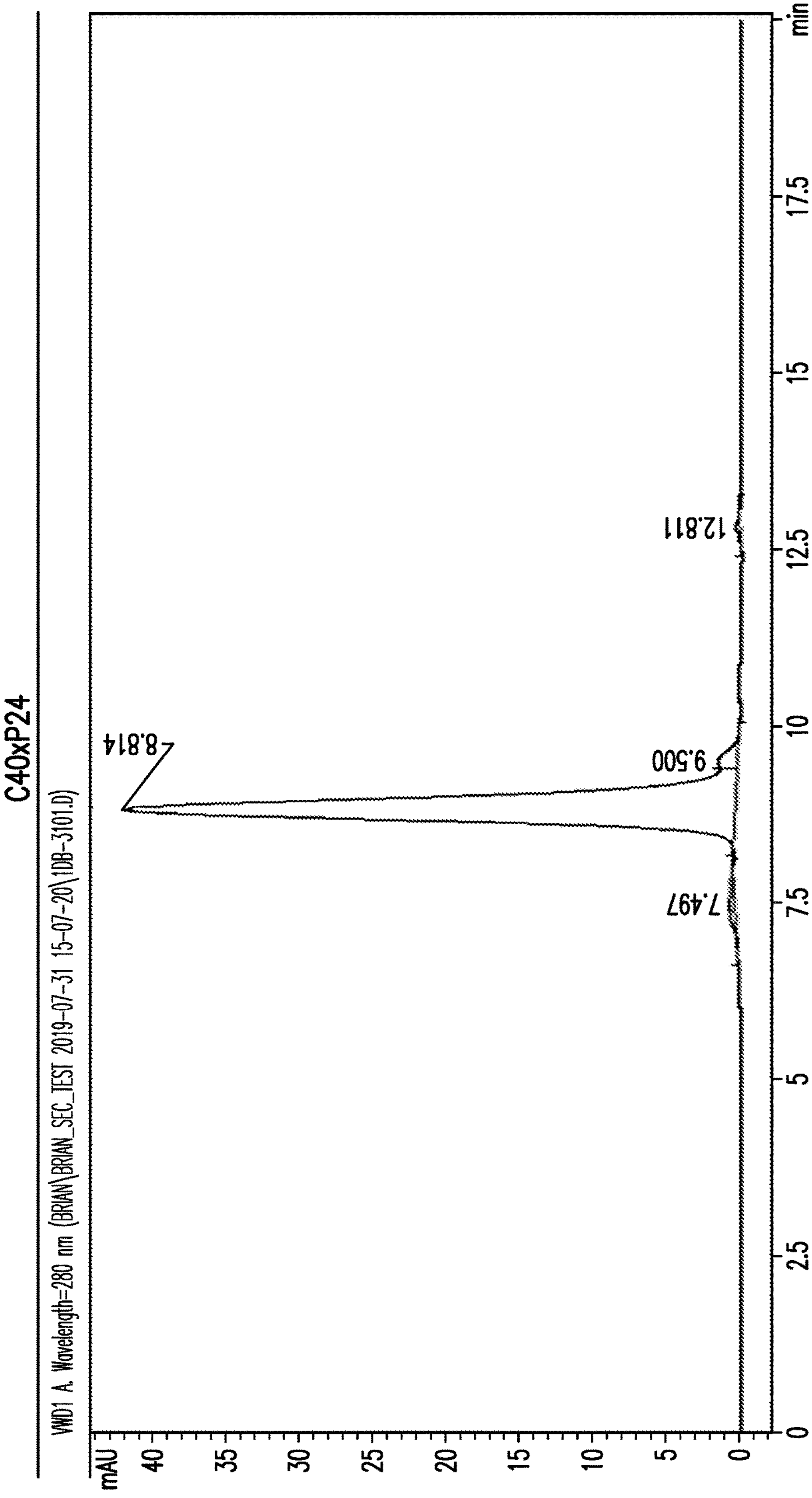
FIGS. 19A-19C illustrate exemplary results from SEC chromatography, further described in Example 8.
Figure 19B:
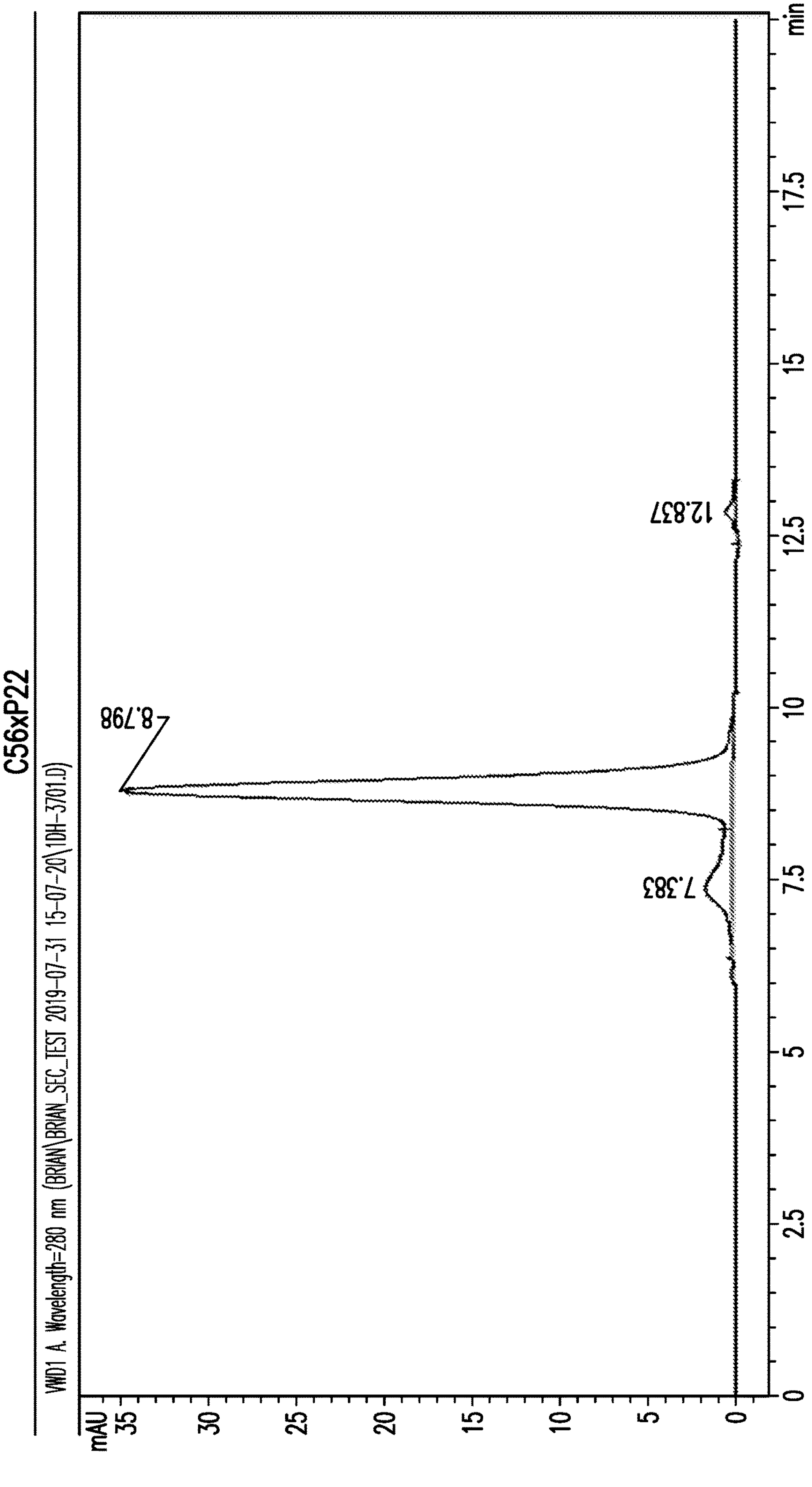
Figure 19C:
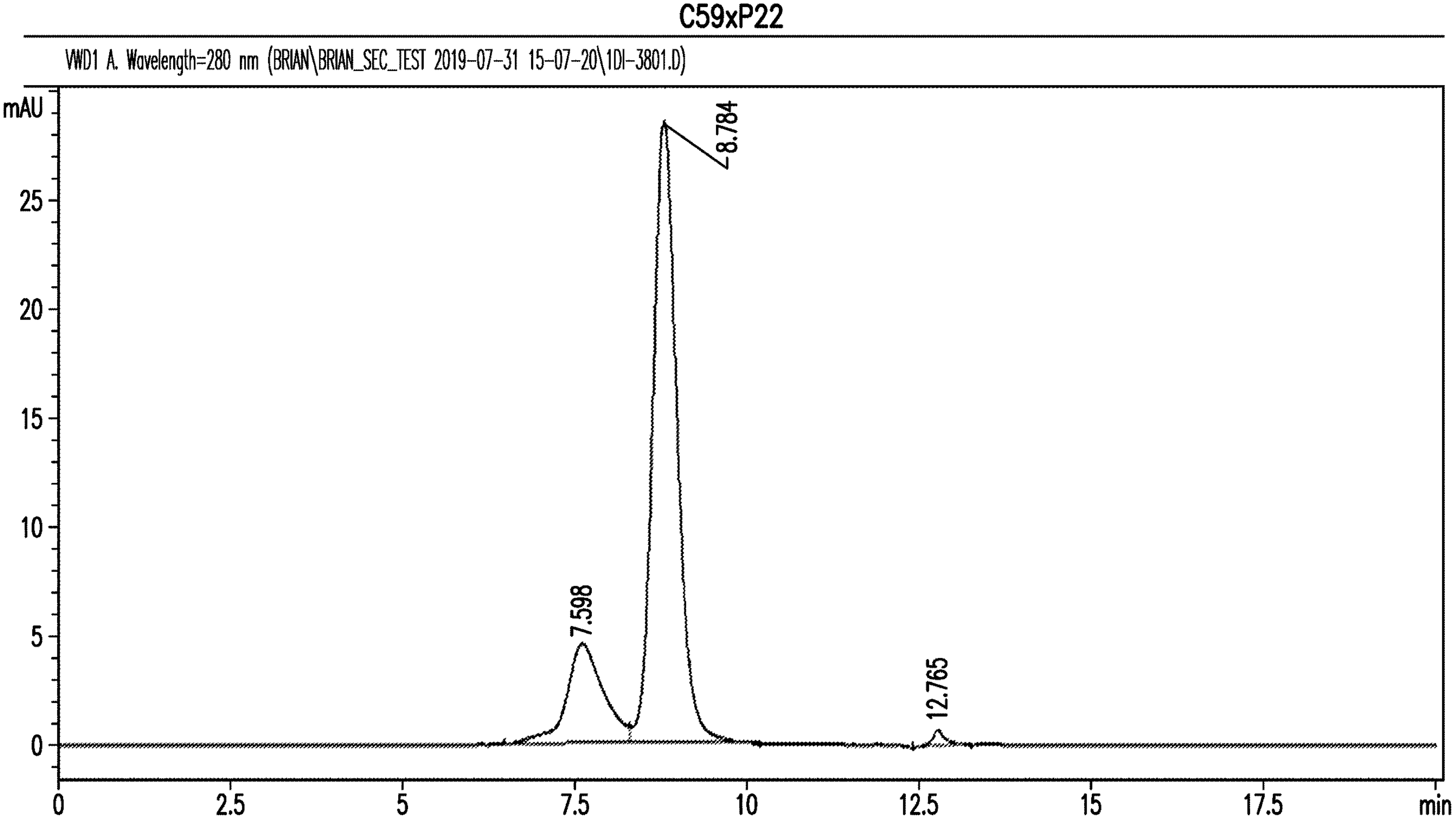
Figure 20A:
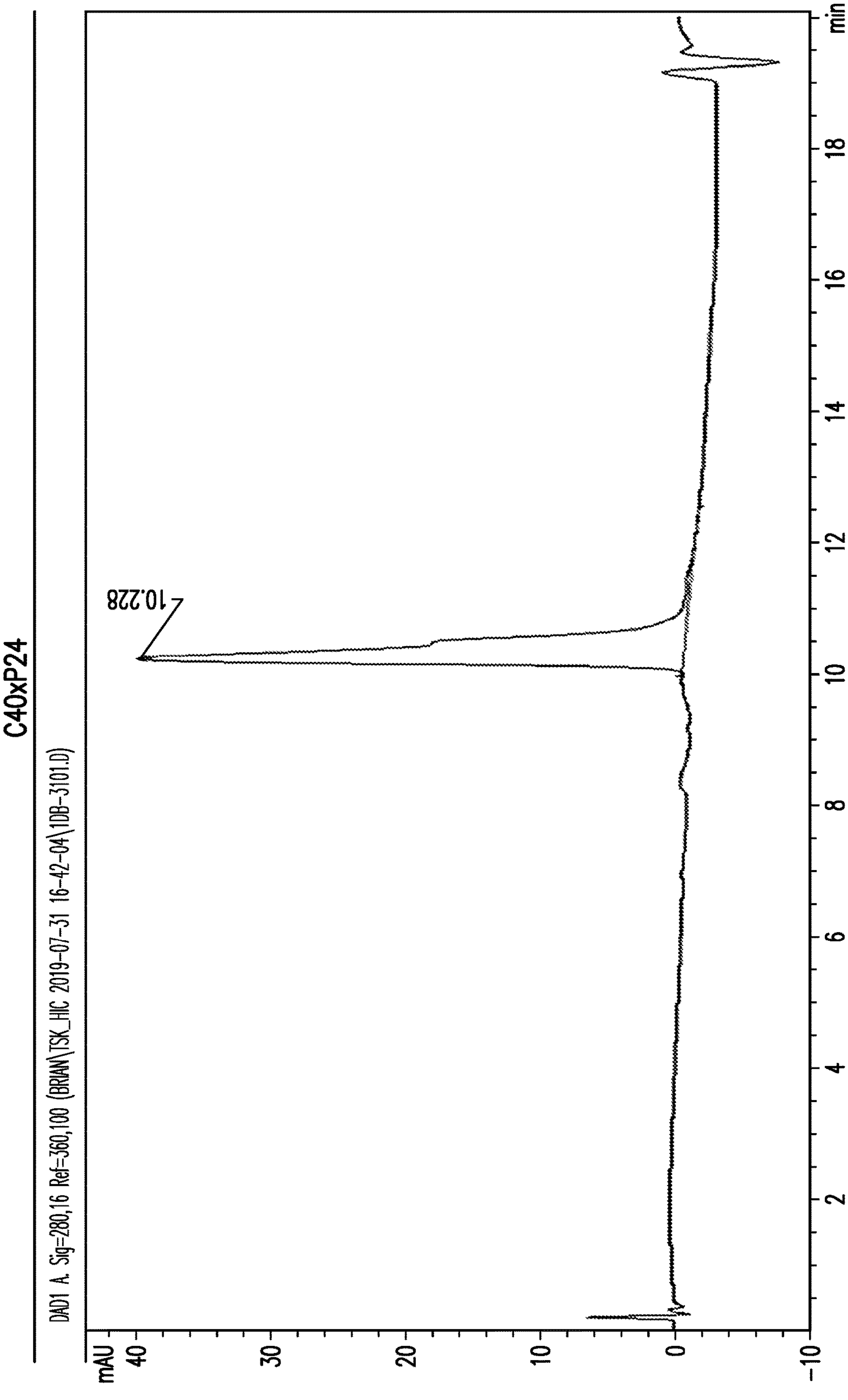
FIGS. 20A-20D illustrate exemplary results from HIC chromatography, further described in Example 8.
Figure 20B:
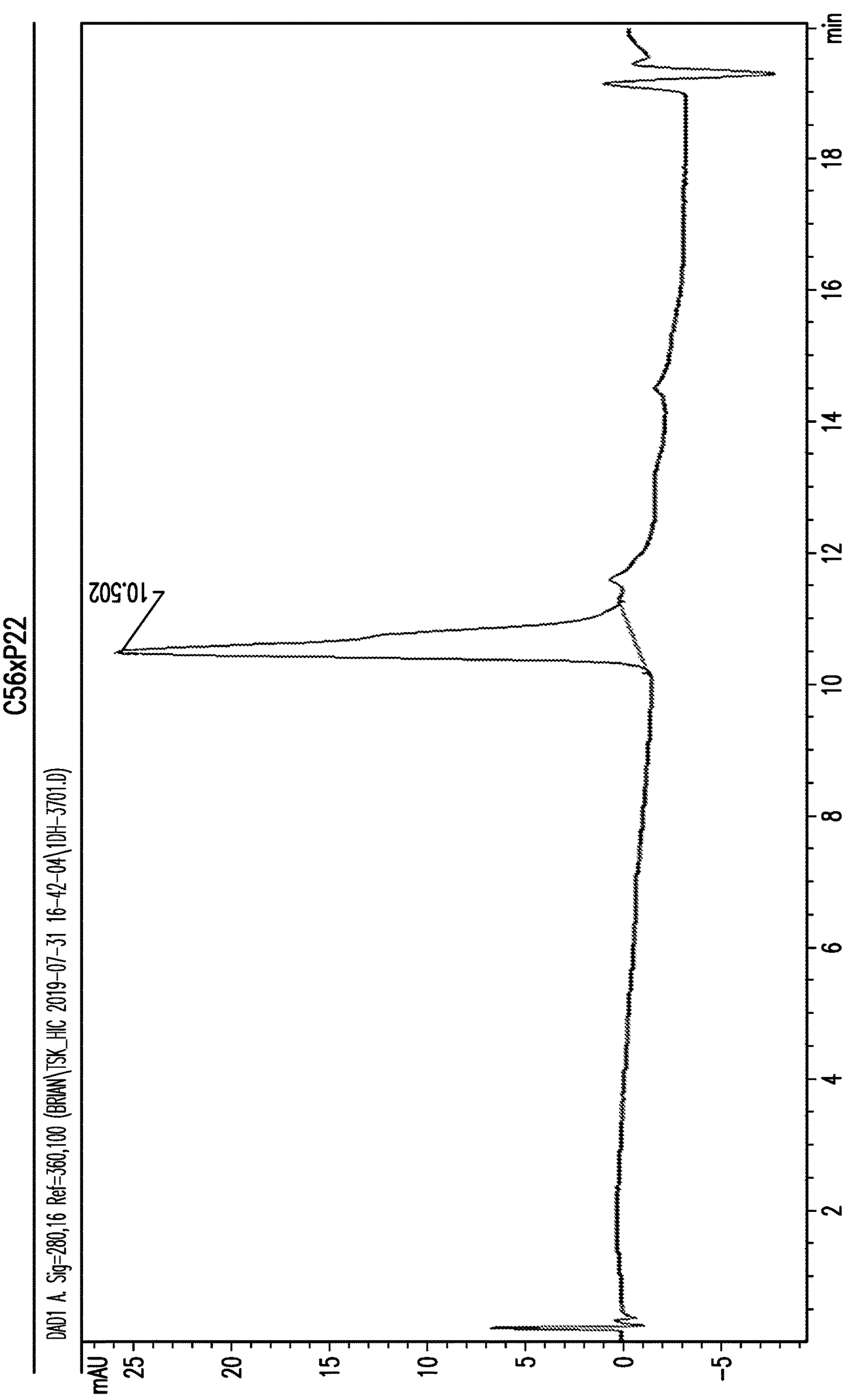
Figure 20C:
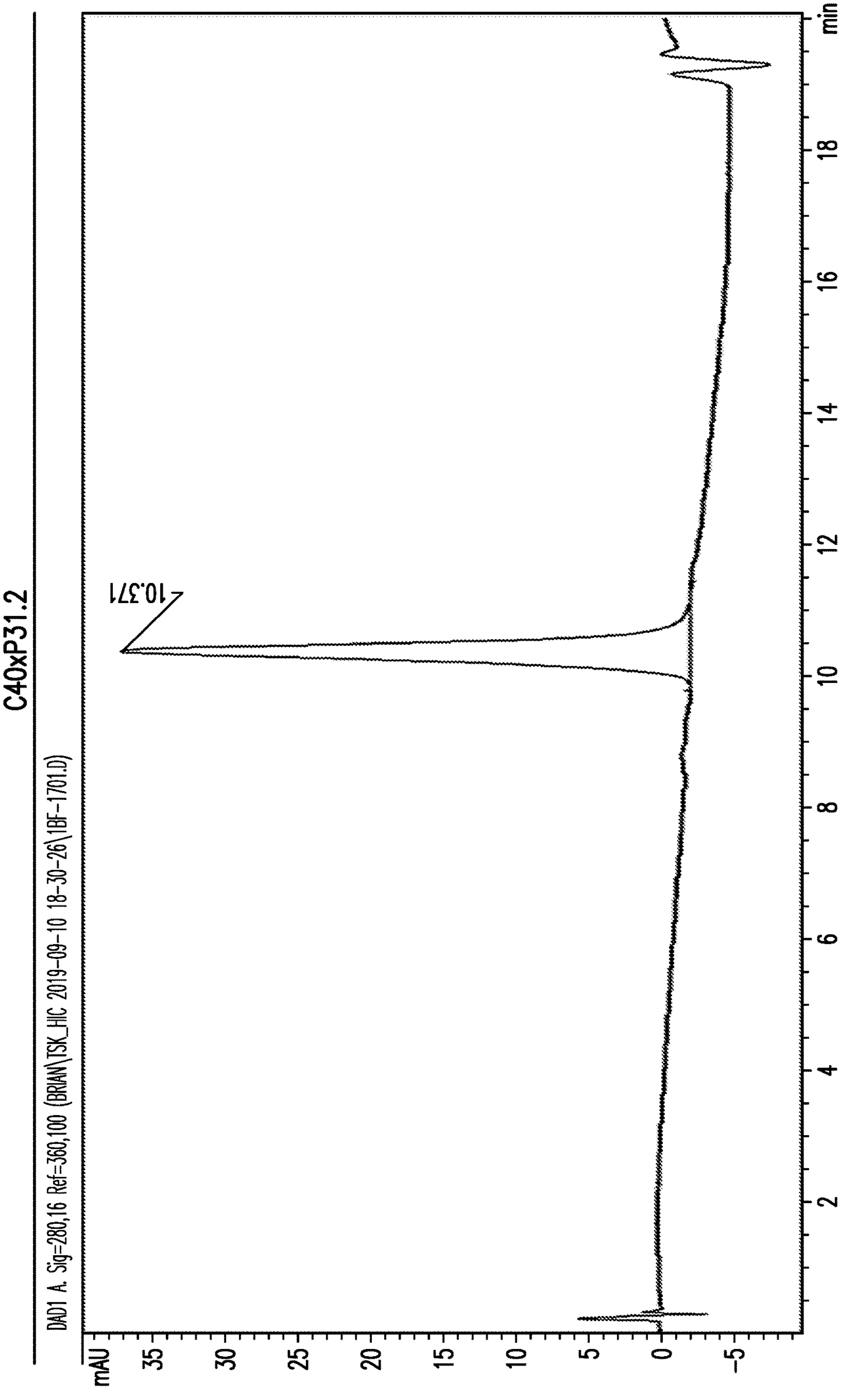
Figure 20D:
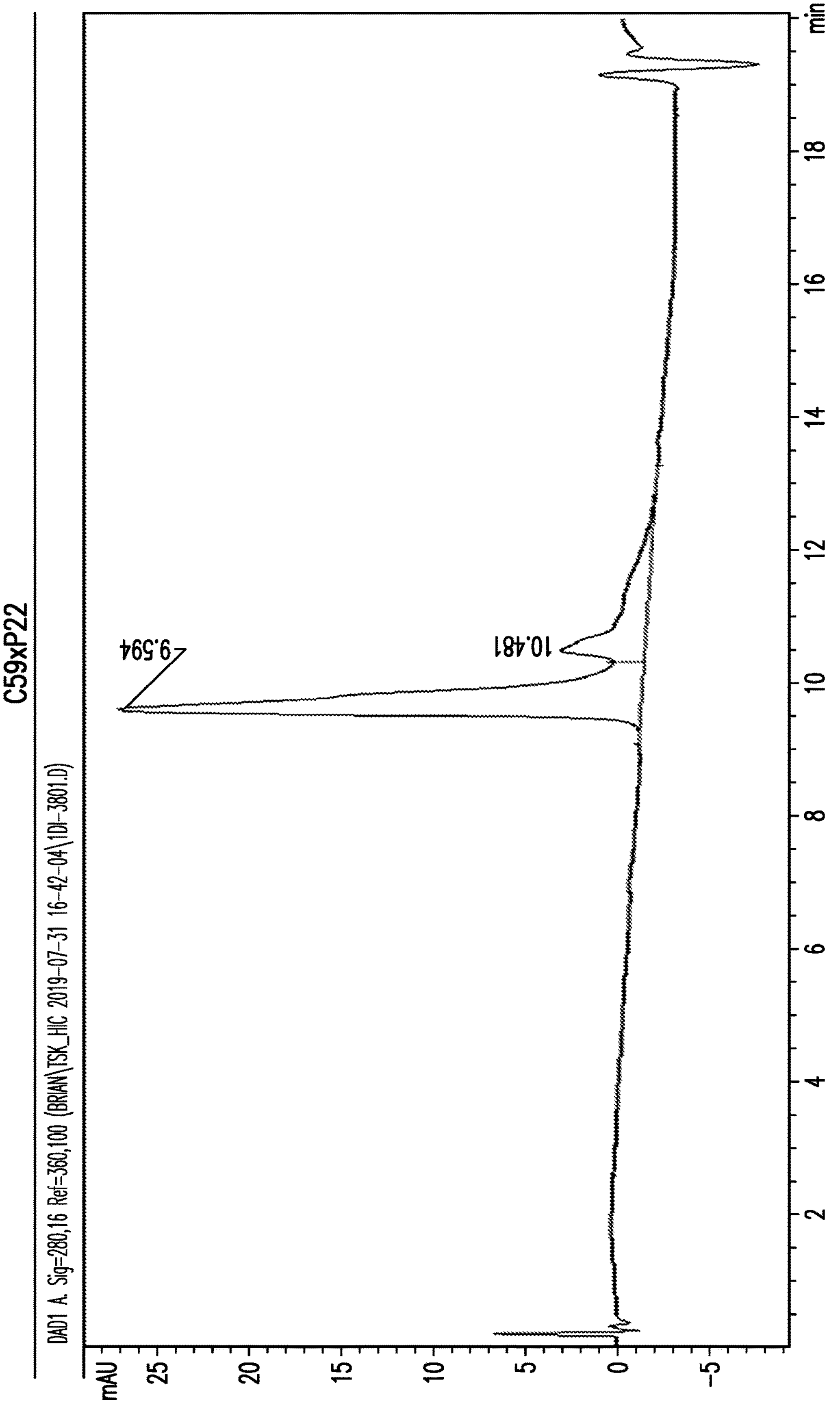
Figure 21A:
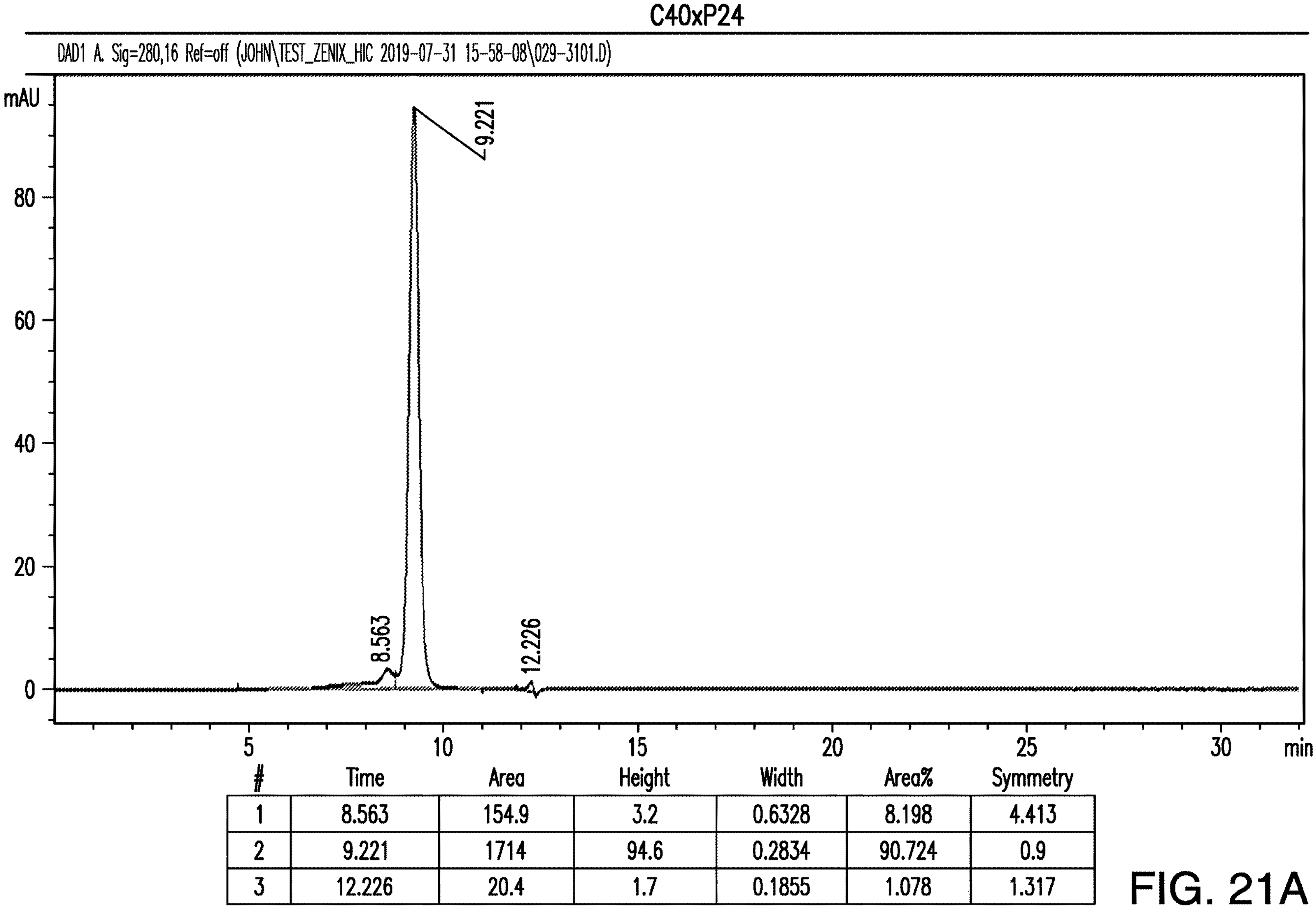
FIGS. 21A-21D illustrate exemplary results from SMAC chromatography, further described in Example 8.
Figure 21B:
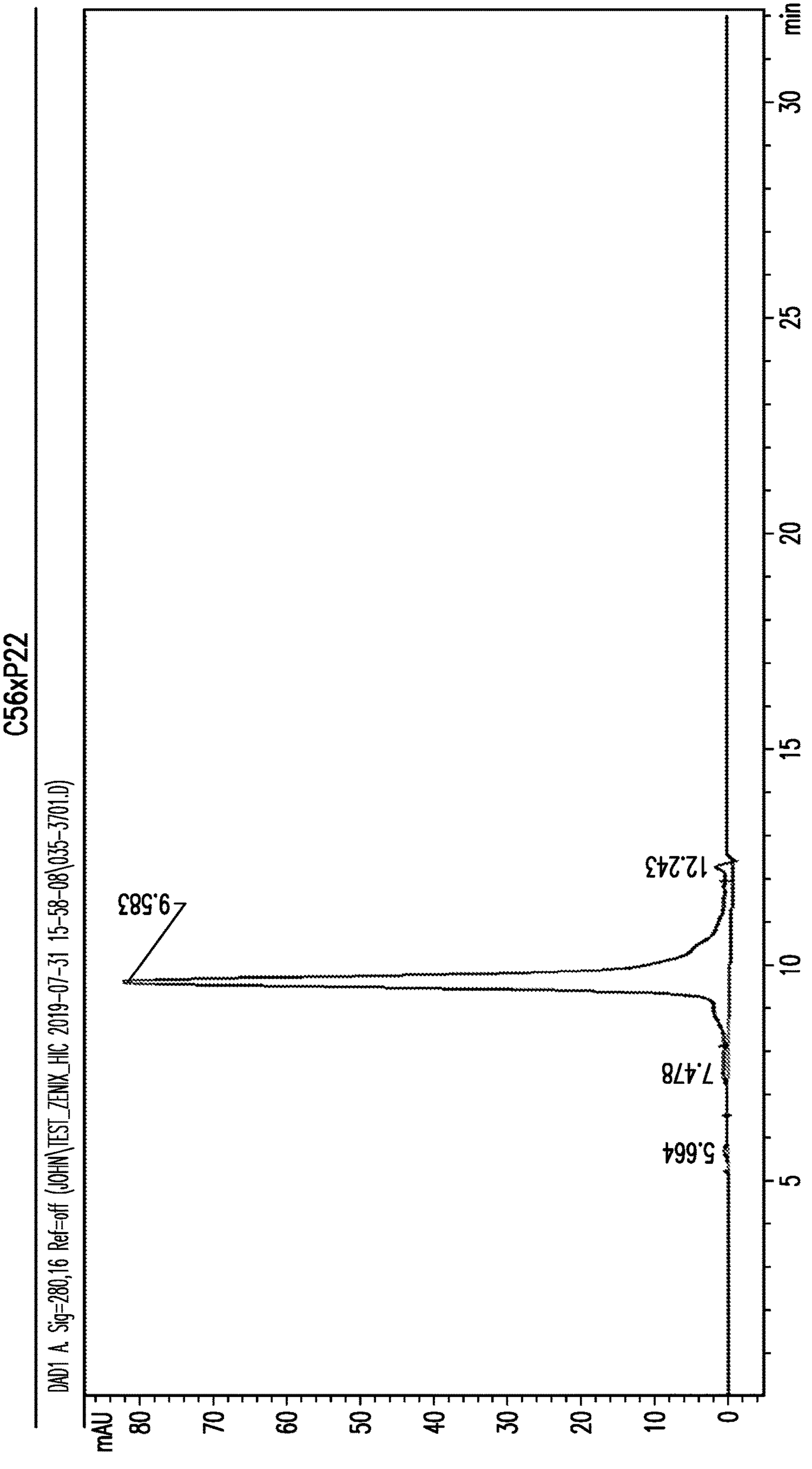
Figure 21C:
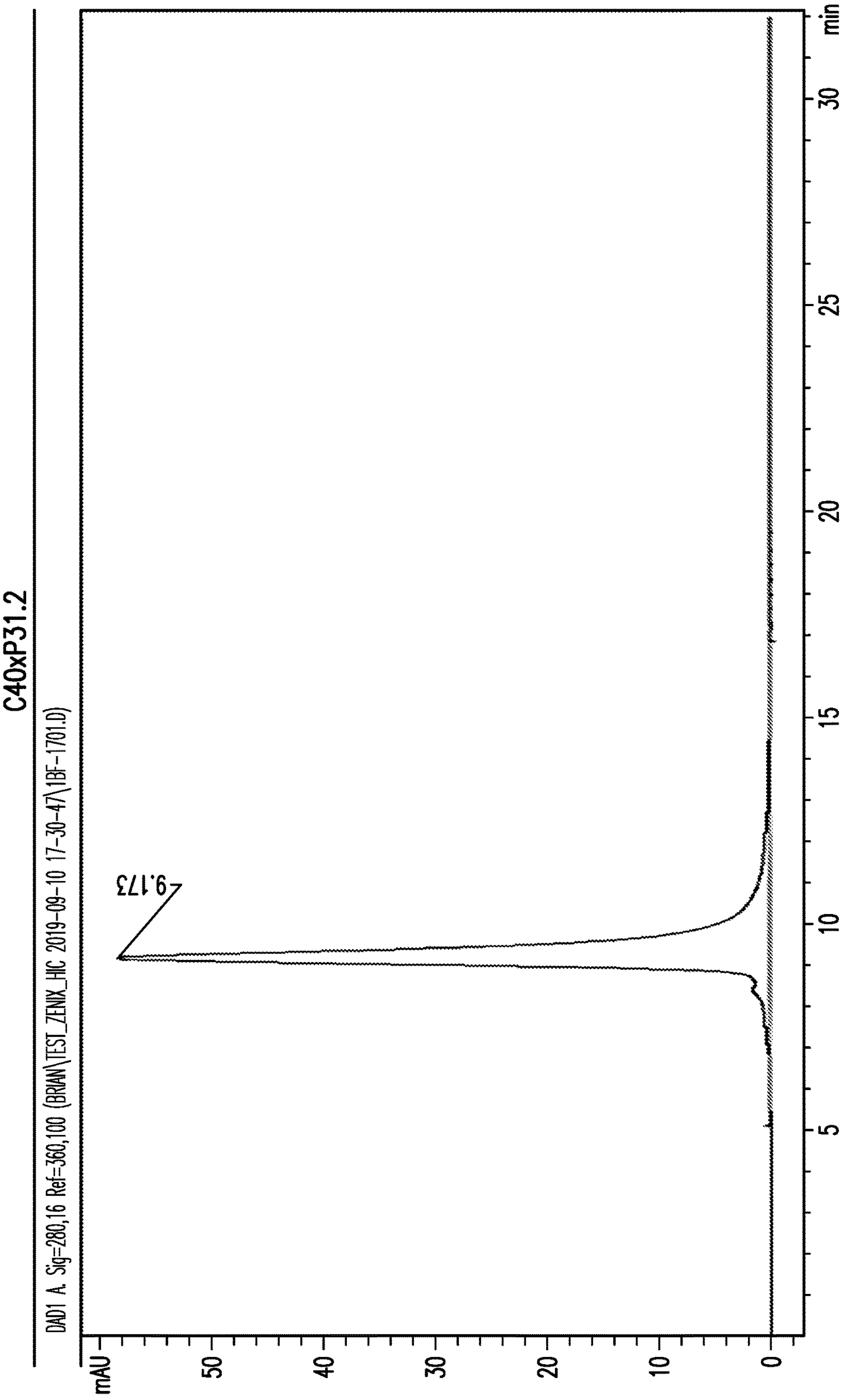
Figure 21D:
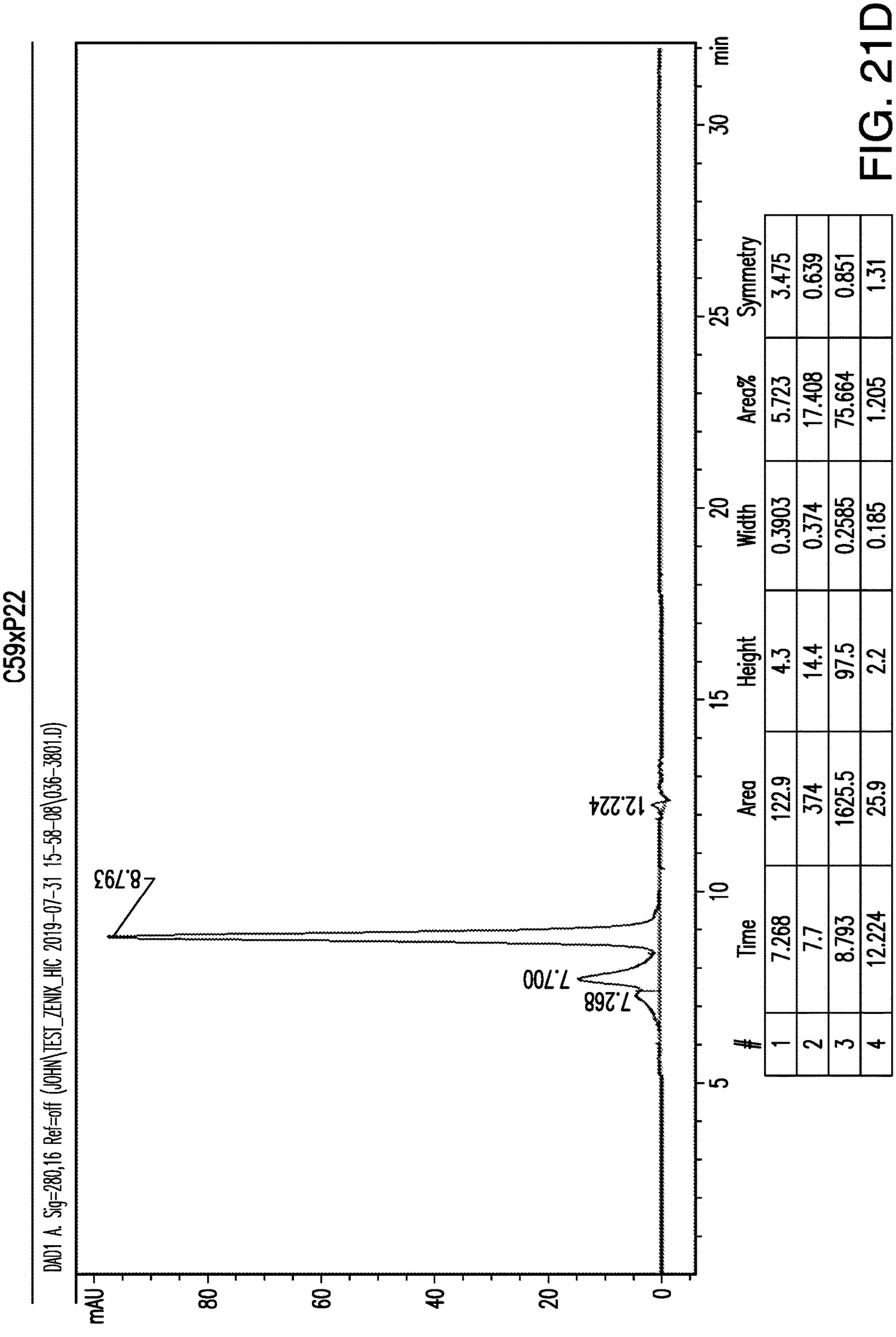

Exemplary SEC results are shown in FIGS. 19A-19C. Results indicate low bispecific antibody aggregation.

Hydrophobic interaction chromatography (HIC) analysis was performed using a 4.6 mm ID×3.5 cm TSKgel® Butyl-NPR column (Tosoh Bioscience LLC, PN 14947) on an Agilent 1100 HPLC. Bispecific antibodies in a BC44 format as described herein were normalized to 2 mg/mL concentration in dPBS (pH 7.4) and then diluted with an equal volume of mobile phase buffer B to a final protein concentration of 1 mg/mL. The column was equilibrated with 100% mobile phase Buffer B (2 M ammonium sulfate/20 mM sodium phosphate, pH 7.0) at a flow rate of 1 mL/min. For each sample, 10 μL was loaded and eluted using a gradient from 100% mobile phase buffer B to 100% mobile phase buffer A (20 mM sodium phosphate, pH 7.0) at 1.0 mL/min over 15 min, held at 100% A for 3 min to wash the column, and returned 100% B for 2 min for equilibration. Absorbance was monitored at 280 nm. Sample retention time was calculated and compared to a set of standard controls to identify bispecific antibodies with increased retention time (increased hydrophobicity).

Exemplary HIC results are shown in FIGS. 20A-20D. Antibody hydrophobicity can impact antibody aggregation, solubility and viscosity. Results show similar retention times for the tested antibodies, and indicates a low propensity for aggregation and precipitation. The HIC elution profiles (e.g., sharpness of elution peak and uniform retention times) of the tested bispecific antibodies suggested low propensities of these bispecific antibodies to aggregate and/or precipitate.

Overall, the results of the developability assays show that the developability criteria are met for tested exemplary bispecific antibodies.

Standup monolayer adsorption chromatography (SMAC) analysis was performed using a 4.6 mm ID×300 mm Zenix® SEC 300 column (Sepax Technologies, PN 213300P-4630) on an Agilent 1100 HPLC. Bispecific antibodies in a BC44 format as described herein were normalized to 1 mg/mL concentration in dPBS (pH 7.4) and clarified via centrifugation to pellet particulates. The mobile phase buffer was dPBS (pH 7.4, without calcium and magnesium). For each sample, 10 μL was loaded and isocratically eluted at 0.25 mL/min over 32 min. Absorbance was monitored at 280 nm. Sample retention time was calculated and compared to a set of standard controls to identify bispecific antibodies with increased retention time (increased propensity to form aggregates).

Exemplary SMAC results are shown in FIGS. 21A-21D. Results show that tested exemplary bispecific antibodies had similar short retention times, indicating colloidal stability and low propensity to aggregate.

Example 9: Competitive Binding Assays and Epitope Binning

Competitive binding assays were employed to determine if antibodies compete for the same or similar binding region of human CD47 or human PD-L1. Using a competitive immunoassay, if antigen binding of one antibody prevents the binding of the other, then these two antibodies are considered to bind to the same or similar, (e.g., overlapping) epitopes, and are considered to be in the same epitope bin. If binding of an antibody does not interfere with the binding of another antibody, then they are considered to bind to distinct epitopes of CD47 or PD-L1, and are in different epitope bins.

An Octet®-based "in tandem" assay format was used for the cross-competition assays to establish competitive binding data and epitope binning. For these assays, 100 nM biotinylated antigen was immobilized on a streptavidin sensor in 10× kinetic buffer (ForteBio). The association of antibodies to CD47 or PD-L1 were monitored by dipping the sensor in consecutive steps into wells containing saturating concentrations of two competing (or non-competing) antibodies. If the saturation with the first antibody did not block the binding (indicated by further increment in the BLI signal) then the antibodies were considered to be binding to distinct or non-overlapping epitopes and belong to different bins.

Results indicate that C40, C56 and C59 bin together. Results also indicate that P22 and P31.2 bin together (data not shown) and bin separately from P24.

```
SEQUENCES
Exemplary Multispecific Binding Agents
Sequences of exemplary bispecific antibodies in a BC1 format:
(1) C40 x P22
C40 First polypeptide chain (VL-BC1-CH2-CH3knob)
                                                  (SEQ ID NO: 157)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C40 Second polypeptide chain (VH-BC1)
                                                  (SEQ ID NO: 158)
EVQLVESGGGLVQPGGSLRLSCAASGFTFSYYYIHWVRQAPGKGLEWVAWIDPYGH

STTYADSVKGRFTISADTSKNTAYLQMNSLRAEDTAVYYCARGGRGAMDYWGQGTLV

TVSSASPREPQVYTDPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSGEC

P22 Third polypeptide chain (VL-Ck-CH2-CH3hole)
                                                  (SEQ ID NO: 159)
DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P22 Fourth polypeptide chain (VH-CH1)
                                                  (SEQ ID NO: 160)
EVQLVESGGGLVQPGGSLRLSCAASGFTFSSYYIHWVRQAPGKGLEWVAWITSHGYS

TKYADSVKGRFTISADTSKNTAYLQMNSLRAEDTAVYYCARDSVIYGLDYWGQGTLVT
```

-continued

VSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPPKSC (2)
C40 x P24
C40 First polypeptide chain (VL-BC1-CH2-CH3knob)
(SEQ ID NO: 157)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C40 Second polypeptide chain (VH-BC1)
(SEQ ID NO: 158)
EVQLVESGGGLVQPGGSLRLSCAASGFTFSYYYIHWVRQAPGKGLEWVAWIDPYGH

STTYADSVKGRFTISADTSKNTAYLQMNSLRAEDTAVYYCARGGRGAMDYWGQGTLV

TVSSASPREPQVYTDPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSGEC

P24 Third polypeptide chain (VL-Ck-CH2-CH3hole)
(SEQ ID NO: 161)
DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P24 Fourth polypeptide chain (VH-CH1)
(SEQ ID NO: 162)
EVQLVESGGGLVQPGGSLRLSCAASGFTFDQYYIHWVRQAPGKGLEWVAEIYPAGSY

TYYADSVKGRFTISADTSKNTAYLQMNSLRAEDTAVYYCARGPYSVRYALDYWGQGT

LVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPPKSC (3) C40 x P31.2
C40 First polypeptide chain (VL-BC1-CH2-CH3knob)
(SEQ ID NO: 157)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

-continued

C40 Second polypeptide chain (VH-BC1)
(SEQ ID NO: 158)
EVQLVESGGGLVQPGGSLRLSCAASGFTFSYYYIHWVRQAPGKGLEWVAWIDPYGH
STTYADSVKGRFTISADTSKNTAYLQMNSLRAEDTAVYYCARGGRGAMDYWGQGTLV
TVSSASPREPQVYTDPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSGEC P31.2 Third polypeptide chain (VL-Ck-CH2-CH3hole)
(SEQ ID NO: 163)
DIQMTQSPSSLSASVGDRVTITCRASQSVSSAVAWYQQKPGKAPKLLIYSASSLYSGV
PSRFSGSRSGTDFTLTISSLQPEDFATYYCQQFGAEPITFGQGTKVEIKRTVAAPSVFIF
PPSDEQLKSGTASVVCLLNNFYPREAKVQWKVDNALQSGNSQESVTEQDSKDSTYSL
SSTLTLSKADYEKHKVYACEVTHQGLSSPVTKSFNRGECDKTHTCPPCPAPELLGGPS
VFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVCTLPPS
REEMTKNQVSLSCAVKGFYPSDIAVEWESNGQPENNYKTTPPVLDSDGSFFLVSKLTV
DKSRWQQGNVFSCSVMHEALHNHYTQKSLSLSPGK P31.2 Fourth polypeptide chain (VH-CH1)
(SEQ ID NO: 164)
EVQLVESGGGLVQPGGSLRLSCAASGFTFSSYYIHWVRQAPGKGLEWVATISSGGGF
TYYADSVKGRFTISADTSKNTAYLQMNSLRAEDTAVYYCARGYTLTPVLDYWGQGTLV
TVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPPKSC (4)
C56 x P22
C56 First polypeptide chain (VL-BC1-CH2-CH3knob)
(SEQ ID NO: 165)
DIQMTQSPSSLSASVGDRVTITCRASQSVSSAVAWYQQKPGKAPKLLIYSASSLYSGV
PSRFSGSRSGTDFTLTISSLQPEDFATYYCQQGRSDLRTFGQGTKVEIKRTPREPQVY
TLPPSRDELTKNQVSLKCLVKGFYPSDIAVEWESNGQPENNYKTTPPVLDSDGSFFLY
SKLTVDKSRWQQGNVFSCSVMHEALHNHYTQKSLSLSKSCDKTHTCPPCPAPELLGG
PSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPP
CRDELTKNQVSLWCLVKGFYPSDIAVEWESNGQPENNYKTTPPVLDSDGSFFLYSKLT
VDKSRWQQGNVFSCSVMHEALHNHYTQKSLSLSPGK C56 Second polypeptide chain (VH-BC1)
(SEQ ID NO: 166)
EVQLVESGGGLVQPGGSLRLSCAASGFTFTYYYIHWVRQAPGKGLEWVAFIDPYSGS
TEYADSVKGRFTISADTSKNTAYLQMNSLRAEDTAVYYCARGGLYALDYWGQGTLVT
VSSASPREPQVYTDPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSGEC P22 Third polypeptide chain (VL-Ck-CH2-CH3hole)
(SEQ ID NO: 159)
DIQMTQSPSSLSASVGDRVTITCRASQSVSSAVAWYQQKPGKAPKLLIYSASSLYSGV
PSRFSGSRSGTDFTLTISSLQPEDFATYYCQQYYTSPYTFGQGTKVEIKRTVAAPSVFI
FPPSDEQLKSGTASVVCLLNNFYPREAKVQWKVDNALQSGNSQESVTEQDSKDSTYS
LSSTLTLSKADYEKHKVYACEVTHQGLSSPVTKSFNRGECDKTHTCPPCPAPELLGGP
SVFLFPPKPKDTLMISRTPEVTCVVVDVSHEDPEVKFNWYVDGVEVHNAKTKPREEQY -continued

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P22 Fourth polypeptide chain (VH-CH1)

(SEQ ID NO: 160)

EVQLVESGGGLVQPGGSLRLSCAASGFTFSSYYIHWVRQAPGKGLEWVAWITSHGYS

TKYADSVKGRFTISADTSKNTAYLQMNSLRAEDTAVYYCARDSVIYGLDYWGQGTLVT

VSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPPKSC (5) C56 x P24

C56 First polypeptide chain (VL-BC1-CH2-CH3knob)

(SEQ ID NO: 165)

DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPELLGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

C56 Second polypeptide chain (VH-BC1)

(SEQ ID NO: 166)

EVQLVESGGGLVQPGGSLRLSCAASGFTFTYYYIHWVRQAPGKGLEWVAFIDPYSGS

TEYADSVKGRFTISADTSKNTAYLQMNSLRAEDTAVYYCARGGLYALDYWGQGTLVT

VSSASPREPQVYTDPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSGEC

P24 Third polypeptide chain (VL-Ck-CH2-CH3hole)

(SEQ ID NO: 161)

DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P24 Fourth polypeptide chain (VH-CH1)

(SEQ ID NO: 162)

EVQLVESGGGLVQPGGSLRLSCAASGFTFDQYYIHWVRQAPGKGLEWVAEIYPAGSY

TYYADSVKGRFTISADTSKNTAYLQMNSLRAEDTAVYYCARGPYSVRYALDYWGQGT

LVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPPKSC (6) C56 x P31.2

C56 First polypeptide chain (VL-BC1-CH2-CH3knob)

(SEQ ID NO: 165)

DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTPREPQVY

TLPPSRDELTKNQVSLKCLVKGFYPSDIAVEWESNGQPENNYKTTPPVLDSDGSFFLY

-continued

SKLTVDKSRWQQGNVFSCSVMHEALHNHYTQKSLSLSKSCDKTHTCPPCPAPELLGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

C56 Second polypeptide chain (VH-BC1)

(SEQ ID NO: 166)

EVQLVESGGGLVQPGGSLRLSCAASGFTFTYYYIHWVRQAPGKGLEWVAFIDPYSGS

TEYADSVKGRFTISADTSKNTAYLQMNSLRAEDTAVYYCARGGLYALDYWGQGTLVT

VSSASPREPQVYTDPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSGEC

P31.2 Third polypeptide chain (VL-Ck-CH2-CH3hole)

(SEQ ID NO: 163)

DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPELLGGPS

VFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P31.2 Fourth polypeptide chain (VH-CH1)

(SEQ ID NO: 164)

EVQLVESGGGLVQPGGSLRLSCAASGFTFSSYYIHWVRQAPGKGLEWVATISSGGGF

TYYADSVKGRFTISADTSKNTAYLQMNSLRAEDTAVYYCARGYTLTPVLDYWGQGTLV

TVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPPKSC (7) C59 x P22

C59 First polypeptide chain (VL-BC1-CH2-CH3knob)

(SEQ ID NO: 167)

DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C59 Second polypeptide chain (VH-BC1)

(SEQ ID NO: 168)

EVQLVESGGGLVQPGGSLRLSCAASGFTFTSYYIHWVRQAPGKGLEWVAYIDSKHGT

TQYADSVKGRFTISADTSKNTAYLQMNSLRAEDTAVYYCARGGRSAMDYWGQGTLVT

VSSASPREPQVYTDPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSGEC

-continued

P22 Third polypeptide chain (VL-Ck-CH2-CH3hole)
(SEQ ID NO: 159)
DIQMTQSPSSLSASVGDRVTITCRASQSVSSAVAWYQQKPGKAPKLLIYSASSLYSGV
PSRFSGSRSGTDFTLTISSLQPEDFATYYCQQYYTSPYTFGQGTKVEIKRTVAAPSVFI
FPPSDEQLKSGTASVVCLLNNFYPREAKVQWKVDNALQSGNSQESVTEQDSKDSTYS
LSSTLTLSKADYEKHKVYACEVTHQGLSSPVTKSFNRGECDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVCTLPPS
REEMTKNQVSLSCAVKGFYPSDIAVEWESNGQPENNYKTTPPVLDSDGSFFLVSKLTV
DKSRWQQGNVFSCSVMHEALHNHYTQKSLSLSPGK P22 Fourth polypeptide chain (VH-CH1)
(SEQ ID NO: 160)
EVQLVESGGGLVQPGGSLRLSCAASGFTFSSYYIHWVRQAPGKGLEWVAWITSHGYS
TKYADSVKGRFTISADTSKNTAYLQMNSLRAEDTAVYYCARDSVIYGLDYWGQGTLVT
VSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPPKSC (8) C59 x P24
C59 First polypeptide chain (VL-BC1-CH2-CH3knob)
(SEQ ID NO: 167)
DIQMTQSPSSLSASVGDRVTITCRASQSVSSAVAWYQQKPGKAPKLLIYSASSLYSGV
PSRFSGSRSGTDFTLTISSLQPEDFATYYCQQRTTSLLTFGQGTKVEIKRTPREPQVYT
LPPSRDELTKNQVSLKCLVKGFYPSDIAVEWESNGQPENNYKTTPPVLDSDGSFFLYS
KLTVDKSRWQQGNVFSCSVMHEALHNHYTQKSLSLSKSCDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPC
RDELTKNQVSLWCLVKGFYPSDIAVEWESNGQPENNYKTTPPVLDSDGSFFLYSKLTV
DKSRWQQGNVFSCSVMHEALHNHYTQKSLSLSPGK C59 Second polypeptide chain (VH-BC1)
(SEQ ID NO: 168)
EVQLVESGGGLVQPGGSLRLSCAASGFTFTSYYIHWVRQAPGKGLEWVAYIDSKHGT
TQYADSVKGRFTISADTSKNTAYLQMNSLRAEDTAVYYCARGGRSAMDYWGQGTLVT
VSSASPREPQVYTDPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSGEC P24 Third polypeptide chain (VL-Ck-CH2-CH3hole)
(SEQ ID NO: 161)
DIQMTQSPSSLSASVGDRVTITCRASQSVSSAVAWYQQKPGKAPKLLIYSASSLYSGV
PSRFSGSRSGTDFTLTISSLQPEDFATYYCQQVSYSPYTFGQGTKVEIKRTVAAPSVFI
FPPSDEQLKSGTASVVCLLNNFYPREAKVQWKVDNALQSGNSQESVTEQDSKDSTYS
LSSTLTLSKADYEKHKVYACEVTHQGLSSPVTKSFNRGECDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVCTLPPS
REEMTKNQVSLSCAVKGFYPSDIAVEWESNGQPENNYKTTPPVLDSDGSFFLVSKLTV
DKSRWQQGNVFSCSVMHEALHNHYTQKSLSLSPGK P24 Fourth polypeptide chain (VH-CH1)
(SEQ ID NO: 162)
EVQLVESGGGLVQPGGSLRLSCAASGFTFDQYYIHWVRQAPGKGLEWVAEIYPAGSY
TYYADSVKGRFTISADTSKNTAYLQMNSLRAEDTAVYYCARGPYSVRYALDYWGQGT -continued

LVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPPKSC (9) C59 x P31.2
C59 First polypeptide chain (VL-BC1-CH2-CH3knob)
(SEQ ID NO: 167)
DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C59 Second polypeptide chain (VH-BC1)
(SEQ ID NO: 168)
EVQLVESGGGLVQPGGSLRLSCAASGFTFTSYYIHWVRQAPGKGLEWVAYIDSKHGT

TQYADSVKGRFTISADTSKNTAYLQMNSLRAEDTAVYYCARGGRSAMDYWGQGTLVT

VSSASPREPQVYTDPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSGEC

P31.2 Third polypeptide chain (VL-Ck-CH2-CH3hole)
(SEQ ID NO: 163)
DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPELLGGPS

VFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P31.2 Fourth polypeptide chain (VH-CH1)
(SEQ ID NO: 164)
EVQLVESGGGLVQPGGSLRLSCAASGFTFSSYYIHWVRQAPGKGLEWVATISSGGGE

TYYADSVKGRFTISADTSKNTAYLQMNSLRAEDTAVYYCARGYTLTPVLDYWGQGTLV

TVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPPKSC

(10) C40 x P22 (silent Fc)
C40 First polypeptide chain (VL-BC1-CH2-CH3knob) silent Fc
(SEQ ID NO: 169)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

-continued

P22 Third polypeptide chain (VL-Ck-CH2-CH3hole) silent Fc
(SEQ ID NO: 170)

DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(11) C40 x P24 (silent Fc)

C40 First polypeptide chain (VL-BC1-CH2-CH3knob) silent Fc
(SEQ ID NO: 169)

DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P24 Third polypeptide chain (VL-Ck-CH2-CH3hole) Silent Fc
(SEQ ID NO: 171)

DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(12) C40 x P31.2 (BC1; silent Fc)

C40 First polypeptide chain (VL-BC1-CH2-CH3knob) silent Fc
(SEQ ID NO: 169)

DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P31.2 Third polypeptide chain (VL-Ck-CH2-CH3hole) Silent Fc
(SEQ ID NO: 172)

DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

-continued

SSTLTLSKADYEKHKVYACEVTHQGLSSPVTKSFNRGECDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

(13) C56 x P22 (silent Fc)
C56 First polypeptide chain (VL-BC1-CH2-CH3knob) Silent Fc
(SEQ ID NO: 173)

DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPEAAG

GPSVFLFPPKPKDTLMISRTPEVTCVVVDVSHEDPEVKFNWYVDGVEVHNAKTKPREE

QYNSTYRVVSVLTVLHQDWLNGKEYKCKVSNKALKAPIEKTISKAKGQPREPQVYTLP

PCRDELTKNQVSLWCLVKGFYPSDIAVEWESNGQPENNYKTTPPVLDSDGSFFLYSK

LTVDKSRWQQGNVFSCSVMHEALHNHYTQKSLSLSPGK

P22 Third polypeptide chain (VL-Ck-CH2-CH3hole) silent Fc
(SEQ ID NO: 170)

DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(14) C56 x P24 (silent Fc)
C56 First polypeptide chain (VL-BC1-CH2-CH3knob) Silent Fc
(SEQ ID NO: 173)

DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPEAAG

GPSVFLFPPKPKDTLMISRTPEVTCVVVDVSHEDPEVKFNWYVDGVEVHNAKTKPREE

QYNSTYRVVSVLTVLHQDWLNGKEYKCKVSNKALKAPIEKTISKAKGQPREPQVYTLP

PCRDELTKNQVSLWCLVKGFYPSDIAVEWESNGQPENNYKTTPPVLDSDGSFFLYSK

LTVDKSRWQQGNVFSCSVMHEALHNHYTQKSLSLSPGK

P24 Third polypeptide chain (VL-Ck-CH2-CH3hole) Silent Fc
(SEQ ID NO: 171)

DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

-continued

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(15) C56 x P31.2 (silent Fc)

C56 First polypeptide chain (VL-BC1-CH2-CH3knob) Silent Fc (SEQ ID NO: 173)

DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPEAAG

GPSVFLFPPKPKDTLMISRTPEVTCVVVDVSHEDPEVKFNWYVDGVEVHNAKTKPREE

QYNSTYRVVSVLTVLHQDWLNGKEYKCKVSNKALKAPIEKTISKAKGQPREPQVYTLP

PCRDELTKNQVSLWCLVKGFYPSDIAVEWESNGQPENNYKTTPPVLDSDGSFFLYSK

LTVDKSRWQQGNVFSCSVMHEALHNHYTQKSLSLSPGK

P31.2 Third polypeptide chain (VL-Ck-CH2-CH3hole) BC1-3 Silent Fc (SEQ ID NO: 172)

DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

(16) C59 x P22 (silent Fc)

C59 First polypeptide chain (VL-BC1-CH2-CH3knob) silent Fc (SEQ ID NO: 174)

DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P22 Third polypeptide chain (VL-Ck-CH2-CH3hole) silent Fc (SEQ ID NO: 170)

DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

-continued

(17) C59 x P24 (silent Fc)
C59 First polypeptide chain (VL-BC1-CH2-CH3knob) silent Fc
(SEQ ID NO: 174)
DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P24 Third polypeptide chain (VL-Ck-CH2-CH3hole) Silent Fc
(SEQ ID NO: 171)
DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(18) C59 x P31.2 (silent Fc)
C59 First polypeptide chain (VL-BC1-CH2-CH3knob) silent Fc
(SEQ ID NO: 174)
DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTPREPQVYT

LPPSRDELTKNQVSLKCLVKGFYPSDIAVEWESNGQPENNYKTTPPVLDSDGSFFLYS

KLTVDKSRWQQGNVFSCSVMHEALHNHYTQKSLSLSKSCDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P31.2 Third polypeptide chain (VL-Ck-CH2-CH3hole) Silent Fc
(SEQ ID NO: 172)
DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

-continued

Sequences of exemplary bispecific antibodies in a BC44 format:
(1)
C40 x P22
C40 First polypeptide chain (VL-BC44-CH2-CH3knob)
(SEQ ID NO: 175)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C40 Second polypeptide chain (VH-BC44)
(SEQ ID NO: 176)
EVQLVESGGGLVQPGGSLRLSCAASGFTFSYYYIHWVRQAPGKGLEWVAWIDPYGH

STTYADSVKGRFTISADTSKNTAYLQMNSLRAEDTAVYYCARGGRGAMDYWGQGTLV

TVSSASPREPQVYTLPPCRDELTKNQVSLTCLVKGFYPSDIAVEWESNGQPENNYKTT

PPVLDSDGSFFLYSKLTVDKSRWQQGNVFSCSVMHEALHNHYTQKSLSLSPGK

P22 Third polypeptide chain (VL-Ck-CH2-CH3hole)
(SEQ ID NO: 159)
DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P22 Fourth polypeptide chain (VH-CH1)
(SEQ ID NO: 160)
EVQLVESGGGLVQPGGSLRLSCAASGFTFSSYYIHWVRQAPGKGLEWVAWITSHGYS

TKYADSVKGRFTISADTSKNTAYLQMNSLRAEDTAVYYCARDSVIYGLDYWGQGTLVT

VSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPPKSC (2)
C40 x P24
C40 First polypeptide chain (VL-BC44-CH2-CH3knob)
(SEQ ID NO: 175)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

-continued

C40 Second polypeptide chain (VH-BC44)
(SEQ ID NO: 176)
EVQLVESGGGLVQPGGSLRLSCAASGFTFSYYYIHWVRQAPGKGLEWVAWIDPYGH

STTYADSVKGRFTISADTSKNTAYLQMNSLRAEDTAVYYCARGGRGAMDYWGQGTLV

TVSSASPREPQVYTLPPCRDELTKNQVSLTCLVKGFYPSDIAVEWESNGQPENNYKTT

PPVLDSDGSFFLYSKLTVDKSRWQQGNVFSCSVMHEALHNHYTQKSLSLSPGK

P24 Third polypeptide chain (VL-Ck-CH2-CH3hole)
(SEQ ID NO: 161)
DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P24 Fourth polypeptide chain (VH-CH1)
(SEQ ID NO: 162)
EVQLVESGGGLVQPGGSLRLSCAASGFTFDQYYIHWVRQAPGKGLEWVAEIYPAGSY

TYYADSVKGRFTISADTSKNTAYLQMNSLRAEDTAVYYCARGPYSVRYALDYWGQGT

LVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPPKSC (3)
C40 x P31.2
C40 First polypeptide chain (VL-BC44-CH2-CH3knob)
(SEQ ID NO: 175)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C40 Second polypeptide chain (VH-BC44)
(SEQ ID NO: 176)
EVQLVESGGGLVQPGGSLRLSCAASGFTFSYYYIHWVRQAPGKGLEWVAWIDPYGH

STTYADSVKGRFTISADTSKNTAYLQMNSLRAEDTAVYYCARGGRGAMDYWGQGTLV

TVSSASPREPQVYTLPPCRDELTKNQVSLTCLVKGFYPSDIAVEWESNGQPENNYKTT

PPVLDSDGSFFLYSKLTVDKSRWQQGNVFSCSVMHEALHNHYTQKSLSLSPGK

P31.2 Third polypeptide chain (VL-Ck-CH2-CH3hole)
(SEQ ID NO: 163)
DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPELLGGPS

VFLFPPKPKDTLMISRTPEVTCVVVDVSHEDPEVKFNWYVDGVEVHNAKTKPREEQY

-continued

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P31.2 Fourth polypeptide chain (VH-CH1)
(SEQ ID NO: 164)
EVQLVESGGGLVQPGGSLRLSCAASGFTFSSYYIHWVRQAPGKGLEWVATISSGGGE

TYYADSVKGRFTISADTSKNTAYLQMNSLRAEDTAVYYCARGYTLTPVLDYWGQGTLV

TVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPPKSC (4)
C56 x P22
C56 First polypeptide chain (VL-BC44-CH2-CH3knob)
(SEQ ID NO: 177)
DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTVREPQVC

TLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKDKTHTCPPCPAPELLGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

C56 Second polypeptide chain (VH-BC44)
(SEQ ID NO: 178)
EVQLVESGGGLVQPGGSLRLSCAASGFTFTYYYIHWVRQAPGKGLEWVAFIDPYSGS

TEYADSVKGRFTISADTSKNTAYLQMNSLRAEDTAVYYCARGGLYALDYWGQGTLVT

VSSASPREPQVYTLPPCRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

P22 Third polypeptide chain (VL-Ck-CH2-CH3hole)
(SEQ ID NO: 159)
DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P22 Fourth polypeptide chain (VH-CH1)
(SEQ ID NO: 160)
EVQLVESGGGLVQPGGSLRLSCAASGFTFSSYYIHWVRQAPGKGLEWVAWITSHGYS

TKYADSVKGRFTISADTSKNTAYLQMNSLRAEDTAVYYCARDSVIYGLDYWGQGTLVT

VSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPPKSC (5)
C56 x P24
C56 First polypeptide chain (VL-BC44-CH2-CH3knob)
(SEQ ID NO: 177)
DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTVREPQVC

-continued

TLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGKDKTHTCPPCPAPELLGG
PSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPP
CRDELTKNQVSLWCLVKGFYPSDIAVEWESNGQPENNYKTTPPVLDSDGSFFLYSKLT
VDKSRWQQGNVFSCSVMHEALHNHYTQKSLSLSPGK

C56 Second polypeptide chain (VH-BC44)
(SEQ ID NO: 178)
EVQLVESGGGLVQPGGSLRLSCAASGFTFTYYYIHWVRQAPGKGLEWVAFIDPYSGS
TEYADSVKGRFTISADTSKNTAYLQMNSLRAEDTAVYYCARGGLYALDYWGQGTLVT
VSSASPREPQVYTLPPCRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK P24 Third polypeptide chain (VL-Ck-CH2-CH3hole)
(SEQ ID NO: 161)
DIQMTQSPSSLSASVGDRVTITCRASQSVSSAVAWYQQKPGKAPKLLIYSASSLYSGV
PSRFSGSRSGTDFTLTISSLQPEDFATYYCQQVSYSPYTFGQGTKVEIKRTVAAPSVFI
FPPSDEQLKSGTASVVCLLNNFYPREAKVQWKVDNALQSGNSQESVTEQDSKDSTYS
LSSTLTLSKADYEKHKVYACEVTHQGLSSPVTKSFNRGECDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVCTLPPS
REEMTKNQVSLSCAVKGFYPSDIAVEWESNGQPENNYKTTPPVLDSDGSFFLVSKLTV
DKSRWQQGNVFSCSVMHEALHNHYTQKSLSLSPGK P24 Fourth polypeptide chain (VH-CH1)
(SEQ ID NO: 162)
EVQLVESGGGLVQPGGSLRLSCAASGFTFDQYYIHWVRQAPGKGLEWVAEIYPAGSY
TYYADSVKGRFTISADTSKNTAYLQMNSLRAEDTAVYYCARGPYSVRYALDYWGQGT
LVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPPKSC (6)
C56 x P31.2
C56 First polypeptide chain (VL-BC44-CH2-CH3knob)
(SEQ ID NO: 177)
DIQMTQSPSSLSASVGDRVTITCRASQSVSSAVAWYQQKPGKAPKLLIYSASSLYSGV
PSRFSGSRSGTDFTLTISSLQPEDFATYYCQQGRSDLRTFGQGTKVEIKRTVREPQVC
TLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGKDKTHTCPPCPAPELLGG
PSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPP
CRDELTKNQVSLWCLVKGFYPSDIAVEWESNGQPENNYKTTPPVLDSDGSFFLYSKLT
VDKSRWQQGNVFSCSVMHEALHNHYTQKSLSLSPGK C56 Second polypeptide chain (VH-BC44)
(SEQ ID NO: 178)
EVQLVESGGGLVQPGGSLRLSCAASGFTFTYYYIHWVRQAPGKGLEWVAFIDPYSGS
TEYADSVKGRFTISADTSKNTAYLQMNSLRAEDTAVYYCARGGLYALDYWGQGTLVT
VSSASPREPQVYTLPPCRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK -continued P31.2 Third polypeptide chain (VL-Ck-CH2-CH3hole)
(SEQ ID NO: 163)

DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPELLGGPS

VFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P31.2 Fourth polypeptide chain (VH-CH1)
(SEQ ID NO: 164)

EVQLVESGGGLVQPGGSLRLSCAASGFTFSSYYIHWVRQAPGKGLEWVATISSGGGF

TYYADSVKGRFTISADTSKNTAYLQMNSLRAEDTAVYYCARGYTLTPVLDYWGQGTLV

TVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPPKSC (7)
C59 x P22
C59 First polypeptide chain (VL-BC44-CH2-CH3knob)
(SEQ ID NO: 179)

DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C59 Second polypeptide chain (VH-BC44)
(SEQ ID NO: 180)

EVQLVESGGGLVQPGGSLRLSCAASGFTFTSYYIHWVRQAPGKGLEWVAYIDSKHGT

TQYADSVKGRFTISADTSKNTAYLQMNSLRAEDTAVYYCARGGRSAMDYWGQGTLVT

VSSASPREPQVYTLPPCRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

P22 Third polypeptide chain (VL-Ck-CH2-CH3hole)
(SEQ ID NO: 159)

DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

-continued

P22 Fourth polypeptide chain (VH-CH1)
(SEQ ID NO: 160)
EVQLVESGGGLVQPGGSLRLSCAASGFTFSSYYIHWVRQAPGKGLEWVAWITSHGYS

TKYADSVKGRFTISADTSKNTAYLQMNSLRAEDTAVYYCARDSVIYGLDYWGQGTLVT

VSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPPKSC (8)
C59 x P24
C59 First polypeptide chain (VL-BC44-CH2-CH3knob)
(SEQ ID NO: 179)
DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C59 Second polypeptide chain (VH-BC44)
(SEQ ID NO: 180)
EVQLVESGGGLVQPGGSLRLSCAASGFTFTSYYIHWVRQAPGKGLEWVAYIDSKHGT

TQYADSVKGRFTISADTSKNTAYLQMNSLRAEDTAVYYCARGGRSAMDYWGQGTLVT

VSSASPREPQVYTLPPCRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

P24 Third polypeptide chain (VL-Ck-CH2-CH3hole)
(SEQ ID NO: 161)
DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P24 Fourth polypeptide chain (VH-CH1)
(SEQ ID NO: 162)
EVQLVESGGGLVQPGGSLRLSCAASGFTFDQYYIHWVRQAPGKGLEWVAEIYPAGSY

TYYADSVKGRFTISADTSKNTAYLQMNSLRAEDTAVYYCARGPYSVRYALDYWGQGT

LVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPPKSC (9)
C59 x P31.2
C59 First polypeptide chain (VL-BC44-CH2-CH3knob)
(SEQ ID NO: 179)
DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPELLGGP

-continued

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

C59 Second polypeptide chain (VH-BC44)

(SEQ ID NO: 180)

EVQLVESGGGLVQPGGSLRLSCAASGFTFTSYYIHWVRQAPGKGLEWVAYIDSKHGT

TQYADSVKGRFTISADTSKNTAYLQMNSLRAEDTAVYYCARGGRSAMDYWGQGTLVT

VSSASPREPQVYTLPPCRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK

P31.2 Third polypeptide chain (VL-Ck-CH2-CH3hole)

(SEQ ID NO: 163)

DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPELLGGPS

VFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

P31.2 Fourth polypeptide chain (VH-CH1)

(SEQ ID NO: 164)

EVQLVESGGGLVQPGGSLRLSCAASGFTFSSYYIHWVRQAPGKGLEWVATISSGGGE

TYYADSVKGRFTISADTSKNTAYLQMNSLRAEDTAVYYCARGYTLTPVLDYWGQGTLV

TVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPPKSC

(10) C40 x P22 (silent Fc)
C40 First polypeptide chain (VL-BC44-CH2-CH3knob) Silent Fc (SEQ ID NO: 181)

DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P22 Third polypeptide chain (VL-Ck-CH2-CH3hole) silent Fc (SEQ ID NO: 170)

DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

-continued

(11) C40 x P24 (silent Fc)
C40 First polypeptide chain (VL-BC44-CH2-CH3knob) Silent Fc
(SEQ ID NO: 181)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P24 Third polypeptide chain (VH-CH1) Silent Fc
(SEQ ID NO: 171)
DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(12) C40 x P31.2 (silent Fc)
C40 First polypeptide chain (VL-BC44-CH2-CH3knob) Silent Fc
(SEQ ID NO: 181)
DIQMTQSPSSLSASVGDRVTITCRASQSVSSAVAWYQQKPGKAPKLLIYSASSLYSGV

PSRFSGSRSGTDFTLTISSLQPEDFATYYCQQRYSSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P31.2 Third polypeptide chain (VL-Ck-CH2-CH3hole) Silent Fc
(SEQ ID NO: 172)
DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

(13) C56 x P22 (silent Fc)
C56 First polypeptide chain (VL-BC44-CH2-CH3knob) Silent Fc
(SEQ ID NO: 182)
DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTVREPQVC

-continued

TLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKDKTHTCPPCPAPEAAG

GPSVFLFPPKPKDTLMISRTPEVTCVVVDVSHEDPEVKFNWYVDGVEVHNAKTKPREE

QYNSTYRVVSVLTVLHQDWLNGKEYKCKVSNKALKAPIEKTISKAKGQPREPQVYTLP

PCRDELTKNQVSLWCLVKGFYPSDIAVEWESNGQPENNYKTTPPVLDSDGSFFLYSK

LTVDKSRWQQGNVFSCSVMHEALHNHYTQKSLSLSPGK

P22 Third polypeptide chain (VL-Ck-CH2-CH3hole) Fc
(SEQ ID NO: 170)

DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(14) C56 x P24 (silent Fc)
C56 First polypeptide chain (VL-BC44-CH2-CH3knob) Silent Fc
(SEQ ID NO: 182)

DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTVREPQVC

TLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKDKTHTCPPCPAPEAAG

GPSVFLFPPKPKDTLMISRTPEVTCVVVDVSHEDPEVKFNWYVDGVEVHNAKTKPREE

QYNSTYRVVSVLTVLHQDWLNGKEYKCKVSNKALKAPIEKTISKAKGQPREPQVYTLP

PCRDELTKNQVSLWCLVKGFYPSDIAVEWESNGQPENNYKTTPPVLDSDGSFFLYSK

LTVDKSRWQQGNVFSCSVMHEALHNHYTQKSLSLSPGK

P24 Third polypeptide chain (VL-Ck-CH2-CH3hole) Silent Fc
(SEQ ID NO: 171)

DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(15) C56 x P31.2 (silent Fc)
C56 First polypeptide chain (VL-BC44-CH2-CH3knob) Silent Fc
(SEQ ID NO: 182)

DIQMTQSPSSLSASVGDRVTITCRASQSVSSAVAWYQQKPGKAPKLLIYSASSLYSGV

PSRFSGSRSGTDFTLTISSLQPEDFATYYCQQGRSDLRTFGQGTKVEIKRTVREPQVC

TLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKDKTHTCPPCPAPEAAG

GPSVFLFPPKPKDTLMISRTPEVTCVVVDVSHEDPEVKFNWYVDGVEVHNAKTKPREE

-continued

QYNSTYRVVSVLTVLHQDWLNGKEYKCKVSNKALKAPIEKTISKAKGQPREPQVYTLP

PCRDELTKNQVSLWCLVKGFYPSDIAVEWESNGQPENNYKTTPPVLDSDGSFFLYSK

LTVDKSRWQQGNVFSCSVMHEALHNHYTQKSLSLSPGK

P31.2 Third polypeptide chain (VL-Ck-CH2-CH3hole) Silent Fc
(SEQ ID NO: 172)

DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

(16) C59 x P22 (silent Fc)
C59 First polypeptide chain (VL-BC44-CH2-CH3knob) silent Fc
(SEQ ID NO: 183)

DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P22 Third polypeptide chain (VL-Ck-CH2-CH3hole) silent Fc
(SEQ ID NO: 170)

DIQMTQSPSSLSASVGDRVTITCRASQSVSSAVAWYQQKPGKAPKLLIYSASSLYSGV

PSRFSGSRSGTDFTLTISSLQPEDFATYYCQQYYTSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(17) C59 x P24 (silent Fc)
C59 First polypeptide chain (VL-BC44-CH2-CH3knob) silent Fc
(SEQ ID NO: 183)

DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

-continued

P24 Third polypeptide chain (VL-Ck-CH2-CH3hole) Silent Fc
(SEQ ID NO: 171)

DIQMTQSPSSLSASVGDRVTITCRASQSVSSAVAWYQQKPGKAPKLLIYSASSLYSGV

PSRFSGSRSGTDFTLTISSLQPEDFATYYCQQVSYSPYTFGQGTKVEIKRTVAAPSVFI

FPPSDEQLKSGTASVVCLLNNFYPREAKVQWKVDNALQSGNSQESVTEQDSKDSTYS

LSSTLTLSKADYEKHKVYACEVTHQGLSSPVTKSFNRGECDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVCTLPP

SREEMTKNQVSLSCAVKGFYPSDIAVEWESNGQPENNYKTTPPVLDSDGSFFLVSKLT

VDKSRWQQGNVFSCSVMHEALHNHYTQKSLSLSPGK

(18) C59 x P31.2 (silent Fc)

C59 First polypeptide chain (VL-BC44-CH2-CH3knob) silent Fc
(SEQ ID NO: 183)

DIQMTQSPSSLSASVGDRVTITCRASQSVSSAVAWYQQKPGKAPKLLIYSASSLYSGV

PSRFSGSRSGTDFTLTISSLQPEDFATYYCQQRTTSLLTFGQGTKVEIKRTVREPQVCT

LPPSRDELTKNQVSLTCLVKGFYPSDIAVEWESNGQPENNYKTTPPVLDSDGSFFLYS

KLTVDKSRWQQGNVFSCSVMHEALHNHYTQKSLSLSPGKDKTHTCPPCPAPEAAGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALKAPIEKTISKAKGQPREPQVYTLPP

CRDELTKNQVSLWCLVKGFYPSDIAVEWESNGQPENNYKTTPPVLDSDGSFFLYSKLT

VDKSRWQQGNVFSCSVMHEALHNHYTQKSLSLSPGK

P31.2 Third polypeptide chain (VL-Ck-CH2-CH3hole) Silent Fc
(SEQ ID NO: 172)

DIQMTQSPSSLSASVGDRVTITCRASQSVSSAVAWYQQKPGKAPKLLIYSASSLYSGV

PSRFSGSRSGTDFTLTISSLQPEDFATYYCQQFGAEPITFGQGTKVEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGECDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

Throughout this application various publications, patents, patent applications and other documents have been referenced. The disclosures of these publications, patents, patent applications and other documents in their entireties are hereby incorporated by reference in this application for all purposes, including in order to more fully describe the state of the art to which this the subject matter disclosed herein pertains. Although the disclosed subject matter has been described with reference to the examples provided above, it should be understood that various modifications can be made without departing from the spirit of the disclosed subject matter. Many variations will become apparent to those skilled in the art upon review of this specification.

What is claimed is:

1. A multispecific antibody or fragment thereof with a first binding domain that binds to CD47 and a second binding domain that binds to PD-L1, wherein the first binding domain comprises all three heavy chain complementarity determining regions (CDRs) and all three light chain CDRs from:

the antibody designated C40 that comprises a VH sequence that is SEQ ID NO:25 and a VL sequence that is SEQ ID NO:26;

the antibody designated C56 that comprises a VH sequence that is SEQ ID NO:51 and a VL sequence that is SEQ ID NO:52; or the antibody designated C59 that comprises a VH sequence that is SEQ ID NO:77 and a VL sequence that is SEQ ID NO:78; and wherein the second binding domain comprises all three heavy chain CDRs and all three light chain CDRs from:

the antibody designated P22 that comprises a VH sequence that is SEQ ID NO:103 and a VL sequence that is SEQ ID NO:104;

the antibody designated P24 that comprises a VH sequence that is SEQ ID NO:129 and a VL sequence that is SEQ ID NO:130; or the antibody designated P31.2 that comprises a VH sequence that is SEQ ID NO:155 and a VL sequence that is SEQ ID NO:156;

wherein the heavy chain CDRs and the light chain CDRs of the first binding domain and the heavy chain CDRs and the light chain CDRs of the second binding domain are determined according to Kabat numbering system, Chothia numbering system, AbM numbering system, Contact numbering system, IMGT numbering system, or Exemplary numbering system.

2. The multispecific antibody or fragment thereof of claim 1, wherein:

(i) the first binding domain comprises:

(a) a heavy chain variable ($V_H$) region comprising:

(1) a $V_H$ CDR1 having the amino acid sequence of SEQ ID NO:1;

(2) a $V_H$ CDR2 having the amino acid sequence of SEQ ID NO:2; and (3) a $V_H$ CDR3 having the amino acid sequence of SEQ ID NO:3; and (b) a light chain variable ($V_L$) region comprising:

(1) a $V_L$ CDR1 having the amino acid sequence of SEQ ID NO:4;

(2) a $V_L$ CDR2 having the amino acid sequence of SEQ ID NO:5; and (3) a $V_L$ CDR3 having the amino acid sequence of SEQ ID NO:6; and the second binding domain comprises:

(a) a heavy chain variable ($V_H$) region comprising:

(1) a $V_H$ CDR1 having the amino acid sequence of SEQ ID NO:79;

(2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising:

(1) a $V_L$ CDR1 having the amino acid sequence of SEQ ID NO: 82;

(2) a $V_L$ CDR2 having the amino acid sequence of SEQ ID NO: 83; and (3) a $V_L$ CDR3 having the amino acid sequence of SEQ ID NO:84;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Exemplary numbering system:

(ii) the first binding domain comprises:

(a) a heavy chain variable ($V_H$) region comprising:

(1) a $V_H$ CDR1 having the amino acid sequence of SEQ ID NO:7;

(2) a $V_H$ CDR2 having the amino acid sequence of SEQ ID NO:8; and (3) a $V_H$ CDR3 having the amino acid sequence of SEQ ID NO:9; and (b) a light chain variable ($V_L$) region comprising:

(1) a $V_L$ CDR1 having the amino acid sequence of SEQ ID NO:10;

(2) a $V_L$ CDR2 having the amino acid sequence of SAS; and (3) a $V_L$ CDR3 having the amino acid sequence of SEQ ID NO:6; and the second binding domain comprises:

(a) a heavy chain variable ($V_H$) region comprising:

(1) a $V_H$ CDR1 having the amino acid sequence of SEQ ID NO: 85;

(2) a $V_H$ CDR2 having the amino acid sequence of SEQ ID NO: 86; and (3) a $V_H$ CDR3 having the amino acid sequence of SEQ ID NO:87; and (b) a light chain variable ($V_L$) region comprising:

(1) a $V_L$ CDR1 having the amino acid sequence of SEQ ID NO:88;

(2) a $V_L$ CDR2 having the amino acid sequence of SAS; and (3) a $V_L$ CDR3 having the amino acid sequence of SEQ ID NO:84;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to IMGT numbering system:

(iii) the first binding domain comprises:

(a) a heavy chain variable ($V_H$) region comprising:

(1) a $V_H$ CDR1 having the amino acid sequence of SEQ ID NO:12;

(2) a $V_H$ CDR2 having the amino acid sequence of SEQ ID NO:2; and (3) a $V_H$ CDR3 having the amino acid sequence of SEQ ID NO:3; and (b) a light chain variable ($V_L$) region comprising:

(1) a $V_L$ CDR1 having the amino acid sequence of SEQ ID NO:4;

(2) a $V_L$ CDR2 having the amino acid sequence of SEQ ID NO:5; and (3) a $V_L$ CDR3 having the amino acid sequence of SEQ ID NO:6; and the second binding domain comprises:

(a) a heavy chain variable ($V_H$) region comprising:

(1) a $V_H$ CDR1 having the amino acid sequence of SEQ ID NO:90;

(2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising:

(1) a $V_L$ CDR1 having the amino acid sequence of SEQ ID NO: 82;

(2) a $V_L$ CDR2 having the amino acid sequence of SEQ ID NO: 83; and (3) a $V_L$ CDR3 having the amino acid sequence of SEQ ID NO:84;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Kabat numbering system:

(iv) the first binding domain comprises:

(a) a heavy chain variable ($V_H$) region comprising:

(1) a $V_H$ CDR1 having the amino acid sequence of SEQ ID NO:13;

(2) a $V_H$ CDR2 having the amino acid sequence of SEQ ID NO:14; and (3) a $V_H$ CDR3 having the amino acid sequence of SEQ ID NO:15; and (b) a light chain variable ($V_L$) region comprising:

(1) a $V_L$ CDR1 having the amino acid sequence of SEQ ID NO:16;

(2) a $V_L$ CDR2 having the amino acid sequence of SAS; and (3) a $V_L$ CDR3 having the amino acid sequence of SEQ ID NO:17; and the second binding domain comprises:

(a) a heavy chain variable ($V_H$) region comprising:

(1) a $V_H$ CDR1 having the amino acid sequence of SEQ ID NO:91;

(2) a $V_H$ CDR2 having the amino acid sequence of SEQ ID NO:92; and (3) a $V_H$ CDR3 having the amino acid sequence of SEQ ID NO:93; and (b) a light chain variable ($V_L$) region comprising:

(1) a $V_L$ CDR1 having the amino acid sequence of SEQ ID NO:94;

(2) a $V_L$ CDR2 having the amino acid sequence of SAS; and (3) a $V_L$ CDR3 having the amino acid sequence of SEQ ID NO:95;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Chothia numbering system:

(v) the first binding domain comprises:

(a) a heavy chain variable ($V_H$) region comprising:

(1) a $V_H$ CDR1 having the amino acid sequence of SEQ ID NO:18;

(2) a $V_H$ CDR2 having the amino acid sequence of SEQ ID NO:19; and (3) a $V_H$ CDR3 having the amino acid sequence of SEQ ID NO:20; and (b) a light chain variable ($V_L$) region comprising:

(1) a $V_L$ CDR1 having the amino acid sequence of SEQ ID NO:21;

(2) a $V_L$ CDR2 having the amino acid sequence of SEQ ID NO:22; and (3) a $V_L$ CDR3 having the amino acid sequence of SEQ ID NO:23; and the second binding domain comprises:

(a) a heavy chain variable ($V_H$) region comprising:

(1) a $V_H$ CDR1 having the amino acid sequence of SEQ ID NO:96;

(2) a $V_H$ CDR2 having the amino acid sequence of SEQ ID NO:97; and (3) a $V_H$ CDR3 having the amino acid sequence of SEQ ID NO:98; and (b) a light chain variable ($V_L$) region comprising:

(1) a $V_L$ CDR1 having the amino acid sequence of SEQ ID NO:99;

(2) a $V_L$ CDR2 having the amino acid sequence of SEQ ID NO:100; and (3) a $V_L$ CDR3 having the amino acid sequence of SEQ ID NO:101;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Contact numbering system; or (vi) the first binding domain comprises:
(a) a heavy chain variable ($V_H$) region comprising:
(1) a $V_H$ CDR1 having the amino acid sequence of SEQ ID NO:1;
(2) a $V_H$ CDR2 having the amino acid sequence of SEQ ID NO:24; and
(3) a $V_H$ CDR3 having the amino acid sequence of SEQ ID NO:3; and
(b) a light chain variable ($V_L$) region comprising:
(1) a $V_L$ CDR1 having the amino acid sequence of SEQ ID NO:4;
(2) a $V_L$ CDR2 having the amino acid sequence of SEQ ID NO:5; and
(3) a $V_L$ CDR3 having the amino acid sequence of SEQ ID NO:6; and
the second binding domain comprises:
(a) a heavy chain variable ($V_H$) region comprising:
(1) a $V_H$ CDR1 having the amino acid sequence of SEQ ID NO:79;
(2) a $V_H$ CDR2 having the amino acid sequence of SEQ ID NO:102; and
(3) a $V_H$ CDR3 having the amino acid sequence of SEQ ID NO:81; and
(b) a light chain variable ($V_L$) region comprising:
(1) a $V_L$ CDR1 having the amino acid sequence of SEQ ID NO: 82;
(2) a $V_L$ CDR2 having the amino acid sequence of SEQ ID NO: 83; and
(3) a $V_L$ CDR3 having the amino acid sequence of SEQ ID NO:84;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to AbM numbering system.

3. The multispecific antibody or fragment thereof of claim 1, wherein:
(i) the first binding domain comprises:
(a) a heavy chain variable ($V_H$) region comprising:
(1) a $V_H$ CDR1 having the amino acid sequence of SEQ ID NO:27;
(2) a $V_H$ CDR2 having the amino acid sequence of SEQ ID NO:28; and
(3) a $V_H$ CDR3 having the amino acid sequence of SEQ ID NO:29; and
(b) a light chain variable ($V_L$) region comprising:
(1) a $V_L$ CDR1 having the amino acid sequence of SEQ ID NO:30;
(2) a $V_L$ CDR2 having the amino acid sequence of SEQ ID NO:31; and
(3) a $V_L$ CDR3 having the amino acid sequence of SEQ ID NO:32; and
the second binding domain comprises:
(a) a heavy chain variable ($V_H$) region comprising:
(1) a $V_H$ CDR1 having the amino acid sequence of SEQ ID NO:79;
(2) a $V_H$ CDR2 having the amino acid sequence of SEQ ID NO:80; and
(3) a $V_H$ CDR3 having the amino acid sequence of SEQ ID NO:81; and
(b) a light chain variable ($V_L$) region comprising:
(1) a $V_L$ CDR1 having the amino acid sequence of SEQ ID NO: 82;
(2) a $V_L$ CDR2 having the amino acid sequence of SEQ ID NO: 83; and
(3) a $V_L$ CDR3 having the amino acid sequence of SEQ ID NO:84;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Exemplary numbering system;
(ii) the first binding domain comprises:
(a) a heavy chain variable ($V_H$) region comprising:
(1) a $V_H$ CDR1 having the amino acid sequence of SEQ ID NO:33;
(2) a $V_H$ CDR2 having the amino acid sequence of SEQ ID NO:34; and
(3) a $V_H$ CDR3 having the amino acid sequence of SEQ ID NO:35; and
(b) a light chain variable ($V_L$) region comprising:
(1) a $V_L$ CDR1 having the amino acid sequence of SEQ ID NO:36;
(2) a $V_L$ CDR2 having the amino acid sequence of SAS; and
(3) a $V_L$ CDR3 having the amino acid sequence of SEQ ID NO:32; and
the second binding domain comprises:
(a) a heavy chain variable ($V_H$) region comprising:
(1) a $V_H$ CDR1 having the amino acid sequence of SEQ ID NO: 85;
(2) a $V_H$ CDR2 having the amino acid sequence of SEQ ID NO: 86; and
(3) a $V_H$ CDR3 having the amino acid sequence of SEQ ID NO:87; and
(b) a light chain variable ($V_L$) region comprising:
(1) a $V_L$ CDR1 having the amino acid sequence of SEQ ID NO:88;
(2) a $V_L$ CDR2 having the amino acid sequence of SAS; and
(3) a $V_L$ CDR3 having the amino acid sequence of SEQ ID NO:84;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to IMGT numbering system:
(iii) the first binding domain comprises:
(a) a heavy chain variable ($V_H$) region comprising:
(1) a $V_H$ CDR1 having the amino acid sequence of SEQ ID NO:38;
(2) a $V_H$ CDR2 having the amino acid sequence of SEQ ID NO:28; and
(3) a $V_H$ CDR3 having the amino acid sequence of SEQ ID NO:29; and (b) a light chain variable ($V_L$) region comprising:
(1) a $V_L$ CDR1 having the amino acid sequence of SEQ ID NO:30;
(2) a $V_L$ CDR2 having the amino acid sequence of SEQ ID NO:31; and
(3) a $V_L$ CDR3 having the amino acid sequence of SEQ ID NO:32; and
the second binding domain comprises:
(a) a heavy chain variable ($V_H$) region comprising:
(1) a $V_H$ CDR1 having the amino acid sequence of SEQ ID NO:90;
(2) a $V_H$ CDR2 having the amino acid sequence of SEQ ID NO:80; and
(3) a $V_H$ CDR3 having the amino acid sequence of SEQ ID NO:81; and
(b) a light chain variable ($V_L$) region comprising:
(1) a $V_L$ CDR1 having the amino acid sequence of SEQ ID NO: 82;
(2) a $V_L$ CDR2 having the amino acid sequence of SEQ ID NO: 83; and
(3) a $V_L$ CDR3 having the amino acid sequence of SEQ ID NO:84;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Kabat numbering system:
(iv) the first binding domain comprises:
(a) a heavy chain variable ($V_H$) region comprising:
(1) a $V_H$ CDR1 having the amino acid sequence of SEQ ID NO:39;
(2) a $V_H$ CDR2 having the amino acid sequence of SEQ ID NO:40; and
(3) a $V_H$ CDR3 having the amino acid sequence of SEQ ID NO:41; and
(b) a light chain variable ($V_L$) region comprising:
(1) a $V_L$ CDR1 having the amino acid sequence of SEQ ID NO:42;
(2) a $V_L$ CDR2 having the amino acid sequence of SAS; and
(3) a $V_L$ CDR3 having the amino acid sequence of SEQ ID NO:43; and
the second binding domain comprises:
(a) a heavy chain variable ($V_H$) region comprising:
(1) a $V_H$ CDR1 having the amino acid sequence of SEQ ID NO:91;
(2) a $V_H$ CDR2 having the amino acid sequence of SEQ ID NO:92; and
(3) a $V_H$ CDR3 having the amino acid sequence of SEQ ID NO:93; and
(b) a light chain variable ($V_L$) region comprising:
(1) a $V_L$ CDR1 having the amino acid sequence of SEQ ID NO:94;
(2) a $V_L$ CDR2 having the amino acid sequence of SAS; and
(3) a $V_L$ CDR3 having the amino acid sequence of SEQ ID NO:95;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Chothia numbering system:
(v) the first binding domain comprises:
(a) a heavy chain variable ($V_H$) region comprising:
(1) a $V_H$ CDR1 having the amino acid sequence of SEQ ID NO:44;
(2) a $V_H$ CDR2 having the amino acid sequence of SEQ ID NO:45; and
(3) a $V_H$ CDR3 having the amino acid sequence of SEQ ID NO:46; and
(b) a light chain variable ($V_L$) region comprising:
(1) a $V_L$ CDR1 having the amino acid sequence of SEQ ID NO:47;
(2) a $V_L$ CDR2 having the amino acid sequence of SEQ ID NO:48; and
(3) a $V_L$ CDR3 having the amino acid sequence of SEQ ID NO:49; and
the second binding domain comprises:
(a) a heavy chain variable ($V_H$) region comprising:
(1) a $V_H$ CDR1 having the amino acid sequence of SEQ ID NO:96;
(2) a $V_H$ CDR2 having the amino acid sequence of SEQ ID NO:97; and
(3) a $V_H$ CDR3 having the amino acid sequence of SEQ ID NO:98; and
(b) a light chain variable ($V_L$) region comprising:
(1) a $V_L$ CDR1 having the amino acid sequence of SEQ ID NO:99;
(2) a $V_L$ CDR2 having the amino acid sequence of SEQ ID NO:100; and
(3) a $V_L$ CDR3 having the amino acid sequence of SEQ ID NO:101;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Contact numbering system; or
(vi) the first binding domain comprises:
(a) a heavy chain variable ($V_H$) region comprising:
(1) a $V_H$ CDR1 having the amino acid sequence of SEQ ID NO:27;
(2) a $V_H$ CDR2 having the amino acid sequence of SEQ ID NO:50; and
(3) a $V_H$ CDR3 having the amino acid sequence of SEQ ID NO:29; and
(b) a light chain variable ($V_L$) region comprising:
(1) a $V_L$ CDR1 having the amino acid sequence of SEQ ID NO:30;
(2) a $V_L$ CDR2 having the amino acid sequence of SEQ ID NO:31; and
(3) a $V_L$ CDR3 having the amino acid sequence of SEQ ID NO:32; and
the second binding domain comprises:
(a) a heavy chain variable ($V_H$) region comprising:
(1) a $V_H$ CDR1 having the amino acid sequence of SEQ ID NO:79;
(2) a $V_H$ CDR2 having the amino acid sequence of SEQ ID NO:102; and
(3) a $V_H$ CDR3 having the amino acid sequence of SEQ ID NO:81; and (b) a light chain variable ($V_L$) region comprising:

(1) a $V_L$ CDR1 having the amino acid sequence of SEQ ID NO: 82;

(2) a $V_L$ CDR2 having the amino acid sequence of SEQ ID NO: 83; and (3) a $V_L$ CDR3 having the amino acid sequence of SEQ ID NO:84, wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to AbM numbering system.

4. The multispecific antibody or fragment thereof of claim 1, wherein:

(i) the first binding domain comprises:

(a) a heavy chain variable ($V_H$) region comprising:

(1) a $V_H$ CDR1 having the amino acid sequence of SEQ ID NO:53;

(2) a $V_H$ CDR2 having the amino acid sequence of SEQ ID NO:54; and (3) a $V_H$ CDR3 having the amino acid sequence of SEQ ID NO:55; and (b) a light chain variable ($V_L$) region comprising:

(1) a $V_L$ CDR1 having the amino acid sequence of SEQ ID NO:56;

(2) a $V_L$ CDR2 having the amino acid sequence of SEQ ID NO:57; and (3) a $V_L$ CDR3 having the amino acid sequence of SEQ ID NO:58; and the second binding domain comprises:

(a) a heavy chain variable ($V_H$) region comprising:

(1) a $V_H$ CDR1 having the amino acid sequence of SEQ ID NO:79;

(2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising:

(1) a $V_L$ CDR1 having the amino acid sequence of SEQ ID NO: 82;

(2) a $V_L$ CDR2 having the amino acid sequence of SEQ ID NO: 83; and (3) a $V_L$ CDR3 having the amino acid sequence of SEQ ID NO:84;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Exemplary numbering system:

(ii) the first binding domain comprises:

(a) a heavy chain variable ($V_H$) region comprising:

(1) a $V_H$ CDR1 having the amino acid sequence of SEQ ID NO:59;

(2) a $V_H$ CDR2 having the amino acid sequence of SEQ ID NO:60; and (3) a $V_H$ CDR3 having the amino acid sequence of SEQ ID NO:61; and (b) a light chain variable ($V_L$) region comprising:

(1) a $V_L$ CDR1 having the amino acid sequence of SEQ ID NO:62;

(2) a $V_L$ CDR2 having the amino acid sequence of SAS; and (3) a $V_L$ CDR3 having the amino acid sequence of SEQ ID NO:58; and the second binding domain comprises:

(a) a heavy chain variable ($V_H$) region comprising:

(1) a $V_H$ CDR1 having the amino acid sequence of SEQ ID NO: 85;

(2) a $V_H$ CDR2 having the amino acid sequence of SEQ ID NO: 86; and (3) a $V_H$ CDR3 having the amino acid sequence of SEQ ID NO:87; and (b) a light chain variable ($V_L$) region comprising:

(1) a $V_L$ CDR1 having the amino acid sequence of SEQ ID NO:88;

(2) a $V_L$ CDR2 having the amino acid sequence of SAS; and (3) a $V_L$ CDR3 having the amino acid sequence of SEQ ID NO:84;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to IMGT numbering system;

(iii) the first binding domain comprises:

(a) a heavy chain variable ($V_H$) region comprising:

(1) a $V_H$ CDR1 having the amino acid sequence of SEQ ID NO:64;

(2) a $V_H$ CDR2 having the amino acid sequence of SEQ ID NO:54; and (3) a $V_H$ CDR3 having the amino acid sequence of SEQ ID NO:55; and (b) a light chain variable ($V_L$) region comprising:

(1) a $V_L$ CDR1 having the amino acid sequence of SEQ ID NO:56;

(2) a $V_L$ CDR2 having the amino acid sequence of SEQ ID NO:57; and (3) a $V_L$ CDR3 having the amino acid sequence of SEQ ID NO:58; and the second binding domain comprises:

(a) a heavy chain variable ($V_H$) region comprising:

(1) a $V_H$ CDR1 having the amino acid sequence of SEQ ID NO:90;

(2) a $V_H$ CDR2 having the amino acid sequence of SEQ ID NO:80; and (3) a $V_H$ CDR3 having the amino acid sequence of SEQ ID NO:81; and (b) a light chain variable ($V_L$) region comprising:

(1) a $V_L$ CDR1 having the amino acid sequence of SEQ ID NO: 82;

(2) a $V_L$ CDR2 having the amino acid sequence of SEQ ID NO: 83; and (3) a $V_L$ CDR3 having the amino acid sequence of SEQ ID NO:84;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Kabat numbering system;

(iv) the first binding domain comprises:
(a) a heavy chain variable ($V_H$) region comprising:
(1) a $V_H$ CDR1 having the amino acid sequence of SEQ ID NO:65;
(2) a $V_H$ CDR2 having the amino acid sequence of SEQ ID NO:66; and
(3) a $V_H$ CDR3 having the amino acid sequence of SEQ ID NO:67; and
(b) a light chain variable ($V_L$) region comprising:
(1) a $V_L$ CDR1 having the amino acid sequence of SEQ ID NO:68;
(2) a $V_L$ CDR2 having the amino acid sequence of SAS; and
(3) a $V_L$ CDR3 having the amino acid sequence of SEQ ID NO:69; and
the second binding domain comprises:
(a) a heavy chain variable ($V_H$) region comprising:
(1) a $V_H$ CDR1 having the amino acid sequence of SEQ ID NO:91;
(2) a $V_H$ CDR2 having the amino acid sequence of SEQ ID NO:92; and
(3) a $V_H$ CDR3 having the amino acid sequence of SEQ ID NO:93; and
(b) a light chain variable ($V_L$) region comprising:
(1) a $V_L$ CDR1 having the amino acid sequence of SEQ ID NO:94;
(2) a $V_L$ CDR2 having the amino acid sequence of SAS; and
(3) a $V_L$ CDR3 having the amino acid sequence of SEQ ID NO:95;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Chothia numbering system:
(v) the first binding domain comprises:
(a) a heavy chain variable ($V_H$) region comprising:
(1) a $V_H$ CDR1 having the amino acid sequence of SEQ ID NO:70;
(2) a $V_H$ CDR2 having the amino acid sequence of SEQ ID NO:71; and
(3) a $V_H$ CDR3 having the amino acid sequence of SEQ ID NO:72; and
(b) a light chain variable ($V_L$) region comprising:
(1) a $V_L$ CDR1 having the amino acid sequence of SEQ ID NO:73;
(2) a $V_L$ CDR2 having the amino acid sequence of SEQ ID NO:74; and
(3) a $V_L$ CDR3 having the amino acid sequence of SEQ ID NO:75; and
the second binding domain comprises:
(a) a heavy chain variable ($V_H$) region comprising:
(1) a $V_H$ CDR1 having the amino acid sequence of SEQ ID NO:96;
(2) a $V_H$ CDR2 having the amino acid sequence of SEQ ID NO:97; and
(3) a $V_H$ CDR3 having the amino acid sequence of SEQ ID NO:98; and
(b) a light chain variable ($V_L$) region comprising:
(1) a $V_L$ CDR1 having the amino acid sequence of SEQ ID NO:99;
(2) a $V_L$ CDR2 having the amino acid sequence of SEQ ID NO:100; and (3) a $V_L$ CDR3 having the amino acid sequence of SEQ ID NO:101;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to Contact numbering system; or
(vi) the first binding domain comprises:
(a) a heavy chain variable ($V_H$) region comprising:
(1) a $V_H$ CDR1 having the amino acid sequence of SEQ ID NO:53;
(2) a $V_H$ CDR2 having the amino acid sequence of SEQ ID NO:76; and
(3) a $V_H$ CDR3 having the amino acid sequence of SEQ ID NO:55; and
(b) a light chain variable ($V_L$) region comprising:
(1) a $V_L$ CDR1 having the amino acid sequence of SEQ ID NO:56;
(2) a $V_L$ CDR2 having the amino acid sequence of SEQ ID NO:57; and
(3) a $V_L$ CDR3 having the amino acid sequence of SEQ ID NO:58; and
the second binding domain comprises:
(a) a heavy chain variable ($V_H$) region comprising:
(1) a $V_H$ CDR1 having the amino acid sequence of SEQ ID NO:79;
(2) a $V_H$ CDR2 having the amino acid sequence of SEQ ID NO:102; and
(3) a $V_H$ CDR3 having the amino acid sequence of SEQ ID NO:81; and
(b) a light chain variable ($V_L$) region comprising:
(1) a $V_L$ CDR1 having the amino acid sequence of SEQ ID NO: 82;
(2) a $V_L$ CDR2 having the amino acid sequence of SEQ ID NO: 83; and
(3) a $V_L$ CDR3 having the amino acid sequence of SEQ ID NO:84;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P22 as determined according to AbM numbering system.

5. The multispecific antibody or fragment thereof of claim 1, wherein the first binding domain and/or the second binding domain further comprises, in its $V_H$ region and/or $V_L$ region, (i) human framework sequences; and/or (ii) a framework 1 (FR1), a framework 2 (FR2), a framework 3 (FR3) and/or a framework 4 (FR4) sequence.

6. The multispecific antibody or fragment thereof of claim 1, wherein
(i) the multispecific antibody is a recombinant antibody;
(ii) the multispecific antibody is a humanized, human or chimeric antibody;
(iii) the multispecific antibody is a bispecific antibody; and/or
(iv) the multispecific antibody or fragment thereof is conjugated or recombinantly fused to a diagnostic agent, detectable agent or therapeutic agent.

7. One or more vectors comprising one or more polynucleotides encoding the multispecific antibody or fragment thereof of claim 1.

8. A pharmaceutical composition that comprises the multispecific antibody or fragment thereof of claim 1, and a pharmaceutically acceptable carrier.

9. A method for treating a cancer or a tumor in a subject, for alleviating one or more symptoms associated with a cancer or a tumor in a subject, for decreasing tumor size in a subject with a tumor, for enhancing tumor cell removal in a subject with a tumor, for treating a phagocytic cell dysfunctional disease, disorder or condition in a subject, for increasing immune cell phagocytosis in a subject, for treating a T cell dysfunctional disease, disorder or condition in a subject, or for enhancing T cell function in a subject, comprising administering to the subject a therapeutically effective amount of the multispecific antibody or fragment thereof of claim 1.

10. The multispecific antibody or fragment thereof of claim 1, wherein the first binding domain comprises a VH comprising the amino acid sequence of SEQ ID NO:25 and a VL comprising the amino acid sequence of SEQ ID NO:26, which are the VH and VL sequences of the antibody designated C40, and the second binding domain comprises a VH comprising the amino acid sequence of SEQ ID NO:103 and a VL comprising the amino acid sequence of SEQ ID NO:104, which are the VH and VL sequences of the antibody designated P22.

11. One or more polynucleotides encoding the multispecific antibody or fragment thereof of claim 1.

12. A cell comprising the one or more vectors of claim 7.

13. The multispecific antibody or fragment thereof of claim 1, wherein:

(i) the first binding domain comprises:
(a) a heavy chain variable ($V_H$) region comprising:
(1) a $V_H$ CDR1 having the amino acid sequence of SEQ ID NO:1;
(2) a $V_H$ CDR2 having the amino acid sequence of SEQ ID NO:2; and
(3) a $V_H$ CDR3 having the amino acid sequence of SEQ ID NO:3; and
(b) a light chain variable ($V_L$) region comprising:
(1) a $V_L$ CDR1 having the amino acid sequence of SEQ ID NO:4;
(2) a $V_L$ CDR2 having the amino acid sequence of SEQ ID NO:5; and
(3) a $V_L$ CDR3 having the amino acid sequence of SEQ ID NO:6; and
the second binding domain comprises:
(a) a heavy chain variable ($V_H$) region comprising:
(1) a $V_H$ CDR1 having the amino acid sequence of SEQ ID NO:105;
(2) a $V_H$ CDR2 having the amino acid sequence of SEQ ID NO:106; and
(3) a $V_H$ CDR3 having the amino acid sequence of SEQ ID NO:107; and
(b) a light chain variable ($V_L$) region comprising:
(1) a $V_L$ CDR1 having the amino acid sequence of SEQ ID NO:108;
(2) a $V_L$ CDR2 having the amino acid sequence of SEQ ID NO:109; and
(3) a $V_L$ CDR3 having the amino acid sequence of SEQ ID NO:110;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Exemplary numbering system:

(ii) the first binding domain comprises:
(a) a heavy chain variable ($V_H$) region comprising:
(1) a $V_H$ CDR1 having the amino acid sequence of SEQ ID NO:7;
(2) a $V_H$ CDR2 having the amino acid sequence of SEQ ID NO:8; and
(3) a $V_H$ CDR3 having the amino acid sequence of SEQ ID NO:9; and
(b) a light chain variable ($V_L$) region comprising:
(1) a $V_L$ CDR1 having the amino acid sequence of SEQ ID NO:10;
(2) a $V_L$ CDR2 having the amino acid sequence of SAS; and
(3) a $V_L$ CDR3 having the amino acid sequence of SEQ ID NO:6; and
the second binding domain comprises:
(a) a heavy chain variable ($V_H$) region comprising:
(1) a $V_H$ CDR1 having the amino acid sequence of SEQ ID NO:111;
(2) a $V_H$ CDR2 having the amino acid sequence of SEQ ID NO:112; and
(3) a $V_H$ CDR3 having the amino acid sequence of SEQ ID NO:113; and
(b) a light chain variable ($V_L$) region comprising:
(1) a $V_L$ CDR1 having the amino acid sequence of SEQ ID NO:114;
(2) a $V_L$ CDR2 having the amino acid sequence of SAS; and
(3) a $V_L$ CDR3 having the amino acid sequence of SEQ ID NO:110;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to IMGT numbering system:

(iii) the first binding domain comprises:
(a) a heavy chain variable ($V_H$) region comprising:
(1) a $V_H$ CDR1 having the amino acid sequence of SEQ ID NO:12;
(2) a $V_H$ CDR2 having the amino acid sequence of SEQ ID NO:2; and
(3) a $V_H$ CDR3 having the amino acid sequence of SEQ ID NO:3; and
(b) a light chain variable ($V_L$) region comprising:
(1) a $V_L$ CDR1 having the amino acid sequence of SEQ ID NO:4;
(2) a $V_L$ CDR2 having the amino acid sequence of SEQ ID NO:5; and
(3) a $V_L$ CDR3 having the amino acid sequence of SEQ ID NO:6; and
the second binding domain comprises:
(a) a heavy chain variable ($V_H$) region comprising:
(1) a $V_H$ CDR1 having the amino acid sequence of SEQ ID NO:116;
(2) a $V_H$ CDR2 having the amino acid sequence of SEQ ID NO:106; and
(3) a $V_H$ CDR3 having the amino acid sequence of SEQ ID NO:107; and (b) a light chain variable ($V_L$) region comprising:
(1) a $V_L$ CDR1 having the amino acid sequence of SEQ ID NO:108;
(2) a $V_L$ CDR2 having the amino acid sequence of SEQ ID NO:109; and
(3) a $V_L$ CDR3 having the amino acid sequence of SEQ ID NO:110;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Kabat numbering system:
(iv) the first binding domain comprises:
(a) a heavy chain variable ($V_H$) region comprising:
(1) a $V_H$ CDR1 having the amino acid sequence of SEQ ID NO:13;
(2) a $V_H$ CDR2 having the amino acid sequence of SEQ ID NO:14; and
(3) a $V_H$ CDR3 having the amino acid sequence of SEQ ID NO:15; and
(b) a light chain variable ($V_L$) region comprising:
(1) a $V_L$ CDR1 having the amino acid sequence of SEQ ID NO:16;
(2) a $V_L$ CDR2 having the amino acid sequence of SAS; and
(3) a $V_L$ CDR3 having the amino acid sequence of SEQ ID NO:17; and
the second binding domain comprises:
(a) a heavy chain variable ($V_H$) region comprising:
(1) a $V_H$ CDR1 having the amino acid sequence of SEQ ID NO:117;
(2) a $V_H$ CDR2 having the amino acid sequence of SEQ ID NO:118; and
(3) a $V_H$ CDR3 having the amino acid sequence of SEQ ID NO:119; and
(b) a light chain variable ($V_L$) region comprising:
(1) a $V_L$ CDR1 having the amino acid sequence of SEQ ID NO:120;
(2) a $V_L$ CDR2 having the amino acid sequence of SAS; and
(3) a $V_L$ CDR3 having the amino acid sequence of SEQ ID NO:121;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Chothia numbering system:
(v) the first binding domain comprises:
(a) a heavy chain variable ($V_H$) region comprising:
(1) a $V_H$ CDR1 having the amino acid sequence of SEQ ID NO:18;
(2) a $V_H$ CDR2 having the amino acid sequence of SEQ ID NO:19; and
(3) a $V_H$ CDR3 having the amino acid sequence of SEQ ID NO:20; and
(b) a light chain variable ($V_L$) region comprising:
(1) a $V_L$ CDR1 having the amino acid sequence of SEQ ID NO:21;
(2) a $V_L$ CDR2 having the amino acid sequence of SEQ ID NO:22; and
(3) a $V_L$ CDR3 having the amino acid sequence of SEQ ID NO:23; and
the second binding domain comprises:
(a) a heavy chain variable ($V_H$) region comprising:
(1) a $V_H$ CDR1 having the amino acid sequence of SEQ ID NO:122;
(2) a $V_H$ CDR2 having the amino acid sequence of SEQ ID NO:123; and
(3) a $V_H$ CDR3 having the amino acid sequence of SEQ ID NO:124; and
(b) a light chain variable ($V_L$) region comprising:
(1) a $V_L$ CDR1 having the amino acid sequence of SEQ ID NO:125;
(2) a $V_L$ CDR2 having the amino acid sequence of SEQ ID NO:126; and
(3) a $V_L$ CDR3 having the amino acid sequence of SEQ ID NO:127;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Contact numbering system; or
(vi) the first binding domain comprises:
(a) a heavy chain variable ($V_H$) region comprising:
(1) a $V_H$ CDR1 having the amino acid sequence of SEQ ID NO:1;
(2) a $V_H$ CDR2 having the amino acid sequence of SEQ ID NO:24; and
(3) a $V_H$ CDR3 having the amino acid sequence of SEQ ID NO:3; and
(b) a light chain variable ($V_L$) region comprising:
(1) a $V_L$ CDR1 having the amino acid sequence of SEQ ID NO:4;
(2) a $V_L$ CDR2 having the amino acid sequence of SEQ ID NO:5; and
(3) a $V_L$ CDR3 having the amino acid sequence of SEQ ID NO:6; and
the second binding domain comprises:
(a) a heavy chain variable ($V_H$) region comprising:
(1) a $V_H$ CDR1 having the amino acid sequence of SEQ ID NO:105;
(2) a $V_H$ CDR2 having the amino acid sequence of SEQ ID NO:128; and
(3) a $V_H$ CDR3 having the amino acid sequence of SEQ ID NO:107; and
(b) a light chain variable ($V_L$) region comprising:
(1) a $V_L$ CDR1 having the amino acid sequence of SEQ ID NO:108;
(2) a $V_L$ CDR2 having the amino acid sequence of SEQ ID NO:109; and
(3) a $V_L$ CDR3 having the amino acid sequence of SEQ ID NO:110,
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to AbM numbering system.

14. The multispecific antibody or fragment thereof of claim 1, wherein:

(i) the first binding domain comprises:

(a) a heavy chain variable ($V_H$) region comprising:

(1) a $V_H$ CDR1 having the amino acid sequence of SEQ ID NO:27;

(2) a $V_H$ CDR2 having the amino acid sequence of SEQ ID NO:28; and (3) a $V_H$ CDR3 having the amino acid sequence of SEQ ID NO:29; and (b) a light chain variable ($V_L$) region comprising:

(1) a $V_L$ CDR1 having the amino acid sequence of SEQ ID NO:30;

(2) a $V_L$ CDR2 having the amino acid sequence of SEQ ID NO:31; and (3) a $V_L$ CDR3 having the amino acid sequence of SEQ ID NO:32; and the second binding domain comprises:

(a) a heavy chain variable ($V_H$) region comprising:

(1) a $V_H$ CDR1 having the amino acid sequence of SEQ ID NO:105;

(2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising:

(1) a $V_L$ CDR1 having the amino acid sequence of SEQ ID NO:108;

(2) a $V_L$ CDR2 having the amino acid sequence of SEQ ID NO:109; and (3) a $V_L$ CDR3 having the amino acid sequence of SEQ ID NO:110;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Exemplary numbering system:

(ii) the first binding domain comprises:

(a) a heavy chain variable ($V_H$) region comprising:

(1) a $V_H$ CDR1 having the amino acid sequence of SEQ ID NO:33;

(2) a $V_H$ CDR2 having the amino acid sequence of SEQ ID NO:34; and (3) a $V_H$ CDR3 having the amino acid sequence of SEQ ID NO:35; and (b) a light chain variable ($V_L$) region comprising:

(1) a $V_L$ CDR1 having the amino acid sequence of SEQ ID NO:36;

(2) a $V_L$ CDR2 having the amino acid sequence of SAS; and (3) a $V_L$ CDR3 having the amino acid sequence of SEQ ID NO:32; and the second binding domain comprises:

(a) a heavy chain variable ($V_H$) region comprising:

(1) a $V_H$ CDR1 having the amino acid sequence of SEQ ID NO:111;

(2) a $V_H$ CDR2 having the amino acid sequence of SEQ ID NO:112; and (3) a $V_H$ CDR3 having the amino acid sequence of SEQ ID NO:113; and (b) a light chain variable ($V_L$) region comprising:

(1) a $V_L$ CDR1 having the amino acid sequence of SEQ ID NO:114;

(2) a $V_L$ CDR2 having the amino acid sequence of SAS; and (3) a $V_L$ CDR3 having the amino acid sequence of SEQ ID NO:110;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to IMGT numbering system:

(iii) the first binding domain comprises:

(a) a heavy chain variable ($V_H$) region comprising:

(1) a $V_H$ CDR1 having the amino acid sequence of SEQ ID NO:38;

(2) a $V_H$ CDR2 having the amino acid sequence of SEQ ID NO:28; and (3) a $V_H$ CDR3 having the amino acid sequence of SEQ ID NO:29; and (b) a light chain variable ($V_L$) region comprising:

(1) a $V_L$ CDR1 having the amino acid sequence of SEQ ID NO:30;

(2) a $V_L$ CDR2 having the amino acid sequence of SEQ ID NO:31; and (3) a $V_L$ CDR3 having the amino acid sequence of SEQ ID NO:32; and the second binding domain comprises:

(a) a heavy chain variable ($V_H$) region comprising:

(1) a $V_H$ CDR1 having the amino acid sequence of SEQ ID NO:116;

(2) a $V_H$ CDR2 having the amino acid sequence of SEQ ID NO:106; and (3) a $V_H$ CDR3 having the amino acid sequence of SEQ ID NO:107; and (b) a light chain variable ($V_L$) region comprising:

(1) a $V_L$ CDR1 having the amino acid sequence of SEQ ID NO:108;

(2) a $V_L$ CDR2 having the amino acid sequence of SEQ ID NO:109; and (3) a $V_L$ CDR3 having the amino acid sequence of SEQ ID NO:110;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Kabat numbering system:

(iv) the first binding domain comprises:

(a) a heavy chain variable ($V_H$) region comprising:

(1) a $V_H$ CDR1 having the amino acid sequence of SEQ ID NO:39;

(2) a $V_H$ CDR2 having the amino acid sequence of SEQ ID NO:40; and (3) a $V_H$ CDR3 having the amino acid sequence of SEQ ID NO:41; and (b) a light chain variable ($V_L$) region comprising:

(1) a $V_L$ CDR1 having the amino acid sequence of SEQ ID NO:42;

(2) a $V_L$ CDR2 having the amino acid sequence of SAS; and (3) a $V_L$ CDR3 having the amino acid sequence of SEQ ID NO:43; and the second binding domain comprises:
(a) a heavy chain variable ($V_H$) region comprising:
(1) a $V_H$ CDR1 having the amino acid sequence of SEQ ID NO:117;
(2) a $V_H$ CDR2 having the amino acid sequence of SEQ ID NO:118; and
(3) a $V_H$ CDR3 having the amino acid sequence of SEQ ID NO:119; and
(b) a light chain variable ($V_L$) region comprising:
(1) a $V_L$ CDR1 having the amino acid sequence of SEQ ID NO:120;
(2) a $V_L$ CDR2 having the amino acid sequence of SAS; and
(3) a $V_L$ CDR3 having the amino acid sequence of SEQ ID NO:121;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Chothia numbering system:
(v) the first binding domain comprises:
(a) a heavy chain variable ($V_H$) region comprising:
(1) a $V_H$ CDR1 having the amino acid sequence of SEQ ID NO:44;
(2) a $V_H$ CDR2 having the amino acid sequence of SEQ ID NO:45; and
(3) a $V_H$ CDR3 having the amino acid sequence of SEQ ID NO:46; and
(b) a light chain variable ($V_L$) region comprising:
(1) a $V_L$ CDR1 having the amino acid sequence of SEQ ID NO:47;
(2) a $V_L$ CDR2 having the amino acid sequence of SEQ ID NO:48; and
(3) a $V_L$ CDR3 having the amino acid sequence of SEQ ID NO:49; and
the second binding domain comprises:
(a) a heavy chain variable ($V_H$) region comprising:
(1) a $V_H$ CDR1 having the amino acid sequence of SEQ ID NO:122;
(2) a $V_H$ CDR2 having the amino acid sequence of SEQ ID NO:123; and
(3) a $V_H$ CDR3 having the amino acid sequence of SEQ ID NO:124; and
(b) a light chain variable ($V_L$) region comprising:
(1) a $V_L$ CDR1 having the amino acid sequence of SEQ ID NO:125;
(2) a $V_L$ CDR2 having the amino acid sequence of SEQ ID NO:126; and
(3) a $V_L$ CDR3 having the amino acid sequence of SEQ ID NO:127;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Contact numbering system; or
(vi) the first binding domain comprises:
(a) a heavy chain variable ($V_H$) region comprising:
(1) a $V_H$ CDR1 having the amino acid sequence of SEQ ID NO:27;
(2) a $V_H$ CDR2 having the amino acid sequence of SEQ ID NO:50; and
(3) a $V_H$ CDR3 having the amino acid sequence of SEQ ID NO:29; and
(b) a light chain variable ($V_L$) region comprising:
(1) a $V_L$ CDR1 having the amino acid sequence of SEQ ID NO:30;
(2) a $V_L$ CDR2 having the amino acid sequence of SEQ ID NO:31; and
(3) a $V_L$ CDR3 having the amino acid sequence of SEQ ID NO:32; and
the second binding domain comprises:
(a) a heavy chain variable ($V_H$) region comprising:
(1) a $V_H$ CDR1 having the amino acid sequence of SEQ ID NO:105;
(2) a $V_H$ CDR2 having the amino acid sequence of SEQ ID NO:128; and
(3) a $V_H$ CDR3 having the amino acid sequence of SEQ ID NO:107; and
(b) a light chain variable ($V_L$) region comprising:
(1) a $V_L$ CDR1 having the amino acid sequence of SEQ ID NO:108;
(2) a $V_L$ CDR2 having the amino acid sequence of SEQ ID NO:109; and
(3) a $V_L$ CDR3 having the amino acid sequence of SEQ ID NO:110,
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to AbM numbering system.

15. The multispecific antibody or fragment thereof of claim 1, wherein:
(i) the first binding domain comprises:
(a) a heavy chain variable ($V_H$) region comprising:
(1) a $V_H$ CDR1 having the amino acid sequence of SEQ ID NO:53;
(2) a $V_H$ CDR2 having the amino acid sequence of SEQ ID NO:54; and
(3) a $V_H$ CDR3 having the amino acid sequence of SEQ ID NO:55; and
(b) a light chain variable ($V_L$) region comprising:
(1) a $V_L$ CDR1 having the amino acid sequence of SEQ ID NO:56;
(2) a $V_L$ CDR2 having the amino acid sequence of SEQ ID NO:57; and
(3) a $V_L$ CDR3 having the amino acid sequence of SEQ ID NO:58; and
the second binding domain comprises:
(a) a heavy chain variable ($V_H$) region comprising:
(1) a $V_H$ CDR1 having the amino acid sequence of SEQ ID NO:105;
(2) a $V_H$ CDR2 having the amino acid sequence of SEQ ID NO:106; and
(3) a $V_H$ CDR3 having the amino acid sequence of SEQ ID NO:107; and
(b) a light chain variable ($V_L$) region comprising:
(1) a $V_L$ CDR1 having the amino acid sequence of SEQ ID NO:108;
(2) a $V_L$ CDR2 having the amino acid sequence of SEQ ID NO:109; and
(3) a $V_L$ CDR3 having the amino acid sequence of SEQ ID NO:110;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Exemplary numbering system:

(ii) the first binding domain comprises:
(a) a heavy chain variable ($V_H$) region comprising:
(1) a $V_H$ CDR1 having the amino acid sequence of SEQ ID NO:59;
(2) a $V_H$ CDR2 having the amino acid sequence of SEQ ID NO:60; and
(3) a $V_H$ CDR3 having the amino acid sequence of SEQ ID NO:61; and
(b) a light chain variable ($V_L$) region comprising:
(1) a $V_L$ CDR1 having the amino acid sequence of SEQ ID NO:62;
(2) a $V_L$ CDR2 having the amino acid sequence of SAS; and
(3) a $V_L$ CDR3 having the amino acid sequence of SEQ ID NO:58; and
the second binding domain comprises:
(a) a heavy chain variable ($V_H$) region comprising:
(1) a $V_H$ CDR1 having the amino acid sequence of SEQ ID NO:111;
(2) a $V_H$ CDR2 having the amino acid sequence of SEQ ID NO:112; and
(3) a $V_H$ CDR3 having the amino acid sequence of SEQ ID NO:113; and
(b) a light chain variable ($V_L$) region comprising:
(1) a $V_L$ CDR1 having the amino acid sequence of SEQ ID NO:114;
(2) a $V_L$ CDR2 having the amino acid sequence of SAS; and
(3) a $V_L$ CDR3 having the amino acid sequence of SEQ ID NO:110;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to IMGT numbering system:

(iii) the first binding domain comprises:
(a) a heavy chain variable ($V_H$) region comprising:
(1) a $V_H$ CDR1 having the amino acid sequence of SEQ ID NO:64;
(2) a $V_H$ CDR2 having the amino acid sequence of SEQ ID NO:54; and
(3) a $V_H$ CDR3 having the amino acid sequence of SEQ ID NO:55; and
(b) a light chain variable ($V_L$) region comprising:
(1) a $V_L$ CDR1 having the amino acid sequence of SEQ ID NO:56;
(2) a $V_L$ CDR2 having the amino acid sequence of SEQ ID NO:57; and
(3) a $V_L$ CDR3 having the amino acid sequence of SEQ ID NO:58; and
the second binding domain comprises:
(a) a heavy chain variable ($V_H$) region comprising:
(1) a $V_H$ CDR1 having the amino acid sequence of SEQ ID NO:116;
(2) a $V_H$ CDR2 having the amino acid sequence of SEQ ID NO:106; and
(3) a $V_H$ CDR3 having the amino acid sequence of SEQ ID NO:107; and
(b) a light chain variable ($V_L$) region comprising:
(1) a $V_L$ CDR1 having the amino acid sequence of SEQ ID NO:108;
(2) a $V_L$ CDR2 having the amino acid sequence of SEQ ID NO:109; and
(3) a $V_L$ CDR3 having the amino acid sequence of SEQ ID NO:110;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Kabat numbering system:

(iv) the first binding domain comprises:
(a) a heavy chain variable ($V_H$) region comprising:
(1) a $V_H$ CDR1 having the amino acid sequence of SEQ ID NO:65;
(2) a $V_H$ CDR2 having the amino acid sequence of SEQ ID NO:66; and
(3) a $V_H$ CDR3 having the amino acid sequence of SEQ ID NO:67; and
(b) a light chain variable ($V_L$) region comprising:
(1) a $V_L$ CDR1 having the amino acid sequence of SEQ ID NO:68;
(2) a $V_L$ CDR2 having the amino acid sequence of SAS; and
(3) a $V_L$ CDR3 having the amino acid sequence of SEQ ID NO:69; and
the second binding domain comprises:
(a) a heavy chain variable ($V_H$) region comprising:
(1) a $V_H$ CDR1 having the amino acid sequence of SEQ ID NO:117;
(2) a $V_H$ CDR2 having the amino acid sequence of SEQ ID NO:118; and
(3) a $V_H$ CDR3 having the amino acid sequence of SEQ ID NO:119; and
(b) a light chain variable ($V_L$) region comprising:
(1) a $V_L$ CDR1 having the amino acid sequence of SEQ ID NO:120;
(2) a $V_L$ CDR2 having the amino acid sequence of SAS; and
(3) a $V_L$ CDR3 having the amino acid sequence of SEQ ID NO:121;
wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Chothia numbering system:

(v) the first binding domain comprises:
(a) a heavy chain variable ($V_H$) region comprising:
(1) a $V_H$ CDR1 having the amino acid sequence of SEQ ID NO:70;
(2) a $V_H$ CDR2 having the amino acid sequence of SEQ ID NO:71; and
(3) a $V_H$ CDR3 having the amino acid sequence of SEQ ID NO:72; and (b) a light chain variable ($V_L$) region comprising:

(1) a $V_L$ CDR1 having the amino acid sequence of SEQ ID NO:73;

(2) a $V_L$ CDR2 having the amino acid sequence of SEQ ID NO:74; and (3) a $V_L$ CDR3 having the amino acid sequence of SEQ ID NO:75; and the second binding domain comprises:

(a) a heavy chain variable ($V_H$) region comprising:

(1) a $V_H$ CDR1 having the amino acid sequence of SEQ ID NO:122;

(2) a $V_H$ CDR2 having the amino acid sequence of SEQ ID NO:123; and (3) a $V_H$ CDR3 having the amino acid sequence of SEQ ID NO:124; and (b) a light chain variable ($V_L$) region comprising:

(1) a $V_L$ CDR1 having the amino acid sequence of SEQ ID NO:125;

(2) a $V_L$ CDR2 having the amino acid sequence of SEQ ID NO:126; and (3) a $V_L$ CDR3 having the amino acid sequence of SEQ ID NO:127;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to Contact numbering system; or (vi) the first binding domain comprises:

(a) a heavy chain variable ($V_H$) region comprising:

(1) a $V_H$ CDR1 having the amino acid sequence of SEQ ID NO:53;

(2) a $V_H$ CDR2 having the amino acid sequence of SEQ ID NO:76; and (3) a $V_H$ CDR3 having the amino acid sequence of SEQ ID NO:55; and (b) a light chain variable ($V_L$) region comprising:

(1) a $V_L$ CDR1 having the amino acid sequence of SEQ ID NO:56;

(2) a $V_L$ CDR2 having the amino acid sequence of SEQ ID NO:57; and (3) a $V_L$ CDR3 having the amino acid sequence of SEQ ID NO:58; and the second binding domain comprises:

(a) a heavy chain variable ($V_H$) region comprising:

(1) a $V_H$ CDR1 having the amino acid sequence of SEQ ID NO:105;

(2) a $V_H$ CDR2 having the amino acid sequence of SEQ ID NO:128; and (3) a $V_H$ CDR3 having the amino acid sequence of SEQ ID NO:107; and (b) a light chain variable ($V_L$) region comprising:

(1) a $V_L$ CDR1 having the amino acid sequence of SEQ ID NO:108;

(2) a $V_L$ CDR2 having the amino acid sequence of SEQ ID NO:109; and (3) a $V_L$ CDR3 having the amino acid sequence of SEQ ID NO:110, wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P24 as determined according to AbM numbering system.

16. The multispecific antibody or fragment thereof of claim 1, wherein:

(i) the first binding domain comprises:

(a) a heavy chain variable ($V_H$) region comprising:

(1) a $V_H$ CDR1 having the amino acid sequence of SEQ ID NO:1;

(2) a $V_H$ CDR2 having the amino acid sequence of SEQ ID NO:2; and (3) a $V_H$ CDR3 having the amino acid sequence of SEQ ID NO:3; and (b) a light chain variable ($V_L$) region comprising:

(1) a $V_L$ CDR1 having the amino acid sequence of SEQ ID NO:4;

(2) a $V_L$ CDR2 having the amino acid sequence of SEQ ID NO:5; and (3) a $V_L$ CDR3 having the amino acid sequence of SEQ ID NO:6; and the second binding domain comprises:

(a) a heavy chain variable ($V_H$) region comprising:

(1) a $V_H$ CDR1 having the amino acid sequence of SEQ ID NO:131;

(2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising:

(1) a $V_L$ CDR1 having the amino acid sequence of SEQ ID NO:134;

(2) a $V_L$ CDR2 having the amino acid sequence of SEQ ID NO:135; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Exemplary numbering system:

(ii) the first binding domain comprises:

(a) a heavy chain variable ($V_H$) region comprising:

(1) a $V_H$ CDR1 having the amino acid sequence of SEQ ID NO:7;

(2) a $V_H$ CDR2 having the amino acid sequence of SEQ ID NO:8; and (3) a $V_H$ CDR3 having the amino acid sequence of SEQ ID NO:9; and (b) a light chain variable ($V_L$) region comprising:

(1) a $V_L$ CDR1 having the amino acid sequence of SEQ ID NO:10;

(2) a $V_L$ CDR2 having the amino acid sequence of SAS; and (3) a $V_L$ CDR3 having the amino acid sequence of SEQ ID NO:6; and the second binding domain comprises:

(a) a heavy chain variable ($V_H$) region comprising:

(1) a $V_H$ CDR1 having the amino acid sequence of SEQ ID NO:137;

(2) a $V_H$ CDR2 having the amino acid sequence of SEQ ID NO:138; and (3) a $V_H$ CDR3 having the amino acid sequence of SEQ ID NO:139; and (b) a light chain variable ($V_L$) region comprising:

(1) a $V_L$ CDR1 having the amino acid sequence of SEQ ID NO:140;

(2) a $V_L$ CDR2 having the amino acid sequence of SAS; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to IMGT numbering system:

(iii) the first binding domain comprises:

(a) a heavy chain variable ($V_H$) region comprising:

(1) a $V_H$ CDR1 having the amino acid sequence of SEQ ID NO:12;

(2) a $V_H$ CDR2 having the amino acid sequence of SEQ ID NO:2; and (3) a $V_H$ CDR3 having the amino acid sequence of SEQ ID NO:3; and (b) a light chain variable ($V_L$) region comprising:

(1) a $V_L$ CDR1 having the amino acid sequence of SEQ ID NO:4;

(2) a $V_L$ CDR2 having the amino acid sequence of SEQ ID NO:5; and (3) a $V_L$ CDR3 having the amino acid sequence of SEQ ID NO:6; and the second binding domain comprises:

(a) a heavy chain variable ($V_H$) region comprising:

(1) a $V_H$ CDR1 having the amino acid sequence of SEQ ID NO:142;

(2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising:

(1) a $V_L$ CDR1 having the amino acid sequence of SEQ ID NO:134;

(2) a $V_L$ CDR2 having the amino acid sequence of SEQ ID NO:135; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Kabat numbering system:

(iv) the first binding domain comprises:

(a) a heavy chain variable ($V_H$) region comprising:

(1) a $V_H$ CDR1 having the amino acid sequence of SEQ ID NO:13;

(2) a $V_H$ CDR2 having the amino acid sequence of SEQ ID NO:14; and (3) a $V_H$ CDR3 having the amino acid sequence of SEQ ID NO:15; and (b) a light chain variable ($V_L$) region comprising:

(1) a $V_L$ CDR1 having the amino acid sequence of SEQ ID NO:16;

(2) a $V_L$ CDR2 having the amino acid sequence of SAS; and (3) a $V_L$ CDR3 having the amino acid sequence of SEQ ID NO:17; and the second binding domain comprises:

(a) a heavy chain variable ($V_H$) region comprising:

(1) a $V_H$ CDR1 having the amino acid sequence of SEQ ID NO:143;

(2) a $V_H$ CDR2 having the amino acid sequence of SEQ ID NO:144; and (3) a $V_H$ CDR3 having the amino acid sequence of SEQ ID NO:145; and (b) a light chain variable ($V_L$) region comprising:

(1) a $V_L$ CDR1 having the amino acid sequence of SEQ ID NO:146;

(2) a $V_L$ CDR2 having the amino acid sequence of SAS; and (3) a $V_L$ CDR3 having the amino acid sequence of SEQ ID NO:147;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Chothia numbering system;

(v) the first binding domain comprises:

(a) a heavy chain variable ($V_H$) region comprising:

(1) a $V_H$ CDR1 having the amino acid sequence of SEQ ID NO:18;

(2) a $V_H$ CDR2 having the amino acid sequence of SEQ ID NO:19; and (3) a $V_H$ CDR3 having the amino acid sequence of SEQ ID NO:20; and (b) a light chain variable ($V_L$) region comprising:

(1) a $V_L$ CDR1 having the amino acid sequence of SEQ ID NO:21;

(2) a $V_L$ CDR2 having the amino acid sequence of SEQ ID NO:22; and (3) a $V_L$ CDR3 having the amino acid sequence of SEQ ID NO:23; and the second binding domain comprises:

(a) a heavy chain variable ($V_H$) region comprising:

(1) a $V_H$ CDR1 having the amino acid sequence of SEQ ID NO:148;

(2) a $V_H$ CDR2 having the amino acid sequence of SEQ ID NO:149; and (3) a $V_H$ CDR3 having the amino acid sequence of SEQ ID NO:150; and (b) a light chain variable ($V_L$) region comprising:

(1) a $V_L$ CDR1 having the amino acid sequence of SEQ ID NO:151;

(2) a $V_L$ CDR2 having the amino acid sequence of SEQ ID NO:152; and (3) a $V_L$ CDR3 having the amino acid sequence of SEQ ID NO:153;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Contact numbering system; or (vi) the first binding domain comprises:

(a) a heavy chain variable ($V_H$) region comprising:

(1) a $V_H$ CDR1 having the amino acid sequence of SEQ ID NO:1;

(2) a $V_H$ CDR2 having the amino acid sequence of SEQ ID NO:24; and (3) a $V_H$ CDR3 having the amino acid sequence of SEQ ID NO:3; and (b) a light chain variable ($V_L$) region comprising:

(1) a $V_L$ CDR1 having the amino acid sequence of SEQ ID NO:4;

(2) a $V_L$ CDR2 having the amino acid sequence of SEQ ID NO:5; and (3) a $V_L$ CDR3 having the amino acid sequence of SEQ ID NO:6; and the second binding domain comprises:

(a) a heavy chain variable ($V_H$) region comprising:

(1) a $V_H$ CDR1 having the amino acid sequence of SEQ ID NO:131;

(2) a $V_H$ CDR2 having the amino acid sequence of SEQ ID NO:154; and (3) a $V_H$ CDR3 having the amino acid sequence of SEQ ID NO:133; and (b) a light chain variable ($V_L$) region comprising:

(1) a $V_L$ CDR1 having the amino acid sequence of SEQ ID NO:134;

(2) a $V_L$ CDR2 having the amino acid sequence of SEQ ID NO:135; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C40 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to AbM numbering system.

17. The multispecific antibody or fragment thereof of claim 1, wherein:

(i) the first binding domain comprises:

(a) a heavy chain variable ($V_H$) region comprising:

(1) a $V_H$ CDR1 having the amino acid sequence of SEQ ID NO:27;

(2) a $V_H$ CDR2 having the amino acid sequence of SEQ ID NO:28; and (3) a $V_H$ CDR3 having the amino acid sequence of SEQ ID NO:29; and (b) a light chain variable ($V_L$) region comprising:

(1) a $V_L$ CDR1 having the amino acid sequence of SEQ ID NO:30;

(2) a $V_L$ CDR2 having the amino acid sequence of SEQ ID NO:31; and (3) a $V_L$ CDR3 having the amino acid sequence of SEQ ID NO:32; and the second binding domain comprises:

(a) a heavy chain variable ($V_H$) region comprising:

(1) a $V_H$ CDR1 having the amino acid sequence of SEQ ID NO:131;

(2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising:

(1) a $V_L$ CDR1 having the amino acid sequence of SEQ ID NO:134;

(2) a $V_L$ CDR2 having the amino acid sequence of SEQ ID NO:135; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Exemplary numbering system:

(ii) the first binding domain comprises:

(a) a heavy chain variable ($V_H$) region comprising:

(1) a $V_H$ CDR1 having the amino acid sequence of SEQ ID NO:33;

(2) a $V_H$ CDR2 having the amino acid sequence of SEQ ID NO:34; and (3) a $V_H$ CDR3 having the amino acid sequence of SEQ ID NO:35; and (b) a light chain variable ($V_L$) region comprising:

(1) a $V_L$ CDR1 having the amino acid sequence of SEQ ID NO:36;

(2) a $V_L$ CDR2 having the amino acid sequence of SAS; and (3) a $V_L$ CDR3 having the amino acid sequence of SEQ ID NO:32; and the second binding domain comprises:

(a) a heavy chain variable ($V_H$) region comprising:

(1) a $V_H$ CDR1 having the amino acid sequence of SEQ ID NO:137;

(2) a $V_H$ CDR2 having the amino acid sequence of SEQ ID NO:138; and (3) a $V_H$ CDR3 having the amino acid sequence of SEQ ID NO:139; and (b) a light chain variable ($V_L$) region comprising:

(1) a $V_L$ CDR1 having the amino acid sequence of SEQ ID NO:140;

(2) a $V_L$ CDR2 having the amino acid sequence of SAS; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to IMGT numbering system;

(iii) the first binding domain comprises:

(a) a heavy chain variable ($V_H$) region comprising:

(1) a $V_H$ CDR1 having the amino acid sequence of SEQ ID NO:38;

(2) a $V_H$ CDR2 having the amino acid sequence of SEQ ID NO:28; and (3) a $V_H$ CDR3 having the amino acid sequence of SEQ ID NO:29; and (b) a light chain variable ($V_L$) region comprising:

(1) a $V_L$ CDR1 having the amino acid sequence of SEQ ID NO:30;

(2) a $V_L$ CDR2 having the amino acid sequence of SEQ ID NO:31; and (3) a $V_L$ CDR3 having the amino acid sequence of SEQ ID NO:32; and the second binding domain comprises:

(a) a heavy chain variable ($V_H$) region comprising:

(1) a $V_H$ CDR1 having the amino acid sequence of SEQ ID NO:142;

(2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising:

(1) a $V_L$ CDR1 having the amino acid sequence of SEQ ID NO:134;

(2) a $V_L$ CDR2 having the amino acid sequence of SEQ ID NO:135; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Kabat numbering system;

(iv) the first binding domain comprises:

(a) a heavy chain variable ($V_H$) region comprising:

(1) a $V_H$ CDR1 having the amino acid sequence of SEQ ID NO:39;

(2) a $V_H$ CDR2 having the amino acid sequence of SEQ ID NO:40; and (3) a $V_H$ CDR3 having the amino acid sequence of SEQ ID NO:41; and (b) a light chain variable ($V_L$) region comprising:

(1) a $V_L$ CDR1 having the amino acid sequence of SEQ ID NO:42;

(2) a $V_L$ CDR2 having the amino acid sequence of SAS; and (3) a $V_L$ CDR3 having the amino acid sequence of SEQ ID NO:43; and the second binding domain comprises:

(a) a heavy chain variable ($V_H$) region comprising:

(1) a $V_H$ CDR1 having the amino acid sequence of SEQ ID NO:143;

(2) a $V_H$ CDR2 having the amino acid sequence of SEQ ID NO:144; and (3) a $V_H$ CDR3 having the amino acid sequence of SEQ ID NO:145; and (b) a light chain variable ($V_L$) region comprising:

(1) a $V_L$ CDR1 having the amino acid sequence of SEQ ID NO:146;

(2) a $V_L$ CDR2 having the amino acid sequence of SAS; and (3) a $V_L$ CDR3 having the amino acid sequence of SEQ ID NO:147;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Chothia numbering system:

(v) the first binding domain comprises:

(a) a heavy chain variable ($V_H$) region comprising:

(1) a $V_H$ CDR1 having the amino acid sequence of SEQ ID NO:44;

(2) a $V_H$ CDR2 having the amino acid sequence of SEQ ID NO:45; and (3) a $V_H$ CDR3 having the amino acid sequence of SEQ ID NO:46; and (b) a light chain variable ($V_L$) region comprising:

(1) a $V_L$ CDR1 having the amino acid sequence of SEQ ID NO:47;

(2) a $V_L$ CDR2 having the amino acid sequence of SEQ ID NO:48; and (3) a $V_L$ CDR3 having the amino acid sequence of SEQ ID NO:49; and the second binding domain comprises:

(a) a heavy chain variable ($V_H$) region comprising:

(1) a $V_H$ CDR1 having the amino acid sequence of SEQ ID NO:148;

(2) a $V_H$ CDR2 having the amino acid sequence of SEQ ID NO:149; and (3) a $V_H$ CDR3 having the amino acid sequence of SEQ ID NO:150; and (b) a light chain variable ($V_L$) region comprising:

(1) a $V_L$ CDR1 having the amino acid sequence of SEQ ID NO:151;

(2) a $V_L$ CDR2 having the amino acid sequence of SEQ ID NO:152; and (3) a $V_L$ CDR3 having the amino acid sequence of SEQ ID NO:153;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Contact numbering system; or (vi) the first binding domain comprises:

(a) a heavy chain variable ($V_H$) region comprising:

(1) a $V_H$ CDR1 having the amino acid sequence of SEQ ID NO:27;

(2) a $V_H$ CDR2 having the amino acid sequence of SEQ ID NO:50; and (3) a $V_H$ CDR3 having the amino acid sequence of SEQ ID NO:29; and (b) a light chain variable ($V_L$) region comprising:

(1) a $V_L$ CDR1 having the amino acid sequence of SEQ ID NO:30;

(2) a $V_L$ CDR2 having the amino acid sequence of SEQ ID NO:31; and (3) a $V_L$ CDR3 having the amino acid sequence of SEQ ID NO:32; and the second binding domain comprises:

(a) a heavy chain variable ($V_H$) region comprising:

(1) a $V_H$ CDR1 having the amino acid sequence of SEQ ID NO:131;

(2) a $V_H$ CDR2 having the amino acid sequence of SEQ ID NO:154; and (3) a $V_H$ CDR3 having the amino acid sequence of SEQ ID NO:133; and (b) a light chain variable ($V_L$) region comprising:

(1) a $V_L$ CDR1 having the amino acid sequence of SEQ ID NO:134;

(2) a $V_L$ CDR2 having the amino acid sequence of SEQ ID NO:135; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C56 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to AbM numbering system.

18. The multispecific antibody or fragment thereof of claim 1, wherein:

(i) the first binding domain comprises:

(a) a heavy chain variable ($V_H$) region comprising:

(1) a $V_H$ CDR1 having the amino acid sequence of SEQ ID NO:53;

(2) a $V_H$ CDR2 having the amino acid sequence of SEQ ID NO:54; and (3) a $V_H$ CDR3 having the amino acid sequence of SEQ ID NO:55; and (b) a light chain variable ($V_L$) region comprising:

(1) a $V_L$ CDR1 having the amino acid sequence of SEQ ID NO:56;

(2) a $V_L$ CDR2 having the amino acid sequence of SEQ ID NO:57; and (3) a $V_L$ CDR3 having the amino acid sequence of SEQ ID NO:58; and the second binding domain comprises:

(a) a heavy chain variable ($V_H$) region comprising:

(1) a $V_H$ CDR1 having the amino acid sequence of SEQ ID NO:131;

(2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising:

(1) a $V_L$ CDR1 having the amino acid sequence of SEQ ID NO:134;

(2) a $V_L$ CDR2 having the amino acid sequence of SEQ ID NO:135; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Exemplary numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Exemplary numbering system:

(ii) the first binding domain comprises:

(a) a heavy chain variable ($V_H$) region comprising:

(1) a $V_H$ CDR1 having the amino acid sequence of SEQ ID NO:59;

(2) a $V_H$ CDR2 having the amino acid sequence of SEQ ID NO:60; and (3) a $V_H$ CDR3 having the amino acid sequence of SEQ ID NO:61; and (b) a light chain variable ($V_L$) region comprising:

(1) a $V_L$ CDR1 having the amino acid sequence of SEQ ID NO:62;

(2) a $V_L$ CDR2 having the amino acid sequence of SAS; and (3) a $V_L$ CDR3 having the amino acid sequence of SEQ ID NO:58; and the second binding domain comprises:

(a) a heavy chain variable ($V_H$) region comprising:

(1) a $V_H$ CDR1 having the amino acid sequence of SEQ ID NO:137;

(2) a $V_H$ CDR2 having the amino acid sequence of SEQ ID NO:138; and (3) a $V_H$ CDR3 having the amino acid sequence of SEQ ID NO:139; and (b) a light chain variable ($V_L$) region comprising:

(1) a $V_L$ CDR1 having the amino acid sequence of SEQ ID NO:140;

(2) a $V_L$ CDR2 having the amino acid sequence of SAS; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to IMGT numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to IMGT numbering system;

(iii) the first binding domain comprises:

(a) a heavy chain variable ($V_H$) region comprising:

(1) a $V_H$ CDR1 having the amino acid sequence of SEQ ID NO:64;

(2) a $V_H$ CDR2 having the amino acid sequence of SEQ ID NO:54; and (3) a $V_H$ CDR3 having the amino acid sequence of SEQ ID NO:55; and (b) a light chain variable ($V_L$) region comprising:

(1) a $V_L$ CDR1 having the amino acid sequence of SEQ ID NO:56;

(2) a $V_L$ CDR2 having the amino acid sequence of SEQ ID NO:57; and (3) a $V_L$ CDR3 having the amino acid sequence of SEQ ID NO:58; and the second binding domain comprises:

(a) a heavy chain variable ($V_H$) region comprising:

(1) a $V_H$ CDR1 having the amino acid sequence of SEQ ID NO:142;

(2) a $V_H$ CDR2 having the amino acid sequence of SEQ ID NO:132; and (3) a $V_H$ CDR3 having the amino acid sequence of SEQ ID NO:133; and (b) a light chain variable ($V_L$) region comprising:

(1) a $V_L$ CDR1 having the amino acid sequence of SEQ ID NO:134;

(2) a $V_L$ CDR2 having the amino acid sequence of SEQ ID NO:135; and (3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Kabat numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Kabat numbering system;

(iv) the first binding domain comprises:

(a) a heavy chain variable ($V_H$) region comprising:

(1) a $V_H$ CDR1 having the amino acid sequence of SEQ ID NO:65;

(2) a $V_H$ CDR2 having the amino acid sequence of SEQ ID NO:66; and (3) a $V_H$ CDR3 having the amino acid sequence of SEQ ID NO:67; and (b) a light chain variable ($V_L$) region comprising:
(1) a $V_L$ CDR1 having the amino acid sequence of SEQ ID NO:68;
(2) a $V_L$ CDR2 having the amino acid sequence of SAS; and
(3) a $V_L$ CDR3 having the amino acid sequence of SEQ ID NO:69; and the second binding domain comprises:
(a) a heavy chain variable ($V_H$) region comprising:
(1) a $V_H$ CDR1 having the amino acid sequence of SEQ ID NO:143;
(2) a $V_H$ CDR2 having the amino acid sequence of SEQ ID NO:144; and
(3) a $V_H$ CDR3 having the amino acid sequence of SEQ ID NO:145; and
(b) a light chain variable ($V_L$) region comprising:
(1) a $V_L$ CDR1 having the amino acid sequence of SEQ ID NO:146;
(2) a $V_L$ CDR2 having the amino acid sequence of SAS; and
(3) a $V_L$ CDR3 having the amino acid sequence of SEQ ID NO:147;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Chothia numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Chothia numbering system:

(v) the first binding domain comprises:
(a) a heavy chain variable ($V_H$) region comprising:
(1) a $V_H$ CDR1 having the amino acid sequence of SEQ ID NO:70;
(2) a $V_H$ CDR2 having the amino acid sequence of SEQ ID NO:71; and
(3) a $V_H$ CDR3 having the amino acid sequence of SEQ ID NO:72; and
(b) a light chain variable ($V_L$) region comprising:
(1) a $V_L$ CDR1 having the amino acid sequence of SEQ ID NO:73;
(2) a $V_L$ CDR2 having the amino acid sequence of SEQ ID NO:74; and
(3) a $V_L$ CDR3 having the amino acid sequence of SEQ ID NO:75; and the second binding domain comprises:
(a) a heavy chain variable ($V_H$) region comprising:
(1) a $V_H$ CDR1 having the amino acid sequence of SEQ ID NO:148;
(2) a $V_H$ CDR2 having the amino acid sequence of SEQ ID NO:149; and
(3) a $V_H$ CDR3 having the amino acid sequence of SEQ ID NO:150; and
(b) a light chain variable ($V_L$) region comprising:
(1) a $V_L$ CDR1 having the amino acid sequence of SEQ ID NO:151;
(2) a $V_L$ CDR2 having the amino acid sequence of SEQ ID NO:152; and
(3) a $V_L$ CDR3 having the amino acid sequence of SEQ ID NO:153;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to Contact numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to Contact numbering system; or (vi) the first binding domain comprises:
(a) a heavy chain variable ($V_H$) region comprising:
(1) a $V_H$ CDR1 having the amino acid sequence of SEQ ID NO:53;
(2) a $V_H$ CDR2 having the amino acid sequence of SEQ ID NO:76; and
(3) a $V_H$ CDR3 having the amino acid sequence of SEQ ID NO:55; and
(b) a light chain variable ($V_L$) region comprising:
(1) a $V_L$ CDR1 having the amino acid sequence of SEQ ID NO:56;
(2) a $V_L$ CDR2 having the amino acid sequence of SEQ ID NO:57; and
(3) a $V_L$ CDR3 having the amino acid sequence of SEQ ID NO:58; and the second binding domain comprises:
(a) a heavy chain variable ($V_H$) region comprising:
(1) a $V_H$ CDR1 having the amino acid sequence of SEQ ID NO:131;
(2) a $V_H$ CDR2 having the amino acid sequence of SEQ ID NO:154; and
(3) a $V_H$ CDR3 having the amino acid sequence of SEQ ID NO:133; and
(b) a light chain variable ($V_L$) region comprising:
(1) a $V_L$ CDR1 having the amino acid sequence of SEQ ID NO:134;
(2) a $V_L$ CDR2 having the amino acid sequence of SEQ ID NO:135; and
(3) a $V_L$ CDR3 having the amino acid sequence of SEQ ID NO:136;

wherein the $V_H$ CDR1, $V_H$ CDR2, $V_H$ CDR3, $V_L$ CDR1, $V_L$ CDR2, and $V_L$ CDR3 of the first binding domain are CDRs from the antibody designated C59 as determined according to AbM numbering system, and the $V_H$ CDR1, $V_H$ CDR2, $V_H$ CDR3, $V_L$ CDR1, $V_L$ CDR2, and $V_L$ CDR3 of the second binding domain are CDRs from the antibody designated P31.2 as determined according to AbM numbering system.

19. The multispecific antibody or fragment thereof of claim 1, wherein the first binding domain comprises a VH comprising the amino acid sequence of SEQ ID NO:51 and a VL comprising the amino acid sequence of SEQ ID NO:52, which are the VH and VL sequences of the antibody designated C56, and the second binding domain comprises a VH comprising the amino acid sequence of SEQ ID NO:103 and a VL comprising the amino acid sequence of SEQ ID NO:104, which are the VH and VL sequences of the antibody designated P22.

20. The multispecific antibody or fragment thereof of claim 1, wherein the first binding domain comprises a VH comprising the amino acid sequence of SEQ ID NO:77 and a VL comprising the amino acid sequence of SEQ ID NO:78, which are the VH and VL sequences of the antibody designated C59, and the second binding domain comprises a VH comprising the amino acid sequence of SEQ ID NO:103 and a VL comprising the amino acid sequence of SEQ ID NO:104, which are the VH and VL sequences of the antibody designated P22.

21. The multispecific antibody or fragment thereof of claim 1, wherein the first binding domain comprises a VH comprising the amino acid sequence of SEQ ID NO:25 and a VL comprising the amino acid sequence of SEQ ID NO:26, which are the VH and VL sequences of the antibody designated C40, and the second binding domain comprises a VH comprising the amino acid sequence of SEQ ID NO:129 and a VL comprising the amino acid sequence of SEQ ID NO:130, which are the VH and VL sequences of the antibody designated P24.

22. The multispecific antibody or fragment thereof of claim 1, wherein the first binding domain comprises a VH comprising the amino acid sequence of SEQ ID NO:51 and a VL comprising the amino acid sequence of SEQ ID NO:52, which are the VH and VL sequences of the antibody designated C56, and the second binding domain comprises a VH comprising the amino acid sequence of SEQ ID NO:129 and a VL comprising the amino acid sequence of SEQ ID NO:130, which are the VH and VL sequences of the antibody designated P24.

23. The multispecific antibody or fragment thereof of claim 1, wherein the first binding domain comprises a VH comprising the amino acid sequence of SEQ ID NO:77 and a VL comprising the amino acid sequence of SEQ ID NO:78, which are the VH and VL sequences of the antibody designated C59, and the second binding domain comprises a VH comprising the amino acid sequence of SEQ ID NO:129 and a VL comprising the amino acid sequence of SEQ ID NO:130, which are the VH and VL sequences of the antibody designated P24.

24. The multispecific antibody or fragment thereof of claim 1, wherein the first binding domain comprises a VH comprising the amino acid sequence of SEQ ID NO:25 and a VL comprising the amino acid sequence of SEQ ID NO:26, which are the VH and VL sequences of the antibody designated C40, and the second binding domain comprises a VH comprising the amino acid sequence of SEQ ID NO:155 and a VL comprising the amino acid sequence of SEQ ID NO:156, which are the VH and VL sequences of the antibody designated P31.2.

25. The multispecific antibody or fragment thereof of claim 1, wherein the first binding domain comprises a VH comprising the amino acid sequence of SEQ ID NO:51 and a VL comprising the amino acid sequence of SEQ ID NO:52, which are the VH and VL sequences of the antibody designated C56, and the second binding domain comprises a VH comprising the amino acid sequence of SEQ ID NO:155 and a VL comprising the amino acid sequence of SEQ ID NO:156, which are the VH and VL sequences of the antibody designated P31.2.

26. The multispecific antibody or fragment thereof of claim 1, wherein the first binding domain comprises a VH comprising the amino acid sequence of SEQ ID NO:77 and a VL comprising the amino acid sequence of SEQ ID NO:78, which are the VH and VL sequences of the antibody designated C59, and the second binding domain comprises a VH comprising the amino acid sequence of SEQ ID NO:155 and a VL comprising the amino acid sequence of SEQ ID NO:156, which are the VH and VL sequences of the antibody designated P31.2.

27. The multispecific antibody or fragment thereof of claim 6, wherein the multispecific antibody or fragment thereof is conjugated or recombinantly fused to a therapeutic agent, wherein the therapeutic agent is a chemotherapeutic agent or cytotoxin.

28. The method of claim 9, wherein the subject is administered one or more therapeutic agents in combination with the multispecific antibody or fragment thereof.

* * * * *

SEQUENCE LISTING

<160> NUMBER OF SEQ ID NOS: 217

<210> SEQ ID NO 1
<211> LENGTH: 10
<212> TYPE: PRT
<213> ORGANISM: Artificial Sequence
<220> FEATURE:
<223> OTHER INFORMATION: Antibody C40 VH CDR1 (Exemplary, AbM)

<400> SEQUENCE: 1

Gly Phe Thr Phe Ser Tyr Tyr Tyr Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Antibody C40 VH CDR2 (Exemplary, Kabat)

<400> SEQUENCE: 2

Trp Ile Asp Pro Tyr Gly His Ser Thr Thr Tyr Ala Asp Ser Val Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Antibody C40 VH CDR3 (Exemplary, Kabat, AbM)

<400> SEQUENCE: 3

Gly Gly Arg Gly Ala Met Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Antibody C40 VL CDR1 (Exemplary, Kabat, AbM)

<400> SEQUENCE: 4

Arg Ala Ser Gln Ser Val Ser Ser Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Antibody C40 VL CDR2 (Exemplary, Kabat, AbM)

<400> SEQUENCE: 5

Ser Ala Ser Ser Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Antibody C40 VL CDR3 (Exemplary, IMGT, Kabat, AbM)

<400> SEQUENCE: 6

Gln Gln Arg Tyr Ser Ser Leu Leu Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Antibody C40 VH CDR1 (IMGT)

<400> SEQUENCE: 7

Gly Phe Thr Phe Ser Tyr Tyr Tyr
1 5

<210> SEQ ID NO 8
<211> LENGTH: 8
<212> TYPE: PRT
<213> ORGANISM: Artificial Sequence
<220> FEATURE:
<223> OTHER INFORMATION: Antibody C40 VH CDR2 (IMGT)

<400> SEQUENCE: 8

Ile Asp Pro Tyr Gly His Ser Thr
1 5

<210> SEQ ID NO 9
<211> LENGTH: 10
<212> TYPE: PRT
<213> ORGANISM: Artificial Sequence
<220> FEATURE:
<223> OTHER INFORMATION: Antibody C40 VH CDR3 (IMGT)

<400> SEQUENCE: 9

Ala Arg Gly Gly Arg Gly Ala Met Asp Tyr
1 5 10

<210> SEQ ID NO 10
<211> LENGTH: 6
<212> TYPE: PRT
<213> ORGANISM: Artificial Sequence
<220> FEATURE:
<223> OTHER INFORMATION: Antibody C40 VL CDR1 (IMGT)

<400> SEQUENCE: 10

Gln Ser Val Ser Ser Ala
1 5

<210> SEQ ID NO 11
<211> LENGTH: 3
<212> TYPE: PRT
<213> ORGANISM: Artificial Sequence
<220> FEATURE:
<223> OTHER INFORMATION: Antibody C40 VL CDR2 (IMGT, Chothia)

<400> SEQUENCE: 11

Ser Ala Ser
1

<210> SEQ ID NO 12
<211> LENGTH: 5
<212> TYPE: PRT
<213> ORGANISM: Artificial Sequence
<220> FEATURE:
<223> OTHER INFORMATION: Antibody C40 VH CDR1 (Kabat)

<400> SEQUENCE: 12

Tyr Tyr Tyr Ile His
1 5

<210> SEQ ID NO 13
<211> LENGTH: 7
<212> TYPE: PRT
<213> ORGANISM: Artificial Sequence
<220> FEATURE:
<223> OTHER INFORMATION: Antibody C40 VH CDR1 (Chothia)

<400> SEQUENCE: 13

Gly Phe Thr Phe Ser Tyr Tyr
1 5

<210> SEQ ID NO 14
<211> LENGTH: 4
<212> TYPE: PRT
<213> ORGANISM: Artificial Sequence
<220> FEATURE:
<223> OTHER INFORMATION: Antibody C40 VH CDR2 (Chothia)

<400> SEQUENCE: 14

Pro Tyr Gly His
1

<210> SEQ ID NO 15
<211> LENGTH: 6
<212> TYPE: PRT
<213> ORGANISM: Artificial Sequence
<220> FEATURE:
<223> OTHER INFORMATION: Antibody C40 VH CDR3 (Chothia)

<400> SEQUENCE: 15

Gly Arg Gly Ala Met Asp
1 5

<210> SEQ ID NO 16
<211> LENGTH: 7
<212> TYPE: PRT
<213> ORGANISM: Artificial Sequence
<220> FEATURE:
<223> OTHER INFORMATION: Antibody C40 VL CDR1 (Chothia)

<400> SEQUENCE: 16

Ser Gln Ser Val Ser Ser Ala
1 5

<210> SEQ ID NO 17
<211> LENGTH: 6
<212> TYPE: PRT
<213> ORGANISM: Artificial Sequence
<220> FEATURE:
<223> OTHER INFORMATION: Antibody C40 VL CDR3 (Chothia)

<400> SEQUENCE: 17

Arg Tyr Ser Ser Leu Leu
1 5

<210> SEQ ID NO 18
<211> LENGTH: 6
<212> TYPE: PRT
<213> ORGANISM: Artificial Sequence
<220> FEATURE:
<223> OTHER INFORMATION: Antibody C40 VH CDR1 (Contact)

<400> SEQUENCE: 18

Ser Tyr Tyr Tyr Ile His
1 5

<210> SEQ ID NO 19
<211> LENGTH: 13
<212> TYPE: PRT
<213> ORGANISM: Artificial Sequence
<220> FEATURE:
<223> OTHER INFORMATION: Antibody C40 VH CDR2 (Contact)

<400> SEQUENCE: 19

Trp Val Ala Trp Ile Asp Pro Tyr Gly His Ser Thr Thr
1 5 10

<210> SEQ ID NO 20
<211> LENGTH: 9
<212> TYPE: PRT
<213> ORGANISM: Artificial Sequence
<220> FEATURE:
<223> OTHER INFORMATION: Antibody C40 VH CDR3 (Contact)

<400> SEQUENCE: 20

Ala Arg Gly Gly Arg Gly Ala Met Asp
1 5

<210> SEQ ID NO 21
<211> LENGTH: 7
<212> TYPE: PRT
<213> ORGANISM: Artificial Sequence
<220> FEATURE:
<223> OTHER INFORMATION: Antibody C40 VL CDR1 (Contact)

<400> SEQUENCE: 21

Ser Ser Ala Val Ala Trp Tyr
1 5

<210> SEQ ID NO 22
<211> LENGTH: 10
<212> TYPE: PRT
<213> ORGANISM: Artificial Sequence
<220> FEATURE:
<223> OTHER INFORMATION: Antibody C40 VL CDR2 (Contact)

<400> SEQUENCE: 22

Leu Leu Ile Tyr Ser Ala Ser Ser Leu Tyr
1 5 10

<210> SEQ ID NO 23
<211> LENGTH: 8
<212> TYPE: PRT
<213> ORGANISM: Artificial Sequence
<220> FEATURE:
<223> OTHER INFORMATION: Antibody C40 VL CDR3 (Contact)

<400> SEQUENCE: 23

Gln Gln Arg Tyr Ser Ser Leu Leu
1 5

<210> SEQ ID NO 24
<211> LENGTH: 10
<212> TYPE: PRT
<213> ORGANISM: Artificial Sequence
<220> FEATURE:
<223> OTHER INFORMATION: Antibody C40 VH CDR2 (AbM)

<400> SEQUENCE: 24

Trp Ile Asp Pro Tyr Gly His Ser Thr Thr
1 5 10

<210> SEQ ID NO 25
<211> LENGTH: 114
<212> TYPE: PRT
<213> ORGANISM: Artificial Sequence
<220> FEATURE:
<223> OTHER INFORMATION: Antibody C40 VH Sequence

<400> SEQUENCE: 25

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Tyr Tyr
20 25 30

Tyr Ile His Trp Val Arg Gln Ala Pro Gly Lys Gly Leu Glu Trp Val
35 40 45

Ala Trp Ile Asp Pro Tyr Gly His Ser Thr Thr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Gly Gly Arg Gly Ala Met Asp Tyr Trp Gly Gln Gly Thr Leu
100 105 110

Val Thr

<210> SEQ ID NO 26
<211> LENGTH: 107
<212> TYPE: PRT
<213> ORGANISM: Artificial Sequence
<220> FEATURE:
<223> OTHER INFORMATION: Antibody C40 VL Sequence

<400> SEQUENCE: 26

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala
20 25 30

Val Ala Trp Tyr Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Arg Tyr Ser Ser Leu Leu
85 90 95

Thr Phe Gly Gln Gly Thr Lys Val Glu Ile Lys
100 105

<210> SEQ ID NO 27
<211> LENGTH: 10
<212> TYPE: PRT
<213> ORGANISM: Artificial Sequence
<220> FEATURE:
<223> OTHER INFORMATION: Antibody C56 VH CDR1 (Exemplary, AbM)

<400> SEQUENCE: 27

Gly Phe Thr Phe Thr Tyr Tyr Tyr Ile His
1 5 10

<210> SEQ ID NO 28
<211> LENGTH: 17
<212> TYPE: PRT
<213> ORGANISM: Artificial Sequence
<220> FEATURE:
<223> OTHER INFORMATION: Antibody C56 VH CDR2 (Exemplary, Kabat)

<400> SEQUENCE: 28

Phe Ile Asp Pro Tyr Ser Gly Ser Thr Glu Tyr Ala Asp Ser Val Lys
1 5 10 15

Gly

<210> SEQ ID NO 29
<211> LENGTH: 8
<212> TYPE: PRT
<213> ORGANISM: Artificial Sequence
<220> FEATURE:
<223> OTHER INFORMATION: Antibody C56 VH CDR3 (Exemplary, Kabat, AbM)

<400> SEQUENCE: 29

Gly Gly Leu Tyr Ala Leu Asp Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: Antibody C56 VL CDR1 (Exemplary, Kabat, AbM)

<400> SEQUENCE: 30

Arg Ala Ser Gln Ser Val Ser Ser Ala Val Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Antibody C56 VL CDR2 (Exemplary, Kabat, AbM)

<400> SEQUENCE: 31

Ser Ala Ser Ser Leu Tyr Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Antibody C56 VL CDR3 (Exemplary, IMGT, Kabat,
AbM)

<400> SEQUENCE: 32

Gln Gln Gly Arg Ser Asp Leu Arg Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Antibody C56 VH CDR1 (IMGT)

<400> SEQUENCE: 33

Gly Phe Thr Phe Thr Tyr Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Antibody C56 VH CDR2 (IMGT)

<400> SEQUENCE: 34

```
Ile Asp Pro Tyr Ser Gly Ser Thr
1               5


<210> SEQ ID NO 35
<211> LENGTH: 10
<212> TYPE: PRT
<213> ORGANISM: Artificial Sequence
<220> FEATURE:
<223> OTHER INFORMATION: Antibody C56 VH CDR3 (IMGT)

<400> SEQUENCE: 35

Ala Arg Gly Gly Leu Tyr Ala Leu Asp Tyr
1               5                   10


<210> SEQ ID NO 36
<211> LENGTH: 6
<212> TYPE: PRT
<213> ORGANISM: Artificial Sequence
<220> FEATURE:
<223> OTHER INFORMATION: Antibody C56 VL CDR1 (IMGT)

<400> SEQUENCE: 36

Gln Ser Val Ser Ser Ala
1               5


<210> SEQ ID NO 37
<211> LENGTH: 3
<212> TYPE: PRT
<213> ORGANISM: Artificial Sequence
<220> FEATURE:
<223> OTHER INFORMATION: Antibody C56 VL CDR2 (IMGT, Chothia)

<400> SEQUENCE: 37

Ser Ala Ser
1


<210> SEQ ID NO 38
<211> LENGTH: 5
<212> TYPE: PRT
<213> ORGANISM: Artificial Sequence
<220> FEATURE:
<223> OTHER INFORMATION: Antibody C56 VH CDR1 (Kabat)

<400> SEQUENCE: 38

Tyr Tyr Tyr Ile His
1               5


<210> SEQ ID NO 39
<211> LENGTH: 7
<212> TYPE: PRT
<213> ORGANISM: Artificial Sequence
<220> FEATURE:
<223> OTHER INFORMATION: Antibody C56 VH CDR1 (Chothia)

<400> SEQUENCE: 39

Gly Phe Thr Phe Thr Tyr Tyr
1               5


<210> SEQ ID NO 40
<211> LENGTH: 4
<212> TYPE: PRT
<213> ORGANISM: Artificial Sequence
<220> FEATURE:
<223> OTHER INFORMATION: Antibody C56 VH CDR2 (Chothia)

<400> SEQUENCE: 40

Pro Tyr Ser Gly
```

1

<210> SEQ ID NO 41
<211> LENGTH: 6
<212> TYPE: PRT
<213> ORGANISM: Artificial Sequence
<220> FEATURE:
<223> OTHER INFORMATION: Antibody C56 VH CDR3 (Chothia)

<400> SEQUENCE: 41

Gly Leu Tyr Ala Leu Asp
1 5

<210> SEQ ID NO 42
<211> LENGTH: 7
<212> TYPE: PRT
<213> ORGANISM: Artificial Sequence
<220> FEATURE:
<223> OTHER INFORMATION: Antibody C56 VL CDR1 (Chothia)

<400> SEQUENCE: 42

Ser Gln Ser Val Ser Ser Ala
1 5

<210> SEQ ID NO 43
<211> LENGTH: 6
<212> TYPE: PRT
<213> ORGANISM: Artificial Sequence
<220> FEATURE:
<223> OTHER INFORMATION: Antibody C56 VL CDR3 (Chothia)

<400> SEQUENCE: 43

Gly Arg Ser Asp Leu Arg
1 5

<210> SEQ ID NO 44
<211> LENGTH: 6
<212> TYPE: PRT
<213> ORGANISM: Artificial Sequence
<220> FEATURE:
<223> OTHER INFORMATION: Antibody C56 VH CDR1 (Contact)

<400> SEQUENCE: 44

Thr Tyr Tyr Tyr Ile His
1 5

<210> SEQ ID NO 45
<211> LENGTH: 13
<212> TYPE: PRT
<213> ORGANISM: Artificial Sequence
<220> FEATURE:
<223> OTHER INFORMATION: Antibody C56 VH CDR2 (Contact)

<400> SEQUENCE: 45

Trp Val Ala Phe Ile Asp Pro Tyr Ser Gly Ser Thr Glu
1 5 10

<210> SEQ ID NO 46
<211> LENGTH: 9
<212> TYPE: PRT
<213> ORGANISM: Artificial Sequence
<220> FEATURE:
<223> OTHER INFORMATION: Antibody C56 VH CDR3 (Contact)

<400> SEQUENCE: 46

Ala Arg Gly Gly Leu Tyr Ala Leu Asp
1 5

<210> SEQ ID NO 47
<211> LENGTH: 7
<212> TYPE: PRT
<213> ORGANISM: Artificial Sequence
<220> FEATURE:
<223> OTHER INFORMATION: Antibody C56 VL CDR1 (Contact)

<400> SEQUENCE: 47

Ser Ser Ala Val Ala Trp Tyr
1               5

<210> SEQ ID NO 48
<211> LENGTH: 10
<212> TYPE: PRT
<213> ORGANISM: Artificial Sequence
<220> FEATURE:
<223> OTHER INFORMATION: Antibody C56 VL CDR2 (Contact)

<400> SEQUENCE: 48

Leu Leu Ile Tyr Ser Ala Ser Ser Leu Tyr
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Antibody C56 VL CDR3 (Contact)

<400> SEQUENCE: 49

Gln Gln Gly Arg Ser Asp Leu Arg
1               5

<210> SEQ ID NO 50
<211> LENGTH: 10
<212> TYPE: PRT
<213> ORGANISM: Artificial Sequence
<220> FEATURE:
<223> OTHER INFORMATION: Antibody C56 VH CDR2 (AbM)

<400> SEQUENCE: 50

Phe Ile Asp Pro Tyr Ser Gly Ser Thr Glu
1               5                   10

<210> SEQ ID NO 51
<211> LENGTH: 114
<212> TYPE: PRT
<213> ORGANISM: Artificial Sequence
<220> FEATURE:
<223> OTHER INFORMATION: Antibody C56 VH Sequence

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Tyr Tyr
            20                  25                  30

Tyr Ile His Trp Val Arg Gln Ala Pro Gly Lys Gly Leu Glu Trp Val
        35                  40                  45

Ala Phe Ile Asp Pro Tyr Ser Gly Ser Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
                85                  90                  95

Ala Arg Gly Gly Leu Tyr Ala Leu Asp Tyr Trp Gly Gln Gly Thr Leu
            100                 105                 110

Val Thr


<210> SEQ ID NO 52
<211> LENGTH: 107
<212> TYPE: PRT
<213> ORGANISM: Artificial Sequence
<220> FEATURE:
<223> OTHER INFORMATION: Antibody C56 VL Sequence

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Ser Asp Leu Arg
                85                  90                  95

Thr Phe Gly Gln Gly Thr Lys Val Glu Ile Lys
            100                 105


<210> SEQ ID NO 53
<211> LENGTH: 10
<212> TYPE: PRT
<213> ORGANISM: Artificial Sequence
<220> FEATURE:
<223> OTHER INFORMATION: Antibody C59 VH CDR1 (Exemplary, AbM)

<400> SEQUENCE: 53

Gly Phe Thr Phe Thr Ser Tyr Tyr Ile His
1               5                   10


<210> SEQ ID NO 54
<211> LENGTH: 17
<212> TYPE: PRT
<213> ORGANISM: Artificial Sequence
<220> FEATURE:
<223> OTHER INFORMATION: Antibody C59 VH CDR2 (Exemplary, Kabat)

<400> SEQUENCE: 54

Tyr Ile Asp Ser Lys His Gly Thr Thr Gln Tyr Ala Asp Ser Val Lys
1               5                   10                  15

Gly


<210> SEQ ID NO 55
<211> LENGTH: 8
<212> TYPE: PRT
<213> ORGANISM: Artificial Sequence
<220> FEATURE:
<223> OTHER INFORMATION: Antibody C59 VH CDR3 (Exemplary, Kabat, AbM)

<400> SEQUENCE: 55

Gly Gly Arg Ser Ala Met Asp Tyr
1               5
```

<210> SEQ ID NO 56
<211> LENGTH: 11
<212> TYPE: PRT
<213> ORGANISM: Artificial Sequence
<220> FEATURE:
<223> OTHER INFORMATION: Antibody C59 VL CDR1 (Exemplary, Kabat, AbM)

<400> SEQUENCE: 56

Arg Ala Ser Gln Ser Val Ser Ser Ala Val Ala
1 5 10

<210> SEQ ID NO 57
<211> LENGTH: 7
<212> TYPE: PRT
<213> ORGANISM: Artificial Sequence
<220> FEATURE:
<223> OTHER INFORMATION: Antibody C59 VL CDR2 (Exemplary, Kabat, AbM)

<400> SEQUENCE: 57

Ser Ala Ser Ser Leu Tyr Ser
1 5

<210> SEQ ID NO 58
<211> LENGTH: 9
<212> TYPE: PRT
<213> ORGANISM: Artificial Sequence
<220> FEATURE:
<223> OTHER INFORMATION: Antibody C59 VL CDR3 (Exemplary, IMGT, Kabat, AbM)

<400> SEQUENCE: 58

Gln Gln Arg Thr Thr Ser Leu Leu Thr
1 5

<210> SEQ ID NO 59
<211> LENGTH: 8
<212> TYPE: PRT
<213> ORGANISM: Artificial Sequence
<220> FEATURE:
<223> OTHER INFORMATION: Antibody C59 VH CDR1 (IMGT)

<400> SEQUENCE: 59

Gly Phe Thr Phe Thr Ser Tyr Tyr
1 5

<210> SEQ ID NO 60
<211> LENGTH: 8
<212> TYPE: PRT
<213> ORGANISM: Artificial Sequence
<220> FEATURE:
<223> OTHER INFORMATION: Antibody C59 VH CDR2 (IMGT)

<400> SEQUENCE: 60

Ile Asp Ser Lys His Gly Thr Thr
1 5

<210> SEQ ID NO 61
<211> LENGTH: 10
<212> TYPE: PRT
<213> ORGANISM: Artificial Sequence
<220> FEATURE:
<223> OTHER INFORMATION: Antibody C59 VH CDR3 (IMGT)

<400> SEQUENCE: 61

Ala Arg Gly Gly Arg Ser Ala Met Asp Tyr
1 5 10

<210> SEQ ID NO 62
<211> LENGTH: 6
<212> TYPE: PRT
<213> ORGANISM: Artificial Sequence
<220> FEATURE:
<223> OTHER INFORMATION: Antibody C59 VL CDR1 (IMGT)

<400> SEQUENCE: 62

Gln Ser Val Ser Ser Ala
1 5

<210> SEQ ID NO 63
<211> LENGTH: 3
<212> TYPE: PRT
<213> ORGANISM: Artificial Sequence
<220> FEATURE:
<223> OTHER INFORMATION: Antibody C59 VL CDR2 (IMGT, Chothia)

<400> SEQUENCE: 63

Ser Ala Ser
1

<210> SEQ ID NO 64
<211> LENGTH: 5
<212> TYPE: PRT
<213> ORGANISM: Artificial Sequence
<220> FEATURE:
<223> OTHER INFORMATION: Antibody C59 VH CDR1 (Kabat)

<400> SEQUENCE: 64

Ser Tyr Tyr Ile His
1 5

<210> SEQ ID NO 65
<211> LENGTH: 7
<212> TYPE: PRT
<213> ORGANISM: Artificial Sequence
<220> FEATURE:
<223> OTHER INFORMATION: Antibody C59 VH CDR1 (Chothia)

<400> SEQUENCE: 65

Gly Phe Thr Phe Thr Ser Tyr
1 5

<210> SEQ ID NO 66
<211> LENGTH: 4
<212> TYPE: PRT
<213> ORGANISM: Artificial Sequence
<220> FEATURE:
<223> OTHER INFORMATION: Antibody C59 VH CDR2 (Chothia)

<400> SEQUENCE: 66

Ser Lys His Gly
1

<210> SEQ ID NO 67
<211> LENGTH: 6
<212> TYPE: PRT
<213> ORGANISM: Artificial Sequence
<220> FEATURE:
<223> OTHER INFORMATION: Antibody C59 VH CDR3 (Chothia)

<400> SEQUENCE: 67

Gly Arg Ser Ala Met Asp
1 5

<210> SEQ ID NO 68
<211> LENGTH: 7
<212> TYPE: PRT
<213> ORGANISM: Artificial Sequence
<220> FEATURE:
<223> OTHER INFORMATION: Antibody C59 VL CDR1 (Chothia)

<400> SEQUENCE: 68

Ser Gln Ser Val Ser Ser Ala
1               5

<210> SEQ ID NO 69
<211> LENGTH: 6
<212> TYPE: PRT
<213> ORGANISM: Artificial Sequence
<220> FEATURE:
<223> OTHER INFORMATION: Antibody C59 VL CDR3 (Chothia)

<400> SEQUENCE: 69

Arg Thr Thr Ser Leu Leu
1               5

<210> SEQ ID NO 70
<211> LENGTH: 6
<212> TYPE: PRT
<213> ORGANISM: Artificial Sequence
<220> FEATURE:
<223> OTHER INFORMATION: Antibody C59 VH CDR1 (Contact)

<400> SEQUENCE: 70

Thr Ser Tyr Tyr Ile His
1               5

<210> SEQ ID NO 71
<211> LENGTH: 13
<212> TYPE: PRT
<213> ORGANISM: Artificial Sequence
<220> FEATURE:
<223> OTHER INFORMATION: Antibody C59 VH CDR2 (Contact)

<400> SEQUENCE: 71

Trp Val Ala Tyr Ile Asp Ser Lys His Gly Thr Thr Gln
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Antibody C59 VH CDR3 (Contact)

<400> SEQUENCE: 72

Ala Arg Gly Gly Arg Ser Ala Met Asp
1               5

<210> SEQ ID NO 73
<211> LENGTH: 7
<212> TYPE: PRT
<213> ORGANISM: Artificial Sequence
<220> FEATURE:
<223> OTHER INFORMATION: Antibody C59 VL CDR1 (Contact)

<400> SEQUENCE: 73

Ser Ser Ala Val Ala Trp Tyr
1               5

<210> SEQ ID NO 74

```
<211> LENGTH: 10
<212> TYPE: PRT
<213> ORGANISM: Artificial Sequence
<220> FEATURE:
<223> OTHER INFORMATION: Antibody C59 VL CDR2 (Contact)

<400> SEQUENCE: 74

Leu Leu Ile Tyr Ser Ala Ser Ser Leu Tyr
1               5                   10


<210> SEQ ID NO 75
<211> LENGTH: 8
<212> TYPE: PRT
<213> ORGANISM: Artificial Sequence
<220> FEATURE:
<223> OTHER INFORMATION: Antibody C59 VL CDR3 (Contact)

<400> SEQUENCE: 75

Gln Gln Arg Thr Thr Ser Leu Leu
1               5


<210> SEQ ID NO 76
<211> LENGTH: 10
<212> TYPE: PRT
<213> ORGANISM: Artificial Sequence
<220> FEATURE:
<223> OTHER INFORMATION: Antibody C59 VH CDR2 (AbM)

<400> SEQUENCE: 76

Tyr Ile Asp Ser Lys His Gly Thr Thr Gln
1               5                   10


<210> SEQ ID NO 77
<211> LENGTH: 114
<212> TYPE: PRT
<213> ORGANISM: Artificial Sequence
<220> FEATURE:
<223> OTHER INFORMATION: Antibody C59 VH Sequence

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Tyr Ile His Trp Val Arg Gln Ala Pro Gly Lys Gly Leu Glu Trp Val
        35                  40                  45

Ala Tyr Ile Asp Ser Lys His Gly Thr Thr Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ser Ala Met Asp Tyr Trp Gly Gln Gly Thr Leu
            100                 105                 110

Val Thr


<210> SEQ ID NO 78
<211> LENGTH: 107
<212> TYPE: PRT
<213> ORGANISM: Artificial Sequence
<220> FEATURE:
<223> OTHER INFORMATION: Antibody C59 VL Sequence

<400> SEQUENCE: 78
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Thr Thr Ser Leu Leu
                85                  90                  95

Thr Phe Gly Gln Gly Thr Lys Val Glu Ile Lys
            100                 105


<210> SEQ ID NO 79
<211> LENGTH: 10
<212> TYPE: PRT
<213> ORGANISM: Artificial Sequence
<220> FEATURE:
<223> OTHER INFORMATION: Antibody P22 VH CDR1 (Exemplary, AbM)

<400> SEQUENCE: 79

Gly Phe Thr Phe Ser Ser Tyr Tyr Ile His
1               5                   10


<210> SEQ ID NO 80
<211> LENGTH: 17
<212> TYPE: PRT
<213> ORGANISM: Artificial Sequence
<220> FEATURE:
<223> OTHER INFORMATION: Antibody P22 VH CDR2 (Exemplary, Kabat)

<400> SEQUENCE: 80

Trp Ile Thr Ser His Gly Tyr Ser Thr Lys Tyr Ala Asp Ser Val Lys
1               5                   10                  15

Gly


<210> SEQ ID NO 81
<211> LENGTH: 9
<212> TYPE: PRT
<213> ORGANISM: Artificial Sequence
<220> FEATURE:
<223> OTHER INFORMATION: Antibody P22 VH CDR3 (Exemplary, Kabat, AbM)

<400> SEQUENCE: 81

Asp Ser Val Ile Tyr Gly Leu Asp Tyr
1               5


<210> SEQ ID NO 82
<211> LENGTH: 11
<212> TYPE: PRT
<213> ORGANISM: Artificial Sequence
<220> FEATURE:
<223> OTHER INFORMATION: Antibody P22 VL CDR1 (Exemplary, Kabat, AbM)

<400> SEQUENCE: 82

Arg Ala Ser Gln Ser Val Ser Ser Ala Val Ala
1               5                   10


<210> SEQ ID NO 83
<211> LENGTH: 7
```

<212> TYPE: PRT
<213> ORGANISM: Artificial Sequence
<220> FEATURE:
<223> OTHER INFORMATION: Antibody P22 VL CDR2 (Exemplary, Kabat, AbM)

<400> SEQUENCE: 83

Ser Ala Ser Ser Leu Tyr Ser
1 5

<210> SEQ ID NO 84
<211> LENGTH: 9
<212> TYPE: PRT
<213> ORGANISM: Artificial Sequence
<220> FEATURE:
<223> OTHER INFORMATION: Antibody P22 VL CDR3 (Exemplary, IMGT, Kabat, AbM)

<400> SEQUENCE: 84

Gln Gln Tyr Tyr Thr Ser Pro Tyr Thr
1 5

<210> SEQ ID NO 85
<211> LENGTH: 8
<212> TYPE: PRT
<213> ORGANISM: Artificial Sequence
<220> FEATURE:
<223> OTHER INFORMATION: Antibody P22 VH CDR1 (IMGT)

<400> SEQUENCE: 85

Gly Phe Thr Phe Ser Ser Tyr Tyr
1 5

<210> SEQ ID NO 86
<211> LENGTH: 8
<212> TYPE: PRT
<213> ORGANISM: Artificial Sequence
<220> FEATURE:
<223> OTHER INFORMATION: Antibody P22 VH CDR2 (IMGT)

<400> SEQUENCE: 86

Ile Thr Ser His Gly Tyr Ser Thr
1 5

<210> SEQ ID NO 87
<211> LENGTH: 11
<212> TYPE: PRT
<213> ORGANISM: Artificial Sequence
<220> FEATURE:
<223> OTHER INFORMATION: Antibody P22 VH CDR3 (IMGT)

<400> SEQUENCE: 87

Ala Arg Asp Ser Val Ile Tyr Gly Leu Asp Tyr
1 5 10

<210> SEQ ID NO 88
<211> LENGTH: 6
<212> TYPE: PRT
<213> ORGANISM: Artificial Sequence
<220> FEATURE:
<223> OTHER INFORMATION: Antibody P22 VL CDR1 (IMGT)

<400> SEQUENCE: 88

Gln Ser Val Ser Ser Ala
1 5

<210> SEQ ID NO 89
<211> LENGTH: 3

<212> TYPE: PRT
<213> ORGANISM: Artificial Sequence
<220> FEATURE:
<223> OTHER INFORMATION: Antibody P22 VL CDR2 (IMGT, Chothia)

<400> SEQUENCE: 89

Ser Ala Ser
1

<210> SEQ ID NO 90
<211> LENGTH: 5
<212> TYPE: PRT
<213> ORGANISM: Artificial Sequence
<220> FEATURE:
<223> OTHER INFORMATION: Antibody P22 VH CDR1 (Kabat)

<400> SEQUENCE: 90

Ser Tyr Tyr Ile His
1               5

<210> SEQ ID NO 91
<211> LENGTH: 7
<212> TYPE: PRT
<213> ORGANISM: Artificial Sequence
<220> FEATURE:
<223> OTHER INFORMATION: Antibody P22 VH CDR1 (Chothia)

<400> SEQUENCE: 91

Gly Phe Thr Phe Ser Ser Tyr
1               5

<210> SEQ ID NO 92
<211> LENGTH: 4
<212> TYPE: PRT
<213> ORGANISM: Artificial Sequence
<220> FEATURE:
<223> OTHER INFORMATION: Antibody P22 VH CDR2 (Chothia)

<400> SEQUENCE: 92

Ser His Gly Tyr
1

<210> SEQ ID NO 93
<211> LENGTH: 7
<212> TYPE: PRT
<213> ORGANISM: Artificial Sequence
<220> FEATURE:
<223> OTHER INFORMATION: Antibody P22 VH CDR3 (Chothia)

<400> SEQUENCE: 93

Ser Val Ile Tyr Gly Leu Asp
1               5

<210> SEQ ID NO 94
<211> LENGTH: 7
<212> TYPE: PRT
<213> ORGANISM: Artificial Sequence
<220> FEATURE:
<223> OTHER INFORMATION: Antibody P22 VL CDR1 (Chothia)

<400> SEQUENCE: 94

Ser Gln Ser Val Ser Ser Ala
1               5

<210> SEQ ID NO 95
<211> LENGTH: 6
<212> TYPE: PRT

<213> ORGANISM: Artificial Sequence
<220> FEATURE:
<223> OTHER INFORMATION: Antibody P22 VL CDR3 (Chothia)

<400> SEQUENCE: 95

Tyr Tyr Thr Ser Pro Tyr
1 5

<210> SEQ ID NO 96
<211> LENGTH: 6
<212> TYPE: PRT
<213> ORGANISM: Artificial Sequence
<220> FEATURE:
<223> OTHER INFORMATION: Antibody P22 VH CDR1 (Contact)

<400> SEQUENCE: 96

Ser Ser Tyr Tyr Ile His
1 5

<210> SEQ ID NO 97
<211> LENGTH: 13
<212> TYPE: PRT
<213> ORGANISM: Artificial Sequence
<220> FEATURE:
<223> OTHER INFORMATION: Antibody P22 VH CDR2 (Contact)

<400> SEQUENCE: 97

Trp Val Ala Trp Ile Thr Ser His Gly Tyr Ser Thr Lys
1 5 10

<210> SEQ ID NO 98
<211> LENGTH: 10
<212> TYPE: PRT
<213> ORGANISM: Artificial Sequence
<220> FEATURE:
<223> OTHER INFORMATION: Antibody P22 VH CDR3 (Contact)

<400> SEQUENCE: 98

Ala Arg Asp Ser Val Ile Tyr Gly Leu Asp
1 5 10

<210> SEQ ID NO 99
<211> LENGTH: 7
<212> TYPE: PRT
<213> ORGANISM: Artificial Sequence
<220> FEATURE:
<223> OTHER INFORMATION: Antibody P22 VL CDR1 (Contact)

<400> SEQUENCE: 99

Ser Ser Ala Val Ala Trp Tyr
1 5

<210> SEQ ID NO 100
<211> LENGTH: 10
<212> TYPE: PRT
<213> ORGANISM: Artificial Sequence
<220> FEATURE:
<223> OTHER INFORMATION: Antibody P22 VL CDR2 (Contact)

<400> SEQUENCE: 100

Leu Leu Ile Tyr Ser Ala Ser Ser Leu Tyr
1 5 10

<210> SEQ ID NO 101
<211> LENGTH: 8
<212> TYPE: PRT
<213> ORGANISM: Artificial Sequence
<220> FEATURE:
<223> OTHER INFORMATION: Antibody P22 VL CDR3 (Contact)

<400> SEQUENCE: 101

Gln Gln Tyr Tyr Thr Ser Pro Tyr
1 5

<210> SEQ ID NO 102
<211> LENGTH: 10
<212> TYPE: PRT
<213> ORGANISM: Artificial Sequence
<220> FEATURE:
<223> OTHER INFORMATION: Antibody P22 VH CDR2 (AbM)

<400> SEQUENCE: 102

Trp Ile Thr Ser His Gly Tyr Ser Thr Lys
1 5 10

<210> SEQ ID NO 103
<211> LENGTH: 115
<212> TYPE: PRT
<213> ORGANISM: Artificial Sequence
<220> FEATURE:
<223> OTHER INFORMATION: Antibody P22 VH Sequence

<400> SEQUENCE: 103

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Tyr Ile His Trp Val Arg Gln Ala Pro Gly Lys Gly Leu Glu Trp Val
35 40 45

Ala Trp Ile Thr Ser His Gly Tyr Ser Thr Lys Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Asp Ser Val Ile Tyr Gly Leu Asp Tyr Trp Gly Gln Gly Thr
100 105 110

Leu Val Thr
115

<210> SEQ ID NO 104
<211> LENGTH: 107
<212> TYPE: PRT
<213> ORGANISM: Artificial Sequence
<220> FEATURE:
<223> OTHER INFORMATION: Antibody P22 VL Sequence

<400> SEQUENCE: 104

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala
20 25 30

Val Ala Trp Tyr Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Thr Ser Pro Tyr
85 90 95

Thr Phe Gly Gln Gly Thr Lys Val Glu Ile Lys
100 105

<210> SEQ ID NO 105
<211> LENGTH: 10
<212> TYPE: PRT
<213> ORGANISM: Artificial Sequence
<220> FEATURE:
<223> OTHER INFORMATION: Antibody P24 VH CDR1 (Exemplary, AbM)

<400> SEQUENCE: 105

Gly Phe Thr Phe Asp Gln Tyr Tyr Ile His
1 5 10

<210> SEQ ID NO 106
<211> LENGTH: 17
<212> TYPE: PRT
<213> ORGANISM: Artificial Sequence
<220> FEATURE:
<223> OTHER INFORMATION: Antibody P24 VH CDR2 (Exemplary, Kabat)

<400> SEQUENCE: 106

Glu Ile Tyr Pro Ala Gly Ser Tyr Thr Tyr Tyr Ala Asp Ser Val Lys
1 5 10 15

Gly

<210> SEQ ID NO 107
<211> LENGTH: 11
<212> TYPE: PRT
<213> ORGANISM: Artificial Sequence
<220> FEATURE:
<223> OTHER INFORMATION: Antibody P24 VH CDR3 (Exemplary, Kabat, AbM)

<400> SEQUENCE: 107

Gly Pro Tyr Ser Val Arg Tyr Ala Leu Asp Tyr
1 5 10

<210> SEQ ID NO 108
<211> LENGTH: 11
<212> TYPE: PRT
<213> ORGANISM: Artificial Sequence
<220> FEATURE:
<223> OTHER INFORMATION: Antibody P24 VL CDR1 (Exemplary, Kabat, AbM)

<400> SEQUENCE: 108

Arg Ala Ser Gln Ser Val Ser Ser Ala Val Ala
1 5 10

<210> SEQ ID NO 109
<211> LENGTH: 7
<212> TYPE: PRT
<213> ORGANISM: Artificial Sequence
<220> FEATURE:
<223> OTHER INFORMATION: Antibody P24 VL CDR2 (Exemplary, Kabat, AbM)

<400> SEQUENCE: 109

Ser Ala Ser Ser Leu Tyr Ser
1 5

<210> SEQ ID NO 110
<211> LENGTH: 9
<212> TYPE: PRT
<213> ORGANISM: Artificial Sequence
<220> FEATURE:
<223> OTHER INFORMATION: Antibody P24 VL CDR3 (Exemplary, IMGT, Kabat, AbM)

<400> SEQUENCE: 110

Gln Gln Val Ser Tyr Ser Pro Tyr Thr
1 5

<210> SEQ ID NO 111
<211> LENGTH: 8
<212> TYPE: PRT
<213> ORGANISM: Artificial Sequence
<220> FEATURE:
<223> OTHER INFORMATION: Antibody P24 VH CDR1 (IMGT)

<400> SEQUENCE: 111

Gly Phe Thr Phe Asp Gln Tyr Tyr
1 5

<210> SEQ ID NO 112
<211> LENGTH: 8
<212> TYPE: PRT
<213> ORGANISM: Artificial Sequence
<220> FEATURE:
<223> OTHER INFORMATION: Antibody P24 VH CDR2 (IMGT)

<400> SEQUENCE: 112

Ile Tyr Pro Ala Gly Ser Tyr Thr
1 5

<210> SEQ ID NO 113
<211> LENGTH: 13
<212> TYPE: PRT
<213> ORGANISM: Artificial Sequence
<220> FEATURE:
<223> OTHER INFORMATION: Antibody P24 VH CDR3 (IMGT)

<400> SEQUENCE: 113

Ala Arg Gly Pro Tyr Ser Val Arg Tyr Ala Leu Asp Tyr
1 5 10

<210> SEQ ID NO 114
<211> LENGTH: 6
<212> TYPE: PRT
<213> ORGANISM: Artificial Sequence
<220> FEATURE:
<223> OTHER INFORMATION: Antibody P24 VL CDR1 (IMGT)

<400> SEQUENCE: 114

Gln Ser Val Ser Ser Ala
1 5

<210> SEQ ID NO 115
<211> LENGTH: 3
<212> TYPE: PRT
<213> ORGANISM: Artificial Sequence
<220> FEATURE:
<223> OTHER INFORMATION: Antibody P24 VL CDR2 (IMGT, Chothia)

<400> SEQUENCE: 115

Ser Ala Ser
1

<210> SEQ ID NO 116
<211> LENGTH: 5
<212> TYPE: PRT
<213> ORGANISM: Artificial Sequence
<220> FEATURE:
<223> OTHER INFORMATION: Antibody P24 VH CDR1 (Kabat)

<400> SEQUENCE: 116

Gln Tyr Tyr Ile His
1 5

<210> SEQ ID NO 117
<211> LENGTH: 7
<212> TYPE: PRT
<213> ORGANISM: Artificial Sequence
<220> FEATURE:
<223> OTHER INFORMATION: Antibody P24 VH CDR1 (Chothia)

<400> SEQUENCE: 117

Gly Phe Thr Phe Asp Gln Tyr
1 5

<210> SEQ ID NO 118
<211> LENGTH: 4
<212> TYPE: PRT
<213> ORGANISM: Artificial Sequence
<220> FEATURE:
<223> OTHER INFORMATION: Antibody P24 VH CDR2 (Chothia)

<400> SEQUENCE: 118

Pro Ala Gly Ser
1

<210> SEQ ID NO 119
<211> LENGTH: 9
<212> TYPE: PRT
<213> ORGANISM: Artificial Sequence
<220> FEATURE:
<223> OTHER INFORMATION: Antibody P24 VH CDR3 (Chothia)

<400> SEQUENCE: 119

Pro Tyr Ser Val Arg Tyr Ala Leu Asp
1 5

<210> SEQ ID NO 120
<211> LENGTH: 7
<212> TYPE: PRT
<213> ORGANISM: Artificial Sequence
<220> FEATURE:
<223> OTHER INFORMATION: Antibody P24 VL CDR1 (Chothia)

<400> SEQUENCE: 120

Ser Gln Ser Val Ser Ser Ala
1 5

<210> SEQ ID NO 121
<211> LENGTH: 6
<212> TYPE: PRT
<213> ORGANISM: Artificial Sequence
<220> FEATURE:
<223> OTHER INFORMATION: Antibody P24 VL CDR3 (Chothia)

<400> SEQUENCE: 121

Val Ser Tyr Ser Pro Tyr
1 5

<210> SEQ ID NO 122
<211> LENGTH: 6
<212> TYPE: PRT
<213> ORGANISM: Artificial Sequence
<220> FEATURE:

<223> OTHER INFORMATION: Antibody P24 VH CDR1 (Contact)

<400> SEQUENCE: 122

Asp Gln Tyr Tyr Ile His
1 5

<210> SEQ ID NO 123
<211> LENGTH: 13
<212> TYPE: PRT
<213> ORGANISM: Artificial Sequence
<220> FEATURE:
<223> OTHER INFORMATION: Antibody P24 VH CDR2 (Contact)

<400> SEQUENCE: 123

Trp Val Ala Glu Ile Tyr Pro Ala Gly Ser Tyr Thr Tyr
1 5 10

<210> SEQ ID NO 124
<211> LENGTH: 12
<212> TYPE: PRT
<213> ORGANISM: Artificial Sequence
<220> FEATURE:
<223> OTHER INFORMATION: Antibody P24 VH CDR3 (Contact)

<400> SEQUENCE: 124

Ala Arg Gly Pro Tyr Ser Val Arg Tyr Ala Leu Asp
1 5 10

<210> SEQ ID NO 125
<211> LENGTH: 7
<212> TYPE: PRT
<213> ORGANISM: Artificial Sequence
<220> FEATURE:
<223> OTHER INFORMATION: Antibody P24 VL CDR1 (Contact)

<400> SEQUENCE: 125

Ser Ser Ala Val Ala Trp Tyr
1 5

<210> SEQ ID NO 126
<211> LENGTH: 10
<212> TYPE: PRT
<213> ORGANISM: Artificial Sequence
<220> FEATURE:
<223> OTHER INFORMATION: Antibody P24 VL CDR2 (Contact)

<400> SEQUENCE: 126

Leu Leu Ile Tyr Ser Ala Ser Ser Leu Tyr
1 5 10

<210> SEQ ID NO 127
<211> LENGTH: 8
<212> TYPE: PRT
<213> ORGANISM: Artificial Sequence
<220> FEATURE:
<223> OTHER INFORMATION: Antibody P24 VL CDR3 (Contact)

<400> SEQUENCE: 127

Gln Gln Val Ser Tyr Ser Pro Tyr
1 5

<210> SEQ ID NO 128
<211> LENGTH: 10
<212> TYPE: PRT
<213> ORGANISM: Artificial Sequence
<220> FEATURE:
<223> OTHER INFORMATION: Antibody P24 VH CDR2 (AbM)

<400> SEQUENCE: 128

Glu Ile Tyr Pro Ala Gly Ser Tyr Thr Tyr
1 5 10

<210> SEQ ID NO 129
<211> LENGTH: 117
<212> TYPE: PRT
<213> ORGANISM: Artificial Sequence
<220> FEATURE:
<223> OTHER INFORMATION: Antibody P24 VH Sequence

<400> SEQUENCE: 129

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asp Gln Tyr
20 25 30

Tyr Ile His Trp Val Arg Gln Ala Pro Gly Lys Gly Leu Glu Trp Val
35 40 45

Ala Glu Ile Tyr Pro Ala Gly Ser Tyr Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Gly Pro Tyr Ser Val Arg Tyr Ala Leu Asp Tyr Trp Gly Gln
100 105 110

Gly Thr Leu Val Thr
115

<210> SEQ ID NO 130
<211> LENGTH: 107
<212> TYPE: PRT
<213> ORGANISM: Artificial Sequence
<220> FEATURE:
<223> OTHER INFORMATION: Antibody P24 VL Sequence

<400> SEQUENCE: 130

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala
20 25 30

Val Ala Trp Tyr Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Val Ser Tyr Ser Pro Tyr
85 90 95

Thr Phe Gly Gln Gly Thr Lys Val Glu Ile Lys
100 105

<210> SEQ ID NO 131
<211> LENGTH: 10
<212> TYPE: PRT
<213> ORGANISM: Artificial Sequence
<220> FEATURE:
<223> OTHER INFORMATION: Antibody P31.2 VH CDR1 (Exemplary, AbM)

<400> SEQUENCE: 131

Gly Phe Thr Phe Ser Ser Tyr Tyr Ile His
1 5 10

<210> SEQ ID NO 132
<211> LENGTH: 17
<212> TYPE: PRT
<213> ORGANISM: Artificial Sequence
<220> FEATURE:
<223> OTHER INFORMATION: Antibody P31.2 VH CDR2 (Exemplary, Kabat)

<400> SEQUENCE: 132

Thr Ile Ser Ser Gly Gly Gly Phe Thr Tyr Tyr Ala Asp Ser Val Lys
1 5 10 15

Gly

<210> SEQ ID NO 133
<211> LENGTH: 10
<212> TYPE: PRT
<213> ORGANISM: Artificial Sequence
<220> FEATURE:
<223> OTHER INFORMATION: Antibody P31.2 VH CDR3 (Exemplary, Kabat, AbM)

<400> SEQUENCE: 133

Gly Tyr Thr Leu Thr Pro Val Leu Asp Tyr
1 5 10

<210> SEQ ID NO 134
<211> LENGTH: 11
<212> TYPE: PRT
<213> ORGANISM: Artificial Sequence
<220> FEATURE:
<223> OTHER INFORMATION: Antibody P31.2 VL CDR1 (Exemplary, Kabat, AbM)

<400> SEQUENCE: 134

Arg Ala Ser Gln Ser Val Ser Ser Ala Val Ala
1 5 10

<210> SEQ ID NO 135
<211> LENGTH: 7
<212> TYPE: PRT
<213> ORGANISM: Artificial Sequence
<220> FEATURE:
<223> OTHER INFORMATION: Antibody P31.2 VL CDR2 (Exemplary, Kabat, AbM)

<400> SEQUENCE: 135

Ser Ala Ser Ser Leu Tyr Ser
1 5

<210> SEQ ID NO 136
<211> LENGTH: 9
<212> TYPE: PRT
<213> ORGANISM: Artificial Sequence
<220> FEATURE:
<223> OTHER INFORMATION: Antibody P31.2 VL CDR3 (Exemplary, IMGT, Kabat, AbM)

<400> SEQUENCE: 136

Gln Gln Phe Gly Ala Glu Pro Ile Thr
1 5

<210> SEQ ID NO 137
<211> LENGTH: 8
<212> TYPE: PRT
<213> ORGANISM: Artificial Sequence
<220> FEATURE:

<223> OTHER INFORMATION: Antibody P31.2 VH CDR1 (IMGT)

<400> SEQUENCE: 137

Gly Phe Thr Phe Ser Ser Tyr Tyr
1               5

<210> SEQ ID NO 138
<211> LENGTH: 8
<212> TYPE: PRT
<213> ORGANISM: Artificial Sequence
<220> FEATURE:
<223> OTHER INFORMATION: Antibody P31.2 VH CDR2 (IMGT)

<400> SEQUENCE: 138

Ile Ser Ser Gly Gly Gly Phe Thr
1               5

<210> SEQ ID NO 139
<211> LENGTH: 12
<212> TYPE: PRT
<213> ORGANISM: Artificial Sequence
<220> FEATURE:
<223> OTHER INFORMATION: Antibody P31.2 VH CDR3 (IMGT)

<400> SEQUENCE: 139

Ala Arg Gly Tyr Thr Leu Thr Pro Val Leu Asp Tyr
1               5                   10

<210> SEQ ID NO 140
<211> LENGTH: 6
<212> TYPE: PRT
<213> ORGANISM: Artificial Sequence
<220> FEATURE:
<223> OTHER INFORMATION: Antibody P31.2 VL CDR1 (IMGT)

<400> SEQUENCE: 140

Gln Ser Val Ser Ser Ala
1               5

<210> SEQ ID NO 141
<211> LENGTH: 3
<212> TYPE: PRT
<213> ORGANISM: Artificial Sequence
<220> FEATURE:
<223> OTHER INFORMATION: Antibody P31.2 VL CDR2 (IMGT, Chothia)

<400> SEQUENCE: 141

Ser Ala Ser
1

<210> SEQ ID NO 142
<211> LENGTH: 5
<212> TYPE: PRT
<213> ORGANISM: Artificial Sequence
<220> FEATURE:
<223> OTHER INFORMATION: Antibody P31.2 VH CDR1 (Kabat)

<400> SEQUENCE: 142

Ser Tyr Tyr Ile His
1               5

<210> SEQ ID NO 143
<211> LENGTH: 7
<212> TYPE: PRT
<213> ORGANISM: Artificial Sequence
<220> FEATURE:
<223> OTHER INFORMATION: Antibody P31.2 VH CDR1 (Chothia)

<400> SEQUENCE: 143

Gly Phe Thr Phe Ser Ser Tyr
1 5

<210> SEQ ID NO 144
<211> LENGTH: 4
<212> TYPE: PRT
<213> ORGANISM: Artificial Sequence
<220> FEATURE:
<223> OTHER INFORMATION: Antibody P31.2 VH CDR2 (Chothia)

<400> SEQUENCE: 144

Ser Gly Gly Gly
1

<210> SEQ ID NO 145
<211> LENGTH: 8
<212> TYPE: PRT
<213> ORGANISM: Artificial Sequence
<220> FEATURE:
<223> OTHER INFORMATION: Antibody P31.2 VH CDR3 (Chothia)

<400> SEQUENCE: 145

Tyr Thr Leu Thr Pro Val Leu Asp
1 5

<210> SEQ ID NO 146
<211> LENGTH: 7
<212> TYPE: PRT
<213> ORGANISM: Artificial Sequence
<220> FEATURE:
<223> OTHER INFORMATION: Antibody P31.2 VL CDR1 (Chothia)

<400> SEQUENCE: 146

Ser Gln Ser Val Ser Ser Ala
1 5

<210> SEQ ID NO 147
<211> LENGTH: 6
<212> TYPE: PRT
<213> ORGANISM: Artificial Sequence
<220> FEATURE:
<223> OTHER INFORMATION: Antibody P31.2 VL CDR3 (Chothia)

<400> SEQUENCE: 147

Phe Gly Ala Glu Pro Ile
1 5

<210> SEQ ID NO 148
<211> LENGTH: 6
<212> TYPE: PRT
<213> ORGANISM: Artificial Sequence
<220> FEATURE:
<223> OTHER INFORMATION: Antibody P31.2 VH CDR1 (Contact)

<400> SEQUENCE: 148

Ser Ser Tyr Tyr Ile His
1 5

<210> SEQ ID NO 149
<211> LENGTH: 13
<212> TYPE: PRT
<213> ORGANISM: Artificial Sequence
<220> FEATURE:
<223> OTHER INFORMATION: Antibody P31.2 VH CDR2 (Contact)

<400> SEQUENCE: 149

Trp Val Ala Thr Ile Ser Ser Gly Gly Gly Phe Thr Tyr
1 5 10

<210> SEQ ID NO 150
<211> LENGTH: 11
<212> TYPE: PRT
<213> ORGANISM: Artificial Sequence
<220> FEATURE:
<223> OTHER INFORMATION: Antibody P31.2 VH CDR3 (Contact)

<400> SEQUENCE: 150

Ala Arg Gly Tyr Thr Leu Thr Pro Val Leu Asp
1 5 10

<210> SEQ ID NO 151
<211> LENGTH: 7
<212> TYPE: PRT
<213> ORGANISM: Artificial Sequence
<220> FEATURE:
<223> OTHER INFORMATION: Antibody P31.2 VL CDR1 (Contact)

<400> SEQUENCE: 151

Ser Ser Ala Val Ala Trp Tyr
1 5

<210> SEQ ID NO 152
<211> LENGTH: 10
<212> TYPE: PRT
<213> ORGANISM: Artificial Sequence
<220> FEATURE:
<223> OTHER INFORMATION: Antibody P31.2 VL CDR2 (Contact)

<400> SEQUENCE: 152

Leu Leu Ile Tyr Ser Ala Ser Ser Leu Tyr
1 5 10

<210> SEQ ID NO 153
<211> LENGTH: 8
<212> TYPE: PRT
<213> ORGANISM: Artificial Sequence
<220> FEATURE:
<223> OTHER INFORMATION: Antibody P31.2 VL CDR3 (Contact)

<400> SEQUENCE: 153

Gln Gln Phe Gly Ala Glu Pro Ile
1 5

<210> SEQ ID NO 154
<211> LENGTH: 10
<212> TYPE: PRT
<213> ORGANISM: Artificial Sequence
<220> FEATURE:
<223> OTHER INFORMATION: Antibody P31.2 VH CDR2 (AbM)

<400> SEQUENCE: 154

Thr Ile Ser Ser Gly Gly Gly Phe Thr Tyr
1 5 10

<210> SEQ ID NO 155
<211> LENGTH: 116
<212> TYPE: PRT
<213> ORGANISM: Artificial Sequence
<220> FEATURE:
<223> OTHER INFORMATION: Antibody P31.2 VH Sequence

<400> SEQUENCE: 155

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Tyr Ile His Trp Val Arg Gln Ala Pro Gly Lys Gly Leu Glu Trp Val
35 40 45

Ala Thr Ile Ser Ser Gly Gly Gly Phe Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Gly Tyr Thr Leu Thr Pro Val Leu Asp Tyr Trp Gly Gln Gly
100 105 110

Thr Leu Val Thr
115

<210> SEQ ID NO 156
<211> LENGTH: 107
<212> TYPE: PRT
<213> ORGANISM: Artificial Sequence
<220> FEATURE:
<223> OTHER INFORMATION: Antibody P31.2 VL Sequence

<400> SEQUENCE: 156

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala
20 25 30

Val Ala Trp Tyr Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Phe Gly Ala Glu Pro Ile
85 90 95

Thr Phe Gly Gln Gly Thr Lys Val Glu Ile Lys
100 105

<210> SEQ ID NO 157
<211> LENGTH: 441
<212> TYPE: PRT
<213> ORGANISM: Artificial Sequence
<220> FEATURE:
<223> OTHER INFORMATION: C40 First polypeptide chain (BC1)

<400> SEQUENCE: 157

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala
20 25 30

Val Ala Trp Tyr Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro

```
65                  70                  75                  80

Glu Asp Phe Ala Thr Tyr Tyr Cys Gln Gln Arg Tyr Ser Ser Leu Leu
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 158
<211> LENGTH: 224
<212> TYPE: PRT
<213> ORGANISM: Artificial Sequence
<220> FEATURE:
<223> OTHER INFORMATION: C40 Second polypeptide chain (BC1)

<400> SEQUENCE: 158

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Tyr Tyr
20 25 30

Tyr Ile His Trp Val Arg Gln Ala Pro Gly Lys Gly Leu Glu Trp Val
35 40 45

Ala Trp Ile Asp Pro Tyr Gly His Ser Thr Thr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Gly Gly Arg Gly Ala Met Asp Tyr Trp Gly Gln Gly Thr Leu
100 105 110

Val Thr Val Ser Ser Ala Ser Pro Arg Glu Pro Gln Val Tyr Thr Asp
115 120 125

Pro Pro Ser Arg Asp Glu Leu Thr Lys Asn Gln Val Ser Leu Thr Cys
130 135 140

Leu Val Lys Gly Phe Tyr Pro Ser Asp Ile Ala Val Glu Trp Glu Ser
145 150 155 160

Asn Gly Gln Pro Glu Asn Asn Tyr Lys Thr Thr Pro Pro Val Leu Asp
165 170 175

Ser Asp Gly Ser Phe Phe Leu Tyr Ser Lys Leu Thr Val Asp Lys Ser
180 185 190

Arg Trp Gln Gln Gly Asn Val Phe Ser Cys Ser Val Met His Glu Ala
195 200 205

Leu His Asn His Tyr Thr Gln Lys Ser Leu Ser Leu Ser Gly Glu Cys
210 215 220

<210> SEQ ID NO 159
<211> LENGTH: 441
<212> TYPE: PRT
<213> ORGANISM: Artificial Sequence
<220> FEATURE:
<223> OTHER INFORMATION: P22 Third polypeptide chain (BC1 and B44)

<400> SEQUENCE: 159

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala
20 25 30

Val Ala Trp Tyr Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Thr Ser Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala

```
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 160
<211> LENGTH: 222
<212> TYPE: PRT
<213> ORGANISM: Artificial Sequence
<220> FEATURE:
<223> OTHER INFORMATION: P22 Fourth polypeptide chain (BC1 and BC44)

<400> SEQUENCE: 160

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Ile His Trp Val Arg Gln Ala Pro Gly Lys Gly Leu Glu Trp Val
        35                  40                  45

Ala Trp Ile Thr Ser His Gly Tyr Ser Thr Lys Tyr Ala Asp Ser Val
```

50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Asp Ser Val Ile Tyr Gly Leu Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Pro Lys Ser Cys
210 215 220

<210> SEQ ID NO 161
<211> LENGTH: 441
<212> TYPE: PRT
<213> ORGANISM: Artificial Sequence
<220> FEATURE:
<223> OTHER INFORMATION: P24 Third polypeptide chain (BC1 and BC44)

<400> SEQUENCE: 161

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala
20 25 30

Val Ala Trp Tyr Gln Gln Lys Pro Gly Lys Ala Pro Lys Leu Leu Ile
35 40 45

Tyr Ser Ala Ser Ser Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln Val Ser Tyr Ser Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser

```
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 162
<211> LENGTH: 224
<212> TYPE: PRT
<213> ORGANISM: Artificial Sequence
<220> FEATURE:
<223> OTHER INFORMATION: P24 Fourth polypeptide chain (BC1 and BC44)

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Gln Tyr
            20                  25                  30

Tyr Ile His Trp Val Arg Gln Ala Pro Gly Lys Gly Leu Glu Trp Val
        35                  40                  45

Ala Glu Ile Tyr Pro Ala Gly Ser Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Tyr Ser Val Arg Tyr Ala Leu Asp Tyr Trp Gly Gln
            100                 105                 110

Gly Thr Leu Val Thr Val Ser Ser Ala Ser Thr Lys Gly Pro Ser Val
```

```
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220


<210> SEQ ID NO 163
<211> LENGTH: 441
<212> TYPE: PRT
<213> ORGANISM: Artificial Sequence
<220> FEATURE:
<223> OTHER INFORMATION: P31.2 Third polypeptide chain (BC1 and BC44)

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Gly Ala Glu Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
```

```
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 164
<211> LENGTH: 223
<212> TYPE: PRT
<213> ORGANISM: Artificial Sequence
<220> FEATURE:
<223> OTHER INFORMATION: P31.2 Fourth polypeptide chain (BC1)

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Ile His Trp Val Arg Gln Ala Pro Gly Lys Gly Leu Glu Trp Val
        35                  40                  45

Ala Thr Ile Ser Ser Gly Gly Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Thr Leu Thr Pro Val Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Pro Lys Ser Cys
    210                 215                 220


<210> SEQ ID NO 165
<211> LENGTH: 441
<212> TYPE: PRT
<213> ORGANISM: Artificial Sequence
<220> FEATURE:
<223> OTHER INFORMATION: C56 First polypeptide chain (BC1)

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Ser Asp Leu Arg
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
```

```
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 166
<211> LENGTH: 224
<212> TYPE: PRT
<213> ORGANISM: Artificial Sequence
<220> FEATURE:
<223> OTHER INFORMATION: C56 Second polypeptide chain (BC1)

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Tyr Tyr
            20                  25                  30

Tyr Ile His Trp Val Arg Gln Ala Pro Gly Lys Gly Leu Glu Trp Val
        35                  40                  45

Ala Phe Ile Asp Pro Tyr Ser Gly Ser Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Ala Leu Asp Tyr Trp Gly Gln Gly Thr Leu
            100                 105                 110

Val Thr Val Ser Ser Ala Ser Pro Arg Glu Pro Gln Val Tyr Thr Asp
        115                 120                 125

Pro Pro Ser Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Gly Glu Cys
    210                 215                 220


<210> SEQ ID NO 167
<211> LENGTH: 441
<212> TYPE: PRT
```

<213> ORGANISM: Artificial Sequence
<220> FEATURE:
<223> OTHER INFORMATION: C59 First polypeptide chain (BC1)

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Thr Thr Ser Leu Leu
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu 385 390 395 400

Tyr Ser Lys Leu Thr Val Asp Lys Ser Arg Trp Gln Gln Gly Asn Val
405 410 415

Phe Ser Cys Ser Val Met His Glu Ala Leu His Asn His Tyr Thr Gln
420 425 430

Lys Ser Leu Ser Leu Ser Pro Gly Lys
435 440

<210> SEQ ID NO 168
<211> LENGTH: 224
<212> TYPE: PRT
<213> ORGANISM: Artificial Sequence
<220> FEATURE:
<223> OTHER INFORMATION: C59 Second polypeptide chain (BC1)

<400> SEQUENCE: 168

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Ser Tyr
20 25 30

Tyr Ile His Trp Val Arg Gln Ala Pro Gly Lys Gly Leu Glu Trp Val
35 40 45

Ala Tyr Ile Asp Ser Lys His Gly Thr Thr Gln Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Gly Gly Arg Ser Ala Met Asp Tyr Trp Gly Gln Gly Thr Leu
100 105 110

Val Thr Val Ser Ser Ala Ser Pro Arg Glu Pro Gln Val Tyr Thr Asp
115 120 125

Pro Pro Ser Arg Asp Glu Leu Thr Lys Asn Gln Val Ser Leu Thr Cys
130 135 140

Leu Val Lys Gly Phe Tyr Pro Ser Asp Ile Ala Val Glu Trp Glu Ser
145 150 155 160

Asn Gly Gln Pro Glu Asn Asn Tyr Lys Thr Thr Pro Pro Val Leu Asp
165 170 175

Ser Asp Gly Ser Phe Phe Leu Tyr Ser Lys Leu Thr Val Asp Lys Ser
180 185 190

Arg Trp Gln Gln Gly Asn Val Phe Ser Cys Ser Val Met His Glu Ala
195 200 205

Leu His Asn His Tyr Thr Gln Lys Ser Leu Ser Leu Ser Gly Glu Cys
210 215 220

<210> SEQ ID NO 169
<211> LENGTH: 441
<212> TYPE: PRT
<213> ORGANISM: Artificial Sequence
<220> FEATURE:
<223> OTHER INFORMATION: C40 First polypeptide chain (BC1; silent Fc)

<400> SEQUENCE: 169

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala
20 25 30

```
Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Ser Leu Leu
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 170
<211> LENGTH: 441
<212> TYPE: PRT
<213> ORGANISM: Artificial Sequence
<220> FEATURE:
<223> OTHER INFORMATION: P22 Third polypeptide chain (BC1; silent Fc and
BC44; silent Fc)

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

```
Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 171
<211> LENGTH: 441
<212> TYPE: PRT
<213> ORGANISM: Artificial Sequence
<220> FEATURE:
<223> OTHER INFORMATION: P24 Third polypeptide chain (BC1; silent Fc and
      BC44; silent Fc)

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ser Tyr Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285
```

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 172
<211> LENGTH: 441
<212> TYPE: PRT
<213> ORGANISM: Artificial Sequence
<220> FEATURE:
<223> OTHER INFORMATION: P31.2 Third polypeptide chain (BC1; silent Fc
      and BC44; silent Fc)

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Gly Ala Glu Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser

```
        195                 200                 205

Phe Asn Arg Gly Glu Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 173
<211> LENGTH: 441
<212> TYPE: PRT
<213> ORGANISM: Artificial Sequence
<220> FEATURE:
<223> OTHER INFORMATION: C56 First polypeptide chain (BC1; silent Fc)

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Ser Asp Leu Arg
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
```

```
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 174
<211> LENGTH: 441
<212> TYPE: PRT
<213> ORGANISM: Artificial Sequence
<220> FEATURE:
<223> OTHER INFORMATION: C59 First polypeptide chain (BC1; silent Fc)

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
```

```
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Thr Thr Ser Leu Leu
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 175

<211> LENGTH: 441
<212> TYPE: PRT
<213> ORGANISM: Artificial Sequence
<220> FEATURE:
<223> OTHER INFORMATION: C40 First polypeptide chain (BC44)

<400> SEQUENCE: 175

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Ser Leu Leu
                85                  90                  95

Thr Phe Gly Gln Gly Thr Lys Val Glu Ile Lys Arg Thr Val Arg Glu
            100                 105                 110

Pro Gln Val Cys Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380
```

Tyr Lys Thr Thr Pro Pro Val Leu Asp Ser Asp Gly Ser Phe Phe Leu
385 390 395 400

Tyr Ser Lys Leu Thr Val Asp Lys Ser Arg Trp Gln Gln Gly Asn Val
405 410 415

Phe Ser Cys Ser Val Met His Glu Ala Leu His Asn His Tyr Thr Gln
420 425 430

Lys Ser Leu Ser Leu Ser Pro Gly Lys
435 440

<210> SEQ ID NO 176
<211> LENGTH: 224
<212> TYPE: PRT
<213> ORGANISM: Artificial Sequence
<220> FEATURE:
<223> OTHER INFORMATION: C40 Second polypeptide chain (BC44)

<400> SEQUENCE: 176

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Tyr Tyr
20 25 30

Tyr Ile His Trp Val Arg Gln Ala Pro Gly Lys Gly Leu Glu Trp Val
35 40 45

Ala Trp Ile Asp Pro Tyr Gly His Ser Thr Thr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Gly Gly Arg Gly Ala Met Asp Tyr Trp Gly Gln Gly Thr Leu
100 105 110

Val Thr Val Ser Ser Ala Ser Pro Arg Glu Pro Gln Val Tyr Thr Leu
115 120 125

Pro Pro Cys Arg Asp Glu Leu Thr Lys Asn Gln Val Ser Leu Thr Cys
130 135 140

Leu Val Lys Gly Phe Tyr Pro Ser Asp Ile Ala Val Glu Trp Glu Ser
145 150 155 160

Asn Gly Gln Pro Glu Asn Asn Tyr Lys Thr Thr Pro Pro Val Leu Asp
165 170 175

Ser Asp Gly Ser Phe Phe Leu Tyr Ser Lys Leu Thr Val Asp Lys Ser
180 185 190

Arg Trp Gln Gln Gly Asn Val Phe Ser Cys Ser Val Met His Glu Ala
195 200 205

Leu His Asn His Tyr Thr Gln Lys Ser Leu Ser Leu Ser Pro Gly Lys
210 215 220

<210> SEQ ID NO 177
<211> LENGTH: 441
<212> TYPE: PRT
<213> ORGANISM: Artificial Sequence
<220> FEATURE:
<223> OTHER INFORMATION: C56 First polypeptide chain (BC44)

<400> SEQUENCE: 177

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ser Ala

```
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Ser Asp Leu Arg
                85                  90                  95

Thr Phe Gly Gln Gly Thr Lys Val Glu Ile Lys Arg Thr Val Arg Glu
            100                 105                 110

Pro Gln Val Cys Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 178
<211> LENGTH: 224
<212> TYPE: PRT
<213> ORGANISM: Artificial Sequence
<220> FEATURE:
<223> OTHER INFORMATION: C56 Second polypeptide chain (BC44)

<400> SEQUENCE: 178

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Tyr Tyr
            20                  25                  30

Tyr Ile His Trp Val Arg Gln Ala Pro Gly Lys Gly Leu Glu Trp Val
        35                  40                  45

Ala Phe Ile Asp Pro Tyr Ser Gly Ser Thr Glu Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Ala Leu Asp Tyr Trp Gly Gln Gly Thr Leu
            100                 105                 110

Val Thr Val Ser Ser Ala Ser Pro Arg Glu Pro Gln Val Tyr Thr Leu
        115                 120                 125

Pro Pro Cys Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220
```

<210> SEQ ID NO 179
<211> LENGTH: 441
<212> TYPE: PRT
<213> ORGANISM: Artificial Sequence
<220> FEATURE:
<223> OTHER INFORMATION: C59 First polypeptide chain (BC44)

<400> SEQUENCE: 179

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Thr Thr Ser Leu Leu
```

```
                85                  90                  95

Thr Phe Gly Gln Gly Thr Lys Val Glu Ile Lys Arg Thr Val Arg Glu
            100                 105                 110

Pro Gln Val Cys Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 180
<211> LENGTH: 224
<212> TYPE: PRT
<213> ORGANISM: Artificial Sequence
<220> FEATURE:
<223> OTHER INFORMATION: C59 Second polypeptide chain (BC44)

<400> SEQUENCE: 180

Glu Val Gln Leu Val Glu Ser Gly Gly Gly Leu Val Gln Pro Gly Gly
```

```
1               5                   10                  15

Ser Leu Arg Leu Ser Cys Ala Ala Ser Gly Phe Thr Phe Thr Ser Tyr
            20                  25                  30

Tyr Ile His Trp Val Arg Gln Ala Pro Gly Lys Gly Leu Glu Trp Val
        35                  40                  45

Ala Tyr Ile Asp Ser Lys His Gly Thr Thr Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Ser Ala Met Asp Tyr Trp Gly Gln Gly Thr Leu
            100                 105                 110

Val Thr Val Ser Ser Ala Ser Pro Arg Glu Pro Gln Val Tyr Thr Leu
        115                 120                 125

Pro Pro Cys Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220


<210> SEQ ID NO 181
<211> LENGTH: 441
<212> TYPE: PRT
<213> ORGANISM: Artificial Sequence
<220> FEATURE:
<223> OTHER INFORMATION: C40 First polypeptide chain (BC44; silent Fc)

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Ser Leu Leu
                85                  90                  95

Thr Phe Gly Gln Gly Thr Lys Val Glu Ile Lys Arg Thr Val Arg Glu
            100                 105                 110

Pro Gln Val Cys Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
```

```
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 182
<211> LENGTH: 441
<212> TYPE: PRT
<213> ORGANISM: Artificial Sequence
<220> FEATURE:
<223> OTHER INFORMATION: C56 First polypeptide chain (BC44; silent Fc)

<400> SEQUENCE: 182

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Gly Arg Ser Asp Leu Arg
                85                  90                  95

Thr Phe Gly Gln Gly Thr Lys Val Glu Ile Lys Arg Thr Val Arg Glu
            100                 105                 110

Pro Gln Val Cys Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 183
<211> LENGTH: 441
<212> TYPE: PRT
<213> ORGANISM: Artificial Sequence
<220> FEATURE:
<223> OTHER INFORMATION: C59 First polypeptide chain (BC44; silent Fc)

<400> SEQUENCE: 183

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Thr Thr Ser Leu Leu
                85                  90                  95

Thr Phe Gly Gln Gly Thr Lys Val Glu Ile Lys Arg Thr Val Arg Glu
            100                 105                 110

Pro Gln Val Cys Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415
```

```
Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 184
<211> LENGTH: 323
<212> TYPE: PRT
<213> ORGANISM: Homo sapiens
<220> FEATURE:
<223> OTHER INFORMATION: Full-length amino acid sequence of human CD47

<400> SEQUENCE: 184

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu
```

<210> SEQ ID NO 185
<211> LENGTH: 504
<212> TYPE: PRT
<213> ORGANISM: Homo sapiens
<220> FEATURE:
<223> OTHER INFORMATION: Full-length amino acid sequence of human SIRPa

<400> SEQUENCE: 185

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365
```

```
Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500


<210> SEQ ID NO 186
<211> LENGTH: 290
<212> TYPE: PRT
<213> ORGANISM: Homo sapiens
<220> FEATURE:
<223> OTHER INFORMATION: Full-length amino acid sequence of human PD-L1

<400> SEQUENCE: 186

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220
```

```
Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 187
<211> LENGTH: 288
<212> TYPE: PRT
<213> ORGANISM: Homo sapiens
<220> FEATURE:
<223> OTHER INFORMATION: Full-length amino acid sequence of human PD-1

<400> SEQUENCE: 187

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 188
<211> LENGTH: 222
<212> TYPE: PRT
<213> ORGANISM: Artificial Sequence
<220> FEATURE:
<223> OTHER INFORMATION: Exemplary Fc region sequence

<400> SEQUENCE: 188

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 189
<211> LENGTH: 222
<212> TYPE: PRT
<213> ORGANISM: Artificial Sequence
<220> FEATURE:
<223> OTHER INFORMATION: Exemplary variant Fc region (silent Fc) sequence

<400> SEQUENCE: 189

```
Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
```

```
                85                  90                  95

Lys Val Ser Asn Lys Ala Leu Lys Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220


<210> SEQ ID NO 190
<211> LENGTH: 110
<212> TYPE: PRT
<213> ORGANISM: Artificial Sequence
<220> FEATURE:
<223> OTHER INFORMATION: Exemplary variant CH2 domain (e.g., silent CH2)
      sequence

<400> SEQUENCE: 190

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Lys Ala Pro Ile Glu Lys Thr Ile Ser Lys Ala Lys
            100                 105                 110


<210> SEQ ID NO 191
<211> LENGTH: 330
<212> TYPE: PRT
<213> ORGANISM: Artificial Sequence
<220> FEATURE:
<223> OTHER INFORMATION: Exemplary IgG heavy chain comprises any VH
      domain

<400> SEQUENCE: 191

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 192
<211> LENGTH: 330
<212> TYPE: PRT
<213> ORGANISM: Artificial Sequence
<220> FEATURE:
<223> OTHER INFORMATION: Exemplary IgG heavy chain comprises any VH
      domain

<400> SEQUENCE: 192

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Lys Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 193
<211> LENGTH: 107
<212> TYPE: PRT
<213> ORGANISM: Artificial Sequence
<220> FEATURE:
<223> OTHER INFORMATION: Exemplary light chain (e.g., for pairing with
      an IgG heavy chain) comprises any VL domain

<400> SEQUENCE: 193

Arg Thr Val Ala Ala Pro Ser Val Phe Ile Phe Pro Pro Ser Asp Ser
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 194
<211> LENGTH: 10
<212> TYPE: PRT
<213> ORGANISM: Artificial Sequence
<220> FEATURE:
<223> OTHER INFORMATION: CD47 VH CDR1
<220> FEATURE:
<221> NAME/KEY: misc_feature
<222> LOCATION: (5)..(6)
<223> OTHER INFORMATION: Xaa can be any naturally occurring amino acid

<400> SEQUENCE: 194

Gly Phe Thr Phe Xaa Xaa Tyr Tyr Ile His
1               5                   10

<210> SEQ ID NO 195
<211> LENGTH: 17
<212> TYPE: PRT
<213> ORGANISM: Artificial Sequence
<220> FEATURE:
<223> OTHER INFORMATION: CD47 VH CDR2
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 195

Xaa Ile Asp Xaa Xaa Xaa Xaa Xaa Thr Xaa Tyr Ala Asp Ser Val Lys
1               5                   10                  15

Gly

<210> SEQ ID NO 196
<211> LENGTH: 8
<212> TYPE: PRT
<213> ORGANISM: Artificial Sequence
<220> FEATURE:
<223> OTHER INFORMATION: CD47 VH CDR3
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 196

Gly Gly Xaa Xaa Ala Xaa Asp Tyr
1               5

<210> SEQ ID NO 197
<211> LENGTH: 11
<212> TYPE: PRT
<213> ORGANISM: Artificial Sequence
<220> FEATURE:
<223> OTHER INFORMATION: CD47 and PD-L1 VL CDR1

<400> SEQUENCE: 197

Arg Ala Ser Gln Ser Val Ser Ser Ala Val Ala
1               5                   10

<210> SEQ ID NO 198
<211> LENGTH: 7
<212> TYPE: PRT
<213> ORGANISM: Artificial Sequence
<220> FEATURE:
<223> OTHER INFORMATION: CD47 and PD-L1 VL CDR2

<400> SEQUENCE: 198

Ser Ala Ser Ser Leu Tyr Ser
1 5

<210> SEQ ID NO 199
<211> LENGTH: 9
<212> TYPE: PRT
<213> ORGANISM: Artificial Sequence
<220> FEATURE:
<223> OTHER INFORMATION: CD47 VL CDR3
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 199

Gln Gln Xaa Xaa Xaa Xaa Leu Xaa Thr
1 5

<210> SEQ ID NO 200
<211> LENGTH: 10
<212> TYPE: PRT
<213> ORGANISM: Artificial Sequence
<220> FEATURE:
<223> OTHER INFORMATION: PD-L1 VH CDR1
<220> FEATURE:
<221> NAME/KEY: misc_feature
<222> LOCATION: (5)..(6)
<223> OTHER INFORMATION: Xaa can be any naturally occurring amino acid

<400> SEQUENCE: 200

Gly Phe Thr Phe Xaa Xaa Tyr Tyr Ile His
1 5 10

<210> SEQ ID NO 201
<211> LENGTH: 17
<212> TYPE: PRT
<213> ORGANISM: Artificial Sequence
<220> FEATURE:
<223> OTHER INFORMATION: PD-L1 VH CDR2
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 201

Xaa Ile Xaa Xaa Xaa Gly Xaa Xaa Thr Xaa Tyr Ala Asp Ser Val Lys
1 5 10 15

Gly

<210> SEQ ID NO 202
<211> LENGTH: 11
<212> TYPE: PRT
<213> ORGANISM: Artificial Sequence
<220> FEATURE:
<223> OTHER INFORMATION: PD-L1 VH CDR3
<220> FEATURE:
<221> NAME/KEY: misc_feature
<222> LOCATION: (1)..(8)
<223> OTHER INFORMATION: Xaa can be any naturally occurring amino acid

<400> SEQUENCE: 202

Xaa Xaa Xaa Xaa Xaa Xaa Xaa Xaa Leu Asp Tyr
1               5                   10

<210> SEQ ID NO 203
<211> LENGTH: 9
<212> TYPE: PRT
<213> ORGANISM: Artificial Sequence
<220> FEATURE:
<223> OTHER INFORMATION: PD-L1 VL CDR3
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 203

Gln Gln Xaa Xaa Xaa Xaa Pro Xaa Thr
1               5

<210> SEQ ID NO 204
<211> LENGTH: 226
<212> TYPE: PRT
<213> ORGANISM: Artificial Sequence
<220> FEATURE:
<223> OTHER INFORMATION: Phage display heavy chain
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(66)
<223> OTHER INFORMATION: Xaa can be any naturally occurring amino acid
<220> FEATURE:
<221> NAME/KEY: misc_feature
<222> LOCATION: (99)..(112)
<223> OTHER INFORMATION: Xaa can be any naturally occurring amino acid

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Xaa Xaa Xaa Xaa Xaa
    50                  55                  60

Xaa Xaa Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
                85                  90                  95

Ala Arg Xaa Xaa Xaa Xaa Xaa Xaa Xaa Xaa Xaa Xaa Xaa Xaa Xaa Xaa
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225


<210> SEQ ID NO 205
<211> LENGTH: 214
<212> TYPE: PRT
<213> ORGANISM: Artificial Sequence
<220> FEATURE:
<223> OTHER INFORMATION: Phage display light chain
<220> FEATURE:
<221> NAME/KEY: misc_feature
<222> LOCATION: (89)..(97)
<223> OTHER INFORMATION: Xaa can be any naturally occurring amino acid

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Xaa Xaa Xaa Xaa Xaa Xaa Xaa Xaa
                85                  90                  95

Xaa Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210


<210> SEQ ID NO 206
<211> LENGTH: 17
<212> TYPE: PRT
<213> ORGANISM: Artificial Sequence
<220> FEATURE:
<223> OTHER INFORMATION: CD47 VH CDR2
<220> FEATURE:
<221> NAME/KEY: MISC_FEATURE
<222> LOCATION: (1)..(1)
<223> OTHER INFORMATION: X is a W, F or Y
<220> FEATURE:
<221> NAME/KEY: MISC_FEATURE
<222> LOCATION: (4)..(4)
<223> OTHER INFORMATION: X is a P or S
<220> FEATURE:
<221> NAME/KEY: MISC_FEATURE
<222> LOCATION: (5)..(5)
<223> OTHER INFORMATION: X is a Y or K
<220> FEATURE:
<221> NAME/KEY: MISC_FEATURE
<222> LOCATION: (6)..(6)
<223> OTHER INFORMATION: X is a G, S or H
<220> FEATURE:
<221> NAME/KEY: MISC_FEATURE
<222> LOCATION: (7)..(7)
<223> OTHER INFORMATION: X is a H or G
<220> FEATURE:
<221> NAME/KEY: MISC_FEATURE
<222> LOCATION: (8)..(8)
<223> OTHER INFORMATION: X is a S or T
<220> FEATURE:
<221> NAME/KEY: MISC_FEATURE
<222> LOCATION: (10)..(10)
<223> OTHER INFORMATION: X is a T, E or Q

<400> SEQUENCE: 206

Xaa Ile Asp Xaa Xaa Xaa Xaa Xaa Thr Xaa Tyr Ala Asp Ser Val Lys
1               5                   10                  15

Gly


<210> SEQ ID NO 207
<211> LENGTH: 8
<212> TYPE: PRT
<213> ORGANISM: Artificial Sequence
<220> FEATURE:
<223> OTHER INFORMATION: CD47 VH CDR3
<220> FEATURE:
<221> NAME/KEY: MISC_FEATURE
<222> LOCATION: (3)..(3)
<223> OTHER INFORMATION: X is a R or L
<220> FEATURE:
<221> NAME/KEY: MISC_FEATURE
<222> LOCATION: (4)..(4)
<223> OTHER INFORMATION: X is a G, Y or S
<220> FEATURE:
<221> NAME/KEY: MISC_FEATURE
<222> LOCATION: (6)..(6)
<223> OTHER INFORMATION: X is a M or L

<400> SEQUENCE: 207

Gly Gly Xaa Xaa Ala Xaa Asp Tyr
1               5


<210> SEQ ID NO 208
<211> LENGTH: 9
<212> TYPE: PRT
<213> ORGANISM: Artificial Sequence
```

<220> FEATURE:
<223> OTHER INFORMATION: CD47 VL CDR3
<220> FEATURE:
<221> NAME/KEY: MISC_FEATURE
<222> LOCATION: (3)..(3)
<223> OTHER INFORMATION: X is a R or G
<220> FEATURE:
<221> NAME/KEY: MISC_FEATURE
<222> LOCATION: (4)..(4)
<223> OTHER INFORMATION: X is a Y, R or T
<220> FEATURE:
<221> NAME/KEY: MISC_FEATURE
<222> LOCATION: (5)..(5)
<223> OTHER INFORMATION: X is a S or T
<220> FEATURE:
<221> NAME/KEY: MISC_FEATURE
<222> LOCATION: (6)..(6)
<223> OTHER INFORMATION: X is a S or D
<220> FEATURE:
<221> NAME/KEY: MISC_FEATURE
<222> LOCATION: (8)..(8)
<223> OTHER INFORMATION: X is a L or R

<400> SEQUENCE: 208

Gln Gln Xaa Xaa Xaa Xaa Leu Xaa Thr
1               5

<210> SEQ ID NO 209
<211> LENGTH: 17
<212> TYPE: PRT
<213> ORGANISM: Artificial Sequence
<220> FEATURE:
<223> OTHER INFORMATION: PD-L1 VH CDR2
<220> FEATURE:
<221> NAME/KEY: MISC_FEATURE
<222> LOCATION: (1)..(1)
<223> OTHER INFORMATION: X is a E, W, or T
<220> FEATURE:
<221> NAME/KEY: MISC_FEATURE
<222> LOCATION: (3)..(3)
<223> OTHER INFORMATION: X is a Y, T, or S
<220> FEATURE:
<221> NAME/KEY: MISC_FEATURE
<222> LOCATION: (4)..(4)
<223> OTHER INFORMATION: X is a P or S
<220> FEATURE:
<221> NAME/KEY: MISC_FEATURE
<222> LOCATION: (5)..(5)
<223> OTHER INFORMATION: X is a A, H, or G
<220> FEATURE:
<221> NAME/KEY: MISC_FEATURE
<222> LOCATION: (7)..(7)
<223> OTHER INFORMATION: X is a S, Y, or G
<220> FEATURE:
<221> NAME/KEY: MISC_FEATURE
<222> LOCATION: (8)..(8)
<223> OTHER INFORMATION: X is a Y, S, or F
<220> FEATURE:
<221> NAME/KEY: MISC_FEATURE
<222> LOCATION: (10)..(10)
<223> OTHER INFORMATION: X is a Y or K

<400> SEQUENCE: 209

Xaa Ile Xaa Xaa Xaa Gly Xaa Xaa Thr Xaa Tyr Ala Asp Ser Val Lys
1               5                   10                  15

Gly

<210> SEQ ID NO 210
<211> LENGTH: 11
<212> TYPE: PRT
<213> ORGANISM: Artificial Sequence
<220> FEATURE:
<223> OTHER INFORMATION: PD-L1 VH CDR3
<220> FEATURE:

<221> NAME/KEY: MISC_FEATURE
<222> LOCATION: (1)..(1)
<223> OTHER INFORMATION: X is a G or D
<220> FEATURE:
<221> NAME/KEY: MISC_FEATURE
<222> LOCATION: (2)..(2)
<223> OTHER INFORMATION: X is a P, S, or Y
<220> FEATURE:
<221> NAME/KEY: MISC_FEATURE
<222> LOCATION: (3)..(3)
<223> OTHER INFORMATION: X is a Y, V, or T
<220> FEATURE:
<221> NAME/KEY: MISC_FEATURE
<222> LOCATION: (4)..(4)
<223> OTHER INFORMATION: X is a S, I, or L
<220> FEATURE:
<221> NAME/KEY: MISC_FEATURE
<222> LOCATION: (5)..(5)
<223> OTHER INFORMATION: X is a V, Y, or T
<220> FEATURE:
<221> NAME/KEY: MISC_FEATURE
<222> LOCATION: (6)..(6)
<223> OTHER INFORMATION: X is a R, G or P
<220> FEATURE:
<221> NAME/KEY: MISC_FEATURE
<222> LOCATION: (7)..(7)
<223> OTHER INFORMATION: X is a Y or V (or not present)
<220> FEATURE:
<221> NAME/KEY: MISC_FEATURE
<222> LOCATION: (8)..(8)
<223> OTHER INFORMATION: X is an A (or not present)

<400> SEQUENCE: 210

Xaa Xaa Xaa Xaa Xaa Xaa Xaa Xaa Leu Asp Tyr
1               5                   10

<210> SEQ ID NO 211
<211> LENGTH: 9
<212> TYPE: PRT
<213> ORGANISM: Artificial Sequence
<220> FEATURE:
<223> OTHER INFORMATION: PD-L1 VL CDR3
<220> FEATURE:
<221> NAME/KEY: MISC_FEATURE
<222> LOCATION: (3)..(3)
<223> OTHER INFORMATION: X is a V, Y, or F
<220> FEATURE:
<221> NAME/KEY: MISC_FEATURE
<222> LOCATION: (4)..(4)
<223> OTHER INFORMATION: X is a S, Y, or G
<220> FEATURE:
<221> NAME/KEY: MISC_FEATURE
<222> LOCATION: (5)..(5)
<223> OTHER INFORMATION: X is a Y, T, or A
<220> FEATURE:
<221> NAME/KEY: MISC_FEATURE
<222> LOCATION: (6)..(6)
<223> OTHER INFORMATION: X is a S or E
<220> FEATURE:
<221> NAME/KEY: MISC_FEATURE
<222> LOCATION: (8)..(8)
<223> OTHER INFORMATION: X is a Y or I

<400> SEQUENCE: 211

Gln Gln Xaa Xaa Xaa Xaa Pro Xaa Thr
1               5

<210> SEQ ID NO 212
<211> LENGTH: 35
<212> TYPE: PRT
<213> ORGANISM: Artificial Sequence
<220> FEATURE:
<223> OTHER INFORMATION: CD47 VH consensus sequence
<220> FEATURE:
<221> NAME/KEY: MISC_FEATURE
<222> LOCATION: (5)..(5)
<223> OTHER INFORMATION: X is a S or T
<220> FEATURE:
<221> NAME/KEY: MISC_FEATURE
<222> LOCATION: (6)..(6)
<223> OTHER INFORMATION: X is a Y or S
<220> FEATURE:
<221> NAME/KEY: MISC_FEATURE
<222> LOCATION: (11)..(11)
<223> OTHER INFORMATION: X is a W, F or Y
<220> FEATURE:
<221> NAME/KEY: MISC_FEATURE
<222> LOCATION: (14)..(14)
<223> OTHER INFORMATION: X is a P or S
<220> FEATURE:
<221> NAME/KEY: MISC_FEATURE
<222> LOCATION: (15)..(15)
<223> OTHER INFORMATION: X is a Y or K
<220> FEATURE:
<221> NAME/KEY: MISC_FEATURE
<222> LOCATION: (16)..(16)
<223> OTHER INFORMATION: X is a G, S or H
<220> FEATURE:
<221> NAME/KEY: MISC_FEATURE
<222> LOCATION: (17)..(17)
<223> OTHER INFORMATION: X is a H or G
<220> FEATURE:
<221> NAME/KEY: MISC_FEATURE
<222> LOCATION: (18)..(18)
<223> OTHER INFORMATION: X is a S or T
<220> FEATURE:
<221> NAME/KEY: MISC_FEATURE
<222> LOCATION: (20)..(20)
<223> OTHER INFORMATION: X is a T, E or Q
<220> FEATURE:
<221> NAME/KEY: MISC_FEATURE
<222> LOCATION: (30)..(30)
<223> OTHER INFORMATION: X is a R or L
<220> FEATURE:
<221> NAME/KEY: MISC_FEATURE
<222> LOCATION: (31)..(31)
<223> OTHER INFORMATION: X is a G, Y or S
<220> FEATURE:
<221> NAME/KEY: MISC_FEATURE
<222> LOCATION: (33)..(33)
<223> OTHER INFORMATION: X is a M or L

<400> SEQUENCE: 212

```
Gly Phe Thr Phe Xaa Xaa Tyr Tyr Ile His Xaa Ile Asp Xaa Xaa Xaa
1               5                   10                  15

Xaa Xaa Thr Xaa Tyr Ala Asp Ser Val Lys Gly Gly Gly Xaa Xaa Ala
            20                  25                  30

Xaa Asp Tyr
        35
```

<210> SEQ ID NO 213
<211> LENGTH: 27
<212> TYPE: PRT
<213> ORGANISM: Artificial Sequence
<220> FEATURE:
<223> OTHER INFORMATION: CD47 VL consensus sequence
<220> FEATURE:
<221> NAME/KEY: MISC_FEATURE
<222> LOCATION: (21)..(21)
<223> OTHER INFORMATION: X is a R or G
<220> FEATURE:
<221> NAME/KEY: MISC_FEATURE
<222> LOCATION: (22)..(22)
<223> OTHER INFORMATION: X is a Y, R or T
<220> FEATURE:
<221> NAME/KEY: MISC_FEATURE
<222> LOCATION: (23)..(23)
<223> OTHER INFORMATION: X is a S or T
<220> FEATURE:
<221> NAME/KEY: MISC_FEATURE
<222> LOCATION: (24)..(24)
<223> OTHER INFORMATION: X is a S or D
<220> FEATURE:
<221> NAME/KEY: MISC_FEATURE
<222> LOCATION: (26)..(26)
<223> OTHER INFORMATION: X is a L or R

<400> SEQUENCE: 213

```
Arg Ala Ser Gln Ser Val Ser Ser Ala Val Ala Ser Ala Ser Ser Leu
1               5                   10                  15

Tyr Ser Gln Gln Xaa Xaa Xaa Xaa Leu Xaa Thr
            20                  25
```

<210> SEQ ID NO 214
<211> LENGTH: 38
<212> TYPE: PRT
<213> ORGANISM: Artificial Sequence
<220> FEATURE:
<223> OTHER INFORMATION: PD-L1 VH consensus sequence
<220> FEATURE:
<221> NAME/KEY: MISC_FEATURE
<222> LOCATION: (5)..(5)
<223> OTHER INFORMATION: X is a D or S
<220> FEATURE:
<221> NAME/KEY: MISC_FEATURE
<222> LOCATION: (6)..(6)
<223> OTHER INFORMATION: X is a Q or S
<220> FEATURE:
<221> NAME/KEY: MISC_FEATURE
<222> LOCATION: (11)..(11)
<223> OTHER INFORMATION: X is a E, W, or T
<220> FEATURE:
<221> NAME/KEY: MISC_FEATURE
<222> LOCATION: (13)..(13)
<223> OTHER INFORMATION: X is a Y, T, or S
<220> FEATURE:
<221> NAME/KEY: MISC_FEATURE
<222> LOCATION: (14)..(14)
<223> OTHER INFORMATION: X is a P or S
<220> FEATURE:
<221> NAME/KEY: MISC_FEATURE
<222> LOCATION: (15)..(15)
<223> OTHER INFORMATION: X is a A, H, or G
<220> FEATURE:
<221> NAME/KEY: MISC_FEATURE
<222> LOCATION: (17)..(17)
<223> OTHER INFORMATION: X is a S, Y, or G
<220> FEATURE:
<221> NAME/KEY: MISC_FEATURE
<222> LOCATION: (18)..(18)
<223> OTHER INFORMATION: X is a Y, S, or F
<220> FEATURE:
<221> NAME/KEY: MISC_FEATURE
<222> LOCATION: (20)..(20)
<223> OTHER INFORMATION: X is a Y or K
<220> FEATURE:
<221> NAME/KEY: MISC_FEATURE
<222> LOCATION: (28)..(28)
<223> OTHER INFORMATION: X is a G or D
<220> FEATURE:
<221> NAME/KEY: MISC_FEATURE
<222> LOCATION: (29)..(29)
<223> OTHER INFORMATION: X is a P, S, or Y
<220> FEATURE:
<221> NAME/KEY: MISC_FEATURE
<222> LOCATION: (30)..(30)
<223> OTHER INFORMATION: X is a Y, V, or T
<220> FEATURE:
<221> NAME/KEY: MISC_FEATURE
<222> LOCATION: (31)..(31)
<223> OTHER INFORMATION: X is a S, I, or L
<220> FEATURE:
<221> NAME/KEY: MISC_FEATURE
<222> LOCATION: (32)..(32)
<223> OTHER INFORMATION: X is a V, Y, or T
<220> FEATURE:

<221> NAME/KEY: MISC_FEATURE
<222> LOCATION: (33)..(33)
<223> OTHER INFORMATION: X is a R, G or P
<220> FEATURE:
<221> NAME/KEY: MISC_FEATURE
<222> LOCATION: (34)..(34)
<223> OTHER INFORMATION: X is a Y or V (or not present)
<220> FEATURE:
<221> NAME/KEY: MISC_FEATURE
<222> LOCATION: (35)..(35)
<223> OTHER INFORMATION: X is an A (or not present)

<400> SEQUENCE: 214

```
Gly Phe Thr Phe Xaa Xaa Tyr Tyr Ile His Xaa Ile Xaa Xaa Xaa Gly
1               5                   10                  15

Xaa Xaa Thr Xaa Tyr Ala Asp Ser Val Lys Gly Xaa Xaa Xaa Xaa Xaa
            20                  25                  30

Xaa Xaa Xaa Leu Asp Tyr
        35
```

<210> SEQ ID NO 215
<211> LENGTH: 27
<212> TYPE: PRT
<213> ORGANISM: Artificial Sequence
<220> FEATURE:
<223> OTHER INFORMATION: PD-L1 VL consensus sequence
<220> FEATURE:
<221> NAME/KEY: MISC_FEATURE
<222> LOCATION: (21)..(21)
<223> OTHER INFORMATION: X is a V, Y, or F
<220> FEATURE:
<221> NAME/KEY: MISC_FEATURE
<222> LOCATION: (22)..(22)
<223> OTHER INFORMATION: X is a S, Y, or G
<220> FEATURE:
<221> NAME/KEY: MISC_FEATURE
<222> LOCATION: (23)..(23)
<223> OTHER INFORMATION: X is a Y, T, or A
<220> FEATURE:
<221> NAME/KEY: MISC_FEATURE
<222> LOCATION: (24)..(24)
<223> OTHER INFORMATION: X is a S or E
<220> FEATURE:
<221> NAME/KEY: MISC_FEATURE
<222> LOCATION: (26)..(26)
<223> OTHER INFORMATION: X is a Y or I

<400> SEQUENCE: 215

```
Arg Ala Ser Gln Ser Val Ser Ser Ala Val Ala Ser Ala Ser Ser Leu
1               5                   10                  15

Tyr Ser Gln Gln Xaa Xaa Xaa Xaa Pro Xaa Thr
            20                  25
```

<210> SEQ ID NO 216
<211> LENGTH: 10
<212> TYPE: PRT
<213> ORGANISM: Artificial Sequence
<220> FEATURE:
<223> OTHER INFORMATION: CD47 VH CDR1
<220> FEATURE:
<221> NAME/KEY: MISC_FEATURE
<222> LOCATION: (5)..(5)
<223> OTHER INFORMATION: X is a S or T
<220> FEATURE:
<221> NAME/KEY: MISC_FEATURE
<222> LOCATION: (6)..(6)
<223> OTHER INFORMATION: X is a Y or S

<400> SEQUENCE: 216

```
Gly Phe Thr Phe Xaa Xaa Tyr Tyr Ile His
1               5                   10
```

```
<210> SEQ ID NO 217
<211> LENGTH: 10
<212> TYPE: PRT
<213> ORGANISM: Artificial Sequence
<220> FEATURE:
<223> OTHER INFORMATION: PD-L1 VH CDR1
<220> FEATURE:
<221> NAME/KEY: MISC_FEATURE
<222> LOCATION: (5)..(5)
<223> OTHER INFORMATION: X is a D or S
<220> FEATURE:
<221> NAME/KEY: MISC_FEATURE
<222> LOCATION: (6)..(6)
<223> OTHER INFORMATION: X is a Q or S

<400> SEQUENCE: 217

Gly Phe Thr Phe Xaa Xaa Tyr Tyr Ile His
1               5                   10
```